United States Patent
Kai et al.

(10) Patent No.: US 9,150,546 B2
(45) Date of Patent: Oct. 6, 2015

(54) TRIAZINE DERIVATIVE AND PHARMACEUTICAL COMPOSITION COMPRISING THE SAME

(75) Inventors: Hiroyuki Kai, Osaka (JP); Takayuki Kameyama, Shiga (JP); Tsuyoshi Hasegawa, Osaka (JP); Miho Oohara, Osaka (JP); Yukio Tada, Osaka (JP); Takeshi Endoh, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 228 days.

(21) Appl. No.: 13/201,209

(22) PCT Filed: Feb. 10, 2010

(86) PCT No.: PCT/JP2010/051920
§ 371 (c)(1),
(2), (4) Date: Aug. 30, 2011

(87) PCT Pub. No.: WO2010/092966
PCT Pub. Date: Aug. 19, 2010

(65) Prior Publication Data
US 2011/0319414 A1    Dec. 29, 2011

(30) Foreign Application Priority Data

Feb. 13, 2009  (JP) .................................. 2009-031520
Nov. 25, 2009  (JP) .................................. 2009-266903

(51) Int. Cl.
| | |
|---|---|
| A61K 31/535 | (2006.01) |
| A61K 31/53 | (2006.01) |
| C07D 403/06 | (2006.01) |
| C07D 251/46 | (2006.01) |
| C07D 251/52 | (2006.01) |

(Continued)

(52) U.S. Cl.
CPC ............ *C07D 403/06* (2013.01); *C07D 251/46* (2013.01); *C07D 251/52* (2013.01); *C07D 401/06* (2013.01); *C07D 401/12* (2013.01); *C07D 401/14* (2013.01); *C07D 403/04* (2013.01); *C07D 403/12* (2013.01); *C07D 405/06* (2013.01); *C07D 405/12* (2013.01); *C07D 409/06* (2013.01); *C07D 413/12* (2013.01)

(58) Field of Classification Search
None
See application file for complete search history.

(56) References Cited

U.S. PATENT DOCUMENTS 3,598,815 A    8/1971 Gilles et al.
4,021,249 A    5/1977 Noguchi et al.

(Continued)

FOREIGN PATENT DOCUMENTS

| | | |
|---|---|---|
| EP | 0 005 911 A1 | 12/1979 |
| EP | 0 547 461 A1 | 6/1993 |

(Continued)

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
CAS RN 857972-98-6 (entered into STN Aug. 3, 2005).*
Anderson (Chem and Biol 10:787-797, 2003).*
Thiel (Nature Biotechnol 2:513-519, 2004).*
Kennedy, "P2X Receptors: Targets for Novel Analgesics?," The Neuroscientist, vol. 11, No. 4, pp. 345-356, (2005).
Cockayne et al., "$P2X_2$ Knockout Mice and $P2X_2/P2X_3$ Double Knockout Mice Reveal a Role for the $P2X_2$ Receptor Subunit in Mediating Multiple Sensory Effects of ATP," J. Physiol. 567.2, The Physiological Society, pp. 621-639, (2005).
Shieh et al., "P2X Receptor Ligands and Pain," Expert Opinion, Ther. Patents, vol. 16, No. 8, pp. 1113-1127, (2006).
North, "$P2X_3$ Receptors and Peripheral Pain Mechanisms," J. Physiol. 554.2, The Physiological Society, pp. 301-308, (2003).

(Continued)

*Primary Examiner* — Craig Ricci
(74) *Attorney, Agent, or Firm* — Finnegan, Henderson, Farabow, Garrett and Dunner, LLP

(57) ABSTRACT

The present invention provides a novel $P2X_3$ and/or $P2X_{2/3}$ receptor antagonist.
A compound represented by the formula (I):

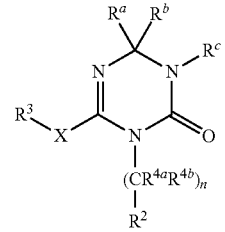

wherein $R^a$, $R^b$ and $R^c$ are,
(a) $R^a$ and $R^b$ are taken together =Z; and $R^c$ is a group represented by $R^{1c}$; or
(b) $R^b$ and $R^c$ are taken together to form a bond; and $R^a$ is a group represented by —Y—$R^{1a}$;
$R^{1a}$ and $R^{1c}$ are each independently hydrogen, substituted or unsubstituted alkyl, etc.;
$R^2$ and $R^3$ are each independently substituted or unsubstituted aryl, etc.;
$R^{4a}$ and $R^{4b}$ are each independently hydrogen, substituted or unsubstituted alkyl, etc.;
X is —N($R^5$)—, etc.;
$R^5$ is hydrogen, substituted or unsubstituted lower alkyl, etc.;
—Y— is —O—, etc.;
=Z is =O, etc.; and
n is an integer of 0 to 4.

5 Claims, No Drawings

(51) Int. Cl.

| | |
|---|---|
| *C07D 401/06* | (2006.01) |
| *C07D 401/12* | (2006.01) |
| *C07D 401/14* | (2006.01) |
| *C07D 403/04* | (2006.01) |
| *C07D 403/12* | (2006.01) |
| *C07D 405/06* | (2006.01) |
| *C07D 405/12* | (2006.01) |
| *C07D 409/06* | (2006.01) |
| *C07D 413/12* | (2006.01) |

(56) References Cited

U.S. PATENT DOCUMENTS

| | | | |
|---|---|---|---|
| 4,127,718 A | | 11/1978 | Illy et al. |
| 4,156,002 A | | 5/1979 | Brown et al. |
| 4,158,724 A | | 6/1979 | Illy et al. |
| 4,254,122 A | * | 3/1981 | Brown .................. 514/245 |
| 4,317,911 A | | 3/1982 | Rasberger et al. |
| 4,518,688 A | | 5/1985 | Leppard et al. |
| 5,232,924 A | | 8/1993 | Watanabe et al. |
| 5,389,599 A | | 2/1995 | Schallner et al. |
| 6,177,437 B1 | | 1/2001 | Wright |
| 7,745,451 B2 | | 6/2010 | Kelly et al. |
| 7,858,632 B2 | | 12/2010 | Broka et al. |
| 2002/0049320 A1 | | 4/2002 | Gopalsamy et al. |
| 2007/0037974 A1 | | 2/2007 | Brotherton-Pleiss et al. |
| 2007/0049534 A1 | | 3/2007 | Dillon et al. |
| 2007/0049609 A1 | | 3/2007 | Broka et al. |
| 2007/0049610 A1 | | 3/2007 | Dillon et al. |
| 2007/0049758 A1 | | 3/2007 | Dillon et al. |
| 2009/0099195 A1 | | 4/2009 | Bayrakdarian et al. |
| 2009/0270369 A1 | | 10/2009 | Ozaki et al. |
| 2010/0317676 A1 | | 12/2010 | Kelly et al. |
| 2011/0077242 A1 | | 3/2011 | Broka et al. |

FOREIGN PATENT DOCUMENTS

| | | | |
|---|---|---|---|
| EP | 2 399 910 | | 12/2011 |
| JP | 57-144269 | | 9/1982 |
| JP | 62-156110 | | 7/1987 |
| JP | 11-189577 | | 7/1999 |
| JP | 2000-072757 A | | 3/2000 |
| JP | 2006528640 | | 2/2005 |
| JP | 2007-526268 | | 9/2007 |
| JP | 2008-546639 | | 12/2008 |
| JP | 2009-7258 | | 1/2009 |
| JP | 2010-526138 | | 7/2010 |
| JP | 2010523667 | | 7/2010 |
| RU | 2057754 | | 4/1996 |
| WO | WO-99/52881 | | 10/1999 |
| WO | WO-00/39101 | | 7/2000 |
| WO | WO-00/51990 | | 9/2000 |
| WO | WO-01/55093 | | 8/2001 |
| WO | WO-02/094767 A2 | | 11/2002 |
| WO | WO-2004/054617 | | 7/2004 |
| WO | WO-2005/009980 A1 | | 2/2005 |
| WO | WO 2005/009980 A1 | | 2/2005 |
| WO | WO-2005/095359 A1 | | 10/2005 |
| WO | WO-2006/074057 | | 7/2006 |
| WO | WO 2006/102112 | * | 9/2006 ................ A61P 1/12 |
| WO | WO-2006/102112 A2 | | 9/2006 |
| WO | WO-2006/104713 A1 | | 10/2006 |
| WO | WO-2006/104715 A1 | | 10/2006 |
| WO | WO 2006/119502 | | 11/2006 |
| WO | WO 2006/119504 | | 11/2006 |
| WO | WO 2007-079163 A2 | | 7/2007 |
| WO | WO-2007/791214 A2 | | 7/2007 |
| WO | WO 2008/005538 | | 1/2008 |
| WO | WO 2008/016522 | | 2/2008 |
| WO | WO-2008/089051 | | 7/2008 |
| WO | WO 2008/089051 | | 7/2008 |
| WO | WO 2008/136756 | | 11/2008 |
| WO | WO 2009/058653 A1 | | 5/2009 |
| WO | WO-2010/051188 A1 | | 5/2010 |
| WO | WO 2008/127591 A2 | | 7/2010 |
| WO | WO 2010/092966 | | 8/2010 |
| WO | WO-2012/016182 | | 2/2012 |
| WO | WO 2012/020749 | | 2/2012 |
| WO | WO 2012/135800 | | 10/2012 |

OTHER PUBLICATIONS

Kennedy et al., "Crossing the Pain Barrier: P2 Receptors as Targets for Novel Analgesics," J. Physiol., 553.3 The Physiological Society, pp. 683-694, (2003).
Gever et al., "Pharmacology of P2X Channels," Pflugers Arch—Eur J Physiol, vol. 452, pp. 513-537, (2006).
Jarvis et al., "A-317491, A Novel Potent and Selective Non-Nucleotide Antagonist of $P2X_3$ and $P2X_{2/3}$ Receptors, Reduces Chronic Inflammatory and Neuropathic Pain in the Rat," PNAS, vol. 99, No. 26, pp. 17179-17184 (2002).
Balboni et al., "Triazine Compounds as Antagonists at Bv8-Prokineticin Receptors," J. Med. Chem. vol. 51, pp. 7635-7639 (2008).
Simov et al., "Triazines and Other 6-Membered Rings," Chemical Abstracts, Heterocyclic Compounds, vol. 67, p. 10245 (1967).
Gopalsamy et al., "Combinatorial Synthesis of Heterocycles: Solid-Phase Synthesis of 6-Amino-2,4-Dioxo-3,4-Dihydro-1,3,5-Triazine Derivatives," J. Comb. Chem., vol. 3, pp. 278-283 (2001).
Akteries et al., "Reactions of Carbonyl Diisocyanate With Amides and Acids," Chem, Ber., vol. 119, pp. 669-682 (1986).
International Search Report from the Japanese Patent Office for International Application No. PCT/JP2010/051920 (Mail date Mar. 30, 2010).
Supplementary European Search Report for European Application No. 10741243, mailed Sep. 13, 2012.
Bernatowicz, et al., 1H-Pyrazole-1-carboxamidine Hydrochloride: An Attractive Reagent for Guanylation of Amines and Its Application to Peptide Synthesis, J. Org. Chem., 57: 2497-2502 (1992).
Carter et al., "Identification and SAR of novel diaminopyrimidines. Part 1: The discovery of RO-4, a dual $P2X_3/p2x_{2/3}$ antagonist for the treatment of pain," Bioorganic & Medicinal Chemistry Letters, 19: 1628-1631 (2009).
Dräger, et al., "A new reagent and its polymer-supported variant for the amidination of amines," Tetrahedron Letters, 43: 1401-1403 (2002).
English-language International Search Report for International Application No. PCT/JP2011/068113 from the Japanese Patent Office mailed Nov. 1, 2011.
English-language International Search Report for International Application No. PCT/JP2011/068097 from the Japanese Patent Office mailed Nov. 15, 2011.
Esayan, et al., Synthesis and sulfuric acid hydrolysis ɣ-chlorocrotylbenzyl (alkyl) isocyanurates, Armyanskii Khimicheskii Zhurnal, 28(4): 332-337 (1975).
Knotz, "1-Chloromethylisatin, an excellent reagent for the identification of carboxylic acids and NH-acid compounds", Scientia Pharmaceutica, 38(4): 227-233 (1970).
Lerchova, et al., "Antioxidants and Stabilizers, L. Transformation of the 1,3,5-Tris(4-hydroxy-3,5-di-tert-butylbenzyl)cyanuric acid into Alkylperoxycyclohexadienones, their Properties and Effects on the Oxidation of Tetralin and Polypropylene", Angewandte Makromolekulare Chemie, 39(1): 107-118, (1974).
Notification of Transmittal of Translation of the International Preliminary Report on Patentability, International Preliminary Report on Patentability, and Translation of the Written Opinion of the International Searching Authority, for International Patent Application No. PCT/JP2010/051920, mailed Sep. 22, 2011 (14 pages).
Notification of Transmittal of Translation of the International Preliminary Report on Patentability, International Preliminary Report on Patentability, and Translation of the Written Opinion of the International Searching Authority, for International Patent Application No. PCT/JP2011/068097, mailed Mar. 21, 2013 (10 pages).
Notification of Transmittal of Translation of the International Preliminary Report on Patentability, International Preliminary Report on Patentability, and Translation of the Written Opinion of the International Searching Authority, for International Patent Application No. PCT/JP2011/068113, mailed Mar. 21, 2013 (15 pages).

(56) References Cited

OTHER PUBLICATIONS

Pecchi, et al., "Identification and structure-activity relationship of 2-morpholino 6-(3-hydroxyphenyl) pyrimidines, a class of potent and selective PI3 kinase inhibitors," Bioorganic & Medicinal Chemistry Letters, 20(23): 6895-6898 (2010).

Schriof-Gregoire, et al., "Preparation of N-alkyl-N-carboalkoxy guanidines: unexpected effective trans-alkoxylation transforming the 2,2,2-trichloroethoxycarbonyl into various carbamates" Tetrahedron Letters 48: 2357-2359 (2007).

Shao, et al., "Strapped porphyrin rosettes based on the melamine-cyanuric acid motif. Self-assembly and supramolecular recognition" Tetrahedron 60(41): 9155-9162, (2004).

Zuen, et al., "Crystalline furanic polyisocyanates" Polymer Bulletin 26(4): 383-390 (1991).

Adriaensen et al., "Functional Morphology of Pulmonary Neuroepithelial Bodies: Extremely Complex Airway Receptors", The Anatomical Record Part A, vol. 270A, pp. 25-40 (2003).

Basoglu, Md, et al., "Effects of Aerosolized Adenosine 5'—Triphosphate vs Adenosine 5'—Monophosphate on Dyspnea and Airway Caliber in Healthy Nonsmokers and Patients with Asthma", Chest, vol. 128, No. 4, pp. 1905-1909 (2005).

Brouns et al., "Intraepithelial Vagal Sensory Nerve Terminals in Rat Pulmonary Neuroepithelial Bodies Express P2X3 Receptors", Am. J. Respir. Cell Mol. Biol., vol. 23, pp. 52-61 (2000).

English-language Abstract of Okano, Natsuko et al., "Preparation of 2-phenylaminopyrimidinones, intermediates as pesticides and herbicides in agriculture", Chem. Abstracts Service, Columbus, OH (1999); STN Accession No. 1999-672770.

English-language Abstract of Fukuchi, T et al., "Novel 2-aminopyrimidinone derivatives, useful as insecticide and acaricide", Thomson Scientific, London, GB (May 15, 2001); STN Accession No. 2001-458100.

English-language Abstract of Fukuchi, T et al., "2-anilino-4(3H)-pyrimidinone derivatives, pesticidally/herbicidally active, useful in agriculture/horticulture and their preparation", Thomson Scientific, London, GB (2003); STN Accession No. 2003-318151.

English-language Abstract of Fukuchi, T et al., "A novel 2-substituted amoni-5,6-dihydro-4(3H)-pyrimidinone derivative", Thomson Scientific, London, GB (2001); STN Accession No. 2001-491646.

English Abstract of WO 9952881 A1 (1999), (via Espacenet).

English Abstract of JP 11-189577 (1999), (Patent Abstracts of Japan).

English Abstract of JP 2009-7258 (2009), (Patent Abstracts of Japan).

English Abstract of WO 01/55093 (2001), (via WIPO Patentscope).

English Abstract of WO 04/054617 (2004), (via WIPO Patentscope).

English Abstract of WO 10/092966 (2010), (via WIPO Patentscope).

English Abstract of WO 12/020749 (2012), (via WIPO Patentscope).

International Search Report from the Japanese Patent Office for International Application No. PCT/JP2013/052991 mailed Mar. 12, 2013.

Ji-Zhen, Li et al., "Polymer Supported Synthesis of Multi-substituted Pyrimidine-4-one Derivatives via Pbf-activated Thiourea", Chem. Research in Chinese Universities, vol. 27, No. 2, (2011) pp. 221-223.

Kennedy et al., "Crossing the pain barrier: P2 receptors as targets for novel analgesics", J. Physiology, vol. 553, No. 3, pp. 683-694 (2003).

Notification of Transmittal of Translation of the International Preliminary Report on Patentability (PCT/IB/338); English-language translation of International Preliminary Report on Patentability (PCT/IB/373) issued Aug. 12, 2014, and Written Opinion from The International Searching Authority (PCT/ISA/237) mailed Mar. 12, 2013, for International Application No. PCT/JP2013/052991.

Office Action dated Jan. 28, 2015 in U.S. Appl. No. 13/816,085.

Office Action dated Feb. 26, 2015 in U.S. Appl. No. 13/814,346.

Supplementary European Search Report for European Application No. 11816406, mailed Oct. 20, 2014.

\* cited by examiner

TRIAZINE DERIVATIVE AND PHARMACEUTICAL COMPOSITION COMPRISING THE SAME

TECHNICAL FIELD

The invention relates to P2X receptor, specifically to a compound useful for the treatment of diseases or conditions associated with a $P2X_3$ receptor, specifically to a $P2X_3$ and/or $P2X_{2/3}$ receptor, and a pharmaceutical composition comprising such compound.

BACKGROUND ART

ATP (adenosine triphosphate) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. ATP thus released mediates various extracellular signal transductions through an ATP receptor (Non-Patent Document 4, Non-Patent Document 5).

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel (Non-Patent Document 6).

ATP is known to cause pain, and studies with $P2X_3$ knockout and knockdown methodologies have shown that $P2X_3$ receptor mediates transmission of chronic pain. $P2X_3$ receptors are expressed in a specific manner on peripheral sensory nerve to form a homo-complex or hetero-complex with $P2X_2$ ($P2X_{2/3}$) (Non-Patent Document 1).

Later, the compound A-317491 was reported as a specific antagonist to $P2X_3$ and $P2X_{2/3}$ receptors. A-317491 is tri-substituted-N-[(1S)-1,2,3,4-tetrahydro-1-naphthalenyl]benzamide derivative represented by the formula:

[Chemical Formula 1]

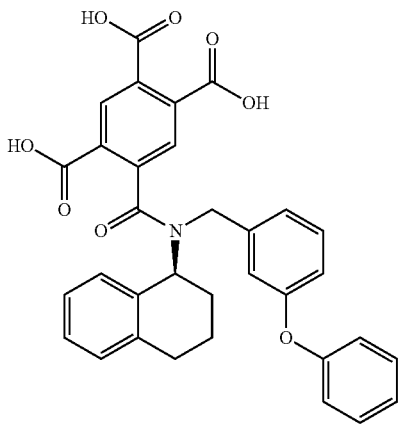

(Patent Document 1). It was reported to exhibit an antagonist activity to $P2X_3$ and $P2X_{2/3}$ receptors and analgesic action in neuropathic pain model and inflammatory pain model (Non-Patent Document 7). This indicates that pain sensation is transmitted via $P2X_3$ or $P2X_{2/3}$ receptor and that a $P2X_3$ or $P2X_{2/3}$ receptor antagonist is useful as an analgesic. Also, compounds that exhibit $P2X_3$ or $P2X_{2/3}$ receptor antagonizing effect are described in Patent Documents 2-7.

Additionally, it was recently reported that vesical reflex was strongly reduced in $P2X_3$ knockout mouse (Non-Patent Document 2), suggesting that a $P2X_3$ antagonist is useful in the treatment of diseases caused by overactive bladder.

Patent document 8, 9, 10 and 11 discloses that the compounds having similar chemical structures to the compound of the invention, however, does not disclose that the compounds having an analgesic effect and a $P2X_3$ or $P2X_{2/3}$ receptor antagonizing effect. Non-Patent documents 8 disclose that the compounds having similar chemical structures to the compound of the invention and an analgesic effect, however, does not disclose that the compound having a $P2X_3$ or $P2X_{2/3}$ receptor antagonizing effect.

[Patent Document 1] WO02/094767
[Patent Document 2] WO2005/095359
[Patent Document 3] US20070037974
[Patent Document 4] US20070049758
[Patent Document 5] US20070049610
[Patent Document 6] US20070049609
[Patent Document 7] US20070049534
[Patent Document 8] JP12-072757
[Patent Document 9] WO2006/104713
[Patent Document 10] WO2006/104715
[Patent Document 11] WO2006/102112
[Non-Patent Document 1] Neuroscientist 11 (2005) 345-356
[Non-Patent Document 2] J. Physiol. 567.2 (2005) 621-639
[Non-Patent Document 3] Expert Opin. Ther. Patens (2006) 16(8) 113-1127
[Non-Patent Document 4] J. Physiol. (2003), 554(2), 301-308
[Non-Patent Document 5] J. Physiology (2003), 553(3), 683-694
[Non-Patent Document 6] Pflungers Arch Eur J physiol (2006), 452, 513-537
[Non-Patent Document 7] PNAS (2002), 99(26), 17179-17184
[Non-Patent Document 8] J. Med. Chem. (2008), 51(23), 7635-7639

DISCLOSURE OF INVENTION

Problems to be Resolved by the Invention

The present invention provides a novel $P2X_3$ and/or $P2X_{2/3}$ receptor antagonist.

Means of Solving the Problems

During studies to solve the problems described above, the inventors have discovered novel compounds that bind specifically to $P2X_3$ and/or $P2X_{2/3}$ receptor and exhibit an antagonizing effect, and thus, achieved the inventions described bellow.

Effect of the Invention

The compound of the invention has antagonizing effect on $P2X_3$ and/or $P2X_{2/3}$ receptor and is useful in the treatment of diseases or conditions associated with a $P2X_3$ and/or $P2X_{2/3}$ receptor, such as chronic pain, overactive bladder, etc.

MODE FOR CARRYING OUT THE INVENTION (1) A compound represented by the formula (I):

[Chemical Formula 2]

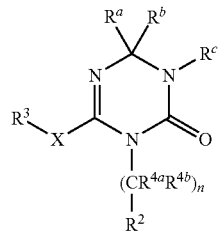

(I)

wherein
$R^a$, $R^b$ and $R^c$ are,
(a) $R^a$ and $R^b$ are taken together =Z;
=Z is =O, =S or =N—$R^6$;
$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^c$ is a group represented by $R^{1c}$;
$R^{1c}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or
(b) $R^b$ and $R^c$ are taken together to form a bond;
$R^a$ is a group represented by —Y—$R^{1a}$;
$R^{1a}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
—Y— is —O—, —S—, —N($R^7$)— or —C($R^{8a}R^{8b}$)—;
$R^7$ is hydrogen, substituted or unsubstituted alkyl, substituted or unsubstituted acyl, or $R^7$ and $R^{1a}$ are taken together to form a substituted or unsubstituted nitrogen-containing non-aromatic heterocyclic group;
$R^{8a}$ and $R^{8b}$ are each independently hydrogen, halogen, or substituted or unsubstituted alkyl;
n is an integer of 0 to 4;
$R^2$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^3$ is substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^{4a}$ and $R^{4b}$ are each independently hydrogen, substituted or unsubstituted alkyl, or
$R^{4a}$ and $R^{4b}$ are taken together oxo;
—X— is —O—, —S— or —N($R^5$)—;
$R^5$ is hydrogen, substituted or unsubstituted alkyl, or substituted or unsubstituted acyl;
provided that $R^3$ is not cyclohexyl substituted with guanidyl when —X— is —NH—,
or its pharmaceutically acceptable salt, or a solvate thereof.

(1') A compound represented by the formula (I'):

[Chemical Formula 3]

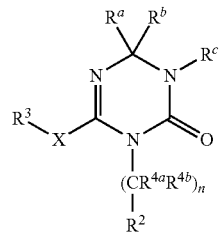

(I')

wherein
$R^a$, $R^b$ and $R^c$ are,
(a) $R^a$ and $R^b$ are taken together =Z; and $R^c$ is $R^{1c}$; or
(b) $R^b$ and $R^c$ are taken together to form a bond; and $R^a$ is —Y—$R^{1a}$;
$R^{1a}$ and $R^{1c}$ are each independently hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
n is an integer of 0 to 4;
$R^2$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^3$ is substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^{4a}$ and $R^{4b}$ are each independently hydrogen, substituted or unsubstituted alkyl;
—X— is —O—, —S— or —N($R^5$)—;
$R^5$ is hydrogen, substituted or unsubstituted alkyl, or substituted or unsubstituted acyl;
when $R^a$, $R^b$ and $R^c$ are (a);
=Z is =O, =S or =N—$R^6$;
$R^6$ is hydrogen, substituted or unsubstituted alkyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
when $R^a$, $R^b$ and $R^c$ are (b),
—Y— is —O—, —S— or —N($R^7$)—;
$R^7$ is hydrogen, substituted or unsubstituted alkyl, or substituted or unsubstituted acyl;
provided that $R^3$ is not cyclohexyl substituted with guanidyl when —X— is —NH—,
or its pharmaceutically acceptable salt, or a solvate thereof.

(1") A compound represented by the formula (I"):

[Chemical Formula 4]

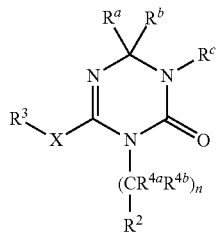

(I")

wherein
$R^a$, $R^b$ and $R^c$ are,
(a) $R^a$ and $R^b$ are taken together =Z; and $R^c$ is $R^{1c}$; or
(b) $R^b$ and $R^c$ are taken together to form a bond; and $R^a$ is —Y—$R^{1a}$;
$R^{1a}$ and $R^{1c}$ are each independently hydrogen, substituted or unsubstituted lower alkyl, substituted or unsubstituted arylalkyl, substituted or unsubstituted heteroarylalkyl, substituted or unsubstituted lower alkenyl, substituted or unsubstituted lower alkynyl, substituted or unsubstituted cycloalkyl, substituted or unsubstituted cycloalkenyl, substituted or unsubstituted acyl, a substituted or unsubstituted non-aromatic heterocyclic group, substituted or unsubstituted aryl, or substituted or unsubstituted heteroaryl;
$R^2$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^{4a}$ and $R^{4b}$ are each independently hydrogen, or substituted or unsubstituted lower alkyl;
—X— is —O—, —S— or —N($R^5$)—;
$R^5$ is hydrogen, or substituted or unsubstituted lower alkyl, or substituted or unsubstituted acyl;
when $R^a$, $R^b$ and $R^c$ are (a);
=Z is =O, =S or =N—$R^6$;
$R^6$ is hydrogen, substituted or unsubstituted lower alkyl, substituted or unsubstituted arylalkyl, substituted or unsubstituted heteroarylalkyl, substituted or unsubstituted aryl, or substituted or unsubstituted heteroaryl;
$R^3$ is substituted or unsubstituted lower alkenyl, substituted or unsubstituted lower alkynyl, substituted or unsubstituted cycloalkenyl, a substituted or unsubstituted non-aromatic heterocyclic group, substituted or unsubstituted aryl, or substituted or unsubstituted heteroaryl;
n is an integer of 1 to 3;
when $R^a$, $R^b$ and $R^c$ are (b);
$R^3$ is substituted or unsubstituted lower alkenyl, substituted or unsubstituted lower alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
—Y— is —O—, —S— or —N($R^7$)—;
$R^7$ is hydrogen, substituted or unsubstituted lower alkyl, or substituted or unsubstituted acyl;
n is an integer of 0 to 3,
or its pharmaceutically acceptable salt, or a solvate thereof.

(2) The compound according to (1), wherein the compound is represented by the formula (II):

[Chemical Formula 5]

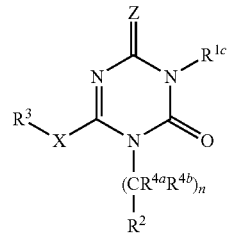

(II)

wherein
$R^{1c}$, $R^{4a}$, $R^{4b}$, —X— and =Z are as defined in (1);
n is an integer of 1 to 4;
$R^2$ and $R^3$ are each independently substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt, or a solvate thereof.

(2') The compound according to (1'), wherein the compound is represented by the formula (II'):

[Chemical Formula 6]

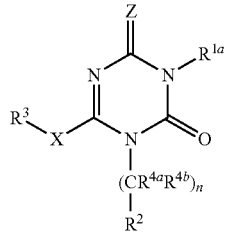

(II')

wherein
$R^{1c}$, $R^{4a}$, $R^{4b}$, —X— and =Z are as defined in (1);
n is an integer of 1 to 4;
$R^2$ and $R^3$ are each independently substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt, or a solvate thereof.

(2") The compound according to (1"), wherein the compound is represented by the formula (II"):

[Chemical Formula 7]

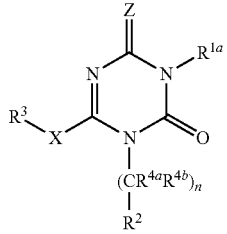

(II")

wherein
$R^{1a}$, $R^2$, $R^3$, $R^{4a}$, $R^{4b}$, —X—, =Z and n are as defined in (1"),
or its pharmaceutically acceptable salt, or a solvate thereof.

(3) The compound according to the abode (1) or (2), wherein —X— is —N(R$^5$)— wherein R$^5$ is as defined in the above (1), or its pharmaceutically acceptable salt, or a solvate thereof.

(3') The compound according to the above (2'), wherein —X— is —N(R$^5$)— wherein R$^5$ is as defined in the above (1'), or its pharmaceutically acceptable salt, or a solvate thereof.

(3") The compound according to the above (2"), wherein —X— is —N(R$^5$)— wherein R$^5$ is as defined in the above (1"), or its pharmaceutically acceptable salt, or a solvate thereof.

(4) The compound according to any one of the above (1) to (3), wherein R$^2$ is substituted or unsubstituted aryl, or substituted or unsubstituted heteroaryl, or its pharmaceutically acceptable salt, or a solvate thereof.

(4') The compound according to any one of the above (2') or (3'), wherein R$^2$ is substituted or unsubstituted aryl, or substituted or unsubstituted heteroaryl, n is 1, or its pharmaceutically acceptable salt, or a solvate thereof.

(4") The compound according to any one of the above (2") or (3"), wherein R$^2$ is substituted or unsubstituted aryl, or substituted or unsubstituted heteroaryl, n is 1, or its pharmaceutically acceptable salt, or a solvate thereof.

(5) The compound according to any one of the above (1) to (4), wherein =Z is =O, or its pharmaceutically acceptable salt, or a solvate thereof.

(6) The compound according to any one of the above (1) to (5), wherein R$^{1c}$ is hydrogen; unsubstituted alkyl; or alkyl substituted with one or more substituents selected from Substituent Group A (Substituent Group A: halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclic ring-oxy-carbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl, or its pharmaceutically acceptable salt, or a solvate thereof.

(6') The compound according to any one of the above (2') to (4'), wherein R$^{1c}$ is hydrogen; unsubstituted alkyl; or alkyl substituted with one or more substituents selected from Substituent Group A (Substituent Group A: halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclic ring-oxy-carbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl, or its pharmaceutically acceptable salt, or a solvate thereof.

(6") The compound according to any one of the above (2") to (4"), wherein R$^{1a}$ is hydrogen; unsubstituted alkyl; or alkyl substituted with one or two or more substituent selected from halogen, hydroxy, substituted or unsubstituted lower alkenyl, substituted or unsubstituted lower alkynyl, substituted or unsubstituted lower alkyloxy, substituted or unsubstituted lower alkylthio, substituted or unsubstituted acyl, carboxy, substituted or unsubstituted lower alkyloxycarbonyl, substituted or unsubstituted benzoyl, substituted or unsubstituted carbamoyl, substituted or unsubstituted lower alkylcarbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl, or its pharmaceutically acceptable salt, or a solvate thereof.

(7) The compound according to any one of the above (1) to (6), wherein R$^3$ is a group represented by the formula:

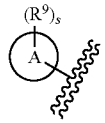

[Chemical Formula 8]

wherein ring A is aryl or heteroaryl;

s is an integer of 0 to 3; and

R$^9$ is each independently halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy, or its pharmaceutically acceptable salt, or a solvate thereof.

(7') The compound according to any one of the above (2') to (4') or (6'), wherein R$^3$ is a group represented by the formula:

[Chemical Formula 9]

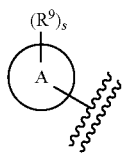

wherein ring A is aryl or heteroaryl;
s is an integer of 0 to 3;
$R^9$ is each independently halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy, or its pharmaceutically acceptable salt, or a solvate thereof.

(7″) The compound according to any one of the above (2″) to (4″) or (6″), wherein $R^3$ is a group represented by the formula:

[Chemical Formula 10]

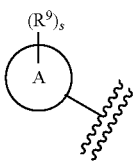

wherein ring A is aryl or heteroaryl;
s is an integer of 0 to 3;
$R^9$ is each independently halogen, hydroxy, substituted or unsubstituted alkyl, substituted or unsubstituted alkyloxy, substituted or unsubstituted lower alkenyl, substituted or unsubstituted lower alkenyloxy, substituted or unsubstituted lower alkynyl, substituted or unsubstituted alkynyloxy, substituted or unsubstituted lower alkylthio, substituted or unsubstituted acyl, carboxy, substituted or unsubstituted lower alkyloxycarbonyl, substituted or unsubstituted carbamoyl, substituted or unsubstituted lower alkylcarbamoyl, substituted or unsubstituted amino, substituted or unsubstituted sulfamoyl, cyano, nitro, nitrile, substituted or unsubstituted cycloalkyl, substituted or unsubstituted cycloalkyloxy, substituted or unsubstituted cycloalkenyl, substituted or unsubstituted cycloalkenyloxy, a substituted or unsubstituted non-aromatic heterocyclic group, substituted or unsubstituted non-aromatic heterocyclic ring-oxy, substituted or unsubstituted aryl, substituted or unsubstituted aryloxy, substituted or unsubstituted heteroaryl, or substituted or unsubstituted heteroaryloxy, or its pharmaceutically acceptable salt, or a solvate thereof.

(8) The compound according to any one of the above (1) to (7), wherein $R^3$ is a group represented by the formula:

[Chemical Formula 11]

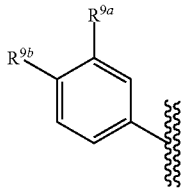

wherein $R^{9a}$ and $R^{9b}$ are each independently halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy, or its pharmaceutically acceptable salt, or a solvate thereof.

(8′) The compound according to any one of the above (2′) to (4′), (6′) or (7′), wherein $R^3$ is a group represented by the formula:

[Chemical Formula 12]

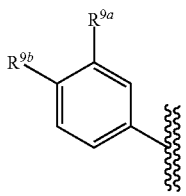

wherein $R^{9a}$ and $R^{9b}$ are each independently halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy, or its pharmaceutically acceptable salt, or a solvate thereof.

(8″) The compound according to any one of the above (2″) to (4″), (6″) or (7″), wherein $R^3$ is a group represented by the formula:

[Chemical Formula 13]

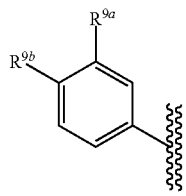

wherein $R^{9a}$ and $R^{9b}$ are each independently halogen, hydroxy, substituted or unsubstituted alkyl, substituted or unsubstituted alkyloxy, substituted or unsubstituted lower alkenyl, substituted or unsubstituted lower alkenyloxy, substituted or unsubstituted lower alkynyl, substituted or unsubstituted alkynyloxy, substituted or unsubstituted lower alkylthio, substituted or unsubstituted acyl, carboxy, substituted or unsubstituted lower alkyloxycarbonyl, substituted or unsubstituted carbamoyl, substituted or unsubstituted lower alkylcarbamoyl, substituted or unsubstituted amino, substituted or unsubstituted sulfamoyl, cyano, nitro, nitrile, substituted or unsubstituted cycloalkyl, substituted or unsubstituted cycloalkyloxy, substituted or unsubstituted cycloalkenyl, substituted or unsubstituted cycloalkenyloxy, a substituted or unsubstituted non-aromatic heterocyclic group, substituted or unsubstituted non-aromatic heterocyclic ring-oxy, substituted or unsubstituted aryl, substituted or unsubstituted aryloxy, substituted or unsubstituted heteroaryl, or substituted or unsubstituted heteroaryloxy, or its pharmaceutically acceptable salt, or a solvate thereof.

(9) The compound according to any one of the above (1) to (8), wherein $R^3$ is a group represented by the formula:

[Chemical Formula 14]

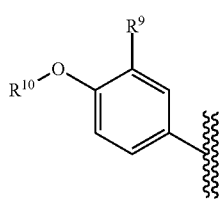

wherein $R^9$ is as defined in the above (7); and $R^{10}$ is substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt, or a solvate thereof.

(9′) The compound according to any one of the above (2′) to (4′) or (6′) to (8′), wherein $R^3$ is a group represented by the formula:

[Chemical Formula 15]

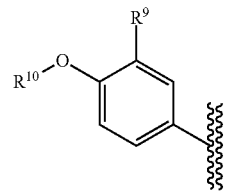

wherein $R^9$ is as defined in the above (7′); and $R^{10}$ is substituted or unsubstituted lower alkyl, substituted or unsubstituted lower alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt, or a solvate thereof.

(9″) The compound according to any one of the above (2″) to (4″) or (6″) to (8″), $R^3$ is a group represented by the formula:

[Chemical Formula 16]

wherein $R^9$ is as defined in the above (7″); and $R^{10}$ is substituted or unsubstituted lower alkyl, substituted or unsubstituted lower alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt, or a solvate thereof.

(10) The compound according to the above (1), wherein the compound is represented by the formula (III):

[Chemical Formula 17]

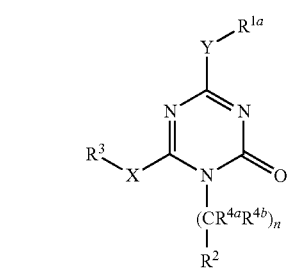

(III)

wherein $R^{1a}$, $R^{4a}$, $R^{4b}$, —X— and —Y— are as defined in the above (1);
n is an integer of 1 to 4; and
$R^2$ and $R^3$ are each independently substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt, or a solvate thereof.

(10') The compound according to the above (1'), wherein the compound is represented by the formula (III');

[Chemical Formula 18]

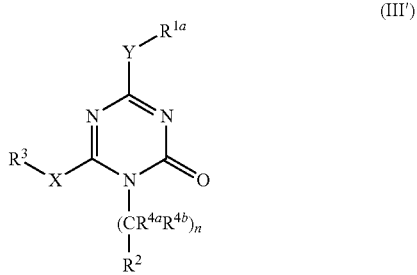

wherein $R^{1a}$, $R^{4a}$, $R^{4b}$, —X—, —Y— and n are as defined in the above (1');
$R^2$ and $R^3$ are each independently substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt, or a solvate thereof.

(10") The compound according to the above (1"), wherein the compound is represented by the formula (III");

[Chemical Formula 19]

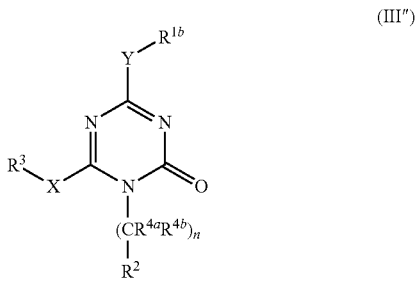

wherein $R^{1b}$, $R^2$, $R^3$, $R^{4a}$, $R^{4b}$, —X—, —Y— and n are as defined in the above (1"), or its pharmaceutically acceptable salt, or a solvate thereof.

(11) The compound according to the above (1) or (10), wherein —X— is —N($R^5$)— wherein $R^5$ is as defined in the above (1), or its pharmaceutically acceptable salt, or a solvate thereof.

(11') The compound according to the above (10'), wherein —X— is —N($R^5$)— wherein $R^5$ is as defined in the above (1'), or its pharmaceutically acceptable salt, or a solvate thereof.

(11") The compound according to the above (10'), wherein —X— is —N($R^5$)— wherein $R^5$ is as defined in the above (1"), or its pharmaceutically acceptable salt, or a solvate thereof.

(12) The compound according to any one of the above (1), (10) or (11), wherein $R^2$ is substituted or unsubstituted aryl, or substituted or unsubstituted heteroaryl, or its pharmaceutically acceptable salt, or a solvate thereof.

(12') The compound according to the above (10') or (11'), wherein $R^2$ is substituted or unsubstituted aryl or substituted or unsubstituted heteroaryl, and n is 1, or its pharmaceutically acceptable salt, or a solvate thereof.

(12") The compound according to the above (10') or (11'), wherein $R^2$ is substituted or unsubstituted aryl or substituted or unsubstituted heteroaryl, and n is 1, or its pharmaceutically acceptable salt, or a solvate thereof.

(13) The compound according to any one of the above (1) or (10) to (12), wherein —Y— is —O—, or its pharmaceutically acceptable salt, or a solvate thereof.

(13') The compound according to the above (10') or (11'), wherein —Y— is —O—, or its pharmaceutically acceptable salt, or a solvate thereof.

(13") The compound according to the above (10") or (11"), wherein —Y— is —O—, or its pharmaceutically acceptable salt, or a solvate thereof.

(14) The compound according to any one of the above (1) or (10) to (13), wherein $R^{1a}$ is hydrogen; unsubstituted alkyl; or alkyl substituted with one or more substituents selected from Substituent Group A (Substituent Group A: halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclic ring-oxy-carbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl), or its pharmaceutically acceptable salt, or a solvate thereof.

(14') The compound according to any one of the above (10") to (13"), wherein $R^{1a}$ is hydrogen; unsubstituted alkyl; or alkyl substituted with one or more substituents selected from Substituent Group A (Substituent Group A: halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclic ring-oxy-carbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl and substituted or unsubstituted heteroaryl), or its pharmaceutically acceptable salt, or a solvate thereof.

(14") The compound according to any one of the above (10") to (13"), wherein $R^{1b}$ is hydrogen; unsubstituted alkyl; or alkyl substituted with one or two or more substituent selected from halogen, hydroxy, substituted or unsubstituted lower alkenyl, substituted or unsubstituted lower alkynyl, substituted or unsubstituted lower alkyloxy, substituted or unsubstituted lower alkylthio, substituted or unsubstituted acyl, carboxy, substituted or unsubstituted lower alkyloxycarbonyl, substituted or unsubstituted benzoyl, substituted or unsubstituted carbamoyl, substituted or unsubstituted lower alkylcarbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl and substituted or unsubstituted heteroaryl, or its pharmaceutically acceptable salt, or a solvate thereof.

(15) The compound according to any one of the above (1) or (10) to (14), wherein $R^3$ is a group represented by the formula:

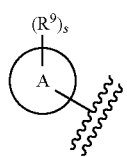

[Chemical Formula 20]

wherein ring A is aryl or heteroaryl;
s is an integer of 0 to 3; and
$R^9$ is as defined in the above (7), or its pharmaceutically acceptable salt, or a solvate thereof.

(15') The compound according to any one of the above (10') to (14'), wherein $R^3$ is a group represented by the formula:

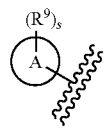

[Chemical Formula 21]

wherein ring A is aryl or heteroaryl;
s is an integer of 0 to 3; and
$R^9$ is as defined in the above (7'), or its pharmaceutically acceptable salt, or a solvate thereof.

(15") The compound according to any one of the above (10") to (13"), wherein $R^3$ is a group represented by the formula:

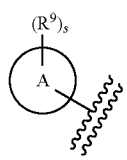

[Chemical Formula 22]

wherein ring A is aryl or heteroaryl;
s is an integer of 0 to 3; and
$R^9$ is as defined in the above (7"), or its pharmaceutically acceptable salt, or a solvate thereof.

(16) The compound according to any one of the above (1) or (10) to (15), wherein $R^3$ is a group represented by the formula:

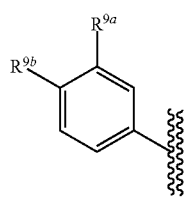

[Chemical Formula 23]

wherein $R^{9a}$ and $R^{9b}$ are as defined in the above (8), or its pharmaceutically acceptable salt, or a solvate thereof.

(16') The compound according to any one of the above (10') to (15'), wherein $R^3$ is a group represented by the formula:

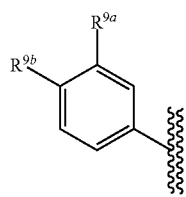

[Chemical Formula 24]

wherein $R^{9a}$ and $R^{9b}$ are as defined in the above (8'), or its pharmaceutically acceptable salt, or a solvate thereof.

(16") The compound according to any one of the above (10") to (15"), wherein $R^3$ is a group represented by the formula:

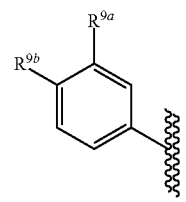

[Chemical Formula 25]

wherein $R^{9a}$ and $R^{9b}$ are as defined in the above (8"), or its pharmaceutically acceptable salt, or a solvate thereof.

(17) The compound according to any one of the above (1) or (10) to (16), wherein $R^3$ is a group represented by the formula:

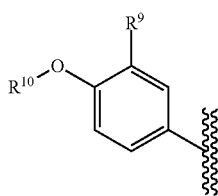

[Chemical Formula 26]

wherein $R^9$ is as defined in the above (7); and $R^{10}$ is as defined in the above (9), or its pharmaceutically acceptable salt, or a solvate thereof.

(17') The compound according to any one of the above (10') to (16'), wherein $R^3$ is a group represented by the formula:

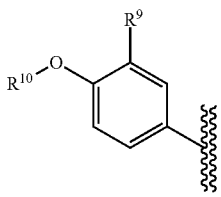

[Chemical Formula 27]

wherein R⁹ is as defined in the above (7'); and R¹⁰ is as defined in the above (9'), or its pharmaceutically acceptable salt, or a solvate thereof.

(17") The compound according to any one of the above (10") to (16"), wherein R³ is a group represented by the formula:

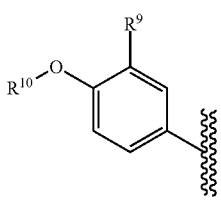

[Chemical Formula 28]

wherein R⁹ is as defined in the above (7"); and R¹⁰ is as defined in the above (9"), or its pharmaceutically acceptable salt, or a solvate thereof.

(18) A pharmaceutical composition comprising the compound according to any one of the above (1) to (17), or its pharmaceutically acceptable salt, or a solvate thereof.

(18') A pharmaceutical composition comprising the compound according to any one of the above (1') to (4') or (6') to (17'), or its pharmaceutically acceptable salt, or a solvate thereof.

(18") A pharmaceutical composition comprising the compound according to any one of the above (1") to (4") or (6") to (17"), or its pharmaceutically acceptable salt, or a solvate thereof.

(19) The pharmaceutical composition according to the above (18), wherein the composition is for a $P2X_3$ and/or $P2X_{2/3}$ receptor antagonist.

(19') The pharmaceutical composition according to the above (18'), wherein the composition is for a $P2X_3$ and/or $P2X_{2/3}$ receptor antagonist.

(19") The pharmaceutical composition according to the above (18"), wherein the composition is for a $P2X_3$ and/or $P2X_{2/3}$ receptor antagonist.

(20) A method for treating and/or preventing a disease related to $P2X_3$ and/or $P2X_{2/3}$ receptor characterized by administration of the compound according to any one of the above (1) to (17), or its pharmaceutically acceptable salt, or a solvate thereof.

(20') A method for preventing and/or treating a disease related to $P2X_3$ and/or $P2X_{2/3}$ receptor characterized by administration of the compound according to any one of the above (1') to (4') or (6') to (17'), or its pharmaceutically acceptable salt, or a solvate thereof.

(20") A method for preventing and/or treating a disease related to $P2X_3$ and/or $P2X_{2/3}$ receptor characterized by administration of the compound according to any one of the above (1") to (4") or (6") to (17"), or its pharmaceutically acceptable salt, or a solvate thereof.

(21) Use of the compound of any one of the above (1) to (17), or its pharmaceutically acceptable salt, or a solvate thereof in the manufacturing of an agent for treating and/or preventing a disease related to $P2X_3$ and/or $P2X_{2/3}$ receptor.

(21') Use of the compound of any one of the above (1') to (4') or (6') to (17'), or its pharmaceutically acceptable salt, or a solvate thereof in the manufacturing of an agent for treating and/or preventing a disease related to $P2X_3$ and/or $P2X_{2/3}$ receptor.

(21") Use of the compound of any one of the above (1") to (4") or (6") to (17"), or its pharmaceutically acceptable salt, or a solvate thereof in the manufacturing of an agent for treating and/or preventing a disease related to $P2X_3$ and/or $P2X_{2/3}$ receptor.

(22) A compound according to any one of the above (1) to (17), or its pharmaceutically acceptable salt, or a solvate thereof for use in a method for treating and/or preventing a disease related to $P2X_3$ and/or $P2X_{2/3}$ receptor.

As used throughout the specification, the following terms have the following meaning unless specifically indicated.

The term "halogen" means fluorine, chlorine, bromine and iodine.

The halogen moiety in said "lower haloalkyl", "lower haloalkyloxy", "haloalkyl" and "haloalkyloxy" is as defined above for "halogen".

The term "alkyl" includes a straight or branched chain monovalent hydrocarbon group containing from 1 to 15, preferably from 1 to 10 more preferably from 1 to 6 carbons. For example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl, n-decyl, n-undecanyl, dodecanyl, tridecanyl, etc. are exemplified.

The term "lower alkyl" includes a straight or branched chain monovalent hydrocarbon group containing from 1 to 6, preferably from 1 to 3 carbons. For example, methyl, ethyl, n-propyl, isopropyl, n-butyl, isobutyl, sec-butyl, tert-butyl, n-pentyl, isopentyl, neo-pentyl, n-hexyl, isohexyl, etc. are exemplified.

The lower alkyl moiety in said "lower haloalkyl", "lower alkylamino", "lower alkylimino", "lower alkylsulfonyl", "lower alkylsulfamoyl" and "lower alkylcarbamoyl" is as defined above for "lower alkyl".

The alkyl moiety in said "haloalkyl", "alkylamino", "alkylimino", "alkylsulfonyl", "alkylsulfamoyl", "alkylcarbamoyl", "arylalkyl" and "arylalkylamino" is as defined above for "alkyl".

The term "lower alkyloxy" includes an alkyloxy group wherein the lower alkyl moiety is as defined above for "lower alkyl". For example, methoxy, ethoxy, propoxy, isopropoxy, butoxy, isobutoxy, sec-butoxy, tert-butoxy, pentoxy, isopentoxy, neopentoxy, hexoxy, etc. are exemplified.

The alkyl moiety in said "alkyloxy" is as defined above for "alkyl".

The lower alkyloxy moiety in said "lower haloalkyloxy" and "lower alkyloxyimino" is as defined above for "lower alkyloxy".

The term "lower alkylthio" includes, for example, methylthio, ethylthio, propylthio, isopropylthio, butylthio, isobutylthio, sec-butylthio, tert-butylthio, pentylthio, isopentylthio, neopentylthio, hexylthio, etc.

The alkyl moiety in said "alkylthio" is as defined above for "alkyl".

The term "lower alkyloxycarbonyl" includes, for example, methyloxycarbonyl, ethyloxycarbonyl, n-propyloxycarbonyl, isopropyloxycarbonyl, n-butyloxycarbonyl, tert-butyloxycarbonyl, n-pentyloxycarbonyl, etc.

The alkyloxy moiety in said "alkyloxycarbonyl" is as defined above for "alkyloxy".

The term "lower alkylcarbamoyl" includes mono- or di-lower alkylcarbamoyl. For example, methylcarbamoyl, ethylcarbamoyl, n-propylcarbamoyl, isopropylcarbamoyl, n-butylcarbamoyl, dimethylcarbamoyl, diethylcarbamoyl, dipropylcarbamoyl, etc. are exemplified.

The alkyl moiety in said "alkylcarbamoyl" is as defined above for "alkyl".

The term "alkenyl" includes a straight or branched chain alkenyl containing from 2 to 15 carbons, preferably containing from 2 to 10 carbons, more preferably containing from 2 to 6 carbons having one or more double bonds at any position. For example, vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, etc. are exemplified.

The term "lower alkenyl" includes a straight or branched chain alkenyl containing from 2 to 6 carbons, preferably containing from 2 to 3 carbons having one or more double bonds at any position. For example, vinyl, propenyl, isopropenyl, butenyl, isobutenyl, prenyl, butadienyl, pentenyl, isopentenyl, pentadienyl, hexenyl, isohexenyl, hexadienyl, etc. are exemplified.

The lower alkenyl moiety of "lower alkenyloxy" and "lower alkenyloxycarbonyl" is as defined above for "lower alkenyl".

The alkenyl moiety of "alkenyloxy" and "alkenyloxycarbonyl" is as defined above for "alkenyl".

The term "alkynyl" includes a straight or branched chain alkynyl containing from 2 to 15 carbons, preferably containing from 2 to 10 carbons, more preferably containing from 2 to 6 carbons. For example, ethynyl, propynyl, butynyl, pentynyl, hexynyl, heptynyl, octynyl, nonynyl, decynyl, etc. are exemplified. They have one or more triple bonds at any position, and optionally, have a double bond.

The term "lower alkynyl" includes a straight or branched chain alkynyl containing from 2 to 6 carbons, preferably containing from 2 to 3 carbons. For example, ethynyl, propynyl, butynyl, pentynyl, hexynyl, etc. are exemplified. They have one or more triple bonds at any position, and optionally, have a double bond.

The lower alkynyl moiety of "lower alkynyloxy" and "lower alkynyloxycarbonyl" is as defined above for "lower alkynyl".

The alkynyl moiety of "alkynyloxy" and "alkynyloxycarbonyl" is as defined above for "alkynyl".

The term "acyl" includes a group of the formula R—C(=O)—, wherein R is, for example, "lower alkyl", "alkyl", "lower alkenyl", "alkenyl", "lower alkynyl", "alkynyl" as defined above or "aryl", "a heterocyclic group", "cycloalkyl", "cycloalkenyl", "arylalkyl" or "heteroarylalkyl" as defined bellow.

The acyl moiety of "acylamino" and "acylimino" is as defined above for "acyl".

The term "cycloalkane" includes a monocyclic or polycyclic saturated cyclic carbocyclic ring containing from 3 to 10 carbons. Monocyclic cycloalkane includes, for example, cyclopropane, cyclobutane, cyclopentane, cyclohexane, cycloheptane, cyclooctane, cyclononane, cyclodecane, etc. Polycyclic cycloalkane includes norbornanane, tetrahydronaphthalene, etc.

The term "cycloalkyl" includes a monovalent group derived from "cycloalkane" as defined above. Monocyclic cycloalkyl includes, for example, cyclopropyl, cyclobutyl, cyclopentyl, cyclohexyl, cycloheptyl, cyclooctyl, cyclononyl, cyclodecyl, etc. Polycyclic cycloalkyl includes norbornanyl, tetrahydronaphthalene-5-yl, tetrahydronaphthalene-6-yl, etc.

Preferable "cycloalkyl" for $R^2$ is cyclopentyl, cyclohexyl, cycloheptyl, cyclooctyl, etc.

The cycloalkyl moiety of "cycloalkyloxycarbonyl" is as defined above for "cycloalkyl".

The term "cycloalkane-diyl" includes a divalent group derived from "cycloalkane" as defined above. Monocyclic cycloalkane-diyl includes, for example, cyclopropane-diyl, cyclobutane-diyl, cyclopentane-diyl, cyclohexane-diyl, cycloheptane-diyl, cyclooctane-diyl, cyclonone-diyl, cyclodecane-diyl, etc. Polycyclic cycloalkane-diyl includes norbornane-diyl, etc.

The term "cycloalkene" includes a non-aromatic monocyclic or polycyclic ring of 3 to 10 carbons containing at least one carbon-carbon double bond. Monocyclic cycloalkene includes, for example, cyclopentene, cyclohexene, etc. Polycyclic cycloalkene includes norborne, indene, etc.

The term "cycloalkenyl" includes a monovalent group derived from "cycloalkene" as defined above. Monocyclic cycloalkenyl includes cyclopentenyl, cyclohexenyl, etc. Polycyclic cycloalkenyl includes norbornyl, indene-1-yl, indene-2-yl, indene-3-yl, etc.

The cycloalkenyl moiety of "cycloalkenyloxycarbonyl" is as defined above for "cycloalkenyl".

The term "cycloalkene-diyl" includes a divalent group derived from "cycloalkene" as defined above. Monocyclic cycloalkene-diyl includes cyclopentene-diyl, cyclohexene-diyl, etc. Polycyclic cycloalkene-diyl includes norbornene-diyl, etc.

The term "aromatic carbocyclic ring" includes an aromatic hydrocarbocyclic ring which is monocyclic or fused-cyclic. For example, benzene ring, naphthalene ring, anthracene ring, phenanthrene ring, etc. are exemplified.

The term "aryl" includes a monovalent group derived from "aromatic carbocyclic ring" as defined above. For example, phenyl, 1-naphthyl, 2-naphthyl, anthryl, phenanthryl, etc. are exemplified.

The aryl moiety of "aryloxycarbonyl" is as defined above for "aryl".

The term "aromatic carbocyclic ring-diyl" includes a divalent group derived from "aromatic carbocyclic ring" as defined above. For example, 1,2-phenylene, 1,3-phenylene, 1,4-phenylene, 1,2-naphthalene etc.

The term "heterocyclic ring" includes an aromatic or a non-aromatic monocyclic or fused-cyclic ring, which includes a five- to seven-membered ring having at least one nitrogen atom, oxygen atom, and/or sulphur atom in the ring; a fused ring consisting of two or more said five- to seven-membered rings; or a fused ring consisting of said five- to seven-membered ring having at least one nitrogen atom, oxygen atom, and/or sulphur atom in the ring fused to one or more "aromatic carbocyclic ring", "cycloalkane" or "cycloalkene" as defined above.

For example, a non-aromatic heterocyclic ring such as pyrroline, pyrrolidine, piperidine, piperazine, morpholine, thiomorpholine, tetrahydropyrane, dihydropyridine, dihydropyridazine, dioxane, oxathiolane, thiane, tetrahydrofuran, tetrahydropyran, tetrahydrothiazole, tetrahydroisothiazole, etc.;

a monocyclic aromatic heterocyclic ring such as pyrrole, pyrazine, pyrazole, tetrazole, furan, thiophene, pyridine, imidazole, triazole, tetrazole, triazine, pyridazine, pyrimidine, isoxazole, thiazole, isothiazole, thiadiazole, oxazole, oxadiazole, etc; and a fused heterocyclic ring such as indole, isoindole, indazole, indolizine, indoline, isoindoline, quinoline, isoquinoline, cinnoline, phthalazine, quinazoline, naphthyridine, quinoxaline, purine, pteridine, benzopyrane, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazole, benzodioxane, tetrahydroquinoline, tetrahydrobenzothiophene, etc. are exemplified.

The term "heterocyclic group" includes a monovalent group derived from "heterocyclic ring" as defined above. For example, non-aromatic heterocyclic groups such as pyrrolinyl, pyrrolidino, pyrrolidinyl, imidazolynyl, imidazolidinyl, pyrazolinyl, pyrazolidinyl, piperidino, piperidyl, piperadino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydroisothiazolinyl, etc.;

monocyclic aromatic heterocyclic groups such as pyrrolyl, pyrazinyl, pyrazolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl and oxadiazolyl, etc; and fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolynyl, benzodioxanyl, tetrahydroquinoline, tetrahydrobenzothienyl, etc. are exemplified.

The term "heterocyclic ring-diyl" includes a divalent group derived from "heterocyclic ring" as defined above. For example, non-aromatic heterocyclic ring-diyl such as pyrrolin-diyl, pyrrolidin-diyl, imidazolidin-diyl, pyrazolin-diyl, pyrazolidin-diyl, piperidin-diyl, piperazine-diyl, morpholin-diyl, thiomorpholin-diyl, tetrahydropyran-diyl, dihydropyridine-diyl, dihydropyridazin-diyl, dihydropyrazin-diyl, dioxan-diyl, oxathiolan-diyl, thian-diyl, tetrahydrofuran-diyl, tetrahydropyran-diyl, tetrahydrothiazol-diyl, tetrahydroisothiazol-diyl, etc.;

a monocyclic aromatic heterocyclic ring-diyl such as pyrrole-diyl, pyrazine-diyl, pyrazole-diyl, tetrazole-diyl, furan-diyl, thiophene-diyl, pyridine-diyl, imidazole-diyl, triazole-diyl, tetrazole-diyl, triazine-diyl, pyridazine-diyl, pyrimidine-diyl, pyrazine-diyl, isoxazole-diyl, thiazole-diyl, isothiazole-diyl, thiadiazole-diyl, oxazole-diyl, oxadiazole-diyl, etc; and a fused heterocyclic ring-diyl such as indole-diyl, isoindole-diyl, indazole-diyl, indolizine-diyl, indoline-diyl, isoindoline-diyl, quinoline-diyl, isoquinoline-diyl, cinnoline-diyl, phthalazine-diyl, quinazoline-diyl, naphthyridine-diyl, quinoxaline-diyl, purine-diyl, pteridine-diyl, benzopyrane-diyl, benzimidazole-diyl, benzisoxazole-diyl, benzoxazole-diyl, benzoxadiazole-diyl, benzisothiazole-diyl, benzothiazole-diyl, benzothiadiazole-diyl, benzofuran-diyl, isobenzofuran-diyl, benzothiophene-diyl, benzotriazole-diyl, imidazopyridine-diyl, triazolopyridine-diyl, imidazothiazole-diyl, pyrazinopyridazine-diyl, benzimidazole-diyl, benzodioxane-diyl, tetrahydroquinoline-diyl, tetrahydrobenzothiophene-diyl, etc. are exemplified.

The term "non-aromatic carbocyclic ring" includes "cycloalkane" as defined above, "cycloalkene" as defined above a fused ring consisting of "aromatic carbocyclic ring" as defined above fused to "cycloalkane" as defined above, and a fused ring consisting of "aromatic carbocyclic ring" as defined above fused to "cycloalkene" as defined above. As a fused ring, indene, etc are exemplified.

The term "aromatic heterocyclic ring" includes aromatic rings of "heterocyclic ring" as defined above. "Aromatic heterocyclic ring" includes a five- to seven-membered aromatic ring having at least one nitrogen atom, oxygen atom, and/or sulphur atom in the ring; a fused aromatic ring consisting of two or more said rings; and a fused ring consisting of a five- to seven-membered aromatic ring having at least one nitrogen atom, oxygen atom, and/or sulphur atom in the ring fused to one or more "aromatic carbocyclic ring" as defined above.

For example, a monocyclic aromatic heterocyclic ring such as pyrazine, pyrazole, tetrazole, furan, thiophene, pyridine, imidazole, triazole, triazine, pyridazine, pyrimidine, pyrazine, isoxazole, thiazole, isothiazole, thiadiazole, oxazole, oxadiazole, etc; and a fused aromatic heterocyclic ring such as indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazoline, etc. are exemplified.

The term "heteroaryl" includes a monovalent group derived from "aromatic heterocyclic ring" as defined above. "Heteroaryl" includes a five- to seven-membered aromatic group having at least one nitrogen atom, oxygen atom, and/or sulphur atom in the ring; a fused aromatic group comprising two or more said rings; and a fused ring comprising a five- to seven-membered aromatic group having at least one nitrogen atom, oxygen atom, and/or sulphur atom in the ring fused to one or more "aromatic carbocyclic ring" as defined above.

For example, monocyclic aromatic heterocyclic groups such as pyrrolyl, pyrazinyl, pyrazolyl, indolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, oxadiazolyl, etc; and fused heterocyclic aromatic groups such as isoindolyl, indazolyl, indolizinyl, isoindolinyl, quinolyl, isoquinolyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolynyl, etc. are exemplified.

The heteroaryl moiety of "heteroaryloxycarbonyl" is as defined above for "heteroaryl".

The term "non-aromatic heterocyclic ring" includes non-aromatic rings of "heterocyclic ring" as defined above. "Non-aromatic heterocyclic ring" includes, a five- to seven-membered non-aromatic ring having at least one nitrogen atom, oxygen atom, and/or sulphur atom in the ring; a fused non-aromatic ring consisting of two or more said rings; a fused ring consisting of a five- to seven-membered aromatic ring having at least one nitrogen atom, oxygen atom, and/or sulphur atom in the ring fused to one or more "cycloalkane" as defined above or "cycloalkene" as defined above; or a fused ring consisting of a five- to seven-membered non-aromatic heterocyclic ring having at least one nitrogen atom, oxygen atom, and/or sulphur atom in the ring fused to one or more "aromatic carbocyclic ring" as defined above or "non-aromatic carbocyclic ring" as defined above For example, non-aromatic heterocyclic ring such as pyrroline, pyrrolidine, imidazoline, imidazolidine, pyrazoline, pyrazolidine, piperidine, piperazine, morpholine, thiomorpholine, thiomorpholine, tetrahydropyrane, dihydropyridine, dihydropyridazine, dihydropyrazine, dioxane, oxathiolane, thiane, tetrahydrofuran, tetrahydropyran, tetrahydrothiazolin, tetrahydroisothiazole, etc.;

a fused non-aromatic heterocyclic ring such as indoline, isoindoline, benzopyrane, benzodioxane, tetrahydroquinoline, benzo[d]oxazole-2(3H)-one, tetrahydrobenzothiophene, etc. are exemplified.

The term "non-aromatic heterocyclic group" includes a monovalent group derived from "non-aromatic heterocyclic ring" as defined above. For example, non-aromatic mono heterocyclic groups such as pyrrolinyl, pyrrolidino, pyrrolidinyl, imidazolynyl, imidazolidinyl, pyrazolinyl, pyrazolidinyl, piperidino, piperidyl, piperidino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydroisothiazolinyl, etc.; and fused heterocyclic groups such as benzodioxanyl, tetrahydroquinoline, tetrahydrobenzothienyl, etc. are exemplified.

The term "nitrogen-containing non-aromatic heterocyclic group" includes a monovalent group derived from a four- to seven-membered aromatic group or a fused aromatic ring consisting of two or more said rings which includes at least one nitrogen atom in the ring and optionally includes one or more atoms selected from an oxygen atom and/or a sulphur atom at any position in the ring.

For example, pyrrolinyl, pyrrolidino, pyrrolidinyl, piperidino, piperidyl, piperadino, piperazinyl, morpholinyl, morpholino, thiomorpholino etc. are exemplified.

The non-aromatic heterocyclic ring moiety of "non-aromatic heterocyclic ring-oxy-carbonyl" is as defined above for "non-aromatic heterocyclic ring".

Substituents for "substituted lower alkyl", "substituted alkyl", "substituted lower alkenyl", "lower alkenyl", "substituted lower alkynyl", "substituted alkynyl", "substituted lower alkyloxy", "substituted alkyloxy", "substituted lower alkenyloxy", "substituted alkenyloxy", "substituted lower alkynyloxy", "substituted alkynyloxy", "substituted lower alkylthio", "substituted alkylthio", "substituted lower alkenylthio", "substituted alkenylthio", "substituted lower alkynylthio", "substituted alkynylthio", "substituted lower alkyloxycarbonyl", "substituted alkyloxycarbonyl", "substituted lower alkenyloxycarbonyl", "substituted alkenyloxycarbonyl", "substituted lower alkynyloxycarbonyl", "substituted alkynyloxycarbonyl", "substituted lower alkylcarbamoyl" and "substituted alkylcarbamoyl" include, but are not limited to, one or more same or different substituents selected from the group comprising: hydroxy, carboxy, halogen (F, Cl, Br, I), lower haloalkyloxy (e.g., $CF_3O$), cycloalkyl (e.g., cyclopropyl), cycloalkenyl (e.g., cyclopropenyl), lower alkyloxy (e.g., methoxy, ethoxy, propoxy, butoxy, etc.), lower alkenyloxy (e.g., vinyloxy, allyloxy, etc.), lower alkyloxycarbonyl (e.g., methoxycarbonyl, ethoxycarbonyl, tert-butoxycarbonyl, etc.), nitro, nitroso, amino, lower alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, imino, hydroxyimino, lower alkylimino (e.g., methylimino, ethylimino, dimethylimino, etc.), lower alkyloxyimino (e.g., methoxyimino, ethoxyimino, etc.), acylimino (e.g., acetylimino, benzoylimino, etc.), azido, aryl (e.g., phenyl, etc.), arylalkyl (e.g., benzyl, phenylethyl, etc.), arylalkyloxy (e.g., benzyloxy), a non-aromatic heterocyclic group (e.g., pyrrolinyl, piperidyl, piperadino, pyrrolidino, pyrrolidinyl, morpholinyl, morpholino, etc.), heteroaryl (e.g., furyl, thienyl, pyridyl, isoxazolyl, thiazolyl, thiadiazolyl, oxazolyl, oxadiazolyl, tetrazolyl, indolyl, benzofuryl, etc.), heteroarylalkyl (e.g., pyridylmethyl, pyridylethyl, etc.), cyano, isocyano, isocyanato, thiocyanato, isothiocyanato, mercapto, lower alkylthio (e.g., methylthio, etc.), lower alkylsulfonyl (e.g., methanesulfonyl, ethanesulfonyl), carbamoyl, lower alkylcarbamoyl (e.g., methylcarbamoyl, ethylcarbamoyl, dimethylcarbamoyl, etc.), sulfamoyl, lower alkylsulfamoyl, acyl (e.g., formyl, acetyl, etc.), formyloxy, thioformyl, thiocarboxy, dithiocarboxy, thiocarbamoyl, sulfino, sulfo, hydrazino, azido, ureido, amidino, guanidino, phthalimido, tri-lower alkylsilyl (e.g., trimethylsilyl, etc.), or oxo.

Substituents for "substituted alkyl" and "substituted lower alkyl" of $R^{1c}$ are exemplified as follows: cyano; halogen; hydroxy; carboxy; unsubstituted lower alkyloxy; lower alkyloxy substituted with one or more substituents selected from Substituent Group B (Substituent Group B: cycloalkyl, cycloalkenyl, a non-aromatic heterocyclic group, aryl, and heteroaryl); unsubstituted lower alkyloxycarbonyl; lower alkyloxycarbonyl substituted with one or more substituents selected from Substituent Group B; unsubstituted carbamoyl; carbamoyl substituted with one or more substituents selected from Substituent Group C (Substituent Group C: unsubstituted lower alkyl, hydroxyalkyl, dihydroxyalkyl, carboxyalkyl, lower alkyloxyalkyl, unsubstituted cycloalkylalkyl, lower alkyloxycarbonylalkyl, carboxycycloalkylalkyl and lower alkyloxycarbonylalkyl); unsubstituted amino; amino substituted with one or more substituents selected from Substituent Group D (Substituent Group D: lower alkyl, acyl, unsubstituted carbamoyl, lower alkylcarbamoyl, lower hydroxyalkylcarbamoyl, and lower carboxyalkylcarbamoyl); unsubstituted cycloalkyl; cycloalkyl substituted with one or more substituents selected from Substituent Group E (Substituent Group E: lower hydroxyalkyl, carboxy, and lower alkyloxycarbonyl); a non-aromatic heterocyclic group; unsubstituted aryl; and aryl substituted with one or more substituents selected from Substituent Group F (Substituent Group F: halogen, lower alkyl, and lower alkyloxy).

Substituents for "substituted alkyl" and "substituted lower alkyl" of $R^{1c}$ are are exemplified as follows: cyano; halogen; hydroxy; carboxy; methoxy; methoxy substituted with tetrahydrofuryl or morpholino; lower alkyloxycarbonyl; unsubstituted carbamoyl; carbamoyl substituted with one or more substituents selected from Substituent Group G (Substituent Group G: methyl, ethyl, hydroxymethyl, hydroxyethyl, carboxymethyl, carboxyethyl, methoxyoxymethyl, dihydroxyisopropyl, carboxyIsopropyl, and carboxycyclopropyl); methoxycarbonyl; ethoxycarbonyl; phenylmethylcarbonyl; cycloalkyl substituted with one or more substituents selected from Substituent Group H (Substituent Group H: hydroxymethyl, carboxy, methoxycarbonyl and ethoxycarbonyl); lower alkylcarbamoyl substituted with one or more substituents selected from Substituent Group I (Substituent Group I: amino, alkyl, acylcarbamoyl, lower alkylcarbamoyl, and hydroxy); unsubstituted phenyl; and phenyl substituted with one or more substituents selected from Substituent Group J (Substituent Group J: halogen, lower alkyl, and lower alkyloxy).

Substituents for "substituted alkyl" and "substituted lower alkyl" of $R^{1a}$ are exemplified as follows: cyano; halogen; hydroxy; carboxy; unsubstituted lower alkyloxy; lower alkyloxy substituted with one or more substituents selected from Substituent Group B (Substituent Group B: cycloalkyl, cycloalkenyl, a non-aromatic heterocyclic group, aryl, and heteroaryl); unsubstituted lower alkyloxycarbonyl; lower alkyloxycarbonyl substituted with one or more substituents selected from Substituent Group B; unsubstituted carbamoyl; carbamoyl substituted with one or more substituents selected from Substituent Group C (Substituent Group C: unsubstituted lower alkyl, hydroxyalkyl, dihydroxyalkyl, carboxyalkyl, lower alkyloxyalkyl, unsubstituted cycloalkylalkyl, lower alkyloxycarbonylalkyl, carboxycycloalkylalkyl and lower alkyloxycarbonylalkyl); unsubstituted amino; amino substituted with one or more substituents selected from Substituent Group D (Substituent Group D: lower alkyl, acyl, unsubstituted carbamoyl, lower alkylcarbamoyl, lower hydroxyalkylcarbamoyl, and lower carboxyalkylcarbamoyl); unsubstituted cycloalkyl; cycloalkyl substituted with one or more substituents selected from Substituent Group E (Substituent Group E: lower hydroxyalkyl, carboxy, and lower alkyloxycarbonyl); a non-aromatic heterocyclic group; unsubstituted aryl; and aryl substituted with one or more substituents selected from Substituent Group F (Substituent Group F: halogen, lower alkyl, and lower alkyloxy).

Substituents for "substituted alkyl" and "substituted lower alkyl" of $R^{1a}$ are exemplified as follows: cyano; halogen; hydroxy; carboxy; methoxy; methoxy substituted with tetrahydrofuryl or morpholino; lower alkyloxycarbonyl; unsubstituted carbamoyl; carbamoyl substituted with one or more substituents selected from Substituent Group G (Substituent Group G: methyl, ethyl, hydroxymethyl, hydroxyethyl, carboxymethyl, carboxyethyl, methoxyoxymethyl, dihydroxyisopropyl, carboxylsopropyl, and carboxycyclopropyl); methoxycarbonyl; ethoxycarbonyl; phenylmethylcarbonyl; cycloalkyl substituted with one or more substituents selected from Substituent Group H (Substituent Group H: hydroxymethyl, carboxy, methoxycarbonyl and ethoxycarbonyl); lower alkylcarbamoyl substituted with one or more substituents selected from Substituent Group I (Substituent Group I: amino, alkyl, acylcarbamoyl, lower alkylcarbamoyl, and hydroxy); unsubstituted phenyl; and phenyl substituted with one or more substituents selected from Substituent Group J (Substituent Group J: halogen, lower alkyl, and lower alkyloxy).

A substituent for "substituted acyl" is selected from the group comprising: substituents for "substituted lower alkyl" as defined above, substituents for "lower alkyl" as defined above, substituents for "lower alkenyl" as defined above, and substituents for "lower alkynyl" as defined above. Especially, when R of acyl (R—C(=O)—) is "cycloalkyl", "cycloalkenyl", "a non-aromatic heterocyclic group", "aryl" or "heteroaryl", a substituent for each ring is lower alkyl (e.g., methyl, ethyl, isopropyl, tert-butyl, etc.), lower haloalkyl (e.g., $CF_3$, $CH_2CF_3$, $CH_2CCl_3$, etc.), lower alkenyl, lower alkynyl (e.g., ethynyl), lower alkyloxy (e.g., methoxy, ethoxy, isopropyloxy), or halogen (e.g., F, Cl, etc.), etc.

For example, a substituent for "substituted carbamoyl" or "substituted sulfamoyl" is, but is not limited to, one or more same or different substituents selected from the group comprising: hydroxy, carboxy, halogen (F, Cl, Br, I), lower alkyl (e.g., methyl, ethyl), lower alkenyl (e.g., vinyl), lower alkynyl (e.g., ethynyl), cycloalkyl (e.g., cyclopropyl), cycloalkenyl (e.g., cyclopropenyl), lower alkyloxycarbonyl (e.g., methoxycarbonyl, ethoxycarbonyl, tert-butoxycarbonyl, etc.), amino, lower alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, aryl (e.g., phenyl, etc.), cyano, isocyano, isocyanato, thiocyanato, isothiocyanato or acyl (e.g., formyl, acetyl, etc.).

For example, a substituent for "substituted amino" is, but is not limited to, one or more same or different substituents selected from the group comprising: lower alkyl (e.g., methyl, ethyl, isopropyl, tert-butyl, etc.), lower haloalkyl (e.g., $CF_3$, $CH_2CF_3$, $CH_2CCl_3$, etc.), lower hydroxyalkyl (e.g., hydroxyethyl, —C(CH_3)_2CH_2OH, etc.), lower alkenyl (e.g., vinyl), lower alkynyl (e.g., ethynyl), cycloalkyl (e.g., cyclopropyl), cycloalkenyl (e.g., cyclopropenyl), lower alkyloxy (e.g., methoxy, ethoxy, propoxy, butoxy, etc.), lower haloalkyloxy (e.g., $CF_3O$), lower alkenyloxy (e.g., vinyloxy, allyloxy, etc.), lower alkyloxycarbonyl(tert-butyloxycarbonyl, etc.), amino, lower alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, imino, hydroxyimino, lower alkylimino (e.g., methylimino, ethylimino, dimethylimino, etc.), lower alkyloxyimino (e.g., methoxyimino, ethoxyimino, etc.), acyl imino (e.g., acetylimino, benzoylimino, etc.), aryl (e.g., phenyl, etc.), arylalkyl (e.g., benzyl, etc.), aryloxy (e.g., phenoxy, etc.), a non-aromatic heterocyclic group (e.g., pyrrolinyl, pyrrolidino, piperidino, piperidyl, piperadino, piperazinyl, morpholinyl, morpholino, etc.), heteroaryl (e.g., pyridyl, thienyl, thiazolyl, furyl, etc.), heteroarylalkyl (e.g., pyridylmethyl, thienylmethyl, thiazolylmethyl, furylmethyl, etc.), non-aromatic heterocyclic ring-oxy(piperadinooxy, piperidinooxy, etc.), heteroaryloxy(pyridyl oxy, etc.), hydroxy, halogen (F, Cl, Br, I), cyano or acyl (e.g., formyl, acetyl, etc.).

For example, a substituent for "substituted cycloalkyl", "substituted cycloalkenyl", "substituted aryl", "a substituted heterocyclic group", "substituted heteroaryl", "substituted arylalkyl", "substituted heteroarylalkyl", "a substituted non-aromatic heterocyclic group" or "a substituted nitrogen-containing non-aromatic heterocyclic group" is, but is not limited to, one or more same or different substituents selected from the group comprising: lower alkyl (e.g., methyl, ethyl, isopropyl, tert-butyl, etc.), lower haloalkyl (e.g., $CF_3$, $CH_2CF_3$, $CH_2CCl_3$, etc.), lower haloalkyloxy (e.g., $CF_3O$, $CHCF_2O$, etc.), lower alkenyl (e.g., vinyl), lower alkynyl (e.g., ethynyl), cycloalkyl (e.g., cyclopropyl), cycloalkenyl (e.g., cyclopropenyl), lower alkyloxy (e.g., methoxy, ethoxy, propoxy, butoxy, etc.), lower alkenyloxy (e.g., vinyloxy, allyloxy, etc.), lower alkyloxycarbonyl (e.g., methoxycarbonyl, ethoxycarbonyl, tert-butoxycarbonyl, etc.), nitro, nitroso, amino, lower alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, imino, hydroxyimino, lower alkylimino (e.g., methylimino, ethylimino, dimethylimino, etc.), lower alkyloxyimino (e.g., methoxyimino, ethoxyimino, etc.), acyl imino (e.g., acetylimino, benzoylimino, etc.), azido, aryl (e.g., phenyl, etc.), arylalkyl (e.g., benzyl, etc.), aryloxy (e.g., phenoxy, etc.), arylalkyloxy (e.g., benzyloxy, etc.), a non-aromatic heterocyclic group (e.g., pyrrolinyl, pyrrolidino, piperidino, piperidyl, piperadino, piperazinyl, morpholinyl, morpholino, etc.), heteroaryl (e.g., pyridyl, thienyl, thiazolyl, furyl, etc.), heteroarylalkyl (e.g., pyridylmethyl, thienylmethyl, thiazolylmethyl, furylmethyl, etc.), non-aromatic heterocyclic ring-oxy(piperadinooxy, piperidinooxy, etc.), heteroaryloxy (pyridyl oxy, etc.), cyano, isocyano, isocyanato, thiocyanato, isothiocyanato, mercapto, lower alkylthio (e.g., methylthio, etc.), lower alkylsulfonyl (e.g., methanesulfonyl, ethanesulfonyl), substituted or unsubstituted carbamoyl (e.g., carbamoyl, N-methyl-N-methoxycarbamoyl, etc.), substituted or unsubstituted lower alkylcarbamoyl (e.g., methylcarbamoyl, ethylcarbamoyl, dimethylcarbamoyl, hydroxyethylcarbamoyl, trifluoromethylcarbamoyl, trifluoroethylcarbamoyl, etc.), sulfamoyl, lower alkylsulfamoyl, hydroxy, carboxy, halogen (F, Cl, Br, I), acyl (e.g., formyl, acetyl, etc.), formyl oxy, thio formyl, thiocarboxy, dithiocarboxy, thiocarbamoyl, sulfino, sulfo, hydrazino, azido, ureido, amidino, guanidino, or phthalimido and oxo.

Substituents for "substituted cycloalkyl", "substituted cycloalkenyl", "a substituted non-aromatic heterocyclic group", "substituted aryl" and "substituted heteroaryl" of $R^{1c}$ are exemplified as follows: halogen, lower alkyl, lower haloalkyl, lower alkyloxy, cyano, nitro; lower alkylamino, etc.

Substituents for "substituted cycloalkyl", "substituted cycloalkenyl", "a substituted non-aromatic heterocyclic group", "substituted aryl" and "substituted heteroaryl" of $R^{1c}$ are exemplified as follows: methyl, ethyl, isopropyl, tert-butyl, trifluoromethyl, methoxy, methylamino, dimethylamino, amino, Cl, F, cyano, etc.

Substituents for "substituted cycloalkyl", "substituted cycloalkenyl", "a substituted non-aromatic heterocyclic group", "substituted aryl" and "substituted heteroaryl" of $R^{1a}$ are exemplified as follows: halogen, lower alkyl, lower haloalkyl, lower alkyloxy, cyano, nitro, lower alkylamino, etc.

Substituents for "substituted cycloalkyl", "substituted cycloalkenyl", "a substituted non-aromatic heterocyclic group", "substituted aryl" and "substituted heteroaryl" of $R^{1a}$ are exemplified as follows: methyl, ethyl, isopropyl, tert-butyl, trifluoromethyl, methoxy, methylamino, dimethylamino, amino, Cl, F, cyano, etc.

Substituents for "a substituted nitrogen-containing non-aromatic heterocyclic group" wherein the ring is formed by $R^7$ and $R^{1a}$ include oxo.

Substituents for "substituted cycloalkyl", "substituted cycloalkenyl", "a substituted non-aromatic heterocyclic group", "substituted aryl" and "substituted heteroaryl" of $R^2$ are exemplified as follows: lower alkyl substituted with halogen, unsubstituted lower alkyl, unsubstituted lower alkenyl, unsubstituted lower alkynyl, unsubstituted lower alkyloxy, unsubstituted lower alkylthio, unsubstituted lower alkylamino, halogen, etc.

Substituents for "substituted cycloalkyl", "substituted cycloalkenyl", "a substituted non-aromatic heterocyclic group", "substituted aryl" and "substituted heteroaryl" of $R^2$ are exemplified as follows: lower alkyl, lower trifluoroalkyl, lower alkyloxy, lower alkylamino, nitro, cyano, halogen, etc.

Substituents for "substituted cycloalkyl", "substituted cycloalkenyl", "a substituted non-aromatic heterocyclic group", "substituted aryl" and "substituted heteroaryl" of $R^2$ are exemplified as follows: methyl, tert-butyl, trifluoromethyl, methoxy, dimethylamino, nitro, cyano, Cl and F, etc.

Substituents for "substituted cycloalkyl", "substituted cycloalkenyl", "a substituted non-aromatic heterocyclic group", "substituted aryl" and "substituted heteroaryl" of $R^3$ are exemplified as follows: halogen, hydroxy, nitro, cyano, carboxy, lower alkyl, lower alkyl substituted with halogen, lower alkyl substituted with amino substituted with lower alkyl, unsubstituted lower alkyloxy, lower alkyloxy substituted with one or more substituents selected from Substituent Group A (Substituent Group A: cyano, lower alkyloxy, and lower alkyloxycarbonyl), cycloalkyloxy, non-aromatic heterocyclic ring-oxy, aryloxy, heteroaryloxy, trifluoromethyl lower alkyloxy, lower difluoroalkyloxy, lower alkylthio, carboxy, lower alkyloxycarbonyl, lower alkylcarbonyl, non-aromatic heterocyclic ring-carbonyl, lower hydroxyalkylcarbamoyl, cycloalkylcarbamoyl, cyclo alkenylcarbamoyl, arylcarbamoyl, non-aromatic heterocyclic ring carbamoyl, heteroarylcarbamoyl, lower alkylamino, lower alkylsulfonylamino, lower alkylsulfonyl, trifluoroalkylsulfonyl, sulfamoyl, lower alkylsulfamoyl, lower alkylsulfino, aryl, heteroaryl, cycloalkyl, cycloalkenyl, a non-aromatic heterocyclic group, etc.

Substituents for "substituted cycloalkyl", "substituted cycloalkenyl", "a substituted non-aromatic heterocyclic group", "substituted aryl" and "substituted heteroaryl" of $R^3$ are exemplified as follows: halogen, nitro, cyano, hydroxy, carboxy, methyl, isopropyl, n-butyl, isobutyl, t-butyl, trifluoromethyl, methoxy, ethoxy, isopropyloxy, cyano methoxy, methoxyethoxy, ethoxycarbonylmethoxy, cyclopenteneoxy, phenoxy, trifluoromethoxy, difluoromethoxy, piperazinyloxy, methylthio, propylthio, t-butylcarbonyl, morpholino carbonyl, piperadinocarbonyl, morpholino ethylcarbonyl, methoxycarbonyl, methylcarbamoyl, dimethylcarbamoyl, hydroxyethylcarbamoyl, isopropylcarbamoyl, cyclopropylcarbamoyl, phenylcarbamoyl, sulfamoyl, trifluoromethylsulfonyl, propylsulfino, methylamino, dimethylamino, ethylamino, diethylamino, methylsulfonylamino, isoxazolyl, furyl, morpholino, tetrahydro-2H-pyranyl, piperadino, etc.

Embodiments of the compound of the present invention are described below.

Embodiments of the compound represented by (II-A) to (II-L) in the below in the formula (II):

[Chemical Formula 29]

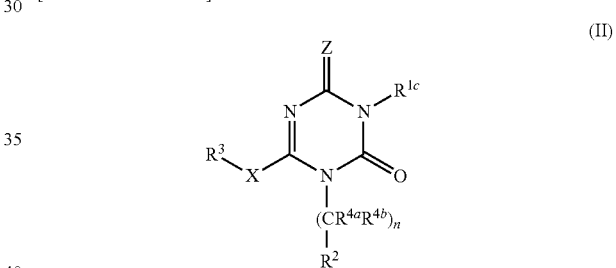

(II)

are as follows.

(II-A): The compound represented by the formula (II), wherein $R^{1c}$, $R^{4a}$, $R^{4b}$, $R^5$ and =Z are as defined in the above (1);

$R^2$ is substituted or unsubstituted aryl, or substituted or unsubstituted heteroaryl;

$R^3$ is substituted or unsubstituted aryl, or substituted or unsubstituted heteroaryl; —X— is —N($R^5$)—; and n is 1, or its pharmaceutically acceptable salt, or a solvate thereof.

(II-B): The compound represented by the formula (II), wherein $R^{1c}$, $R^{4a}$, $R^{4b}$, and $R^5$ are as defined in the above (1);

$R^2$ is substituted or unsubstituted aryl, or substituted or unsubstituted heteroaryl;

$R^3$ is substituted or unsubstituted aryl, or substituted or unsubstituted heteroaryl; —X— is —N($R^5$)—;

=Z is =O; and n is 1, or its pharmaceutically acceptable salt, or a solvate thereof.

(II-C): The compound represented by the formula (II), wherein $R^{4a}$, $R^{4b}$, and $R^5$ are as defined in the above (1);

$R^{1c}$ and $R^2$ are each independently substituted or unsubstituted aryl, or substituted or unsubstituted heteroaryl;

$R^3$ is a group represented by the formula:

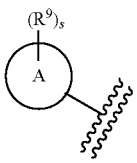
[Chemical Formula 30]

wherein ring A is aryl or heteroaryl;
s is an integer of 0 to 3;
$R^9$ is each independently halogen, hydroxy, substituted or unsubstituted alkyl, substituted or unsubstituted alkyloxy, substituted or unsubstituted lower alkenyl, substituted or unsubstituted lower alkenyloxy, substituted or unsubstituted lower alkynyl, substituted or unsubstituted lower alkynyloxy, substituted or unsubstituted lower alkylthio, substituted or unsubstituted acyl, carboxy, substituted or unsubstituted lower alkyloxycarbonyl, substituted or unsubstituted carbamoyl, substituted or unsubstituted lower alkylcarbamoyl, substituted or unsubstituted amino, substituted or unsubstituted sulfamoyl, cyano, nitro, nitrile, substituted or unsubstituted cycloalkyl, substituted or unsubstituted cycloalkyloxy, substituted or unsubstituted cycloalkenyl, substituted or unsubstituted cycloalkenyloxy, a substituted or unsubstituted non-aromatic heterocyclic group, substituted or unsubstituted non-aromatic heterocyclic ring-oxy, substituted or unsubstituted aryl, substituted or unsubstituted aryloxy, substituted or unsubstituted heteroaryl or substituted or unsubstituted heteroaryloxy;
—X— is —N($R^5$)—;
=Z is =O; and
n is 1, or its pharmaceutically acceptable salt, or a solvate thereof.

(II-D): The compound represented by the formula (II), wherein $R^{1c}$ is substituted lower alkyl;
$R^2$ is substituted or unsubstituted aryl, or substituted or unsubstituted heteroaryl;
$R^3$ is a group represented by the formula:

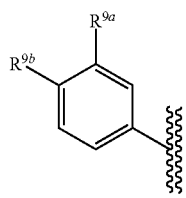
[Chemical Formula 31]

wherein $R^{9a}$ and $R^{9b}$ are as defined in the above (8);
both of $R^{4a}$ and $R^{4b}$ are hydrogen;
—X— is —NH—; and
=Z is =O;
n is 1, or its pharmaceutically acceptable salt, or a solvate thereof.

(II-E): The compound represented by the formula (II), wherein $R^{1c}$ is lower alkyl substituted with one or more substituents selected from Substituent Group L (cyano, halogen, hydroxy, carboxy, unsubstituted lower alkyloxy, lower alkyloxy substituted with cycloalkyl, lower alkyloxy substituted with cycloalkenyl, lower alkyloxy substituted with a non-aromatic heterocyclic group, lower alkyloxy substituted with non-aryl, unsubstituted lower alkyloxy, lower alkyloxy substituted with heteroaryl, lower alkyloxycarbonyl, lower alkyloxycarbonyl substituted with cycloalkyl, lower alkyloxycarbonyl substituted with cycloalkenyl, lower alkyloxycarbonyl substituted with a non-aromatic heterocyclic group, lower alkyloxycarbonyl substituted with non-aryl, lower alkyloxycarbonyl substituted with heteroaryl, lower alkyloxycarbonylcarbonyl, unsubstituted carbamoyl, lower alkylcarbamoyl, lower alkylcarbamoyl substituted with hydroxy, lower alkylcarbamoyl substituted with carboxy, lower alkylcarbamoyl substituted with lower alkyloxy, lower alkylcarbamoyl substituted with unsubstituted cycloalkyl, and lower alkylcarbamoyl substituted with carboxycycloalkyl, unsubstituted amino, lower alkyl, acyl, unsubstituted carbamoyl, lower alkylcarbamoyl, lower alkylcarbamoyl substituted with hydroxy, and lower alkylcarbamoyl substituted with carboxy, amino substituted with lower alkyl, amino substituted with acyl, amino substituted with unsubstituted carbamoyl, amino substituted with lower alkylcarbamoyl, amino substituted with lower hydroxyalkylcarbamoyl, amino substituted with lower carboxyalkylcarbamoyl, a non-aromatic heterocyclic ring substituted with lower hydroxyalkyl, a non-aromatic heterocyclic ring substituted with carboxy, a non-aromatic heterocyclic ring substituted with lower alkyloxycarbonyl, a non-aromatic heterocyclic ring substituted with lower hydroxyalkyl, a non-aromatic heterocyclic ring substituted with carboxy, a non-aromatic heterocyclic ring substituted with lower alkyloxycarbonyl, halogen and lower alkyloxy);
$R^2$ is aryl substituted with one or more substituents selected from Substituent Group S (Substituent Group S lower alkyl, lower alkyloxy, trifluoromethyl, dimethylamino, nitro, cyano, and halogen), or heteroaryl substituted with one or more substituents selected from Substituent Group S;
$R^3$ is a group represented by the formula:

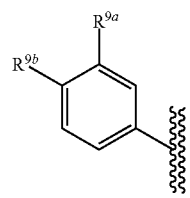
[Chemical Formula 32]

wherein $R^{9a}$ and $R^{9b}$ are each independently halogen, hydroxy, cyano, nitro, substituted or unsubstituted lower alkyl, substituted or unsubstituted lower alkenyl, substituted or unsubstituted lower alkynyl, substituted or unsubstituted lower alkyloxy, substituted or unsubstituted lower alkenyloxy, substituted or unsubstituted lower alkynyloxy, substituted or unsubstituted lower alkylthio, substituted or unsubstituted acyl, carboxy, substituted or unsubstituted lower alkyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, substituted or unsubstituted a non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy;
both of $R^{4a}$ and $R^{4b}$ are hydrogen;
—X— is —NH—;
=Z is =O; and n is 1, or its pharmaceutically acceptable salt, or a solvate thereof.

(II-F): The compound represented by the formula (II), wherein =Z is =O;
$R^{1c}$ is substituted alkyl;
$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
n is 1;
$R^3$ is substituted or unsubstituted aryl, or substituted or unsubstituted heteroaryl;
$R^{4a}$ and $R^{4b}$ are hydrogen; and
—X— is —NH—, or its pharmaceutically acceptable salt, or a solvate thereof.

(II-G): The compound represented by the formula (II), wherein =Z is =O;
$R^{1c}$ is substituted alkyl;
$R^2$ is substituted or unsubstituted aryl, or substituted or unsubstituted heteroaryl;
n is 1;
$R^3$ is substituted or unsubstituted aryl, or substituted or unsubstituted heteroaryl;
$R^{4a}$ and $R^{4b}$ are hydrogen; and
—X— is —NH—, or its pharmaceutically acceptable salt, or a solvate thereof.

(II-H): The compound represented by the formula (II), wherein =Z is =O;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen;
—X— is —NH—; and
$R^{1c}$ is a group represented by the formula:

[Chemical Formula 33]

wherein $R^{1c'}$ is carboxy or substituted or unsubstituted alkyloxycarbonyl, or its pharmaceutically acceptable salt, or a solvate thereof.

(II-I): The compound represented by the formula (II), wherein =Z is =O;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen;
—X— is —NH—; and
$R^{1c}$ is a group represented by the formula:

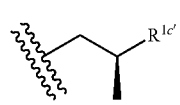

[Chemical Formula 34]

wherein $R^{1c'}$ is carboxy, or substituted or unsubstituted alkyloxycarbonyl, or its pharmaceutically acceptable salt, or a solvate thereof.

(II-J): The compound represented by the formula (II), wherein =Z is =O;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen;
—X— is —NH—; and
$R^{1c}$ is a group represented by the formula:

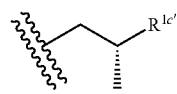

[Chemical Formula 35]

wherein $R^{1c'}$ is carboxy, or substituted or unsubstituted alkyloxycarbonyl, or its pharmaceutically acceptable salt, or a solvate thereof.

(II-K): The compound represented by the formula (II), wherein =Z is =O;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen;
—X— is —NH—; and
$R^{1c}$ is a group represented by the formula:

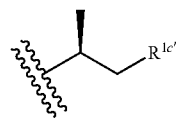

[Chemical Formula 36]

wherein $R^{1c'}$ is carboxy, or substituted or unsubstituted alkyloxycarbonyl, or its pharmaceutically acceptable salt, or a solvate thereof.

(II-L): The compound represented by the formula (II), wherein =Z is =O;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen;
—X— is —NH—; and
$R^{1c}$ is a group represented by the formula:

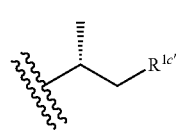

[Chemical Formula 37]

wherein $R^{1c'}$ is carboxy, or substituted or unsubstituted alkyloxycarbonyl, or its pharmaceutically acceptable salt, or a solvate thereof.

Embodiments of the compound represented by (III-A) to (III-I) in the below in the formula (III):

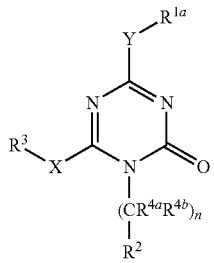

[Chemical Formula 38]

are as follows.

(III-A): The compound represented by the formula (III), wherein $R^{1a}$, $R^{4a}$, $R^{4b}$, $R^5$ and —Y— are as defined in the above (1);
$R^2$ is substituted or unsubstituted aryl, or substituted or unsubstituted heteroaryl;
$R^3$ is substituted or unsubstituted aryl, or substituted or unsubstituted heteroaryl;
—X— is —N($R^5$)—; and
n is 1, or its pharmaceutically acceptable salt, or a solvate thereof.

(III-B): The compound represented by the formula (III), wherein $R^{1a}$, $R^{4a}$, $R^{4b}$ and $R^5$ are as defined in the above (1);
$R^2$ is substituted or unsubstituted aryl, or substituted or unsubstituted heteroaryl;
$R^3$ is substituted or unsubstituted aryl, or substituted or unsubstituted heteroaryl;
—X— is —N($R^5$)—;
—Y— is —O—; and
n is 1, or its pharmaceutically acceptable salt, or a solvate thereof.

(III-C): The compound represented by the formula (III), wherein $R^{1a}$ and $R^2$ are each independently substituted or unsubstituted aryl, or substituted or unsubstituted heteroaryl;
$R^3$ is a group represented by the formula:

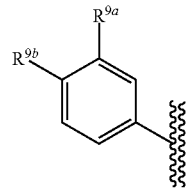

[Chemical Formula 39]

wherein ring A is aryl or heteroaryl;
s is an integer of 0 to 3;
$R^9$ is each independently halogen, hydroxy, substituted or unsubstituted alkyl, substituted or unsubstituted alkyloxy, substituted or unsubstituted lower alkenyl, substituted or unsubstituted lower alkenyloxy, substituted or unsubstituted lower alkynyl, substituted or unsubstituted lower alkynyloxy, substituted or unsubstituted lower alkylthio, substituted or unsubstituted acyl, carboxy, substituted or unsubstituted lower alkyloxycarbonyl, substituted or unsubstituted carbamoyl, substituted or unsubstituted lower alkylcarbamoyl, substituted or unsubstituted amino, substituted or unsubstituted sulfamoyl, cyano, nitro, nitrile, substituted or unsubstituted cycloalkyl, substituted or unsubstituted cycloalkyloxy, substituted or unsubstituted cycloalkenyl, substituted or unsubstituted cycloalkenyloxy, substituted or unsubstituted a non-aromatic heterocyclic group, substituted or unsubstituted non-aromatic heterocyclic ring-oxy, substituted or unsubstituted aryl, substituted or unsubstituted aryloxy, substituted or unsubstituted heteroaryl or substituted or unsubstituted heteroaryloxy;
—X— is —N($R^5$)—;
—Y— is —O—; and
n is 1, or its pharmaceutically acceptable salt, or a solvate thereof.

(III-D): The compound represented by the formula (III), wherein $R^{1a}$ is substituted lower alkyl;
$R^2$ is substituted or unsubstituted aryl, or substituted or unsubstituted heteroaryl;
$R^3$ is a group represented by the formula:

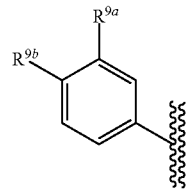

[Chemical Formula 40]

wherein $R^{9a}$ and $R^{9b}$ are as defined in the above (8);
both of $R^{4a}$ and $R^{4b}$ are hydrogen;
—X— is —NH—;
—Y— is —O—; and
n is 1, or its pharmaceutically acceptable salt, or a solvate thereof.

(III-E): The compound represented by the formula (III), wherein $R^{1a}$ is lower alkyl substituted with one or more substituents selected from Substituent Group L;
$R^2$ is aryl substituted with one or more substituents selected from Substituent Group L, or heteroaryl substituted with one or more substituents selected from Substituent Group S;
$R^3$ is a group represented by the formula:

[Chemical Formula 41]

wherein $R^{9a}$ and $R^{9b}$ are each independently halogen, hydroxy, cyano, nitro, substituted or unsubstituted lower alkyl, substituted or unsubstituted lower alkenyl, substituted or unsubstituted lower alkynyl, substituted or unsubstituted lower alkyloxy, substituted or unsubstituted lower alkenyloxy, substituted or unsubstituted lower alkynyloxy, substituted or unsubstituted lower alkylthio, substituted or unsubstituted acyl, carboxy, substituted or unsubstituted lower alkyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, substituted or unsubstituted a non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy;
both of $R^{4a}$ and $R^{4b}$ are hydrogen;
—X— is —NH—;
—Y— is —O—; and
n is 1, or its pharmaceutically acceptable salt, or a solvate thereof.

(III-F): The compound represented by the formula (III), wherein —Y— is —O— or —N($R^7$)—;
$R^7$ is hydrogen, substituted or unsubstituted alkyl, or substituted or unsubstituted acyl;
$R^{1a}$ is hydrogen, substituted or unsubstituted alkyl, substituted or unsubstituted alkenyl, or substituted or unsubstituted alkynyl;
$R^2$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
n is 1;
$R^3$ is substituted or unsubstituted aryl, or substituted or unsubstituted heteroaryl;
$R^{4a}$ and $R^{4b}$ are hydrogen; and
—X— is —NH—, or its pharmaceutically acceptable salt, or a solvate thereof.

(III-G): The compound represented by the formula (III), wherein —Y— is —O— or —N($R^7$)—;
$R^7$ is hydrogen, or substituted or unsubstituted alkyl;
$R^{1a}$ is hydrogen, substituted or unsubstituted alkyl, substituted or unsubstituted alkenyl, or substituted or unsubstituted alkynyl;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen; and
—X— is —NH—, or its pharmaceutically acceptable salt, or a solvate thereof.

(III-H): The compound represented by the formula (III), wherein —Y— is —N($R^7$)—;
$R^7$ and $R^{1a}$ are taken together a substituted or unsubstituted nitrogen-containing non-aromatic heterocyclic group;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen; and
—X— is —NH—, or its pharmaceutically acceptable salt, or a solvate thereof.

(III-I): The compound represented by the formula (III), wherein —Y— is —O— or —N($R^7$)—;
$R^7$ is hydrogen, or substituted or unsubstituted alkyl;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen;
—X— is —NH—; and
$R^{1a}$ is a group represented by the formula:

[Chemical Formula 42]

wherein $R^{1a'}$ is carboxy, or substituted or unsubstituted alkyloxycarbonyl, or its pharmaceutically acceptable salt, or a solvate thereof.

(III-J): The compound represented by the formula (III), wherein —Y— is —O— or —N($R^7$)—;
$R^7$ is hydrogen, or substituted or unsubstituted alkyl;
$R^2$ is substituted or unsubstituted aryl;
n is 1;
$R^3$ is substituted or unsubstituted aryl or substituted or unsubstituted heteroaryl;
$R^{4a}$ and $R^{4b}$ are hydrogen;
—X— is —NH—; and
$R^{1a}$ is a group represented by the formula:

[Chemical Formula 43]

wherein $R^{1a'}$ is carboxy, or substituted or unsubstituted alkyloxycarbonyl, or its pharmaceutically acceptable salt, or a solvate thereof.

The compound represented by the formula (III), wherein —Y— is —O— or —N($R^7$)—;
$R^7$ is hydrogen, or substituted or unsubstituted alkyl;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen;
—X— is —NH—; and
$R^{1a}$ is a group represented by the formula:

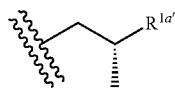

[Chemical Formula 44]

wherein $R^{1a'}$ is carboxy, or substituted or unsubstituted alkyloxycarbonyl, or its pharmaceutically acceptable salt, or a solvate thereof.

(III-L): The compound represented by the formula (III), wherein —Y— is —O— or —N($R^7$)—;
$R^7$ is hydrogen, or substituted or unsubstituted alkyl;
$R^2$ is substituted or unsubstituted aryl;
n is 1;
$R^3$ is substituted or unsubstituted aryl;
$R^{4a}$ and $R^{4b}$ are hydrogen;
—X— is —NH—; and
$R^{1a}$ is a group represented by the formula:

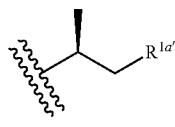

[Chemical Formula 45]

wherein $R^{1a'}$ is carboxy, or substituted or unsubstituted alkyloxycarbonyl, or its pharmaceutically acceptable salt, or a solvate thereof.

(III-M): The compound represented by the formula (III), wherein —Y— is —O— or —N($R^7$)—;

$R^7$ is hydrogen, or substituted or unsubstituted alkyl;
$R^2$ is substituted or unsubstituted aryl;
n is 1;
$R^3$ is substituted or unsubstituted aryl, or substituted or unsubstituted heteroaryl;
$R^{4a}$ and $R^{4b}$ are hydrogen;
—X— is —NH—; and
$R^{1a}$ is a group represented by the formula:

[Chemical Formula 46]

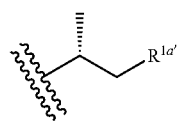

wherein $R^{1a'}$ is carboxy, or substituted or unsubstituted alkyloxycarbonyl, or its pharmaceutically acceptable salt, or a solvate thereof.

General procedures for the synthesis of the compound of the invention are described bellow. Starting materials and reaction reagents used in such synthesis are commercially available or can be prepared according to methods well known in the art using compounds commercially available.

The compound of the present invention represented by the general formula (I), (II) and (III) is able to be prepared in accordance with the synthetic methods as described bellow.

[Method A]

[Process 1]
Compound (i) or a salt thereof such as hydrochloride salt or hydrobromide salt is reacted with isocyanate (ii) in a solvent such as N,N-dimethylformamide, N,N-dimethylacetamide, N,N-dimethylimidazolidinone or dimethylsulfoxide, in the presence of a base such as DBU, triethylamine or pyridine, at temperature of −20° C. to 50° C., preferably ice-cooling. Then, the obtained reaction mixture is reacted with a condensing agent such as 1,1'-carbonyldiimidazole, and a base such as DBU, triethylamine or pyridine, at temperature of −20° C. to 50° C., preferably ice-cooling to give compound (iii).

[Process 2]
Compound (v) may be prepared by the reaction of compound (iii) and compound (iv) in a solvent such as acetonitrile, acetone, DMF or DMSO, in the presence of a base such as potassium carbonate or sodium carbonate, at temperature of 50° C. to reflux temperature, preferably reflux temperature.

[Process 3]
The compound represented by the general formula (II) may be prepared by the reaction of compound (v) and compound (vi) in a solvent such as NMP, DMF or DMSO, or without solvent, at temperature of 150° C. to 250° C., preferably 200° C. to 230° C., under microwave radiation. Also this compound may be prepared by the reaction of compound (v) and compound (vi) in a solvent such as t-butanol, in the presence of an acid such as acetic acid, at temperature of 60° C. to 150° C., preferably 80° C. to 120° C.

The chiral compound (II) may be prepared by using chiral isocyanate

[Method B]

[Chemical Formula 47]

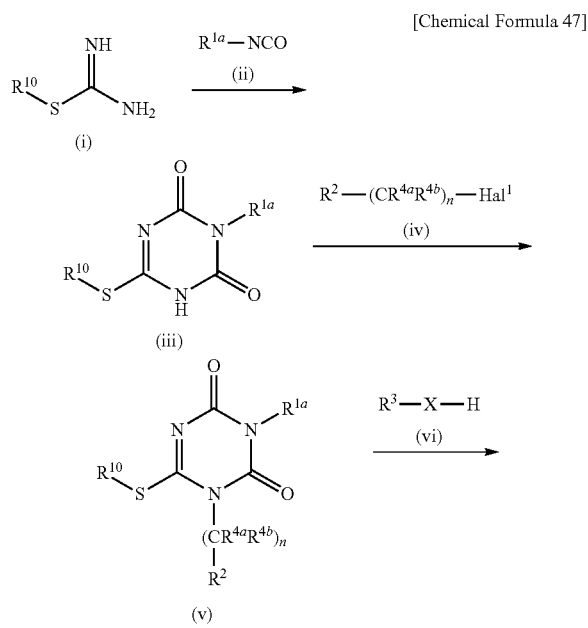

[Chemical Formula 48]

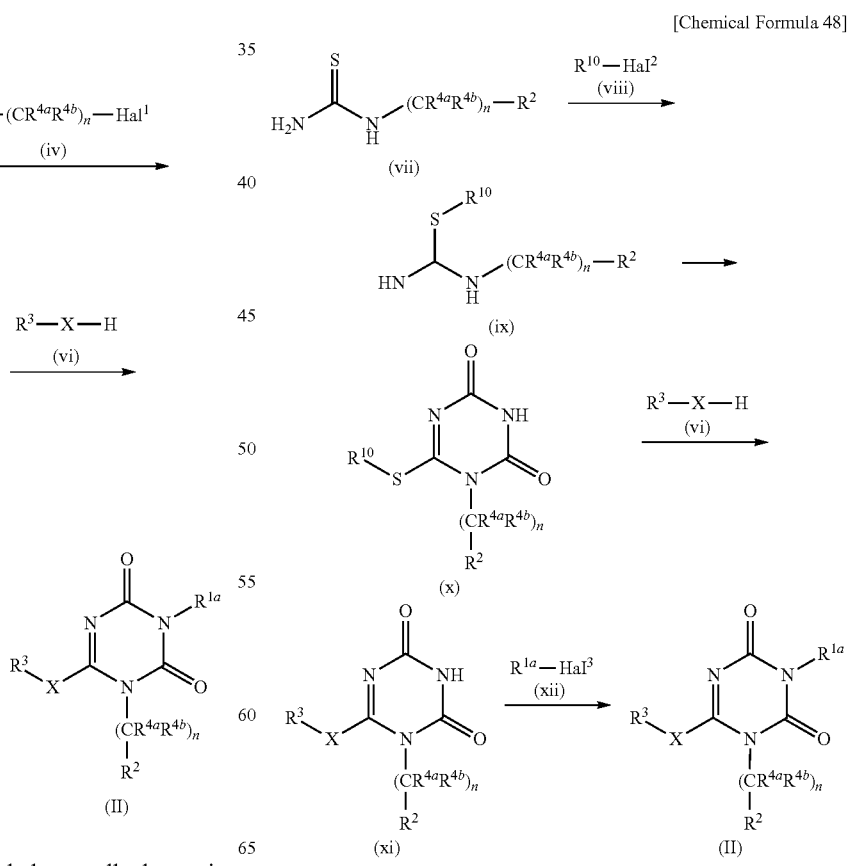

wherein, $R^{10}$ is lower alkyl; $Hal^1$ is halogen; all other variables are as defined above.

wherein, Hal² and Hal³ are halogen; all other variables are as defined above.

[Process 1]
Compound (ix) may be prepared by the reaction of compound (vii) and alkylating reagent (viii) in a solvent such as methanol or ethanol at temperature of −40° C. to 30° C., preferably ice-cooling.

[Process 2]
Compound (x) may be prepared by the reaction of compound (ix) and isocyanate such as N-chlorocarbonylisocyanate in a solvent such as dichloromethane, chloroform or 1,2-dichloroethane, in the presence of a base such as triethylamine or N,N-diisopropylamine, at temperature of −20° C. to 30° C., preferably ice-cooling.

[Process 3]
Compound (xi) may be prepared by the reaction of compound (x) and compound (vi) in a solvent such as t-butanol, iso-propanol, ethanol or acetonitrile, in the presence of an acid such as acetic acid, formic acid or methanesulfonic acid, at reflux temperature.

[Process 4]
The compound represented by the general formula (II) may be prepared by the reaction of compound (xi) and compound (xii) in a solvent such as DMF or NMP, in the presence of a base such as potassium t-butoxide or sodium hydride, at temperature of 40° C. to 100° C., preferably 50° C. to 70° C.

The chiral compound (II) may be prepared by using chiral compound (xii).

[Method C]

[Chemical Formula 49]

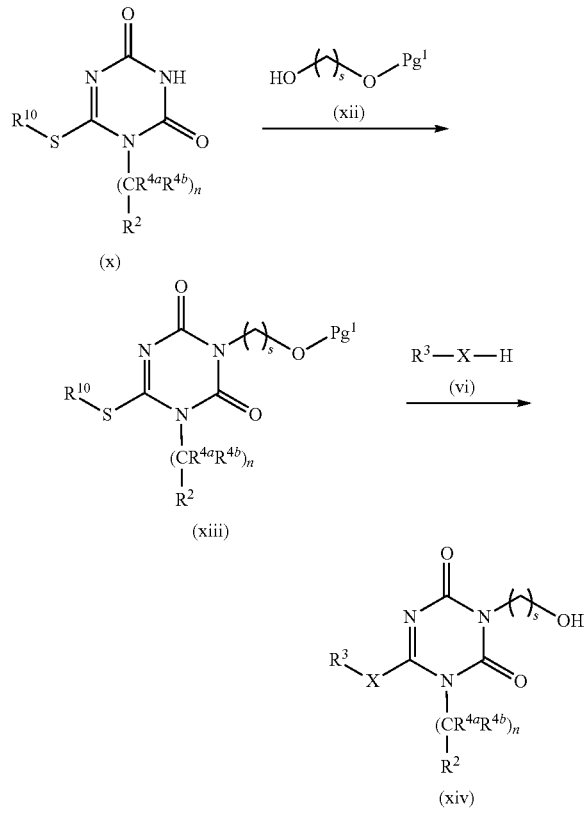

wherein, $Pg^1$ is an appropriate hydroxy protecting group; s is an integer of 1 to 4; all other variables are as defined above.

[Process 1]
The mixture of compound (x) obtained by Method B and alcohol (xii) such as 2-(tetrahydro-2H-pyran-2-yloxy)ethanol, where the other hydroxy group is protected, in a solvent such as THF or dioxane, is reacted with triphenylphosphine or the like and diethyl azodicarboxylate or the like to give compound (xiii).

[Process 2]
Compound (xiv) may be prepared by the reaction of compound (xiii) and compound (vi) in the presence of an acid such as formic acid or acetic acid, at reflux temperature.

[Method D]

[Chemical Formula 50]

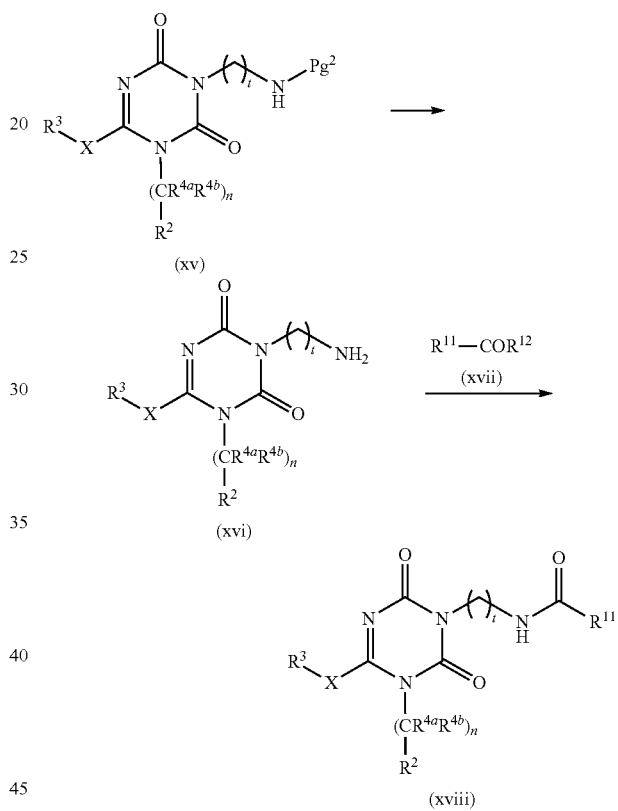

wherein, $Pg^2$ is an appropriate amino protecting group; $R^{11}$ is substituted or unsubstituted lower alkyl, substituted or unsubstituted aryl alkyl, substituted or unsubstituted heteroaryl alkyl, substituted or unsubstituted lower alkenyl, substituted or unsubstituted lower alkynyl, substituted or unsubstituted cycloalkyl, substituted or unsubstituted cycloalkenyl, substituted or unsubstituted acyl, substituted or unsubstituted a non-aromatic heterocyclic group, substituted or unsubstituted aryl, substituted or unsubstituted heteroaryl; $R^{12}$ is hydroxy or halogen; t is an integer of 1 to 4; all other variables are as defined above.

[Process 1]
Compound (xv) obtained by Method A or B is reacted with an acid such as a solution of hydrochloric acid in dioxane, a solution of hydrochloric acid in methanol, a solution of hydrochloric acid in ethyl acetate, or trifluoroacetic acid to give compound (xvi).

[Process 2]
Compound (xviii) may be prepared by a reaction of compound (xvi) and an acid halide compound (xvii) wherein $R^{12}$ is halogen, in the presence of a base such as triethylamine or diisopropylethylamine in a solvent such as THF or dioxane. Dimethylaminopyridine may be added, if necessary.

Also, compound (xvi) is reacted with carboxylic acid (xvii) wherein $R^{12}$ is hydroxy, in a solvent such as THF or DMF, in the presence of a condensing agent such as 1-ethyl-3-(3-dimethylaminopropyl carbodiimide hydrochloride and a base such as triethylamine or diisopropylethylamine, and 1-hydroxybenzotriazole to give compound (xviii).

[Method E]

isopropanol, ethanol or acetonitrile, in the presence of an acid such as formic acid, acetic acid or metanesulfonic acid at reflux temperature.

[Process 3]

Compound (xxii) may be prepared by the reaction of compound (xxi) and a reagent such as aqueous lithium hydroxide, aqueous sodium hydroxide or aqueous potassium hydroxide, in a solvent such as methanol, ethanol or a mixed solvent thereof with THF, dioxane, and the like.

[Method F]

[Chemical Formula 51]

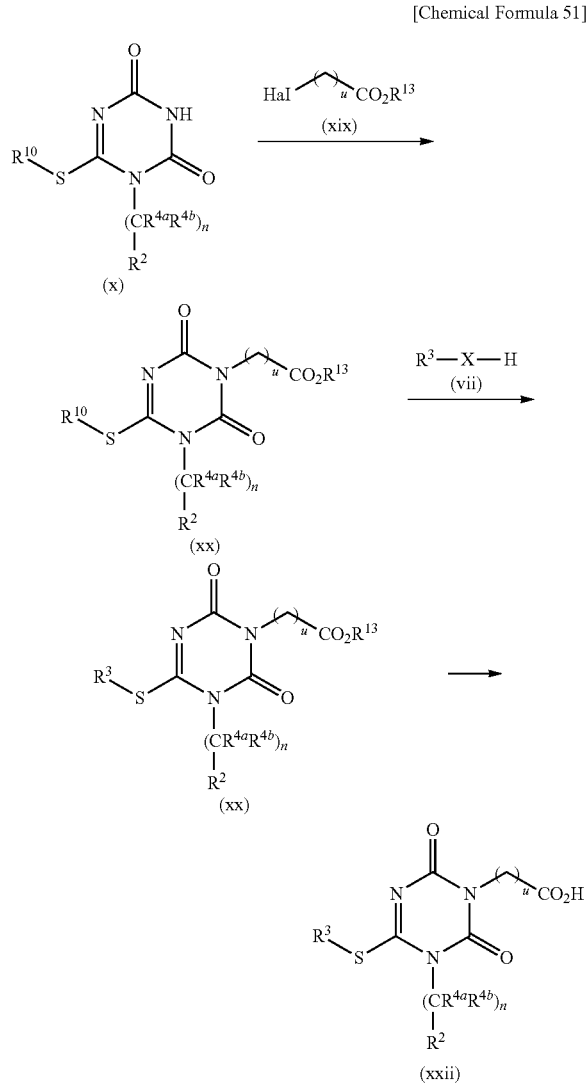

[Chemical Formula 52]

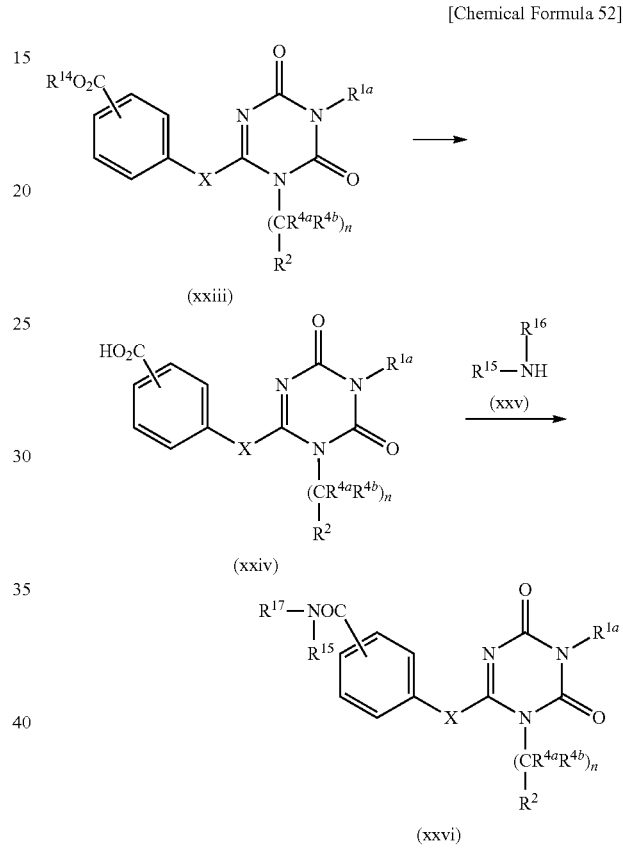

wherein, $R^{13}$ is substituted or unsubstituted lower alkyl; u is an integer of 1 to 4; all other variables are as defined above.

[Process 1]

Compound (xx) may be prepared by the reaction of compound (x) obtained by Method B and compound (xix) in a solvent such as DMF, NMP or THF, in the presence of a base such as DBU, potassium t-butoxide or sodium hydride at temperature of 0° C. to 80° C., preferably 30° C. to 50° C.

[Process 2]

Compound (xxi) may be prepared by the reaction of compound (xx) and compound (vii) in a solvent such as t-butanol, wherein, $R^{14}$ is substituted or unsubstituted lower alkyl; $R^{15}$ and $R^{16}$ are each independently substituted or unsubstituted lower alkyl, substituted or unsubstituted aryl alkyl, substituted or unsubstituted heteroaryl alkyl, substituted or unsubstituted lower alkenyl, substituted or unsubstituted lower alkynyl, substituted or unsubstituted cycloalkyl, substituted or unsubstituted cycloalkenyl, substituted or unsubstituted acyl, substituted or unsubstituted a non-aromatic heterocyclic group, substituted or unsubstituted aryl, or substituted or unsubstituted heteroaryl; u is an integer of 1 to 4; all other variables are as defined above.

[Process 1]

Compound (xxiv) may be prepared by the reaction of compound (xxiii) obtained by Method A or B and aqueous lithium hydroxide, aqueous sodium hydroxide or aqueous potassium hydroxide, in a solvent such as methanol, ethanol or a mixed thereof solvent with THF, dioxane and the like.

[Process 2]

Compound (xxiv) is reacted with compound (xxv) in a solvent such as THF, DMF or NMP, in the presence of a condensing agent such as 1-hydroxybenzotriazole, HOAt, 1-ethyl-3-(3-dimethylamiknopropyl)carbodiimide hydrochloride, HATU or PyBOP, and a base such as triethylamine or diisopropylethylamine to give compound (xxvi).

[Method G]

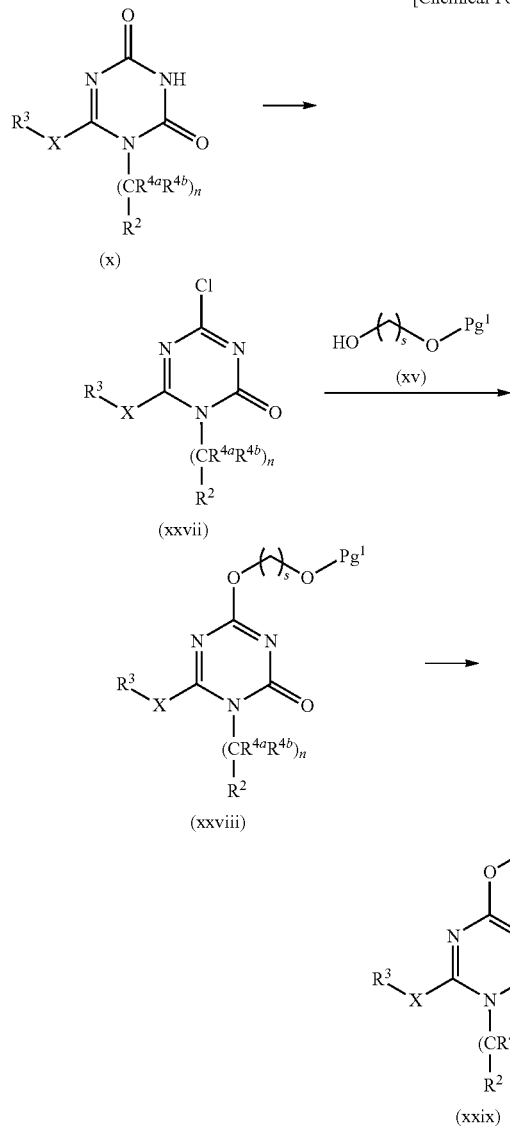

wherein, $Pg^1$ is an appropriate hydroxy protecting group; all other variables are as defined above.

[Process 1]

Compound (xxvii) may be prepared by the reaction of compound (x) obtained by Method B and a halogenating agent such as phosphorous oxychloride or phosphorous oxybromide, without solvent or in a solvent such as toluene or tetrahydrofuran at temperature of 0° C. to 100° C., preferably 40° C. to 60° C.

[Process 2]

To a mixture of alcohol (xv) such as 2-(tetrahydro-2H-pyran-2-yloxy)ethanol, where the other hydroxy group is protected, in a solvent such as THF, dioxane or DMF, is added a base, such as sodium hydride or potassium t-butoxide, and the resulting mixture is reacted with compound (xv) to give compound (xxviii).

[Process 3]

Compound (xxix) may be prepared by the reaction of compound (xxviii) and an acid such as hydrochloric acid, p-toluenesulfonic acid or a hydrate thereof, or p-toluenesulfonic acid pyridinium salt, in a solvent such as methanol.

[Method H]

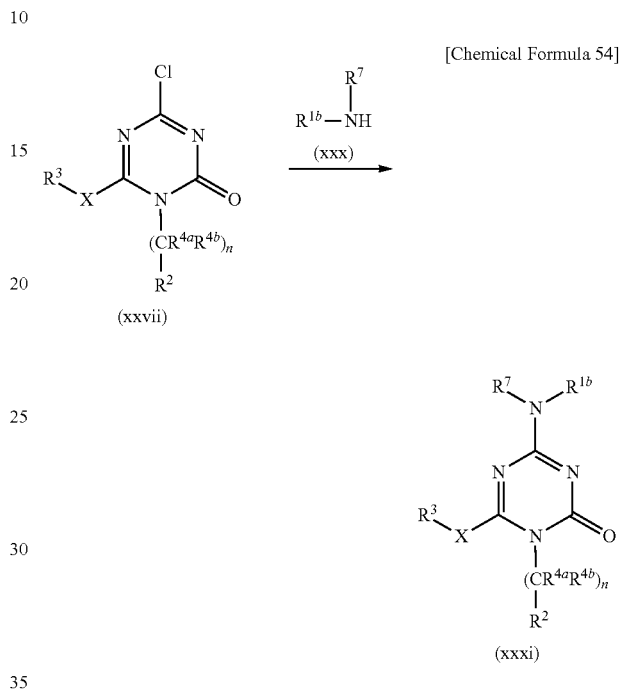

wherein, $R^7$ is substituted or unsubstituted lower alkyl, substituted or unsubstituted aryl alkyl, substituted or unsubstituted heteroaryl alkyl, substituted or unsubstituted lower alkenyl, substituted or unsubstituted lower alkynyl, substituted or unsubstituted cycloalkyl, substituted or unsubstituted cycloalkenyl, substituted or unsubstituted acyl, substituted or unsubstituted a non-aromatic heterocyclic group, substituted or unsubstituted aryl, or substituted or unsubstituted heteroaryl; all other variables are as defined above.

[Process 1]

Compound (xxxi) may be prepared by the reaction of compound (xxvii) obtained by Method G and compound (xxx) in a solvent such as THF or dioxane.

[Method I]

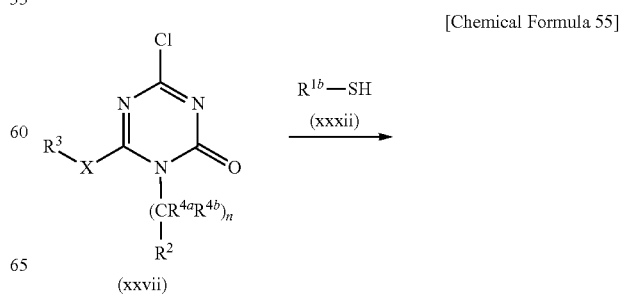

-continued

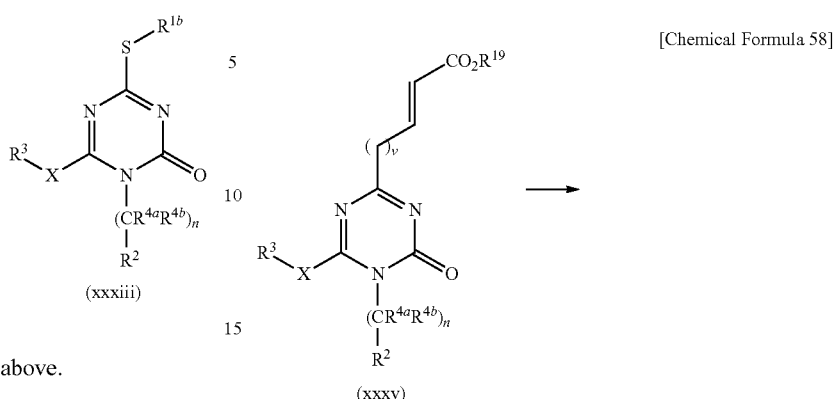

(xxxiii)

wherein all variables are as defined above.

[Process 1]

Compound (xxvii) obtained by Method G in a solvent such as THF or dioxane, in the presence of a base such as sodium hydride is reacted with compound (xxxii) to give compound (xxxiii).

[Method J]

[Chemical Formula 56]

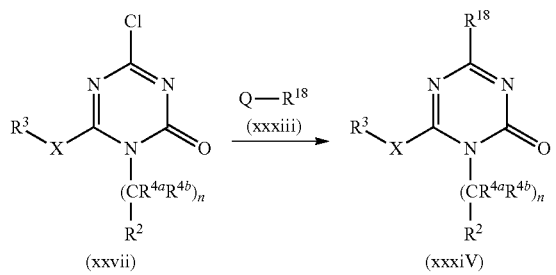

wherein, $R^{18}$ is substituted or unsubstituted alkyl, substituted or unsubstituted alkenyl, substituted or unsubstituted alkynyl; Q is dihydroxyborane, dialkoxyborane or dialkylborane,

[Chemical Formula 57]

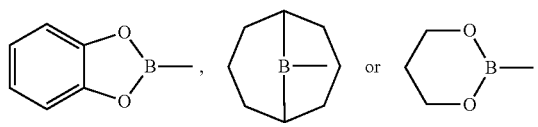

and all other variants are as defined above.

Compound (xxxiv) may be prepared by the reaction of compound (xxvii) obtained by Method G and compound (xxxiii) in a solvent such as THF or dioxane, in the presence a palladium catalyst and an aqueous potassium carbonate, aqueous cesium carbonate or aqueous sodium carbonate, at temperature of 50° C. to reflux temperature, preferably reflux temperature or 120° C. to 200° C., preferably 130° C. to 150° C. under microwave radiation.

[Method K]

[Chemical Formula 58]

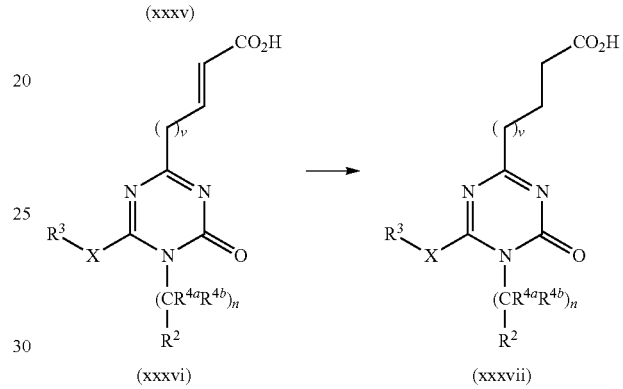

wherein, $R^{19}$ is substituted or unsubstituted alkyl; v is an integer of 0 to 4; all other variables are as defined above.

A mixture of compound (xxxv) in a mixed solvent is hydrolyzed with a base such as sodium hydroxide or lithium hydroxide to give compound (xxxvi). In the above step, ethers such as dioxane, THF or DME, alcohols such as ethanol or methanol, DMF, DMA, DMSO or NMP is mixed with water as a mixed solvent. The room temperature is preferable. When the progress of the reaction is slow, the reaction temperature may be raised further.

[Process 2]

Compound (xxxvi) is solved in an alcohol such as methanol or ethanol, and the solution is applied for a catalytic reduction by using a hydrogenation reactor (e.g., H-Cube (10% Pt—C, H2=1 atm)) or a metallic catalyst such as palladium-carbon, platinum oxide or chlorotris(triphenylphosphine)rhodium(I) to give compound (xxxvii).

[Method L]

[Chemical Formula 59]

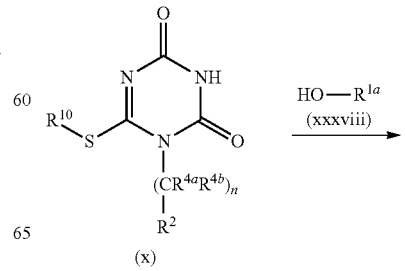

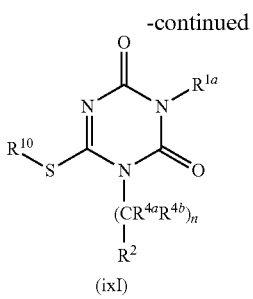

(ixI)

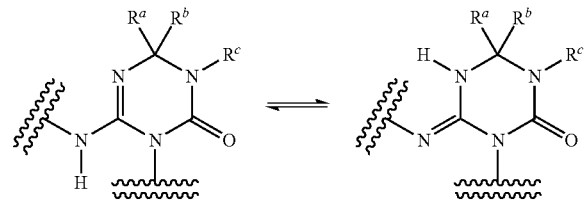

(II)

wherein the variables are as defined above.

[Process 1]

The mixture of compound (x) obtained by Method B and alcohol (xxxviii) in a solvent such as THF or dioxane, is reacted with triphenylphosphine or the like and diethyl azodicarboxylate or the like to give compound (ixl).

[Process 2]

Compound (II) may be prepared by the reaction of compound (ixl) and compound (vi) in the presence of an acid such as formic acid or acetic acid at reflux temperature.

The chiral compound (II) may be prepared by using chiral alcohol (xxxviii).

The compound (I) of the invention includes but is not limited to all possible isomers and racemates. For example, the compound (I) of the invention includes tautomers represented by formula:

[Chemical Formula 60]

In addition, one or more hydrogen, carbon or other atoms of a compound of Formula (I) can be replaced by an isotope of the hydrogen, carbon or other atoms. Compounds of Formula (I) include all radiolabeled forms of compounds of Formula (I) "radiolabeled," "radiolabeled form", and the like of a compound of Formula I, each of which is encompassed by the invention, is useful as a research and/or diagnostic tool in metabolism pharmacokinetic studies and in binding assays.

Examples of isotopes that can be incorporated into a compound of Formula (I) of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the invention can be prepared by methods known in the art. For example, tritiated compounds of Formula (I) can be prepared by introducing tritium into the particular compound of Formula (I), for example, by catalytic dehalogenation with tritium. This method may include reacting a suitably halogen-substituted precursor of a compound of Formula (I) with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," Chapter 6, pp. 155-192 in *Isotopes in the Physical and Biomedical Sciences, Vol. 1, Labeled Compounds (Part A)* (1987). $^{14}C$-labeled compounds can be prepared by employing starting materials having a $^{14}C$ carbon.

Also, the compounds of the invention represented above by the general formula (I) or pharmaceutically acceptable salts thereof can be prepared in a form of hydrate or solvate thereof by published methods. Preferable solvate includes solvates with acetone, 2-butanol, 2-propanol, ethanol, ethyl acetate, tetrahydrofuran, diethylether, etc. For example, such solvate includes hydrate or solvate (For example, with ethanol, etc.) which has non-toxicity and solubility.

The compound of the invention represented above by the general formula (I) has an antagonizing action on $P2X_3$ and/or $P2X_{2/3}$ receptor, and therefore, is useful as a therapeutic agent for diseases associated with a $P2X_3$ and/or $P2X_{2/3}$ receptor. Since $P2X_3$ and/or $P2X_{2/3}$ receptor is believed to associate with pain and diseases in urinary system (Nature 407, 26, 1011-1015 (2000), Nature, Vol. 407, No. 26, 1015-1017 (2000), Non-Patent Document 1, Non-Patent Document 2, etc.), the compound of the invention is useful in the treatment of, alleviation of symptoms or prevention of diseases, such as for example, pain associated with rheumatoid arthritis, pain associated with osteoarthritis, headache, migraine, orofacial pain, toothache, glossagra, pain associated with temporomandibular arthrosis, trigeminal neuralgia, shoulder pain, pain associated with hernia of intervertebral disk, pain associated with cervical spondylosis deformans, pain associated with spinal canal stenosis, pain associated with thoracic outlet syndrome, pain associated with traumatic brachial plexus injury syndrome, pain associated with shoulder-hand syndrome, pain associated with whiplash injury, chest pain, abdominal pain, colic pain, pain associated with cholelithiasis, pain associated with pancreatitis, pain associated with urinary calculosis, pain associated with irritable bowel syndrome, lumbar backache, sciatica, pain associated with bone fracture, pain associated with osteoporosis, joint pain, pain associated with gout, pain associated with cauda equina syndrome, pain associated with ankylosing spondylitis, sore muscle, pain associated with painful spasm, pain associated with myofascial pain syndrome, pain associated with fibromyalgia syndrome, pain associated with arteriosclerosis obliterans, pain associated with Buerger's disease, pain associated with Raynaud's phenomenon, pain associated with zoster, causalgic pain, pain associated with entrapment neuropathy, pain associated with carpal canal syndrome, pain associated with diabetes, pain associated with Guillain-Barre syndrome, pain associated with Hansen's disease, pain associated with drug therapy, pain associated with radiation therapy, pain associated with cord injury, pain associated with syringomyelia, pain associated with stroke, thalamic pain, pain associated with deafferentation, sympathetically-maintained pain, pain associated with ABC syndrome, pain associated with multiple sclerosis, pain associated with skin disease, cancer pain, postoperative pain, pain associated with injury, pain associated with gangrene, pain associated with somatoform disorder, pain associated with somatization disorder, pain associated with depression, pain associated with Parkinson's disease, knee joint pain, pain associated with arthritis, neuropathic pain such as menstrual pain, intermenstrual pain, labor pain, etc., inflammatory pain, nociceptive pain, psychogenic pain, and overactive bladder, incontinence, pollakiuria, urinary urgency, cystatrophia, prostatic hypertrophy, prostatitis, prostate pain, detrusor hyperfleswia, dysuria, nervous pollakiuria, chronic prostatitis, chronic cystitis, etc.

The compound of the invention can be a drug with reduced side-effect such as effect on motor function because it has a high affinity for ATP receptor, especially P2X$_3$ receptor, and also has high subtype selectivity and high selectivity for other receptors. Also, the compound of the invention is advantageous because of its high stability and high oral absorptivity, good bioavailability, low clearance, long half-life, prolonged duration of action, and/or low activity of hepatic enzyme inhibition, etc.

In another embodiment, the invention provides a pharmaceutical composition comprising an effective amount of the compound of the invention, in combination with a pharmaceutically acceptable carrier For use of the compound of the invention as a medicament, a pharmaceutical composition can be prepared according to conventional methods, using pharmaceutically acceptable carriers well known in the art, such as excipients, binders, disintegrants, lubricants, colourants, flavors, surfactants, etc.

For the pharmaceutical composition of the invention to be administered in the treatment of mammals including human, an appropriate unit dosage form may be selected depending on the purpose of the treatment and the route of administration. Specifically, such unit dosage form includes oral formulations such as tablet, coated tablet, powder, granule, capsule, liquid, pill, suspension, emulsion, etc., and parenteral formulations such as injectable solution, suppository, ointment, patch, aerosol, etc. Such unit dosage form can be formulated according to methods well known in the art.

The amount of the compound in a formulation can be varied depending on its dosage form, route for administration, dosing regimen, etc.

Means for administration of the pharmaceutical composition may be selected depending on dosage form, age, sex, body weight, severity of the disease, and other factors, etc., and route for administration can be selected from various routes such as oral, subcutaneous, transdermal, rectal, intranasal, buccal, etc.

Dose of the compound of the invention in a pharmaceutical composition of the invention can be determined depending on the choice of route for administration, age, sex, body weight, severity of the disease, the compound to be administered, and other factors, etc., and can be generally from 0.05 to 1000 mg/kg/day, preferably from 0.1 to 10 mg/kg/day, for oral administration to adults. For parenteral administration, dose can be varied widely depending on its route but generally from 0.005 to 100 mg/kg/day, preferably from 0.01 to 1 mg/kg/day. Such pharmaceutical composition of the invention may be administered once a day or in several times at a divided dosage in a day.

Embodiments of the compound of the invention include compounds represented by the general formula (IV) and the general formula (V):

[Chemical Formula 61]

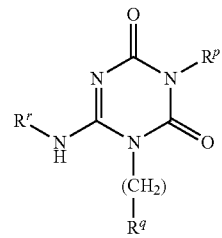
(IV)

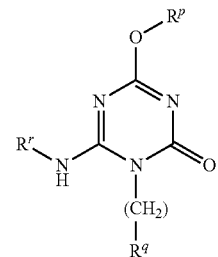
(V)

wherein each substituent is as shown below:

TABLE 1

| | Rp |
|---|---|
| Rp1 | Et |
| Rp2 | Pr |
| Rp3 | i-Pr |
| Rp4 | Bu |
| Rp5 | t-Bu |
| Rp6 | c-PrCH2 |
| Rp7 | HO(CH2)2 |
| Rp8 | HO(CH2)3 |
| Rp9 | (HOCH2)2CH |
| Rp10 | (HOCH2)2CHCH2 |
| Rp11 | (HOCH2)2C(Me)CH2 |
| Rp12 | EtOCOCH2 |
| Rp13 | EtOCO(CH2)2 |
| Rp14 | EtOCOCF2CH2 |
| Rp15 | HOCOCH2 |
| Rp16 | HOCO(CH2)2 |
| Rp17 | HOCOCF2CH2 |
| Rp18 | Ph—CH2 |
| Rp19 | 3-pyridylmethyl |
| Rp20 | NCCH2 |
| Rp21 | NC(CH2)2 |
| Rp22 | allyl |
| Rp23 | propargyl |
| Rp24 | H2N(CH2)2 |
| Rp25 | Me2N(CH2)2 |
| Rp26 | AcHN(CH2)2 |
| Rp27 | (morpholino)methyl |
| Rp28 | 2-(morpholino)ethyl |
| Rp29 | (piperidino)methyl |
| Rp30 | 2-(piperidino)ethyl |
| Rp31 | HOCOC(Me)2CH2 |
| Rp32 | (1-hydroxycarbonyl-c-propyl) methyl |
| Rp33 | HOCOC(CH2)3 |
| Rp34 | HOCOC(Me)2(CH2)2 |
| Rp35 | H2NCOCH2 |
| Rp36 | MeNHCOCH2 |
| Rp37 | HOCH2NHCOCH2 |
| Rp38 | HOCOCH2NHCOCH2 |
| Rp39 | HOCOCH(Me)CH2 |
| Rp40 | HOCOCH2CH(Me) |
| Rp41 | (2-HOCO)PhCH2 |
| Rp42 | (3-HOCO)PhCH2 |
| Rp43 | (4-HOCO)PhCH2 |

TABLE 2

| | Rq |
|---|---|
| Rq1 | Ph |
| Rq2 | 4-Me—Ph |
| Rq3 | 4-MeO—Ph |
| Rq4 | 4-F—Ph |
| Rq5 | 4-Cl—Ph |
| Rq6 | 4-Br—Ph |
| Rq7 | 3,4-Cl$_2$—Ph |
| Rq8 | 5-Cl-2-pyridyl |
| Rq9 | 6-Cl-3-pyridyl |
| Rq10 | c-hexyl |
| Rq11 | 3-F-4-Cl—Ph |
| Rq12 | c-heptyl |

TABLE 3

| | Rr |
|---|---|
| Rr1 | 3-Br—Ph |
| Rr2 | 3-CF$_3$—Ph |
| Rr3 | 4-EtO—Ph |
| Rr4 | 4-i-PrO—Ph |
| Rr5 | 4-PhO—Ph |
| Rr6 | 4-CHF$_2$O—Ph |
| Rr7 | 3-F-4-MeO—Ph |
| Rr8 | 3-F-4-EtO—Ph |
| Rr9 | 3-F-4-PrO—Ph |
| Rr10 | 3-F-4-i-PrO—Ph |
| Rr11 | 3-F-4-CHF$_2$O—Ph |
| Rr12 | 3-Cl-4-MeO—Ph |
| Rr13 | 3-Cl-4-EtO—Ph |
| Rr14 | 3-Cl-4-PrO—Ph |
| Rr15 | 3-Cl-4-i-PrO—Ph |
| Rr16 | 3-Cl-4-CHF$_2$O—Ph |
| Rr17 | 3-Me-4-EtO—Ph |
| Rr18 | 3-Me-4-PrO—Ph |
| Rr19 | 3-Me-4-i-PrO—Ph |
| Rr20 | 2-Me-benzofuran-5-yl |
| Rr21 | 3-MeS |
| Rr22 | 3,4-Cl2 |

In the above Tables, Ac indicates acetyl, Ms indicates mesyl, Me indicates methyl, Et indicates ethyl, Pr indicates propyl, i-Pr indicates isopropyl, Bu indicates n-butyl, t-Bu indicates tert-butyl, c-Pr indicates cyclopropyl, cBu indicates cyclobutyl, cPent indicates cyclopentyl, cHex indicates cyclohexyl and Ph indicates phenyl The compounds represented by the following ($R_p$,$R_q$,$R_r$) which show the combination of $R^p$, $R^q$ and $R^r$ are exemplified:

(Rp,Rq,Rr)=(Rp1,Rq1,Rr1), (Rp1,Rq1,Rr2), (Rp1,Rq1,Rr3), (Rp1,Rq1,Rr4), (Rp1,Rq1,Rr5), (Rp1,Rq1,Rr6), (Rp1,Rq1,Rr7), (Rp1,Rq1,Rr8), (Rp1,Rq1,Rr9), (Rp1,Rq1,Rr10), (Rp1,Rq1,Rr11), (Rp1,Rq1,Rr12), (Rp1,Rq1,Rr13), (Rp1,Rq1,Rr14), (Rp1,Rq1,Rr15), (Rp1,Rq1, Rr16), (Rp1,Rq1,Rr17), (Rp1,Rq1,Rr18), (Rp1,Rq1,Rr19), (Rp1,Rq1,Rr20), (Rp1,Rq1,Rr21), (Rp1,Rq1,Rr22), (Rp1,Rq2,Rr1), (Rp1,Rq2,Rr2), (Rp1,Rq2,Rr3), (Rp1,Rq2,Rr4), (Rp1,Rq2,Rr5), (Rp1,Rq2,Rr6), (Rp1,R$_q$2,Rr7), (Rp1,R$_q$2,Rr8), (Rp1,Rq2,Rr9), (Rp1,Rq2,Rr10), (Rp1,Rq2,Rr11), (Rp1,Rq2,Rr12), (Rp1,Rq2,Rr13), (Rp1,Rq2,Rr14), (Rp1,Rq2,Rr15), (Rp1,Rq2, Rr16), (Rp1,Rq2,Rr17), (Rp1,Rq2,Rr18), (Rp1,Rq2,Rr19), (Rp1,Rq2,Rr20), (Rp1,Rq2,Rr21), (Rp1,Rq2,Rr22), (Rp1,Rq3,Rr1), (Rp1,Rq3,Rr2), (Rp1,Rq3,Rr3), (Rp1,Rq3,Rr4), (Rp1,Rq3,Rr5), (Rp1,Rq3,Rr6), (Rp1,Rq3,Rr7), (Rp1,Rq3,Rr8), (Rp1,Rq3,Rr9), (Rp1,Rq3,Rr10), (Rp1,Rq3,Rr11), (Rp1,Rq3,Rr12), (Rp1,Rq3,Rr13), (Rp1,Rq3,Rr14), (Rp1,Rq3,Rr15), (Rp1,Rq3, Rr16), (Rp1,Rq3,Rr17), (Rp1,Rq3,Rr18), (Rp1,Rq3,Rr19), (Rp1,Rq3,Rr20), (Rp1,Rq3,Rr21), (Rp1,Rq3,Rr22), (Rp1,Rq4,Rr1), (Rp1,Rq4,Rr2), (Rp1,Rq4,Rr3), (Rp1,Rq4,Rr4), (Rp1,Rq4,Rr5), (Rp1,Rq4, Rr6), (Rp1,Rq4,Rr7), (Rp1,Rq4,Rr8), (Rp1,Rq4,Rr9), (Rp1,Rq4,Rr10), (Rp1,Rq4,Rr11), (Rp1,Rq4,Rr12), (Rp1,Rq4,Rr13), (Rp1,Rq4,Rr14), (Rp1,Rq4,Rr15), (Rp1,Rq4, Rr16), (Rp1,Rq4,Rr17), (Rp1,Rq4,Rr18), (Rp1,Rq4,Rr19), (Rp1,Rq4,Rr20), (Rp1,Rq4,Rr21), (Rp1,Rq4,Rr22), (Rp1,Rq5,Rr1), (Rp1,Rq5,Rr2), (Rp1,Rq5,Rr3), (Rp1,Rq5,Rr4), (Rp1,Rq5,Rr5), (Rp1,Rq5,Rr6), (Rp1,Rq5,Rr7), (Rp1,Rq5,Rr8), (Rp1,Rq5,Rr9), (Rp1,Rq5,Rr10), (Rp1,Rq5,Rr11), (Rp1,Rq5,Rr12), (Rp1,Rq5,Rr13), (Rp1,Rq5,Rr14), (Rp1,Rq5,Rr15), (Rp1,Rq5, Rr16), (Rp1,Rq5,Rr17), (Rp1,Rq5,Rr18), (Rp1,Rq5,Rr19), (Rp1,Rq5,Rr20), (Rp1,Rq5,Rr21), (Rp1,Rq5,Rr22), (Rp1,Rq6,Rr1), (Rp1,Rq6,Rr2), (Rp1,Rq6,Rr3), (Rp1,Rq6,Rr4), (Rp1,Rq6,Rr5), (Rp1,Rq6,Rr6), (Rp1,Rq6,Rr7), (Rp1,Rq6,Rr8), (Rp1,Rq6,Rr9), (Rp1,Rq6,Rr10), (Rp1,Rq6,Rr11), (Rp1,Rq6,Rr12), (Rp1,Rq6,Rr13), (Rp1,Rq6,Rr14), (Rp1,Rq6,Rr15), (Rp1,Rq6, Rr16), (Rp1,Rq6,Rr17), (Rp1,Rq6,Rr18), (Rp1,Rq6,Rr19), (Rp1,Rq6,Rr20), (Rp1,Rq6,Rr21), (Rp1,Rq6,Rr22), (Rp1,Rq7,Rr1), (Rp1,Rq7,Rr2), (Rp1,Rq7,Rr3), (Rp1,Rq7,Rr4), (Rp1,Rq7,Rr5), (Rp1,Rq7,Rr6), (Rp1,Rq7,Rr7), (Rp1,Rq7,Rr8), (Rp1,Rq7,Rr9), (Rp1,Rq7,Rr10), (Rp1,Rq7,Rr11), (Rp1,Rq7,Rr12), (Rp1,Rq7,Rr13), (Rp1,Rq7,Rr14), (Rp1,Rq7,Rr15), (Rp1,Rq7,Rr16), (Rp1,Rq7,Rr17), (Rp1,Rq7,Rr18), (Rp1,Rq7,Rr19), (Rp1,Rq7,Rr20), (Rp1,Rq7,Rr21), (Rp1,Rq7,Rr22), (Rp1,Rq8,Rr1), (Rp1,Rq8,Rr2), (Rp1,Rq8,Rr3), (Rp1,Rq8,Rr4), (Rp1,Rq8,Rr5), (Rp1,Rq8,Rr6), (Rp1,Rq8,Rr7), (Rp1,Rq8,Rr8), (Rp1,Rq8,Rr9), (Rp1,Rq8,Rr10), (Rp1,Rq8,Rr11), (Rp1,Rq8,Rr12), (Rp1,Rq8,Rr13), (Rp1,Rq8,Rr14), (Rp1,Rq8,Rr15), (Rp1,Rq8,Rr16), (Rp1,Rq8,Rr17), (Rp1,Rq8,Rr18), (Rp1,Rq8,Rr19), (Rp1,Rq8,Rr20), (Rp1,Rq8,Rr21), (Rp1,Rq8,Rr22), (Rp1,Rq9,Rr1), (Rp1,Rq9,Rr2), (Rp1,Rq9,Rr3), (Rp1,Rq9,Rr4), (Rp1,Rq9,Rr5), (Rp1,Rq9,Rr6), (Rp1,Rq9,Rr7), (Rp1,Rq9,Rr8), (Rp1,Rq9,Rr9), (Rp1,Rq9,Rr10), (Rp1,Rq9,Rr11), (Rp1,Rq9,Rr12), (Rp1,Rq9,Rr13), (Rp1,Rq9,Rr14), (Rp1,Rq9,Rr15), (Rp1,Rq9,Rr16), (Rp1,Rq9,Rr17), (Rp1,Rq9,Rr18), (Rp1,Rq9,Rr19), (Rp1,Rq9,Rr20), (Rp1,Rq9,Rr21), (Rp1,Rq9,Rr22), (Rp1,Rq10,Rr1), (Rp1,Rq10,Rr2), (Rp1,Rq10,Rr3), (Rp1,Rq10,Rr4), (Rp1,Rq10,Rr5), (Rp1,Rq10,Rr6), (Rp1,Rq10,Rr7), (Rp1,Rq10,Rr8), (Rp1,Rq10,Rr9), (Rp1,Rq10,Rr10), (Rp1,Rq10,Rr11), (Rp1,Rq10,Rr12), (Rp1,Rq10,Rr13), (Rp1,Rq10,Rr14), (Rp1,Rq10,Rr15), (Rp1,Rq10,Rr16), (Rp1,Rq10,Rr17), (Rp1,Rq10,Rr18), (Rp1,Rq10,Rr19), (Rp1,Rq10,Rr20), (Rp1,Rq10,Rr21), (Rp1,Rq10,Rr22), (Rp1,Rq11,Rr1), (Rp1,Rq11,Rr2), (Rp1,Rq11,Rr3), (Rp1,Rq11,Rr4), (Rp1,Rq11,Rr5), (Rp1,Rq11,Rr6), (Rp1,Rq11,Rr7), (Rp1,Rq11,Rr8), (Rp1,Rq11,Rr9), (Rp1,Rq11,Rr10), (Rp1,Rq11,Rr11), (Rp1,Rq11,Rr12), (Rp1,Rq11,Rr13), (Rp1,Rq11,Rr14), (Rp1,Rq11,Rr15), (Rp1,Rq11,Rr16), (Rp1,Rq11,Rr17), (Rp1,Rq11,Rr18), (Rp1,Rq11,Rr19), (Rp1,Rq11,Rr20), (Rp1,Rq11,Rr21), (Rp1,Rq11,Rr22), (Rp1,Rq12,Rr1), (Rp1,Rq12,Rr2), (Rp1,Rq12,Rr3), (Rp1,Rq12,Rr4), (Rp1,Rq12,Rr5), (Rp1,Rq12,Rr6), (Rp1,Rq12,Rr7), (Rp1,Rq12,Rr8), (Rp1,Rq12,Rr9), (Rp1,Rq12,Rr10), (Rp1,Rq12,Rr11), (Rp1,Rq12,Rr12), (Rp1,Rq12,Rr13), (Rp1,Rq12,Rr14), (Rp1,Rq12,Rr15), (Rp1,Rq12,Rr16), (Rp1,Rq12,Rr17), (Rp1,Rq12,Rr18), (Rp1,Rq12,Rr19), (Rp1,Rq12,Rr20), (Rp1,Rq12,Rr21), (Rp1,Rq12,Rr22), (Rp2,Rq1,Rr1), (Rp2,Rq1,Rr2), (Rp2,Rq1,Rr3), (Rp2,Rq1,Rr4), (Rp2,Rq1,Rr5), (Rp2,Rq1,Rr6), (Rp2,Rq1,Rr7), (Rp2,Rq1,Rr8), (Rp2,Rq1,Rr9), (Rp2,Rq1,Rr10), (Rp2,Rq1,Rr11), (Rp2,Rq1,Rr12), (Rp2,Rq1,Rr13), (Rp2,Rq1,Rr14), (Rp2,Rq1,Rr15), (Rp2,Rq1,Rr16), (Rp2,Rq1,Rr17), (Rp2,Rq1,Rr18), (Rp2,Rq1,Rr19), (Rp2,Rq1,Rr20), (Rp2,Rq1,Rr21), (Rp2,Rq1,Rr22), (Rp2,Rq2,Rr1), (Rp2,Rq2,Rr2), (Rp2,Rq2,Rr3), (Rp2,Rq2,Rr4), (Rp2,Rq2,Rr5), (Rp2,Rq2,Rr6), (Rp2,Rq2,Rr7), (Rp2,Rq2,Rr8), (Rp2,Rq2,Rr9), (Rp2,Rq2,Rr10), (Rp2,Rq2,Rr11), (Rp2,Rq2,Rr12), (Rp2,Rq2,Rr13), (Rp2,Rq2,Rr14), (Rp2,Rq2,Rr15), (Rp2,Rq2,Rr16), (Rp2,Rq2,Rr17), (Rp2,Rq2,Rr18), (Rp2,Rq2,Rr19), (Rp2,Rq2,Rr20), (Rp2,Rq2,Rr21), (Rp2,Rq2,Rr22), (Rp2,Rq3,Rr1), (Rp2,Rq3,Rr2), (Rp2,Rq3,Rr3), (Rp2,Rq3,Rr4), (Rp2,Rq3,Rr5), (Rp2,Rq3,Rr6), (Rp2,Rq3,Rr7), (Rp2,Rq3,Rr8), (Rp2,Rq3,Rr9), (Rp2,Rq3,Rr10), (Rp2, Rq3,Rr11), (Rp2,Rq3,Rr12), (Rp2,Rq3,Rr13), (Rp2,Rq3,Rr14), (Rp2,Rq3,Rr15), (Rp2,Rq3,Rr16), (Rp2,Rq3,Rr17), (Rp2,Rq3,Rr18), (Rp2,Rq3,Rr19), (Rp2,Rq3,Rr20), (Rp2,Rq3,Rr21), (Rp2,Rq3,Rr22), (Rp2,Rq4,Rr1), (Rp2,Rq4,Rr2), (Rp2,Rq4,Rr3), (Rp2,Rq4,Rr4), (Rp2,Rq4,Rr5), (Rp2,Rq4,Rr6), (Rp2,Rq4,Rr7), (Rp2,Rq4,Rr8), (Rp2,Rq4,Rr9), (Rp2,Rq4,Rr10), (Rp2,Rq4,Rr11), (Rp2,Rq4,Rr12), (Rp2,Rq4,Rr13), (Rp2,Rq4,Rr14), (Rp2,Rq4,Rr15), (Rp2,Rq4,Rr16), (Rp2,Rq4,Rr17), (Rp2,Rq4,Rr18), (Rp2,Rq4,Rr19), (Rp2,Rq4,Rr20), (Rp2,Rq4,Rr21), (Rp2,Rq4,Rr22), (Rp2,Rq5,Rr1), (Rp2,Rq5,Rr2), (Rp2,Rq5,Rr3), (Rp2,Rq5,Rr4), (Rp2,Rq5,Rr5), (Rp2,Rq5,Rr6), (Rp2,Rq5,Rr7), (Rp2,Rq5,Rr8), (Rp2,Rq5,Rr9), (Rp2,Rq5,Rr10), (Rp2,Rq5,Rr11), (Rp2,Rq5,Rr12), (Rp2,Rq5,Rr13), (Rp2,Rq5,Rr14), (Rp2,Rq5,Rr15), (Rp2,Rq5,Rr16), (Rp2,Rq5,Rr17), (Rp2,Rq5,Rr18), (Rp2,Rq5,Rr19), (Rp2,Rq5,Rr20), (Rp2,Rq5,Rr21), (Rp2,Rq5,Rr22), (Rp2,Rq6,Rr1), (Rp2,Rq6,Rr2), (Rp2,Rq6,Rr3), (Rp2,Rq6,Rr4), (Rp2,Rq6,Rr5), (Rp2,Rq6,Rr6), (Rp2,Rq6,Rr7), (Rp2,Rq6,Rr8), (Rp2,Rq6,Rr9), (Rp2,Rq6,Rr10), (Rp2,Rq6,Rr11), (Rp2,Rq6,Rr12), (Rp2,Rq6,Rr13), (Rp2,Rq6,Rr14), (Rp2,Rq6,Rr15), (Rp2,Rq6,Rr16), (Rp2,Rq6,Rr17), (Rp2,Rq6,Rr18), (Rp2,Rq6,Rr19), (Rp2,Rq6,Rr20), (Rp2,Rq6,Rr21), (Rp2,Rq6,Rr22), (Rp2,Rq7,Rr1), (Rp2,Rq7,Rr2), (Rp2,Rq7,Rr3), (Rp2,Rq7,Rr4), (Rp2,Rq7,Rr5), (Rp2,Rq7,Rr6), (Rp2,Rq7,Rr7), (Rp2,Rq7,Rr8), (Rp2,Rq7,Rr9), (Rp2,Rq7,Rr10), (Rp2,Rq7,Rr11), (Rp2,Rq7,Rr12), (Rp2,Rq7,Rr13), (Rp2,Rq7,Rr14), (Rp2,Rq7,Rr15), (Rp2,Rq7,Rr16), (Rp2,Rq7,Rr17), (Rp2,Rq7,Rr18), (Rp2,Rq7,Rr19), (Rp2,Rq7,Rr20), (Rp2,Rq7,Rr21), (Rp2,Rq7,Rr22), (Rp2,Rq8,Rr1), (Rp2,Rq8,Rr2), (Rp2,Rq8,Rr3), (Rp2,Rq8,Rr4), (Rp2,Rq8,Rr5), (Rp2,Rq8,Rr6), (Rp2,Rq8,Rr7), (Rp2,Rq8,Rr8), (Rp2,Rq8,Rr9), (Rp2,Rq8,Rr10), (Rp2,Rq8,Rr11), (Rp2,Rq8,Rr12), (Rp2,Rq8,Rr13), (Rp2,Rq8,Rr14), (Rp2,Rq8,Rr15), (Rp2, Rq8, Rr16), (Rp2,Rq8,Rr17), (Rp2,Rq8,Rr18), (Rp2,Rq8,Rr19), (Rp2,Rq8,Rr20), (Rp2,Rq8,Rr21), (Rp2,Rq8,Rr22), (Rp2,Rq9,Rr1), (Rp2,Rq9,Rr2), (Rp2,Rq9,Rr3), (Rp2,Rq9,Rr4), (Rp2,Rq9,Rr5), (Rp2,Rq9,Rr6), (Rp2,Rq9,Rr7), (Rp2,Rq9,Rr8), (Rp2,Rq9,Rr9), (Rp2,Rq9,Rr10), (Rp2,Rq9,Rr11), (Rp2,Rq9,Rr12), (Rp2,Rq9,Rr13), (Rp2,Rq9,Rr14), (Rp2,Rq9,Rr15), (Rp2,Rq9,Rr16), (Rp2,Rq9,Rr17), (Rp2,Rq9,Rr18), (Rp2,Rq9,Rr19), (Rp2,Rq9,Rr20), (Rp2,Rq9,Rr21), (Rp2,Rq9,Rr22), (Rp2,Rq10,Rr1), (Rp2,Rq10,Rr2), (Rp2,Rq10,Rr3), (Rp2,Rq10,Rr4), (Rp2,Rq10,Rr5), (Rp2,Rq10,Rr6), (Rp2,Rq10,Rr7), (Rp2,Rq10,Rr8), (Rp2,Rq10,Rr9), (Rp2,Rq10,Rr10), (Rp2,Rq10,Rr11), (Rp2,Rq10,Rr12), (Rp2,Rq10,Rr13), (Rp2,Rq10,Rr14), (Rp2,Rq10,Rr15), (Rp2,Rq10,Rr16), (Rp2,Rq10,Rr17), (Rp2,Rq10,Rr18), (Rp2,Rq10,Rr19), (Rp2,Rq10,Rr20), (Rp2,Rq10,Rr21), (Rp2,Rq10,Rr22), (Rp2,Rq11,Rr1), (Rp2,Rq11,Rr2), (Rp2,Rq11,Rr3), (Rp2,Rq11,Rr4), (Rp2,Rq11,Rr5), (Rp2,Rq11,Rr6), (Rp2,Rq11,Rr7), (Rp2,Rq11, Rr8), (Rp2,Rq11,Rr9), (Rp2,Rq11,Rr10), (Rp2,Rq11,Rr11), (Rp2,Rq11,Rr12), (Rp2,Rq11,Rr13), (Rp2,Rq11,Rr14), (Rp2,Rq11,Rr15), (Rp2,Rq11,Rr16), (Rp2,Rq11,Rr17), (Rp2,Rq11,Rr18), (Rp2,Rq11,Rr19), (Rp2,Rq11,Rr20), (Rp2,Rq11,Rr21), (Rp2,Rq11,Rr22), (Rp2,Rq12,Rr1), (Rp2,Rq12,Rr2), (Rp2,Rq12,Rr3), (Rp2,Rq12,Rr4), (Rp2,Rq12,Rr5), (Rp2,Rq12,Rr6), (Rp2,Rq12,Rr7), (Rp2,Rq12,Rr8), (Rp2,Rq12,Rr9), (Rp2,Rq12,Rr10), (Rp2,Rq12,Rr11), (Rp2,Rq12,Rr12), (Rp2,Rq12,Rr13), (Rp2,Rq12,Rr14), (Rp2,Rq12,Rr15), (Rp2,Rq12,Rr16), (Rp2,Rq12,Rr17), (Rp2,Rq12,Rr18), (Rp2,Rq12,Rr19), (Rp2,Rq12,Rr20), (Rp2,Rq12,Rr21), (Rp2,Rq12,Rr22), (Rp3,Rq1,Rr1), (Rp3,Rq1,Rr2), (Rp3,Rq1,Rr3), (Rp3,Rq1,Rr4), (Rp3,Rq1,Rr5), (Rp3,Rq1,Rr6), (Rp3,Rq1,Rr7), (Rp3,Rq1,Rr8), (Rp3,Rq1,Rr9), (Rp3,Rq1,Rr10), (Rp3,Rq1,Rr11), (Rp3,Rq1,Rr12), (Rp3,Rq1,Rr13), (Rp3,Rq1,Rr14), (Rp3,Rq1,Rr15), (Rp3,Rq1,Rr16), (Rp3,Rq1,Rr17), (Rp3,Rq1,Rr18), (Rp3,Rq1,Rr19), (Rp3,Rq1,Rr20), (Rp3,Rq1,Rr21), (Rp3,Rq1,Rr22), (Rp3,Rq2,Rr1), (Rp3,Rq2,Rr2), (Rp3,Rq2,Rr3), (Rp3,Rq2,Rr4), (Rp3,Rq2,Rr5), (Rp3,Rq2,Rr6), (Rp3,Rq2,Rr7), (Rp3,Rq2,Rr8), (Rp3,Rq2,Rr9), (Rp3,Rq2,Rr10), (Rp3,Rq2,Rr11), (Rp3,Rq2,Rr12), (Rp3,Rq2,Rr13), (Rp3,Rq2,Rr14), (Rp3,Rq2,Rr15), (Rp3,Rq2,Rr16), (Rp3,Rq2,Rr17), (Rp3,Rq2,Rr18), (Rp3,Rq2,Rr19), (Rp3,Rq2,Rr20), (Rp3,Rq2,Rr21), (Rp3,Rq2,Rr22), (Rp3,Rq3,Rr1), (Rp3,Rq3,Rr2), (Rp3,Rq3,Rr3), (Rp3,Rq3,Rr4), (Rp3,Rq3,Rr5), (Rp3,Rq3,Rr6), (Rp3,Rq3,Rr7), (Rp3,Rq3,Rr8), (Rp3,Rq3,Rr9), (Rp3,Rq3,Rr10), (Rp3,Rq3,Rr11), (Rp3,Rq3,Rr12), (Rp3,Rq3,Rr13), (Rp3,Rq3,Rr14), (Rp3,Rq3,Rr15), (Rp3,Rq3,Rr16), (Rp3,Rq3,Rr17), (Rp3,Rq3,Rr18), (Rp3,Rq3,Rr19), (Rp3,Rq3,Rr20), (Rp3,Rq3,Rr21), (Rp3,Rq3,Rr22), (Rp3,Rq4,Rr1), (Rp3,Rq4,Rr2), (Rp3,Rq4,Rr3), (Rp3,Rq4,Rr4), (Rp3,Rq4,Rr5), (Rp3,Rq4,Rr6), (Rp3,Rq4,Rr7), (Rp3,Rq4,Rr8), (Rp3,Rq4,Rr9), (Rp3,Rq4,Rr10), (Rp3,Rq4,Rr11), (Rp3,Rq4,Rr12), (Rp3,Rq4,Rr13), (Rp3,Rq4,Rr14), (Rp3,Rq4,Rr15), (Rp3,Rq4,Rr16), (Rp3,Rq4,Rr17), (Rp3,Rq4,Rr18), (Rp3,Rq4,Rr19), (Rp3,Rq4,Rr20), (Rp3,Rq4,Rr21), (Rp3,Rq4,Rr22), (Rp3,Rq5,Rr1), (Rp3,Rq5,Rr2), (Rp3,Rq5,Rr3), (Rp3,Rq5,Rr4), (Rp3,Rq5,Rr5), (Rp3,Rq5,Rr6), (Rp3,Rq5,Rr7), (Rp3,Rq5,Rr8), (Rp3,Rq5,Rr9), (Rp3,Rq5,Rr10), (Rp3,Rq5,Rr11), (Rp3,Rq5,Rr12), (Rp3,Rq5,Rr13), (Rp3,Rq5,Rr14), (Rp3,Rq5,Rr15), (Rp3,Rq5,Rr16), (Rp3,Rq5,Rr17), (Rp3,Rq5,Rr18), (Rp3,Rq5,Rr19), (Rp3,Rq5,Rr20), (Rp3,Rq5,Rr21), (Rp3,Rq5,Rr22), (Rp3,Rq6,Rr1), (Rp3,Rq6,Rr2), (Rp3,Rq6,Rr3), (Rp3,Rq6,Rr4), (Rp3,Rq6,Rr5), (Rp3,Rq6,Rr6), (Rp3,Rq6,Rr7), (Rp3,Rq6,Rr8), (Rp3,Rq6,Rr9), (Rp3,Rq6,Rr10), (Rp3,Rq6, Rr11), (Rp3,Rq6,Rr12), (Rp3,Rq6,Rr13), (Rp3,Rq6,Rr14), (Rp3,Rq6,Rr15), (Rp3,Rq6,Rr16), (Rp3,Rq6,Rr17), (Rp3,Rq6,Rr18), (Rp3,Rq6,Rr19), (Rp3,Rq6,Rr20), (Rp3,Rq6,Rr21), (Rp3, Rq6,Rr22), (Rp3,Rq7,Rr1), (Rp3,Rq7,Rr2), (Rp3,Rq7,Rr3), (Rp3,Rq7,Rr4), (Rp3,Rq7,Rr5), (Rp3,Rq7,Rr6), (Rp3,Rq7,Rr7), (Rp3,Rq7,Rr8), (Rp3,Rq7,Rr9), (Rp3,Rq7,Rr10), (Rp3,Rq7, Rr11), (Rp3,Rq7,Rr12), (Rp3,Rq7,Rr13), (Rp3,Rq7,Rr14), (Rp3,Rq7,Rr15), (Rp3,Rq7,Rr16), (Rp3,Rq7,Rr17), (Rp3,Rq7,Rr18), (Rp3,Rq7,Rr19), (Rp3,Rq7,Rr20), (Rp3,Rq7,Rr21), (Rp3,Rq7,Rr22), (Rp3,Rq8,Rr1), (Rp3,Rq8,Rr2), (Rp3,Rq8,Rr3), (Rp3,Rq8,Rr4), (Rp3,Rq8,Rr5), (Rp3,Rq8,Rr6), (Rp3,Rq8,Rr7), (Rp3,Rq8,Rr8), (Rp3,Rq8,Rr9), (Rp3,Rq8,Rr10), (Rp3,Rq8,Rr11), (Rp3,Rq8,Rr12), (Rp3,Rq8,Rr13), (Rp3,Rq8,Rr14), (Rp3,Rq8,Rr15), (Rp3,Rq8,Rr16), (Rp3,Rq8,Rr17), (Rp3,Rq8,Rr18), (Rp3,Rq8,Rr19), (Rp3,Rq8,Rr20), (Rp3,Rq8,Rr21), (Rp3,Rq8,Rr22), (Rp3,Rq9,Rr1), (Rp3,Rq9,Rr2), (Rp3,Rq9,Rr3), (Rp3,Rq9,Rr4), (Rp3,Rq9,Rr5), (Rp3,Rq9,Rr6), (Rp3,Rq9,Rr7), (Rp3,Rq9,Rr8), (Rp3,Rq9,Rr9), (Rp3,Rq9,Rr10), (Rp3,Rq9,Rr11), (Rp3,Rq9,Rr12), (Rp3,Rq9,Rr13), (Rp3,Rq9,Rr14), (Rp3,Rq9,Rr15), (Rp3,Rq9,Rr16), (Rp3,Rq9,Rr17), (Rp3,Rq9,Rr18), (Rp3,Rq9,Rr19), (Rp3,Rq9,Rr20), (Rp3,Rq9,Rr21), (Rp3,Rq9,Rr22), (Rp3,Rq10,Rr1), (Rp3,Rq10,Rr2), (Rp3,Rq10,Rr3), (Rp3,Rq10,Rr4), (Rp3,Rq10,Rr5), (Rp3,Rq10,Rr6), (Rp3,Rq10,Rr7), (Rp3,Rq10,Rr8), (Rp3,Rq10,Rr9), (Rp3,Rq10,Rr10), (Rp3,Rq10,Rr11), (Rp3,Rq10,Rr12), (Rp3,Rq10,Rr13), (Rp3,Rq10,Rr14), (Rp3,Rq10,Rr15), (Rp3,Rq10,Rr16), (Rp3,Rq10,Rr17), (Rp3,Rq10,Rr18), (Rp3,Rq10,Rr19), (Rp3,Rq10,Rr20), (Rp3,Rq10,Rr21), (Rp3,Rq10,Rr22), (Rp3,Rq11,Rr1), (Rp3,Rq11,Rr2), (Rp3,Rq11,Rr3), (Rp3,Rq11,Rr4), (Rp3,Rq11,Rr5), (Rp3,Rq11,Rr6), (Rp3,Rq11,Rr7), (Rp3,Rq11, Rr8), (Rp3,Rq11,Rr9), (Rp3,Rq11,Rr10), (Rp3,Rq11,Rr11), (Rp3,Rq11,Rr12), (Rp3,Rq11,Rr13), (Rp3,Rq11,Rr14), (Rp3,Rq11,Rr15), (Rp3,Rq11,Rr16), (Rp3,Rq11,Rr17), (Rp3,Rq11,Rr18), (Rp3,Rq11,Rr19), (Rp3,Rq11,Rr20), (Rp3,Rq11,Rr21), (Rp3,Rq11,Rr22), (Rp3,Rq12,Rr1), (Rp3,Rq12,Rr2), (Rp3,Rq12,Rr3), (Rp3,Rq12,Rr4), (Rp3,Rq12,Rr5), (Rp3,Rq12,Rr6), (Rp3,Rq12,Rr7), (Rp3,Rq12,Rr8), (Rp3,Rq12,Rr9), (Rp3,Rq12,Rr10), (Rp3,Rq12,Rr11), (Rp3,Rq12,Rr12), (Rp3,Rq12,Rr13), (Rp3,Rq12,Rr14), (Rp3,Rq12,Rr15), (Rp3,Rq12,Rr16), (Rp3,Rq12,Rr17), (Rp3,Rq12,Rr18), (Rp3,Rq12,Rr19), (Rp3,Rq12,Rr20), (Rp3,Rq12,Rr21), (Rp3,Rq12,Rr22), (Rp4,Rq1,Rr1), (Rp4,Rq1,Rr2), (Rp4,Rq1,Rr3), (Rp4,Rq1,Rr4), (Rp4,Rq1,Rr5), (Rp4,Rq1,Rr6), (Rp4,Rq1,Rr7), (Rp4,Rq1,Rr8), (Rp4,Rq1,Rr9), (Rp4,Rq1,Rr10), (Rp4,Rq1,Rr11), (Rp4,Rq1,Rr12), (Rp4,Rq1,Rr13), (Rp4,Rq1,Rr14), (Rp4,Rq1,Rr15), (Rp4,Rq1,Rr16), (Rp4,Rq1,Rr17), (Rp4,Rq1,Rr18), (Rp4,Rq1,Rr19), (Rp4,Rq1,Rr20), (Rp4,Rq1,Rr21), (Rp4,Rq1,Rr22), (Rp4,Rq2,Rr1), (Rp4,Rq2,Rr2), (Rp4,Rq2,Rr3), (Rp4,Rq2,Rr4), (Rp4,Rq2,Rr5), (Rp4,Rq2,Rr6), (Rp4,Rq2,Rr7), (Rp4,Rq2,Rr8), (Rp4,Rq2,Rr9), (Rp4,Rq2,Rr10), (Rp4,Rq2,Rr11), (Rp4,Rq2,Rr12), (Rp4,Rq2,Rr13), (Rp4,Rq2,Rr14), (Rp4,Rq2,Rr15), (Rp4,Rq2,Rr16), (Rp4,Rq2,Rr17), (Rp4,Rq2,Rr18), (Rp4,Rq2,Rr19), (Rp4,Rq2,Rr20), (Rp4,Rq2,Rr21), (Rp4,Rq2,Rr22), (Rp4,Rq3,Rr1), (Rp4,Rq3,Rr2), (Rp4,Rq3,Rr3), (Rp4,Rq3,Rr4), (Rp4,Rq3,Rr5), (Rp4,Rq3,Rr6), (Rp4,Rq3,Rr7), (Rp4,Rq3,Rr8), (Rp4,Rq3,Rr9), (Rp4,Rq3,Rr10), (Rp4,Rq3,Rr11), (Rp4,Rq3,Rr12), (Rp4,Rq3,Rr13), (Rp4,Rq3,Rr14), (Rp4,Rq3,Rr15), (Rp4,Rq3,Rr16), (Rp4,Rq3,Rr17), (Rp4,Rq3,Rr18), (Rp4,Rq3,Rr19), (Rp4,Rq3,Rr20), (Rp4,Rq3,Rr21), (Rp4,Rq3,Rr22), (Rp4,Rq4,Rr1), (Rp4,Rq4,Rr2), (Rp4,Rq4,Rr3), (Rp4,Rq4,Rr4), (Rp4,Rq4,Rr5), (Rp4,Rq4,Rr6), (Rp4,Rq4,Rr7), (Rp4,Rq4,Rr8), (Rp4,Rq4,Rr9), (Rp4,Rq4,Rr10), (Rp4,Rq4,Rr11), (Rp4,Rq4,Rr12), (Rp4,Rq4,Rr13), (Rp4,Rq4,Rr14), (Rp4,Rq4,Rr15), (Rp4,Rq4,Rr16), (Rp4,Rq4,Rr17), (Rp4,Rq4,Rr18), (Rp4,Rq4,Rr19), (Rp4,Rq4,Rr20), (Rp4,Rq4,Rr21), (Rp4,Rq4,Rr22), (Rp4,Rq5,Rr1), (Rp4,Rq5,Rr2), (Rp4,Rq5,Rr3), (Rp4,Rq5,Rr4), (Rp4,Rq5,Rr5), (Rp4,Rq5,Rr6), (Rp4,Rq5,Rr7), (Rp4,Rq5,Rr8), (Rp4,Rq5,Rr9), (Rp4,Rq5,Rr10), (Rp4,Rq5,Rr11), (Rp4,Rq5,Rr12), (Rp4,Rq5,Rr13), (Rp4,Rq5,Rr14), (Rp4,Rq5,Rr15), (Rp4,Rq5,Rr16), (Rp4,Rq5,Rr17), (Rp4,Rq5,Rr18), (Rp4,Rq5,Rr19), (Rp4,Rq5,Rr20), (Rp4,Rq5,Rr21), (Rp4,Rq5,Rr22), (Rp4,Rq6,Rr1), (Rp4,Rq6,Rr2), (Rp4,Rq6,Rr3), (Rp4,Rq6,Rr4), (Rp4,Rq6,Rr5), (Rp4,Rq6,Rr6), (Rp4,Rq6,Rr7), (Rp4,Rq6,Rr8), (Rp4,Rq6,Rr9), (Rp4,Rq6,Rr10), (Rp4,Rq6,Rr11), (Rp4,Rq6,Rr12), (Rp4,Rq6,Rr13), (Rp4,Rq6,Rr14), (Rp4,Rq6,Rr15), (Rp4,Rq6,Rr16), (Rp4,Rq6,Rr17), (Rp4,Rq6,Rr18), (Rp4,Rq6,Rr19), (Rp4,Rq6,Rr20), (Rp4,Rq6,Rr21), (Rp4,Rq6,Rr22), (Rp4,Rq7,Rr1), (Rp4,Rq7,Rr2), (Rp4,Rq7,Rr3), (Rp4,Rq7,Rr4), (Rp4,Rq7,Rr5), (Rp4,Rq7,Rr6), (Rp4,Rq7,Rr7), (Rp4,Rq7,Rr8), (Rp4,Rq7,Rr9), (Rp4,Rq7,Rr10), (Rp4,Rq7,Rr11), (Rp4,Rq7,Rr12), (Rp4,Rq7,Rr13), (Rp4,Rq7,Rr14), (Rp4,Rq7,Rr15), (Rp4,Rq7,Rr16), (Rp4,Rq7,Rr17), (Rp4,Rq7,Rr18), (Rp4,Rq7,Rr19), (Rp4,Rq7,Rr20), (Rp4,Rq7,Rr21), (Rp4,Rq7,Rr22), (Rp4,Rq8,Rr1), (Rp4,Rq8,Rr2), (Rp4,Rq8,Rr3), (Rp4,Rq8,Rr4), (Rp4,Rq8,Rr5), (Rp4,Rq8,Rr6), (Rp4,Rq8,Rr7), (Rp4,Rq8,Rr8), (Rp4,Rq8,Rr9), (Rp4,Rq8,Rr10), (Rp4,Rq8,Rr11), (Rp4,Rq8,Rr12), (Rp4,Rq8,Rr13), (Rp4,Rq8,Rr14), (Rp4,Rq8,Rr15), (Rp4,Rq8,Rr16), (Rp4,Rq8,Rr17), (Rp4,Rq8,Rr18), (Rp4,Rq8,Rr19), (Rp4,Rq8,Rr20), (Rp4,Rq8,Rr21), (Rp4,Rq8,Rr22), (Rp4,Rq9,Rr1), (Rp4,Rq9,Rr2), (Rp4,Rq9,Rr3), (Rp4,Rq9,Rr4), (Rp4,Rq9,Rr5), (Rp4,Rq9,Rr6), (Rp4,Rq9,Rr7), (Rp4,Rq9,Rr8), (Rp4,Rq9,Rr9), (Rp4,Rq9,Rr10), (Rp4,Rq9,Rr11), (Rp4,Rq9,Rr12), (Rp4,Rq9,Rr13), (Rp4,Rq9,Rr14), (Rp4,Rq9,Rr15), (Rp4,Rq9,Rr16), (Rp4,Rq9,Rr17), (Rp4,Rq9,Rr18), (Rp4,Rq9,Rr19), (Rp4,Rq9,Rr20), (Rp4,Rq9,Rr21), (Rp4,Rq9,Rr22), (Rp4,Rq10,Rr1), (Rp4,Rq10,Rr2), (Rp4,Rq10,Rr3), (Rp4,Rq10,Rr4), (Rp4,Rq10,Rr5), (Rp4,Rq10,Rr6), (Rp4,Rq10,Rr7), (Rp4,Rq10,Rr8), (Rp4,Rq10,Rr9), (Rp4,Rq10,Rr10), (Rp4,Rq10,Rr11), (Rp4,Rq10,Rr12), (Rp4,Rq10,Rr13), (Rp4,Rq10,Rr14), (Rp4,Rq10,Rr15), (Rp4,Rq10,Rr16), (Rp4,Rq10,Rr17), (Rp4,Rq10,Rr18), (Rp4,Rq10,Rr19), (Rp4,Rq10,Rr20), (Rp4,Rq10,Rr21), (Rp4,Rq10,Rr22), (Rp4,Rq11,Rr1), (Rp4,Rq11,Rr2), (Rp4,Rq11,Rr3), (Rp4,Rq11,Rr4), (Rp4,Rq11,Rr5), (Rp4,Rq11,Rr6), (Rp4,Rq11,Rr7), (Rp4,Rq11,Rr8), (Rp4,Rq11,Rr9), (Rp4,Rq11,Rr10), (Rp4,Rq11,Rr11), (Rp4,Rq11,Rr12), (Rp4,Rq11,Rr13), (Rp4,Rq11,Rr14), (Rp4,Rq11,Rr15), (Rp4,Rq11,Rr16), (Rp4,Rq11,Rr17), (Rp4,Rq11,Rr18), (Rp4,Rq11,Rr19), (Rp4,Rq11,Rr20), (Rp4,Rq11,Rr21), (Rp4,Rq11,Rr22), (Rp4,Rq12,Rr1), (Rp4,Rq12,Rr2), (Rp4,Rq12,Rr3), (Rp4,Rq12,Rr4), (Rp4,Rq12,Rr5), (Rp4,Rq12,Rr6), (Rp4,Rq12,Rr7), (Rp4,Rq12,Rr8), (Rp4,Rq12,Rr9), (Rp4,Rq12,Rr10), (Rp4,Rq12,Rr11), (Rp4,Rq12,Rr12), (Rp4,Rq12,Rr13), (Rp4,Rq12,Rr14), (Rp4,Rq12,Rr15), (Rp4,Rq12,Rr16), (Rp4,Rq12,Rr17), (Rp4,Rq12,Rr18), (Rp4,Rq12,Rr19), (Rp4,Rq12,Rr20), (Rp4,Rq12,Rr21), (Rp4,Rq12,Rr22), (Rp5,Rq1,Rr1), (Rp5,Rq1,Rr2), (Rp5,Rq1,Rr3), (Rp5,Rq1,Rr4), (Rp5,Rq1,Rr5), (Rp5,Rq1,Rr6), (Rp5,Rq1,Rr7), (Rp5,Rq1,Rr8), (Rp5,Rq1,Rr9), (Rp5,Rq1,Rr10), (Rp5,Rq1,Rr11), (Rp5,Rq1,Rr12), (Rp5,Rq1,Rr13), (Rp5,Rq1,Rr14), (Rp5,Rq1,Rr15), (Rp5,Rq1,Rr16), (Rp5,Rq1,Rr17), (Rp5,Rq1,Rr18), (Rp5,Rq1,Rr19), (Rp5,Rq1,Rr20), (Rp5,Rq1,Rr21), (Rp5,Rq1,Rr22), (Rp5,Rq2,Rr1), (Rp5,Rq2,Rr2), (Rp5,Rq2,Rr3), (Rp5,Rq2,Rr4), (Rp5,Rq2,Rr5), (Rp5,Rq2,Rr6), (Rp5,Rq2,Rr7), (Rp5,Rq2,Rr8), (Rp5,Rq2,Rr9), (Rp5,Rq2,Rr10), (Rp5,Rq2,Rr11), (Rp5,Rq2,Rr12), (Rp5,Rq2,Rr13), (Rp5,Rq2,Rr14), (Rp5,Rq2,Rr15), (Rp5,Rq2,Rr16), (Rp5,Rq2,Rr17), (Rp5,Rq2,Rr18), (Rp5,Rq2,Rr19), (Rp5,Rq2,Rr20), (Rp5,Rq2,Rr21), (Rp5,Rq2,Rr22), (Rp5,Rq3,Rr1), (Rp5,Rq3,Rr2), (Rp5,Rq3,Rr3), (Rp5,Rq3,Rr4), (Rp5,Rq3,Rr5), (Rp5,Rq3,Rr6), (Rp5,Rq3,Rr7), (Rp5,Rq3,Rr8), (Rp5,Rq3,Rr9), (Rp5,Rq3,Rr10), (Rp5,Rq3,Rr11), (Rp5,Rq3,Rr12), (Rp5,Rq3,Rr13), (Rp5,Rq3,Rr14), (Rp5,Rq3,Rr15), (Rp5,Rq3,Rr16), (Rp5,Rq3,Rr17), (Rp5,Rq3,Rr18), (Rp5,Rq3,Rr19), (Rp5,Rq3,Rr20), (Rp5,Rq3,Rr21), (Rp5,Rq3,Rr22), (Rp5,Rq4,Rr1), (Rp5,Rq4,Rr2), (Rp5,Rq4,Rr3), (Rp5,Rq4,Rr4), (Rp5,Rq4,Rr5), (Rp5,Rq4,Rr6), (Rp5,Rq4,Rr7), (Rp5,Rq4,Rr8), (Rp5,Rq4,Rr9), (Rp5,Rq4,Rr10), (Rp5,Rq4,Rr11), (Rp5,Rq4,Rr12), (Rp5,Rq4,Rr13), (Rp5,Rq4,Rr14), (Rp5,Rq4,Rr15), (Rp5,Rq4,Rr16), (Rp5,Rq4,Rr17), (Rp5,Rq4,Rr18), (Rp5,Rq4,Rr19), (Rp5,Rq4,Rr20), (Rp5,Rq4,Rr21), (Rp5,Rq4,Rr22), (Rp5,Rq5,Rr1), (Rp5,Rq5,Rr2), (Rp5,Rq5,Rr3), (Rp5,Rq5,Rr4), (Rp5,Rq5,Rr5), (Rp5,Rq5,Rr6), (Rp5,Rq5,Rr7), (Rp5,Rq5,Rr8), (Rp5,Rq5,Rr9), (Rp5,Rq5,Rr10), (Rp5,Rq5,Rr11), (Rp5,Rq5,Rr12), (Rp5,Rq5,Rr13), (Rp5,Rq5,Rr14), (Rp5,Rq5,Rr15), (Rp5,Rq5,Rr16), (Rp5,Rq5,Rr17), (Rp5,Rq5,Rr18), (Rp5,Rq5,Rr19), (Rp5,Rq5,Rr20), (Rp5,Rq5,Rr21), (Rp5,Rq5,Rr22), (Rp5,Rq6,Rr1), (Rp5,Rq6,Rr2), (Rp5,Rq6,Rr3), (Rp5,Rq6,Rr4), (Rp5,Rq6,Rr5), (Rp5,Rq6,Rr6), (Rp5,Rq6,Rr7), (Rp5,Rq6,Rr8), (Rp5,Rq6,Rr9), (Rp5,Rq6,Rr10), (Rp5,Rq6,Rr11), (Rp5,Rq6,Rr12), (Rp5,Rq6,Rr13), (Rp5,Rq6,Rr14), (Rp5,Rq6,Rr15), (Rp5,Rq6,Rr16), (Rp5,Rq6,Rr17), (Rp5,Rq6,Rr18), (Rp5,Rq6,Rr19), (Rp5,Rq6,Rr20), (Rp5,Rq6,Rr21), (Rp5,Rq6,Rr22), (Rp5,Rq7,Rr1), (Rp5,Rq7,Rr2), (Rp5,Rq7,Rr3), (Rp5,Rq7,Rr4), (Rp5,Rq7,Rr5), (Rp5,Rq7,Rr6), (Rp5,Rq7,Rr7), (Rp5,Rq7,Rr8), (Rp5,Rq7,Rr9), (Rp5,Rq7,Rr10), (Rp5,Rq7,Rr11), (Rp5,

Rq7,Rr12), (Rp5,Rq7,Rr13), (Rp5,Rq7,Rr14), (Rp5,Rq7,Rr15), (Rp5,Rq7,Rr16), (Rp5,Rq7,Rr17), (Rp5,Rq7,Rr18), (Rp5,Rq7,Rr19), (Rp5,Rq7,Rr20), (Rp5,Rq7,Rr21), (Rp5,Rq7,Rr22), (Rp5,Rq8,Rr1), (Rp5,Rq8,Rr2), (Rp5,Rq8,Rr3), (Rp5,Rq8,Rr4), (Rp5,Rq8,Rr5), (Rp5,Rq8,Rr6), (Rp5,Rq8,Rr7), (Rp5,Rq8,Rr8), (Rp5,Rq8,Rr9), (Rp5,Rq8,Rr10), (Rp5,Rq8,Rr11), (Rp5,Rq8,Rr12), (Rp5,Rq8,Rr13), (Rp5,Rq8,Rr14), (Rp5,Rq8,Rr15), (Rp5,Rq8,Rr16), (Rp5,Rq8,Rr17), (Rp5,Rq8,Rr18), (Rp5,Rq8,Rr19), (Rp5,Rq8,Rr20), (Rp5,Rq8,Rr21), (Rp5,Rq8,Rr22), (Rp5,Rq9,Rr1), (Rp5,Rq9,Rr2), (Rp5,Rq9,Rr3), (Rp5,Rq9,Rr4), (Rp5,Rq9,Rr5), (Rp5,Rq9,Rr6), (Rp5,Rq9,Rr7), (Rp5,Rq9,Rr8), (Rp5,Rq9,Rr9), (Rp5,Rq9,Rr10), (Rp5,Rq9,Rr11), (Rp5,Rq9,Rr12), (Rp5,Rq9,Rr13), (Rp5,Rq9,Rr14), (Rp5,Rq9,Rr15), (Rp5,Rq9,Rr16), (Rp5,Rq9,Rr17), (Rp5,Rq9,Rr18), (Rp5,Rq9,Rr19), (Rp5,Rq9,Rr20), (Rp5,Rq9,Rr21), (Rp5,Rq9,Rr22), (Rp5,Rq10,Rr1), (Rp5,Rq10,Rr2), (Rp5,Rq10,Rr3), (Rp5,Rq10,Rr4), (Rp5,Rq10,Rr5), (Rp5,Rq10,Rr6), (Rp5,Rq10,Rr7), (Rp5,Rq10,Rr8), (Rp5,Rq10,Rr9), (Rp5,Rq10,Rr10), (Rp5,Rq10,Rr11), (Rp5,Rq10,Rr12), (Rp5,Rq10,Rr13), (Rp5,Rq10,Rr14), (Rp5,Rq10,Rr15), (Rp5,Rq10,Rr16), (Rp5,Rq10,Rr17), (Rp5,Rq10,Rr18), (Rp5,Rq10,Rr19), (Rp5,Rq10,Rr20), (Rp5,Rq10,Rr21), (Rp5,Rq10,Rr22), (Rp5,Rq11,Rr1), (Rp5,Rq11,Rr2), (Rp5,Rq11,Rr3), (Rp5,Rq11,Rr4), (Rp5,Rq11,Rr5), (Rp5,Rq11,Rr6), (Rp5,Rq11,Rr7), (Rp5,Rq11,Rr8), (Rp5,Rq11,Rr9), (Rp5,Rq11,Rr10), (Rp5,Rq11,Rr11), (Rp5,Rq11,Rr12), (Rp5,Rq11,Rr13), (Rp5,Rq11,Rr14), (Rp5,Rq11,Rr15), (Rp5,Rq11,Rr16), (Rp5,Rq11,Rr17), (Rp5,Rq11,Rr18), (Rp5,Rq11,Rr19), (Rp5,Rq11,Rr20), (Rp5,Rq11,Rr21), (Rp5,Rq11,Rr22), (Rp5,Rq12,Rr1), (Rp5,Rq12,Rr2), (Rp5,Rq12,Rr3), (Rp5,Rq12,Rr4), (Rp5,Rq12,Rr5), (Rp5,Rq12,Rr6), (Rp5,Rq12,Rr7), (Rp5,Rq12,Rr8), (Rp5,Rq12,Rr9), (Rp5,Rq12,Rr10), (Rp5,Rq12,Rr11), (Rp5,Rq12,Rr12), (Rp5,Rq12,Rr13), (Rp5,Rq12,Rr14), (Rp5,Rq12,Rr15), (Rp5,Rq12,Rr16), (Rp5,Rq12,Rr17), (Rp5,Rq12,Rr18), (Rp5,Rq12,Rr19), (Rp5,Rq12,Rr20), (Rp5,Rq12,Rr21), (Rp5,Rq12,Rr22), (Rp6,Rq1,Rr1), (Rp6,Rq1,Rr2), (Rp6,Rq1,Rr3), (Rp6,Rq1,Rr4), (Rp6,Rq1,Rr5), (Rp6,Rq1,Rr6), (Rp6,Rq1,Rr7), (Rp6,Rq1,Rr8), (Rp6,Rq1,Rr9), (Rp6,Rq1,Rr10), (Rp6,Rq1,Rr11), (Rp6,Rq1,Rr12), (Rp6,Rq1,Rr13), (Rp6,Rq1,Rr14), (Rp6,Rq1,Rr15), (Rp6,Rq1,Rr16), (Rp6,Rq1,Rr17), (Rp6,Rq1,Rr18), (Rp6,Rq1,Rr19), (Rp6,Rq1,Rr20), (Rp6,Rq1,Rr21), (Rp6,Rq1,Rr22), (Rp6,Rq2,Rr1), (Rp6,Rq2,Rr2), (Rp6,Rq2,Rr3), (Rp6,Rq2,Rr4), (Rp6,Rq2,Rr5), (Rp6,Rq2,Rr6), (Rp6,Rq2,Rr7), (Rp6,Rq2,Rr8), (Rp6,Rq2,Rr9), (Rp6,Rq2,Rr10), (Rp6,Rq2,Rr11), (Rp6,Rq2,Rr12), (Rp6,Rq2,Rr13), (Rp6,Rq2,Rr14), (Rp6,Rq2,Rr15), (Rp6,Rq2,Rr16), (Rp6,Rq2,Rr17), (Rp6,Rq2,Rr18), (Rp6,Rq2,Rr19), (Rp6,Rq2,Rr20), (Rp6,Rq2,Rr21), (Rp6,Rq2,Rr22), (Rp6,Rq3,Rr1), (Rp6,Rq3,Rr2), (Rp6,Rq3,Rr3), (Rp6,Rq3,Rr4), (Rp6,Rq3,Rr5), (Rp6,Rq3,Rr6), (Rp6,Rq3,Rr7), (Rp6,Rq3,Rr8), (Rp6,Rq3,Rr9), (Rp6,Rq3,Rr10), (Rp6,Rq3,Rr11), (Rp6,Rq3,Rr12), (Rp6,Rq3,Rr13), (Rp6,Rq3,Rr14), (Rp6,Rq3,Rr15), (Rp6,Rq3,Rr16), (Rp6,Rq3,Rr17), (Rp6,Rq3,Rr18), (Rp6,Rq3,Rr19), (Rp6,Rq3,Rr20), (Rp6,Rq3,Rr21), (Rp6,Rq3,Rr22), (Rp6,Rq4,Rr1), (Rp6,Rq4,Rr2), (Rp6,Rq4,Rr3), (Rp6,Rq4,Rr4), (Rp6,Rq4,Rr5), (Rp6,Rq4,Rr6), (Rp6,Rq4,Rr7), (Rp6,Rq4,Rr8), (Rp6,Rq4,Rr9), (Rp6,Rq4,Rr10), (Rp6,Rq4,Rr11), (Rp6,$R_q$4,Rr12), (Rp6,Rq4,Rr13), (Rp6,Rq4,Rr14), (Rp6,Rq4,Rr15), (Rp6,Rq4,Rr16), (Rp6,Rq4,Rr17), (Rp6,Rq4,Rr18), (Rp6,Rq4,Rr19), (Rp6,Rq4,Rr20), (Rp6,Rq4,Rr21), (Rp6,Rq4,Rr22), (Rp6,Rq5,Rr1), (Rp6,Rq5,Rr2), (Rp6,Rq5,Rr3), (Rp6,Rq5,Rr4), (Rp6,Rq5,Rr5), (Rp6, Rq5,Rr6), (Rp6,Rq5,Rr7), (Rp6,Rq5,Rr8), (Rp6,Rq5,Rr9), (Rp6,Rq5,Rr10), (Rp6,Rq5,Rr11), (Rp6,Rq5,Rr12), (Rp6,Rq5,Rr13), (Rp6,Rq5,Rr14), (Rp6,Rq5,Rr15), (Rp6,Rq5,Rr16), (Rp6,Rq5,Rr17), (Rp6,Rq5,Rr18), (Rp6,Rq5,Rr19), (Rp6,Rq5,Rr20), (Rp6,Rq5,Rr21), (Rp6,Rq5,Rr22), (Rp6,Rq6,Rr1), (Rp6,Rq6,Rr2), (Rp6,Rq6,Rr3), (Rp6,Rq6,Rr4), (Rp6,Rq6,Rr5), (Rp6,Rq6,Rr6), (Rp6,Rq6,Rr7), (Rp6,Rq6,Rr8), (Rp6,Rq6,Rr9), (Rp6,Rq6,Rr10), (Rp6,Rq6,Rr11), (Rp6,Rq6,Rr12), (Rp6,Rq6,Rr13), (Rp6,Rq6,Rr14), (Rp6,Rq6,Rr15), (Rp6,Rq6,Rr16), (Rp6,Rq6,Rr17), (Rp6,Rq6,Rr18), (Rp6,Rq6,Rr19), (Rp6,Rq6,Rr20), (Rp6,Rq6,Rr21), (Rp6,Rq6,Rr22), (Rp6,Rq7,Rr1), (Rp6,Rq7,Rr2), (Rp6,Rq7,Rr3), (Rp6,Rq7,Rr4), (Rp6,Rq7,Rr5), (Rp6,Rq7,Rr6), (Rp6,Rq7,Rr7), (Rp6,Rq7,Rr8), (Rp6,Rq7,Rr9), (Rp6,Rq7,Rr10), (Rp6,Rq7,Rr11), (Rp6,Rq7,Rr12), (Rp6,Rq7,Rr13), (Rp6,Rq7,Rr14), (Rp6,Rq7,Rr15), (Rp6,Rq7,Rr16), (Rp6,Rq7,Rr17), (Rp6,Rq7,Rr18), (Rp6,Rq7,Rr19), (Rp6,Rq7,Rr20), (Rp6,Rq7,Rr21), (Rp6,Rq7,Rr22), (Rp6,Rq8,Rr1), (Rp6,Rq8,Rr2), (Rp6,Rq8,Rr3), (Rp6,Rq8,Rr4), (Rp6,Rq8,Rr5), (Rp6,Rq8,Rr6), (Rp6,Rq8,Rr7), (Rp6,Rq8,Rr8), (Rp6,Rq8,Rr9), (Rp6,Rq8,Rr10), (Rp6,Rq8,Rr11), (Rp6,Rq8,Rr12), (Rp6,Rq8,Rr13), (Rp6,Rq8,Rr14), (Rp6,Rq8,Rr15), (Rp6,Rq8,Rr16), (Rp6,Rq8,Rr17), (Rp6,Rq8,Rr18), (Rp6,Rq8,Rr19), (Rp6,Rq8,Rr20), (Rp6,Rq8,Rr21), (Rp6,Rq8,Rr22), (Rp6,Rq9,Rr1), (Rp6,Rq9,Rr2), (Rp6,Rq9,Rr3), (Rp6,Rq9,Rr4), (Rp6,Rq9,Rr5), (Rp6,Rq9,Rr6), (Rp6,Rq9,Rr7), (Rp6,Rq9,Rr8), (Rp6,Rq9,Rr9), (Rp6,Rq9,Rr10), (Rp6,Rq9,Rr11), (Rp6,Rq9,Rr12), (Rp6,Rq9,Rr13), (Rp6,Rq9,Rr14), (Rp6,Rq9,Rr15), (Rp6,Rq9,Rr16), (Rp6,Rq9,Rr17), (Rp6,Rq9,Rr18), (Rp6,$R_{49}$,Rr19), (Rp6,Rq9,Rr20), (Rp6,Rq9,Rr21), (Rp6,Rq9,Rr22), (Rp6,Rq10,Rr1), (Rp6,Rq10,Rr2), (Rp6,Rq10,Rr3), (Rp6,Rq10,Rr4), (Rp6,Rq10,Rr5), (Rp6,$R_q$10,Rr6), ($R_p$ 6,$R_q$10,Rr7), (Rp6,Rq10,Rr8), (Rp6,Rq10,Rr9), (Rp6,Rq10,Rr10), (Rp6,Rq10,Rr11), (Rp6,Rq10,Rr12), (Rp6,Rq10,Rr13), (Rp6,Rq10,Rr14), (Rp6,Rq10,Rr15), (Rp6,Rq10,Rr16), (Rp6,Rq10,Rr17), (Rp6,Rq10,Rr18), (Rp6,Rq10,Rr19), (Rp6,Rq10,Rr20), (Rp6,Rq10,Rr21), (Rp6,Rq10,Rr22), (Rp6,Rq11,Rr1), (Rp6,Rq11,Rr2), (Rp6,Rq11,Rr3), (Rp6,Rq11,Rr4), (Rp6,Rq11,Rr5), (Rp6,Rq11,Rr6), (Rp6,Rq11,Rr7), (Rp6,Rq11,Rr8), (Rp6,Rq11,Rr9), (Rp6,Rq11,Rr10), (Rp6,Rq11,Rr11), (Rp6,Rq11,Rr12), (Rp6,Rq11, Rr13), (Rp6,Rq11,Rr14), (Rp6,Rq11,Rr15), (Rp6,Rq11,Rr16), (Rp6,Rq11,Rr17), (Rp6,Rq11,Rr18), (Rp6,Rq11,Rr19), (Rp6,Rq11,Rr20), (Rp6,Rq11,Rr21), (Rp6,Rq11,Rr22), (Rp6,Rq12,Rr1), (Rp6,Rq12,Rr2), (Rp6,Rq12,Rr3), (Rp6,Rq12,Rr4), (Rp6,Rq12,Rr5), (Rp6,Rq12,Rr6), (Rp6,Rq12,Rr7), (Rp6,Rq12,Rr8), (Rp6,Rq12,Rr9), (Rp6,Rq12,Rr10), (Rp6,Rq12,Rr11), (Rp6,Rq12,Rr12), (Rp6,Rq12,Rr13), (Rp6,Rq12,Rr14), (Rp6,Rq12,Rr15), (Rp6,Rq12,Rr16), (Rp6,Rq12,Rr17), (Rp6,Rq12,Rr18), (Rp6,Rq12,Rr19), (Rp6,Rq12,Rr20), (Rp6,Rq12,Rr21), (Rp6,Rq12,Rr22), (Rp7,Rq1,Rr1), (Rp7,Rq1,Rr2), (Rp7,Rq1,Rr3), (Rp7,Rq1,Rr4), (Rp7,Rq1,Rr5), (Rp7,Rq1,Rr6), (Rp7,Rq1,Rr7), (Rp7,Rq1,Rr8), (Rp7,Rq1,Rr9), (Rp7,Rq1,Rr10), (Rp7,Rq1,Rr11), (Rp7,Rq1,Rr12), (Rp7,Rq1,Rr13), (Rp7,Rq1,Rr14), (Rp7,Rq1,Rr15), (Rp7,Rq1, Rr16), (Rp7,Rq1, Rr17), (Rp7,Rq1,Rr18), (Rp7,Rq1,Rr19), (Rp7,Rq1,Rr20), (Rp7,Rq1,Rr21), (Rp7,Rq1,Rr22), (Rp7,Rq2,Rr1), (Rp7,Rq2,Rr2), (Rp7,Rq2,Rr3), (Rp7,Rq2,Rr4), (Rp7,Rq2,Rr5), (Rp7,Rq2,Rr6), (Rp7,Rq2,Rr7), (Rp7,Rq2,Rr8), (Rp7,Rq2,Rr9), (Rp7,Rq2,Rr10), (Rp7,Rq2,Rr11), (Rp7,Rq2,Rr12), (Rp7,Rq2,Rr13), (Rp7,Rq2,Rr14), (Rp7,Rq2,Rr15), (Rp7,Rq2,Rr16), (Rp7,Rq2,Rr17), (Rp7,Rq2,Rr18), (Rp7,Rq2,Rr19), (Rp7,Rq2,Rr20), (Rp7,Rq2,Rr21), (Rp7,Rq2,Rr22), (Rp7,Rq3,Rr1), (Rp7,Rq3,Rr2), (Rp7,Rq3,Rr3), (Rp7,Rq3,Rr4), (Rp7,Rq3,Rr5), (Rp7,Rq3,Rr6), (Rp7,Rq3,Rr7), (Rp7,Rq3,Rr8), (Rp7,Rq3,Rr9), (Rp7,Rq3,Rr10), (Rp7,Rq3,Rr11), (Rp7,Rq3,Rr12), (Rp7,Rq3,Rr13), (Rp7,Rq3,Rr14), (Rp7,Rq3,Rr15), (Rp7,Rq3,Rr16), (Rp7,Rq3,Rr17), (Rp7,Rq3,Rr18), (Rp7,Rq3,Rr19), (Rp7,Rq3,Rr20), (Rp7,Rq3,Rr21), (Rp7,Rq3,Rr22), (Rp7,Rq4,Rr1), (Rp7, Rq4,Rr2), (Rp7,Rq4,Rr3), (Rp7,Rq4,Rr4), (Rp7,Rq4,Rr5), (Rp7,Rq4,Rr6), (Rp7,Rq4,Rr7), (Rp7,Rq4,Rr8), (Rp7,Rq4, Rr9), (Rp7,Rq4,Rr10), (Rp7,Rq4,Rr11), (Rp7,Rq4,Rr12), (Rp7,Rq4,Rr13), (Rp7,Rq4,Rr14), (Rp7,Rq4,Rr15), (Rp7, Rq4,Rr16), (Rp7,Rq4,Rr17), (Rp7,Rq4,Rr18), (Rp7,Rq4, Rr19), (Rp7,Rq4,Rr20), (Rp7,Rq4,Rr21), (Rp7,Rq4,Rr22), (Rp7,Rq5,Rr1), (Rp7,Rq5,Rr2), (Rp7,Rq5,Rr3), (Rp7,Rq5, Rr4), (Rp7,Rq5,Rr5), (Rp7,Rq5,Rr6), (Rp7,Rq5,Rr7), (Rp7, Rq5,Rr8), (Rp7,Rq5,Rr9), (Rp7,Rq5,Rr10), (Rp7,Rq5, Rr11), (Rp7,Rq5,Rr12), (Rp7,Rq5,Rr13), (Rp7,Rq5,Rr14), (Rp7,Rq5,Rr15), (Rp7,Rq5,Rr16), (Rp7,Rq5,Rr17), (Rp7, Rq5,Rr18), (Rp7,Rq5,Rr19), (Rp7,Rq5,Rr20), (Rp7,Rq5, Rr21), (Rp7,Rq5, Rr22), (Rp7,Rq6,Rr1), (Rp7,Rq6,Rr2), (Rp7,Rq6,Rr3), (Rp7,Rq6,Rr4), (Rp7,Rq6,Rr5), (Rp7, Rq6, Rr6), (Rp7,Rq6,Rr7), (Rp7,Rq6,Rr8), (Rp7,Rq6,Rr9), (Rp7, Rq6,Rr10), (Rp7,Rq6,Rr11), (Rp7,Rq6,Rr12), (Rp7,Rq6, Rr13), (Rp7,Rq6,Rr14), (Rp7,Rq6,Rr15), (Rp7,Rq6,Rr16), (Rp7,Rq6,Rr17), (Rp7,Rq6,Rr18), (Rp7,Rq6,Rr19), (Rp7, Rq6,Rr20), (Rp7,Rq6,Rr21), (Rp7,Rq6, Rr22), (Rp7,Rq7, Rr1), (Rp7,Rq7,Rr2), (Rp7,Rq7,Rr3), (Rp7,Rq7,Rr4), (Rp7, Rq7,Rr5), (Rp7, Rq7,Rr6), (Rp7,Rq7,Rr7), (Rp7,Rq7,Rr8), (Rp7,Rq7,Rr9), (Rp7,Rq7,Rr10), (Rp7,Rq7,Rr11), (Rp7, Rq7,Rr12), (Rp7,Rq7,Rr13), (Rp7,Rq7,Rr14), (Rp7,Rq7, Rr15), (Rp7,Rq7,Rr16), (Rp7,Rq7,Rr17), (Rp7,Rq7,Rr18), (Rp7,Rq7,Rr19), (Rp7,Rq7,Rr20), (Rp7,Rq7,Rr21), (Rp7, Rq7, Rr22), (Rp7,Rq8,Rr1), (Rp7,Rq8,Rr2), (Rp7,Rq8,Rr3), (Rp7,Rq8,Rr4), (Rp7,Rq8,Rr5), (Rp7, Rq8,Rr6), (Rp7,Rq8, Rr7), (Rp7,Rq8,Rr8), (Rp7,Rq8,Rr9), (Rp7,Rq8,Rr10), (Rp7,Rq8,Rr11), (Rp7,Rq8,Rr12), (Rp7,Rq8,Rr13), (Rp7, Rq8,Rr14), (Rp7,Rq8,Rr15), (Rp7,Rq8,Rr16), (Rp7,Rq8, Rr17), (Rp7,Rq8,Rr18), (Rp7,Rq8,Rr19), (Rp7,Rq8,Rr20), (Rp7,Rq8,Rr21), (Rp7,Rq8, Rr22), (Rp7,Rq9,Rr1), (Rp7, Rq9,Rr2), (Rp7,Rq9,Rr3), (Rp7,Rq9,Rr4), (Rp7,Rq9,Rr5), (Rp7, Rq9,Rr6), (Rp7,Rq9,Rr7), (Rp7,Rq9,Rr8), (Rp7,Rq9, Rr9), (Rp7,Rq9,Rr10), (Rp7,Rq9,Rr11), (Rp7,Rq9,Rr12), (Rp7,Rq9,Rr13), (Rp7,Rq9,Rr14), (Rp7,Rq9,Rr15), (Rp7, Rq9,Rr16), (Rp7,Rq9,Rr17), (Rp7,Rq9,Rr18), (Rp7,Rq9, Rr19), (Rp7,Rq9,Rr20), (Rp7,Rq9,Rr21), (Rp7,Rq9, Rr22), (Rp7,Rq10,Rr1), (Rp7,Rq10,Rr2), (Rp7,Rq10,Rr3), (Rp7, Rq10,Rr4), (Rp7,Rq10,Rr5), (Rp7,Rq10,Rr6), (Rp7,Rq10, Rr7), (Rp7,Rq10,Rr8), (Rp7,Rq10,Rr9), (Rp7,Rq10,Rr10), (Rp7,Rq10,Rr11), (Rp7,Rq10,Rr12), (Rp7,Rq10,Rr13), (Rp7,Rq10,Rr14), (Rp7,Rq10,Rr15), (Rp7,Rq10,Rr16), (Rp7,Rq10,Rr17), (Rp7,Rq10,Rr18), (Rp7,Rq10,Rr19), (Rp7,Rq10,Rr20), (Rp7,Rq10,Rr21), (Rp7,Rq10,Rr22), (Rp7,Rq11,Rr1), (Rp7,Rq11,Rr2), (Rp7,Rq11,Rr3), (Rp7, Rq11,Rr4), (Rp7,Rq11,Rr5), (Rp7,Rq11,Rr6), (Rp7,Rq11, Rr7), (Rp7,Rq11,Rr8), (Rp7,Rq11,Rr9), (Rp7,Rq11,Rr10), (Rp7,Rq11, Rr11), (Rp7,Rq11,Rr12), (Rp7,Rq11, Rr13), (Rp7,Rq11,Rr14), (Rp7,Rq11,Rr15), (Rp7,Rq11,Rr16), (Rp7,Rq11, Rr17), (Rp7,Rq11,Rr18), (Rp7,Rq11,Rr19), (Rp7,Rq11,Rr20), (Rp7,Rq11,Rr21), (Rp7,Rq11,Rr22), (Rp7,Rq12,Rr1), (Rp7,Rq12,Rr2), (Rp7,Rq12,Rr3), (Rp7, Rq12,Rr4), (Rp7,Rq12,Rr5), (Rp7,Rq12,Rr6), (Rp7,Rq12, Rr7), (Rp7,Rq12,Rr8), (Rp7,Rq12,Rr9), (Rp7,Rq12,Rr10), (Rp7,Rq12,Rr11), (Rp7,Rq12,Rr12), (Rp7,Rq12,Rr13), (Rp7,Rq12,Rr14), (Rp7,Rq12,Rr15), (Rp7,Rq12,Rr16), (Rp7,Rq12,Rr17), (Rp7,Rq12,Rr18), (Rp7,Rq12,Rr19), (Rp7,Rq12,Rr20), (Rp7,Rq12,Rr21), (Rp7,Rq12,Rr22), (Rp8,Rq1,Rr1), (Rp8,Rq1,Rr2), (Rp8,Rq1,Rr3), (Rp8,Rq1, Rr4), (Rp8,Rq1,Rr5), (Rp8,Rq1,Rr6), (Rp8,Rq1,Rr7), (Rp8, Rq1, Rr8), (Rp8,Rq1,Rr9), (Rp8,Rq1,Rr10), (Rp8,Rq1, Rr11), (Rp8,Rq1,Rr12), (Rp8,Rq1,Rr13), (Rp8,Rq1,Rr14), (Rp8,Rq1,Rr15), (Rp8,Rq1,Rr16), (Rp8,Rq1,Rr17), (Rp8, Rq1,Rr18), (Rp8,Rq1,Rr19), (Rp8,Rq1,Rr20), (Rp8,Rq1, Rr21), (Rp8,Rq1,Rr22), (Rp8,Rq2,Rr1), (Rp8,Rq2,Rr2), (Rp8,Rq2,Rr3), (Rp8,Rq2,Rr4), (Rp8,Rq2,Rr5), (Rp8,Rq2, Rr6), (Rp8,Rq2,Rr7), (Rp8,Rq2,Rr8), (Rp8,Rq2,Rr9), (Rp8, Rq2,Rr10), (Rp8,Rq2,Rr11), (Rp8,Rq2,Rr12), (Rp8,Rq2, Rr13), (Rp8,Rq2,Rr14), (Rp8,Rq2,Rr15), (Rp8,Rq2,Rr16), (Rp8, Rq2,Rr17), (Rp8,Rq2,Rr18), (Rp8,Rq2,Rr19), (Rp8, Rq2,Rr20), (Rp8,Rq2,Rr21), (Rp8,Rq2, Rr22), (Rp8,Rq3, Rr1), (Rp8,Rq3,Rr2), (Rp8,Rq3,Rr3), (Rp8,Rq3,Rr4), (Rp8, Rq3,Rr5), (Rp8, Rq3,Rr6), (Rp8,Rq3,Rr7), (Rp8,Rq3,Rr8), (Rp8,Rq3,Rr9), (Rp8,Rq3,Rr10), (Rp8,Rq3,Rr11), (Rp8, Rq3,Rr12), (Rp8,Rq3,Rr13), (Rp8,Rq3,Rr14), (Rp8,Rq3, Rr15), (Rp8,Rq3,Rr16), (Rp8,Rq3,Rr17), (Rp8,Rq3,Rr18), (Rp8,Rq3,Rr19), (Rp8,Rq3,Rr20), (Rp8,Rq3,Rr21), (Rp8, Rq3, Rr22), (Rp8,Rq4,Rr1), (Rp8,Rq4,Rr2), (Rp8,Rq4,Rr3), (Rp8,Rq4,Rr4), (Rp8,Rq4,Rr5), (Rp8,Rq4,Rr6), (Rp8,Rq4, Rr7), (Rp8,Rq4,Rr8), (Rp8,Rq4,Rr9), (Rp8,Rq4,Rr10), (Rp8,Rq4,Rr11), (Rp8,Rq4,Rr12), (Rp8,Rq4,Rr13), (Rp8, Rq4,Rr14), (Rp8,Rq4,Rr15), (Rp8,Rq4,Rr16), (Rp8,Rq4, Rr17), (Rp8,Rq4,Rr18), (Rp8,Rq4,Rr19), (Rp8,Rq4,Rr20), (Rp8,Rq4,Rr21), (Rp8,Rq4, Rr22), (Rp8,Rq5,Rr1), (Rp8, Rq5,Rr2), (Rp8,Rq5,Rr3), (Rp8,Rq5,Rr4), (Rp8,Rq5,Rr5), (Rp8, Rq5,Rr6), (Rp8,Rq5,Rr7), (Rp8,Rq5,Rr8), (Rp8,Rq5, Rr9), (Rp8,Rq5,Rr10), (Rp8,Rq5,Rr11), (Rp8,Rq5,Rr12), (Rp8,Rq5,Rr13), (Rp8,Rq5,Rr14), (Rp8,Rq5,Rr15), (Rp8, Rq5,Rr16), (Rp8,Rq5,Rr17), (Rp8,Rq5,Rr18), (Rp8,Rq5, Rr19), (Rp8,Rq5,Rr20), (Rp8,Rq5,Rr21), (Rp8,Rq5, Rr22), (Rp8,Rq6,Rr1), (Rp8,Rq6,Rr2), (Rp8,Rq6,Rr3), (Rp8,Rq6, Rr4), (Rp8,Rq6,Rr5), (Rp8, Rq6,Rr6), (Rp8,Rq6,Rr7), (Rp8, Rq6,Rr8), (Rp8,Rq6,Rr9), (Rp8,Rq6,Rr10), (Rp8,Rq6, Rr11), (Rp8,Rq6,Rr12), (Rp8,Rq6,Rr13), (Rp8,Rq6,Rr14), (Rp8,Rq6,Rr15), (Rp8,Rq6,Rr16), (Rp8,Rq6,Rr17), (Rp8, Rq6,Rr18), (Rp8,Rq6,Rr19), (Rp8,Rq6,Rr20), (Rp8,Rq6, Rr21), (Rp8,Rq6, Rr22), (Rp8,Rq7,Rr1), (Rp8,Rq7,Rr2), (Rp8,Rq7,Rr3), (Rp8,Rq7,Rr4), (Rp8,Rq7,Rr5), (Rp8, Rq7, Rr6), (Rp8,Rq7,Rr7), (Rp8,Rq7,Rr8), (Rp8,Rq7,Rr9), (Rp8, Rq7,Rr10), (Rp8,Rq7,Rr11), (Rp8,Rq7,Rr12), (Rp8,Rq7, Rr13), (Rp8,Rq7,Rr14), (Rp8,Rq7,Rr15), (Rp8,Rq7,Rr16), (Rp8,Rq7,Rr17), (Rp8,Rq7,Rr18), (Rp8,Rq7,Rr19), (Rp8, Rq7,Rr20), (Rp8,Rq7,Rr21), (Rp8,Rq7, Rr22), (Rp8,Rq8, Rr1), (Rp8,Rq8,Rr2), (Rp8,Rq8,Rr3), (Rp8,Rq8,Rr4), (Rp8, Rq8,Rr5), (Rp8, Rq8,Rr6), (Rp8,Rq8,Rr7), (Rp8,Rq8,Rr8), (Rp8,Rq8,Rr9), (Rp8,Rq8,Rr10), (Rp8,Rq8,Rr11), (Rp8, Rq8,Rr12), (Rp8,Rq8,Rr13), (Rp8,Rq8,Rr14), (Rp8,Rq8, Rr15), (Rp8,Rq8,Rr16), (Rp8,Rq8,Rr17), (Rp8,Rq8,Rr18), (Rp8,Rq8,Rr19), (Rp8,Rq8,Rr20), (Rp8,Rq8,Rr21), (Rp8, Rq8, Rr22), (Rp8,Rq9,Rr1), (Rp8,Rq9,Rr2), (Rp8,Rq9,Rr3), (Rp8,Rq9,Rr4), (Rp8,Rq9,Rr5), (Rp8, Rq9,Rr6), (Rp8,Rq9, Rr7), (Rp8,Rq9,Rr8), (Rp8,Rq9,Rr9), (Rp8,Rq9,Rr10), (Rp8,Rq9,Rr11), (Rp8,Rq9,Rr12), (Rp8,Rq9,Rr13), (Rp8, Rq9,Rr14), (Rp8,Rq9,Rr15), (Rp8,Rq9,Rr16), (Rp8, Rq9, Rr17), (Rp8,Rq9,Rr18), (Rp8,Rq9,Rr19), (Rp8,Rq9,Rr20), (Rp8,Rq9,Rr21), (Rp8,Rq9, Rr22), (Rp8,Rq10,Rr1), (Rp8, Rq10,Rr2), (Rp8,Rq10,Rr3), (Rp8,Rq10,Rr4), (Rp8,Rq10, Rr5), (Rp8,Rq10,Rr6), (Rp8,Rq10,Rr7), (Rp8,Rq10,Rr8), (Rp8,Rq10,Rr9), (Rp8,Rq10,Rr10), (Rp8,Rq10,Rr11), (Rp8, Rq10,Rr12), (Rp8,Rq10,Rr13), (Rp8,Rq10,Rr14), (Rp8, Rq10,Rr15), (Rp8,Rq10,Rr16), (Rp8,Rq10,Rr17), (Rp8, Rq10,Rr18), (Rp8,Rq10,Rr19), (Rp8,Rq10,Rr20), (Rp8, Rq10,Rr21), (Rp8,Rq10,Rr22), (Rp8,Rq11,Rr1), (Rp8, Rq11,Rr2), (Rp8,Rq11,Rr3), (Rp8,Rq11,Rr4), (Rp8,Rq11, Rr5), (Rp8,Rq11,Rr6), (Rp8,Rq11,Rr7), (Rp8,Rq11,Rr8), (Rp8,Rq11,Rr9), (Rp8,Rq11,Rr10), (Rp8,Rq11,Rr11), (Rp8, Rq11,Rr12), (Rp8,Rq11,Rr13), (Rp8,Rq11,Rr14), (Rp8, Rq11,Rr15), (Rp8,Rq11,Rr16), (Rp8,Rq11,Rr17), (Rp8, Rq11,Rr18), (Rp8,Rq11,Rr19), (Rp8,Rq11,Rr20), (Rp8, Rq11,Rr21), (Rp8,Rq11,Rr22), (Rp8,Rq12,Rr1), (Rp8, Rq12,Rr2), (Rp8,Rq12,Rr3), (Rp8,Rq12,Rr4), (Rp8,Rq12, Rr5), (Rp8,Rq12,Rr6), (Rp8,Rq12,Rr7), (Rp8,Rq12,Rr8), (Rp8,Rq12,Rr9), (Rp8,Rq12,Rr10), (Rp8,Rq12,Rr11), (Rp8, Rq12,Rr12), (Rp8,Rq12,Rr13), (Rp8,Rq12,Rr14), (Rp8, Rq12,Rr15), (Rp8,Rq12,Rr16), (Rp8,Rq12,Rr17), (Rp8, Rq12,Rr18), (Rp8,Rq12,Rr19), (Rp8,Rq12,Rr20), (Rp8, Rq12,Rr21), (Rp8,Rq12,Rr22), (Rp9,Rq1,Rr1), (Rp9,Rq1, Rr2), (Rp9,Rq1,Rr3), (Rp9,Rq1,Rr4), (Rp9,Rq1,Rr5), (Rp9, Rq1,Rr6), (Rp9,Rq1,Rr7), (Rp9,Rq1,Rr8), (Rp9,Rq1,Rr9), (Rp9,Rq1,Rr10), (Rp9,Rq1,Rr11), (Rp9,Rq1,Rr12), (Rp9, Rq1,Rr13), (Rp9,Rq1,Rr14), (Rp9,Rq1,Rr15), (Rp9,Rq1, Rr16), (Rp9,Rq1,Rr17), (Rp9,Rq1,Rr18), (Rp9,Rq1,Rr19), (Rp9,Rq1,Rr20), (Rp9,Rq1,Rr21), (Rp9,Rq1,Rr22), (Rp9, Rq2,Rr1), (Rp9,Rq2,Rr2), (Rp9,Rq2,Rr3), (Rp9,Rq2,Rr4), (Rp9,Rq2,Rr5), (Rp9,Rq2,Rr6), (Rp9,Rq2,Rr7), (Rp9,Rq2, Rr8), (Rp9,Rq2,Rr9), (Rp9,Rq2,Rr10), (Rp9,Rq2,Rr11), (Rp9,Rq2,Rr12), (Rp9,Rq2,Rr13), (Rp9,Rq2,Rr14), (Rp9, Rq2,Rr15), (Rp9,Rq2,Rr16), (Rp9, Rq2,Rr17), (Rp9,Rq2, Rr18), (Rp9,Rq2,Rr19), (Rp9,Rq2,Rr20), (Rp9,Rq2,Rr21), (Rp9,Rq2, Rr22), (Rp9,Rq3,Rr1), (Rp9,Rq3,Rr2), (Rp9, Rq3,Rr3), (Rp9,Rq3,Rr4), (Rp9,Rq3,Rr5), (Rp9, Rq3,Rr6), (Rp9,Rq3,Rr7), (Rp9,Rq3,Rr8), (Rp9,Rq3,Rr9), (Rp9,Rq3, Rr10), (Rp9,Rq3,Rr11), (Rp9,Rq3,Rr12), (Rp9,Rq3,Rr13), (Rp9,Rq3,Rr14), (Rp9,Rq3,Rr15), (Rp9,Rq3,Rr16), (Rp9, Rq3,Rr17), (Rp9,Rq3,Rr18), (Rp9,Rq3,Rr19), (Rp9,Rq3, Rr20), (Rp9,Rq3,Rr21), (Rp9,Rq3, Rr22), (Rp9,Rq4,Rr1), (Rp9,Rq4,Rr2), (Rp9,Rq4,Rr3), (Rp9,Rq4,Rr4), (Rp9,Rq4, Rr5), (Rp9,Rq4,Rr6), (Rp9,Rq4,Rr7), (Rp9,Rq4,Rr8), (Rp9, Rq4,Rr9), (Rp9,Rq4,Rr10), (Rp9,Rq4,Rr11), (Rp9,Rq4, Rr12), (Rp9,Rq4,Rr13), (Rp9,Rq4,Rr14), (Rp9,Rq4,Rr15), (Rp9,Rq4,Rr16), (Rp9,Rq4,Rr17), (Rp9,Rq4,Rr18), (Rp9, Rq4,Rr19), (Rp9,Rq4,Rr20), (Rp9,Rq4,Rr21), (Rp9,Rq4, Rr22), (Rp9,Rq5,Rr1), (Rp9,Rq5,Rr2), (Rp9,Rq5,Rr3), (Rp9,Rq5,Rr4), (Rp9,Rq5,Rr5), (Rp9, Rq5,Rr6), (Rp9,Rq5, Rr7), (Rp9,Rq5,Rr8), (Rp9,Rq5,Rr9), (Rp9,Rq5,Rr10), (Rp9,Rq5,Rr11), (Rp9,Rq5,Rr12), (Rp9,Rq5,Rr13), (Rp9, Rq5,Rr14), (Rp9,Rq5,Rr15), (Rp9,Rq5,Rr16), (Rp9,Rq5, Rr17), (Rp9,Rq5,Rr18), (Rp9,Rq5,Rr19), (Rp9,Rq5,Rr20), (Rp9,Rq5,Rr21), (Rp9,Rq5, Rr22), (Rp9,Rq6,Rr1), (Rp9, Rq6,Rr2), (Rp9,Rq6,Rr3), (Rp9,Rq6,Rr4), (Rp9,Rq6,Rr5), (Rp9, Rq6,Rr6), (Rp9,Rq6,Rr7), (Rp9,Rq6,Rr8), (Rp9,Rq6, Rr9), (Rp9,Rq6,Rr10), (Rp9,Rq6,Rr11), (Rp9,Rq6,Rr12), (Rp9,Rq6,Rr13), (Rp9,Rq6,Rr14), (Rp9,Rq6,Rr15), (Rp9, Rq6,Rr16), (Rp9,Rq6,Rr17), (Rp9,Rq6,Rr18), (Rp9,Rq6, Rr19), (Rp9,Rq6,Rr20), (Rp9,Rq6,Rr21), (Rp9,Rq6, Rr22), (Rp9,Rq7,Rr1), (Rp9,Rq7,Rr2), (Rp9,Rq7,Rr3), (Rp9,Rq7, Rr4), (Rp9,Rq7,Rr5), (Rp9, Rq7,Rr6), (Rp9,Rq7,Rr7), (Rp9, Rq7,Rr8), (Rp9,Rq7,Rr9), (Rp9,Rq7,Rr10), (Rp9,Rq7, Rr11), (Rp9,Rq7,Rr12), (Rp9,Rq7,Rr13), (Rp9,Rq7,Rr14), (Rp9,Rq7,Rr15), (Rp9,Rq7,Rr16), (Rp9,Rq7,Rr17), (Rp9, Rq7,Rr18), (Rp9,Rq7,Rr19), (Rp9,Rq7,Rr20), (Rp9,Rq7, Rr21), (Rp9,Rq7, Rr22), (Rp9,Rq8,Rr1), (Rp9,Rq8,Rr2), (Rp9,Rq8,Rr3), (Rp9,Rq8,Rr4), (Rp9,Rq8,Rr5), (Rp9, Rq8, Rr6), (Rp9,Rq8,Rr7), (Rp9,Rq8,Rr8), (Rp9,Rq8,Rr9), (Rp9, Rq8,Rr10), (Rp9,Rq8,Rr11), (Rp9,Rq8,Rr12), (Rp9,Rq8, Rr13), (Rp9,Rq8,Rr14), (Rp9,Rq8,Rr15), (Rp9,Rq8,Rr16), (Rp9,Rq8,Rr17), (Rp9,Rq8,Rr18), (Rp9,Rq8,Rr19), (Rp9, Rq8,Rr20), (Rp9,Rq8,Rr21), (Rp9,Rq8, Rr22), (Rp9,Rq9, Rr1), (Rp9,Rq9,Rr2), (Rp9,Rq9,Rr3), (Rp9,Rq9,Rr4), (Rp9, Rq9,Rr5), (Rp9, Rq9,Rr6), (Rp9,Rq9,Rr7), (Rp9,Rq9,Rr8), (Rp9,Rq9,Rr9), (Rp9,Rq9,Rr10), (Rp9,Rq9,Rr11), (Rp9, Rq9,Rr12), (Rp9,Rq9,Rr13), (Rp9,Rq9,Rr14), (Rp9,Rq9, Rr15), (Rp9,Rq9,Rr16), (Rp9,Rq9,Rr17), (Rp9,Rq9,Rr18), (Rp9,Rq9,Rr19), (Rp9,Rq9,Rr20), (Rp9,Rq9,Rr21), (Rp9, Rq9, Rr22), (Rp9,Rq10,Rr1), (Rp9,Rq10,Rr2), (Rp9,Rq10, Rr3), (Rp9,Rq10,Rr4), (Rp9,Rq10,Rr5), (Rp9,Rq10,Rr6), (Rp9,Rq10,Rr7), (Rp9,Rq10,Rr8), (Rp9,Rq10,Rr9), (Rp9, Rq10,Rr10), (Rp9,Rq10,Rr11), (Rp9,Rq10,Rr12), (Rp9, Rq10,Rr13), (Rp9,Rq10,Rr14), (Rp9,Rq10,Rr15), (Rp9, Rq10,Rr16), (Rp9,Rq10,Rr17), (Rp9,Rq10,Rr18), (Rp9, Rq10,Rr19), (Rp9,Rq10,Rr20), (Rp9,Rq10,Rr21), (Rp9, Rq10,Rr22), (Rp9,Rq11,Rr1), (Rp9,Rq11,Rr2), (Rp9,Rq11, Rr3), (Rp9,Rq11,Rr4), (Rp9,Rq11,Rr5), (Rp9,Rq11,Rr6), (Rp9,Rq11,Rr7), (Rp9,Rq11,Rr8), (Rp9,Rq11,Rr9), (Rp9, Rq11, Rr10), (Rp9,Rq11,Rr11), (Rp9,Rq11,Rr12), (Rp9, Rq11,Rr13), (Rp9,Rq11,Rr14), (Rp9,Rq11,Rr15), (Rp9, Rq11,Rr16), (Rp9,Rq11,Rr17), (Rp9,Rq11, Rr18), (Rp9, Rq11,Rr19), (Rp9,Rq11,Rr20), (Rp9,Rq11,Rr21), (Rp9, Rq11,Rr22), (Rp9,Rq12,Rr1), (Rp9,Rq12,Rr2), (Rp9,Rq12, Rr3), (Rp9,Rq12,Rr4), (Rp9,Rq12,Rr5), (Rp9,Rq12,Rr6), (Rp9,Rq12,Rr7), (Rp9,Rq12,Rr8), (Rp9,Rq12,Rr9), (Rp9, Rq12,Rr10), (Rp9,Rq12,Rr11), (Rp9,Rq12,Rr12), (Rp9, Rq12,Rr13), (Rp9,Rq12,Rr14), (Rp9,Rq12,Rr15), (Rp9, Rq12,Rr16), (Rp9,Rq12,Rr17), (Rp9,Rq12,Rr18), (Rp9, Rq12,Rr19), (Rp9,Rq12,Rr20), (Rp9,Rq12,Rr21), (Rp9, Rq12,Rr22), (Rp10,Rq1,Rr1), (Rp10,Rq1,Rr2), (Rp10,Rq1, Rr3), (Rp10,Rq1,Rr4), (Rp10,Rq1,Rr5), (Rp10,Rq1,Rr6), (Rp10,Rq1,Rr7), (Rp10,Rq1,Rr8), (Rp10,Rq1,Rr9), (Rp10, Rq1,Rr10), (Rp10, Rq1,Rr11), (Rp10,Rq1,Rr12), (Rp10, Rq1,Rr13), (Rp10,Rq1,Rr14), (Rp10,Rq1,Rr15), (Rp10, Rq1,Rr16), (Rp10,Rq1,Rr17), (Rp10,Rq1,Rr18), (Rp10, Rq1,Rr19), (Rp10,Rq1,Rr20), (Rp10,Rq1,Rr21), (Rp10, Rq1,Rr22), (Rp10,Rq2,Rr1), (Rp10,Rq2,Rr2), (Rp10,Rq2, Rr3), (Rp10,Rq2,Rr4), (Rp10,Rq2,Rr5), (Rp10,Rq2,Rr6), (Rp10,Rq2,Rr7), (Rp10,Rq2,Rr8), (Rp10,Rq2,Rr9), (Rp10, Rq2,Rr10), (Rp10,Rq2,Rr11), (Rp10,Rq2,Rr12), (Rp10, Rq2,Rr13), (Rp10,Rq2,Rr14), (Rp10,Rq2,Rr15), (Rp10, Rq2,Rr16), (Rp10,Rq2,Rr17), (Rp10,Rq2,Rr18), (Rp10, Rq2,Rr19), (Rp10,Rq2,Rr20), (Rp10,Rq2,Rr21), (Rp10, Rq2,Rr22), (Rp10,Rq3,Rr1), (Rp10,Rq3,Rr2), (Rp10,Rq3, Rr3), (Rp10,Rq3,Rr4), (Rp10,Rq3,Rr5), (Rp10,Rq3,Rr6), (Rp10,Rq3,Rr7), (Rp10,Rq3,Rr8), (Rp10,Rq3,Rr9), (Rp10, Rq3,Rr10), (Rp10,Rq3,Rr11), (Rp10,Rq3,Rr12), (Rp10, Rq3,Rr13), (Rp10,Rq3,Rr14), (Rp10,Rq3,Rr15), (Rp10, Rq3,Rr16), (Rp10,Rq3,Rr17), (Rp10,Rq3,Rr18), (Rp10, Rq3,Rr19), (Rp10,Rq3,Rr20), (Rp10,Rq3,Rr21), (Rp10, Rq3,Rr22), (Rp10,Rq4,Rr1), (Rp10,Rq4,Rr2), (Rp10,Rq4, Rr3), (Rp10,Rq4,Rr4), (Rp10,Rq4,Rr5), (Rp10,Rq4,Rr6), (Rp10,Rq4,Rr7), (Rp10,Rq4,Rr8), (Rp10,Rq4,Rr9), (Rp10, Rq4,Rr10), (Rp10,Rq4,Rr11), (Rp10,Rq4,Rr12), (Rp10, Rq4,Rr13), (Rp10,Rq4,Rr14), (Rp10,Rq4,Rr15), (Rp10, Rq4,Rr16), (Rp10,Rq4,Rr17), (Rp10,Rq4,Rr18), (Rp10, Rq4,Rr19), (Rp10,Rq4,Rr20), (Rp10,Rq4,Rr21), (Rp10, Rq4,Rr22), (Rp10,Rq5,Rr1), (Rp10,Rq5,Rr2), (Rp10,Rq5, Rr3), (Rp10,Rq5, Rr4), (Rp10,Rq5,Rr5), (Rp10,Rq5,Rr6), (Rp10,Rq5,Rr7), (Rp10,Rq5,Rr8), (Rp10,Rq5,Rr9), (Rp10, Rq5,Rr10), (Rp10,Rq5,Rr11), (Rp10,Rq5,Rr12), (Rp10, Rq5,Rr13), (Rp10,Rq5,Rr14), (Rp10,Rq5,Rr15), (Rp10, Rq5,Rr16), (Rp10,Rq5,Rr17), (Rp10,Rq5,Rr18), (Rp10, Rq5,Rr19), (Rp10,Rq5,Rr20), (Rp10,Rq5,Rr21), (Rp10, Rq5,Rr22), (Rp10,Rq6,Rr1), (Rp10,Rq6,Rr2), (Rp10,Rq6, Rr3), (Rp10,Rq6,Rr4), (Rp10,Rq6,Rr5), (Rp10,Rq6,Rr6), (Rp10,Rq6,Rr7), (Rp10,Rq6,Rr8), (Rp10,Rq6,Rr9), (Rp10, Rq6,Rr10), (Rp10,Rq6,Rr11), (Rp10,Rq6,Rr12), (Rp10, Rq6,Rr13), (Rp10,Rq6,Rr14), (Rp10,Rq6,Rr15), (Rp10, Rq6,Rr16), (Rp10,Rq6,Rr17), (Rp10, Rq6,Rr18), (Rp10, Rq6,Rr19), (Rp10,Rq6,Rr20), (Rp10,Rq6,Rr21), (Rp10, Rq6,Rr22), (Rp10,Rq7,Rr1), (Rp10,Rq7,Rr2), (Rp10,Rq7, Rr3), (Rp10,Rq7,Rr4), (Rp10,Rq7,Rr5), (Rp10,Rq7, Rr6), (Rp10,Rq7,Rr7), (Rp10,Rq7,Rr8), (Rp10,Rq7,Rr9), (Rp10, Rq7,Rr10), (Rp10,Rq7,Rr11), (Rp10,Rq7,Rr12), (Rp10, Rq7,Rr13), (Rp10,Rq7,Rr14), (Rp10,Rq7,Rr15), (Rp10, Rq7,Rr16), (Rp10,Rq7,Rr17), (Rp10,Rq7,Rr18), (Rp10, Rq7,Rr19), (Rp10,Rq7,Rr20), (Rp10,Rq7,Rr21), (Rp10, Rq7,Rr22), (Rp10,Rq8,Rr1), (Rp10,Rq8,Rr2), (Rp10,Rq8, Rr3), (Rp10,Rq8,Rr4), (Rp10,Rq8,Rr5), (Rp10,Rq8,Rr6), (Rp10,Rq8,Rr7), (Rp10,Rq8,Rr8), (Rp10,Rq8,Rr9), (Rp10, Rq8,Rr10), (Rp10,Rq8,Rr11), (Rp10,Rq8,Rr12), (Rp10, Rq8,Rr13), (Rp10,Rq8,Rr14), (Rp10,Rq8,Rr15), (Rp10, Rq8,Rr16), (Rp10,Rq8,Rr17), (Rp10,Rq8,Rr18), (Rp10, Rq8,Rr19), (Rp10,Rq8,Rr20), (Rp10,Rq8,Rr21), (Rp10, Rq8,Rr22), (Rp10,Rq9,Rr1), (Rp10,Rq9,Rr2), (Rp10,Rq9, Rr3), (Rp10,Rq9,Rr4), (Rp10,Rq9,Rr5), (Rp10,Rq9,Rr6), (Rp10,Rq9,Rr7), (Rp10,Rq9,Rr8), (Rp10,Rq9,Rr9), (Rp10, Rq9,Rr10), (Rp10,Rq9,Rr11), (Rp10,Rq9,Rr12), (Rp10, Rq9, Rr13), (Rp10,Rq9,Rr14), (Rp10,Rq9,Rr15), (Rp10, Rq9,Rr16), (Rp10,Rq9,Rr17), (Rp10,Rq9,Rr18), (Rp10, Rq9,Rr19), (Rp10,Rq9,Rr20), (Rp10,Rq9,Rr21), (Rp10, Rq9,Rr22), (Rp10,Rq10,Rr1), (Rp10,Rq10,Rr2), (Rp10, Rq10,Rr3), (Rp10,Rq10,Rr4), (Rp10,Rq10,Rr5), (Rp10, Rq10,Rr6), (Rp10,Rq10,Rr7), (Rp10,Rq10,Rr8), (Rp10, Rq10,Rr9), (Rp10,Rq10,Rr10), (Rp10, Rq10,Rr11), (Rp10, Rq10,Rr12), (Rp10,Rq10,Rr13), (Rp10,Rq10,Rr14), (Rp10, Rq10,Rr15), (Rp10,Rq10,Rr16), (Rp10,Rq10,Rr17), (Rp10, Rq10,Rr18), (Rp10,Rq10,Rr19), (Rp10,Rq10, Rr20), (Rp10, Rq10,Rr21), (Rp10,Rq10,Rr22), (Rp10,Rq11,Rr1), (Rp10, Rq11,Rr2), (Rp10,Rq11,Rr3), (Rp10,Rq11,Rr4), (Rp10, Rq11,Rr5), (Rp10,Rq11,Rr6), (Rp10,Rq11,Rr7), (Rp10, Rq11,Rr8), (Rp10,Rq11,Rr9), (Rp10,Rq11,Rr10), (Rp10, Rq11,Rr11), (Rp10,Rq11,Rr12), (Rp10,Rq11,Rr13), (Rp10, Rq11,Rr14), (Rp10,Rq11,Rr15), (Rp10,Rq11,Rr16), (Rp10, Rq11,Rr17), (Rp10,Rq11,Rr18), (Rp10,Rq11,Rr19), (Rp10, Rq11,Rr20), (Rp10,Rq11,Rr21), (Rp10, Rq11,Rr22), (Rp10, Rq12,Rr1), (Rp10,Rq12,Rr2), (Rp10,Rq12,Rr3), (Rp10, Rq12,Rr4), (Rp10,Rq12,Rr5), (Rp10,Rq12,Rr6), (Rp10, Rq12,Rr7), (Rp10,Rq12,Rr8), (Rp10,Rq12,Rr9), (Rp10, Rq12,Rr10), (Rp10,Rq12,Rr11), (Rp10,Rq12,Rr12), (Rp10, Rq12,Rr13), (Rp10,Rq12,Rr14), (Rp10,Rq12,Rr15), (Rp10, Rq12,Rr16), (Rp10,Rq12,Rr17), (Rp10,Rq12,Rr18), (Rp10, Rq12,Rr19), (Rp10,Rq12,Rr20), (Rp10,Rq12,Rr21), (Rp10, Rq12,Rr22), (Rp11,Rq1,Rr1), (Rp11,Rq1,Rr2), (Rp11,Rq1, Rr3), (Rp11,Rq1,Rr4), (Rp11,Rq1,Rr5), (Rp11,Rq1,Rr6), (Rp11,Rq1,Rr7), (Rp11,Rq1,Rr8), (Rp11,Rq1,Rr9), (Rp11, Rq1,Rr10), (Rp11,Rq1,Rr11), (Rp11,Rq1,Rr12), (Rp11, Rq1,Rr13), (Rp11,Rq1,Rr14), (Rp11,Rq1,Rr15), (Rp11, Rq1,Rr16), (Rp11,Rq1, Rr17), (Rp11,Rq1,Rr18), (Rp11, Rq1,Rr19), (Rp11,Rq1,Rr20), (Rp11,Rq1,Rr21), (Rp11, Rq1,Rr22), (Rp11,Rq2,Rr1), (Rp11,Rq2,Rr2), (Rp11,Rq2, Rr3), (Rp11,Rq2,Rr4), (Rp11,Rq2,Rr5), (Rp11,Rq2,Rr6), (Rp11,Rq2,Rr7), (Rp11,Rq2,Rr8), (Rp11,Rq2,Rr9), (Rp11, Rq2,Rr10), (Rp11,Rq2,Rr11), (Rp11,Rq2,Rr12), (Rp11, Rq2,Rr13), (Rp11,Rq2,Rr14), (Rp11,Rq2,Rr15), (Rp11, Rq2,Rr16), (Rp11,Rq2,Rr17), (Rp11,Rq2,Rr18), (Rp11, Rq2,Rr19), (Rp11,Rq2,Rr20), (Rp11,Rq2,Rr21), (Rp11, Rq2,Rr22), (Rp11,Rq3,Rr1), (Rp11,Rq3,Rr2), (Rp11,Rq3, Rr3), (Rp11,Rq3,Rr4), (Rp11,Rq3,Rr5), (Rp11,Rq3,Rr6), (Rp11,Rq3,Rr7), (Rp11,Rq3,Rr8), (Rp11, Rq3,Rr9), (Rp11, Rq3,Rr10), (Rp11,Rq3,Rr11), (Rp11,Rq3,Rr12), (Rp11, Rq3,Rr13), (Rp11, Rq3,Rr14), (Rp11,Rq3,Rr15), (Rp11, Rq3,Rr16), (Rp11,Rq3,Rr17), (Rp11,Rq3,Rr18), (Rp11, Rq3,Rr19), (Rp11,Rq3,Rr20), (Rp11,Rq3,Rr21), (Rp11, Rq3,Rr22), (Rp11,Rq4,Rr1), (Rp11, Rq4,Rr2), (Rp11,Rq4, Rr3), (Rp11,Rq4,Rr4), (Rp11,Rq4,Rr5), (Rp11,Rq4,Rr6), (Rp11,Rq4, Rr7), (Rp11,Rq4,Rr8), (Rp11,Rq4,Rr9), (Rp11, Rq4,Rr10), (Rp11,Rq4,Rr11), (Rp11,Rq4,Rr12), (Rp11, Rq4,Rr13), (Rp11,Rq4,Rr14), (Rp11,Rq4,Rr15), (Rp11, Rq4,Rr16), (Rp11,Rq4,Rr17), (Rp11,Rq4,Rr18), (Rp11, Rq4,Rr19), (Rp11,Rq4,Rr20), (Rp11,Rq4,Rr21), (Rp11, Rq4, Rr22), (Rp11,Rq5,Rr1), (Rp11,Rq5,Rr2), (Rp11,Rq5, Rr3), (Rp11,Rq5,Rr4), (Rp11,Rq5,Rr5), (Rp11,Rq5,Rr6), (Rp11,Rq5,Rr7), (Rp11,Rq5,Rr8), (Rp11,Rq5,Rr9), (Rp11, Rq5,Rr10), (Rp11,Rq5,Rr11), (Rp11,Rq5,Rr12), (Rp11, Rq5,Rr13), (Rp11,Rq5,Rr14), (Rp11,Rq5,Rr15), (Rp11, Rq5,Rr16), (Rp11,Rq5,Rr17), (Rp11,Rq5,Rr18), (Rp11, Rq5,Rr19), (Rp11,Rq5,Rr20), (Rp11,Rq5,Rr21), (Rp11, Rq5,Rr22), (Rp11,Rq6,Rr1), (Rp11,Rq6,Rr2), (Rp11,Rq6, Rr3), (Rp11,Rq6,Rr4), (Rp11,Rq6,Rr5), (Rp11,Rq6,Rr6), (Rp11,Rq6,Rr7), (Rp11,Rq6,Rr8), (Rp11,Rq6,Rr9), (Rp11, Rq6,Rr10), (Rp11,Rq6,Rr11), (Rp11,Rq6,Rr12), (Rp11, Rq6,Rr13), (Rp11,Rq6,Rr14), (Rp11,Rq6,Rr15), (Rp11, Rq6,Rr16), (Rp11,Rq6,Rr17), (Rp11,Rq6,Rr18), (Rp11, Rq6,Rr19), (Rp11,Rq6,Rr20), (Rp11,Rq6,Rr21), (Rp11, Rq6,Rr22), (Rp11,Rq7,Rr1), (Rp11,Rq7,Rr2), (Rp11,Rq7, Rr3), (Rp11,Rq7,Rr4), (Rp11,Rq7,Rr5), (Rp11,Rq7,Rr6), (Rp11,Rq7,Rr7), (Rp11,Rq7,Rr8), (Rp11,Rq7,Rr9), (Rp11, Rq7,Rr10), (Rp11,Rq7,Rr11), (Rp11,Rq7,Rr12), (Rp11, Rq7,Rr13), (Rp11,Rq7,Rr14), (Rp11,Rq7,Rr15), (Rp11, Rq7,Rr16), (Rp11,Rq7,Rr17), (Rp11,Rq7,Rr18), (Rp11, Rq7,Rr19), (Rp11,Rq7,Rr20), (Rp11,Rq7,Rr21), (Rp11, Rq7,Rr22), (Rp11,Rq8,Rr1), (Rp11,Rq8,Rr2), (Rp11,Rq8, Rr3), (Rp11,Rq8,Rr4), (Rp11,Rq8,Rr5), (Rp11,Rq8,Rr6), (Rp11,Rq8,Rr7), (Rp11,Rq8,Rr8), (Rp11,Rq8,Rr9), (Rp11, Rq8,Rr10), (Rp11, Rq8,Rr11), (Rp11,Rq8,Rr12), (Rp11, Rq8,Rr13), (Rp11,Rq8,Rr14), (Rp11,Rq8,Rr15), (Rp11, Rq8,Rr16), (Rp11,Rq8,Rr17), (Rp11,Rq8,Rr18), (Rp11, Rq8,Rr19), (Rp11,Rq8,Rr20), (Rp11,Rq8,Rr21), (Rp11, Rq8,Rr22), (Rp11,Rq9,Rr1), (Rp11,Rq9,Rr2), (Rp11,Rq9, Rr3), (Rp11,Rq9,Rr4), (Rp11,Rq9,Rr5), (Rp11,Rq9,Rr6), (Rp11,Rq9,Rr7), (Rp11,Rq9,Rr8), (Rp11,Rq9,Rr9), (Rp11, Rq9,Rr10), (Rp11,Rq9,Rr11), (Rp11,Rq9,Rr12), (Rp11, Rq9,Rr13), (Rp11,Rq9,Rr14), (Rp11,Rq9,Rr15), (Rp11, Rq9,Rr16), (Rp11,Rq9,Rr17), (Rp11,Rq9,Rr18), (Rp11, Rq9,Rr19), (Rp11,Rq9,Rr20), (Rp11,Rq9,Rr21), (Rp11, Rq9,Rr22), (Rp11,Rq10,Rr1), (Rp11,Rq10, Rr2), (Rp11, Rq10,Rr3), (Rp11,Rq10,Rr4), (Rp11,Rq10,Rr5), (Rp11, Rq10,Rr6), (Rp11,Rq10,Rr7), (Rp11,Rq10,Rr8), (Rp11, Rq10,Rr9), (Rp11,Rq10,Rr10), (Rp11,Rq10,Rr11), (Rp11, Rq10,Rr12), (Rp11,Rq10,Rr13), (Rp11,Rq10,Rr14), (Rp11, Rq10,Rr15), (Rp11,Rq10,Rr16), (Rp11,Rq10,Rr17), (Rp11, Rq10,Rr18), (Rp11,Rq10,Rr19), (Rp11,Rq10,Rr20), (Rp11, Rq10, Rr21), (Rp11,Rq10,Rr22), (Rp11,Rq11,Rr1), (Rp11, Rq11,Rr2), (Rp11,Rq11,Rr3), (Rp11,Rq11,Rr4), (Rp11, Rq11,Rr5), (Rp11,Rq11,Rr6), (Rp11,Rq11,Rr7), (Rp11, Rq11,Rr8), (Rp11,Rq11,Rr9), (Rp11,Rq11,Rr10), (Rp11, Rq11,Rr11), (Rp11,Rq11,Rr12), (Rp11,Rq11,Rr13), (Rp11, Rq11,Rr14), (Rp11,Rq11,Rr15), (Rp11,Rq11,Rr16), (Rp11, Rq11,Rr17), (Rp11,Rq11,Rr18), (Rp11,Rq11,Rr19), (Rp11, Rq11,Rr20), (Rp11,Rq11,Rr21), (Rp11,Rq11,Rr22), (Rp11, Rq12,Rr1), (Rp11,Rq12,Rr2), (Rp11,Rq12,Rr3), (Rp11, Rq12,Rr4), (Rp11,Rq12,Rr5), (Rp11,Rq12,Rr6), (Rp11, Rq12,Rr7), (Rp11,Rq12,Rr8), (Rp11,Rq12,Rr9), (Rp11, Rq12,Rr10), (Rp11,Rq12,Rr11), (Rp11,Rq12,Rr12), (Rp11, Rq12,Rr13), (Rp11,Rq12,Rr14), (Rp11,Rq12,Rr15), (Rp11, Rq12,Rr16), (Rp11,Rq12,Rr17), (Rp11,Rq12,Rr18), (Rp11, Rq12,Rr19), (Rp11,Rq12,Rr20), (Rp11,Rq12,Rr21), (Rp11, Rq12,Rr22), (Rp12,Rq1,Rr1), (Rp12,Rq1,Rr2), (Rp12, Rq1, Rr3), (Rp12,Rq1,Rr4), (Rp12,Rq1,Rr5), (Rp12,Rq1,Rr6), (Rp12,Rq1,Rr7), (Rp12,Rq1,Rr8), (Rp12,Rq1,Rr9), (Rp12, Rq1,Rr10), (Rp12,Rq1,Rr11), (Rp12,Rq1,Rr12), (Rp12, Rq1,Rr13), (Rp12,Rq1,Rr14), (Rp12,Rq1,Rr15), (Rp12, Rq1,Rr16), (Rp12,Rq1,Rr17), (Rp12,Rq1,Rr18), (Rp12, Rq1,Rr19), (Rp12,Rq1,Rr20), (Rp12,Rq1,Rr21), (Rp12, Rq1,Rr22), (Rp12,Rq2,Rr1), (Rp12,Rq2,Rr2), (Rp12,Rq2, Rr3), (Rp12,Rq2,Rr4), (Rp12,Rq2,Rr5), (Rp12,Rq2,Rr6), (Rp12,Rq2,Rr7), (Rp12,Rq2,Rr8), (Rp12,Rq2,Rr9), (Rp12, Rq2,Rr10), (Rp12,Rq2,Rr11), (Rp12,Rq2,Rr12), (Rp12, Rq2,Rr13), (Rp12,Rq2,Rr14), (Rp12,Rq2,Rr15), (Rp12, Rq2,Rr16), (Rp12,Rq2,Rr17), (Rp12,Rq2,Rr18), (Rp12, Rq2,Rr19), (Rp12,Rq2,Rr20), (Rp12,Rq2,Rr21), (Rp12, Rq2,Rr22), (Rp12,Rq3,Rr1), (Rp12,Rq3,Rr2), (Rp12,Rq3,

Rr3), (Rp12,Rq3,Rr4), (Rp12,Rq3,Rr5), (Rp12,Rq3,Rr6), (Rp12,Rq3,Rr7), (Rp12,Rq3,Rr8), (Rp12,Rq3,Rr9), (Rp12, Rq3,Rr10), (Rp12,Rq3,Rr11), (Rp12,Rq3,Rr12), (Rp12, Rq3,Rr13), (Rp12,Rq3,Rr14), (Rp12,Rq3,Rr15), (Rp12, Rq3,Rr16), (Rp12,Rq3,Rr17), (Rp12,Rq3,Rr18), (Rp12, Rq3,Rr19), (Rp12, Rq3,Rr20), (Rp12,Rq3,Rr21), (Rp12, Rq3,Rr22), (Rp12,Rq4,Rr1), (Rp12,Rq4,Rr2), (Rp12,Rq4, Rr3), (Rp12,Rq4,Rr4), (Rp12,Rq4,Rr5), (Rp12,Rq4,Rr6), (Rp12,Rq4,Rr7), (Rp12,Rq4,Rr8), (Rp12,Rq4,Rr9), (Rp12, Rq4,Rr10), (Rp12,Rq4,Rr11), (Rp12,Rq4,Rr12), (Rp12, Rq4,Rr13), (Rp12,Rq4,Rr14), (Rp12,Rq4,Rr15), (Rp12, Rq4,Rr16), (Rp12,Rq4,Rr17), (Rp12,Rq4,Rr18), (Rp12, Rq4,Rr19), (Rp12,Rq4,Rr20), (Rp12,Rq4,Rr21), (Rp12, Rq4,Rr22), (Rp12,Rq5,Rr1), (Rp12,Rq5,Rr2), (Rp12,Rq5, Rr3), (Rp12,Rq5,Rr4), (Rp12,Rq5,Rr5), (Rp12,Rq5,Rr6), (Rp12,Rq5,Rr7), (Rp12,Rq5,Rr8), (Rp12,Rq5,Rr9), (Rp12, Rq5,Rr10), (Rp12,Rq5,Rr11), (Rp12,Rq5,Rr12), (Rp12, Rq5,Rr13), (Rp12,Rq5,Rr14), (Rp12,Rq5,Rr15), (Rp12, Rq5,Rr16), (Rp12,Rq5,Rr17), (Rp12,Rq5,Rr18), (Rp12, Rq5,Rr19), (Rp12,Rq5,Rr20), (Rp12,Rq5,Rr21), (Rp12, Rq5,Rr22), (Rp12,Rq6,Rr1), (Rp12,Rq6,Rr2), (Rp12,Rq6, Rr3), (Rp12,Rq6,Rr4), (Rp12,Rq6,Rr5), (Rp12,Rq6,Rr6), (Rp12,Rq6,Rr7), (Rp12,Rq6,Rr8), (Rp12,Rq6,Rr9), (Rp12, Rq6,Rr10), (Rp12,Rq6,Rr11), (Rp12,Rq6,Rr12), (Rp12, Rq6,Rr13), (Rp12,Rq6,Rr14), (Rp12,Rq6,Rr15), (Rp12, Rq6,Rr16), (Rp12,Rq6,Rr17), (Rp12,Rq6,Rr18), (Rp12, Rq6,Rr19), (Rp12,Rq6,Rr20), (Rp12,Rq6,Rr21), (Rp12, Rq6,Rr22), (Rp12,Rq7,Rr1), (Rp12,Rq7,Rr2), (Rp12,Rq7, Rr3), (Rp12,Rq7,Rr4), (Rp12,Rq7,Rr5), (Rp12,Rq7,Rr6), (Rp12,Rq7,Rr7), (Rp12,Rq7,Rr8), (Rp12,Rq7,Rr9), (Rp12, Rq7,Rr10), (Rp12,Rq7,Rr11), (Rp12,Rq7,Rr12), (Rp12, Rq7,Rr13), (Rp12,Rq7,Rr14), (Rp12,Rq7,Rr15), (Rp12, Rq7,Rr16), (Rp12,Rq7,Rr17), (Rp12,Rq7,Rr18), (Rp12, Rq7,Rr19), (Rp12,Rq7,Rr20), (Rp12,Rq7,Rr21), (Rp12, Rq7,Rr22), (Rp12,Rq8,Rr1), (Rp12,Rq8,Rr2), (Rp12,Rq8, Rr3), (Rp12,Rq8,Rr4), (Rp12,Rq8,Rr5), (Rp12,Rq8,Rr6), (Rp12,Rq8,Rr7), (Rp12,Rq8,Rr8), (Rp12,Rq8,Rr9), (Rp12, Rq8,Rr10), (Rp12,Rq8,Rr11), (Rp12,Rq8,Rr12), (Rp12, Rq8,Rr13), (Rp12,Rq8,Rr14), (Rp12,Rq8,Rr15), (Rp12, Rq8,Rr16), (Rp12, Rq8,Rr17), (Rp12,Rq8,Rr18), (Rp12, Rq8,Rr19), (Rp12,Rq8,Rr20), (Rp12,Rq8,Rr21), (Rp12, Rq8,Rr22), (Rp12,Rq9,Rr1), (Rp12,Rq9,Rr2), (Rp12,Rq9, Rr3), (Rp12,Rq9,Rr4), (Rp12,Rq9,Rr5), (Rp12,Rq9,Rr6), (Rp12,Rq9,Rr7), (Rp12,Rq9,Rr8), (Rp12,Rq9,Rr9), (Rp12, Rq9,Rr10), (Rp12,Rq9,Rr11), (Rp12,Rq9,Rr12), (Rp12, Rq9,Rr13), (Rp12,Rq9,Rr14), (Rp12,Rq9,Rr15), (Rp12, Rq9,Rr16), (Rp12,Rq9,Rr17), (Rp12,Rq9,Rr18), (Rp12, Rq9,Rr19), (Rp12,Rq9,Rr20), (Rp12,Rq9,Rr21), (Rp12, Rq9,Rr22), (Rp12,Rq10,Rr1), (Rp12,Rq10,Rr2), (Rp12, Rq10, Rr3), (Rp12,Rq10,Rr4), (Rp12,Rq10,Rr5), (Rp12, Rq10,Rr6), (Rp12,Rq10,Rr7), (Rp12,Rq10,Rr8), (Rp12, Rq10,Rr9), (Rp12,Rq10,Rr10), (Rp12,Rq10,Rr11), (Rp12, Rq10,Rr12), (Rp12, Rq10,Rr13), (Rp12,Rq10,Rr14), (Rp12, Rq10,Rr15), (Rp12,Rq10,Rr16), (Rp12,Rq10,Rr17), (Rp12, Rq10,Rr18), (Rp12,Rq10,Rr19), (Rp12,Rq10,Rr20), (Rp12, Rq10,Rr21), (Rp12,Rq10, Rr22), (Rp12,Rq11,Rr1), (Rp12, Rq11,Rr2), (Rp12,Rq11,Rr3), (Rp12,Rq11,Rr4), (Rp12, Rq11,Rr5), (Rp12,Rq11,Rr6), (Rp12,Rq11,Rr7), (Rp12, Rq11,Rr8), (Rp12,Rq11,Rr9), (Rp12,Rq11,Rr10), (Rp12, Rq11,Rr11), (Rp12,Rq11,Rr12), (Rp12,Rq11,Rr13), (Rp12, Rq11,Rr14), (Rp12,Rq11,Rr15), (Rp12,Rq11,Rr16), (Rp12, Rq11,Rr17), (Rp12,Rq11,Rr18), (Rp12,Rq11,Rr19), (Rp12, Rq11,Rr20), (Rp12,Rq11,Rr21), (Rp12,Rq11,Rr22), (Rp12, Rq12,Rr1), (Rp12,Rq12,Rr2), (Rp12,Rq12,Rr3), (Rp12, Rq12,Rr4), (Rp12,Rq12,Rr5), (Rp12,Rq12,Rr6), (Rp12, Rq12,Rr7), (Rp12,Rq12,Rr8), (Rp12,Rq12,Rr9), (Rp12, Rq12,Rr10), (Rp12,Rq12,Rr11), (Rp12,Rq12,Rr12), (Rp12, Rq12,Rr13), (Rp12,Rq12,Rr14), (Rp12,Rq12,Rr15), (Rp12, Rq12,Rr16), (Rp12,Rq12,Rr17), (Rp12,Rq12,Rr18), (Rp12, Rq12,Rr19), (Rp12,Rq12,Rr20), (Rp12,Rq12,Rr21), (Rp12, Rq12,Rr22), (Rp13,Rq1,Rr1), (Rp13,Rq1,Rr2), (Rp13,Rq1, Rr3), (Rp13,Rq1,Rr4), (Rp13,Rq1,Rr5), (Rp13,Rq1,Rr6), (Rp13,Rq1,Rr7), (Rp13,Rq1,Rr8), (Rp13,Rq1,Rr9), (Rp13, Rq1,Rr10), (Rp13,Rq1,Rr11), (Rp13,Rq1,Rr12), (Rp13, Rq1,Rr13), (Rp13,Rq1,Rr14), (Rp13,Rq1,Rr15), (Rp13, Rq1,Rr16), (Rp13,Rq1,Rr17), (Rp13,Rq1,Rr18), (Rp13, Rq1,Rr19), (Rp13,Rq1,Rr20), (Rp13,Rq1,Rr21), (Rp13, Rq1,Rr22), (Rp13,Rq2,Rr1), (Rp13,Rq2,Rr2), (Rp13,Rq2, Rr3), (Rp13,Rq2,Rr4), (Rp13,Rq2,Rr5), (Rp13,Rq2,Rr6), (Rp13,Rq2,Rr7), (Rp13,Rq2,Rr8), (Rp13,Rq2,Rr9), (Rp13, Rq2,Rr10), (Rp13,Rq2,Rr11), (Rp13,Rq2,Rr12), (Rp13, Rq2,Rr13), (Rp13,Rq2,Rr14), (Rp13,Rq2,Rr15), (Rp13, Rq2,Rr16), (Rp13,Rq2,Rr17), (Rp13,Rq2,Rr18), (Rp13, Rq2,Rr19), (Rp13,Rq2,Rr20), (Rp13,Rq2,Rr21), (Rp13, Rq2,Rr22), (Rp13,Rq3,Rr1), (Rp13,Rq3,Rr2), (Rp13,Rq3, Rr3), (Rp13,Rq3,Rr4), (Rp13,Rq3,Rr5), (Rp13,Rq3,Rr6), (Rp13,Rq3,Rr7), (Rp13,Rq3,Rr8), (Rp13,Rq3,Rr9), (Rp13, Rq3,Rr10), (Rp13,Rq3,Rr11), (Rp13,Rq3,Rr12), (Rp13, Rq3,Rr13), (Rp13,Rq3,Rr14), (Rp13,Rq3,Rr15), (Rp13, Rq3,Rr16), (Rp13,Rq3,Rr17), (Rp13,Rq3,Rr18), (Rp13, Rq3,Rr19), (Rp13,Rq3,Rr20), (Rp13,Rq3,Rr21), (Rp13, Rq3,Rr22), (Rp13,Rq4,Rr1), (Rp13,Rq4,Rr2), (Rp13,Rq4, Rr3), (Rp13,Rq4, Rr4), (Rp13,Rq4,Rr5), (Rp13,Rq4,Rr6), (Rp13,Rq4,Rr7), (Rp13,Rq4,Rr8), (Rp13,Rq4,Rr9), (Rp13, Rq4,Rr10), (Rp13,Rq4,Rr11), (Rp13,Rq4,Rr12), (Rp13, Rq4,Rr13), (Rp13,Rq4,Rr14), (Rp13,Rq4,Rr15), (Rp13, Rq4,Rr16), (Rp13,Rq4,Rr17), (Rp13,Rq4,Rr18), (Rp13, Rq4,Rr19), (Rp13,Rq4,Rr20), (Rp13,Rq4,Rr21), (Rp13, Rq4,Rr22), (Rp13,Rq5,Rr1), (Rp13,Rq5,Rr2), (Rp13,Rq5, Rr3), (Rp13,Rq5,Rr4), (Rp13,Rq5,Rr5), (Rp13,Rq5,Rr6), (Rp13,Rq5,Rr7), (Rp13,Rq5,Rr8), (Rp13,Rq5,Rr9), (Rp13, Rq5,Rr10), (Rp13,Rq5,Rr11), (Rp13,Rq5,Rr12), (Rp13, Rq5,Rr13), (Rp13,Rq5,Rr14), (Rp13,Rq5,Rr15), (Rp13, Rq5,Rr16), (Rp13,Rq5,Rr17), (Rp13, Rq5,Rr18), (Rp13, Rq5,Rr19), (Rp13,Rq5,Rr20), (Rp13,Rq5,Rr21), (Rp13, Rq5,Rr22), (Rp13,Rq6,Rr1), (Rp13,Rq6,Rr2), (Rp13,Rq6, Rr3), (Rp13,Rq6,Rr4), (Rp13,Rq6,Rr5), (Rp13,Rq6, Rr6), (Rp13,Rq6,Rr7), (Rp13,Rq6,Rr8), (Rp13,Rq6,Rr9), (Rp13, Rq6,Rr10), (Rp13,Rq6,Rr11), (Rp13,Rq6,Rr12), (Rp13, Rq6,Rr13), (Rp13,Rq6,Rr14), (Rp13,Rq6,Rr15), (Rp13, Rq6,Rr16), (Rp13,Rq6,Rr17), (Rp13,Rq6,Rr18), (Rp13, Rq6,Rr19), (Rp13,Rq6,Rr20), (Rp13,Rq6,Rr21), (Rp13, Rq6,Rr22), (Rp13,Rq7,Rr1), (Rp13,Rq7,Rr2), (Rp13,Rq7, Rr3), (Rp13,Rq7,Rr4), (Rp13,Rq7,Rr5), (Rp13,Rq7,Rr6), (Rp13,Rq7,Rr7), (Rp13,Rq7,Rr8), (Rp13,Rq7,Rr9), (Rp13, Rq7,Rr10), (Rp13,Rq7,Rr11), (Rp13,Rq7,Rr12), (Rp13, Rq7,Rr13), (Rp13,Rq7,Rr14), (Rp13,Rq7,Rr15), (Rp13, Rq7,Rr16), (Rp13,Rq7,Rr17), (Rp13,Rq7,Rr18), (Rp13, Rq7,Rr19), (Rp13,Rq7,Rr20), (Rp13,Rq7,Rr21), (Rp13, Rq7,Rr22), (Rp13,Rq8,Rr1), (Rp13,Rq8,Rr2), (Rp13,Rq8, Rr3), (Rp13,Rq8,Rr4), (Rp13,Rq8,Rr5), (Rp13,Rq8,Rr6), (Rp13,Rq8,Rr7), (Rp13,Rq8,Rr8), (Rp13,Rq8,Rr9), (Rp13, Rq8,Rr10), (Rp13,Rq8,Rr11), (Rp13,Rq8,Rr12), (Rp13, Rq8, Rr13), (Rp13,Rq8,Rr14), (Rp13,Rq8,Rr15), (Rp13, Rq8,Rr16), (Rp13,Rq8,Rr17), (Rp13,Rq8,Rr18), (Rp13, Rq8,Rr19), (Rp13,Rq8,Rr20), (Rp13,Rq8,Rr21), (Rp13, Rq8,Rr22), (Rp13,Rq9,Rr1), (Rp13,Rq9,Rr2), (Rp13,Rq9, Rr3), (Rp13,Rq9,Rr4), (Rp13,Rq9,Rr5), (Rp13,Rq9,Rr6), (Rp13,Rq9,Rr7), (Rp13,Rq9,Rr8), (Rp13,Rq9,Rr9), (Rp13, Rq9,Rr10), (Rp13,Rq9,Rr11), (Rp13,Rq9,Rr12), (Rp13, Rq9,Rr13), (Rp13,Rq9,Rr14), (Rp13,Rq9,Rr15), (Rp13, Rq9,Rr16), (Rp13,Rq9,Rr17), (Rp13,Rq9,Rr18), (Rp13, Rq9,Rr19), (Rp13,Rq9,Rr20), (Rp13,Rq9,Rr21), (Rp13, Rq9,Rr22), (Rp13,Rq10,Rr1), (Rp13,Rq10,Rr2), (Rp13,

Rq10,Rr3), (Rp13,Rq10,Rr4), (Rp13,Rq10,Rr5), (Rp13, Rq10,Rr6), (Rp13,Rq10,Rr7), (Rp13,Rq10,Rr8), (Rp13, Rq10,Rr9), (Rp13,Rq10,Rr10), (Rp13,Rq10,Rr11), (Rp13, Rq10,Rr12), (Rp13,Rq10,Rr13), (Rp13,Rq10,Rr14), (Rp13, Rq10,Rr15), (Rp13,Rq10,Rr16), (Rp13,Rq10,Rr17), (Rp13, Rq10,Rr18), (Rp13,Rq10,Rr19), (Rp13,Rq10,Rr20), (Rp13, Rq10,Rr21), (Rp13,Rq10,Rr22), (Rp13,Rq11,R r1) (Rp13, Rq11,Rr2), (Rp13,Rq11,Rr3), (Rp13,Rq11,Rr4), (Rp13, Rq11,Rr5), (Rp13,Rq11, Rr6), (Rp13,Rq11,Rr7), (Rp13, Rq11,Rr8), (Rp13,Rq11,Rr9), (Rp13,Rq11,Rr10), (Rp13, Rq11,Rr11), (Rp13,Rq11,Rr12), (Rp13,Rq11,Rr13), (Rp13, Rq11,Rr14), (Rp13,Rq11,Rr15), (Rp13,Rq11,Rr16), (Rp13, Rq11,Rr17), (Rp13,Rq11,Rr18), (Rp13,Rq11,Rr19), (Rp13, Rq11,Rr20), (Rp13,Rq11,Rr21), (Rp13,Rq11,Rr22), (Rp13, Rq12,Rr1), (Rp13,Rq12,Rr2), (Rp13,Rq12,Rr3), (Rp13, Rq12,Rr4), (Rp13,Rq12,Rr5), (Rp13,Rq12,Rr6), (Rp13, Rq12,Rr7), (Rp13,Rq12,Rr8), (Rp13,Rq12,Rr9), (Rp13, Rq12,Rr10), (Rp13,Rq12,Rr11), (Rp13,Rq12,Rr12), (Rp13, Rq12,Rr13), (Rp13,Rq12,Rr14), (Rp13,Rq12,Rr15), (Rp13, Rq12,Rr16), (Rp13,Rq12,Rr17), (Rp13,Rq12,Rr18), (Rp13, Rq12,Rr19), (Rp13,Rq12,Rr20), (Rp13,Rq12,Rr21), (Rp13, Rq12,Rr22), (Rp14,Rq1,Rr1), (Rp14,Rq1,Rr2), (Rp14,Rq1, Rr3), (Rp14,Rq1,Rr4), (Rp14,Rq1,Rr5), (Rp14,Rq1,Rr6), (Rp14,Rq1,Rr7), (Rp14,Rq1,Rr8), (Rp14,Rq1,Rr9), (Rp14, Rq1,Rr10), (Rp14,Rq1,Rr11), (Rp14,Rq1,Rr12), (Rp14, Rq1,Rr13), (Rp14,Rq1,Rr14), (Rp14,Rq1,Rr15), (Rp14, Rq1,Rr16), (Rp14,Rq1,Rr17), (Rp14,Rq1,Rr18), (Rp14, Rq1,Rr19), (Rp14,Rq1,Rr20), (Rp14,Rq1,Rr21), (Rp14, Rq1,Rr22), (Rp14,Rq2,Rr1), (Rp14,Rq2,Rr2), (Rp14,Rq2, Rr3), (Rp14,Rq2,Rr4), (Rp14,Rq2,Rr5), (Rp14,Rq2,Rr6), (Rp14,Rq2,Rr7), (Rp14,Rq2,Rr8), (Rp14, Rq2,Rr9), (Rp14, Rq2,Rr10), (Rp14,Rq2,Rr11), (Rp14,Rq2,Rr12), (Rp14, Rq2,Rr13), (Rp14, Rq2,Rr14), (Rp14,Rq2,Rr15), (Rp14, Rq2,Rr16), (Rp14,Rq2,Rr17), (Rp14,Rq2,Rr18), (Rp14, Rq2,Rr19), (Rp14,Rq2,Rr20), (Rp14,Rq2,Rr21), (Rp14, Rq2,Rr22), (Rp14,Rq3,Rr1), (Rp14, Rq3,Rr2), (Rp14,Rq3, Rr3), (Rp14,Rq3,Rr4), (Rp14,Rq3,Rr5), (Rp14,Rq3,Rr6), (Rp14,Rq3, Rr7), (Rp14,Rq3,Rr8), (Rp14,Rq3,Rr9), (Rp14, Rq3,Rr10), (Rp14,Rq3,Rr11), (Rp14,Rq3,Rr12), (Rp14, Rq3,Rr13), (Rp14,Rq3,Rr14), (Rp14,Rq3,Rr15), (Rp14, Rq3,Rr16), (Rp14,Rq3,Rr17), (Rp14,Rq3,Rr18), (Rp14, Rq3,Rr19), (Rp14,Rq3,Rr20), (Rp14,Rq3,Rr21), (Rp14, Rq3, Rr22), (Rp14,Rq4,Rr1), (Rp14,Rq4,Rr2), (Rp14,Rq4, Rr3), (Rp14,Rq4,Rr4), (Rp14,Rq4,Rr5), (Rp14,Rq4,Rr6), (Rp14,Rq4,Rr7), (Rp14,Rq4,Rr8), (Rp14,Rq4,Rr9), (Rp14, Rq4,Rr10), (Rp14,Rq4,Rr11), (Rp14,Rq4,Rr12), (Rp14, Rq4,Rr13), (Rp14,Rq4,Rr14), (Rp14,Rq4,Rr15), (Rp14, Rq4,Rr16), (Rp14,Rq4,Rr17), (Rp14,Rq4,Rr18), (Rp14, Rq4,Rr19), (Rp14,Rq4,Rr20), (Rp14,Rq4,Rr21), (Rp14, Rq4,Rr22), (Rp14,Rq5,Rr1), (Rp14,Rq5,Rr2), (Rp14,Rq5, Rr3), (Rp14,Rq5,Rr4), (Rp14,Rq5,Rr5), (Rp14,Rq5,Rr6), (Rp14,Rq5,Rr7), (Rp14,Rq5,Rr8), (Rp14,Rq5,Rr9), (Rp14, Rq5,Rr10), (Rp14,Rq5,Rr11), (Rp14,Rq5,Rr12), (Rp14, Rq5,Rr13), (Rp14,Rq5,Rr14), (Rp14,Rq5,Rr15), (Rp14, Rq5,Rr16), (Rp14,Rq5,Rr17), (Rp14,Rq5,Rr18), (Rp14, Rq5,Rr19), (Rp14,Rq5,Rr20), (Rp14,Rq5,Rr21), (Rp14, Rq5,Rr22), (Rp14,Rq6,Rr1), (Rp14,Rq6,Rr2), (Rp14,Rq6, Rr3), (Rp14,Rq6,Rr4), (Rp14,Rq6,Rr5), (Rp14,Rq6,Rr6), (Rp14,Rq6,Rr7), (Rp14,Rq6,Rr8), (Rp14,Rq6,Rr9), (Rp14, Rq6,Rr10), (Rp14,Rq6,Rr11), (Rp14,Rq6,Rr12), (Rp14, Rq6,Rr13), (Rp14,Rq6,Rr14), (Rp14,Rq6,Rr15), (Rp14, Rq6,Rr16), (Rp14,Rq6,Rr17), (Rp14,Rq6,Rr18), (Rp14, Rq6,Rr19), (Rp14,Rq6,Rr20), (Rp14,Rq6,Rr21), (Rp14, Rq6,Rr22), (Rp14,Rq7,Rr1), (Rp14,Rq7,Rr2), (Rp14,Rq7, Rr3), (Rp14,Rq7,Rr4), (Rp14,Rq7,Rr5), (Rp14,Rq7,Rr6), (Rp14,Rq7,Rr7), (Rp14,Rq7,Rr8), (Rp14,Rq7,Rr9), (Rp14, Rq7,Rr10), (Rp14, Rq7,Rr11), (Rp14,Rq7,Rr12), (Rp14, Rq7,Rr13), (Rp14,Rq7,Rr14), (Rp14,Rq7,Rr15), (Rp14, Rq7,Rr16), (Rp14,Rq7,Rr17), (Rp14,Rq7,Rr18), (Rp14, Rq7,Rr19), (Rp14,Rq7,Rr20), (Rp14,Rq7,Rr21), (Rp14, Rq7,Rr22), (Rp14,Rq8,Rr1), (Rp14,Rq8,Rr2), (Rp14,Rq8, Rr3), (Rp14,Rq8,Rr4), (Rp14,Rq8,Rr5), (Rp14,Rq8,Rr6), (Rp14,Rq8,Rr7), (Rp14,Rq8,Rr8), (Rp14,Rq8,Rr9), (Rp14, Rq8,Rr10), (Rp14,Rq8,Rr11), (Rp14,Rq8,Rr12), (Rp14, Rq8,Rr13), (Rp14,Rq8,Rr14), (Rp14,Rq8,Rr15), (Rp14, Rq8,Rr16), (Rp14,Rq8,Rr17), (Rp14,Rq8,Rr18), (Rp14, Rq8,Rr19), (Rp14,Rq8,Rr20), (Rp14,Rq8,Rr21), (Rp14, Rq8,Rr22), (Rp14,Rq9,Rr1), (Rp14,Rq9,Rr2), (Rp14,Rq9, Rr3), (Rp14,Rq9,Rr4), (Rp14,Rq9,Rr5), (Rp14,Rq9,Rr6), (Rp14,Rq9,Rr7), (Rp14,Rq9,Rr8), (Rp14,Rq9,Rr9), (Rp14, Rq9,Rr10), (Rp14,Rq9,Rr11), (Rp14,Rq9,Rr12), (Rp14, Rq9,Rr13), (Rp14,Rq9,Rr14), (Rp14,Rq9,Rr15), (Rp14, Rq9,Rr16), (Rp14,Rq9,Rr17), (Rp14,Rq9,Rr18), (Rp14, Rq9,Rr19), (Rp14,Rq9,Rr20), (Rp14,Rq9,Rr21), (Rp14, Rq9,Rr22), (Rp14,Rq10,Rr1), (Rp14,Rq10,Rr2), (Rp14, Rq10,Rr3), (Rp14,Rq10,Rr4), (Rp14,Rq10,Rr5), (Rp14, Rq10,Rr6), (Rp14,Rq10,Rr7), (Rp14,Rq10,Rr8), (Rp14, Rq10,Rr9), (Rp14,Rq10,Rr10), (Rp14,Rq10,Rr11), (Rp14, Rq10,Rr12), (Rp14,Rq10,Rr13), (Rp14,Rq10,Rr14), (Rp14, Rq10,Rr15), (Rp14,Rq10,Rr16), (Rp14,Rq10,Rr17), (Rp14, Rq10,Rr18), (Rp14,Rq10,Rr19), (Rp14,Rq10,Rr20), (Rp14, Rq10,Rr21), (Rp14,Rq10,Rr22), (Rp14,Rq11,Rr1), (Rp14, Rq11,Rr2), (Rp14,Rq11,Rr3), (Rp14,Rq11,Rr4), (Rp14, Rq11,Rr5), (Rp14,Rq11,Rr6), (Rp14,Rq11,Rr7), (Rp14, Rq11,Rr8), (Rp14,Rq11,Rr9), (Rp14,Rq11,Rr10), (Rp14, Rq11,Rr11), (Rp14,Rq11, Rr12), (Rp14,Rq11,Rr13), (Rp14, Rq11,Rr14), (Rp14,Rq11,Rr15), (Rp14,Rq11,Rr16), (Rp14, Rq11,Rr17), (Rp14,Rq11,Rr18), (Rp14,Rq11,Rr19), (Rp14, Rq11,Rr20), (Rp14,Rq11,Rr21), (Rp14,Rq11,Rr22), (Rp14, Rq12,Rr1), (Rp14,Rq12,Rr2), (Rp14,Rq12,Rr3), (Rp14, Rq12,Rr4), (Rp14,Rq12,Rr5), (Rp14,Rq12,Rr6), (Rp14, Rq12,Rr7), (Rp14,Rq12,Rr8), (Rp14,Rq12,Rr9), (Rp14, Rq12,Rr10), (Rp14,Rq12,Rr11), (Rp14,Rq12,Rr12), (Rp14, Rq12,Rr13), (Rp14,Rq12,Rr14), (Rp14,Rq12,Rr15), (Rp14, Rq12,Rr16), (Rp14,Rq12,Rr17), (Rp14,Rq12,Rr18), (Rp14, Rq12,Rr19), (Rp14,Rq12,Rr20), (Rp14,Rq12,Rr21), (Rp14, Rq12,Rr22), (Rp15,Rq1,Rr1), (Rp15,Rq1,Rr2), (Rp15,Rq1, Rr3), (Rp15,Rq1,Rr4), (Rp15,Rq1,Rr5), (Rp15,Rq1,Rr6), (Rp15,Rq1,Rr7), (Rp15,Rq1,Rr8), (Rp15,Rq1,Rr9), (Rp15, Rq1,Rr10), (Rp15,Rq1,Rr11), (Rp15,Rq1,Rr12), (Rp15, Rq1,Rr13), (Rp15,Rq1,Rr14), (Rp15,Rq1,Rr15), (Rp15, Rq1,Rr16), (Rp15,Rq1,Rr17), (Rp15,Rq1,Rr18), (Rp15, Rq1,Rr19), (Rp15,Rq1,Rr20), (Rp15,Rq1,Rr21), (Rp15, Rq1,Rr22), (Rp15,Rq2,Rr1), (Rp15,Rq2,Rr2), (Rp15,Rq2, Rr3), (Rp15,Rq2,Rr4), (Rp15,Rq2,Rr5), (Rp15,Rq2,Rr6), (Rp15,Rq2,Rr7), (Rp15,Rq2,Rr8), (Rp15,Rq2,Rr9), (Rp15, Rq2,Rr10), (Rp15,Rq2,Rr11), (Rp15,Rq2,Rr12), (Rp15, Rq2,Rr13), (Rp15,Rq2,Rr14), (Rp15,Rq2,Rr15), (Rp15, Rq2,Rr16), (Rp15,Rq2,Rr17), (Rp15,Rq2,Rr18), (Rp15, Rq2,Rr19), (Rp15,Rq2,Rr20), (Rp15,Rq2,Rr21), (Rp15, Rq2,Rr22), (Rp15,Rq3,Rr1), (Rp15,Rq3,Rr2), (Rp15,Rq3, Rr3), (Rp15,Rq3,Rr4), (Rp15,Rq3,Rr5), (Rp15,Rq3,Rr6), (Rp15,Rq3,Rr7), (Rp15,Rq3,Rr8), (Rp15,Rq3,Rr9), (Rp15, Rq3,Rr10), (Rp15,Rq3,Rr11), (Rp15,Rq3,Rr12), (Rp15, Rq3,Rr13), (Rp15,Rq3,Rr14), (Rp15,Rq3,Rr15), (Rp15, Rq3,Rr16), (Rp15,Rq3,Rr17), (Rp15,Rq3,Rr18), (Rp15, Rq3,Rr19), (Rp15,Rq3,Rr20), (Rp15,Rq3,Rr21), (Rp15, Rq3,Rr22), (Rp15,Rq4,Rr1), (Rp15,Rq4,Rr2), (Rp15,Rq4, Rr3), (Rp15,Rq4,Rr4), (Rp15,Rq4,Rr5), (Rp15,Rq4,Rr6), (Rp15,Rq4,Rr7), (Rp15,Rq4,Rr8), (Rp15,Rq4,Rr9), (Rp15, Rq4,Rr10), (Rp15,Rq4,Rr11), (Rp15,Rq4,Rr12), (Rp15, Rq4,Rr13), (Rp15,Rq4,Rr14), (Rp15,Rq4,Rr15), (Rp15, Rq4,Rr16), (Rp15, Rq4,Rr17), (Rp15,Rq4,Rr18), (Rp15, Rq4,Rr19), (Rp15,Rq4,Rr20), (Rp15,Rq4,Rr21), (Rp15,

Rq4,Rr22), (Rp15,Rq5,Rr1), (Rp15,Rq5,Rr2), (Rp15,Rq5, Rr3), (Rp15,Rq5,Rr4), (Rp15,Rq5,Rr5), (Rp15,Rq5,Rr6), (Rp15,Rq5,Rr7), (Rp15,Rq5,Rr8), (Rp15,Rq5,Rr9), (Rp15, Rq5,Rr10), (Rp15,Rq5,Rr11), (Rp15,Rq5,Rr12), (Rp15, Rq5,Rr13), (Rp15,Rq5,Rr14), (Rp15,Rq5,Rr15), (Rp15, Rq5,Rr16), (Rp15,Rq5,Rr17), (Rp15,Rq5,Rr18), (Rp15, Rq5,Rr19), (Rp15,Rq5,Rr20), (Rp15,Rq5,Rr21), (Rp15, Rq5,Rr22), (Rp15,Rq6,Rr1), (Rp15,Rq6,Rr2), (Rp15,Rq6, Rr3), (Rp15,Rq6,Rr4), (Rp15,Rq6,Rr5), (Rp15,Rq6,Rr6), (Rp15,Rq6,Rr7), (Rp15,Rq6,Rr8), (Rp15,Rq6,Rr9), (Rp15, Rq6,Rr10), (Rp15,Rq6,Rr11), (Rp15,Rq6,Rr12), (Rp15, Rq6,Rr13), (Rp15,Rq6,Rr14), (Rp15,Rq6,Rr15), (Rp15, Rq6,Rr16), (Rp15,Rq6,Rr17), (Rp15,Rq6,Rr18), (Rp15, Rq6,Rr19), (Rp15,Rq6,Rr20), (Rp15,Rq6,Rr21), (Rp15, Rq6,Rr22), (Rp15,Rq7,Rr1), (Rp15,Rq7,Rr2), (Rp15,Rq7, Rr3), (Rp15,Rq7,Rr4), (Rp15,Rq7,Rr5), (Rp15,Rq7,Rr6), (Rp15,Rq7,Rr7), (Rp15,Rq7,Rr8), (Rp15,Rq7,Rr9), (Rp15, Rq7,Rr10), (Rp15,Rq7,Rr11), (Rp15,Rq7,Rr12), (Rp15, Rq7,Rr13), (Rp15,Rq7,Rr14), (Rp15,Rq7,Rr15), (Rp15, Rq7,Rr16), (Rp15,Rq7, Rr17), (Rp15,Rq7,Rr18), (Rp15, Rq7,Rr19), (Rp15,Rq7,Rr20), (Rp15,Rq7,Rr21), (Rp15, Rq7,Rr22), (Rp15,Rq8,Rr1), (Rp15,Rq8,Rr2), (Rp15,Rq8, Rr3), (Rp15,Rq8,Rr4), (Rp15,Rq8,Rr5), (Rp15,Rq8,Rr6), (Rp15,Rq8,Rr7), (Rp15,Rq8,Rr8), (Rp15,Rq8,Rr9), (Rp15, Rq8,Rr10), (Rp15,Rq8,Rr11), (Rp15,Rq8,Rr12), (Rp15, Rq8,Rr13), (Rp15,Rq8,Rr14), (Rp15,Rq8,Rr15), (Rp15, Rq8,Rr16), (Rp15,Rq8,Rr17), (Rp15,Rq8,Rr18), (Rp15, Rq8,Rr19), (Rp15,Rq8,Rr20), (Rp15,Rq8,Rr21), (Rp15, Rq8,Rr22), (Rp15,Rq9,Rr1), (Rp15,Rq9,Rr2), (Rp15,Rq9, Rr3), (Rp15,Rq9,Rr4), (Rp15,Rq9,Rr5), (Rp15,Rq9,Rr6), (Rp15,Rq9,Rr7), (Rp15,Rq9,Rr8), (Rp15, Rq9,Rr9), (Rp15, Rq9,Rr10), (Rp15,Rq9,Rr11), (Rp15,Rq9,Rr12), (Rp15, Rq9,Rr13), (Rp15, Rq9,Rr14), (Rp15,Rq9,Rr15), (Rp15, Rq9,Rr16), (Rp15,Rq9,Rr17), (Rp15,Rq9,Rr18), (Rp15, Rq9,Rr19), (Rp15,Rq9,Rr20), (Rp15,Rq9,Rr21), (Rp15, Rq9,Rr22), (Rp15,Rq10,Rr1), (Rp15,Rq10,Rr2), (Rp15, Rq10,Rr3), (Rp15,Rq10,Rr4), (Rp15,Rq10,Rr5), (Rp15, Rq10,Rr6), (Rp15,Rq10,Rr7), (Rp15,Rq10,Rr8), (Rp15, Rq10,Rr9), (Rp15,Rq10,Rr10), (Rp15,Rq10,Rr11), (Rp15, Rq10,Rr12), (Rp15,Rq10,Rr13), (Rp15,Rq10,Rr14), (Rp15, Rq10,Rr15), (Rp15,Rq10, Rr16), (Rp15,Rq10,Rr17), (Rp15, Rq10,Rr18), (Rp15,Rq10,Rr19), (Rp15,Rq10,Rr20), (Rp15, Rq10,Rr21), (Rp15,Rq10,Rr22), (Rp15,Rq11,Rr1), (Rp15, Rq11,Rr2), (Rp15,Rq11,Rr3), (Rp15,Rq11,Rr4), (Rp15, Rq11,Rr5), (Rp15,Rq11,Rr6), (Rp15,Rq11,Rr7), (Rp15, Rq11,Rr8), (Rp15,Rq11,Rr9), (Rp15,Rq11,Rr10), (Rp15, Rq11,Rr11), (Rp15,Rq11,Rr12), (Rp15,Rq11,Rr13), (Rp15, Rq11,Rr14), (Rp15,Rq11,Rr15), (Rp15,Rq11,Rr16), (Rp15, Rq11,Rr17), (Rp15, Rq11,Rr18), (Rp15,Rq11,Rr19), (Rp15, Rq11,Rr20), (Rp15,Rq11,Rr21), (Rp15,Rq11,Rr22), (Rp15, Rq12,Rr1), (Rp15,Rq12,Rr2), (Rp15,Rq12,Rr3), (Rp15, Rq12,Rr4), (Rp15,Rq12,Rr5), (Rp15,Rq12,Rr6), (Rp15, Rq12,Rr7), (Rp15,Rq12,Rr8), (Rp15,Rq12,Rr9), (Rp15, Rq12,Rr10), (Rp15,Rq12,Rr11), (Rp15,Rq12,Rr12), (Rp15, Rq12,Rr13), (Rp15,Rq12,Rr14), (Rp15,Rq12,Rr15), (Rp15, Rq12,Rr16), (Rp15,Rq12,Rr17), (Rp15,Rq12,Rr18), (Rp15, Rq12,Rr19), (Rp15,Rq12,Rr20), (Rp15,Rq12,Rr21), (Rp15, Rq12,Rr22), (Rp16,Rq1,Rr1), (Rp16,Rq1,Rr2), (Rp16,Rq1, Rr3), (Rp16,Rq1,Rr4), (Rp16,Rq1,Rr5), (Rp16,Rq1,Rr6), (Rp16,Rq1,Rr7), (Rp16,Rq1,Rr8), (Rp16,Rq1,Rr9), (Rp16, Rq1,Rr10), (Rp16,Rq1,Rr11), (Rp16,Rq1,Rr12), (Rp16, Rq1,Rr13), (Rp16,Rq1,Rr14), (Rp16,Rq1,Rr15), (Rp16, Rq1,Rr16), (Rp16,Rq1,Rr17), (Rp16, Rq1,Rr18), (Rp16, Rq1,Rr19), (Rp16,Rq1,Rr20), (Rp16,Rq1,Rr21), (Rp16, Rq1,Rr22), (Rp16,Rq2,Rr1), (Rp16,Rq2,Rr2), (Rp16,Rq2, Rr3), (Rp16,Rq2,Rr4), (Rp16,Rq2,Rr5), (Rp16,Rq2, Rr6), (Rp16,Rq2,Rr7), (Rp16,Rq2,Rr8), (Rp16,Rq2,Rr9), (Rp16, Rq2,Rr10), (Rp16,Rq2,Rr11), (Rp16,Rq2,Rr12), (Rp16, Rq2,Rr13), (Rp16,Rq2,Rr14), (Rp16,Rq2,Rr15), (Rp16, Rq2,Rr16), (Rp16,Rq2,Rr17), (Rp16,Rq2,Rr18), (Rp16, Rq2,Rr19), (Rp16,Rq2,Rr20), (Rp16,Rq2,Rr21), (Rp16, Rq2,Rr22), (Rp16,Rq3,Rr1), (Rp16,Rq3,Rr2), (Rp16,Rq3, Rr3), (Rp16,Rq3,Rr4), (Rp16,Rq3,Rr5), (Rp16,Rq3,Rr6), (Rp16,Rq3,Rr7), (Rp16,Rq3,Rr8), (Rp16,Rq3,Rr9), (Rp16, Rq3,Rr10), (Rp16,Rq3,Rr11), (Rp16,Rq3,Rr12), (Rp16, Rq3,Rr13), (Rp16,Rq3,Rr14), (Rp16,Rq3,Rr15), (Rp16, Rq3,Rr16), (Rp16,Rq3,Rr17), (Rp16,Rq3,Rr18), (Rp16, Rq3,Rr19), (Rp16,Rq3,Rr20), (Rp16,Rq3,Rr21), (Rp16, Rq3,Rr22), (Rp16,Rq4,Rr1), (Rp16,Rq4,Rr2), (Rp16,Rq4, Rr3), (Rp16,Rq4,Rr4), (Rp16,Rq4,Rr5), (Rp16,Rq4,Rr6), (Rp16,Rq4,Rr7), (Rp16,Rq4,Rr8), (Rp16,Rq4,Rr9), (Rp16, Rq4,Rr10), (Rp16,Rq4,Rr11), (Rp16,Rq4,Rr12), (Rp16, Rq4, Rr13), (Rp16,Rq4,Rr14), (Rp16,Rq4,Rr15), (Rp16, Rq4,Rr16), (Rp16,Rq4,Rr17), (Rp16,Rq4,Rr18), (Rp16, Rq4,Rr19), (Rp16,Rq4,Rr20), (Rp16,Rq4,Rr21), (Rp16, Rq4,Rr22), (Rp16,Rq5,Rr1), (Rp16,Rq5,Rr2), (Rp16,Rq5, Rr3), (Rp16,Rq5,Rr4), (Rp16,Rq5,Rr5), (Rp16,Rq5,Rr6), (Rp16,Rq5,Rr7), (Rp16,Rq5,Rr8), (Rp16,Rq5,Rr9), (Rp16, Rq5,Rr10), (Rp16,Rq5,Rr11), (Rp16,Rq5,Rr12), (Rp16, Rq5,Rr13), (Rp16,Rq5,Rr14), (Rp16,Rq5,Rr15), (Rp16, Rq5,Rr16), (Rp16,Rq5,Rr17), (Rp16,Rq5,Rr18), (Rp16, Rq5,Rr19), (Rp16,Rq5,Rr20), (Rp16,Rq5,Rr21), (Rp16, Rq5,Rr22), (Rp16,Rq6,Rr1), (Rp16,Rq6,Rr2), (Rp16,Rq6, Rr3), (Rp16,Rq6,Rr4), (Rp16,Rq6,Rr5), (Rp16,Rq6,Rr6), (Rp16,Rq6,Rr7), (Rp16,Rq6,Rr8), (Rp16,Rq6,Rr9), (Rp16, Rq6,Rr10), (Rp16,Rq6,Rr11), (Rp16,Rq6,Rr12), (Rp16, Rq6,Rr13), (Rp16,Rq6,Rr14), (Rp16,Rq6,Rr15), (Rp16, Rq6,Rr16), (Rp16,Rq6,Rr17), (Rp16,Rq6,Rr18), (Rp16, Rq6,Rr19), (Rp16, Rq6,Rr20), (Rp16,Rq6,Rr21), (Rp16, Rq6,Rr22), (Rp16,Rq7,Rr1), (Rp16,Rq7,Rr2), (Rp16,Rq7, Rr3), (Rp16,Rq7,Rr4), (Rp16,Rq7,Rr5), (Rp16,Rq7,Rr6), (Rp16,Rq7,Rr7), (Rp16,Rq7,Rr8), (Rp16,Rq7,Rr9), (Rp16, Rq7,Rr10), (Rp16,Rq7,Rr11), (Rp16,Rq7,Rr12), (Rp16, Rq7,Rr13), (Rp16,Rq7,Rr14), (Rp16,Rq7,Rr15), (Rp16, Rq7,Rr16), (Rp16,Rq7,Rr17), (Rp16,Rq7,Rr18), (Rp16, Rq7,Rr19), (Rp16,Rq7,Rr20), (Rp16,Rq7,Rr21), (Rp16, Rq7,Rr22), (Rp16,Rq8,Rr1), (Rp16,Rq8,Rr2), (Rp16,Rq8, Rr3), (Rp16,Rq8,Rr4), (Rp16,Rq8,Rr5), (Rp16,Rq8,Rr6), (Rp16,Rq8,Rr7), (Rp16,Rq8,Rr8), (Rp16,Rq8,Rr9), (Rp16, Rq8,Rr10), (Rp16,Rq8,Rr11), (Rp16,Rq8,Rr12), (Rp16, Rq8,Rr13), (Rp16,Rq8,Rr14), (Rp16,Rq8,Rr15), (Rp16, Rq8,Rr16), (Rp16,Rq8,Rr17), (Rp16,Rq8,Rr18), (Rp16, Rq8,Rr19), (Rp16,Rq8,Rr20), (Rp16,Rq8,Rr21), (Rp16, Rq8,Rr22), (Rp16,Rq9,Rr1), (Rp16,Rq9,Rr2), (Rp16,Rq9, Rr3), (Rp16,Rq9,Rr4), (Rp16,Rq9,Rr5), (Rp16,Rq9,Rr6), (Rp16,Rq9,Rr7), (Rp16,Rq9,Rr8), (Rp16,Rq9,Rr9), (Rp16, Rq9,Rr10), (Rp16,Rq9,Rr11), (Rp16,Rq9,Rr12), (Rp16, Rq9,Rr13), (Rp16,Rq9,Rr14), (Rp16,Rq9,Rr15), (Rp16, Rq9,Rr16), (Rp16,Rq9,Rr17), (Rp16,Rq9,Rr18), (Rp16, Rq9,Rr19), (Rp16,Rq9,Rr20), (Rp16,Rq9,Rr21), (Rp16, Rq9,Rr22), (Rp16,Rq10,Rr1), (Rp16,Rq10,Rr2), (Rp16, Rq10,Rr3), (Rp16,Rq10,Rr4), (Rp16,Rq10,Rr5), (Rp16, Rq10,Rr6), (Rp16,Rq10,Rr7), (Rp16,Rq10,Rr8), (Rp16, Rq10,Rr9), (Rp16,Rq10,Rr10), (Rp16,Rq10,Rr11), (Rp16, Rq10,Rr12), (Rp16,Rq10,Rr13), (Rp16,Rq10,Rr14), (Rp16, Rq10,Rr15), (Rp16,Rq10,Rr16), (Rp16,Rq10, Rr17), (Rp16, Rq10,Rr18), (Rp16,Rq10,Rr19), (Rp16,Rq10,Rr20), (Rp16, Rq10,Rr21), (Rp16,Rq10,Rr22), (Rp16,Rq11,Rr1), (Rp16, Rq11,Rr2), (Rp16,Rq11,Rr3), (Rp16,Rq11,Rr4), (Rp16, Rq11,Rr5), (Rp16,Rq11,Rr6), (Rp16,Rq11,Rr7), (Rp16, Rq11,Rr8), (Rp16,Rq11,Rr9), (Rp16,Rq11,Rr10), (Rp16, Rq11,Rr11), (Rp16,Rq11,Rr12), (Rp16,Rq11,Rr13), (Rp16, Rq11,Rr14), (Rp16,Rq11,Rr15), (Rp16,Rq11,Rr16), (Rp16, Rq11,Rr17), (Rp16,Rq11,Rr18), (Rp16, Rq11,Rr19), (Rp16,

Rq11,Rr20), (Rp16,Rq11,Rr21), (Rp16,Rq11,Rr22), (Rp16, Rq12,Rr1), (Rp16,Rq12,Rr2), (Rp16,Rq12,Rr3), (Rp16, Rq12,Rr4), (Rp16,Rq12,Rr5), (Rp16,Rq12,Rr6), (Rp16, Rq12,Rr7), (Rp16,Rq12,Rr8), (Rp16,Rq12,Rr9), (Rp16, Rq12,Rr10), (Rp16,Rq12,Rr11), (Rp16,Rq12,Rr12), (Rp16, Rq12,Rr13), (Rp16,Rq12,Rr14), (Rp16,Rq12,Rr15), (Rp16, Rq12,Rr16), (Rp16,Rq12,Rr17), (Rp16,Rq12,Rr18), (Rp16, Rq12,Rr19), (Rp16,Rq12,Rr20), (Rp16,Rq12,Rr21), (Rp16, Rq12,Rr22), (Rp17,Rq1,Rr1), (Rp17,Rq1,Rr2), (Rp17,Rq1, Rr3), (Rp17,Rq1,Rr4), (Rp17,Rq1,Rr5), (Rp17,Rq1,Rr6), (Rp17,Rq1,Rr7), (Rp17,Rq1,Rr8), (Rp17, Rq1,Rr9), (Rp17, Rq1,Rr10), (Rp17,Rq1,Rr11), (Rp17,Rq1,Rr12), (Rp17, Rq1,Rr13), (Rp17, Rq1,Rr14), (Rp17,Rq1,Rr15), (Rp17, Rq1,Rr16), (Rp17,Rq1,Rr17), (Rp17,Rq1,Rr18), (Rp17, Rq1,Rr19), (Rp17,Rq1,Rr20), (Rp17,Rq1,Rr21), (Rp17, Rq1,Rr22), (Rp17,Rq2,Rr1), (Rp17, Rq2,Rr2), (Rp17,Rq2, Rr3), (Rp17,Rq2,Rr4), (Rp17,Rq2,Rr5), (Rp17,Rq2,Rr6), (Rp17,Rq2, Rr7), (Rp17,Rq2,Rr8), (Rp17,Rq2,Rr9), (Rp17, Rq2,Rr10), (Rp17,Rq2,Rr11), (Rp17,Rq2,Rr12), (Rp17, Rq2,Rr13), (Rp17,Rq2,Rr14), (Rp17,Rq2,Rr15), (Rp17, Rq2,Rr16), (Rp17,Rq2,Rr17), (Rp17,Rq2,Rr18), (Rp17, Rq2,Rr19), (Rp17,Rq2,Rr20), (Rp17,Rq2,Rr21), (Rp17, Rq2, Rr22), (Rp17,Rq3,Rr1), (Rp17,Rq3,Rr2), (Rp17,Rq3, Rr3), (Rp17,Rq3,Rr4), (Rp17,Rq3,Rr5), (Rp17,Rq3,Rr6), (Rp17,Rq3,Rr7), (Rp17,Rq3,Rr8), (Rp17,Rq3,Rr9), (Rp17, Rq3,Rr10), (Rp17,Rq3,Rr11), (Rp17,Rq3,Rr12), (Rp17, Rq3,Rr13), (Rp17,Rq3,Rr14), (Rp17,Rq3,Rr15), (Rp17, Rq3,Rr16), (Rp17,Rq3,Rr17), (Rp17,Rq3,Rr18), (Rp17, Rq3,Rr19), (Rp17,Rq3,Rr20), (Rp17,Rq3,Rr21), (Rp17, Rq3,Rr22), (Rp17,Rq4,Rr1), (Rp17,Rq4,Rr2), (Rp17,Rq4, Rr3), (Rp17,Rq4,Rr4), (Rp17,Rq4,Rr5), (Rp17,Rq4,Rr6), (Rp17,Rq4,Rr7), (Rp17,Rq4,Rr8), (Rp17,Rq4,Rr9), (Rp17, Rq4,Rr10), (Rp17,Rq4,Rr11), (Rp17,Rq4,Rr12), (Rp17, Rq4,Rr13), (Rp17,Rq4,Rr14), (Rp17,Rq4,Rr15), (Rp17, Rq4,Rr16), (Rp17,Rq4,Rr17), (Rp17,Rq4,Rr18), (Rp17, Rq4,Rr19), (Rp17,Rq4,Rr20), (Rp17,Rq4,Rr21), (Rp17, Rq4,Rr22), (Rp17,Rq5,Rr1), (Rp17,Rq5,Rr2), (Rp17,Rq5, Rr3), (Rp17,Rq5,Rr4), (Rp17,Rq5,Rr5), (Rp17,Rq5,Rr6), (Rp17,Rq5,Rr7), (Rp17,Rq5,Rr8), (Rp17,Rq5,Rr9), (Rp17, Rq5,Rr10), (Rp17,Rq5,Rr11), (Rp17,Rq5,Rr12), (Rp17, Rq5,Rr13), (Rp17,Rq5,Rr14), (Rp17,Rq5,Rr15), (Rp17, Rq5,Rr16), (Rp17,Rq5,Rr17), (Rp17,Rq5,Rr18), (Rp17, Rq5,Rr19), (Rp17,Rq5,Rr20), (Rp17,Rq5,Rr21), (Rp17, Rq5,Rr22), (Rp17,Rq6,Rr1), (Rp17,Rq6,Rr2), (Rp17,Rq6, Rr3), (Rp17,Rq6,Rr4), (Rp17,Rq6,Rr5), (Rp17,Rq6,Rr6), (Rp17,Rq6,Rr7), (Rp17,Rq6,Rr8), (Rp17,Rq6,Rr9), (Rp17, Rq6,Rr10), (Rp17, Rq6,Rr11), (Rp17,Rq6,Rr12), (Rp17, Rq6,Rr13), (Rp17,Rq6,Rr14), (Rp17,Rq6,Rr15), (Rp17, Rq6,Rr16), (Rp17,Rq6,Rr17), (Rp17,Rq6,Rr18), (Rp17, Rq6,Rr19), (Rp17,Rq6,Rr20), (Rp17,Rq6,Rr21), (Rp17, Rq6,Rr22), (Rp17,Rq7,Rr1), (Rp17,Rq7,Rr2), (Rp17,Rq7, Rr3), (Rp17,Rq7,Rr4), (Rp17,Rq7,Rr5), (Rp17,Rq7,Rr6), (Rp17,Rq7,Rr7), (Rp17,Rq7,Rr8), (Rp17,Rq7,Rr9), (Rp17, Rq7,Rr10), (Rp17,Rq7,Rr11), (Rp17,Rq7,Rr12), (Rp17, Rq7,Rr13), (Rp17,Rq7,Rr14), (Rp17,Rq7,Rr15), (Rp17, Rq7,Rr16), (Rp17,Rq7,Rr17), (Rp17,Rq7,Rr18), (Rp17, Rq7,Rr19), (Rp17,Rq7,Rr20), (Rp17,Rq7,Rr21), (Rp17, Rq7,Rr22), (Rp17,Rq8,Rr1), (Rp17,Rq8,Rr2), (Rp17,Rq8, Rr3), (Rp17,Rq8,Rr4), (Rp17,Rq8,Rr5), (Rp17,Rq8,Rr6), (Rp17,Rq8,Rr7), (Rp17,Rq8,Rr8), (Rp17,Rq8,Rr9), (Rp17, Rq8,Rr10), (Rp17,Rq8,Rr11), (Rp17,Rq8,Rr12), (Rp17, Rq8,Rr13), (Rp17,Rq8,Rr14), (Rp17,Rq8,Rr15), (Rp17, Rq8,Rr16), (Rp17,Rq8,Rr17), (Rp17,Rq8,Rr18), (Rp17, Rq8,Rr19), (Rp17,Rq8,Rr20), (Rp17,Rq8,Rr21), (Rp17, Rq8,Rr22), (Rp17,Rq9,Rr1), (Rp17,Rq9,Rr2), (Rp17,Rq9, Rr3), (Rp17,Rq9,Rr4), (Rp17,Rq9,Rr5), (Rp17,Rq9,Rr6), (Rp17,Rq9,Rr7), (Rp17,Rq9,Rr8), (Rp17,Rq9,Rr9), (Rp17, Rq9,Rr10), (Rp17,Rq9,Rr11), (Rp17,Rq9,Rr12), (Rp17, Rq9,Rr13), (Rp17,Rq9,Rr14), (Rp17,Rq9,Rr15), (Rp17, Rq9,Rr16), (Rp17,Rq9,Rr17), (Rp17,Rq9,Rr18), (Rp17, Rq9,Rr19), (Rp17,Rq9,Rr20), (Rp17,Rq9,Rr21), (Rp17, Rq9,Rr22), (Rp17,Rq10,Rr1), (Rp17,Rq10,Rr2), (Rp17, Rq10,Rr3), (Rp17, Rq10,Rr4), (Rp17,Rq10,Rr5), (Rp17, Rq10,Rr6), (Rp17,Rq10,Rr7), (Rp17,Rq10,Rr8), (Rp17, Rq10,Rr9), (Rp17,Rq10,Rr10), (Rp17,Rq10,Rr11), (Rp17, Rq10,Rr12), (Rp17,Rq10,Rr13), (Rp17,Rq10,Rr14), (Rp17, Rq10,Rr15), (Rp17,Rq10,Rr16), (Rp17,Rq10,Rr17), (Rp17, Rq10, Rr18), (Rp17,Rq10,Rr19), (Rp17,Rq10,Rr20), (Rp17, Rq10,Rr21), (Rp17,Rq10,Rr22), (Rp17,Rq11,Rr1), (Rp17, Rq11,Rr2), (Rp17,Rq11,Rr3), (Rp17,Rq11,Rr4), (Rp17, Rq11,Rr5), (Rp17,Rq11,Rr6), (Rp17,Rq11,Rr7), (Rp17, Rq11,Rr8), (Rp17,Rq11,Rr9), (Rp17,Rq11,Rr10), (Rp17, Rq11,Rr11), (Rp17,Rq11,Rr12), (Rp17,Rq11,Rr13), (Rp17, Rq11,Rr14), (Rp17,Rq11,Rr15), (Rp17,Rq11,Rr16), (Rp17, Rq11,Rr17), (Rp17,Rq11,Rr18), (Rp17,Rq11,Rr19), (Rp17, Rq11,Rr20), (Rp17,Rq11,Rr21), (Rp17,Rq11,Rr22), (Rp17, Rq12,Rr1), (Rp17,Rq12,Rr2), (Rp17,Rq12,Rr3), (Rp17, Rq12,Rr4), (Rp17,Rq12,Rr5), (Rp17,Rq12,Rr6), (Rp17, Rq12,Rr7), (Rp17,Rq12,Rr8), (Rp17,Rq12,Rr9), (Rp17, Rq12,Rr10), (Rp17,Rq12,Rr11), (Rp17,Rq12,Rr12), (Rp17, Rq12,Rr13), (Rp17,Rq12,Rr14), (Rp17,Rq12,Rr15), (Rp17, Rq12,Rr16), (Rp17,Rq12,Rr17), (Rp17,Rq12,Rr18), (Rp17, Rq12,Rr19), (Rp17,Rq12,Rr20), (Rp17,Rq12,Rr21), (Rp17, Rq12,Rr22), (Rp18,Rq1,Rr1), (Rp18,Rq1,Rr2), (Rp18,Rq1, Rr3), (Rp18,Rq1,Rr4), (Rp18,Rq1,Rr5), (Rp18,Rq1,Rr6), (Rp18,Rq1,Rr7), (Rp18,Rq1,Rr8), (Rp18,Rq1,Rr9), (Rp18, Rq1,Rr10), (Rp18,Rq1,Rr11), (Rp18,Rq1,Rr12), (Rp18, Rq1,Rr13), (Rp18,Rq1,Rr14), (Rp18,Rq1,Rr15), (Rp18, Rq1,Rr16), (Rp18,Rq1,Rr17), (Rp18,Rq1,Rr18), (Rp18, Rq1,Rr19), (Rp18, Rq1,Rr20), (Rp18,Rq1,Rr21), (Rp18, Rq1,Rr22), (Rp18,Rq2,Rr1), (Rp18,Rq2,Rr2), (Rp18,Rq2, Rr3), (Rp18,Rq2,Rr4), (Rp18,Rq2,Rr5), (Rp18,Rq2,Rr6), (Rp18,Rq2,Rr7), (Rp18,Rq2,Rr8), (Rp18,Rq2,Rr9), (Rp18, Rq2,Rr10), (Rp18,Rq2,Rr11), (Rp18,Rq2,Rr12), (Rp18, Rq2,Rr13), (Rp18,Rq2,Rr14), (Rp18,Rq2,Rr15), (Rp18, Rq2,Rr16), (Rp18,Rq2,Rr17), (Rp18,Rq2,Rr18), (Rp18, Rq2,Rr19), (Rp18,Rq2,Rr20), (Rp18,Rq2,Rr21), (Rp18, Rq2,Rr22), (Rp18,Rq3,Rr1), (Rp18,Rq3,Rr2), (Rp18,Rq3, Rr3), (Rp18,Rq3,Rr4), (Rp18,Rq3,Rr5), (Rp18,Rq3,Rr6), (Rp18,Rq3,Rr7), (Rp18,Rq3,Rr8), (Rp18,Rq3,Rr9), (Rp18, Rq3,Rr10), (Rp18,Rq3,Rr11), (Rp18,Rq3,Rr12), (Rp18, Rq3,Rr13), (Rp18,Rq3,Rr14), (Rp18,Rq3,Rr15), (Rp18, Rq3,Rr16), (Rp18,Rq3,Rr17), (Rp18,Rq3,Rr18), (Rp18, Rq3,Rr19), (Rp18,Rq3,Rr20), (Rp18,Rq3,Rr21), (Rp18, Rq3,Rr22), (Rp18,Rq4,Rr1), (Rp18,Rq4,Rr2), (Rp18,Rq4, Rr3), (Rp18,Rq4,Rr4), (Rp18,Rq4,Rr5), (Rp18,Rq4,Rr6), (Rp18,Rq4,Rr7), (Rp18,Rq4,Rr8), (Rp18,Rq4,Rr9), (Rp18, Rq4,Rr10), (Rp18,Rq4,Rr11), (Rp18,Rq4,Rr12), (Rp18, Rq4,Rr13), (Rp18,Rq4,Rr14), (Rp18,Rq4,Rr15), (Rp18, Rq4,Rr16), (Rp18,Rq4,Rr17), (Rp18,Rq4,Rr18), (Rp18, Rq4,Rr19), (Rp18,Rq4,Rr20), (Rp18,Rq4,Rr21), (Rp18, Rq4,Rr22), (Rp18,Rq5,Rr1), (Rp18,Rq5,Rr2), (Rp18,Rq5, Rr3), (Rp18,Rq5,Rr4), (Rp18,Rq5,Rr5), (Rp18,Rq5,Rr6), (Rp18,Rq5,Rr7), (Rp18,Rq5,Rr8), (Rp18,Rq5,Rr9), (Rp18, Rq5,Rr10), (Rp18,Rq5,Rr11), (Rp18,Rq5,Rr12), (Rp18, Rq5,Rr13), (Rp18,Rq5,Rr14), (Rp18,Rq5,Rr15), (Rp18, Rq5,Rr16), (Rp18,Rq5,Rr17), (Rp18,Rq5,Rr18), (Rp18, Rq5,Rr19), (Rp18,Rq5,Rr20), (Rp18,Rq5,Rr21), (Rp18, Rq5,Rr22), (Rp18,Rq6,Rr1), (Rp18,Rq6,Rr2), (Rp18,Rq6, Rr3), (Rp18,Rq6,Rr4), (Rp18,Rq6,Rr5), (Rp18,Rq6,Rr6), (Rp18,Rq6,Rr7), (Rp18,Rq6,Rr8), (Rp18,Rq6,Rr9), (Rp18, Rq6,Rr10), (Rp18,Rq6,Rr11), (Rp18,Rq6,Rr12), (Rp18, Rq6,Rr13), (Rp18,Rq6,Rr14), (Rp18,Rq6,Rr15), (Rp18, Rq6,Rr16), (Rp18, Rq6,Rr17), (Rp18,Rq6,Rr18), (Rp18,

Rq6,Rr19), (Rp18,Rq6,Rr20), (Rp18,Rq6,Rr21), (Rp18, Rq6,Rr22), (Rp18,Rq7,Rr1), (Rp18,Rq7,Rr2), (Rp18,Rq7, Rr3), (Rp18,Rq7,Rr4), (Rp18,Rq7,Rr5), (Rp18,Rq7,Rr6), (Rp18,Rq7,Rr7), (Rp18,Rq7,Rr8), (Rp18,Rq7,Rr9), (Rp18, Rq7,Rr10), (Rp18,Rq7,Rr11), (Rp18,Rq7,Rr12), (Rp18, Rq7,Rr13), (Rp18,Rq7,Rr14), (Rp18,Rq7,Rr15), (Rp18, Rq7,Rr16), (Rp18,Rq7,Rr17), (Rp18,Rq7,Rr18), (Rp18, Rq7,Rr19), (Rp18,Rq7,Rr20), (Rp18,Rq7,Rr21), (Rp18, Rq7,Rr22), (Rp18,Rq8,Rr1), (Rp18,Rq8,Rr2), (Rp18,Rq8, Rr3), (Rp18,Rq8,Rr4), (Rp18,Rq8,Rr5), (Rp18,Rq8,Rr6), (Rp18,Rq8,Rr7), (Rp18,Rq8,Rr8), (Rp18,Rq8,Rr9), (Rp18, Rq8,Rr10), (Rp18,Rq8,Rr11), (Rp18,Rq8,Rr12), (Rp18, Rq8,Rr13), (Rp18,Rq8,Rr14), (Rp18,Rq8,Rr15), (Rp18, Rq8,Rr16), (Rp18,Rq8,Rr17), (Rp18,Rq8,Rr18), (Rp18, Rq8,Rr19), (Rp18,Rq8,Rr20), (Rp18,Rq8,Rr21), (Rp18, Rq8,Rr22), (Rp18,Rq9,Rr1), (Rp18,Rq9,Rr2), (Rp18,Rq9, Rr3), (Rp18,Rq9,Rr4), (Rp18,Rq9,Rr5), (Rp18,Rq9,Rr6), (Rp18,Rq9,Rr7), (Rp18,Rq9,Rr8), (Rp18,Rq9,Rr9), (Rp18, Rq9,Rr10), (Rp18,Rq9,Rr11), (Rp18,Rq9,Rr12), (Rp18, Rq9,Rr13), (Rp18,Rq9,Rr14), (Rp18,Rq9,Rr15), (Rp18, Rq9,Rr16), (Rp18,Rq9, Rr17), (Rp18,Rq9,Rr18), (Rp18, Rq9,Rr19), (Rp18,Rq9,Rr20), (Rp18,Rq9,Rr21), (Rp18, Rq9,Rr22), (Rp18,Rq10,Rr1), (Rp18,Rq10,Rr2), (Rp18, Rq10,Rr3), (Rp18,Rq10,Rr4), (Rp18,Rq10,Rr5), (Rp18, Rq10,Rr6), (Rp18,Rq10,Rr7), (Rp18,Rq10,Rr8), (Rp18, Rq10,Rr9), (Rp18,Rq10,Rr10), (Rp18,Rq10,Rr11), (Rp18, Rq10,Rr12), (Rp18,Rq10,Rr13), (Rp18,Rq10,Rr14), (Rp18, Rq10,Rr15), (Rp18,Rq10,Rr16), (Rp18,Rq10,Rr17), (Rp18, Rq10,Rr18), (Rp18,Rq10, Rr19), (Rp18,Rq10,Rr20), (Rp18, Rq10,Rr21), (Rp18,Rq10,Rr22), (Rp18,Rq11,Rr1), (Rp18, Rq11,Rr2), (Rp18,Rq11,Rr3), (Rp18,Rq11,Rr4), (Rp18, Rq11,Rr5), (Rp18,Rq11,Rr6), (Rp18,Rq11,Rr7), (Rp18, Rq11,Rr8), (Rp18,Rq11,Rr9), (Rp18,Rq11,Rr10), (Rp18, Rq11,Rr11), (Rp18,Rq11,Rr12), (Rp18,Rq11,Rr13), (Rp18, Rq11,Rr14), (Rp18,Rq11,Rr15), (Rp18,Rq11,Rr16), (Rp18, Rq11,Rr17), (Rp18,Rq11,Rr18), (Rp18,Rq11,Rr19), (Rp18, Rq11,Rr20), (Rp18, Rq11,Rr21), (Rp18,Rq11,Rr22), (Rp18, Rq12,Rr1), (Rp18,Rq12,Rr2), (Rp18,Rq12,Rr3), (Rp18, Rq12,Rr4), (Rp18,Rq12,Rr5), (Rp18,Rq12,Rr6), (Rp18, Rq12,Rr7), (Rp18,Rq12,Rr8), (Rp18,Rq12,Rr9), (Rp18, Rq12,Rr10), (Rp18,Rq12,Rr11), (Rp18,Rq12,Rr12), (Rp18, Rq12,Rr13), (Rp18,Rq12,Rr14), (Rp18,Rq12,Rr15), (Rp18, Rq12,Rr16), (Rp18,Rq12,Rr17), (Rp18,Rq12,Rr18), (Rp18, Rq12,Rr19), (Rp18,Rq12,Rr20), (Rp18,Rq12,Rr21), (Rp18, Rq12,Rr22), (Rp19,Rq1,Rr1), (Rp19,Rq1,Rr2), (Rp19,Rq1, Rr3), (Rp19,Rq1,Rr4), (Rp19,Rq1,Rr5), (Rp19,Rq1,Rr6), (Rp19,Rq1,Rr7), (Rp19,Rq1,Rr8), (Rp19,Rq1,Rr9), (Rp19, Rq1,Rr10), (Rp19,Rq1,Rr11), (Rp19,Rq1,Rr12), (Rp19, Rq1,Rr13), (Rp19,Rq1,Rr14), (Rp19,Rq1,Rr15), (Rp19, Rq1,Rr16), (Rp19,Rq1,Rr17), (Rp19,Rq1,Rr18), (Rp19, Rq1,Rr19), (Rp19,Rq1,Rr20), (Rp19,Rq1,Rr21), (Rp19, Rq1,Rr22), (Rp19,Rq2,Rr1), (Rp19,Rq2,Rr2), (Rp19,Rq2, Rr3), (Rp19,Rq2, Rr4), (Rp19,Rq2,Rr5), (Rp19,Rq2,Rr6), (Rp19,Rq2,Rr7), (Rp19,Rq2,Rr8), (Rp19,Rq2,Rr9), (Rp19, Rq2,Rr10), (Rp19,Rq2,Rr11), (Rp19,Rq2,Rr12), (Rp19, Rq2,Rr13), (Rp19,Rq2,Rr14), (Rp19,Rq2,Rr15), (Rp19, Rq2,Rr16), (Rp19,Rq2,Rr17), (Rp19,Rq2,Rr18), (Rp19, Rq2,Rr19), (Rp19,Rq2,Rr20), (Rp19,Rq2,Rr21), (Rp19, Rq2,Rr22), (Rp19,Rq3,Rr1), (Rp19,Rq3,Rr2), (Rp19,Rq3, Rr3), (Rp19,Rq3,Rr4), (Rp19,Rq3,Rr5), (Rp19,Rq3,Rr6), (Rp19,Rq3,Rr7), (Rp19,Rq3,Rr8), (Rp19,Rq3,Rr9), (Rp19, Rq3,Rr10), (Rp19,Rq3,Rr11), (Rp19,Rq3,Rr12), (Rp19, Rq3,Rr13), (Rp19,Rq3,Rr14), (Rp19,Rq3,Rr15), (Rp19, Rq3,Rr16), (Rp19,Rq3,Rr17), (Rp19, Rq3,Rr18), (Rp19, Rq3,Rr19), (Rp19,Rq3,Rr20), (Rp19,Rq3,Rr21), (Rp19, Rq3,Rr22), (Rp19,Rq4,Rr1), (Rp19,Rq4,Rr2), (Rp19,Rq4, Rr3), (Rp19,Rq4,Rr4), (Rp19,Rq4,Rr5), (Rp19,Rq4, Rr6), (Rp19,Rq4,Rr7), (Rp19,Rq4,Rr8), (Rp19,Rq4,Rr9), (Rp19, Rq4,Rr10), (Rp19,Rq4,Rr11), (Rp19,Rq4,Rr12), (Rp19, Rq4,Rr13), (Rp19,Rq4,Rr14), (Rp19,Rq4,Rr15), (Rp19, Rq4,Rr16), (Rp19,Rq4,Rr17), (Rp19,Rq4,Rr18), (Rp19, Rq4,Rr19), (Rp19,Rq4,Rr20), (Rp19,Rq4,Rr21), (Rp19, Rq4,Rr22), (Rp19,Rq5,Rr1), (Rp19,Rq5,Rr2), (Rp19,Rq5, Rr3), (Rp19,Rq5,Rr4), (Rp19,Rq5,Rr5), (Rp19,Rq5,Rr6), (Rp19,Rq5,Rr7), (Rp19,Rq5,Rr8), (Rp19,Rq5,Rr9), (Rp19, Rq5,Rr10), (Rp19,Rq5,Rr11), (Rp19,Rq5,Rr12), (Rp19, Rq5,Rr13), (Rp19,Rq5,Rr14), (Rp19,Rq5,Rr15), (Rp19, Rq5,Rr16), (Rp19,Rq5,Rr17), (Rp19,Rq5,Rr18), (Rp19, Rq5,Rr19), (Rp19,Rq5,Rr20), (Rp19,Rq5,Rr21), (Rp19, Rq5,Rr22), (Rp19,Rq6,Rr1), (Rp19,Rq6,Rr2), (Rp19,Rq6, Rr3), (Rp19,Rq6,Rr4), (Rp19,Rq6,Rr5), (Rp19,Rq6,Rr6), (Rp19,Rq6,Rr7), (Rp19,Rq6,Rr8), (Rp19,Rq6,Rr9), (Rp19, Rq6,Rr10), (Rp19,Rq6,Rr11), (Rp19,Rq6,Rr12), (Rp19, Rq6, Rr13), (Rp19,Rq6,Rr14), (Rp19,Rq6,Rr15), (Rp19, Rq6,Rr16), (Rp19,Rq6,Rr17), (Rp19,Rq6,Rr18), (Rp19, Rq6,Rr19), (Rp19,Rq6,Rr20), (Rp19,Rq6,Rr21), (Rp19, Rq6,Rr22), (Rp19,Rq7,Rr1), (Rp19,Rq7,Rr2), (Rp19,Rq7, Rr3), (Rp19,Rq7,Rr4), (Rp19,Rq7,Rr5), (Rp19,Rq7,Rr6), (Rp19,Rq7,Rr7), (Rp19,Rq7,Rr8), (Rp19,Rq7,Rr9), (Rp19, Rq7,Rr10), (Rp19,Rq7,Rr11), (Rp19,Rq7,Rr12), (Rp19, Rq7,Rr13), (Rp19,Rq7,Rr14), (Rp19,Rq7,Rr15), (Rp19, Rq7,Rr16), (Rp19,Rq7,Rr17), (Rp19,Rq7,Rr18), (Rp19, Rq7,Rr19), (Rp19,Rq7,Rr20), (Rp19,Rq7,Rr21), (Rp19, Rq7,Rr22), (Rp19,Rq8,Rr1), (Rp19,Rq8,Rr2), (Rp19,Rq8, Rr3), (Rp19,Rq8,Rr4), (Rp19,Rq8,Rr5), (Rp19,Rq8,Rr6), (Rp19,Rq8,Rr7), (Rp19,Rq8,Rr8), (Rp19,Rq8,Rr9), (Rp19, Rq8,Rr10), (Rp19,Rq8,Rr11), (Rp19,Rq8,Rr12), (Rp19, Rq8,Rr13), (Rp19,Rq8,Rr14), (Rp19,Rq8,Rr15), (Rp19, Rq8,Rr16), (Rp19,Rq8,Rr17), (Rp19,Rq8,Rr18), (Rp19, Rq8,Rr19), (Rp19, Rq8,Rr20), (Rp19,Rq8,Rr21), (Rp19, Rq8,Rr22), (Rp19,Rq9,Rr1), (Rp19,Rq9,Rr2), (Rp19,Rq9, Rr3), (Rp19,Rq9,Rr4), (Rp19,Rq9,Rr5), (Rp19,Rq9,Rr6), (Rp19,Rq9,Rr7), (Rp19,Rq9,Rr8), (Rp19,Rq9,Rr9), (Rp19, Rq9,Rr10), (Rp19,Rq9,Rr11), (Rp19,Rq9,Rr12), (Rp19, Rq9,Rr13), (Rp19,Rq9,Rr14), (Rp19,Rq9,Rr15), (Rp19, Rq9,Rr16), (Rp19,Rq9,Rr17), (Rp19,Rq9,Rr18), (Rp19, Rq9,Rr19), (Rp19,Rq9,Rr20), (Rp19,Rq9,Rr21), (Rp19, Rq9,Rr22), (Rp19,Rq10, Rr1), (Rp19,Rq10,Rr2), (Rp19, Rq10,Rr3), (Rp19,Rq10,Rr4), (Rp19,Rq10,Rr5), (Rp19, Rq10,Rr6), (Rp19,Rq10,Rr7), (Rp19,Rq10,Rr8), (Rp19, Rq10,Rr9), (Rp19,Rq10,Rr10), (Rp19,Rq10,Rr11), (Rp19, Rq10,Rr12), (Rp19,Rq10,Rr13), (Rp19,Rq10,Rr14), (Rp19, Rq10,Rr15), (Rp19,Rq10,Rr16), (Rp19,Rq10,Rr17), (Rp19, Rq10,Rr18), (Rp19,Rq10,Rr19), (Rp19,Rq10,Rr20), (Rp19, Rq10,Rr21), (Rp19,Rq10,Rr22), (Rp19,Rq11,Rr1), (Rp19, Rq11,Rr2), (Rp19,Rq11,Rr3), (Rp19,Rq11,Rr4), (Rp19, Rq11,Rr5), (Rp19,Rq11,Rr6), (Rp19,Rq11,Rr7), (Rp19, Rq11,Rr8), (Rp19,Rq11,Rr9), (Rp19,Rq11,Rr10), (Rp19, Rq11,Rr11), (Rp19,Rq11,Rr12), (Rp19,Rq11,Rr13), (Rp19, Rq11,Rr14), (Rp19,Rq11,Rr15), (Rp19,Rq11,Rr16), (Rp19, Rq11,Rr17), (Rp19,Rq11,Rr18), (Rp19,Rq11,Rr19), (Rp19, Rq11,Rr20), (Rp19,Rq11,Rr21), (Rp19,Rq11,Rr22), (Rp19, Rq12,Rr1), (Rp19,Rq12,Rr2), (Rp19,Rq12,Rr3), (Rp19, Rq12,Rr4), (Rp19, Rq12,Rr5), (Rp19,Rq12,Rr6), (Rp19, Rq12,Rr7), (Rp19,Rq12,Rr8), (Rp19,Rq12,Rr9), (Rp19, Rq12,Rr10), (Rp19,Rq12,Rr11), (Rp19,Rq12,Rr12), (Rp19, Rq12,Rr13), (Rp19,Rq12,Rr14), (Rp19,Rq12,Rr15), (Rp19, Rq12,Rr16), (Rp19,Rq12,Rr17), (Rp19,Rq12,Rr18), (Rp19, Rq12,Rr19), (Rp19,Rq12,Rr20), (Rp19,Rq12,Rr21), (Rp19, Rq12,Rr22), (Rp20,Rq1,Rr1), (Rp20, Rq1,Rr2), (Rp20,Rq1, Rr3), (Rp20,Rq1,Rr4), (Rp20,Rq1,Rr5), (Rp20,Rq1,Rr6), (Rp20,Rq1,Rr7), (Rp20,Rq1,Rr8), (Rp20,Rq1,Rr9), (Rp20, Rq1,Rr10), (Rp20,Rq1,Rr11), (Rp20,Rq1,Rr12), (Rp20, Rq1,Rr13), (Rp20,Rq1,Rr14), (Rp20,Rq1,Rr15), (Rp20,

Rq1,Rr16), (Rp20,Rq1,Rr17), (Rp20,Rq1,Rr18), (Rp20, Rq1,Rr19), (Rp20,Rq1,Rr20), (Rp20,Rq1,Rr21), (Rp20, Rq1,Rr22), (Rp20,Rq2,Rr1), (Rp20,Rq2,Rr2), (Rp20,Rq2, Rr3), (Rp20,Rq2,Rr4), (Rp20,Rq2,Rr5), (Rp20,Rq2,Rr6), (Rp20,Rq2,Rr7), (Rp20,Rq2,Rr8), (Rp20,Rq2,Rr9), (Rp20, Rq2,Rr10), (Rp20,Rq2,Rr11), (Rp20,Rq2,Rr12), (Rp20, Rq2,Rr13), (Rp20,Rq2,Rr14), (Rp20,Rq2,Rr15), (Rp20, Rq2,Rr16), (Rp20,Rq2,Rr17), (Rp20,Rq2,Rr18), (Rp20, Rq2,Rr19), (Rp20,Rq2,Rr20), (Rp20,Rq2,Rr21), (Rp20, Rq2,Rr22), (Rp20,Rq3,Rr1), (Rp20,Rq3,Rr2), (Rp20,Rq3, Rr3), (Rp20,Rq3,Rr4), (Rp20,Rq3,Rr5), (Rp20,Rq3,Rr6), (Rp20,Rq3,Rr7), (Rp20,Rq3,Rr8), (Rp20,Rq3,Rr9), (Rp20, Rq3,Rr10), (Rp20,Rq3,Rr11), (Rp20,Rq3,Rr12), (Rp20, Rq3,Rr13), (Rp20,Rq3,Rr14), (Rp20,Rq3,Rr15), (Rp20, Rq3,Rr16), (Rp20,Rq3,Rr17), (Rp20,Rq3,Rr18), (Rp20, Rq3,Rr19), (Rp20,Rq3,Rr20), (Rp20,Rq3,Rr21), (Rp20, Rq3,Rr22), (Rp20,Rq4,Rr1), (Rp20,Rq4,Rr2), (Rp20,Rq4, Rr3), (Rp20,Rq4,Rr4), (Rp20,Rq4,Rr5), (Rp20,Rq4,Rr6), (Rp20,Rq4,Rr7), (Rp20,Rq4,Rr8), (Rp20,Rq4,Rr9), (Rp20, Rq4,Rr10), (Rp20,Rq4,Rr11), (Rp20,Rq4,Rr12), (Rp20, Rq4,Rr13), (Rp20,Rq4,Rr14), (Rp20,Rq4,Rr15), (Rp20, Rq4,Rr16), (Rp20,Rq4,Rr17), (Rp20,Rq4,Rr18), (Rp20, Rq4,Rr19), (Rp20,Rq4,Rr20), (Rp20,Rq4,Rr21), (Rp20, Rq4,Rr22), (Rp20,Rq5,Rr1), (Rp20,Rq5,Rr2), (Rp20,Rq5, Rr3), (Rp20,Rq5,Rr4), (Rp20,Rq5,Rr5), (Rp20,Rq5,Rr6), (Rp20,Rq5,Rr7), (Rp20,Rq5,Rr8), (Rp20,Rq5,Rr9), (Rp20, Rq5,Rr10), (Rp20, Rq5,Rr11), (Rp20,Rq5,Rr12), (Rp20, Rq5,Rr13), (Rp20,Rq5,Rr14), (Rp20,Rq5,Rr15), (Rp20, Rq5,Rr16), (Rp20,Rq5,Rr17), (Rp20,Rq5,Rr18), (Rp20, Rq5,Rr19), (Rp20,Rq5,Rr20), (Rp20,Rq5,Rr21), (Rp20, Rq5,Rr22), (Rp20,Rq6,Rr1), (Rp20,Rq6,Rr2), (Rp20,Rq6, Rr3), (Rp20,Rq6,Rr4), (Rp20,Rq6,Rr5), (Rp20,Rq6,Rr6), (Rp20,Rq6,Rr7), (Rp20,Rq6,Rr8), (Rp20,Rq6,Rr9), (Rp20, Rq6,Rr10), (Rp20,Rq6,Rr11), (Rp20,Rq6,Rr12), (Rp20, Rq6,Rr13), (Rp20,Rq6,Rr14), (Rp20,Rq6,Rr15), (Rp20, Rq6,Rr16), (Rp20,Rq6,Rr17), (Rp20,Rq6,Rr18), (Rp20, Rq6,Rr19), (Rp20,Rq6,Rr20), (Rp20,Rq6,Rr21), (Rp20, Rq6,Rr22), (Rp20,Rq7,Rr1), (Rp20,Rq7,Rr2), (Rp20,Rq7, Rr3), (Rp20,Rq7,Rr4), (Rp20,Rq7,Rr5), (Rp20,Rq7,Rr6), (Rp20,Rq7,Rr7), (Rp20,Rq7,Rr8), (Rp20,Rq7,Rr9), (Rp20, Rq7,Rr10), (Rp20,Rq7,Rr11), (Rp20,Rq7,Rr12), (Rp20, Rq7,Rr13), (Rp20,Rq7,Rr14), (Rp20,Rq7,Rr15), (Rp20, Rq7,Rr16), (Rp20,Rq7,Rr17), (Rp20,Rq7,Rr18), (Rp20, Rq7,Rr19), (Rp20,Rq7,Rr20), (Rp20,Rq7,Rr21), (Rp20, Rq7,Rr22), (Rp20,Rq8,Rr1), (Rp20,Rq8,Rr2), (Rp20,Rq8, Rr3), (Rp20,Rq8,Rr4), (Rp20,Rq8,Rr5), (Rp20,Rq8,Rr6), (Rp20,Rq8,Rr7), (Rp20,Rq8,Rr8), (Rp20,Rq8,Rr9), (Rp20, Rq8,Rr10), (Rp20,Rq8,Rr11), (Rp20,Rq8,Rr12), (Rp20, Rq8,Rr13), (Rp20,Rq8,Rr14), (Rp20,Rq8,Rr15), (Rp20, Rq8,Rr16), (Rp20,Rq8,Rr17), (Rp20,Rq8,Rr18), (Rp20, Rq8,Rr19), (Rp20,Rq8,Rr20), (Rp20,Rq8,Rr21), (Rp20, Rq8,Rr22), (Rp20,Rq9,Rr1), (Rp20,Rq9,Rr2), (Rp20,Rq9, Rr3), (Rp20,Rq9, Rr4), (Rp20,Rq9,Rr5), (Rp20,Rq9,Rr6), (Rp20,Rq9,Rr7), (Rp20,Rq9,Rr8), (Rp20,Rq9,Rr9), (Rp20, Rq9,Rr10), (Rp20,Rq9,Rr11), (Rp20,Rq9,Rr12), (Rp20, Rq9,Rr13), (Rp20,Rq9,Rr14), (Rp20,Rq9,Rr15), (Rp20, Rq9,Rr16), (Rp20,Rq9,Rr17), (Rp20,Rq9,Rr18), (Rp20, Rq9,Rr19), (Rp20,Rq9,Rr20), (Rp20,Rq9,Rr21), (Rp20, Rq9,Rr22), (Rp20,Rq10,Rr1), (Rp20,Rq10,Rr2), (Rp20, Rq10,Rr3), (Rp20,Rq10,Rr4), (Rp20,Rq10,Rr5), (Rp20, Rq10,Rr6), (Rp20,Rq10,Rr7), (Rp20,Rq10,Rr8), (Rp20, Rq10,Rr9), (Rp20,Rq10,Rr10), (Rp20,Rq10,Rr11), (Rp20, Rq10,Rr12), (Rp20,Rq10,Rr13), (Rp20,Rq10,Rr14), (Rp20, Rq10,Rr15), (Rp20,Rq10,Rr16), (Rp20,Rq10,Rr17), (Rp20, Rq10,Rr18), (Rp20,Rq10,Rr19), (Rp20,Rq10,Rr20), (Rp20, Rq10,Rr21), (Rp20,Rq10,Rr22), (Rp20,Rq11,Rr1), (Rp20, Rq11,Rr2), (Rp20,Rq11,Rr3), (Rp20,Rq11,Rr4), (Rp20, Rq11,Rr5), (Rp20,Rq11,Rr6), (Rp20,Rq11,Rr7), (Rp20, Rq11,Rr8), (Rp20,Rq11,Rr9), (Rp20,Rq11,Rr10), (Rp20, Rq11,Rr11), (Rp20,Rq11,Rr12), (Rp20,Rq11,Rr13), (Rp20, Rq11,Rr14), (Rp20,Rq11,Rr15), (Rp20,Rq11,Rr16), (Rp20, Rq11,Rr17), (Rp20,Rq11,Rr18), (Rp20,Rq11,Rr19), (Rp20, Rq11,Rr20), (Rp20,Rq11,Rr21), (Rp20,Rq11,Rr22), (Rp20, Rq12,Rr1), (Rp20,Rq12,Rr2), (Rp20,Rq12,Rr3), (Rp20, Rq12,Rr4), (Rp20,Rq12,Rr5), (Rp20,Rq12,Rr6), (Rp20, Rq12,Rr7), (Rp20,Rq12,Rr8), (Rp20,Rq12,Rr9), (Rp20, Rq12,Rr10), (Rp20, Rq12,Rr11), (Rp20,Rq12,Rr12), (Rp20, Rq12,Rr13), (Rp20,Rq12,Rr14), (Rp20,Rq12,Rr15), (Rp20, Rq12,Rr16), (Rp20,Rq12,Rr17), (Rp20,Rq12,Rr18), (Rp20, Rq12,Rr19), (Rp20,Rq12, Rr20), (Rp20,Rq12,Rr21), (Rp20, Rq12,Rr22), (Rp21,Rq1,Rr1), (Rp21,Rq1,Rr2), (Rp21,Rq1, Rr3), (Rp21,Rq1,Rr4), (Rp21,Rq1,Rr5), (Rp21,Rq1,Rr6), (Rp21,Rq1,Rr7), (Rp21,Rq1,Rr8), (Rp21,Rq1,Rr9), (Rp21, Rq1,Rr10), (Rp21,Rq1,Rr11), (Rp21,Rq1,Rr12), (Rp21, Rq1,Rr13), (Rp21,Rq1,Rr14), (Rp21,Rq1,Rr15), (Rp21, Rq1,Rr16), (Rp21,Rq1,Rr17), (Rp21,Rq1,Rr18), (Rp21, Rq1,Rr19), (Rp21,Rq1,Rr20), (Rp21,Rq1,Rr21), (Rp21, Rq1,Rr22), (Rp21,Rq2,Rr1), (Rp21,Rq2,Rr2), (Rp21,Rq2, Rr3), (Rp21,Rq2,Rr4), (Rp21,Rq2,Rr5), (Rp21,Rq2,Rr6), (Rp21,Rq2,Rr7), (Rp21,Rq2,Rr8), (Rp21,Rq2,Rr9), (Rp21, Rq2,Rr10), (Rp21,Rq2,Rr11), (Rp21,Rq2,Rr12), (Rp21, Rq2,Rr13), (Rp21,Rq2,Rr14), (Rp21,Rq2,Rr15), (Rp21, Rq2,Rr16), (Rp21,Rq2,Rr17), (Rp21,Rq2,Rr18), (Rp21, Rq2,Rr19), (Rp21,Rq2,Rr20), (Rp21,Rq2,Rr21), (Rp21, Rq2,Rr22), (Rp21,Rq3,Rr1), (Rp21,Rq3,Rr2), (Rp21,Rq3, Rr3), (Rp21,Rq3,Rr4), (Rp21,Rq3, Rr5), (Rp21,Rq3,Rr6), (Rp21,Rq3,Rr7), (Rp21,Rq3,Rr8), (Rp21,Rq3,Rr9), (Rp21, Rq3,Rr10), (Rp21,Rq3,Rr11), (Rp21,Rq3,Rr12), (Rp21, Rq3,Rr13), (Rp21,Rq3,Rr14), (Rp21,Rq3,Rr15), (Rp21, Rq3,Rr16), (Rp21,Rq3,Rr17), (Rp21,Rq3,Rr18), (Rp21, Rq3,Rr19), (Rp21,Rq3,Rr20), (Rp21,Rq3,Rr21), (Rp21, Rq3,Rr22), (Rp21,Rq4,Rr1), (Rp21,Rq4,Rr2), (Rp21,Rq4, Rr3), (Rp21,Rq4,Rr4), (Rp21,Rq4,Rr5), (Rp21,Rq4,Rr6), (Rp21,Rq4,Rr7), (Rp21,Rq4,Rr8), (Rp21,Rq4,Rr9), (Rp21, Rq4,Rr10), (Rp21,Rq4,Rr11), (Rp21,Rq4,Rr12), (Rp21, Rq4,Rr13), (Rp21, Rq4,Rr14), (Rp21,Rq4,Rr15), (Rp21, Rq4,Rr16), (Rp21,Rq4,Rr17), (Rp21,Rq4,Rr18), (Rp21, Rq4,Rr19), (Rp21,Rq4,Rr20), (Rp21,Rq4,Rr21), (Rp21, Rq4,Rr22), (Rp21,Rq5,Rr1), (Rp21, Rq5,Rr2), (Rp21,Rq5, Rr3), (Rp21,Rq5,Rr4), (Rp21,Rq5,Rr5), (Rp21,Rq5,Rr6), (Rp21,Rq5, Rr7), (Rp21,Rq5,Rr8), (Rp21,Rq5,Rr9), (Rp21, Rq5,Rr10), (Rp21,Rq5,Rr11), (Rp21,Rq5,Rr12), (Rp21, Rq5,Rr13), (Rp21,Rq5,Rr14), (Rp21,Rq5,Rr15), (Rp21, Rq5,Rr16), (Rp21,Rq5,R r17), (Rp21,Rq5,Rr18), (Rp21, Rq5,Rr19), (Rp21,Rq5,Rr20), (Rp21,Rq5,Rr21), (Rp21, Rq5, Rr22), (Rp21,Rq6,Rr1), (Rp21,Rq6,Rr2), (Rp21,Rq6, Rr3), (Rp21,Rq6,Rr4), (Rp21,Rq6,Rr5), (Rp21,Rq6,Rr6), (Rp21,Rq6,Rr7), (Rp21,Rq6,Rr8), (Rp21,Rq6,Rr9), (Rp21, Rq6,Rr10), (Rp21,Rq6,Rr11), (Rp21,Rq6,Rr12), (Rp21, Rq6,Rr13), (Rp21,Rq6,Rr14), (Rp21,Rq6,Rr15), (Rp21, Rq6,Rr16), (Rp21,Rq6,Rr17), (Rp21,Rq6,Rr18), (Rp21, Rq6,Rr19), (Rp21,Rq6,Rr20), (Rp21,Rq6,Rr21), (Rp21, Rq6,Rr22), (Rp21,Rq7,Rr1), (Rp21,Rq7,Rr2), (Rp21,Rq7, Rr3), (Rp21,Rq7,Rr4), (Rp21,Rq7,Rr5), (Rp21,Rq7,Rr6), (Rp21,Rq7,Rr7), (Rp21,Rq7,Rr8), (Rp21,Rq7,Rr9), (Rp21, Rq7,Rr10), (Rp21,Rq7,Rr11), (Rp21,Rq7,Rr12), (Rp21, Rq7,Rr13), (Rp21,Rq7,Rr14), (Rp21,Rq7,Rr15), (Rp21, Rq7,Rr16), (Rp21,Rq7,Rr17), (Rp21,Rq7,Rr18), (Rp21, Rq7,Rr19), (Rp21,Rq7,Rr20), (Rp21,Rq7,Rr21), (Rp21, Rq7,Rr22), (Rp21,Rq8,Rr1), (Rp21,Rq8,Rr2), (Rp21,Rq8, Rr3), (Rp21,Rq8,Rr4), (Rp21,Rq8,Rr5), (Rp21,Rq8,Rr6), (Rp21,Rq8,Rr7), (Rp21,Rq8,Rr8), (Rp21,Rq8,Rr9), (Rp21, Rq8,Rr10), (Rp21,Rq8,Rr11), (Rp21,Rq8,Rr12), (Rp21, Rq8,Rr13), (Rp21,Rq8,Rr14), (Rp21,Rq8,Rr15), (Rp21,

Rq8,Rr16), (Rp21,Rq8,Rr17), (Rp21,Rq8,Rr18), (Rp21, Rq8,Rr19), (Rp21,Rq8,Rr20), (Rp21,Rq8,Rr21), (Rp21, Rq8,Rr22), (Rp21,Rq9,Rr1), (Rp21,Rq9,Rr2), (Rp21,Rq9, Rr3), (Rp21,Rq9,Rr4), (Rp21,Rq9,Rr5), (Rp21,Rq9,Rr6), (Rp21,Rq9,Rr7), (Rp21,Rq9,Rr8), (Rp21,Rq9,Rr9), (Rp21, Rq9,Rr10), (Rp21, Rq9,Rr11), (Rp21,Rq9,Rr12), (Rp21, Rq9,Rr13), (Rp21,Rq9,Rr14), (Rp21,Rq9,Rr15), (Rp21, Rq9,Rr16), (Rp21,Rq9,Rr17), (Rp21,Rq9,Rr18), (Rp21, Rq9,Rr19), (Rp21,Rq9,Rr20), (Rp21,Rq9,Rr21), (Rp21, Rq9,Rr22), (Rp21,Rq10,Rr1), (Rp21,Rq10,Rr2), (Rp21, Rq10,Rr3), (Rp21,Rq10,Rr4), (Rp21,Rq10,Rr5), (Rp21, Rq10,Rr6), (Rp21,Rq10,Rr7), (Rp21,Rq10,Rr8), (Rp21, Rq10,Rr9), (Rp21,Rq10,Rr10), (Rp21,Rq10,Rr11), (Rp21, Rq10,Rr12), (Rp21,Rq10,Rr13), (Rp21,Rq10,Rr14), (Rp21, Rq10,Rr15), (Rp21,Rq10,Rr16), (Rp21,Rq10,Rr17), (Rp21, Rq10,Rr18), (Rp21,Rq10,Rr19), (Rp21,Rq10,Rr20), (Rp21, Rq10,Rr21), (Rp21,Rq10,Rr22), (Rp21,Rq11,Rr1), (Rp21, Rq11,Rr2), (Rp21,Rq11,Rr3), (Rp21,Rq11,Rr4), (Rp21, Rq11,Rr5), (Rp21,Rq11,Rr6), (Rp21,Rq11,Rr7), (Rp21, Rq11,Rr8), (Rp21,Rq11,Rr9), (Rp21,Rq11,Rr10), (Rp21, Rq11,Rr11), (Rp21,Rq11,Rr12), (Rp21,Rq11,Rr13), (Rp21, Rq11,Rr14), (Rp21,Rq11,Rr15), (Rp21,Rq11,Rr16), (Rp21, Rq11,Rr17), (Rp21,Rq11,Rr18), (Rp21,Rq11,Rr19), (Rp21, Rq11,Rr20), (Rp21,Rq11,Rr21), (Rp21,Rq11,Rr22), (Rp21, Rq12,Rr1), (Rp21,Rq12,Rr2), (Rp21,Rq12,Rr3), (Rp21, Rq12,Rr4), (Rp21,Rq12,Rr5), (Rp21,Rq12,Rr6), (Rp21, Rq12,Rr7), (Rp21,Rq12,Rr8), (Rp21,Rq12,Rr9), (Rp21, Rq12,Rr10), (Rp21,Rq12,Rr11), (Rp21,Rq12, Rr12), (Rp21, Rq12,Rr13), (Rp21,Rq12,Rr14), (Rp21,Rq12,Rr15), (Rp21, Rq12,Rr16), (Rp21,Rq12,Rr17), (Rp21,Rq12,Rr18), (Rp21, Rq12,Rr19), (Rp21,Rq12,Rr20), (Rp21,Rq12,Rr21), (Rp21, Rq12,Rr22), (Rp22,Rq1,Rr1), (Rp22,Rq1,Rr2), (Rp22,Rq1, Rr3), (Rp22,Rq1,Rr4), (Rp22,Rq1,Rr5), (Rp22,Rq1,Rr6), (Rp22,Rq1,Rr7), (Rp22,Rq1,Rr8), (Rp22,Rq1,Rr9), (Rp22, Rq1,Rr10), (Rp22,Rq1,Rr11), (Rp22,Rq1,Rr12), (Rp22, Rq1,Rr13), (Rp22,Rq1,Rr14), (Rp22,Rq1,Rr15), (Rp22, Rq1,Rr16), (Rp22,Rq1,Rr17), (Rp22,Rq1,Rr18), (Rp22, Rq1,Rr19), (Rp22,Rq1,Rr20), (Rp22,Rq1,Rr21), (Rp22, Rq1,Rr22), (Rp22,Rq2,Rr1), (Rp22,Rq2,Rr2), (Rp22, Rq2, Rr3), (Rp22,Rq2,Rr4), (Rp22,Rq2,Rr5), (Rp22,Rq2,Rr6), (Rp22,Rq2,Rr7), (Rp22,Rq2, Rr8), (Rp22,Rq2,Rr9), (Rp22, Rq2,Rr10), (Rp22,Rq2,Rr11), (Rp22,Rq2,Rr12), (Rp22, Rq2,Rr13), (Rp22,Rq2,Rr14), (Rp22,Rq2,Rr15), (Rp22, Rq2,Rr16), (Rp22,Rq2,Rr17), (Rp22,Rq2, Rr18), (Rp22, Rq2,Rr19), (Rp22,Rq2,Rr20), (Rp22,Rq2,Rr21), (Rp22, Rq2,Rr22), (Rp22,Rq3,Rr1), (Rp22,Rq3,Rr2), (Rp22,Rq3, Rr3), (Rp22,Rq3,Rr4), (Rp22,Rq3,Rr5), (Rp22,Rq3,Rr6), (Rp22,Rq3,Rr7), (Rp22,Rq3,Rr8), (Rp22,Rq3,Rr9), (Rp22, Rq3,Rr10), (Rp22,Rq3,Rr11), (Rp22,Rq3,Rr12), (Rp22, Rq3,Rr13), (Rp22,Rq3,Rr14), (Rp22,Rq3,Rr15), (Rp22, Rq3,Rr16), (Rp22,Rq3,Rr17), (Rp22,Rq3,Rr18), (Rp22, Rq3,Rr19), (Rp22,Rq3,Rr20), (Rp22,Rq3,Rr21), (Rp22, Rq3,Rr22), (Rp22,Rq4,Rr1), (Rp22,Rq4,Rr2), (Rp22,Rq4, Rr3), (Rp22,Rq4,Rr4), (Rp22,Rq4,Rr5), (Rp22,Rq4,Rr6), (Rp22,Rq4,Rr7), (Rp22,Rq4,Rr8), (Rp22,Rq4,Rr9), (Rp22, Rq4,Rr10), (Rp22,Rq4,Rr11), (Rp22,Rq4,Rr12), (Rp22, Rq4,Rr13), (Rp22,Rq4,Rr14), (Rp22,Rq4,Rr15), (Rp22, Rq4,Rr16), (Rp22,Rq4,Rr17), (Rp22,Rq4,Rr18), (Rp22, Rq4,Rr19), (Rp22,Rq4,Rr20), (Rp22,Rq4,Rr21), (Rp22, Rq4,Rr22), (Rp22,Rq5,Rr1), (Rp22,Rq5,Rr2), (Rp22,Rq5, Rr3), (Rp22,Rq5,Rr4), (Rp22,Rq5,Rr5), (Rp22,Rq5,Rr6), (Rp22,Rq5,Rr7), (Rp22,Rq5,Rr8), (Rp22,Rq5,Rr9), (Rp22, Rq5,Rr10), (Rp22,Rq5,Rr11), (Rp22,Rq5,Rr12), (Rp22, Rq5,Rr13), (Rp22,Rq5,Rr14), (Rp22,Rq5,Rr15), (Rp22, Rq5,Rr16), (Rp22,Rq5,Rr17), (Rp22,Rq5,Rr18), (Rp22, Rq5,Rr19), (Rp22,Rq5,Rr20), (Rp22,Rq5,Rr21), (Rp22, Rq5,Rr22), (Rp22,Rq6,Rr1), (Rp22,Rq6,Rr2), (Rp22,Rq6, Rr3), (Rp22,Rq6,Rr4), (Rp22,Rq6,Rr5), (Rp22,Rq6,Rr6), (Rp22,Rq6,Rr7), (Rp22,Rq6,Rr8), (Rp22,Rq6,Rr9), (Rp22, Rq6,Rr10), (Rp22,Rq6,Rr11), (Rp22,Rq6,Rr12), (Rp22, Rq6,Rr13), (Rp22,Rq6,Rr14), (Rp22,Rq6,Rr15), (Rp22, Rq6,Rr16), (Rp22,Rq6,Rr17), (Rp22,Rq6,Rr18), (Rp22, Rq6,Rr19), (Rp22,Rq6,Rr20), (Rp22,Rq6,Rr21), (Rp22, Rq6,Rr22), (Rp22,Rq7,Rr1), (Rp22,Rq7,Rr2), (Rp22,Rq7, Rr3), (Rp22,Rq7,Rr4), (Rp22,Rq7,Rr5), (Rp22,Rq7,Rr6), (Rp22,Rq7,Rr7), (Rp22,Rq7,Rr8), (Rp22,Rq7,Rr9), (Rp22, Rq7,Rr10), (Rp22,Rq7,Rr11), (Rp22,Rq7,Rr12), (Rp22, Rq7,Rr13), (Rp22,Rq7,Rr14), (Rp22,Rq7,Rr15), (Rp22, Rq7,Rr16), (Rp22,Rq7,Rr17), (Rp22,Rq7,Rr18), (Rp22, Rq7,Rr19), (Rp22,Rq7,Rr20), (Rp22,Rq7,Rr21), (Rp22, Rq7,Rr22), (Rp22,Rq8,Rr1), (Rp22,Rq8,Rr2), (Rp22,Rq8, Rr3), (Rp22,Rq8,Rr4), (Rp22,Rq8,Rr5), (Rp22,Rq8,Rr6), (Rp22,Rq8,Rr7), (Rp22,Rq8,Rr8), (Rp22,Rq8,Rr9), (Rp22, Rq8,Rr10), (Rp22,Rq8,Rr11), (Rp22,Rq8,Rr12), (Rp22, Rq8,Rr13), (Rp22,Rq8,Rr14), (Rp22,Rq8,Rr15), (Rp22, Rq8,Rr16), (Rp22,Rq8,Rr17), (Rp22,Rq8,Rr18), (Rp22, Rq8,Rr19), (Rp22,Rq8,Rr20), (Rp22,Rq8,Rr21), (Rp22, Rq8,Rr22), (Rp22,Rq9,Rr1), (Rp22,Rq9,Rr2), (Rp22,Rq9, Rr3), (Rp22,Rq9,Rr4), (Rp22,Rq9,Rr5), (Rp22,Rq9,Rr6), (Rp22,Rq9,Rr7), (Rp22,Rq9,Rr8), (Rp22,Rq9,Rr9), (Rp22, Rq9,Rr10), (Rp22,Rq9,Rr11), (Rp22,Rq9,Rr12), (Rp22, Rq9,Rr13), (Rp22,Rq9,Rr14), (Rp22,Rq9,Rr15), (Rp22, Rq9,Rr16), (Rp22, Rq9,Rr17), (Rp22,Rq9,Rr18), (Rp22, Rq9,Rr19), (Rp22,Rq9,Rr20), (Rp22,Rq9,Rr21), (Rp22, Rq9,Rr22), (Rp22,Rq10,Rr1), (Rp22,Rq10,Rr2), (Rp22, Rq10,Rr3), (Rp22,Rq10,Rr4), (Rp22,Rq10,Rr5), (Rp22, Rq10,Rr6), (Rp22,Rq10,Rr7), (Rp22,Rq10,Rr8), (Rp22, Rq10,Rr9), (Rp22,Rq10,Rr10), (Rp22,Rq10,Rr11), (Rp22, Rq10,Rr12), (Rp22,Rq10,Rr13), (Rp22,Rq10,Rr14), (Rp22, Rq10,Rr15), (Rp22,Rq10,Rr16), (Rp22,Rq10,Rr17), (Rp22, Rq10,Rr18), (Rp22,Rq10,Rr19), (Rp22,Rq10,Rr20), (Rp22, Rq10,Rr21), (Rp22,Rq10,Rr22), (Rp22,Rq11,Rr1), (Rp22, Rq11,Rr2), (Rp22,Rq11,Rr3), (Rp22,Rq11,Rr4), (Rp22, Rq11,Rr5), (Rp22,Rq11,Rr6), (Rp22,Rq11,Rr7), (Rp22, Rq11,Rr8), (Rp22,Rq11,Rr9), (Rp22,Rq11,Rr10), (Rp22, Rq11, Rr11), (Rp22,Rq11,Rr12), (Rp22,Rq11,Rr13), (Rp22, Rq11,Rr14), (Rp22,Rq11,Rr15), (Rp22,Rq11,Rr16), (Rp22, Rq11,Rr17), (Rp22,Rq11,Rr18), (Rp22,Rq11,Rr19), (Rp22, Rq11,Rr20), (Rp22,Rq11,Rr21), (Rp22,Rq11,Rr22), (Rp22, Rq12,Rr1), (Rp22,Rq12,Rr2), (Rp22,Rq12,Rr3), (Rp22, Rq12,Rr4), (Rp22,Rq12,Rr5), (Rp22,Rq12,Rr6), (Rp22, Rq12,Rr7), (Rp22,Rq12,Rr8), (Rp22,Rq12,Rr9), (Rp22, Rq12,Rr10), (Rp22,Rq12,Rr11), (Rp22,Rq12,Rr12), (Rp22, Rq12,Rr13), (Rp22,Rq12,Rr14), (Rp22,Rq12,Rr15), (Rp22, Rq12,Rr16), (Rp22,Rq12,Rr17), (Rp22,Rq12,Rr18), (Rp22, Rq12,Rr19), (Rp22,Rq12,Rr20), (Rp22,Rq12,Rr21), (Rp22, Rq12,Rr22), (Rp23,Rq1,Rr1), (Rp23,Rq1,Rr2), (Rp23,Rq1, Rr3), (Rp23,Rq1,Rr4), (Rp23,Rq1,Rr5), (Rp23,Rq1,Rr6), (Rp23,Rq1,Rr7), (Rp23,Rq1,Rr8), (Rp23,Rq1,Rr9), (Rp23, Rq1,Rr10), (Rp23, Rq1,Rr11), (Rp23,Rq1,Rr12), (Rp23, Rq1,Rr13), (Rp23,Rq1,Rr14), (Rp23,Rq1,Rr15), (Rp23, Rq1,Rr16), (Rp23,Rq1,Rr17), (Rp23,Rq1,Rr18), (Rp23, Rq1,Rr19), (Rp23,Rq1,Rr20), (Rp23,Rq1,Rr21), (Rp23, Rq1,Rr22), (Rp23,Rq2,Rr1), (Rp23,Rq2,Rr2), (Rp23,Rq2, Rr3), (Rp23,Rq2,Rr4), (Rp23,Rq2,Rr5), (Rp23,Rq2,Rr6), (Rp23,Rq2,Rr7), (Rp23,Rq2,Rr8), (Rp23,Rq2,Rr9), (Rp23, Rq2,Rr10), (Rp23,Rq2,Rr11), (Rp23,Rq2,Rr12), (Rp23, Rq2,Rr13), (Rp23,Rq2,Rr14), (Rp23,Rq2,Rr15), (Rp23, Rq2,Rr16), (Rp23,Rq2,Rr17), (Rp23,Rq2,Rr18), (Rp23, Rq2,Rr19), (Rp23,Rq2,Rr20), (Rp23,Rq2,Rr21), (423,Rq2, Rr22), (Rp23,Rq3,Rr1), (Rp23,Rq3,Rr2), (Rp23,Rq3,Rr3), (Rp23,Rq3,Rr4), (Rp23,Rq3,Rr5), (Rp23,Rq3,Rr6), (Rp23, Rq3,Rr7), (Rp23,Rq3,Rr8), (Rp23,Rq3,Rr9), (Rp23,Rq3, Rr10), (Rp23,Rq3,Rr11), (Rp23,Rq3,Rr12), (Rp23,Rq3,

Rr13), (Rp23,Rq3,Rr14), (Rp23,Rq3,Rr15), (Rp23,Rq3, Rr16), (Rp23,Rq3,Rr17), (Rp23,Rq3,Rr18), (Rp23,Rq3, Rr19), (Rp23,Rq3,Rr20), (Rp23,Rq3,Rr21), (Rp23,Rq3, Rr22), (Rp23,Rq4,Rr1), (Rp23,Rq4,Rr2), (Rp23,Rq4,Rr3), (Rp23,Rq4,Rr4), (Rp23,Rq4,Rr5), (Rp23,Rq4,Rr6), (Rp23, Rq4,Rr7), (Rp23,Rq4,Rr8), (Rp23,Rq4,Rr9), (Rp23,Rq4, Rr10), (Rp23,Rq4,Rr11), (Rp23,Rq4,Rr12), (Rp23,Rq4, Rr13), (Rp23,Rq4,Rr14), (Rp23,Rq4,Rr15), (Rp23,Rq4, Rr16), (Rp23,Rq4,Rr17), (Rp23,Rq4,Rr18), (Rp23,Rq4, Rr19), (Rp23,Rq4,Rr20), (Rp23,Rq4,Rr21), (Rp23,Rq4, Rr22), (Rp23,Rq5,Rr1), (Rp23,Rq5,Rr2), (Rp23,Rq5,Rr3), (Rp23,Rq5, Rr4), (Rp23,Rq5,Rr5), (Rp23,Rq5,Rr6), (Rp23, Rq5,Rr7), (Rp23,Rq5,Rr8), (Rp23,Rq5,Rr9), (Rp23,Rq5, Rr10), (Rp23,Rq5,Rr11), (Rp23,Rq5,Rr12), (Rp23,Rq5, Rr13), (Rp23,Rq5,Rr14), (Rp23,Rq5,Rr15), (Rp23,Rq5, Rr16), (Rp23,Rq5,Rr17), (Rp23,Rq5,Rr18), (Rp23,Rq5, Rr19), (Rp23,Rq5,Rr20), (Rp23,Rq5,Rr21), (Rp23,Rq5, Rr22), (Rp23,Rq6,Rr1), (Rp23,Rq6,Rr2), (Rp23,Rq6,Rr3), (Rp23,Rq6,Rr4), (Rp23,Rq6,Rr5), (Rp23,Rq6,Rr6), (Rp23, Rq6,Rr7), (Rp23,Rq6,Rr8), (Rp23,Rq6,Rr9), (Rp23,Rq6, Rr10), (Rp23,Rq6,Rr11), (Rp23,Rq6,Rr12), (Rp23,Rq6, Rr13), (Rp23,Rq6,Rr14), (Rp23,Rq6,Rr15), (Rp23,Rq6, Rr16), (Rp23,Rq6,Rr17), (Rp23, Rq6,Rr18), (Rp23,Rq6, Rr19), (Rp23,Rq6,Rr20), (Rp23,Rq6,Rr21), (Rp23,Rq6, Rr22), (Rp23,Rq7,Rr1), (Rp23,Rq7,Rr2), (Rp23,Rq7,Rr3), (Rp23,Rq7,Rr4), (Rp23,Rq7,Rr5), (Rp23,Rq7, Rr6), (Rp23, Rq7,Rr7), (Rp23,Rq7,Rr8), (Rp23,Rq7,Rr9), (Rp23,Rq7, Rr10), (Rp23,Rq7,Rr11), (Rp23,Rq7,Rr12), (Rp23,Rq7, Rr13), (Rp23,Rq7,Rr14), (Rp23,Rq7,Rr15), (Rp23,Rq7, Rr16), (Rp23,Rq7,Rr17), (Rp23,Rq7,Rr18), (Rp23,Rq7, Rr19), (Rp23,Rq7,Rr20), (Rp23,Rq7,Rr21), (Rp23,Rq7, Rr22), (Rp23,Rq8,Rr1), (Rp23,Rq8,Rr2), (Rp23,Rq8,Rr3), (Rp23,Rq8,Rr4), (Rp23,Rq8,Rr5), (Rp23,Rq8,Rr6), (Rp23, Rq8,Rr7), (Rp23,Rq8,Rr8), (Rp23,Rq8,Rr9), (Rp23,Rq8, Rr10), (Rp23,Rq8,Rr11), (Rp23,Rq8,Rr12), (Rp23,Rq8, Rr13), (Rp23,Rq8,Rr14), (Rp23,Rq8,Rr15), (Rp23,Rq8, Rr16), (Rp23,Rq8,Rr17), (Rp23,Rq8,Rr18), (Rp23,Rq8, Rr19), (Rp23,Rq8,Rr20), (Rp23,Rq8,Rr21), (Rp23,Rq8, Rr22), (Rp23,Rq9,Rr1), (Rp23,Rq9,Rr2), (Rp23,Rq9,Rr3), (Rp23,Rq9,Rr4), (Rp23,Rq9,Rr5), (Rp23,Rq9,Rr6), (Rp23, Rq9,Rr7), (Rp23,Rq9,Rr8), (Rp23,Rq9,Rr9), (Rp23,Rq9, Rr10), (Rp23,Rq9,Rr11), (Rp23,Rq9,Rr12), (Rp23,Rq9, Rr13), (Rp23,Rq9,Rr14), (Rp23,Rq9,Rr15), (Rp23,Rq9, Rr16), (Rp23,Rq9,Rr17), (Rp23,Rq9,Rr18), (Rp23,Rq9, Rr19), (Rp23,Rq9,Rr20), (Rp23,Rq9,Rr21), (Rp23,Rq9, Rr22), (Rp23,Rq10,Rr1), (Rp23,Rq10,Rr2), (Rp23,Rq10, Rr3), (Rp23,Rq10,Rr4), (Rp23,Rq10,Rr5), (Rp23,Rq10, Rr6), (Rp23,Rq10,Rr7), (Rp23,Rq10,Rr8), (Rp23,Rq10, Rr9), (Rp23,Rq10,Rr10), (Rp23, Rq10,Rr11), (Rp23,Rq10, Rr12), (Rp23,Rq10,Rr13), (Rp23,Rq10,Rr14), (Rp23,Rq10, Rr15), (Rp23,Rq10,Rr16), (Rp23,Rq10,Rr17), (Rp23,Rq10, Rr18), (Rp23,Rq10,Rr19), (Rp23,Rq10, Rr20), (Rp23,Rq10, Rr21), (Rp23,Rq10,Rr22), (Rp23,Rq11,Rr1), (Rp23,Rq11, Rr2), (Rp23,Rq11,Rr3), (Rp23,Rq11,Rr4), (Rp23,Rq11, Rr5), (Rp23,Rq11,Rr6), (Rp23,Rq11,Rr7), (Rp23, Rq11, Rr8), (Rp23,Rq11,Rr9), (Rp23,Rq11,Rr10), (Rp23,Rq11, Rr11), (Rp23,Rq11,Rr12), (Rp23,Rq11,Rr13), (Rp23,Rq11, Rr14), (Rp23,Rq11,Rr15), (Rp23,Rq11,Rr16), (Rp23,Rq11, Rr17), (Rp23,Rq11,Rr18), (Rp23,Rq11,Rr19), (Rp23,Rq11, Rr20), (Rp23,Rq11,Rr21), (Rp23, Rq11,Rr22), (Rp23,Rq12, Rr1), (Rp23,Rq12,Rr2), (Rp23,Rq12,Rr3), (Rp23,Rq12, Rr4), (Rp23,Rq12,Rr5), (Rp23,Rq12,Rr6), (Rp23,Rq12, Rr7), (Rp23,Rq12,Rr8), (Rp23,Rq12,Rr9), (Rp23,Rq12, Rr10), (Rp23,Rq12,Rr11), (Rp23,Rq12,Rr12), (Rp23,Rq12, Rr13), (Rp23,Rq12,Rr14), (Rp23,Rq12,Rr15), (Rp23,Rq12, Rr16), (Rp23,Rq12,Rr17), (Rp23,Rq12,Rr18), (Rp23,Rq12, Rr19), (Rp23,Rq12,Rr20), (Rp23,Rq12,Rr21), (Rp23,Rq12, Rr22), (Rp24,Rq1,Rr1), (Rp24,Rq1,Rr2), (Rp24,Rq1,Rr3), (Rp24,Rq1,Rr4), (Rp24,Rq1,Rr5), (Rp24,Rq1,Rr6), (Rp24, Rq1,Rr7), (Rp24,Rq1,Rr8), (Rp24,Rq1,Rr9), (Rp24,Rq1, Rr10), (Rp24,Rq1,Rr11), (Rp24,Rq1,Rr12), (Rp24,Rq1, Rr13), (Rp24,Rq1,Rr14), (Rp24,Rq1,Rr15), (Rp24,Rq1, Rr16), (Rp24,Rq1, Rr17), (Rp24,Rq1,Rr18), (Rp24,Rq1, Rr19), (Rp24,Rq1,Rr20), (Rp24,Rq1,Rr21), (Rp24,Rq1, Rr22), (Rp24,Rq2,Rr1), (Rp24,Rq2,Rr2), (Rp24,Rq2,Rr3), (Rp24,Rq2,Rr4), (Rp24,Rq2,Rr5), (Rp24,Rq2,Rr6), (Rp24, Rq2,Rr7), (Rp24,Rq2,Rr8), (Rp24,Rq2,Rr9), (Rp24,Rq2, Rr10), (Rp24,Rq2,Rr11), (Rp24,Rq2,Rr12), (Rp24,Rq2, Rr13), (Rp24,Rq2,Rr14), (Rp24,Rq2,Rr15), (Rp24,Rq2, Rr16), (Rp24,Rq2,Rr17), (Rp24,Rq2,Rr18), (Rp24,Rq2, Rr19), (Rp24,Rq2,Rr20), (Rp24,Rq2,Rr21), (Rp24,Rq2, Rr22), (Rp24,Rq3,Rr1), (Rp24,Rq3,Rr2), (Rp24,Rq3,Rr3), (Rp24,Rq3,Rr4), (Rp24,Rq3,Rr5), (Rp24,Rq3,Rr6), (Rp24, Rq3,Rr7), (Rp24,Rq3,Rr8), (Rp24, Rq3,Rr9), (Rp24,Rq3, Rr10), (Rp24,Rq3,Rr11), (Rp24,Rq3,Rr12), (Rp24,Rq3, Rr13), (Rp24, Rq3,Rr14), (Rp24,Rq3,Rr15), (Rp24,Rq3, Rr16), (Rp24,Rq3,Rr17), (Rp24,Rq3,Rr18), (Rp24,Rq3, Rr19), (Rp24,Rq3,Rr20), (Rp24,Rq3,Rr21), (Rp24,Rq3, Rr22), (Rp24,Rq4,Rr1), (Rp24, Rq4,Rr2), (Rp24,Rq4,Rr3), (Rp24,Rq4,Rr4), (Rp24,Rq4,Rr5), (Rp24,Rq4,Rr6), (Rp24, Rq4, Rr7), (Rp24,Rq4,Rr8), (Rp24,Rq4,Rr9), (Rp24,Rq4, Rr10), (Rp24,Rq4,Rr11), (Rp24,Rq4,Rr12), (Rp24,Rq4, Rr13), (Rp24,Rq4,Rr14), (Rp24,Rq4,Rr15), (Rp24,Rq4, Rr16), (Rp24,Rq4,Rr17), (Rp24,Rq4,Rr18), (Rp24,Rq4, Rr19), (Rp24,Rq4,Rr20), (Rp24,Rq4,Rr21), (Rp24,Rq4, Rr22), (Rp24,Rq5,Rr1), (Rp24,Rq5,Rr2), (Rp24,Rq5,Rr3), (Rp24,Rq5,Rr4), (Rp24,Rq5,Rr5), (Rp24,Rq5,Rr6), (Rp24, Rq5,Rr7), (Rp24,Rq5,Rr8), (Rp24,Rq5,Rr9), (Rp24,Rq5, Rr10), (Rp24,Rq5,Rr11), (Rp24,Rq5,Rr12), (Rp24,Rq5, Rr13), (Rp24,Rq5,Rr14), (Rp24,Rq5,Rr15), (Rp24,Rq5, Rr16), (Rp24,Rq5,Rr17), (Rp24,Rq5,Rr18), (Rp24,Rq5, Rr19), (Rp24,Rq5,Rr20), (Rp24,Rq5,Rr21), (Rp24,Rq5, Rr22), (Rp24,Rq6,Rr1), (Rp24,Rq6,Rr2), (Rp24,Rq6,Rr3), (Rp24,Rq6,Rr4), (Rp24,Rq6,Rr5), (Rp24,Rq6,Rr6), (Rp24, Rq6,Rr7), (Rp24,Rq6,Rr8), (Rp24,Rq6,Rr9), (Rp24,Rq6, Rr10), (Rp24,Rq6,Rr11), (Rp24,Rq6,Rr12), (Rp24,Rq6, Rr13), (Rp24,Rq6,Rr14), (Rp24,Rq6,Rr15), (Rp24,Rq6, Rr16), (Rp24,Rq6,Rr17), (Rp24,Rq6,Rr18), (Rp24,Rq6, Rr19), (Rp24,Rq6,Rr20), (Rp24,Rq6,Rr21), (Rp24,Rq6, Rr22), (Rp24,Rq7,Rr1), (Rp24,Rq7,Rr2), (Rp24,Rq7,Rr3), (Rp24,Rq7,Rr4), (Rp24,Rq7,Rr5), (Rp24,Rq7,Rr6), (Rp24, Rq7,Rr7), (Rp24,Rq7,Rr8), (Rp24,Rq7,Rr9), (Rp24,Rq7, Rr10), (Rp24,Rq7,Rr11), (Rp24,Rq7,Rr12), (Rp24,Rq7, Rr13), (Rp24,Rq7,Rr14), (Rp24,Rq7,Rr15), (Rp24,Rq7, Rr16), (Rp24,Rq7,Rr17), (Rp24,Rq7,Rr18), (Rp24,Rq7, Rr19), (Rp24,Rq7,Rr20), (Rp24,Rq7,Rr21), (Rp24,Rq7, Rr22), (Rp24,Rq8,Rr1), (Rp24,Rq8,Rr2), (Rp24,Rq8,Rr3), (Rp24,Rq8,Rr4), (Rp24,Rq8,Rr5), (Rp24,Rq8,Rr6), (Rp24, Rq8,Rr7), (Rp24,Rq8,Rr8), (Rp24,Rq8,Rr9), (Rp24,Rq8, Rr10), (Rp24, Rq8,Rr11), (Rp24,Rq8,Rr12), (Rp24,Rq8, Rr13), (Rp24,Rq8,Rr14), (Rp24,Rq8,Rr15), (Rp24,Rq8, Rr16), (Rp24,Rq8,Rr17), (Rp24,Rq8,Rr18), (Rp24,Rq8, Rr19), (Rp24,Rq8,Rr20), (Rp24,Rq8,Rr21), (Rp24,Rq8, Rr22), (Rp24,Rq9,Rr1), (Rp24,Rq9,Rr2), (Rp24,Rq9,Rr3), (Rp24,Rq9,Rr4), (Rp24,Rq9,Rr5), (Rp24,Rq9,Rr6), (Rp24, Rq9,Rr7), (Rp24,Rq9,Rr8), (Rp24,Rq9,Rr9), (Rp24,Rq9, Rr10), (Rp24,Rq9,Rr11), (Rp24,Rq9,Rr12), (Rp24,Rq9, Rr13), (Rp24,Rq9,Rr14), (Rp24,Rq9,Rr15), (Rp24,Rq9, Rr16), (Rp24,Rq9,Rr17), (Rp24,Rq9,Rr18), (Rp24,Rq9, Rr19), (Rp24,Rq9,Rr20), (Rp24,Rq9,Rr21), (Rp24,Rq9, Rr22), (Rp24,Rq10,Rr1), (Rp24,Rq10, Rr2), (Rp24,Rq10, Rr3), (Rp24,Rq10,Rr4), (Rp24,Rq10,Rr5), (Rp24,Rq10, Rr6), (Rp24,Rq10,Rr7), (Rp24,Rq10,Rr8), (Rp24,Rq10, Rr9), (Rp24,Rq10,Rr10), (Rp24,Rq10,Rr11), (Rp24,Rq10,

Rr12), (Rp24,Rq10,Rr13), (Rp24,Rq10,Rr14), (Rp24,Rq10, Rr15), (Rp24,Rq10,Rr16), (Rp24,Rq10,Rr17), (Rp24,Rq10, Rr18), (Rp24,Rq10,Rr19), (Rp24,Rq10,Rr20), (Rp24,Rq10, Rr21), (Rp24,Rq10,Rr22), (Rp24,Rq11,Rr1), (Rp24,Rq11, Rr2), (Rp24,Rq11,Rr3), (Rp24,Rq11,Rr4), (Rp24,Rq11, Rr5), (Rp24,Rq11,Rr6), (Rp24,Rq11,Rr7), (Rp24,Rq11, Rr8), (Rp24,Rq11,Rr9), (Rp24,Rq11,Rr10), (Rp24,Rq11, Rr11), (Rp24,Rq11,Rr12), (Rp24,Rq11,Rr13), (Rp24,Rq11, Rr14), (Rp24,Rq11,Rr15), (Rp24,Rq11,Rr16), (Rp24,Rq11, Rr17), (Rp24,Rq11,Rr18), (Rp24,Rq11,Rr19), (Rp24,Rq11, Rr20), (Rp24,Rq11,Rr21), (Rp24,Rq11,Rr22), (Rp24, Rq12, Rr1), (Rp24,Rq12,Rr2), (Rp24,Rq12,Rr3), (Rp24,Rq12, Rr4), (Rp24,Rq12,Rr5), (Rp24,Rq12,Rr6), (Rp24,Rq12, Rr7), (Rp24,Rq12,Rr8), (Rp24,Rq12,Rr9), (Rp24,Rq12, Rr10), (Rp24,Rq12,Rr11), (Rp24,Rq12,Rr12), (Rp24,Rq12, Rr13), (Rp24,Rq12,Rr14), (Rp24,Rq12,Rr15), (Rp24,Rq12, Rr16), (Rp24,Rq12,Rr17), (Rp24,Rq12,Rr18), (Rp24,Rq12, Rr19), (Rp24,Rq12,Rr20), (Rp24,Rq12,Rr21), (Rp24,Rq12, Rr22), (Rp25,Rq1,Rr1), (Rp25,Rq1,Rr2), (Rp25, Rq1,Rr3), (Rp25,Rq1,Rr4), (Rp25,Rq1,Rr5), (Rp25,Rq1,Rr6), (Rp25, Rq1,Rr7), (Rp25,Rq1,Rr8), (Rp25,Rq1,Rr9), (Rp25,Rq1, Rr10), (Rp25,Rq1,Rr11), (Rp25,Rq1,Rr12), (Rp25,Rq1, Rr13), (Rp25,Rq1,Rr14), (Rp25,Rq1,Rr15), (Rp25,Rq1, Rr16), (Rp25,Rq1,Rr17), (Rp25,Rq1, Rr18), (Rp25,Rq1, Rr19), (Rp25,Rq1,Rr20), (Rp25,Rq1,Rr21), (Rp25,Rq1, Rr22), (Rp25,Rq2,Rr1), (Rp25,Rq2,Rr2), (Rp25,Rq2,Rr3), (Rp25,Rq2,Rr4), (Rp25,Rq2,Rr5), (Rp25,Rq2,Rr6), (Rp25, Rq2,Rr7), (Rp25,Rq2,Rr8), (Rp25,Rq2,Rr9), (Rp25,Rq2, Rr10), (Rp25,Rq2,Rr11), (Rp25,Rq2,Rr12), (Rp25,Rq2, Rr13), (Rp25,Rq2,Rr14), (Rp25,Rq2,Rr15), (Rp25,Rq2, Rr16), (Rp25,Rq2,Rr17), (Rp25,Rq2,Rr18), (Rp25,Rq2, Rr19), (Rp25,Rq2,Rr20), (Rp25,Rq2,Rr21), (Rp25,Rq2, Rr22), (Rp25,Rq3,Rr1), (Rp25,Rq3,Rr2), (Rp25,Rq3,Rr3), (Rp25,Rq3,Rr4), (Rp25,Rq3,Rr5), (Rp25,Rq3,Rr6), (Rp25, Rq3,Rr7), (Rp25,Rq3,Rr8), (Rp25,Rq3,Rr9), (Rp25,Rq3, Rr10), (Rp25,Rq3,Rr11), (Rp25,Rq3,Rr12), (Rp25,Rq3, Rr13), (Rp25,Rq3,Rr14), (Rp25,Rq3,Rr15), (Rp25,Rq3, Rr16), (Rp25,Rq3,Rr17), (Rp25,Rq3,Rr18), (Rp25,Rq3, Rr19), (Rp25, Rq3,Rr20), (Rp25,Rq3,Rr21), (Rp25,Rq3, Rr22), (Rp25,Rq4,Rr1), (Rp25,Rq4,Rr2), (Rp25,Rq4,Rr3), (Rp25,Rq4,Rr4), (Rp25,Rq4,Rr5), (Rp25,Rq4,Rr6), (Rp25, Rq4,Rr7), (Rp25,Rq4,Rr8), (Rp25,Rq4,Rr9), (Rp25,Rq4, Rr10), (Rp25,Rq4,Rr11), (Rp25,Rq4,Rr12), (Rp25,Rq4, Rr13), (Rp25,Rq4,Rr14), (Rp25,Rq4,Rr15), (Rp25,Rq4, Rr16), (Rp25,Rq4,Rr17), (Rp25,Rq4,Rr18), (Rp25,Rq4, Rr19), (Rp25,Rq4,Rr20), (Rp25,Rq4,Rr21), (Rp25,Rq4, Rr22), (Rp25,Rq5,Rr1), (Rp25,Rq5,Rr2), (Rp25,Rq5,Rr3), (Rp25,Rq5,Rr4), (Rp25,Rq5,Rr5), (Rp25,Rq5,Rr6), (Rp25, Rq5,Rr7), (Rp25,Rq5,Rr8), (Rp25,Rq5,Rr9), (Rp25,Rq5, Rr10), (Rp25,Rq5,Rr11), (Rp25,Rq5,Rr12), (Rp25,Rq5, Rr13), (Rp25,Rq5,Rr14), (Rp25,Rq5,Rr15), (Rp25,Rq5, Rr16), (Rp25,Rq5,Rr17), (Rp25,Rq5,Rr18), (Rp25,Rq5, Rr19), (Rp25,Rq5,Rr20), (Rp25,Rq5,Rr21), (Rp25,Rq5, Rr22), (Rp25,Rq6,Rr1), (Rp25,Rq6,Rr2), (Rp25,Rq6,Rr3), (Rp25,Rq6,Rr4), (Rp25,Rq6,Rr5), (Rp25,Rq6,Rr6), (Rp25, Rq6,Rr7), (Rp25,Rq6,Rr8), (Rp25,Rq6,Rr9), (Rp25,Rq6, Rr10), (Rp25,Rq6,Rr11), (Rp25,Rq6,Rr12), (Rp25,Rq6, Rr13), (Rp25,Rq6,Rr14), (Rp25,Rq6,Rr15), (Rp25,Rq6, Rr16), (Rp25,Rq6,Rr17), (Rp25,Rq6,Rr18), (Rp25,Rq6, Rr19), (Rp25,Rq6,Rr20), (Rp25,Rq6,Rr21), (Rp25,Rq6, Rr22), (Rp25,Rq7,Rr1), (Rp25,Rq7,Rr2), (Rp25,Rq7,Rr3), (Rp25,Rq7,Rr4), (Rp25,Rq7,Rr5), (Rp25,Rq7,Rr6), (Rp25, Rq7,Rr7), (Rp25,Rq7,Rr8), (Rp25,Rq7,Rr9), (Rp25,Rq7, Rr10), (Rp25,Rq7,Rr11), (Rp25,Rq7,Rr12), (Rp25,Rq7, Rr13), (Rp25,Rq7,Rr14), (Rp25,Rq7,Rr15), (Rp25,Rq7, Rr16), (Rp25,Rq7,Rr17), (Rp25,Rq7,Rr18), (Rp25,Rq7, Rr19), (Rp25,Rq7,Rr20), (Rp25,Rq7,Rr21), (Rp25,Rq7, Rr22), (Rp25,Rq8,Rr1), (Rp25,Rq8,Rr2), (Rp25,Rq8,Rr3), (Rp25,Rq8,Rr4), (Rp25,Rq8,Rr5), (Rp25,Rq8,Rr6), (Rp25, Rq8,Rr7), (Rp25,Rq8,Rr8), (Rp25,Rq8,Rr9), (Rp25,Rq8, Rr10), (Rp25,Rq8,Rr11), (Rp25,Rq8,Rr12), (Rp25,Rq8, Rr13), (Rp25,Rq8,Rr14), (Rp25,Rq8,Rr15), (Rp25,Rq8, Rr16), (Rp25, Rq8,Rr17), (Rp25,Rq8,Rr18), (Rp25,Rq8, Rr19), (Rp25,Rq8,Rr20), (Rp25,Rq8,Rr21), (Rp25,Rq8, Rr22), (Rp25,Rq9,Rr1), (Rp25,Rq9,Rr2), (Rp25,Rq9,Rr3), (Rp25,Rq9,Rr4), (Rp25,Rq9,Rr5), (Rp25,Rq9,Rr6), (Rp25, Rq9,Rr7), (Rp25,Rq9,Rr8), (Rp25,Rq9,Rr9), (Rp25,Rq9, Rr10), (Rp25,Rq9,Rr11), (Rp25,Rq9,Rr12), (Rp25,Rq9, Rr13), (Rp25,Rq9,Rr14), (Rp25,Rq9,Rr15), (Rp25,Rq9, Rr16), (Rp25,Rq9,Rr17), (Rp25,Rq9,Rr18), (Rp25,Rq9, Rr19), (Rp25,Rq9,Rr20), (Rp25,Rq9,Rr21), (Rp25,Rq9, Rr22), (Rp25,Rq10,Rr1), (Rp25,Rq10,Rr2), (Rp25,Rq10, Rr3), (Rp25,Rq10,Rr4), (Rp25,Rq10,Rr5), (Rp25,Rq10, Rr6), (Rp25,Rq10,Rr7), (Rp25,Rq10,Rr8), (Rp25,Rq10, Rr9), (Rp25,Rq10,Rr10), (Rp25,Rq10,Rr11), (Rp25,Rq10, Rr12), (Rp25, Rq10,Rr13), (Rp25,Rq10,Rr14), (Rp25,Rq10, Rr15), (Rp25,Rq10,Rr16), (Rp25,Rq10,Rr17), (Rp25,Rq10, Rr18), (Rp25,Rq10,Rr19), (Rp25,Rq10,Rr20), (Rp25,Rq10, Rr21), (Rp25,Rq10, Rr22), (Rp25,Rq11,Rr1), (Rp25,Rq11, Rr2), (Rp25,Rq11,Rr3), (Rp25,Rq11,Rr4), (Rp25,Rq11, Rr5), (Rp25,Rq11,Rr6), (Rp25,Rq11,Rr7), (Rp25,Rq11, Rr8), (Rp25,Rq11,Rr9), (Rp25,Rq11,Rr10), (Rp25,Rq11, Rr11), (Rp25,Rq11,Rr12), (Rp25,Rq11,Rr13), (Rp25,Rq11, Rr14), (Rp25,Rq11,Rr15), (Rp25,Rq11,Rr16), (Rp25,Rq11, Rr17), (Rp25,Rq11,Rr18), (Rp25,Rq11,Rr19), (Rp25,Rq11, Rr20), (Rp25,Rq11,Rr21), (Rp25,Rq11,Rr22), (Rp25,Rq12, Rr1), (Rp25,Rq12,Rr2), (Rp25,Rq12,Rr3), (Rp25,Rq12, Rr4), (Rp25,Rq12,Rr5), (Rp25,Rq12,Rr6), (Rp25, Rq12, Rr7), (Rp25,Rq12,Rr8), (Rp25,Rq12,Rr9), (Rp25,Rq12, Rr10), (Rp25,Rq12,Rr11), (Rp25,Rq12,Rr12), (Rp25,Rq12, Rr13), (Rp25,Rq12,Rr14), (Rp25,Rq12,Rr15), (Rp25,Rq12, Rr16), (Rp25,Rq12,Rr17), (Rp25,Rq12,Rr18), (Rp25,Rq12, Rr19), (Rp25,Rq12,Rr20), (Rp25,Rq12,Rr21), (Rp25,Rq12, Rr22), (Rp26,Rq1,Rr1), (Rp26,Rq1,Rr2), (Rp26,Rq1,Rr3), (Rp26,Rq1,Rr4), (Rp26,Rq1,Rr5), (Rp26,Rq1,Rr6), (Rp26, Rq1,Rr7), (Rp26,Rq1,Rr8), (Rp26,Rq1,Rr9), (Rp26,Rq1, Rr10), (Rp26,Rq1,Rr11), (Rp26,Rq1,Rr12), (Rp26,Rq1, Rr13), (Rp26,Rq1,Rr14), (Rp26,Rq1,Rr15), (Rp26,Rq1, Rr16), (Rp26,Rq1,Rr17), (Rp26,Rq1,Rr18), (Rp26,Rq1, Rr19), (Rp26,Rq1,Rr20), (Rp26,Rq1,Rr21), (Rp26,Rq1, Rr22), (Rp26,Rq2,Rr1), (Rp26,Rq2,Rr2), (Rp26,Rq2,Rr3), (Rp26,Rq2,Rr4), (Rp26,Rq2,Rr5), (Rp26,Rq2,Rr6), (Rp26, Rq2,Rr7), (Rp26,Rq2,Rr8), (Rp26,Rq2,Rr9), (Rp26,Rq2, Rr10), (Rp26,Rq2,Rr11), (Rp26,Rq2,Rr12), (Rp26,Rq2, Rr13), (Rp26,Rq2,Rr14), (Rp26,Rq2,Rr15), (Rp26,Rq2, Rr16), (Rp26,Rq2,Rr17), (Rp26,Rq2,Rr18), (Rp26,Rq2, Rr19), (Rp26,Rq2,Rr20), (Rp26,Rq2,Rr21), (Rp26,Rq2, Rr22), (Rp26,Rq3,Rr1), (Rp26,Rq3,Rr2), (Rp26,Rq3,Rr3), (Rp26,Rq3,Rr4), (Rp26,Rq3,Rr5), (Rp26,Rq3,Rr6), (Rp26, Rq3,Rr7), (Rp26,Rq3,Rr8), (Rp26,Rq3,Rr9), (Rp26,Rq3, Rr10), (Rp26,Rq3,Rr11), (Rp26,Rq3,Rr12), (Rp26,Rq3, Rr13), (Rp26,Rq3,Rr14), (Rp26,Rq3,Rr15), (Rp26,Rq3, Rr16), (Rp26,Rq3,Rr17), (Rp26,Rq3,Rr18), (Rp26,Rq3, Rr19), (Rp26,Rq3,Rr20), (Rp26,Rq3,Rr21), (Rp26,Rq3, Rr22), (Rp26,Rq4,Rr1), (Rp26,Rq4,Rr2), (Rp26,Rq4,Rr3), (Rp26,Rq4, Rr4), (Rp26,Rq4,Rr5), (Rp26,Rq4,Rr6), (Rp26, Rq4,Rr7), (Rp26,Rq4,Rr8), (Rp26,Rq4,Rr9), (Rp26,Rq4, Rr10), (Rp26,Rq4,Rr11), (Rp26,Rq4,Rr12), (Rp26,Rq4, Rr13), (Rp26,Rq4,Rr14), (Rp26,Rq4,Rr15), (Rp26,Rq4, Rr16), (Rp26,Rq4,Rr17), (Rp26,Rq4,Rr18), (Rp26,Rq4, Rr19), (Rp26,Rq4,Rr20), (Rp26,Rq4,Rr21), (Rp26,Rq4, Rr22), (Rp26,Rq5,Rr1), (Rp26,Rq5,Rr2), (Rp26,Rq5,Rr3), (Rp26,Rq5,Rr4), (Rp26,Rq5,Rr5), (Rp26,Rq5,Rr6), (Rp26, Rq5,Rr7), (Rp26,Rq5,Rr8), (Rp26,Rq5,Rr9), (Rp26,Rq5,

Rr10), (Rp26,Rq5,Rr11), (Rp26,Rq5,Rr12), (Rp26,Rq5, Rr13), (Rp26,Rq5,Rr14), (Rp26,Rq5,Rr15), (Rp26,Rq5, Rr16), (Rp26,Rq5,Rr17), (Rp26, Rq5,Rr18), (Rp26,Rq5, Rr19), (Rp26,Rq5,Rr20), (Rp26,Rq5,Rr21), (Rp26,Rq5, Rr22), (Rp26,Rq6,Rr1), (Rp26,Rq6,Rr2), (Rp26,Rq6,Rr3), (Rp26,Rq6,Rr4), (Rp26,Rq6,Rr5), (Rp26,Rq6, Rr6), (Rp26, Rq6,Rr7), (Rp26,Rq6,Rr8), (Rp26,Rq6,Rr9), (Rp26,Rq6, Rr10), (Rp26,Rq6,Rr11), (Rp26,Rq6,Rr12), (Rp26,Rq6, Rr13), (Rp26,Rq6,Rr14), (Rp26,Rq6,Rr15), (Rp26,Rq6, Rr16), (Rp26,Rq6,Rr17), (Rp26,Rq6,Rr18), (Rp26,Rq6, Rr19), (Rp26,Rq6,Rr20), (Rp26,Rq6,Rr21), (Rp26,Rq6, Rr22), (Rp26,Rq7,Rr1), (Rp26,Rq7,Rr2), (Rp26,Rq7,Rr3), (Rp26,Rq7,Rr4), (Rp26,Rq7,Rr5), (Rp26,Rq7,Rr6), (Rp26, Rq7,Rr7), (Rp26,Rq7,Rr8), (Rp26,Rq7,Rr9), (Rp26,Rq7, Rr10), (Rp26,Rq7,Rr11), (Rp26,Rq7,Rr12), (Rp26,Rq7, Rr13), (Rp26,Rq7,Rr14), (Rp26,Rq7,Rr15), (Rp26,Rq7, Rr16), (Rp26,Rq7,Rr17), (Rp26,Rq7,Rr18), (Rp26,Rq7, Rr19), (Rp26,Rq7,Rr20), (Rp26,Rq7,Rr21), (Rp26,Rq7, Rr22), (Rp26,Rq8,Rr1), (Rp26,Rq8,Rr2), (Rp26,Rq8,Rr3), (Rp26,Rq8,Rr4), (Rp26,Rq8,Rr5), (Rp26,Rq8,Rr6), (Rp26, Rq8,Rr7), (Rp26,Rq8,Rr8), (Rp26,Rq8,Rr9), (Rp26,Rq8, Rr10), (Rp26,Rq8,Rr11), (Rp26,Rq8,Rr12), (Rp26,Rq8, Rr13), (Rp26,Rq8,Rr14), (Rp26,Rq8,Rr15), (Rp26,Rq8, Rr16), (Rp26,Rq8,Rr17), (Rp26,Rq8,Rr18), (Rp26,Rq8, Rr19), (Rp26,Rq8,Rr20), (Rp26,Rq8,Rr21), (Rp26,Rq8, Rr22), (Rp26,Rq9,Rr1), (Rp26,Rq9,Rr2), (Rp26,Rq9,Rr3), (Rp26,Rq9,Rr4), (Rp26,Rq9,Rr5), (Rp26,Rq9,Rr6), (Rp26, Rq9,Rr7), (Rp26,Rq9,Rr8), (Rp26,Rq9,Rr9), (Rp26,Rq9, Rr10), (Rp26,Rq9,Rr11), (Rp26,Rq9,Rr12), (Rp26,Rq9, Rr13), (Rp26,Rq9,Rr14), (Rp26,Rq9,Rr15), (Rp26,Rq9, Rr16), (Rp26,Rq9,Rr17), (Rp26,Rq9,Rr18), (Rp26,Rq9, Rr19), (Rp26,Rq9,Rr20), (Rp26,Rq9,Rr21), (Rp26,Rq9, Rr22), (Rp26,Rq10,Rr1), (Rp26,Rq10,Rr2), (Rp26,Rq10, Rr3), (Rp26,Rq10,Rr4), (Rp26,Rq10,Rr5), (Rp26,Rq10, Rr6), (Rp26,Rq10,Rr7), (Rp26,Rq10,Rr8), (Rp26,Rq10, Rr9), (Rp26,Rq10,Rr10), (Rp26,Rq10,Rr11), (Rp26,Rq10, Rr12), (Rp26,Rq10,Rr13), (Rp26,Rq10,Rr14), (Rp26,Rq10, Rr15), (Rp26,Rq10,Rr16), (Rp26,Rq10,Rr17), (Rp26,Rq10, Rr18), (Rp26,Rq10,Rr19), (Rp26,Rq10,Rr20), (Rp26,Rq10, Rr21), (Rp26,Rq10,Rr22), (Rp26,Rq11,Rr1), (Rp26,Rq11, Rr2), (Rp26,Rq11,Rr3), (Rp26,Rq11,Rr4), (Rp26,Rq11, Rr5), (Rp26,Rq11, Rr6), (Rp26,Rq11,Rr7), (Rp26,Rq11, Rr8), (Rp26,Rq11,Rr9), (Rp26,Rq11,Rr10), (Rp26,Rq11, Rr11), (Rp26,Rq11,Rr12), (Rp26,Rq11,Rr13), (Rp26,Rq11, Rr14), (Rp26,Rq11,Rr15), (Rp26,Rq11,Rr16), (Rp26,Rq11, Rr17), (Rp26,Rq11,Rr18), (Rp26,Rq11,Rr19), (Rp26,Rq11, Rr20), (Rp26,Rq11,Rr21), (Rp26,Rq11,Rr22), (Rp26,Rq12, Rr1), (Rp26,Rq12,Rr2), (Rp26,Rq12,Rr3), (Rp26,Rq12, Rr4), (Rp26,Rq12,Rr5), (Rp26,Rq12,Rr6), (Rp26,Rq12, Rr7), (Rp26,Rq12,Rr8), (Rp26,Rq12,Rr9), (Rp26,Rq12, Rr10), (Rp26,Rq12,Rr11), (Rp26,Rq12,Rr12), (Rp26,Rq12, Rr13), (Rp26,Rq12,Rr14), (Rp26,Rq12,Rr15), (Rp26,Rq12, Rr16), (Rp26,Rq12,Rr17), (Rp26,Rq12,Rr18), (Rp26,Rq12, Rr19), (Rp26,Rq12,Rr20), (Rp26,Rq12,Rr21), (Rp26,Rq12, Rr22), (Rp27,Rq1,Rr1), (Rp27,Rq1,Rr2), (Rp27,Rq1,Rr3), (Rp27,Rq1,Rr4), (Rp27,Rq1,Rr5), (Rp27,Rq1,Rr6), (Rp27, Rq1,Rr7), (Rp27,Rq1,Rr8), (Rp27,Rq1,Rr9), (Rp27,Rq1, Rr10), (Rp27,Rq1,Rr11), (Rp27,Rq1,Rr12), (Rp27,Rq1, Rr13), (Rp27,Rq1,Rr14), (Rp27,Rq1,Rr15), (Rp27,Rq1, Rr16), (Rp27,Rq1,Rr17), (Rp27,Rq1,Rr18), (Rp27,Rq1, Rr19), (Rp27,Rq1,Rr20), (Rp27,Rq1,Rr21), (Rp27,Rq1, Rr22), (Rp27,Rq2,Rr1), (Rp27,Rq2,Rr2), (Rp27,Rq2,Rr3), (Rp27,Rq2,Rr4), (Rp27,Rq2,Rr5), (Rp27,Rq2,Rr6), (Rp27, Rq2,Rr7), (Rp27,Rq2,Rr8), (Rp27, Rq2,Rr9), (Rp27,Rq2, Rr10), (Rp27,Rq2,Rr11), (Rp27,Rq2,Rr12), (Rp27,Rq2, Rr13), (Rp27, Rq2,Rr14), (Rp27,Rq2,Rr15), (Rp27,Rq2, Rr16), (Rp27,Rq2,Rr17), (Rp27,Rq2,Rr18), (Rp27,Rq2, Rr19), (Rp27,Rq2,Rr20), (Rp27,Rq2,Rr21), (Rp27,Rq2, Rr22), (Rp27,Rq3,Rr1), (Rp27, Rq3,Rr2), (Rp27,Rq3,Rr3), (Rp27,Rq3,Rr4), (Rp27,Rq3,Rr5), (Rp27,Rq3,Rr6), (Rp27, Rq3, Rr7), (Rp27,Rq3,Rr8), (Rp27,Rq3,Rr9), (Rp27,Rq3, Rr10), (Rp27,Rq3,Rr11), (Rp27,Rq3,Rr12), (Rp27,Rq3, Rr13), (Rp27,Rq3,Rr14), (Rp27,Rq3,Rr15), (Rp27,Rq3, Rr16), (Rp27,Rq3,Rr17), (Rp27,Rq3,Rr18), (Rp27,Rq3, Rr19), (Rp27,Rq3,Rr20), (Rp27,Rq3,Rr21), (Rp27,Rq3, Rr22), (Rp27,Rq4,Rr1), (Rp27,Rq4,Rr2), (Rp27,Rq4,Rr3), (Rp27,Rq4,Rr4), (Rp27,Rq4,Rr5), (Rp27,Rq4,Rr6), (Rp27, Rq4,Rr7), (Rp27,Rq4,Rr8), (Rp27,Rq4,Rr9), (Rp27,Rq4, Rr10), (Rp27,Rq4,Rr11), (Rp27,Rq4,Rr12), (Rp27,Rq4, Rr13), (Rp27,Rq4,Rr14), (Rp27,Rq4,Rr15), (Rp27,Rq4, Rr16), (Rp27,Rq4,Rr17), (Rp27,Rq4,Rr18), (Rp27,Rq4, Rr19), (Rp27,Rq4,Rr20), (Rp27,Rq4,Rr21), (Rp27,Rq4, Rr22), (Rp27,Rq5,Rr1), (Rp27,Rq5,Rr2), (Rp27,Rq5,Rr3), (Rp27,Rq5,Rr4), (Rp27,Rq5,Rr5), (Rp27,Rq5,Rr6), (Rp27, Rq5,Rr7), (Rp27,Rq5,Rr8), (Rp27,Rq5,Rr9), (Rp27,Rq5, Rr10), (Rp27,Rq5,Rr11), (Rp27,Rq5,Rr12), (Rp27,Rq5, Rr13), (Rp27,Rq5,Rr14), (Rp27,Rq5,Rr15), (Rp27,Rq5, Rr16), (Rp27,Rq5,Rr17), (Rp27,Rq5,Rr18), (Rp27,Rq5, Rr19), (Rp27,Rq5,Rr20), (Rp27,Rq5,Rr21), (Rp27,Rq5, Rr22), (Rp27,Rq6,Rr1), (Rp27,Rq6,Rr2), (Rp27,Rq6,Rr3), (Rp27,Rq6,Rr4), (Rp27,Rq6,Rr5), (Rp27,Rq6,Rr6), (Rp27, Rq6,Rr7), (Rp27,Rq6,Rr8), (Rp27,Rq6,Rr9), (Rp27,Rq6, Rr10), (Rp27,Rq6,Rr11), (Rp27,Rq6,Rr12), (Rp27,Rq6, Rr13), (Rp27,Rq6,Rr14), (Rp27,Rq6,Rr15), (Rp27,Rq6, Rr16), (Rp27,Rq6,Rr17), (Rp27,Rq6,Rr18), (Rp27,Rq6, Rr19), (Rp27,Rq6,Rr20), (Rp27,Rq6,Rr21), (Rp27,Rq6, Rr22), (Rp27,Rq7,Rr1), (Rp27,Rq7,Rr2), (Rp27,Rq7,Rr3), (Rp27,Rq7,Rr4), (Rp27,Rq7,Rr5), (Rp27,Rq7,Rr6), (Rp27, Rq7,Rr7), (Rp27,Rq7,Rr8), (Rp27,Rq7,Rr9), (Rp27,Rq7, Rr10), (Rp27, Rq7,Rr11), (Rp27,Rq7,Rr12), (Rp27,Rq7, Rr13), (Rp27,Rq7,Rr14), (Rp27,Rq7,Rr15), (Rp27,Rq7, Rr16), (Rp27,Rq7,Rr17), (Rp27,Rq7,Rr18), (Rp27,Rq7, Rr19), (Rp27,Rq7,Rr20), (Rp27,Rq7,Rr21), (Rp27,Rq7, Rr22), (Rp27,Rq8,Rr1), (Rp27,Rq8,Rr2), (Rp27,Rq8,Rr3), (Rp27,Rq8,Rr4), (Rp27,Rq8,Rr5), (Rp27,Rq8,Rr6), (Rp27, Rq8,Rr7), (Rp27,Rq8,Rr8), (Rp27,Rq8,Rr9), (Rp27,Rq8, Rr10), (Rp27,Rq8,Rr11), (Rp27,Rq8,Rr12), (Rp27,Rq8, Rr13), (Rp27,Rq8,Rr14), (Rp27,Rq8,Rr15), (Rp27,Rq8, Rr16), (Rp27,Rq8,Rr17), (Rp27,Rq8,Rr18), (Rp27,Rq8, Rr19), (Rp27,Rq8,Rr20), (Rp27,Rq8,Rr21), (Rp27,Rq8, Rr22), (Rp27,Rq9,Rr1), (Rp27,Rq9,Rr2), (Rp27,Rq9,Rr3), (Rp27,Rq9,Rr4), (Rp27,Rq9,Rr5), (Rp27,Rq9,Rr6), (Rp27, Rq9,Rr7), (Rp27,Rq9,Rr8), (Rp27,Rq9,Rr9), (Rp27,Rq9, Rr10), (Rp27,Rq9,Rr11), (Rp27,Rq9,Rr12), (Rp27,Rq9, Rr13), (Rp27,Rq9,Rr14), (Rp27,Rq9,Rr15), (Rp27,Rq9, Rr16), (Rp27,Rq9,Rr17), (Rp27,Rq9,Rr18), (Rp27,Rq9, Rr19), (Rp27,Rq9,Rr20), (Rp27,Rq9,Rr21), (Rp27,Rq9, Rr22), (Rp27,Rq10,Rr1), (Rp27,Rq10,Rr2), (Rp27,Rq10, Rr3), (Rp27,Rq10,Rr4), (Rp27,Rq10,Rr5), (Rp27,Rq10, Rr6), (Rp27,Rq10,Rr7), (Rp27,Rq10,Rr8), (Rp27,Rq10, Rr9), (Rp27,Rq10,Rr10), (Rp27,Rq10,Rr11), (Rp27,Rq10, Rr12), (Rp27,Rq10,Rr13), (Rp27,Rq10,Rr14), (Rp27,Rq10, Rr15), (Rp27,Rq10,Rr16), (Rp27,Rq10,Rr17), (Rp27,Rq10, Rr18), (Rp27,Rq10,Rr19), (Rp27,Rq10,Rr20), (Rp27,Rq10, Rr21), (Rp27,Rq10,Rr22), (Rp27,Rq11,Rr1), (Rp27,Rq11, Rr2), (Rp27,Rq11,Rr3), (Rp27,Rq11,Rr4), (Rp27,Rq11, Rr5), (Rp27,Rq11,Rr6), (Rp27,Rq11,Rr7), (Rp27,Rq11, Rr8), (Rp27,Rq11,Rr9), (Rp27,Rq11,Rr10), (Rp27,Rq11, Rr11), (Rp27,Rq11, Rr12), (Rp27,Rq11,Rr13), (Rp27,Rq11, Rr14), (Rp27,Rq11,Rr15), (Rp27,Rq11,Rr16), (Rp27,Rq11, Rr17), (Rp27,Rq11,Rr18), (Rp27,Rq11,Rr19), (Rp27,Rq11, Rr20), (Rp27,Rq11,Rr21), (Rp27,Rq11,Rr22), (Rp27,Rq12, Rr1), (Rp27,Rq12,Rr2), (Rp27,Rq12,Rr3), (Rp27,Rq12, Rr4), (Rp27,Rq12,Rr5), (Rp27,Rq12,Rr6), (Rp27,Rq12,

Rr7), (Rp27,Rq12,Rr8), (Rp27,Rq12,Rr9), (Rp27,Rq12, Rr10), (Rp27,Rq12,Rr11), (Rp27,Rq12,Rr12), (Rp27,Rq12, Rr13), (Rp27,Rq12,Rr14), (Rp27,Rq12,Rr15), (Rp27,Rq12, Rr16), (Rp27,Rq12,Rr17), (Rp27,Rq12,Rr18), (Rp27,Rq12, Rr19), (Rp27,Rq12,Rr20), (Rp27,Rq12,Rr21), (Rp27,Rq12, Rr22), (Rp28,Rq1,Rr1), (Rp28,Rq1,Rr2), (Rp28,Rq1,Rr3), (Rp28,Rq1,Rr4), (Rp28,Rq1,Rr5), (Rp28,Rq1,Rr6), (Rp28, Rq1,Rr7), (Rp28,Rq1,Rr8), (Rp28,Rq1,Rr9), (Rp28,Rq1, Rr10), (Rp28,Rq1,Rr11), (Rp28,Rq1,Rr12), (Rp28,Rq1, Rr13), (Rp28,Rq1,Rr14), (Rp28,Rq1,Rr15), (Rp28,Rq1, Rr16), (Rp28,Rq1,Rr17), (Rp28,Rq1,Rr18), (Rp28,Rq1, Rr19), (Rp28,Rq1,Rr20), (Rp28,Rq1,Rr21), (Rp28,Rq1, Rr22), (Rp28,Rq2,Rr1), (Rp28,Rq2,Rr2), (Rp28,Rq2,Rr3), (Rp28,Rq2,Rr4), (Rp28,Rq2,Rr5), (Rp28,Rq2,Rr6), (Rp28, Rq2,Rr7), (Rp28,Rq2,Rr8), (Rp28,Rq2,Rr9), (Rp28,Rq2, Rr10), (Rp28,Rq2,Rr11), (Rp28,Rq2,Rr12), (Rp28,Rq2, Rr13), (Rp28,Rq2,Rr14), (Rp28,Rq2,Rr15), (Rp28,Rq2, Rr16), (Rp28,Rq2,Rr17), (Rp28,Rq2,Rr18), (Rp28,Rq2, Rr19), (Rp28,Rq2,Rr20), (Rp28,Rq2,Rr21), (Rp28,Rq2, Rr22), (Rp28,Rq3,Rr1), (Rp28,Rq3,Rr2), (Rp28,Rq3,Rr3), (Rp28,Rq3,Rr4), (Rp28,Rq3,Rr5), (Rp28,Rq3,Rr6), (Rp28, Rq3,Rr7), (Rp28,Rq3,Rr8), (Rp28,Rq3,Rr9), (Rp28,Rq3, Rr10), (Rp28,Rq3,Rr11), (Rp28,Rq3,Rr12), (Rp28,Rq3, Rr13), (Rp28,Rq3,Rr14), (Rp28,Rq3,Rr15), (Rp28,Rq3, Rr16), (Rp28,Rq3,Rr17), (Rp28,Rq3,Rr18), (Rp28,Rq3, Rr19), (Rp28,Rq3,Rr20), (Rp28,Rq3,Rr21), (Rp28,Rq3, Rr22), (Rp28,Rq4,Rr1), (Rp28,Rq4,Rr2), (Rp28,Rq4,Rr3), (Rp28,Rq4,Rr4), (Rp28,Rq4,Rr5), (Rp28,Rq4,Rr6), (Rp28, Rq4,Rr7), (Rp28,Rq4,Rr8), (Rp28,Rq4,Rr9), (Rp28,Rq4, Rr10), (Rp28,Rq4,Rr11), (Rp28,Rq4,Rr12), (Rp28,Rq4, Rr13), (Rp28,Rq4,Rr14), (Rp28,Rq4,Rr15), (Rp28,Rq4, Rr16), (Rp28, Rq4,Rr17), (Rp28,Rq4,Rr18), (Rp28,Rq4, Rr19), (Rp28,Rq4,Rr20), (Rp28,Rq4,Rr21), (Rp28,Rq4, Rr22), (Rp28,Rq5,Rr1), (Rp28,Rq5,Rr2), (Rp28,Rq5,Rr3), (Rp28,Rq5,Rr4), (Rp28,Rq5,Rr5), (Rp28,Rq5,Rr6), (Rp28, Rq5,Rr7), (Rp28,Rq5,Rr8), (Rp28,Rq5,Rr9), (Rp28,Rq5, Rr10), (Rp28,Rq5,Rr11), (Rp28,Rq5,Rr12), (Rp28,Rq5, Rr13), (Rp28,Rq5,Rr14), (Rp28,Rq5,Rr15), (Rp28,Rq5, Rr16), (Rp28,Rq5,Rr17), (Rp28,Rq5,Rr18), (Rp28,Rq5, Rr19), (Rp28,Rq5,Rr20), (Rp28,Rq5,Rr21), (Rp28,Rq5, Rr22), (Rp28,Rq6,Rr1), (Rp28,Rq6,Rr2), (Rp28,Rq6,Rr3), (Rp28,Rq6,Rr4), (Rp28,Rq6,Rr5), (Rp28,Rq6,Rr6), (Rp28, Rq6,Rr7), (Rp28,Rq6,Rr8), (Rp28,Rq6,Rr9), (Rp28,Rq6, Rr10), (Rp28,Rq6,Rr11), (Rp28,Rq6,Rr12), (Rp28,Rq6, Rr13), (Rp28,Rq6,Rr14), (Rp28,Rq6,Rr15), (Rp28,Rq6, Rr16), (Rp28,Rq6,Rr17), (Rp28,Rq6,Rr18), (Rp28,Rq6, Rr19), (Rp28,Rq6,Rr20), (Rp28,Rq6,Rr21), (Rp28,Rq6, Rr22), (Rp28,Rq7,Rr1), (Rp28,Rq7,Rr2), (Rp28,Rq7,Rr3), (Rp28,Rq7,Rr4), (Rp28,Rq7,Rr5), (Rp28,Rq7,Rr6), (Rp28, Rq7,Rr7), (Rp28,Rq7,Rr8), (Rp28,Rq7,Rr9), (Rp28,Rq7, Rr10), (Rp28,Rq7,Rr11), (Rp28,Rq7,Rr12), (Rp28,Rq7, Rr13), (Rp28,Rq7,Rr14), (Rp28,Rq7,Rr15), (Rp28,Rq7, Rr16), (Rp28,Rq7, Rr17), (Rp28,Rq7,Rr18), (Rp28,Rq7, Rr19), (Rp28,Rq7,Rr20), (Rp28,Rq7,Rr21), (Rp28,Rq7, Rr22), (Rp28,Rq8,Rr1), (Rp28,Rq8,Rr2), (Rp28,Rq8,Rr3), (Rp28,Rq8,Rr4), (Rp28,Rq8,Rr5), (Rp28,Rq8,Rr6), (Rp28, Rq8,Rr7), (Rp28,Rq8,Rr8), (Rp28,Rq8,Rr9), (Rp28,Rq8, Rr10), (Rp28,Rq8,Rr11), (Rp28,Rq8,Rr12), (Rp28,Rq8, Rr13), (Rp28,Rq8,Rr14), (Rp28,Rq8,Rr15), (Rp28,Rq8, Rr16), (Rp28,Rq8,Rr17), (Rp28,Rq8,Rr18), (Rp28,Rq8, Rr19), (Rp28,Rq8,Rr20), (Rp28,Rq8,Rr21), (Rp28,Rq8, Rr22), (Rp28,Rq9,Rr1), (Rp28,Rq9,Rr2), (Rp28,Rq9,Rr3), (Rp28,Rq9,Rr4), (Rp28,Rq9,Rr5), (Rp28,Rq9,Rr6), (Rp28, Rq9,Rr7), (Rp28,Rq9,Rr8), (Rp28, Rq9,Rr9), (Rp28,Rq9, Rr10), (Rp28,Rq9,Rr11), (Rp28,Rq9,Rr12), (Rp28,Rq9, Rr13), (Rp28, Rq9,Rr14), (Rp28,Rq9,Rr15), (Rp28,Rq9, Rr16), (Rp28,Rq9,Rr17), (Rp28,Rq9,Rr18), (Rp28,Rq9, Rr19), (Rp28,Rq9,Rr20), (Rp28,Rq9,Rr21), (Rp28,Rq9, Rr22), (Rp28,Rq10,Rr1), (Rp28,Rq10,Rr2), (Rp28,Rq10, Rr3), (Rp28,Rq10,Rr4), (Rp28,Rq10,Rr5), (Rp28,Rq10, Rr6), (Rp28,Rq10,Rr7), (Rp28,Rq10,Rr8), (Rp28,Rq10, Rr9), (Rp28,Rq10,Rr10), (Rp28,Rq10,Rr11), (Rp28,Rq10, Rr12), (Rp28,Rq10,Rr13), (Rp28,Rq10,Rr14), (Rp28,Rq10, Rr15), (Rp28,Rq10, Rr16), (Rp28,Rq10,Rr17), (Rp28,Rq10, Rr18), (Rp28,Rq10,Rr19), (Rp28,Rq10,Rr20), (Rp28,Rq10, Rr21), (Rp28,Rq10,Rr22), (Rp28,Rq11,Rr1), (Rp28,Rq11, Rr2), (Rp28,Rq11,Rr3), (Rp28,Rq11,Rr4), (Rp28,Rq11, Rr5), (Rp28,Rq11,Rr6), (Rp28,Rq11,Rr7), (Rp28,Rq11, Rr8), (Rp28,Rq11,Rr9), (Rp28,Rq11,Rr10), (Rp28,Rq11, Rr11), (Rp28,Rq11,Rr12), (Rp28,Rq11,Rr13), (Rp28,Rq11, Rr14), (Rp28,Rq11,Rr15), (Rp28,Rq11,Rr16), (Rp28,Rq11, Rr17), (Rp28, Rq11,Rr18), (Rp28,Rq11,Rr19), (Rp28,Rq11, Rr20), (Rp28,Rq11,Rr21), (Rp28,Rq11,Rr22), (Rp28,Rq12, Rr1), (Rp28,Rq12,Rr2), (Rp28,Rq12,Rr3), (Rp28,Rq12, Rr4), (Rp28,Rq12,Rr5), (Rp28,Rq12,Rr6), (Rp28,Rq12, Rr7), (Rp28,Rq12,Rr8), (Rp28,Rq12,Rr9), (Rp28,Rq12, Rr11), (Rp28,Rq12,Rr11), (Rp28,Rq12,Rr12), (Rp28,Rq12, Rr13), (Rp28,Rq12,Rr14), (Rp28,Rq12,Rr15), (Rp28,Rq12, Rr16), (Rp28,Rq12,Rr17), (Rp28,Rq12,Rr18), (Rp28,Rq12, Rr19), (Rp28,Rq12,Rr20), (Rp28,Rq12,Rr21), (Rp28,Rq12, Rr22), (Rp29,Rq1,Rr1), (Rp29,Rq1,Rr2), (Rp29,Rq1,Rr3), (Rp29,Rq1,Rr4), (Rp29,Rq1,Rr5), (Rp29,Rq1,Rr6), (Rp29, Rq1,Rr7), (Rp29,Rq1,Rr8), (Rp29,Rq1,Rr9), (Rp29,Rq1, Rr10), (Rp29,Rq1,Rr11), (Rp29,Rq1,Rr12), (Rp29,Rq1, Rr13), (Rp29,Rq1,Rr14), (Rp29,Rq1,Rr15), (Rp29,Rq1, Rr16), (Rp29,Rq1,Rr17), (Rp29, Rq1,Rr18), (Rp29,Rq1, Rr19), (Rp29,Rq1,Rr20), (Rp29,Rq1,Rr21), (Rp29,Rq1, Rr22), (Rp29,Rq2,Rr1), (Rp29,Rq2,Rr2), (Rp29,Rq2,Rr3), (Rp29,Rq2,Rr4), (Rp29,Rq2,Rr5), (Rp29,Rq2, Rr6), (Rp29, Rq2,Rr7), (Rp29,Rq2,Rr8), (Rp29,Rq2,Rr9), (Rp29,Rq2, Rr10), (Rp29,Rq2,Rr11), (Rp29,Rq2,Rr12), (Rp29,Rq2, Rr13), (Rp29,Rq2,Rr14), (Rp29,Rq2,Rr15), (Rp29,Rq2, Rr16), (Rp29,Rq2,Rr17), (Rp29,Rq2,Rr18), (Rp29,Rq2, Rr19), (Rp29,Rq2,Rr20), (Rp29,Rq2,Rr21), (Rp29,Rq2, Rr22), (Rp29,Rq3,Rr1), (Rp29,Rq3,Rr2), (Rp29,Rq3,Rr3), (Rp29,Rq3,Rr4), (Rp29,Rq3,Rr5), (Rp29,Rq3,Rr6), (Rp29, Rq3,Rr7), (Rp29,Rq3,Rr8), (Rp29,Rq3,Rr9), (Rp29,Rq3, Rr10), (Rp29,Rq3,Rr11), (Rp29,Rq3,Rr12), (Rp29,Rq3, Rr13), (Rp29,Rq3,Rr14), (Rp29,Rq3,Rr15), (Rp29,Rq3, Rr16), (Rp29,Rq3,Rr17), (Rp29,Rq3,Rr18), (Rp29,Rq3, Rr19), (Rp29,Rq3,Rr20), (Rp29,Rq3,Rr21), (Rp29,Rq3, Rr22), (Rp29,Rq4,Rr1), (Rp29,Rq4,Rr2), (Rp29,Rq4,Rr3), (Rp29,Rq4,Rr4), (Rp29,Rq4,Rr5), (Rp29,Rq4,Rr6), (Rp29, Rq4,Rr7), (Rp29,Rq4,Rr8), (Rp29,Rq4,Rr9), (Rp29,Rq4, Rr10), (Rp29,Rq4,Rr11), (Rp29,Rq4,Rr12), (Rp29,Rq4, Rr13), (Rp29,Rq4,Rr14), (Rp29,Rq4,Rr15), (Rp29,Rq4, Rr16), (Rp29,Rq4,Rr17), (Rp29,Rq4,Rr18), (Rp29,Rq4, Rr19), (Rp29,Rq4,Rr20), (Rp29,Rq4,Rr21), (Rp29,Rq4, Rr22), (Rp29,Rq5,Rr1), (Rp29,Rq5,Rr2), (Rp29,Rq5,Rr3), (Rp29,Rq5,Rr4), (Rp29,Rq5,Rr5), (Rp29,Rq5,Rr6), (Rp29, Rq5,Rr7), (Rp29,Rq5,Rr8), (Rp29,Rq5,Rr9), (Rp29,Rq5, Rr10), (Rp29,Rq5,Rr11), (Rp29,Rq5,Rr12), (Rp29,Rq5, Rr13), (Rp29,Rq5,Rr14), (Rp29,Rq5,Rr15), (Rp29,Rq5, Rr16), (Rp29,Rq5,Rr17), (Rp29,Rq5,Rr18), (Rp29,Rq5, Rr19), (Rp29,Rq5,Rr20), (Rp29,Rq5,Rr21), (Rp29,Rq5, Rr22), (Rp29,Rq6,Rr1), (Rp29,Rq6,Rr2), (Rp29,Rq6,Rr3), (Rp29,Rq6,Rr4), (Rp29,Rq6,Rr5), (Rp29,Rq6,Rr6), (Rp29, Rq6,Rr7), (Rp29,Rq6,Rr8), (Rp29,Rq6,Rr9), (Rp29,Rq6, Rr10), (Rp29,Rq6,Rr11), (Rp29,Rq6,Rr12), (Rp29,Rq6, Rr13), (Rp29,Rq6,Rr14), (Rp29,Rq6,Rr15), (Rp29,Rq6, Rr16), (Rp29,Rq6,Rr17), (Rp29,Rq6,Rr18), (Rp29,Rq6, Rr19), (Rp29, Rq6,Rr20), (Rp29,Rq6,Rr21), (Rp29,Rq6, Rr22), (Rp29,Rq7,Rr1), (Rp29,Rq7,Rr2), (Rp29,Rq7,Rr3), (Rp29,Rq7,Rr4), (Rp29,Rq7,Rr5), (Rp29,Rq7,Rr6), (Rp29,

Rq7,Rr7), (Rp29,Rq7,Rr8), (Rp29,Rq7,Rr9), (Rp29,Rq7, Rr10), (Rp29,Rq7,Rr11), (Rp29,Rq7,Rr12), (Rp29,Rq7, Rr13), (Rp29,Rq7,Rr14), (Rp29,Rq7,Rr15), (Rp29,Rq7, Rr16), (Rp29,Rq7,Rr17), (Rp29,Rq7,Rr18), (Rp29,Rq7, Rr19), (Rp29,Rq7,Rr20), (Rp29,Rq7,Rr21), (Rp29,Rq7, Rr22), (Rp29,Rq8,Rr1), (Rp29,Rq8,Rr2), (Rp29,Rq8,Rr3), (Rp29,Rq8,Rr4), (Rp29,Rq8,Rr5), (Rp29,Rq8,Rr6), (Rp29, Rq8,Rr7), (Rp29,Rq8,Rr8), (Rp29,Rq8,Rr9), (Rp29,Rq8, Rr10), (Rp29,Rq8,Rr11), (Rp29,Rq8,Rr12), (Rp29,Rq8, Rr13), (Rp29,Rq8,Rr14), (Rp29,Rq8,Rr15), (Rp29,Rq8, Rr16), (Rp29,Rq8,Rr17), (Rp29,Rq8,Rr18), (Rp29,Rq8, Rr19), (Rp29,Rq8,Rr20), (Rp29,Rq8,Rr21), (Rp29,Rq8, Rr22), (Rp29,Rq9,Rr1), (Rp29,Rq9,Rr2), (Rp29,Rq9,Rr3), (Rp29,Rq9,Rr4), (Rp29,Rq9,Rr5), (Rp29,Rq9,Rr6), (Rp29, Rq9,Rr7), (Rp29,Rq9,Rr8), (Rp29,Rq9,Rr9), (Rp29,Rq9, Rr10), (Rp29,Rq9,Rr11), (Rp29,Rq9,Rr12), (Rp29,Rq9, Rr13), (Rp29,Rq9,Rr14), (Rp29,Rq9,Rr15), (Rp29,Rq9, Rr16), (Rp29,Rq9,Rr17), (Rp29,Rq9,Rr18), (Rp29,Rq9, Rr19), (Rp29,Rq9,Rr20), (Rp29,Rq9,Rr21), (Rp29,Rq9, Rr22), (Rp29,Rq10,Rr1), (Rp29,Rq10,Rr2), (Rp29,Rq10, Rr3), (Rp29,Rq10,Rr4), (Rp29,Rq10,Rr5), (Rp29,Rq10, Rr6), (Rp29,Rq10,Rr7), (Rp29,Rq10,Rr8), (Rp29,Rq10, Rr9), (Rp29,Rq10,Rr10), (Rp29,Rq10,Rr11), (Rp29,Rq10, Rr12), (Rp29,Rq10,Rr13), (Rp29,Rq10,Rr14), (Rp29,Rq10, Rr15), (Rp29,Rq10,Rr16), (Rp29,Rq10,Rr17), (Rp29,Rq10, Rr18), (Rp29,Rq10,Rr19), (Rp29,Rq10,Rr20), (Rp29,Rq10, Rr21), (Rp29,Rq10,Rr22), (Rp29,Rq11,Rr1), (Rp29,Rq11, Rr2), (Rp29,Rq11,Rr3), (Rp29,Rq11,Rr4), (Rp29,Rq11, Rr5), (Rp29,Rq11,Rr6), (Rp29,Rq11,Rr7), (Rp29,Rq11, Rr8), (Rp29,Rq11,Rr9), (Rp29,Rq11,Rr10), (Rp29,Rq11, Rr11), (Rp29,Rq11,Rr12), (Rp29,Rq11,Rr13), (Rp29,Rq11, Rr14), (Rp29,Rq11,Rr15), (Rp29,Rq11,Rr16), (Rp29,Rq11, Rr17), (Rp29,Rq11,Rr18), (Rp29, Rq11,Rr19), (Rp29,Rq11, Rr20), (Rp29,Rq11,Rr21), (Rp29,Rq11,Rr22), (Rp29,Rq12, Rr1), (Rp29,Rq12,Rr2), (Rp29,Rq12,Rr3), (Rp29,Rq12, Rr4), (Rp29,Rq12,Rr5), (Rp29,Rq12,Rr6), (Rp29,Rq12, Rr7), (Rp29,Rq12,Rr8), (Rp29,Rq12,Rr9), (Rp29,Rq12, Rr10), (Rp29,Rq12,Rr11), (Rp29,Rq12,Rr12), (Rp29,Rq12, Rr13), (Rp29,Rq12,Rr14), (Rp29,Rq12,Rr15), (Rp29,Rq12, Rr16), (Rp29,Rq12,Rr17), (Rp29,Rq12,Rr18), (Rp29,Rq12, Rr19), (Rp29,Rq12,Rr20), (Rp29,Rq12,Rr21), (Rp29,Rq12, Rr22), (Rp30,Rq1,Rr1), (Rp30,Rq1,Rr2), (Rp30,Rq1,Rr3), (Rp30,Rq1,Rr4), (Rp30,Rq1,Rr5), (Rp30,Rq1,Rr6), (Rp30, Rq1,Rr7), (Rp30,Rq1,Rr8), (Rp30, Rq1,Rr9), (Rp30,Rq1, Rr10), (Rp30,Rq1,Rr11), (Rp30,Rq1,Rr12), (Rp30,Rq1, Rr13), (Rp30, Rq1,Rr14), (Rp30,Rq1,Rr15), (Rp30,Rq1, Rr16), (Rp30,Rq1,Rr17), (Rp30,Rq1,Rr18), (Rp30,Rq1, Rr19), (Rp30,Rq1,Rr20), (Rp30,Rq1,Rr21), (Rp30,Rq1, Rr22), (Rp30,Rq2,Rr1), (Rp30, Rq2,Rr2), (Rp30,Rq2,Rr3), (Rp30,Rq2,Rr4), (Rp30,Rq2,Rr5), (Rp30,Rq2,Rr6), (Rp30, Rq2, Rr7), (Rp30,Rq2,Rr8), (Rp30,Rq2,Rr9), (Rp30,Rq2, Rr10), (Rp30,Rq2,Rr11), (Rp30,Rq2,Rr12), (Rp30,Rq2, Rr13), (Rp30,Rq2,Rr14), (Rp30,Rq2,Rr15), (Rp30,Rq2, Rr16), (Rp30,Rq2,Rr17), (Rp30,Rq2,Rr18), (Rp30,Rq2, Rr19), (Rp30,Rq2,Rr20), (Rp30,Rq2,Rr21), (Rp30,Rq2, Rr22), (Rp30,Rq3,Rr1), (Rp30,Rq3,Rr2), (Rp30,Rq3,Rr3), (Rp30,Rq3,Rr4), (Rp30,Rq3,Rr5), (Rp30,Rq3,Rr6), (Rp30, Rq3,Rr7), (Rp30,Rq3,Rr8), (Rp30,Rq3,Rr9), (Rp30,Rq3, Rr10), (Rp30,Rq3,Rr11), (Rp30,Rq3,Rr12), (Rp30,Rq3, Rr13), (Rp30,Rq3,Rr14), (Rp30,Rq3,Rr15), (Rp30,Rq3, Rr16), (Rp30,Rq3,Rr17), (Rp30,Rq3,Rr18), (Rp30,Rq3, Rr19), (Rp30,Rq3,Rr20), (Rp30,Rq3,Rr21), (Rp30,Rq3, Rr22), (Rp30,Rq4,Rr1), (Rp30,Rq4,Rr2), (Rp30,Rq4,Rr3), (Rp30,Rq4,Rr4), (Rp30,Rq4,Rr5), (Rp30,Rq4,Rr6), (Rp30, Rq4,Rr7), (Rp30,Rq4,Rr8), (Rp30,Rq4,Rr9), (Rp30,Rq4, Rr10), (Rp30,Rq4,Rr11), (Rp30,Rq4,Rr12), (Rp30,Rq4, Rr13), (Rp30,Rq4,Rr14), (Rp30,Rq4,Rr15), (Rp30,Rq4, Rr16), (Rp30,Rq4,Rr17), (Rp30,Rq4,Rr18), (Rp30,Rq4, Rr19), (Rp30,Rq4,Rr20), (Rp30,Rq4,Rr21), (Rp30,Rq4, Rr22), (Rp30,Rq5,Rr1), (Rp30,Rq5,Rr2), (Rp30,Rq5,Rr3), (Rp30,Rq5,Rr4), (Rp30,Rq5,Rr5), (Rp30,Rq5,Rr6), (Rp30, Rq5,Rr7), (Rp30,Rq5,Rr8), (Rp30,Rq5,Rr9), (Rp30,Rq5, Rr10), (Rp30,Rq5,Rr11), (Rp30,Rq5,Rr12), (Rp30,Rq5, Rr13), (Rp30,Rq5,Rr14), (Rp30,Rq5,Rr15), (Rp30,Rq5, Rr16), (Rp30,Rq5,Rr17), (Rp30,Rq5,Rr18), (Rp30,Rq5, Rr19), (Rp30,Rq5,Rr20), (Rp30,Rq5,Rr21), (Rp30,Rq5, Rr22), (Rp30,Rq6,Rr1), (Rp30,Rq6,Rr2), (Rp30,Rq6,Rr3), (Rp30,Rq6,Rr4), (Rp30,Rq6,Rr5), (Rp30,Rq6,Rr6), (Rp30, Rq6,Rr7), (Rp30,Rq6,Rr8), (Rp30,Rq6,Rr9), (Rp30,Rq6, Rr10), (Rp30, Rq6,Rr11), (Rp30,Rq6,Rr12), (Rp30,Rq6, Rr13), (Rp30,Rq6,Rr14), (Rp30,Rq6,Rr15), (Rp30,Rq6, Rr16), (Rp30,Rq6,Rr17), (Rp30,Rq6,Rr18), (Rp30,Rq6, Rr19), (Rp30,Rq6,Rr20), (Rp30,Rq6,Rr21), (Rp30,Rq6, Rr22), (Rp30,Rq7,Rr1), (Rp30,Rq7,Rr2), (Rp30,Rq7,Rr3), (Rp30,Rq7,Rr4), (Rp30,Rq7,Rr5), (Rp30,Rq7,Rr6), (Rp30, Rq7,Rr7), (Rp30,Rq7,Rr8), (Rp30,Rq7,Rr9), (Rp30,Rq7, Rr10), (Rp30,Rq7,Rr11), (Rp30,Rq7,Rr12), (Rp30,Rq7, Rr13), (Rp30,Rq7,Rr14), (Rp30,Rq7,Rr15), (Rp30,Rq7, Rr16), (Rp30,Rq7,Rr17), (Rp30,Rq7,Rr18), (Rp30,Rq7, Rr19), (Rp30,Rq7,Rr20), (Rp30,Rq7,Rr21), (Rp30,Rq7, Rr22), (Rp30,Rq8,Rr1), (Rp30,Rq8,Rr2), (Rp30,Rq8,Rr3), (Rp30,Rq8,Rr4), (Rp30,Rq8,Rr5), (Rp30,Rq8,Rr6), (Rp30, Rq8,Rr7), (Rp30,Rq8,Rr8), (Rp30,Rq8,Rr9), (Rp30,Rq8, Rr10), (Rp30,Rq8,Rr11), (Rp30,Rq8,Rr12), (Rp30,Rq8, Rr13), (Rp30,Rq8,Rr14), (Rp30,Rq8,Rr15), (Rp30,Rq8, Rr16), (Rp30,Rq8,Rr17), (Rp30,Rq8,Rr18), (Rp30,Rq8, Rr19), (Rp30,Rq8,Rr20), (Rp30,Rq8,Rr21), (Rp30,Rq8, Rr22), (Rp30,Rq9,Rr1), (Rp30,Rq9,Rr2), (Rp30,Rq9,Rr3), (Rp30,Rq9,Rr4), (Rp30,Rq9,Rr5), (Rp30,Rq9,Rr6), (Rp30, Rq9,Rr7), (Rp30,Rq9,Rr8), (Rp30,Rq9,Rr9), (Rp30,Rq9, Rr10), (Rp30,Rq9,Rr11), (Rp30,Rq9,Rr12), (Rp30,Rq9, Rr13), (Rp30,Rq9,Rr14), (Rp30,Rq9,Rr15), (Rp30,Rq9, Rr16), (Rp30,Rq9,Rr17), (Rp30,Rq9,Rr18), (Rp30,Rq9, Rr19), (Rp30,Rq9,Rr20), (Rp30,Rq9,Rr21), (Rp30,Rq9, Rr22), (Rp30,Rq10,Rr1), (Rp30,Rq10,Rr2), (Rp30,Rq10, Rr3), (Rp30, Rq10,Rr4), (Rp30,Rq10,Rr5), (Rp30,Rq10, Rr6), (Rp30,Rq10,Rr7), (Rp30,Rq10,Rr8), (Rp30,Rq10, Rr9), (Rp30,Rq10,Rr10), (Rp30,Rq10,Rr11), (Rp30,Rq10, Rr12), (Rp30,Rq10,Rr13), (Rp30,Rq10,Rr14), (Rp30,Rq10, Rr15), (Rp30,Rq10,Rr16), (Rp30,Rq10,Rr17), (Rp30,Rq10, Rr18), (Rp30,Rq10,Rr19), (Rp30,Rq10,Rr20), (Rp30,Rq10, Rr21), (Rp30,Rq10,Rr22), (Rp30,Rq11,Rr1), (Rp30,Rq11, Rr2), (Rp30,Rq11,Rr3), (Rp30,Rq11,Rr4), (Rp30,Rq11, Rr5), (Rp30,Rq11,Rr6), (Rp30,Rq11,Rr7), (Rp30,Rq11, Rr8), (Rp30,Rq11,Rr9), (Rp30,Rq11,Rr10), (Rp30,Rq11, Rr11), (Rp30,Rq11,Rr12), (Rp30,Rq11,Rr13), (Rp30,Rq11, Rr14), (Rp30,Rq11,Rr15), (Rp30,Rq11,Rr16), (Rp30,Rq11, Rr17), (Rp30,Rq11,Rr18), (Rp30,Rq11,Rr19), (Rp30, Rq11, Rr20), (Rp30,Rq11,Rr21), (Rp30,Rq11,Rr22), (Rp30,Rq12, Rr1), (Rp30,Rq12,Rr2), (Rp30,Rq12,Rr3), (Rp30,Rq12, Rr4), (Rp30,Rq12,Rr5), (Rp30,Rq12,Rr6), (Rp30,Rq12, Rr7), (Rp30,Rq12,Rr8), (Rp30,Rq12,Rr9), (Rp30,Rq12, Rr10), (Rp30,Rq12,Rr11), (Rp30,Rq12,Rr12), (Rp30,Rq12, Rr13), (Rp30,Rq12,Rr14), (Rp30,Rq12,Rr15), (Rp30,Rq12, Rr16), (Rp30,Rq12,Rr17), (Rp30,Rq12,Rr18), (Rp30,Rq12, Rr19), (Rp30,Rq12,Rr20), (Rp30,Rq12,Rr21), (Rp30,Rq12, Rr22), (Rp31,Rq1,Rr1), (Rp31,Rq1,Rr2), (Rp31,Rq1,Rr3), (Rp31,Rq1,Rr4), (Rp31,Rq1,Rr5), (Rp31,Rq1,Rr6), (Rp31, Rq1,Rr7), (Rp31,Rq1,Rr8), (Rp31,Rq1,Rr9), (Rp31,Rq1, Rr10), (Rp31,Rq1,Rr11), (Rp31,Rq1,Rr12), (Rp31,Rq1, Rr13), (Rp31,Rq1,Rr14), (Rp31,Rq1,Rr15), (Rp31,Rq1, Rr16), (Rp31,Rq1,Rr17), (Rp31,Rq1,Rr18), (Rp31,Rq1, Rr19), (Rp31, Rq1,Rr20), (Rp31,Rq1,Rr21), (Rp31,Rq1, Rr22), (Rp31,Rq2,Rr1), (Rp31,Rq2,Rr2), (Rp31,Rq2,Rr3), (Rp31,Rq2,Rr4), (Rp31,Rq2,Rr5), (Rp31,Rq2,Rr6), (Rp31,Rq2,Rr7), (Rp31,Rq2,Rr8), (Rp31,Rq2,Rr9), (Rp31,Rq2,Rr10), (Rp31,Rq2,Rr11), (Rp31,Rq2,Rr12), (Rp31,Rq2,Rr13), (Rp31,Rq2,Rr14), (Rp31,Rq2,Rr15), (Rp31,Rq2,Rr16), (Rp31,Rq2,Rr17), (Rp31,Rq2,Rr18), (Rp31,Rq2,Rr19), (Rp31,Rq2,Rr20), (Rp31,Rq2,Rr21), (Rp31,Rq2,Rr22), (Rp31,Rq3,Rr1), (Rp31,Rq3,Rr2), (Rp31,Rq3,Rr3), (Rp31,Rq3,Rr4), (Rp31,Rq3,Rr5), (Rp31,Rq3,Rr6), (Rp31,Rq3,Rr7), (Rp31,Rq3,Rr8), (Rp31,Rq3,Rr9), (Rp31,Rq3,Rr10), (Rp31,Rq3,Rr11), (Rp31,Rq3,Rr12), (Rp31,Rq3,Rr13), (Rp31,Rq3,Rr14), (Rp31,Rq3,Rr15), (Rp31,Rq3,Rr16), (Rp31,Rq3,Rr17), (Rp31,Rq3,Rr18), (Rp31,Rq3,Rr19), (Rp31,Rq3,Rr20), (Rp31,Rq3,Rr21), (Rp31,Rq3,Rr22), (Rp31,Rq4,Rr1), (Rp31,Rq4,Rr2), (Rp31,Rq4,Rr3), (Rp31,Rq4,Rr4), (Rp31,Rq4,Rr5), (Rp31,Rq4,Rr6), (Rp31,Rq4,Rr7), (Rp31,Rq4,Rr8), (Rp31,Rq4,Rr9), (Rp31,Rq4,Rr10), (Rp31,Rq4,Rr11), (Rp31,Rq4,Rr12), (Rp31,Rq4,Rr13), (Rp31,Rq4,Rr14), (Rp31,Rq4,Rr15), (Rp31,Rq4,Rr16), (Rp31,Rq4,Rr17), (Rp31,Rq4,Rr18), (Rp31,Rq4,Rr19), (Rp31,Rq4,Rr20), (Rp31,Rq4,Rr21), (Rp31,Rq4,Rr22), (Rp31,Rq5,Rr1), (Rp31,Rq5,Rr2), (Rp31,Rq5,Rr3), (Rp31,Rq5,Rr4), (Rp31,Rq5,Rr5), (Rp31,Rq5,Rr6), (Rp31,Rq5,Rr7), (Rp31,Rq5,Rr8), (Rp31,Rq5,Rr9), (Rp31,Rq5,Rr10), (Rp31,Rq5,Rr11), (Rp31,Rq5,Rr12), (Rp31,Rq5,Rr13), (Rp31,Rq5,Rr14), (Rp31,Rq5,Rr15), (Rp31,Rq5,Rr16), (Rp31,Rq5,Rr17), (Rp31,Rq5,Rr18), (Rp31,Rq5,Rr19), (Rp31,Rq5,Rr20), (Rp31,Rq5,Rr21), (Rp31,Rq5,Rr22), (Rp31,Rq6,Rr1), (Rp31,Rq6,Rr2), (Rp31,Rq6,Rr3), (Rp31,Rq6,Rr4), (Rp31,Rq6,Rr5), (Rp31,Rq6,Rr6), (Rp31,Rq6,Rr7), (Rp31,Rq6,Rr8), (Rp31,Rq6,Rr9), (Rp31,Rq6,Rr10), (Rp31,Rq6,Rr11), (Rp31,Rq6,Rr12), (Rp31,Rq6,Rr13), (Rp31,Rq6,Rr14), (Rp31,Rq6,Rr15), (Rp31,Rq6,Rr16), (Rp31, Rq6,Rr17), (Rp31,Rq6,Rr18), (Rp31,Rq6,Rr19), (Rp31, Rq6,Rr20), (Rp31,Rq6,Rr21), (Rp31,Rq6,Rr22), (Rp31,Rq7,Rr1), (Rp31,Rq7,Rr2), (Rp31,Rq7,Rr3), (Rp31,Rq7,Rr4), (Rp31,Rq7,Rr5), (Rp31,Rq7,Rr6), (Rp31,Rq7,Rr7), (Rp31,Rq7,Rr8), (Rp31,Rq7,Rr9), (Rp31,Rq7,Rr10), (Rp31,Rq7,Rr11), (Rp31,Rq7,Rr12), (Rp31,Rq7,Rr13), (Rp31,Rq7,Rr14), (Rp31,Rq7,Rr15), (Rp31,Rq7,Rr16), (Rp31,Rq7,Rr17), (Rp31,Rq7,Rr18), (Rp31,Rq7,Rr19), (Rp31,Rq7,Rr20), (Rp31,Rq7,Rr21), (Rp31,Rq7,Rr22), (Rp31,Rq8,Rr1), (Rp31,Rq8,Rr2), (Rp31,Rq8,Rr3), (Rp31,Rq8,Rr4), (Rp31,Rq8,Rr5), (Rp31,Rq8,Rr6), (Rp31,Rq8,Rr7), (Rp31,Rq8,Rr8), (Rp31,Rq8,Rr9), (Rp31,Rq8,Rr10), (Rp31,Rq8,Rr11), (Rp31,Rq8,Rr12), (Rp31,Rq8,Rr13), (Rp31,Rq8,Rr14), (Rp31,Rq8,Rr15), (Rp31,Rq8,Rr16), (Rp31,Rq8,Rr17), (Rp31,Rq8,Rr18), (Rp31,Rq8,Rr19), (Rp31,Rq8,Rr20), (Rp31,Rq8,Rr21), (Rp31,Rq8,Rr22), (Rp31,Rq9,Rr1), (Rp31,Rq9,Rr2), (Rp31,Rq9,Rr3), (Rp31,Rq9,Rr4), (Rp31,Rq9,Rr5), (Rp31,Rq9,Rr6), (Rp31,Rq9,Rr7), (Rp31,Rq9,Rr8), (Rp31,Rq9,Rr9), (Rp31,Rq9,Rr10), (Rp31,Rq9,Rr11), (Rp31,Rq9,Rr12), (Rp31,Rq9,Rr13), (Rp31,Rq9,Rr14), (Rp31,Rq9,Rr15), (Rp31,Rq9,Rr16), (Rp31,Rq9, Rr17), (Rp31,Rq9,Rr18), (Rp31,Rq9,Rr19), (Rp31,Rq9,Rr20), (Rp31,Rq9,Rr21), (Rp31,Rq9,Rr22), (Rp31,Rq10,Rr1), (Rp31,Rq10,Rr2), (Rp31,Rq10,Rr3), (Rp31,Rq10,Rr4), (Rp31,Rq10,Rr5), (Rp31,Rq10,Rr6), (Rp31,Rq10,Rr7), (Rp31,Rq10,Rr8), (Rp31,Rq10,Rr9), (Rp31,Rq10,Rr10), (Rp31,Rq10,Rr11), (Rp31,Rq10,Rr12), (Rp31,Rq10,Rr13), (Rp31,Rq10,Rr14), (Rp31,Rq10,Rr15), (Rp31,Rq10,Rr16), (Rp31,Rq10,Rr17), (Rp31,Rq10,Rr18), (Rp31,Rq10, Rr19), (Rp31,Rq10,Rr20), (Rp31,Rq10,Rr21), (Rp31,Rq10,Rr22), (Rp31,Rq11,Rr1), (Rp31, Rq11,Rr2), (Rp31,Rq11,Rr3), (Rp31,Rq11,Rr4), (Rp31,Rq11,Rr5), (Rp31,Rq11,Rr6), (Rp31,Rq11,Rr7), (Rp31,Rq11,Rr8), (Rp31,Rq11,Rr9), (Rp31,Rq11,Rr10), (Rp31,Rq11,Rr11), (Rp31,Rq11,Rr12), (Rp31,Rq11,Rr13), (Rp31,Rq11,Rr14), (Rp31,Rq11,Rr15), (Rp31,Rq11,Rr16), (Rp31,Rq11,Rr17), (Rp31,Rq11,Rr18), (Rp31,Rq11,Rr19), (Rp31,Rq11,Rr20), (Rp31, Rq11,Rr21), (Rp31,Rq11,Rr22), (Rp31,Rq12,Rr1), (Rp31,Rq12,Rr2), (Rp31,Rq12,Rr3), (Rp31,Rq12,Rr4), (Rp31,Rq12,Rr5), (Rp31,Rq12,Rr6), (Rp31,Rq12,Rr7), (Rp31,Rq12,Rr8), (Rp31,Rq12,Rr9), (Rp31,Rq12,Rr10), (Rp31,Rq12,Rr11), (Rp31,Rq12,Rr12), (Rp31,Rq12,Rr13), (Rp31,Rq12,Rr14), (Rp31,Rq12,Rr15), (Rp31,Rq12,Rr16), (Rp31,Rq12,Rr17), (Rp31,Rq12,Rr18), (Rp31,Rq12,Rr19), (Rp31,Rq12,Rr20), (Rp31,Rq12,Rr21), (Rp31,Rq12,Rr22), (Rp32,Rq1,Rr1), (Rp32,Rq1,Rr2), (Rp32,Rq1,Rr3), (Rp32,Rq1,Rr4), (Rp32,Rq1,Rr5), (Rp32,Rq1,Rr6), (Rp32,Rq1,Rr7), (Rp32,Rq1,Rr8), (Rp32,Rq1,Rr9), (Rp32,Rq1,Rr10), (Rp32,Rq1,Rr11), (Rp32,Rq1,Rr12), (Rp32,Rq1,Rr13), (Rp32,Rq1,Rr14), (Rp32,Rq1,Rr15), (Rp32,Rq1,Rr16), (Rp32,Rq1,Rr17), (Rp32,Rq1,Rr18), (Rp32,Rq1,Rr19), (Rp32,Rq1,Rr20), (Rp32,Rq1,Rr21), (Rp32,Rq1,Rr22), (Rp32,Rq2,Rr1), (Rp32,Rq2,Rr2), (Rp32,Rq2,Rr3), (Rp32,Rq2, Rr4), (Rp32,Rq2,Rr5), (Rp32,Rq2,Rr6), (Rp32,Rq2,Rr7), (Rp32,Rq2,Rr8), (Rp32,Rq2,Rr9), (Rp32,Rq2,Rr10), (Rp32,Rq2,Rr11), (Rp32,Rq2,Rr12), (Rp32,Rq2,Rr13), (Rp32,Rq2,Rr14), (Rp32,Rq2,Rr15), (Rp32,Rq2,Rr11), (Rp32,Rq2,Rr17), (Rp32,Rq2,Rr18), (Rp32,Rq2,Rr19), (Rp32,Rq2,Rr20), (Rp32,Rq2,Rr21), (Rp32,Rq2,Rr22), (Rp32,Rq3,Rr1), (Rp32,Rq3,Rr2), (Rp32,Rq3,Rr3), (Rp32,Rq3,Rr4), (Rp32,Rq3,Rr5), (Rp32,Rq3,Rr6), (Rp32,Rq3,Rr7), (Rp32,Rq3,Rr8), (Rp32,Rq3,Rr9), (Rp32,Rq3,Rr10), (Rp32,Rq3,Rr11), (Rp32,Rq3,Rr12), (Rp32,Rq3,Rr13), (Rp32,Rq3,Rr14), (Rp32,Rq3,Rr15), (Rp32,Rq3,Rr16), (Rp32,Rq3,Rr17), (Rp32, Rq3,Rr18), (Rp32,Rq3,Rr19), (Rp32,Rq3,Rr20), (Rp32,Rq3,Rr21), (Rp32,Rq3,Rr22), (Rp32,Rq4,Rr1), (Rp32,Rq4,Rr2), (Rp32,Rq4,Rr3), (Rp32,Rq4,Rr4), (Rp32,Rq4,Rr5), (Rp32,Rq4, Rr6), (Rp32,Rq4,Rr7), (Rp32,Rq4,Rr8), (Rp32,Rq4,Rr9), (Rp32,Rq4,Rr10), (Rp32,Rq4,Rr11), (Rp32,Rq4,Rr12), (Rp32,Rq4,Rr13), (Rp32,Rq4,Rr14), (Rp32,Rq4,Rr15), (Rp32,Rq4,Rr16), (Rp32,Rq4,Rr17), (Rp32,Rq4,Rr18), (Rp32,Rq4,Rr19), (Rp32,Rq4,Rr20), (Rp32,Rq4,Rr21), (Rp32,Rq4,Rr22), (Rp32,Rq5,Rr1), (Rp32,Rq5,Rr2), (Rp32,Rq5,Rr3), (Rp32,Rq5,Rr4), (Rp32,Rq5,Rr5), (Rp32,Rq5,Rr6), (Rp32,Rq5,Rr7), (Rp32,Rq5,Rr8), (Rp32,Rq5,Rr9), (Rp32,Rq5,Rr10), (Rp32,Rq5,Rr11), (Rp32,Rq5,Rr12), (Rp32,Rq5,Rr13), (Rp32,Rq5,Rr14), (Rp32,Rq5,Rr15), (Rp32,Rq5,Rr16), (Rp32,Rq5,Rr17), (Rp32,Rq5,Rr18), (Rp32,Rq5,Rr19), (Rp32,Rq5,Rr20), (Rp32,Rq5,Rr21), (Rp32,Rq5,Rr22), (Rp32,Rq6,Rr1), (Rp32,Rq6,Rr2), (Rp32,Rq6,Rr3), (Rp32,Rq6,Rr4), (Rp32,Rq6,Rr5), (Rp32,Rq6,Rr6), (Rp32,Rq6,Rr7), (Rp32,Rq6,Rr8), (Rp32,Rq6,Rr9), (Rp32,Rq6,Rr10), (Rp32,Rq6,Rr11), (Rp32,Rq6,Rr12), (Rp32,Rq6,Rr13), (Rp32,Rq6,Rr14), (Rp32,Rq6,Rr15), (Rp32,Rq6,Rr16), (Rp32,Rq6,Rr17), (Rp32,Rq6,Rr18), (Rp32,Rq6,Rr19), (Rp32,Rq6,Rr20), (Rp32,Rq6,Rr21), (Rp32,Rq6,Rr22), (Rp32,Rq7,Rr1), (Rp32,Rq7,Rr2), (Rp32,Rq7,Rr3), (Rp32,Rq7,Rr4), (Rp32,Rq7,Rr5), (Rp32,Rq7,Rr6), (Rp32,Rq7,Rr7), (Rp32,Rq7,Rr8), (Rp32,Rq7,Rr9), (Rp32,Rq7,Rr10), (Rp32,Rq7,Rr11), (Rp32,Rq7,Rr12), (Rp32,Rq7,Rr13), (Rp32,Rq7,Rr14), (Rp32,Rq7,Rr15), (Rp32,Rq7,Rr16), (Rp32,Rq7,Rr17), (Rp32,Rq7,Rr18), (Rp32,Rq7,Rr19), (Rp32,Rq7,Rr20), (Rp32,Rq7,Rr21), (Rp32,Rq7,Rr22), (Rp32,Rq8,Rr1), (Rp32,Rq8,Rr2), (Rp32,Rq8,Rr3), (Rp32,Rq8,Rr4), (Rp32,Rq8,Rr5), (Rp32,Rq8,Rr6), (Rp32,Rq8,Rr7), (Rp32,Rq8,Rr8), (Rp32,Rq8,Rr9), (Rp32,Rq8,Rr10), (Rp32,Rq8,Rr11), (Rp32,Rq8,Rr12), (Rp32,Rq8,Rr13), (Rp32,Rq8,Rr14), (Rp32,Rq8,Rr15), (Rp32,Rq8,Rr16), (Rp32,Rq8,Rr17), (Rp32,Rq8,Rr18), (Rp32,Rq8,Rr19), (Rp32, Rq8,Rr20), (Rp32,Rq8,Rr21), (Rp32,Rq8,Rr22), (Rp32,Rq9,Rr1), (Rp32,Rq9,Rr2), (Rp32,Rq9,Rr3), (Rp32,Rq9,Rr4), (Rp32,Rq9,Rr5), (Rp32,Rq9,Rr6), (Rp32, Rq9,Rr7), (Rp32,Rq9,Rr8), (Rp32,Rq9,Rr9), (Rp32,Rq9, Rr10), (Rp32,Rq9,Rr11), (Rp32,Rq9,Rr12), (Rp32,Rq9, Rr13), (Rp32,Rq9,Rr14), (Rp32,Rq9,Rr15), (Rp32,Rq9, Rr16), (Rp32,Rq9,Rr17), (Rp32,Rq9,Rr18), (Rp32,Rq9, Rr19), (Rp32,Rq9,Rr20), (Rp32,Rq9,Rr21), (Rp32,Rq9, Rr22), (Rp32,Rq10, Rr1), (Rp32,Rq10,Rr2), (Rp32,Rq10, Rr3), (Rp32,Rq10,Rr4), (Rp32,Rq10,Rr5), (Rp32,Rq10, Rr6), (Rp32,Rq10,Rr7), (Rp32,Rq10,Rr8), (Rp32,Rq10, Rr9), (Rp32,Rq10,Rr10), (Rp32,Rq10,Rr11), (Rp32,Rq10, Rr12), (Rp32,Rq10,Rr13), (Rp32,Rq10,Rr14), (Rp32,Rq10, Rr15), (Rp32,Rq10,Rr16), (Rp32,Rq10,Rr17), (Rp32,Rq10, Rr18), (Rp32,Rq10,Rr19), (Rp32,Rq10,Rr20), (Rp32,Rq10, Rr21), (Rp32,Rq10,Rr22), (Rp32,Rq11,Rr1), (Rp32,Rq11, Rr2), (Rp32,Rq11,Rr3), (Rp32,Rq11,Rr4), (Rp32,Rq11, Rr5), (Rp32,Rq11,Rr6), (Rp32,Rq11,Rr7), (Rp32,Rq11, Rr8), (Rp32,Rq11,Rr9), (Rp32,Rq11,Rr10), (Rp32,Rq11, Rr11), (Rp32,Rq11, Rr12), (Rp32,Rq11,Rr13), (Rp32,Rq11, Rr14), (Rp32,Rq11,Rr15), (Rp32,Rq11,Rr16), (Rp32,Rq11, Rr17), (Rp32,Rq11,Rr18), (Rp32,Rq11,Rr19), (Rp32,Rq11, Rr20), (Rp32,Rq11,Rr21), (Rp32,Rq11,Rr22), (Rp32,Rq12, Rr1), (Rp32,Rq12,Rr2), (Rp32,Rq12,Rr3), (Rp32,Rq12, Rr4), (Rp32, Rq12,Rr5), (Rp32,Rq12,Rr6), (Rp32,Rq12, Rr7), (Rp32,Rq12,Rr8), (Rp32,Rq12,Rr9), (Rp32,Rq12, Rr10), (Rp32,Rq12,Rr11), (Rp32,Rq12,Rr12), (Rp32,Rq12, Rr13), (Rp32,Rq12,Rr14), (Rp32,Rq12,Rr15), (Rp32,Rq12, Rr16), (Rp32,Rq12,Rr17), (Rp32,Rq12,Rr18), (Rp32,Rq12, Rr19), (Rp32,Rq12,Rr20), (Rp32,Rq12,Rr21), (Rp32,Rq12, Rr22), (Rp33,Rq1,Rr1), (Rp33, Rq1,Rr2), (Rp33,Rq1,Rr3), (Rp33,Rq1,Rr4), (Rp33,Rq1,Rr5), (Rp33,Rq1,Rr6), (Rp33, Rq1,Rr7), (Rp33,Rq1,Rr8), (Rp33,Rq1,Rr9), (Rp33,Rq1, Rr10), (Rp33,Rq1,Rr11), (Rp33,Rq1,Rr12), (Rp33,Rq1, Rr13), (Rp33,Rq1,Rr14), (Rp33,Rq1,Rr15), (Rp33,Rq1, Rr16), (Rp33,Rq1,Rr17), (Rp33,Rq1,Rr18), (Rp33,Rq1, Rr19), (Rp33,Rq1,Rr20), (Rp33,Rq1,Rr21), (Rp33,Rq1, Rr22), (Rp33,Rq2,Rr1), (Rp33,Rq2,Rr2), (Rp33,Rq2,Rr3), (Rp33,Rq2,Rr4), (Rp33,Rq2,Rr5), (Rp33,Rq2,Rr6), (Rp33, Rq2,Rr7), (Rp33,Rq2,Rr8), (Rp33,Rq2,Rr9), (Rp33,Rq2, Rr10), (Rp33,Rq2,Rr11), (Rp33,Rq2,Rr12), (Rp33,Rq2, Rr13), (Rp33,Rq2,Rr14), (Rp33,Rq2,Rr15), (Rp33,Rq2, Rr16), (Rp33,Rq2,Rr17), (Rp33,Rq2,Rr18), (Rp33,Rq2, Rr19), (Rp33,Rq2,Rr20), (Rp33,Rq2,Rr21), (Rp33,Rq2, Rr22), (Rp33,Rq3,Rr1), (Rp33,Rq3,Rr2), (Rp33,Rq3,Rr3), (Rp33,Rq3,Rr4), (Rp33,Rq3,Rr5), (Rp33,Rq3,Rr6), (Rp33, Rq3,Rr7), (Rp33,Rq3,Rr8), (Rp33,Rq3,Rr9), (Rp33,Rq3, Rr10), (Rp33,Rq3,Rr11), (Rp33,Rq3,Rr12), (Rp33,Rq3, Rr13), (Rp33,Rq3,Rr14), (Rp33,Rq3,Rr15), (Rp33,Rq3, Rr16), (Rp33,Rq3,Rr17), (Rp33,Rq3,Rr18), (Rp33,Rq3, Rr19), (Rp33,Rq3,Rr20), (Rp33,Rq3,Rr21), (Rp33,Rq3, Rr22), (Rp33,Rq4,Rr1), (Rp33,Rq4,Rr2), (Rp33,Rq4,Rr3), (Rp33,Rq4,Rr4), (Rp33,Rq4,Rr5), (Rp33,Rq4,Rr6), (Rp33, Rq4,Rr7), (Rp33,Rq4,Rr8), (Rp33,Rq4,Rr9), (Rp33,Rq4, Rr10), (Rp33,Rq4,Rr11), (Rp33,Rq4,Rr12), (Rp33,Rq4, Rr13), (Rp33,Rq4,Rr14), (Rp33,Rq4,Rr15), (Rp33,Rq4, Rr16), (Rp33,Rq4,Rr17), (Rp33,Rq4,Rr18), (Rp33,Rq4, Rr19), (Rp33,Rq4,Rr20), (Rp33,Rq4,Rr21), (Rp33,Rq4, Rr22), (Rp33,Rq5,Rr1), (Rp33,Rq5,Rr2), (Rp33,Rq5,Rr3), (Rp33,Rq5,Rr4), (Rp33,Rq5,Rr5), (Rp33,Rq5,Rr6), (Rp33, Rq5,Rr7), (Rp33,Rq5,Rr8), (Rp33,Rq5,Rr9), (Rp33,Rq5, Rr10), (Rp33, Rq5,Rr11), (Rp33,Rq5,Rr12), (Rp33,Rq5, Rr13), (Rp33,Rq5,Rr14), (Rp33,Rq5,Rr15), (Rp33,Rq5, Rr16), (Rp33,Rq5,Rr17), (Rp33,Rq5,Rr18), (Rp33,Rq5, Rr19), (Rp33,Rq5,Rr20), (Rp33,Rq5,Rr21), (Rp33,Rq5, Rr22), (Rp33,Rq6,Rr1), (Rp33,Rq6,Rr2), (Rp33,Rq6,Rr3), (Rp33,Rq6,Rr4), (Rp33,Rq6,Rr5), (Rp33,Rq6,Rr6), (Rp33, Rq6,Rr7), (Rp33,Rq6,Rr8), (Rp33,Rq6,Rr9), (Rp33,Rq6, Rr10), (Rp33,Rq6,Rr11), (Rp33,Rq6,Rr12), (Rp33,Rq6, Rr13), (Rp33,Rq6,Rr14), (Rp33,Rq6,Rr15), (Rp33,Rq6, Rr16), (Rp33,Rq6,Rr17), (Rp33,Rq6,Rr18), (Rp33,Rq6, Rr19), (Rp33,Rq6,Rr20), (Rp33,Rq6,Rr21), (Rp33,Rq6, Rr22), (Rp33,Rq7,Rr1), (Rp33,Rq7,Rr2), (Rp33,Rq7,Rr3), (Rp33,Rq7,Rr4), (Rp33,Rq7,Rr5), (Rp33,Rq7,Rr6), (Rp33, Rq7,Rr7), (Rp33,Rq7,Rr8), (Rp33,Rq7,Rr9), (Rp33,Rq7, Rr10), (Rp33,Rq7,Rr11), (Rp33,Rq7,Rr12), (Rp33,Rq7, Rr13), (Rp33,Rq7,Rr14), (Rp33,Rq7,Rr15), (Rp33,Rq7, Rr16), (Rp33,Rq7,Rr17), (Rp33,Rq7,Rr18), (Rp33,Rq7, Rr19), (Rp33,Rq7,Rr20), (Rp33,Rq7,Rr21), (Rp33,Rq7, Rr22), (Rp33,Rq8,Rr1), (Rp33,Rq8,Rr2), (Rp33,Rq8,Rr3), (Rp33,Rq8,Rr4), (Rp33,Rq8,Rr5), (Rp33,Rq8,Rr6), (Rp33, Rq8,Rr7), (Rp33,Rq8,Rr8), (Rp33,Rq8,Rr9), (Rp33,Rq8, Rr10), (Rp33,Rq8,Rr11), (Rp33,Rq8,Rr12), (Rp33,Rq8, Rr13), (Rp33,Rq8,Rr14), (Rp33,Rq8,Rr15), (Rp33,Rq8, Rr16), (Rp33,Rq8,Rr17), (Rp33,Rq8,Rr18), (Rp33,Rq8, Rr19), (Rp33,Rq8,Rr20), (Rp33,Rq8,Rr21), (Rp33,Rq8, Rr22), (Rp33,Rq9,Rr1), (Rp33,Rq9,Rr2), (Rp33,Rq9,Rr3), (Rp33,Rq9, Rr4), (Rp33,Rq9,Rr5), (Rp33,Rq9,Rr6), (Rp33, Rq9,Rr7), (Rp33,Rq9,Rr8), (Rp33,Rq9,Rr9), (Rp33,Rq9, Rr10), (Rp33,Rq9,Rr11), (Rp33,Rq9,Rr12), (Rp33,Rq9, Rr13), (Rp33,Rq9,Rr14), (Rp33,Rq9,Rr15), (Rp33,Rq9, Rr16), (Rp33,Rq9,Rr17), (Rp33,Rq9,Rr18), (Rp33,Rq9, Rr19), (Rp33,Rq9,Rr20), (Rp33,Rq9,Rr21), (Rp33,Rq9, Rr22), (Rp33,Rq10,Rr1), (Rp33,Rq10,Rr2), (Rp33,Rq10, Rr3), (Rp33,Rq10,Rr4), (Rp33,Rq10,Rr5), (Rp33,Rq10, Rr6), (Rp33,Rq10,Rr7), (Rp33,Rq10,Rr8), (Rp33,Rq10, Rr9), (Rp33,Rq10,Rr10), (Rp33,Rq10,Rr11), (Rp33,Rq10, Rr12), (Rp33,Rq10,Rr13), (Rp33,Rq10,Rr14), (Rp33,Rq10, Rr15), (Rp33,Rq10,Rr16), (Rp33,Rq10,Rr17), (Rp33,Rq10, Rr18), (Rp33,Rq10,Rr19), (Rp33,Rq10,Rr20), (Rp33,Rq10, Rr21), (Rp33,Rq10,Rr22), (Rp33,Rq11,Rr1), (Rp33,Rq11, Rr2), (Rp33,Rq11,Rr3), (Rp33,Rq11,Rr4), (Rp33,Rq11, Rr5), (Rp33,Rq11,Rr6), (Rp33,Rq11,Rr7), (Rp33,Rq11, Rr8), (Rp33,Rq11,Rr9), (Rp33,Rq11,Rr10), (Rp33,Rq11, Rr11), (Rp33,Rq11,Rr12), (Rp33,Rq11,Rr13), (Rp33,Rq11, Rr14), (Rp33,Rq11,Rr15), (Rp33,Rq11,Rr16), (Rp33,Rq11, Rr17), (Rp33,Rq11,Rr18), (Rp33,Rq11,Rr19), (Rp33,Rq11, Rr20), (Rp33,Rq11,Rr21), (Rp33,Rq11,Rr22), (Rp33,Rq12, Rr1), (Rp33,Rq12,Rr2), (Rp33,Rq12,Rr3), (Rp33,Rq12, Rr4), (Rp33,Rq12,Rr5), (Rp33,Rq12,Rr6), (Rp33,Rq12, Rr7), (Rp33,Rq12,Rr8), (Rp33,Rq12,Rr9), (Rp33,Rq12, Rr10), (Rp33, Rq12,Rr11), (Rp33,Rq12,Rr12), (Rp33,Rq12, Rr13), (Rp33,Rq12,Rr14), (Rp33,Rq12,Rr15), (Rp33,Rq12, Rr16), (Rp33,Rq12,Rr17), (Rp33,Rq12,Rr18), (Rp33,Rq12, Rr19), (Rp33,Rq12, Rr20), (Rp33,Rq12,Rr21), (Rp33,Rq12, Rr22), (Rp34,Rq1,Rr1), (Rp34,Rq1,Rr2), (Rp34,Rq1,Rr3), (Rp34,Rq1,Rr4), (Rp34,Rq1,Rr5), (Rp34,Rq1,Rr6), (Rp34, Rq1,Rr7), (Rp34,Rq1,Rr8), (Rp34,Rq1,Rr9), (Rp34,Rq1, Rr10), (Rp34,Rq1,Rr11), (Rp34,Rq1,Rr12), (Rp34,Rq1, Rr13), (Rp34,Rq1,Rr14), (Rp34,Rq1,Rr15), (Rp34,Rq1, Rr16), (Rp34,Rq1,Rr17), (Rp34,Rq1,Rr18), (Rp34,Rq1, Rr19), (Rp34,Rq1,Rr20), (Rp34,Rq1,Rr21), (Rp34,Rq1, Rr22), (Rp34,Rq2,Rr1), (Rp34,Rq2,Rr2), (Rp34,Rq2,Rr3), (Rp34,Rq2,Rr4), (Rp34,Rq2,Rr5), (Rp34,Rq2,Rr6), (Rp34, Rq2,Rr7), (Rp34,Rq2,Rr8), (Rp34,Rq2,Rr9), (Rp34,Rq2, Rr10), (Rp34,Rq2,Rr11), (Rp34,Rq2,Rr12), (Rp34,Rq2, Rr13), (Rp34,Rq2,Rr14), (Rp34,Rq2,Rr15), (Rp34,Rq2, Rr16), (Rp34,Rq2,Rr17), (Rp34,Rq2,Rr18), (Rp34,Rq2, Rr19), (Rp34,Rq2,Rr20), (Rp34,Rq2,Rr21), (Rp34, Rq2, Rr22), (Rp34,Rq3,Rr1), (Rp34,Rq3,Rr2), (Rp34,Rq3,Rr3), (Rp34,Rq3,Rr4), (Rp34,Rq3, Rr5), (Rp34,Rq3,Rr6), (Rp34, Rq3,Rr7), (Rp34,Rq3,Rr8), (Rp34,Rq3,Rr9), (Rp34,Rq3, Rr10), (Rp34,Rq3,Rr11), (Rp34,Rq3,Rr12), (Rp34,Rq3, Rr13), (Rp34,Rq3,Rr14), (Rp34,Rq3,Rr15), (Rp34,Rq3, Rr16), (Rp34,Rq3,Rr17), (Rp34,Rq3,Rr18), (Rp34,Rq3, Rr19), (Rp34,Rq3,Rr20), (Rp34,Rq3,Rr21), (Rp34,Rq3,

Rr22), (Rp34,Rq4,Rr1), (Rp34,Rq4,Rr2), (Rp34,Rq4,Rr3), (Rp34,Rq4,Rr4), (Rp34,Rq4,Rr5), (Rp34,Rq4,Rr6), (Rp34, Rq4,Rr7), (Rp34,Rq4,Rr8), (Rp34,Rq4,Rr9), (Rp34,Rq4, Rr10), (Rp34,Rq4,Rr11), (Rp34,Rq4,Rr12), (Rp34,Rq4, Rr13), (Rp34, Rq4,Rr14), (Rp34,Rq4,Rr15), (Rp34,Rq4, Rr16), (Rp34,Rq4,Rr17), (Rp34,Rq4,Rr18), (Rp34,Rq4, Rr19), (Rp34,Rq4,Rr20), (Rp34,Rq4,Rr21), (Rp34,Rq4, Rr22), (Rp34,Rq5,Rr1), (Rp34, Rq5,Rr2), (Rp34,Rq5,Rr3), (Rp34,Rq5,Rr4), (Rp34,Rq5,Rr5), (Rp34,Rq5,Rr6), (Rp34, Rq5, Rr7), (Rp34,Rq5,Rr8), (Rp34,Rq5,Rr9), (Rp34,Rq5, Rr10), (Rp34,Rq5,Rr11), (Rp34,Rq5,Rr12), (Rp34,Rq5, Rr13), (Rp34,Rq5,Rr14), (Rp34,Rq5,Rr15), (Rp34,Rq5, Rr16), (Rp34,Rq5,R r17), (Rp34,Rq5,Rr18), (Rp34,Rq5, Rr19), (Rp34,Rq5,Rr20), (Rp34,Rq5,Rr21), (Rp34,Rq5, Rr22), (Rp34,Rq6,Rr1), (Rp34,Rq6,Rr2), (Rp34,Rq6,Rr3), (Rp34,Rq6,Rr4), (Rp34,Rq6,Rr5), (Rp34,Rq6,Rr6), (Rp34, Rq6,Rr7), (Rp34,Rq6,Rr8), (Rp34,Rq6,Rr9), (Rp34,Rq6, Rr10), (Rp34,Rq6,Rr11), (Rp34,Rq6,Rr12), (Rp34,Rq6, Rr13), (Rp34,Rq6,Rr14), (Rp34,Rq6,Rr15), (Rp34,Rq6, Rr16), (Rp34,Rq6,Rr17), (Rp34,Rq6,Rr18), (Rp34,Rq6, Rr19), (Rp34,Rq6,Rr20), (Rp34,Rq6,Rr21), (Rp34,Rq6, Rr22), (Rp34,Rq7,Rr1), (Rp34,Rq7,Rr2), (Rp34,Rq7,Rr3), (Rp34,Rq7,Rr4), (Rp34,Rq7,Rr5), (Rp34,Rq7,Rr6), (Rp34, Rq7,Rr7), (Rp34,Rq7,Rr8), (Rp34,Rq7,Rr9), (Rp34,Rq7, Rr10), (Rp34,Rq7,Rr11), (Rp34,Rq7,Rr12), (Rp34,Rq7, Rr13), (Rp34,Rq7,Rr14), (Rp34,Rq7,Rr15), (Rp34,Rq7, Rr16), (Rp34,Rq7,Rr17), (Rp34,Rq7,Rr18), (Rp34,Rq7, Rr19), (Rp34,Rq7,Rr20), (Rp34,Rq7,Rr21), (Rp34,Rq7, Rr22), (Rp34,Rq8,Rr1), (Rp34,Rq8,Rr2), (Rp34,Rq8,Rr3), (Rp34,Rq8,Rr4), (Rp34,Rq8,Rr5), (Rp34,Rq8,Rr6), (Rp34, Rq8,Rr7), (Rp34,Rq8,Rr8), (Rp34,Rq8,Rr9), (Rp34,Rq8, Rr10), (Rp34,Rq8,Rr11), (Rp34,Rq8,Rr12), (Rp34,Rq8, Rr13), (Rp34,Rq8,Rr14), (Rp34,Rq8,Rr15), (Rp34,Rq8, Rr16), (Rp34,Rq8,Rr17), (Rp34,Rq8,Rr18), (Rp34,Rq8, Rr19), (Rp34,Rq8,Rr20), (Rp34,Rq8,Rr21), (Rp34,Rq8, Rr22), (Rp34,Rq9,Rr1), (Rp34,Rq9,Rr2), (Rp34,Rq9,Rr3), (Rp34,Rq9,Rr4), (Rp34,Rq9,Rr5), (Rp34,Rq9,Rr6), (Rp34, Rq9,Rr7), (Rp34,Rq9,Rr8), (Rp34,Rq9,Rr9), (Rp34,Rq9, Rr10), (Rp34, Rq9,Rr11), (Rp34,Rq9,Rr12), (Rp34,Rq9, Rr13), (Rp34,Rq9,Rr14), (Rp34,Rq9,Rr15), (Rp34,Rq9, Rr16), (Rp34,Rq9,Rr17), (Rp34,Rq9,Rr18), (Rp34,Rq9, Rr19), (Rp34,Rq9,Rr20), (Rp34,Rq9,Rr21), (Rp34,Rq9, Rr22), (Rp34,Rq10,Rr1), (Rp34,Rq10,Rr2), (Rp34,Rq10, Rr3), (Rp34,Rq10,Rr4), (Rp34,Rq10,Rr5), (Rp34,Rq10, Rr6), (Rp34,Rq10,Rr7), (Rp34,Rq10,Rr8), (Rp34,Rq10, Rr9), (Rp34,Rq10,Rr10), (Rp34,Rq10,Rr11), (Rp34,Rq10, Rr12), (Rp34,Rq10,Rr13), (Rp34,Rq10,Rr14), (Rp34,Rq10, Rr15), (Rp34,Rq10,Rr16), (Rp34,Rq10,Rr17), (Rp34,Rq10, Rr18), (Rp34,Rq10,Rr19), (Rp34,Rq10,Rr20), (Rp34,Rq10, Rr21), (Rp34,Rq10,Rr22), (Rp34,Rq11,Rr1), (Rp34,Rq11, Rr2), (Rp34,Rq11,Rr3), (Rp34,Rq11,Rr4), (Rp34,Rq11, Rr5), (Rp34,Rq11,Rr6), (Rp34,Rq11,Rr7), (Rp34,Rq11, Rr8), (Rp34,Rq11,Rr9), (Rp34,Rq11, Rr10), (Rp34,Rq11, Rr11), (Rp34,Rq11,Rr12), (Rp34,Rq11,Rr13), (Rp34,Rq11, Rr14), (Rp34,Rq11,Rr15), (Rp34,Rq11,Rr16), (Rp34,Rq11, Rr17), (Rp34,Rq11,Rr18), (Rp34,Rq11,Rr19), (Rp34,Rq11, Rr20), (Rp34,Rq11,Rr21), (Rp34,Rq11,Rr22), (Rp34,Rq12, Rr1), (Rp34,Rq12,Rr2), (Rp34,Rq12,Rr3), (Rp34,Rq12, Rr4), (Rp34,Rq12,Rr5), (Rp34,Rq12,Rr6), (Rp34,Rq12, Rr7), (Rp34,Rq12,Rr8), (Rp34,Rq12,Rr9), (Rp34,Rq12, Rr10), (Rp34,Rq12,Rr11), (Rp34,Rq12, Rr12), (Rp34,Rq12, Rr13), (Rp34,Rq12,Rr14), (Rp34,Rq12,Rr15), (Rp34,Rq12, Rr16), (Rp34,Rq12,Rr17), (Rp34,Rq12,Rr18), (Rp34,Rq12, Rr19), (Rp34,Rq12,Rr20), (Rp34,Rq12,Rr21), (Rp34,Rq12, Rr22), (Rp35,Rq1,Rr1), (Rp35,Rq1,Rr2), (Rp35,Rq1,Rr3), (Rp35,Rq1,Rr4), (Rp35,Rq1,Rr5), (Rp35,Rq1,Rr6), (Rp35, Rq1,Rr7), (Rp35,Rq1,Rr8), (Rp35,Rq1,Rr9), (Rp35, Rq1, Rr10), (Rp35,Rq1,Rr11), (Rp35,Rq1,Rr12), (Rp35,Rq1, Rr13), (Rp35,Rq1,Rr14), (Rp35,Rq1,Rr15), (Rp35,Rq1, Rr16), (Rp35,Rq1,Rr17), (Rp35,Rq1,Rr18), (Rp35,Rq1, Rr19), (Rp35,Rq1,Rr20), (Rp35,Rq1,Rr21), (Rp35,Rq1, Rr22), (Rp35,Rq2,Rr1), (Rp35,Rq2,Rr2), (Rp35, Rq2,Rr3), (Rp35,Rq2,Rr4), (Rp35,Rq2,Rr5), (Rp35,Rq2,Rr6), (Rp35, Rq2,Rr7), (Rp35,Rq2, Rr8), (Rp35,Rq2,Rr9), (Rp35,Rq2, Rr10), (Rp35,Rq2,Rr11), (Rp35,Rq2,Rr12), (Rp35,Rq2, Rr13), (Rp35,Rq2,Rr14), (Rp35,Rq2,Rr15), (Rp35,Rq2, Rr16), (Rp35,Rq2,Rr17), (Rp35,Rq2, Rr18), (Rp35,Rq2, Rr19), (Rp35,Rq2,Rr20), (Rp35,Rq2,Rr21), (Rp35,Rq2, Rr22), (Rp35,Rq3,Rr1), (Rp35,Rq3,Rr2), (Rp35,Rq3,Rr3), (Rp35,Rq3,Rr4), (Rp35,Rq3,Rr5), (Rp35,Rq3,Rr6), (Rp35, Rq3,Rr7), (Rp35,Rq3,Rr8), (Rp35,Rq3,Rr9), (Rp35,Rq3, Rr10), (Rp35,Rq3,Rr11), (Rp35,Rq3,Rr12), (Rp35,Rq3, Rr13), (Rp35,Rq3,Rr14), (Rp35,Rq3,Rr15), (Rp35,Rq3, Rr16), (Rp35,Rq3,Rr17), (Rp35,Rq3,Rr18), (Rp35,Rq3, Rr19), (Rp35,Rq3,Rr20), (Rp35,Rq3,Rr21), (Rp35,Rq3, Rr22), (Rp35,Rq4,Rr1), (Rp35,Rq4,Rr2), (Rp35,Rq4,Rr3), (Rp35,Rq4,Rr4), (Rp35,Rq4,Rr5), (Rp35,Rq4,Rr6), (Rp35, Rq4,Rr7), (Rp35,Rq4,Rr8), (Rp35,Rq4,Rr9), (Rp35,Rq4, Rr10), (Rp35,Rq4,Rr11), (Rp35,Rq4,Rr12), (Rp35,Rq4, Rr13), (Rp35,Rq4,Rr14), (Rp35,Rq4,Rr15), (Rp35,Rq4, Rr16), (Rp35,Rq4,Rr17), (Rp35,Rq4,Rr18), (Rp35,Rq4, Rr19), (Rp35,Rq4,Rr20), (Rp35,Rq4,Rr21), (Rp35,Rq4, Rr22), (Rp35,Rq5,Rr1), (Rp35,Rq5,Rr2), (Rp35,Rq5,Rr3), (Rp35,Rq5,Rr4), (Rp35,Rq5,Rr5), (Rp35,Rq5,Rr6), (Rp35, Rq5,Rr7), (Rp35,Rq5,Rr8), (Rp35,Rq5,Rr9), (Rp35,Rq5, Rr10), (Rp35,Rq5,Rr11), (Rp35,Rq5,Rr12), (Rp35,Rq5, Rr13), (Rp35,Rq5,Rr14), (Rp35,Rq5,Rr15), (Rp35,Rq5, Rr16), (Rp35,Rq5,Rr17), (Rp35,Rq5,Rr18), (Rp35,Rq5, Rr19), (Rp35,Rq5,Rr20), (Rp35,Rq5,Rr21), (Rp35,Rq5, Rr22), (Rp35,Rq6,R r1), (Rp35,Rq6,Rr2), (Rp35,Rq6,Rr3), (Rp35,Rq6,Rr4), (Rp35,Rq6,Rr5), (Rp35,Rq6,Rr6), (Rp35, Rq6,Rr7), (Rp35,Rq6,Rr8), (Rp35,Rq6,Rr9), (Rp35,Rq6, Rr10), (Rp35,Rq6,Rr11), (Rp35,Rq6,Rr12), (Rp35,Rq6, Rr13), (Rp35,Rq6,Rr14), (Rp35,Rq6,Rr15), (Rp35,Rq6, Rr16), (Rp35,Rq6,Rr17), (Rp35,Rq6,Rr18), (Rp35,Rq6, Rr19), (Rp35,Rq6,Rr20), (Rp35,Rq6,Rr21), (Rp35,Rq6, Rr22), (Rp35,Rq7,Rr1), (Rp35,Rq7,Rr2), (Rp35,Rq7,Rr3), (Rp35,Rq7,Rr4), (Rp35,Rq7,Rr5), (Rp35,Rq7,Rr6), (Rp35, Rq7,Rr7), (Rp35,Rq7,Rr8), (Rp35,Rq7,Rr9), (Rp35,Rq7, Rr10), (Rp35,Rq7,Rr11), (Rp35,Rq7,Rr12), (Rp35,Rq7, Rr13), (Rp35,Rq7,Rr14), (Rp35,Rq7,Rr15), (Rp35,Rq7, Rr16), (Rp35,Rq7,Rr17), (Rp35,Rq7,Rr18), (Rp35,Rq7, Rr19), (Rp35,Rq7,Rr20), (Rp35,Rq7,Rr21), (Rp35,Rq7, Rr22), (Rp35,Rq8,Rr1), (Rp35,Rq8,Rr2), (Rp35,Rq8,Rr3), (Rp35,Rq8,Rr4), (Rp35,Rq8,Rr5), (Rp35,Rq8,Rr6), (Rp35, Rq8,Rr7), (Rp35,Rq8,Rr8), (Rp35,Rq8,Rr9), (Rp35,Rq8, Rr10), (Rp35,Rq8,Rr11), (Rp35,Rq8,Rr12), (Rp35,Rq8, Rr13), (Rp35,Rq8,Rr14), (Rp35,Rq8,Rr15), (Rp35,Rq8, Rr16), (Rp35,Rq8,Rr17), (Rp35,Rq8,Rr18), (Rp35,Rq8, Rr19), (Rp35,Rq8,Rr20), (Rp35,Rq8,Rr21), (Rp35,Rq8, Rr22), (Rp35,Rq9,Rr1), (Rp35,Rq9,Rr2), (Rp35,Rq9,Rr3), (Rp35,Rq9,Rr4), (Rp35,Rq9,Rr5), (Rp35,Rq9,Rr6), (Rp35, Rq9,Rr7), (Rp35,Rq9,Rr8), (Rp35,Rq9,Rr9), (Rp35,Rq9, Rr10), (Rp35,Rq9,Rr11), (Rp35,Rq9,Rr12), (Rp35,Rq9, Rr13), (Rp35,Rq9,Rr14), (Rp35,Rq9,Rr15), (Rp35,Rq9, Rr16), (Rp35, Rq9,Rr17), (Rp35,Rq9,Rr18), (Rp35,Rq9, Rr19), (Rp35,Rq9,Rr20), (Rp35,Rq9,Rr21), (Rp35,Rq9, Rr22), (Rp35,Rq10,Rr1), (Rp35,Rq10,Rr2), (Rp35,Rq10, Rr3), (Rp35,Rq10,Rr4), (Rp35,Rq10,Rr5), (Rp35,Rq10, Rr6), (Rp35,Rq10,Rr7), (Rp35,Rq10,Rr8), (Rp35,Rq10, Rr9), (Rp35,Rq10,Rr10), (Rp35,Rq10,Rr11), (Rp35,Rq10, Rr12), (Rp35,Rq10,Rr13), (Rp35,Rq10,Rr14), (Rp35,Rq10, Rr15), (Rp35,Rq10,Rr16), (Rp35,Rq10,Rr17), (Rp35,Rq10, Rr18), (Rp35,Rq10,Rr19), (Rp35,Rq10,Rr20), (Rp35,Rq10,

Rr21), (Rp35,Rq10,Rr22), (Rp35,Rq11,Rr1), (Rp35,Rq11, Rr2), (Rp35,Rq11,Rr3), (Rp35,Rq11,Rr4), (Rp35,Rq11, Rr5), (Rp35,Rq11,Rr6), (Rp35,Rq11,Rr7), (Rp35,Rq11, Rr8), (Rp35,Rq11,Rr9), (Rp35,Rq11,Rr10), (Rp35,Rq11, Rr11), (Rp35,Rq11,Rr12), (Rp35,Rq11,Rr13), (Rp35,Rq11, Rr14), (Rp35,Rq11,Rr15), (Rp35,Rq11,Rr16), (Rp35,Rq11, Rr17), (Rp35,Rq11,Rr18), (Rp35,Rq11,Rr19), (Rp35,Rq11, Rr20), (Rp35,Rq11,Rr21), (Rp35,Rq11,Rr22), (Rp35,Rq12, Rr1), (Rp35,Rq12,Rr2), (Rp35,Rq12,Rr3), (Rp35,Rq12, Rr4), (Rp35,Rq12,Rr5), (Rp35,Rq12,Rr6), (Rp35,Rq12, Rr7), (Rp35,Rq12,Rr8), (Rp35,Rq12,Rr9), (Rp35,Rq12, Rr10), (Rp35,Rq12,Rr11), (Rp35,Rq12,Rr12), (Rp35,Rq12, Rr13), (Rp35,Rq12,Rr14), (Rp35,Rq12,Rr15), (Rp35,Rq12, Rr16), (Rp35,Rq12,Rr17), (Rp35,Rq12,Rr18), (Rp35,Rq12, Rr19), (Rp35,Rq12,Rr20), (Rp35,Rq12,Rr21), (Rp35,Rq12, Rr22), (Rp36,Rq1,Rr1), (Rp36,Rq1,Rr2), (Rp36,Rq1,Rr3), (Rp36,Rq1,Rr4), (Rp36,Rq1,Rr5), (Rp36,Rq1,Rr6), (Rp36, Rq1,Rr7), (Rp36,Rq1,Rr8), (Rp36,Rq1,Rr9), (Rp36,Rq1, Rr10), (Rp36, Rq1,Rr11), (Rp36,Rq1,Rr12), (Rp36,Rq1, Rr13), (Rp36,Rq1,Rr14), (Rp36,Rq1,Rr15), (Rp36,Rq1, Rr16), (Rp36,Rq1,Rr17), (Rp36,Rq1,Rr18), (Rp36,Rq1, Rr19), (Rp36,Rq1,Rr20), (Rp36,Rq1,Rr21), (Rp36,Rq1, Rr22), (Rp36,Rq2,Rr1), (Rp36,Rq2,Rr2), (Rp36,Rq2,Rr3), (Rp36,Rq2,Rr4), (Rp36,Rq2,Rr5), (Rp36,Rq2,Rr6), (Rp36, Rq2,Rr7), (Rp36,Rq2,Rr8), (Rp36,Rq2,Rr9), (Rp36,Rq2, Rr10), (Rp36,Rq2,Rr11), (Rp36,Rq2,Rr12), (Rp36,Rq2, Rr13), (Rp36,Rq2,Rr14), (Rp36,Rq2,Rr15), (Rp36,Rq2, Rr16), (Rp36,Rq2,Rr17), (Rp36,Rq2,Rr18), (Rp36,Rq2, Rr19), (Rp36,Rq2,Rr20), (Rp36,Rq2,Rr2 (Rp36,Rq2,Rr22), (Rp36,Rq3,Rr1), (Rp36,Rq3,Rr2), (Rp36,Rq3,Rr3), (Rp36, Rq3,Rr4), (Rp36,Rq3,Rr5), (Rp36,Rq3,Rr6), (Rp36,Rq3, Rr7), (Rp36,Rq3,Rr8), (Rp36,Rq3,Rr9), (Rp36,Rq3,Rr10), (Rp36,Rq3,Rr11), (Rp36,Rq3,Rr12), (Rp36,Rq3,Rr13), (Rp36,Rq3,Rr14), (Rp36,Rq3,Rr15), (Rp36,Rq3,Rr16), (Rp36,Rq3,Rr17), (Rp36,Rq3,Rr18), (Rp36,Rq3,Rr19), (Rp36,Rq3,Rr20), (Rp36,Rq3,Rr21), (Rp36,Rq3,Rr22), (Rp36,Rq4,Rr1), (Rp36,Rq4,Rr2), (Rp36,Rq4,Rr3), (Rp36, Rq4,Rr4), (Rp36,Rq4,Rr5), (Rp36,Rq4,Rr6), (Rp36,Rq4, Rr7), (Rp36,Rq4,Rr8), (Rp36,Rq4,Rr9), (Rp36,Rq4,Rr10), (Rp36,Rq4,Rr11), (Rp36,Rq4,Rr12), (Rp36,Rq4,Rr13), (Rp36,Rq4,Rr14), (Rp36,Rq4,Rr15), (Rp36,Rq4,Rr16), (Rp36,Rq4,Rr17), (Rp36,Rq4,Rr18), (Rp36,Rq4,Rr19), (Rp36,Rq4,Rr20), (Rp36,Rq4,Rr21), (Rp36,Rq4,Rr22), (Rp36,Rq5,Rr1), (Rp36,Rq5,Rr2), (Rp36,Rq5,Rr3), (Rp36, Rq5, Rr4), (Rp36,Rq5,Rr5), (Rp36,Rq5,Rr6), (Rp36,Rq5, Rr7), (Rp36,Rq5,Rr8), (Rp36,Rq5,Rr9), (Rp36,Rq5,Rr10), (Rp36,Rq5,Rr11), (Rp36,Rq5,Rr12), (Rp36,Rq5,Rr13), (Rp36,Rq5,Rr14), (Rp36,Rq5,Rr15), (Rp36,Rq5,Rr16), (Rp36,Rq5,Rr17), (Rp36,Rq5,Rr18), (Rp36,Rq5,Rr19), (Rp36,Rq5,Rr20), (Rp36,Rq5,Rr21), (Rp36,Rq5,Rr22), (Rp36,Rq6,Rr1), (Rp36,Rq6,Rr2), (Rp36,Rq6,Rr3), (Rp36, Rq6,Rr4), (Rp36,Rq6,Rr5), (Rp36,Rq6,Rr6), (Rp36,Rq6, Rr7), (Rp36,Rq6,Rr8), (Rp36,Rq6,Rr9), (Rp36,Rq6,Rr10), (Rp36,Rq6,Rr11), (Rp36,Rq6,Rr12), (Rp36,Rq6,Rr13), (Rp36,Rq6,Rr14), (Rp36,Rq6,Rr15), (Rp36,Rq6,Rr16), (Rp36,Rq6,Rr17), (Rp36, Rq6,Rr18), (Rp36,Rq6,Rr19), (Rp36,Rq6,Rr20), (Rp36,Rq6,Rr21), (Rp36,Rq6,Rr22), (Rp36,Rq7,Rr1), (Rp36,Rq7,Rr2), (Rp36,Rq7,Rr3), (Rp36, Rq7,Rr4), (Rp36,Rq7,Rr5), (Rp36,Rq7, Rr6), (Rp36,Rq7, Rr7), (Rp36,Rq7,Rr8), (Rp36,Rq7,Rr9), (Rp36,Rq7,Rr10), (Rp36,Rq7,Rr11), (Rp36,Rq7,Rr12), (Rp36,Rq7,Rr13), (Rp36,Rq7,Rr14), (Rp36,Rq7,Rr15), (Rp36,Rq7,Rr16), (Rp36,Rq7,Rr17), (Rp36,Rq7,Rr18), (Rp36,Rq7,Rr19), (Rp36,Rq7,Rr20), (Rp36,Rq7,Rr21), (Rp36,Rq7,Rr22), (Rp36,Rq8,Rr1), (Rp36,Rq8,Rr2), (Rp36,Rq8,Rr3), (Rp36, Rq8,Rr4), (Rp36,Rq8,Rr5), (Rp36,Rq8,Rr6), (Rp36,Rq8, Rr7), (Rp36,Rq8,Rr8), (Rp36,Rq8,Rr9), (Rp36,Rq8,Rr10), (Rp36,Rq8,Rr11), (Rp36,Rq8,Rr12), (Rp36,Rq8,Rr13), (Rp36,Rq8,Rr14), (Rp36,Rq8,Rr15), (Rp36,Rq8,Rr16), (Rp36,Rq8,Rr17), (Rp36,Rq8,Rr18), (Rp36,Rq8,Rr19), (Rp36,Rq8,Rr20), (Rp36,Rq8,Rr21), (Rp36,Rq8,Rr22), (Rp36,Rq9,Rr1), (Rp36,Rq9,Rr2), (Rp36,Rq9,Rr3), (Rp36, Rq9,Rr4), (Rp36,Rq9,Rr5), (Rp36,Rq9,Rr6), (Rp36,Rq9, Rr7), (Rp36,Rq9,Rr8), (Rp36,Rq9,Rr9), (Rp36,Rq9,Rr10), (Rp36,Rq9,Rr11), (Rp36,Rq9,Rr12), (Rp36,Rq9, Rr13), (Rp36,Rq9,Rr14), (Rp36,Rq9,Rr15), (Rp36,Rq9,Rr16), (Rp36,Rq9,Rr17), (Rp36,Rq9,Rr18), (Rp36,Rq9,Rr19), (Rp36,Rq9,Rr20), (Rp36,Rq9,Rr21), (Rp36,Rq9,Rr22), (Rp36,Rq10,Rr1), (Rp36,Rq10,Rr2), (Rp36,Rq10,Rr3), (Rp36,Rq10,Rr4), (Rp36,Rq10,Rr5), (Rp36,Rq10,Rr6), (Rp36,Rq10,Rr7), (Rp36,Rq10,Rr8), (Rp36,Rq10,Rr9), (Rp36,Rq10,Rr10), (Rp36, Rq10,Rr11), (Rp36,Rq10,Rr12), (Rp36,Rq10,Rr13), (Rp36,Rq10,Rr14), (Rp36,Rq10,Rr15), (Rp36,Rq10,Rr16), (Rp36,Rq10,Rr17), (Rp36,Rq10,Rr18), (Rp36,Rq10,Rr19), (Rp36,Rq10, Rr20), (Rp36,Rq10,Rr21), (Rp36,Rq10,Rr22), (Rp36,Rq11,Rr1), (Rp36,Rq11,Rr2), (Rp36,Rq11,Rr3), (Rp36,Rq11,Rr4), (Rp36,Rq11,Rr5), (Rp36,Rq11,Rr6), (Rp36,Rq11,Rr7), (Rp36, Rq11,Rr8), (Rp36,Rq11,Rr9), (Rp36,Rq11,Rr10), (Rp36,Rq11, Rr11), (Rp36,Rq11,Rr12), (Rp36,Rq11,Rr13), (Rp36,Rq11,Rr14), (Rp36,Rq11,Rr15), (Rp36,Rq11,Rr16), (Rp36,Rq11,Rr17), (Rp36,Rq11,Rr18), (Rp36,Rq11,Rr19), (Rp36,Rq11,Rr20), (Rp36,Rq11,Rr21), (Rp36, Rq11,Rr22), (Rp36,Rq12,Rr1), (Rp36,Rq12,Rr2), (Rp36,Rq12,Rr3), (Rp36,Rq12,Rr4), (Rp36,Rq12,Rr5), (Rp36,Rq12,Rr6), (Rp36,Rq12,Rr7), (Rp36,Rq12,Rr8), (Rp36,Rq12,Rr9), (Rp36,Rq12,Rr10), (Rp36,Rq12,Rr11), (Rp36,Rq12,Rr12), (Rp36,Rq12,Rr13), (Rp36,Rq12,Rr14), (Rp36,Rq12,Rr15), (Rp36,Rq12,Rr16), (Rp36,Rq12,Rr17), (Rp36,Rq12,Rr18), (Rp36,Rq12,Rr19), (Rp36,Rq12,Rr20), (Rp36,Rq12,Rr21), (Rp36,Rq12,Rr22), (Rp37,Rq1,Rr1), (Rp37,Rq1,Rr2), (Rp37,Rq1,Rr3), (Rp37, Rq1,Rr4), (Rp37,Rq1,Rr5), (Rp37,Rq1,Rr6), (Rp37,Rq1, Rr7), (Rp37,Rq1,Rr8), (Rp37,Rq1,Rr9), (Rp37,Rq1,Rr10), (Rp37,Rq1,Rr11), (Rp37,Rq1,Rr12), (Rp37,Rq1,Rr13), (Rp37,Rq1,Rr14), (Rp37,Rq1,Rr15), (Rp37,Rq1,Rr16), (Rp37,Rq1, Rr17), (Rp37,Rq1,Rr18), (Rp37,Rq1,Rr19), (Rp37,Rq1,Rr20), (Rp37,Rq1,Rr21), (Rp37,Rq1,Rr22), (Rp37,Rq2,Rr1), (Rp37,Rq2,Rr2), (Rp37,Rq2,Rr3), (Rp37, Rq2,Rr4), (Rp37,Rq2,Rr5), (Rp37,Rq2,Rr6), (Rp37,Rq2, Rr7), (Rp37,Rq2,Rr8), (Rp37,Rq2,Rr9), (Rp37,Rq2,Rr10), (Rp37,Rq2,Rr11), (Rp37,Rq2,Rr12), (Rp37,Rq2,Rr13), (Rp37,Rq2,Rr14), (Rp37,Rq2,Rr15), (Rp37,Rq2,Rr16), (Rp37,Rq2,Rr17), (Rp37,Rq2,Rr18), (Rp37,Rq2,Rr19), (Rp37,Rq2,Rr20), (Rp37,Rq2,Rr21), (Rp37,Rq2,Rr22), (Rp37,Rq3,Rr1), (Rp37,Rq3,Rr2), (Rp37,Rq3,Rr3), (Rp37, Rq3,Rr4), (Rp37,Rq3,Rr5), (Rp37,Rq3,Rr6), (Rp37,Rq3, Rr7), (Rp37,Rq3,Rr8), (Rp37, Rq3,Rr9), (Rp37,Rq3,Rr10), (Rp37,Rq3,Rr11), (Rp37,Rq3,Rr12), (Rp37,Rq3,Rr13), (Rp37, Rq3,Rr14), (Rp37,Rq3,Rr15), (Rp37,Rq3,Rr16), (Rp37,Rq3,Rr17), (Rp37,Rq3,Rr18), (Rp37,Rq3,Rr19), (Rp37,Rq3,Rr20), (Rp37,Rq3,Rr21), (Rp37,Rq3,Rr22), (Rp37,Rq4,Rr1), (Rp37, Rq4,Rr2), (Rp37,Rq4,Rr3), (Rp37, Rq4,Rr4), (Rp37,Rq4,Rr5), (Rp37,Rq4,Rr6), (Rp37,Rq4, Rr7), (Rp37,Rq4,Rr8), (Rp37,Rq4,Rr9), (Rp37,Rq4,Rr10), (Rp37,Rq4,Rr11), (Rp37,Rq4,Rr12), (Rp37,Rq4,Rr13), (Rp37,Rq4,Rr14), (Rp37,Rq4,Rr15), (Rp37,Rq4,Rr16), (Rp37,Rq4,Rr17), (Rp37,Rq4,Rr18), (Rp37,Rq4,Rr19), (Rp37,Rq4,Rr20), (Rp37,Rq4,Rr21), (Rp37,Rq4, Rr22), (Rp37,Rq5,Rr1), (Rp37,Rq5,Rr2), (Rp37,Rq5,Rr3), (Rp37, Rq5,Rr4), (Rp37,Rq5,Rr5), (Rp37,Rq5,Rr6), (Rp37,Rq5, Rr7), (Rp37,Rq5,Rr8), (Rp37,Rq5,Rr9), (Rp37,Rq5,Rr10), (Rp37,Rq5,Rr11), (Rp37,Rq5,Rr12), (Rp37,Rq5,Rr13), (Rp37,Rq5,Rr14), (Rp37,Rq5,Rr15), (Rp37,Rq5,Rr16), (Rp37,Rq5,Rr17), (Rp37,Rq5,Rr18), (Rp37,Rq5,Rr19), (Rp37,Rq5,Rr20), (Rp37,Rq5,Rr21), (Rp37,Rq5,Rr22), (Rp37,Rq6,Rr1), (Rp37,Rq6,Rr2), (Rp37,Rq6,Rr3), (Rp37,Rq6,Rr4), (Rp37,Rq6,Rr5), (Rp37,Rq6,Rr6), (Rp37,Rq6,Rr7), (Rp37,Rq6,Rr8), (Rp37,Rq6,Rr9), (Rp37,Rq6,Rr10), (Rp37,Rq6,Rr11), (Rp37,Rq6,Rr12), (Rp37,Rq6,Rr13), (Rp37,Rq6,Rr14), (Rp37,Rq6,Rr15), (Rp37,Rq6,Rr16), (Rp37,Rq6,Rr17), (Rp37,Rq6,Rr18), (Rp37,Rq6,Rr19), (Rp37,Rq6,Rr20), (Rp37,Rq6,Rr21), (Rp37,Rq6,Rr22), (Rp37,Rq7,Rr1), (Rp37,Rq7,Rr2), (Rp37,Rq7,Rr3), (Rp37,Rq7,Rr4), (Rp37,Rq7,Rr5), (Rp37,Rq7,Rr6), (Rp37,Rq7,Rr7), (Rp37,Rq7,Rr8), (Rp37,Rq7,Rr9), (Rp37,Rq7,Rr10), (Rp37,Rq7,Rr11), (Rp37,Rq7,Rr12), (Rp37,Rq7,Rr13), (Rp37,Rq7,Rr14), (Rp37,Rq7,Rr15), (Rp37,Rq7,Rr16), (Rp37,Rq7,Rr17), (Rp37,Rq7,Rr18), (Rp37,Rq7,Rr19), (Rp37,Rq7,Rr20), (Rp37,Rq7,Rr21), (Rp37,Rq7,Rr22), (Rp37,Rq8,Rr1), (Rp37,Rq8,Rr2), (Rp37,Rq8,Rr3), (Rp37,Rq8,Rr4), (Rp37,Rq8,Rr5), (Rp37,Rq8,Rr6), (Rp37,Rq8,Rr7), (Rp37,Rq8,Rr8), (Rp37,Rq8,Rr9), (Rp37,Rq8,Rr10), (Rp37, Rq8,Rr11), (Rp37,Rq8,Rr12), (Rp37,Rq8,Rr13), (Rp37,Rq8,Rr14), (Rp37,Rq8,Rr15), (Rp37,Rq8,Rr16), (Rp37,Rq8,Rr17), (Rp37,Rq8,Rr18), (Rp37,Rq8,Rr19), (Rp37,Rq8,Rr20), (Rp37,Rq8,Rr21), (Rp37,Rq8,Rr22), (Rp37,Rq9,Rr1), (Rp37,Rq9,Rr2), (Rp37,Rq9,Rr3), (Rp37,Rq9,Rr4), (Rp37,Rq9,Rr5), (Rp37,Rq9,Rr6), (Rp37,Rq9,Rr7), (Rp37,Rq9,Rr8), (Rp37,Rq9,Rr9), (Rp37,Rq9,Rr10), (Rp37,Rq9,Rr11), (Rp37,Rq9,Rr12), (Rp37,Rq9,Rr13), (Rp37,Rq9,Rr14), (Rp37,Rq9,Rr15), (Rp37,Rq9,Rr16), (Rp37,Rq9,Rr17), (Rp37,Rq9,Rr18), (Rp37,Rq9,Rr19), (Rp37,Rq9,Rr20), (Rp37,Rq9,Rr21), (Rp37,Rq9,Rr22), (Rp37,Rq10,Rr1), (Rp37,Rq10, Rr2), (Rp37,Rq10,Rr3), (Rp37,Rq10,Rr4), (Rp37,Rq10,Rr5), (Rp37,Rq10,Rr6), (Rp37,Rq10,Rr7), (Rp37,Rq10,Rr8), (Rp37,Rq10,Rr9), (Rp37,Rq10,Rr10), (Rp37,Rq10,Rr11), (Rp37,Rq10,Rr12), (Rp37,Rq10,Rr13), (Rp37,Rq10,Rr14), (Rp37,Rq10,Rr15), (Rp37,Rq10,Rr16), (Rp37,Rq10,Rr17), (Rp37,Rq10,Rr18), (Rp37,Rq10,Rr19), (Rp37,Rq10,Rr20), (Rp37,Rq10, Rr21), (Rp37,Rq10,Rr22), (Rp37,Rq11,Rr1), (Rp37,Rq11,Rr2), (Rp37,Rq11,Rr3), (Rp37,Rq11,Rr4), (Rp37,Rq11,Rr5), (Rp37,Rq11,Rr6), (Rp37,Rq11,Rr7), (Rp37,Rq11,Rr8), (Rp37,Rq11,Rr9), (Rp37,Rq11,Rr10), (Rp37,Rq11,Rr11), (Rp37,Rq11,Rr12), (Rp37,Rq11,Rr13), (Rp37,Rq11,Rr14), (Rp37,Rq11,Rr15), (Rp37,Rq11,Rr16), (Rp37,Rq11,Rr17), (Rp37,Rq11,Rr18), (Rp37,Rq11,Rr19), (Rp37,Rq11,Rr20), (Rp37,Rq11,Rr21), (Rp37,Rq11,Rr22), (Rp37, Rq12,Rr1), (Rp37,Rq12,Rr2), (Rp37,Rq12,Rr3), (Rp37,Rq12,Rr4), (Rp37,Rq12,Rr5), (Rp37,Rq12,Rr6), (Rp37,Rq12,Rr7), (Rp37,Rq12,Rr8), (Rp37,Rq12,Rr9), (Rp37,Rq12,Rr10), (Rp37,Rq12,Rr11), (Rp37,Rq12,Rr12), (Rp37,Rq12,Rr13), (Rp37,Rq12,Rr14), (Rp37,Rq12,Rr15), (Rp37,Rq12,Rr16), (Rp37,Rq12,Rr17), (Rp37,Rq12,Rr18), (Rp37,Rq12,Rr19), (Rp37,Rq12,Rr20), (Rp37,Rq12,Rr21), (Rp37,Rq12,Rr22), (Rp38,Rq1,Rr1), (Rp38,Rq1,Rr2), (Rp38, Rq1,Rr3), (Rp38,Rq1,Rr4), (Rp38,Rq1,Rr5), (Rp38,Rq1,Rr6), (Rp38,Rq1,Rr7), (Rp38,Rq1,Rr8), (Rp38,Rq1,Rr9), (Rp38,Rq1,Rr10), (Rp38,Rq1,Rr11), (Rp38,Rq1,Rr12), (Rp38,Rq1,Rr13), (Rp38,Rq1,Rr14), (Rp38,Rq1,Rr15), (Rp38,Rq1,Rr16), (Rp38,Rq1,Rr17), (Rp38,Rq1, Rr18), (Rp38,Rq1,Rr19), (Rp38,Rq1,Rr20), (Rp38,Rq1,Rr21), (Rp38,Rq1,Rr22), (Rp38,Rq2,Rr1), (Rp38,Rq2,Rr2), (Rp38,Rq2,Rr3), (Rp38, Rq2,Rr4), (Rp38,Rq2,Rr5), (Rp38,Rq2,Rr6), (Rp38,Rq2,Rr7), (Rp38,Rq2,Rr8), (Rp38,Rq2,Rr9), (Rp38,Rq2,Rr10), (Rp38,Rq2,Rr11), (Rp38,Rq2,Rr12), (Rp38,Rq2,Rr13), (Rp38,Rq2,Rr14), (Rp38,Rq2,Rr15), (Rp38,Rq2,Rr16), (Rp38,Rq2,Rr17), (Rp38,Rq2,Rr18), (Rp38,Rq2,Rr19), (Rp38,Rq2,Rr20), (Rp38,Rq2,Rr21), (Rp38,Rq2,Rr22), (Rp38,Rq3,Rr1), (Rp38,Rq3,Rr2), (Rp38,Rq3,Rr3), (Rp38, Rq3,Rr4), (Rp38,Rq3,Rr5), (Rp38,Rq3,Rr6), (Rp38,Rq3, Rr7), (Rp38,Rq3,Rr8), (Rp38,Rq3,Rr9), (Rp38,Rq3,Rr10), (Rp38,Rq3,Rr11), (Rp38,Rq3,Rr12), (Rp38,Rq3,Rr13), (Rp38,Rq3,Rr14), (Rp38,Rq3,Rr15), (Rp38,Rq3,Rr16), (Rp38,Rq3,Rr17), (Rp38,Rq3,Rr18), (Rp38,Rq3,Rr19), (Rp38, Rq3,Rr20), (Rp38,Rq3,Rr21), (Rp38,Rq3,Rr22), (Rp38,Rq4,Rr1), (Rp38,Rq4,Rr2), (Rp38,Rq4,Rr3), (Rp38, Rq4,Rr4), (Rp38,Rq4,Rr5), (Rp38,Rq4,Rr6), (Rp38,Rq4, Rr7), (Rp38,Rq4,Rr8), (Rp38,Rq4,Rr9), (Rp38,Rq4,Rr10), (Rp38,Rq4,Rr11), (Rp38,Rq4,Rr12), (Rp38,Rq4,Rr13), (Rp38,Rq4,Rr14), (Rp38,Rq4,Rr15), (Rp38,Rq4,Rr16), (Rp38,Rq4,Rr17), (Rp38,Rq4,Rr18), (Rp38,Rq4,Rr19), (Rp38,Rq4,Rr20), (Rp38,Rq4,Rr21), (Rp38,Rq4,Rr22), (Rp38,Rq5,Rr1), (Rp38,Rq5,Rr2), (Rp38,Rq5,Rr3), (Rp38, Rq5,Rr4), (Rp38,Rq5,Rr5), (Rp38,Rq5,Rr6), (Rp38,Rq5, Rr7), (Rp38,Rq5,Rr8), (Rp38,Rq5,Rr9), (Rp38,Rq5,Rr10), (Rp38,Rq5,Rr11), (Rp38,Rq5,Rr12), (Rp38,Rq5,Rr13), (Rp38,Rq5,Rr14), (Rp38,Rq5,Rr15), (Rp38,Rq5,Rr16), (Rp38,Rq5,Rr17), (Rp38,Rq5,Rr18), (Rp38,Rq5,Rr19), (Rp38,Rq5,Rr20), (Rp38,Rq5,Rr21), (Rp38,Rq5,Rr22), (Rp38,Rq6,Rr1), (Rp38,Rq6,Rr2), (Rp38,Rq6,Rr3), (Rp38, Rq6,Rr4), (Rp38,Rq6,Rr5), (Rp38,Rq6,Rr6), (Rp38,Rq6, Rr7), (Rp38,Rq6,Rr8), (Rp38,Rq6,Rr9), (Rp38,Rq6,Rr10), (Rp38,Rq6,Rr11), (Rp38,Rq6,Rr12), (Rp38,Rq6,Rr13), (Rp38,Rq6,Rr14), (Rp38,Rq6,Rr15), (Rp38,Rq6,Rr12), (Rp38,Rq6,Rr17), (Rp38,Rq6,Rr18), (Rp38,Rq6,Rr19), (Rp38,Rq6,Rr20), (Rp38,Rq6,Rr21), (Rp38,Rq6,Rr22), (Rp38,Rq7,Rr1), (Rp38,Rq7,Rr2), (Rp38,Rq7,Rr3), (Rp38, Rq7,Rr4), (Rp38,Rq7,Rr5), (Rp38,Rq7,Rr6), (Rp38,Rq7, Rr7), (Rp38,Rq7,Rr8), (Rp38,Rq7,Rr9), (Rp38,Rq7,Rr10), (Rp38,Rq7,Rr11), (Rp38,Rq7,Rr12), (Rp38,Rq7,Rr13), (Rp38,Rq7,Rr14), (Rp38,Rq7,Rr15), (Rp38,Rq7,Rr16), (Rp38,Rq7,Rr17), (Rp38,Rq7,Rr18), (Rp38,Rq7,Rr19), (Rp38,Rq7,Rr20), (Rp38,Rq7,Rr21), (Rp38,Rq7,Rr22), (Rp38,Rq8,Rr1), (Rp38,Rq8,Rr2), (Rp38,Rq8,Rr3), (Rp38, Rq8,Rr4), (Rp38,Rq8,Rr5), (Rp38,Rq8,Rr6), (Rp38,Rq8, Rr7), (Rp38,Rq8,Rr8), (Rp38,Rq8,Rr9), (Rp38,Rq8,Rr10), (Rp38,Rq8,Rr11), (Rp38,Rq8,Rr12), (Rp38,Rq8,Rr13), (Rp38,Rq8,Rr14), (Rp38,Rq8,Rr15), (Rp38,Rq8,Rr16), (Rp38, Rq8,Rr17), (Rp38,Rq8,Rr18), (Rp38,Rq8,Rr19), (Rp38,Rq8,Rr20), (Rp38,Rq8,Rr21), (Rp38,Rq8,Rr22), (Rp38,Rq9,Rr1), (Rp38,Rq9,Rr2), (Rp38,Rq9,Rr3), (Rp38, Rq9,Rr4), (Rp38,Rq9,Rr5), (Rp38,Rq9,Rr6), (Rp38,Rq9, Rr7), (Rp38,Rq9,Rr8), (Rp38,Rq9,Rr9), (Rp38,Rq9,Rr10), (Rp38,Rq9,Rr11), (Rp38,Rq9,Rr12), (Rp38,Rq9,Rr13), (Rp38,Rq9,Rr14), (Rp38,Rq9,Rr15), (Rp38,Rq9,Rr16), (Rp38,Rq9,Rr17), (Rp38,Rq9,Rr18), (Rp38,Rq9,Rr19), (Rp38,Rq9,Rr20), (Rp38,Rq9,Rr21), (Rp38,Rq9,Rr22), (Rp38,Rq10,Rr1), (Rp38,Rq10,Rr2), (Rp38,Rq10, Rr3), (Rp38,Rq10,Rr4), (Rp38,Rq10,Rr5), (Rp38,Rq10,Rr6), (Rp38,Rq10,Rr7), (Rp38,Rq10,Rr8), (Rp38,Rq10,Rr9), (Rp38,Rq10,Rr10), (Rp38,Rq10,Rr11), (Rp38,Rq10,Rr12), (Rp38, Rq10,Rr13), (Rp38,Rq10,Rr14), (Rp38,Rq10,Rr15), (Rp38,Rq10,Rr16), (Rp38,Rq10,Rr17), (Rp38,Rq10,Rr18), (Rp38,Rq10,Rr19), (Rp38,Rq10,Rr20), (Rp38,Rq10,Rr21), (Rp38,Rq10, Rr22), (Rp38,Rq11,Rr1), (Rp38,Rq11,Rr2), (Rp38,Rq11,Rr3), (Rp38,Rq11,Rr4), (Rp38,Rq11,Rr5), (Rp38,Rq11,Rr6), (Rp38,Rq11,Rr7), (Rp38,Rq11,Rr8), (Rp38,Rq11,Rr9), (Rp38,Rq11,Rr10), (Rp38,Rq11,Rr11), (Rp38,Rq11,Rr12), (Rp38,Rq11,Rr13), (Rp38,Rq11,Rr14), (Rp38,Rq11,Rr15), (Rp38,Rq11,Rr16), (Rp38,Rq11,Rr17), (Rp38,Rq11,Rr18), (Rp38,Rq11,Rr19), (Rp38,Rq11,Rr20), (Rp38,Rq11,Rr21), (Rp38,Rq11,Rr22), (Rp38,Rq12,Rr1), (Rp38,Rq12,Rr2), (Rp38,Rq12,Rr3), (Rp38,Rq12,Rr4), (Rp38,Rq12,Rr5), (Rp38,Rq12,Rr6), (Rp38, Rq12,Rr7), (Rp38,Rq12,Rr8), (Rp38,Rq12,Rr9), (Rp38,Rq12,Rr10), (Rp38,Rq12,Rr11), (Rp38,Rq12,Rr12), (Rp38,Rq12,Rr13), (Rp38,Rq12,Rr14), (Rp38,Rq12,Rr15), (Rp38,Rq12,Rr16), (Rp38,Rq12,Rr17), (Rp38,Rq12,Rr18), (Rp38,Rq12,Rr19), (Rp38,Rq12,Rr20), (Rp38,Rq12,Rr21), (Rp38,Rq12,Rr22), (Rp39,Rq1,Rr1), (Rp39,Rq1,Rr2), (Rp39,Rq1,Rr3), (Rp39,Rq1,Rr4), (Rp39,Rq1,Rr5), (Rp39,Rq1,Rr6), (Rp39,Rq1,Rr7), (Rp39,Rq1,Rr8), (Rp39,Rq1,Rr9), (Rp39,Rq1,Rr10), (Rp39,Rq1,Rr11), (Rp39,Rq1,Rr12), (Rp39,Rq1,Rr13), (Rp39,Rq1,Rr14), (Rp39,Rq1,Rr15), (Rp39,Rq1,Rr16), (Rp39,Rq1,Rr17), (Rp39,Rq1,Rr18), (Rp39,Rq1,Rr19), (Rp39,Rq1,Rr20), (Rp39,Rq1,Rr21), (Rp39,Rq1,Rr22), (Rp39,Rq2,Rr1), (Rp39,Rq2,Rr2), (Rp39,Rq2,Rr3), (Rp39,Rq2,Rr4), (Rp39,Rq2,Rr5), (Rp39,Rq2,Rr6), (Rp39,Rq2,Rr7), (Rp39,Rq2,Rr8), (Rp39,Rq2,Rr9), (Rp39,Rq2,Rr10), (Rp39,Rq2,Rr11), (Rp39,Rq2,Rr12), (Rp39,Rq2,Rr13), (Rp39,Rq2,Rr14), (Rp39,Rq2,Rr15), (Rp39,Rq2,Rr16), (Rp39,Rq2,Rr17), (Rp39,Rq2,Rr18), (Rp39,Rq2,Rr19), (Rp39,Rq2,Rr20), (Rp39,Rq2,Rr21), (Rp39,Rq2,Rr22), (Rp39,Rq3,Rr1), (Rp39,Rq3,Rr2), (Rp39,Rq3,Rr3), (Rp39,Rq3,Rr4), (Rp39,Rq3,Rr5), (Rp39,Rq3,Rr6), (Rp39,Rq3,Rr7), (Rp39,Rq3,Rr8), (Rp39,Rq3,Rr9), (Rp39,Rq3,Rr10), (Rp39,Rq3,Rr11), (Rp39,Rq3,Rr12), (Rp39,Rq3,Rr13), (Rp39,Rq3,Rr14), (Rp39,Rq3,Rr15), (Rp39,Rq3,Rr16), (Rp39,Rq3,Rr17), (Rp39,Rq3,Rr18), (Rp39,Rq3,Rr19), (Rp39,Rq3,Rr20), (Rp39,Rq3,Rr21), (Rp39,Rq3,Rr22), (Rp39,Rq4,Rr1), (Rp39,Rq4,Rr2), (Rp39,Rq4,Rr3), (Rp39,Rq4,Rr4), (Rp39,Rq4,Rr5), (Rp39,Rq4,Rr6), (Rp39,Rq4,Rr7), (Rp39,Rq4,Rr8), (Rp39,Rq4,Rr9), (Rp39,Rq4,Rr10), (Rp39,Rq4,Rr11), (Rp39,Rq4,Rr12), (Rp39,Rq4,Rr13), (Rp39,Rq4,Rr14), (Rp39,Rq4,Rr15), (Rp39,Rq4,Rr16), (Rp39,Rq4,Rr17), (Rp39,Rq4,Rr18), (Rp39,Rq4,Rr19), (Rp39,Rq4,Rr20), (Rp39,Rq4,Rr21), (Rp39,Rq4,Rr22), (Rp39,Rq5,Rr1), (Rp39,Rq5,Rr2), (Rp39,Rq5,Rr3), (Rp39,Rq5,Rr4), (Rp39,Rq5,Rr5), (Rp39,Rq5,Rr6), (Rp39,Rq5,Rr7), (Rp39,Rq5,Rr8), (Rp39,Rq5,Rr9), (Rp39,Rq5,Rr10), (Rp39,Rq5,Rr11), (Rp39,Rq5,Rr12), (Rp39,Rq5,Rr13), (Rp39,Rq5,Rr14), (Rp39,Rq5,Rr15), (Rp39,Rq5,Rr16), (Rp39,Rq5,Rr17), (Rp39, Rq5,Rr18), (Rp39,Rq5,Rr19), (Rp39,Rq5,Rr20), (Rp39,Rq5,Rr21), (Rp39,Rq5,Rr22), (Rp39,Rq6,Rr1), (Rp39,Rq6,Rr2), (Rp39,Rq6,Rr3), (Rp39,Rq6,Rr4), (Rp39,Rq6,Rr5), (Rp39,Rq6, Rr6), (Rp39,Rq6,Rr2), (Rp39,Rq6,Rr8), (Rp39,Rq6,Rr9), (Rp39,Rq6,Rr10), (Rp39,Rq6,Rr11), (Rp39,Rq6,Rr12), (Rp39,Rq6,Rr13), (Rp39,Rq6,Rr14), (Rp39,Rq6,Rr15), (Rp39,Rq6,Rr16), (Rp39,Rq6,Rr17), (Rp39,Rq6,Rr18), (Rp39,Rq6,Rr19), (Rp39,Rq6,Rr20), (Rp39,Rq6,Rr21), (Rp39,Rq6,Rr22), (Rp39,Rq7,Rr1), (Rp39,Rq7,Rr2), (Rp39,Rq7,Rr3), (Rp39,Rq7,Rr4), (Rp39,Rq7,Rr5), (Rp39,Rq7,Rr6), (Rp39,Rq7,Rr7), (Rp39,Rq7,Rr8), (Rp39,Rq7,Rr9), (Rp39,Rq7,Rr10), (Rp39,Rq7,Rr11), (Rp39,Rq7,Rr12), (Rp39,Rq7,Rr13), (Rp39,Rq7,Rr14), (Rp39,Rq7,Rr15), (Rp39,Rq7,Rr16), (Rp39,Rq7,Rr17), (Rp39,Rq7,Rr18), (Rp39,Rq7,Rr19), (Rp39,Rq7,Rr20), (Rp39,Rq7,Rr21), (Rp39,Rq7,Rr22), (Rp39,Rq8,Rr1), (Rp39,Rq8,Rr2), (Rp39,Rq8,Rr3), (Rp39,Rq8,Rr4), (Rp39,Rq8,Rr5), (Rp39,Rq8,Rr6), (Rp39,Rq8,Rr7), (Rp39,Rq8,Rr8), (Rp39,Rq8,Rr9), (Rp39,Rq8,Rr10), (Rp39,Rq8,Rr11), (Rp39,Rq8,Rr12), (Rp39,Rq8, Rr13), (Rp39,Rq8,Rr14), (Rp39,Rq8,Rr15), (Rp39,Rq8,Rr16), (Rp39,Rq8,Rr17), (Rp39,Rq8,Rr18), (Rp39,Rq8,Rr19), (Rp39,Rq8,Rr20), (Rp39,Rq8,Rr21), (Rp39,Rq8,Rr22), (Rp39,Rq9,Rr1), (Rp39,Rq9,Rr2), (Rp39,Rq9,Rr3), (Rp39,Rq9,Rr4), (Rp39,Rq9,Rr5), (Rp39,Rq9,Rr6), (Rp39,Rq9,Rr7), (Rp39,Rq9,Rr8), (Rp39,Rq9,Rr9), (Rp39,Rq9,Rr10), (Rp39,Rq9,Rr11), (Rp39,Rq9,Rr12), (Rp39,Rq9,Rr13), (Rp39,Rq9,Rr14), (Rp39,Rq9,Rr15), (Rp39,Rq9,Rr16), (Rp39,Rq9,Rr17), (Rp39,Rq9,Rr18), (Rp39,Rq9,Rr19), (Rp39,Rq9,Rr20), (Rp39,Rq9,Rr21), (Rp39,Rq9,Rr22), (Rp39,Rq10,Rr1), (Rp39,Rq10,Rr2), (Rp39,Rq10,Rr3), (Rp39,Rq10,Rr4), (Rp39,Rq10,Rr5), (Rp39,Rq10,Rr6), (Rp39,Rq10,Rr7), (Rp39,Rq10,Rr8), (Rp39,Rq10,Rr9), (Rp39,Rq10,Rr10), (Rp39,Rq10,Rr11), (Rp39,Rq10,Rr12), (Rp39,Rq10,Rr13), (Rp39,Rq10,Rr14), (Rp39,Rq10,Rr15), (Rp39,Rq10,Rr16), (Rp39,Rq10,Rr17), (Rp39,Rq10,Rr18), (Rp39,Rq10,Rr19), (Rp39,Rq10,Rr20), (Rp39,Rq10,Rr21), (Rp39,Rq10,Rr22), (Rp39,Rq11,Rr2), (Rp39,Rq11,Rr2), (Rp39,Rq11,Rr3), (Rp39,Rq11,Rr4), (Rp39,Rq11,Rr5), (Rp39,Rq11,Rr6), (Rp39,Rq11,Rr7), (Rp39,Rq11,Rr8), (Rp39,Rq11,Rr9), (Rp39,Rq11,Rr10), (Rp39,Rq11,Rr11), (Rp39,Rq11,Rr12), (Rp39,Rq11,Rr13), (Rp39,Rq11,Rr14), (Rp39,Rq11,Rr15), (Rp39,Rq11,Rr16), (Rp39,Rq11,Rr17), (Rp39,Rq11,Rr18), (Rp39,Rq11,Rr19), (Rp39,Rq11,Rr20), (Rp39,Rq11,Rr21), (Rp39,Rq11,Rr22), (Rp39,Rq12,Rr1), (Rp39,Rq12,Rr2), (Rp39,Rq12,Rr3), (Rp39,Rq12,Rr4), (Rp39,Rq12,Rr5), (Rp39,Rq12,Rr6), (Rp39,Rq12,Rr7), (Rp39,Rq12,Rr8), (Rp39,Rq12,Rr9), (Rp39,Rq12,Rr10), (Rp39,Rq12,Rr11), (Rp39,Rq12,Rr12), (Rp39,Rq12,Rr13), (Rp39,Rq12,Rr14), (Rp39,Rq12,Rr15), (Rp39,Rq12,Rr16), (Rp39,Rq12,Rr17), (Rp39,Rq12,Rr18), (Rp39,Rq12,Rr19), (Rp39,Rq12,Rr20), (Rp39,Rq12,Rr21), (Rp39,Rq12,Rr22), (Rp40,Rq1,Rr1), (Rp40,Rq1,Rr2), (Rp40,Rq1,Rr3), (Rp40,Rq1,Rr4), (Rp40,Rq1,Rr5), (Rp40,Rq1,Rr6), (Rp40,Rq1,Rr7), (Rp40,Rq1,Rr8), (Rp40,Rq1,Rr9), (Rp40,Rq1,Rr10), (Rp40,Rq1,Rr11), (Rp40,Rq1,Rr12), (Rp40,Rq1,Rr13), (Rp40,Rq1,Rr14), (Rp40,Rq1,Rr15), (Rp40,Rq1,Rr16), (Rp40,Rq1,Rr17), (Rp40,Rq1,Rr18), (Rp40,Rq1,Rr19), (Rp40,Rq1,Rr20), (Rp40,Rq11,Rr21), (Rp40,Rq1,Rr22), (Rp40,Rq2,Rr1), (Rp40,Rq2,Rr2), (Rp40,Rq2,Rr3), (Rp40,Rq2,Rr4), (Rp40,Rq2,Rr5), (Rp40,Rq2,Rr6), (Rp40,Rq2,Rr7), (Rp40,Rq2,Rr8), (Rp40, Rq2,Rr9), (Rp40,Rq2,Rr10), (Rp40,Rq2,Rr11), (Rp40,Rq2,Rr12), (Rp40,Rq2,Rr13), (Rp40, Rq2,Rr14), (Rp40,Rq2,Rr15), (Rp40,Rq2,Rr16), (Rp40,Rq2,Rr17), (Rp40,Rq2,Rr18), (Rp40,Rq2,Rr19), (Rp40,Rq2,Rr20), (Rp40,Rq2,Rr21), (Rp40,Rq2,Rr22), (Rp40,Rq3,Rr1), (Rp40, Rq3,Rr2), (Rp40,Rq3,Rr3), (Rp40,Rq3,Rr4), (Rp40,Rq3,Rr5), (Rp40,Rq3,Rr6), (Rp40,Rq3,Rr7), (Rp40,Rq3,Rr8), (Rp40,Rq3,Rr9), (Rp40,Rq3,Rr10), (Rp40,Rq3,Rr11), (Rp40,Rq3,Rr12), (Rp40,Rq3,Rr13), (Rp40,Rq3,Rr14), (Rp40,Rq3,Rr15), (Rp40,Rq3,Rr16), (Rp40,Rq3,Rr17), (Rp40,Rq3,Rr18), (Rp40,Rq3,Rr19), (Rp40,Rq3,Rr20), (Rp40,Rq3,Rr21), (Rp40,Rq3, Rr22), (Rp40,Rq4,Rr1), (Rp40,Rq4,Rr2), (Rp40,Rq4,Rr3), (Rp40,Rq4,Rr4), (Rp40,Rq4,Rr5), (Rp40,Rq4,Rr6), (Rp40,Rq4,Rr7), (Rp40,Rq4,Rr8), (Rp40,Rq4,Rr9), (Rp40,Rq4,Rr10), (Rp40,Rq4,Rr11), (Rp40,Rq4,Rr12), (Rp40,Rq4,Rr13), (Rp40,Rq4,Rr14), (Rp40,Rq4,Rr15), (Rp40,Rq4,Rr16), (Rp40,Rq4,Rr17), (Rp40,Rq4,Rr18), (Rp40,Rq4,Rr19), (Rp40,Rq4,Rr20), (Rp40,Rq4,Rr21), (Rp40,Rq4,Rr22), (Rp40,Rq5,Rr1), (Rp40,Rq5,Rr2), (Rp40,Rq5,Rr3), (Rp40,Rq5,Rr4), (Rp40,Rq5,Rr5), (Rp40,Rq5,Rr6), (Rp40,Rq5,Rr7), (Rp40,Rq5,Rr8), (Rp40,Rq5,Rr9), (Rp40,Rq5,Rr10), (Rp40,Rq5,Rr11), (Rp40,Rq5,Rr12), (Rp40,Rq5,Rr13), (Rp40,Rq5,Rr14), (Rp40,Rq5,Rr15), (Rp40,Rq5,Rr16), (Rp40,Rq5,Rr17), (Rp40,Rq5,Rr18), (Rp40,Rq5,Rr19), (Rp40,Rq5,Rr20), (Rp40,Rq5,Rr21), (Rp40,Rq5,Rr22), (Rp40,Rq6,Rr1), (Rp40,Rq6,Rr2), (Rp40,Rq6,Rr3), (Rp40,Rq6,Rr4), (Rp40,Rq6,Rr5), (Rp40,Rq6,Rr6), (Rp40,Rq6,Rr7), (Rp40,Rq6,Rr8), (Rp40,Rq6,Rr9), (Rp40,Rq6,Rr10), (Rp40,Rq6,Rr11), (Rp40,Rq6,Rr12), (Rp40,Rq6,Rr13), (Rp40,Rq6,Rr14), (Rp40,Rq6,Rr15), (Rp40,Rq6,Rr16), (Rp40,Rq6,Rr17), (Rp40,Rq6,Rr18), (Rp40,Rq6,Rr19), (Rp40,Rq6,Rr20), (Rp40,Rq6,Rr21), (Rp40,Rq6,Rr22), (Rp40,Rq7,Rr1), (Rp40,Rq7,Rr2), (Rp40,Rq7,Rr3), (Rp40,Rq7,Rr4), (Rp40,Rq7,Rr5), (Rp40,Rq7,Rr6), (Rp40,Rq7,Rr7), (Rp40,Rq7,Rr8), (Rp40,Rq7,Rr9), (Rp40,Rq7,Rr10), (Rp40, Rq7,Rr11), (Rp40,Rq7,Rr12), (Rp40,Rq7,Rr13), (Rp40,Rq7,Rr14), (Rp40,Rq7,Rr15), (Rp40,Rq7,Rr16), (Rp40,Rq7,Rr17), (Rp40,Rq7,Rr18), (Rp40,Rq7,Rr19), (Rp40,Rq7,Rr20), (Rp40,Rq7,Rr21), (Rp40,Rq7,Rr22), (Rp40,Rq8,Rr1), (Rp40,Rq8,Rr2), (Rp40,Rq8,Rr3), (Rp40,Rq8,Rr4), (Rp40,Rq8,Rr5), (Rp40,Rq8,Rr6), (Rp40,Rq8,Rr7), (Rp40,Rq8,Rr8), (Rp40,Rq8,Rr9), (Rp40,Rq8,Rr10), (Rp40,Rq8,Rr11), (Rp40,Rq8,Rr12), (Rp40,Rq8,Rr13), (Rp40,Rq8,Rr14), (Rp40,Rq8,Rr15), (Rp40,Rq8,Rr16), (Rp40,Rq8,Rr17), (Rp40,Rq8,Rr18), (Rp40,Rq8,Rr19), (Rp40,Rq8,Rr20), (Rp40,Rq8,Rr21), (Rp40,Rq8,Rr22), (Rp40,Rq9,Rr1), (Rp40,Rq9,Rr2), (Rp40,Rq9,Rr3), (Rp40,Rq9,Rr4), (Rp40,Rq9,Rr5), (Rp40,Rq9,Rr6), (Rp40,Rq9,Rr7), (Rp40,Rq9,Rr8), (Rp40,Rq9,Rr9), (Rp40,Rq9,Rr10), (Rp40,Rq9,Rr11), (Rp40,Rq9,Rr12), (Rp40,Rq9,Rr13), (Rp40,Rq9,Rr14), (Rp40,Rq9,Rr15), (Rp40,Rq9,Rr16), (Rp40,Rq9,Rr17), (Rp40,Rq9,Rr18), (Rp40,Rq9,Rr19), (Rp40,Rq9,Rr20), (Rp40,Rq9,Rr21), (Rp40,Rq9,Rr22), (Rp40,Rq10,Rr1), (Rp40,Rq10,Rr2), (Rp40,Rq10,Rr3), (Rp40,Rq10,Rr4), (Rp40,Rq10,Rr5), (Rp40,Rq10,Rr6), (Rp40,Rq10,Rr7), (Rp40,Rq10,Rr8), (Rp40,Rq10,Rr9), (Rp40,Rq10,Rr10), (Rp40,Rq10,Rr11), (Rp40,Rq10,Rr12), (Rp40,Rq10,Rr13), (Rp40,Rq10,Rr14), (Rp40,Rq10,Rr15), (Rp40,Rq10,Rr16), (Rp40,Rq10,Rr17), (Rp40,Rq10,Rr18), (Rp40,Rq10,Rr19), (Rp40,Rq10,Rr20), (Rp40,Rq10,Rr21), (Rp40,Rq10,Rr22), (Rp40,Rq11,Rr1), (Rp40,Rq11,Rr2), (Rp40,Rq11,Rr3), (Rp40,Rq11,Rr4), (Rp40,Rq11,Rr5), (Rp40,Rq11,Rr6), (Rp40,Rq11,Rr7), (Rp40,Rq11,Rr8), (Rp40,Rq11,Rr9), (Rp40,Rq11,Rr10), (Rp40,Rq11,Rr11), (Rp40,Rq11, Rr12), (Rp40,Rq11,Rr13), (Rp40,Rq11,Rr14), (Rp40,Rq11,Rr15), (Rp40,Rq11,Rr16), (Rp40,Rq11,Rr17), (Rp40,Rq11,Rr18), (Rp40,Rq11,Rr19), (Rp40,Rq11,Rr20), (Rp40,Rq11,Rr21), (Rp40,Rq11,Rr22), (Rp40,Rq12,Rr1), (Rp40,Rq12,Rr2), (Rp40,Rq12,Rr3), (Rp40,Rq12,Rr4), (Rp40,Rq12,Rr5), (Rp40,Rq12,Rr6), (Rp40,Rq12,Rr7), (Rp40,Rq12,Rr8), (Rp40,Rq12,Rr9), (Rp40,Rq12,Rr10), (Rp40,Rq12,Rr11), (Rp40,Rq12,Rr12), (Rp40,Rq12,Rr13), (Rp40,Rq12,Rr14), (Rp40,Rq12,Rr15), (Rp40,Rq12,Rr16), (Rp40,Rq12,Rr17), (Rp40,Rq12,Rr18), (Rp40,Rq12,Rr19), (Rp40,Rq12,Rr20), (Rp40,Rq12,Rr21), (Rp40,Rq12,Rr22), (Rp41,Rq1,R r1), (Rp41,Rq1,Rr2), (Rp41,Rq1,Rr3), (Rp41,Rq1,Rr4), (Rp41,Rq1,Rr5), (Rp41,Rq1,Rr6), (Rp41,Rq1,Rr7), (Rp41,Rq1,Rr8), (Rp41,Rq1,Rr9), (Rp41,Rq1,Rr10), (Rp41,Rq1,Rr11), (Rp41,Rq1,Rr12), (Rp41,Rq1,Rr13), (Rp41,Rq1,Rr14), (Rp41,Rq1,Rr15), (Rp41,Rq1,Rr16), (Rp41,Rq1,Rr17), (Rp41,Rq1,Rr18), (Rp41,Rq1,Rr19), (Rp41,Rq1,Rr20), (Rp41,Rq1,Rr21), (Rp41,Rq1,Rr22), (Rp41,Rq2,Rr1), (Rp41,Rq2,Rr2), (Rp41,Rq2,Rr3), (Rp41,Rq2,Rr4), (Rp41,Rq2,Rr5), (Rp41,Rq2,Rr6), (Rp41,Rq2,Rr7), (Rp41,Rq2,Rr8), (Rp41,Rq2,Rr9), (Rp41,Rq2,Rr10), (Rp41,Rq2,Rr11), (Rp41,Rq2,Rr12), (Rp41,Rq2,Rr13), (Rp41,Rq2,Rr14), (Rp41,Rq2,Rr15), (Rp41,Rq2,Rr16), (Rp41,Rq2,Rr17), (Rp41,Rq2,Rr18), (Rp41,Rq2,Rr19), (Rp41,Rq2,Rr20), (Rp41,Rq2,Rr21), (Rp41,Rq2,Rr22), (Rp41,Rq3,Rr1), (Rp41,Rq3,Rr2), (Rp41,Rq3,Rr3), (Rp41,Rq3,Rr4), (Rp41,Rq3,Rr5), (Rp41,Rq3,Rr6), (Rp41,Rq3,Rr7), (Rp41,Rq3,Rr8), (Rp41,Rq3,Rr9), (Rp41,Rq3,Rr10), (Rp41,Rq3,Rr11), (Rp41,Rq3,Rr12), (Rp41,Rq3,Rr13), (Rp41,Rq3,Rr14), (Rp41,Rq3,Rr15), (Rp41,Rq3,Rr16), (Rp41,Rq3,Rr17), (Rp41,Rq3,Rr18), (Rp41,Rq3,Rr19), (Rp41,Rq3,Rr20), (Rp41,Rq3,Rr21), (Rp41,Rq3,Rr22), (Rp41,Rq4,Rr1), (Rp41,Rq4,Rr2), (Rp41,Rq4,Rr3), (Rp41,Rq4,Rr4), (Rp41,Rq4,Rr5), (Rp41,Rq4,Rr6), (Rp41,Rq4,Rr7), (Rp41,Rq4,Rr8), (Rp41,Rq4,Rr9), (Rp41,Rq4,Rr10), (Rp41,Rq4,Rr11), (Rp41,Rq4,Rr12), (Rp41,Rq4,Rr13), (Rp41,Rq4,Rr14), (Rp41,Rq4,Rr15), (Rp41,Rq4,Rr16), (Rp41, Rq4,Rr17), (Rp41,Rq4,Rr18), (Rp41,Rq4,Rr19), (Rp41,Rq4,Rr20), (Rp41,Rq4,Rr21), (Rp41,Rq4,Rr22), (Rp41,Rq5,Rr1), (Rp41,Rq5,Rr2), (Rp41,Rq5,Rr3), (Rp41,Rq5,Rr4), (Rp41,Rq5,Rr5), (Rp41,Rq5,Rr6), (Rp41,Rq5,Rr7), (Rp41,Rq5,Rr8), (Rp41,Rq5,Rr9), (Rp41,Rq5,Rr10), (Rp41,Rq5,Rr11), (Rp41,Rq5,Rr12), (Rp41,Rq5,Rr13), (Rp41,Rq5,Rr14), (Rp41,Rq5,Rr15), (Rp41,Rq5,Rr16), (Rp41,Rq5,Rr17), (Rp41,Rq5,Rr18), (Rp41,Rq5,Rr19), (Rp41,Rq5,Rr20), (Rp41,Rq5,Rr21), (Rp41,Rq5,Rr22), (Rp41,Rq6,Rr1), (Rp41,Rq6,Rr2), (Rp41,Rq6,Rr3), (Rp41,Rq6,Rr4), (Rp41,Rq6,Rr5), (Rp41,Rq6,Rr6), (Rp41,Rq6,Rr7), (Rp41,Rq6,Rr8), (Rp41,Rq6,Rr9), (Rp41,Rq6,Rr10), (Rp41,Rq6,Rr11), (Rp41,Rq6,Rr12), (Rp41,Rq6,Rr13), (Rp41,Rq6,Rr14), (Rp41,Rq6,Rr15), (Rp41,Rq6,Rr16), (Rp41,Rq6,Rr17), (Rp41,Rq6,Rr18), (Rp41,Rq6,Rr19), (Rp41,Rq6,Rr20), (Rp41,Rq6,Rr21), (Rp41,Rq6,Rr22), (Rp41,Rq7,Rr1), (Rp41,Rq7,Rr2), (Rp41,Rq7,Rr3), (Rp41,Rq7,Rr4), (Rp41,Rq7,Rr5), (Rp41,Rq7,Rr6), (Rp41,Rq7,Rr7), (Rp41,Rq7,Rr8), (Rp41,Rq7,Rr9), (Rp41,Rq7,Rr10), (Rp41,Rq7,Rr11), (Rp41,Rq7,Rr12), (Rp41,Rq7,Rr13), (Rp41,Rq7,Rr14), (Rp41,Rq7,Rr15), (Rp41,Rq7,Rr16), (Rp41,Rq7, Rr17), (Rp41,Rq7,Rr18), (Rp41,Rq7,Rr19), (Rp41,Rq7,Rr20), (Rp41,Rq7,Rr21), (Rp41,Rq7,Rr22), (Rp41,Rq8,Rr1), (Rp41,Rq8,Rr2), (Rp41,Rq8,Rr3), (Rp41,Rq8,Rr4), (Rp41,Rq8,Rr5), (Rp41,Rq8,Rr6), (Rp41,Rq8,Rr7), (Rp41,Rq8,Rr8), (Rp41,Rq8,Rr9), (Rp41,Rq8,Rr10), (Rp41,Rq8,Rr11), (Rp41,Rq8,Rr12), (Rp41,Rq8,Rr13), (Rp41,Rq8,Rr14), (Rp41,Rq8,Rr15), (Rp41,Rq8,Rr16), (Rp41,Rq8,Rr17), (Rp41,Rq8,Rr18), (Rp41,Rq8,Rr19), (Rp41,Rq8,Rr20), (Rp41,Rq8,Rr21), (Rp41,Rq8,Rr22), (Rp41,Rq9,Rr1), (Rp41,Rq9,Rr2), (Rp41,Rq9,Rr3), (Rp41,Rq9,Rr4), (Rp41,Rq9,Rr5), (Rp41,Rq9,Rr6), (Rp41,Rq9,Rr7), (Rp41,Rq9,Rr8), (Rp41, Rq9,Rr9), (Rp41,Rq9,Rr10), (Rp41,Rq9,Rr11), (Rp41,Rq9,Rr12), (Rp41,Rq9,Rr13), (Rp41, Rq9,Rr14), (Rp41,Rq9,Rr15), (Rp41,Rq9,Rr16), (Rp41,Rq9,Rr17), (Rp41,Rq9,Rr18), (Rp41,Rq9,Rr19), (Rp41,Rq9,Rr20), (Rp41,Rq9,Rr21), (Rp41,Rq9,Rr22), (Rp41,Rq10,Rr1), (Rp41,Rq10,Rr2), (Rp41,Rq10,Rr3), (Rp41,Rq10,Rr4), (Rp41,Rq10,Rr5), (Rp41,Rq10,Rr6), (Rp41,Rq10,Rr7), (Rp41,Rq10,Rr8), (Rp41,Rq10,Rr9), (Rp41,Rq10,Rr10), (Rp41,Rq10,Rr11), (Rp41,Rq10,Rr12), (Rp41,Rq10,Rr13), (Rp41,Rq10,Rr14), (Rp41,Rq10,Rr15), (Rp41,Rq10, Rr16), (Rp41,Rq10,Rr17), (Rp41,Rq10,Rr18), (Rp41,Rq10,Rr19), (Rp41,Rq10,Rr20), (Rp41,Rq10,Rr21), (Rp41,Rq10,Rr22), (Rp41,Rq11,Rr1), (Rp41,Rq11,Rr2), (Rp41,Rq11,Rr3), (Rp41,Rq11,Rr4), (Rp41,Rq11,Rr5), (Rp41,Rq11,Rr6), (Rp41,Rq11,Rr7), (Rp41,Rq11,Rr8), (Rp41,Rq11,Rr9), (Rp41,Rq11,Rr10), (Rp41,Rq11,Rr11), (Rp41,Rq11,Rr12), (Rp41,Rq11,Rr13), (Rp41,Rq11,Rr14), (Rp41,Rq11,Rr15), (Rp41,Rq11,Rr16), (Rp41,Rq11,Rr17), (Rp41, Rq11,Rr18), (Rp41,Rq11,Rr19), (Rp41,Rq11,Rr20), (Rp41,Rq11,Rr21), (Rp41,Rq11,Rr22), (Rp41,Rq12,Rr1), (Rp41,Rq12,Rr2), (Rp41,Rq12,Rr3), (Rp41,Rq12,Rr4), (Rp41,Rq12,Rr5), (Rp41,Rq12,Rr6), (Rp41,Rq12,Rr7), (Rp41,Rq12,Rr8), (Rp41,Rq12,Rr9), (Rp41,Rq12,Rr10), (Rp41,Rq12,Rr11), (Rp41,Rq12,Rr12), (Rp41,Rq12,Rr13), (Rp41,Rq12,Rr14), (Rp41,Rq12,Rr15), (Rp41,Rq12,Rr16), (Rp41,Rq12,Rr17), (Rp41,Rq12,Rr18), (Rp41,Rq12,Rr19), (Rp41,Rq12,Rr20), (Rp41,Rq12,Rr21), (Rp41,Rq12,Rr22), (Rp42,Rq1,Rr1), (Rp42,Rq1,Rr2), (Rp42,Rq1,Rr3), (Rp42,Rq1,Rr4), (Rp42,Rq1,Rr5), (Rp42,Rq1,Rr6), (Rp42,Rq1,Rr7), (Rp42,Rq1,Rr8), (Rp42,Rq1,Rr9), (Rp42,Rq1,Rr10), (Rp42,Rq1,Rr11), (Rp42,Rq1,Rr12), (Rp42,Rq1,Rr13), (Rp42,Rq1,Rr14), (Rp42,Rq1,Rr15), (Rp42,Rq1,Rr16), (Rp42,Rq1,Rr17), (Rp42, Rq1,Rr18), (Rp42,Rq1,Rr19), (Rp42,Rq1,Rr20), (Rp42,Rq1,Rr21), (Rp42,Rq1,Rr22), (Rp42,Rq2,Rr1), (Rp42,Rq2,Rr2), (Rp42,Rq2,Rr3), (Rp42,Rq2,Rr4), (Rp42,Rq2,Rr5), (Rp42,Rq2, Rr6), (Rp42,Rq2,Rr7), (Rp42,Rq2,Rr8), (Rp42,Rq2,Rr9), (Rp42,Rq2,Rr10), (Rp42,Rq2,Rr11), (Rp42,Rq2,Rr12), (Rp42,Rq2,Rr13), (Rp42,Rq2,Rr14), (Rp42,Rq2,Rr15), (Rp42,Rq2,Rr16), (Rp42,Rq2,Rr17), (Rp42,Rq2,Rr18), (Rp42,Rq2,Rr19), (Rp42,Rq2,Rr20), (Rp42,Rq2,Rr21), (Rp42,Rq2,Rr22), (Rp42,Rq3,Rr1), (Rp42,Rq3,Rr2), (Rp42,Rq3,Rr3), (Rp42,Rq3,Rr4), (Rp42,Rq3,Rr5), (Rp42,Rq3,Rr6), (Rp42,Rq3,Rr7), (Rp42,Rq3,Rr8), (Rp42,Rq3,Rr9), (Rp42,Rq3,Rr10), (Rp42,Rq3,Rr11), (Rp42,Rq3,Rr12), (Rp42,Rq3,Rr13), (Rp42,Rq3,Rr14), (Rp42,Rq3,Rr15), (Rp42,Rq3,Rr16), (Rp42,Rq3,Rr17), (Rp42,Rq3,Rr18), (Rp42,Rq3,Rr19), (Rp42,Rq3,Rr20), (Rp42,Rq3,Rr21), (Rp42,Rq3,Rr22), (Rp42,Rq4,Rr1), (Rp42,Rq4,Rr2), (Rp42,Rq4,Rr3), (Rp42, Rq4,Rr4), (Rp42,Rq4,Rr5), (Rp42,Rq4,Rr6), (Rp42,Rq4, Rr7), (Rp42,Rq4,Rr8), (Rp42,Rq4,Rr9), (Rp42,Rq4,Rr10), (Rp42,Rq4,Rr11), (Rp42,Rq4,Rr12), (Rp42,Rq4, Rr13), (Rp42,Rq4,Rr14), (Rp42,Rq4,Rr15), (Rp42,Rq4,Rr16), (Rp42,Rq4,Rr17), (Rp42,Rq4,Rr18), (Rp42,Rq4,Rr19), (Rp42,Rq4,Rr20), (Rp42,Rq4,Rr21), (Rp42,Rq4,Rr22), (Rp42,Rq5,Rr1), (Rp42,Rq5,Rr2), (Rp42,Rq5,Rr3), (Rp42, Rq5,Rr4), (Rp42,Rq5,Rr5), (Rp42,Rq5,Rr6), (Rp42,Rq5, Rr7), (Rp42,Rq5,Rr8), (Rp42,Rq5,Rr9), (Rp42,Rq5,Rr10), (Rp42,Rq5,Rr11), (Rp42,Rq5,Rr12), (Rp42,Rq5,Rr13), (Rp42,Rq5,Rr14), (Rp42,Rq5,Rr15), (Rp42,Rq5,Rr16), (Rp42,Rq5,Rr17), (Rp42,Rq5,Rr18), (Rp42,Rq5,Rr19), (Rp42,Rq5,Rr20), (Rp42,Rq5,Rr21), (Rp42,Rq5,Rr22), (Rp42,Rq6,Rr1), (Rp42,Rq6,Rr2), (Rp42,Rq6,Rr3), (Rp42, Rq6,Rr4), (Rp42,Rq6,Rr5), (Rp42,Rq6,Rr6), (Rp42,Rq6, Rr7), (Rp42,Rq6,Rr8), (Rp42,Rq6,Rr9), (Rp42,Rq6,Rr10), (Rp42,Rq6,Rr11), (Rp42,Rq6,Rr12), (Rp42,Rq6,Rr13), (Rp42,Rq6,Rr14), (Rp42,Rq6,Rr15), (Rp42,Rq6,Rr16), (Rp42,Rq6,Rr17), (Rp42,Rq6,Rr18), (Rp42,Rq6,Rr19), (Rp42, Rq6,Rr20), (Rp42,Rq6,Rr21), (Rp42,Rq6,Rr22), (Rp42,Rq7,Rr1), (Rp42,Rq7,Rr2), (Rp42,Rq7,Rr3), (Rp42, Rq7,Rr4), (Rp42,Rq7,Rr5), (Rp42,Rq7,Rr6), (Rp42,Rq7, Rr7), (Rp42,Rq7,Rr8), (Rp42,Rq7,Rr9), (Rp42,Rq7,Rr10), (Rp42,Rq7,Rr11), (Rp42,Rq7,Rr12), (Rp42,Rq7,Rr13), (Rp42,Rq7,Rr14), (Rp42,Rq7,Rr15), (Rp42,Rq7,Rr16), (Rp42,Rq7,Rr17), (Rp42,Rq7,Rr18), (Rp42,Rq7,Rr19), (Rp42,Rq7,Rr20), (Rp42,Rq7,Rr21), (Rp42,Rq7,Rr22), (Rp42,Rq8,Rr1), (Rp42,Rq8,Rr2), (Rp42,Rq8,Rr3), (Rp42, Rq8,Rr4), (Rp42,Rq8,Rr5), (Rp42,Rq8,Rr6), (Rp42,Rq8, Rr7), (Rp42,Rq8,Rr8), (Rp42,Rq8,Rr9), (Rp42,Rq8,Rr10), (Rp42,Rq8,Rr11), (Rp42,Rq8,Rr12), (Rp42,Rq8,Rr13), (Rp42,Rq8,Rr14), (Rp42,Rq8,Rr15), (Rp42,Rq8,Rr16), (Rp42,Rq8,Rr17), (Rp42,Rq8,Rr18), (Rp42,Rq8,Rr19), (Rp42,Rq8,Rr20), (Rp42,Rq8,Rr21), (Rp42,Rq8,Rr22), (Rp42,Rq9,Rr1), (Rp42,Rq9,Rr2), (Rp42,Rq9,Rr3), (Rp42, Rq9,Rr4), (Rp42,Rq9,Rr5), (Rp42,Rq9,Rr6), (Rp42,Rq9, Rr7), (Rp42,Rq9,Rr8), (Rp42,Rq9,Rr9), (Rp42,Rq9,Rr10), (Rp42,Rq9,Rr11), (Rp42,Rq9,Rr12), (Rp42,Rq9,Rr13), (Rp42,Rq9,Rr14), (Rp42,Rq9,Rr15), (Rp42,Rq9,Rr16), (Rp42,Rq9,Rr17), (Rp42,Rq9,Rr18), (Rp42,Rq9,Rr19), (Rp42,Rq9,Rr20), (Rp42,Rq9,Rr21), (Rp42,Rq9,Rr22), (Rp42,Rq10,Rr1), (Rp42,Rq10,Rr2), (Rp42,Rq10,Rr3), (Rp42,Rq10,Rr4), (Rp42,Rq10,Rr5), (Rp42,Rq10,Rr6), (Rp42,Rq10,Rr7), (Rp42,Rq10,Rr8), (Rp42,Rq10,Rr9), (Rp42,Rq10,Rr10), (Rp42,Rq10,Rr11), (Rp42,Rq10,Rr12), (Rp42,Rq10,Rr13), (Rp42,Rq10,Rr14), (Rp42,Rq10,Rr15), (Rp42,Rq10,Rr16), (Rp42,Rq10, Rr17), (Rp42,Rq10,Rr18), (Rp42,Rq10,Rr19), (Rp42,Rq10,Rr20), (Rp42,Rq10,Rr21), (Rp42,Rq10,Rr22), (Rp42,Rq11, Rr1), (Rp42,Rq11,Rr2), (Rp42,Rq11,Rr3), (Rp42,Rq11,Rr4), (Rp42,Rq11,Rr5), (Rp42,Rq11,Rr6), (Rp42,Rq11,Rr7), (Rp42,Rq11,Rr8), (Rp42,Rq11,Rr9), (Rp42,Rq11,Rr10), (Rp42,Rq11,Rr11), (Rp42,Rq11,Rr12), (Rp42,Rq11,Rr13), (Rp42,Rq11,Rr14), (Rp42,Rq11,Rr15), (Rp42,Rq11,Rr16), (Rp42,Rq11,Rr17), (Rp42,Rq11,Rr18), (Rp42, Rq11,Rr19), (Rp42,Rq11,Rr20), (Rp42,Rq11,Rr21), (Rp42,Rq11,Rr22), (Rp42,Rq12,Rr1), (Rp42,Rq12,Rr2), (Rp42,Rq12,Rr3), (Rp42,Rq12,Rr4), (Rp42,Rq12,Rr5), (Rp42,Rq12,Rr6), (Rp42,Rq12,Rr7), (Rp42,Rq12,Rr8), (Rp42,Rq12,Rr9), (Rp42,Rq12,Rr10), (Rp42,Rq12,Rr11), (Rp42,Rq12,Rr12), (Rp42,Rq12,Rr13), (Rp42,Rq12,Rr14), (Rp42,Rq12,Rr15), (Rp42,Rq12,Rr16), (Rp42,Rq12,Rr17), (Rp42,Rq12,Rr18), (Rp42,Rq12,Rr19), (Rp42,Rq12,Rr20), (Rp42,Rq12,Rr21), (Rp42,Rq12,Rr22), (Rp43,Rq1,Rr1), (Rp43,Rq1,Rr2), (Rp43,Rq1,Rr3), (Rp43, Rq1,Rr4), (Rp43,Rq1,Rr5), (Rp43,Rq1,Rr6), (Rp43,Rq1, Rr7), (Rp43,Rq1,Rr8), (Rp43, Rq1,Rr9), (Rp43,Rq1,Rr10), (Rp43,Rq1,Rr11), (Rp43,Rq1,Rr12), (Rp43,Rq1,Rr13), (Rp43, Rq1,Rr14), (Rp43,Rq1,Rr15), (Rp43,Rq1,Rr16), (Rp43,Rq1,Rr17), (Rp43,Rq1,Rr18), (Rp43,Rq1,Rr19), (Rp43,Rq1,Rr20), (Rp43,Rq1,Rr21), (Rp43,Rq1,Rr22), (Rp43,Rq2,Rr1), (Rp43, Rq2,Rr2), (Rp43,Rq2,Rr3), (Rp43, Rq2,Rr4), (Rp43,Rq2,Rr5), (Rp43,Rq2,Rr6), (Rp43,Rq2, Rr7), (Rp43,Rq2,Rr8), (Rp43,Rq2,Rr9), (Rp43,Rq2,Rr10), (Rp43,Rq2,Rr11), (Rp43,Rq2,Rr12), (Rp43,Rq2,Rr13), (Rp43,Rq2,Rr14), (Rp43,Rq2,Rr15), (Rp43,Rq2,Rr16), (Rp43,Rq2,Rr17), (Rp43,Rq2,Rr18), (Rp43,Rq2,Rr19), (Rp43,Rq2,Rr20), (Rp43,Rq2,Rr21), (Rp43,Rq2, Rr22), (Rp43,Rq3,Rr1), (Rp43,Rq3,Rr2), (Rp43,Rq3,Rr3), (Rp43, Rq3,Rr4), (Rp43,Rq3,Rr5), (Rp43,Rq3,Rr6), (Rp43,Rq3, Rr7), (Rp43,Rq3,Rr8), (Rp43,Rq3,Rr9), (Rp43,Rq3,Rr10), (Rp43,Rq3,Rr11), (Rp43,Rq3,Rr12), (Rp43,Rq3,Rr13), (Rp43,Rq3,Rr14), (Rp43,Rq3,Rr15), (Rp43,Rq3,Rr16), (Rp43,Rq3,Rr17), (Rp43,Rq3,Rr18), (Rp43,Rq3,Rr19), (Rp43,Rq3,Rr20), (Rp43,Rq3,Rr21), (Rp43,Rq3,Rr22), (Rp43,Rq4,Rr1), (Rp43,Rq4,Rr2), (Rp43,Rq4,Rr3), (Rp43, Rq4,Rr4), (Rp43,Rq4,Rr5), (Rp43,Rq4,Rr6), (Rp43,Rq4, Rr7), (Rp43,Rq4,Rr8), (Rp43,Rq4,Rr9), (Rp43,Rq4,Rr10), (Rp43,Rq4,Rr11), (Rp43,Rq4,Rr12), (Rp43,Rq4,Rr13), (Rp43,Rq4,Rr14), (Rp43,Rq4,Rr15), (Rp43,Rq4,Rr16), (Rp43,Rq4,Rr17), (Rp43,Rq4,Rr18), (Rp43,Rq4,Rr19), (Rp43,Rq4,Rr20), (Rp43,Rq4,Rr21), (Rp43,Rq4,Rr22), (Rp43,Rq5,Rr1), (Rp43,Rq5,Rr2), (Rp43,Rq5,Rr3), (Rp43, Rq5,Rr4), (Rp43,Rq5,Rr5), (Rp43,Rq5,Rr6), (Rp43,Rq5, Rr7), (Rp43,Rq5,Rr8), (Rp43,Rq5,Rr9), (Rp43,Rq5,Rr10), (Rp43,Rq5,Rr11), (Rp43,Rq5,Rr12), (Rp43,Rq5,Rr13), (Rp43,Rq5,Rr14), (Rp43,Rq5,Rr15), (Rp43,Rq5,Rr16), (Rp43,Rq5,Rr17), (Rp43,Rq5,Rr18), (Rp43,Rq5,Rr19), (Rp43,Rq5,Rr20), (Rp43,Rq5,Rr21), (Rp43,Rq5,Rr22), (Rp43,Rq6,Rr1), (Rp43,Rq6,Rr2), (Rp43,Rq6,Rr3), (Rp43, Rq6,Rr4), (Rp43,Rq6,Rr5), (Rp43,Rq6,Rr6), (Rp43,Rq6, Rr7), (Rp43,Rq6,Rr8), (Rp43,Rq6,Rr9), (Rp43,Rq6,Rr10), (Rp43, Rq6,Rr11), (Rp43,Rq6,Rr12), (Rp43,Rq6,Rr13), (Rp43,Rq6,Rr14), (Rp43,Rq6,Rr15), (Rp43,Rq6,Rr16), (Rp43,Rq6,Rr17), (Rp43,Rq6,Rr18), (Rp43,Rq6,Rr19), (Rp43,Rq6,Rr20), (Rp43,Rq6,Rr21), (Rp43,Rq6,Rr22), (Rp43,Rq7,Rr1), (Rp43,Rq7,Rr2), (Rp43,Rq7,Rr3), (Rp43, Rq7,Rr4), (Rp43,Rq7,Rr5), (Rp43,Rq7,Rr6), (Rp43,Rq7, Rr7), (Rp43,Rq7,Rr8), (Rp43,Rq7,Rr9), (Rp43,Rq7,Rr10), (Rp43,Rq7,Rr11), (Rp43,Rq7,Rr12), (Rp43,Rq7,Rr13), (Rp43,Rq7,Rr14), (Rp43,Rq7,Rr15), (Rp43,Rq7,Rr16), (Rp43,Rq7,Rr17), (Rp43,Rq7,Rr18), (Rp43,Rq7,Rr19), (Rp43,Rq7,Rr20), (Rp43,Rq7,Rr21), (Rp43,Rq7,Rr22), (Rp43,Rq8,Rr1), (Rp43,Rq8,Rr2), (Rp43,Rq8,Rr3), (Rp43, Rq8,Rr4), (Rp43,Rq8,Rr5), (Rp43,Rq8,Rr6), (Rp43,Rq8, Rr7), (Rp43,Rq8,Rr8), (Rp43,Rq8,Rr9), (Rp43,Rq8,Rr10), (Rp43,Rq8,Rr11), (Rp43,Rq8,Rr12), (Rp43,Rq8,Rr13), (Rp43,Rq8,Rr14), (Rp43,Rq8,Rr15), (Rp43,Rq8,Rr16), (Rp43,Rq8,Rr17), (Rp43,Rq8,Rr18), (Rp43,Rq8,Rr19), (Rp43,Rq8,Rr20), (Rp43,Rq8,Rr21), (Rp43,Rq8,Rr22), (Rp43,Rq9,Rr1), (Rp43,Rq9,Rr2), (Rp43,Rq9,Rr3), (Rp43, Rq9,Rr4), (Rp43,Rq9,Rr5), (Rp43,Rq9,Rr6), (Rp43,Rq9, Rr7), (Rp43,Rq9,Rr8), (Rp43,Rq9,Rr9), (Rp43,Rq9,Rr10), (Rp43,Rq9,Rr11), (Rp43,Rq9,Rr12), (Rp43,Rq9,Rr13), (Rp43,Rq9,Rr14), (Rp43,Rq9,Rr15), (Rp43,Rq9,Rr16), (Rp43,Rq9,Rr17), (Rp43,Rq9,Rr18), (Rp43,Rq9,Rr19), (Rp43,Rq9,Rr20), (Rp43,Rq9,Rr21), (Rp43,Rq9,Rr22), (Rp43,Rq10,Rr1), (Rp43,Rq10,Rr2), (Rp43,Rq10,Rr3), (Rp43, Rq10,Rr4), (Rp43,Rq10,Rr5), (Rp43,Rq10,Rr6), (Rp43,Rq10,Rr7), (Rp43,Rq10,Rr8), (Rp43,Rq10,Rr9), (Rp43,Rq10,Rr10), (Rp43,Rq10,Rr11), (Rp43,Rq10,Rr12), (Rp43,Rq10,Rr13), (Rp43,Rq10,Rr14), (Rp43,Rq10,Rr15), (Rp43,Rq10,Rr16), (Rp43,Rq10,Rr17), (Rp43,Rq10, Rr18), (Rp43,Rq10,Rr19), (Rp43,Rq10,Rr20), (Rp43,Rq10,Rr21), (Rp43,Rq10,Rr22), (Rp43,Rq11,Rr1), (Rp43,Rq11,Rr2), (Rp43,Rq11,Rr3), (Rp43,Rq11,Rr4), (Rp43,Rq11,Rr5), (Rp43,Rq11,Rr6), (Rp43,Rq11,Rr7), (Rp43,Rq11,Rr8), (Rp43,Rq11,Rr9), (Rp43,Rq11, Rr10), (Rp43,Rq11,Rr11), (Rp43,Rq11,Rr12), (Rp43,Rq11,Rr13), (Rp43,Rq11,Rr14), (Rp43,Rq11,Rr15), (Rp43,Rq11,Rr16), (Rp43,Rq11,Rr17), (Rp43,Rq11,Rr18), (Rp43,Rq11,Rr19), (Rp43, Rq11,Rr20), (Rp43,Rq11,Rr21), (Rp43,Rq11,Rr22), (Rp43,Rq12,Rr1), (Rp43,Rq12,Rr2), (Rp43,Rq12,Rr3), (Rp43,Rq12,Rr4), (Rp43,Rq12,Rr5), (Rp43,Rq12,Rr6), (Rp43,Rq12,Rr7), (Rp43,Rq12,Rr8), (Rp43,Rq12,Rr9), (Rp43,Rq12,Rr10), (Rp43,Rq12,Rr11), (Rp43,Rq12,Rr12), (Rp43,Rq12,Rr13), (Rp43,Rq12,Rr14), (Rp43,Rq12,Rr15), (Rp43,Rq12,Rr16), (Rp43,Rq12,Rr17), (Rp43,Rq12,Rr18), (Rp43,Rq12,Rr19), (Rp43,Rq12,Rr20), (Rp43,Rq12,Rr21), (Rp43,Rq12,Rr22).

Following examples illustrate the present invention in more detail, however, the present invention is not limited to these examples. The meaning of each abbreviation is as follows.

Me: methyl
Et: ethyl
Bu: butyl
Ac: acetyl
TMS: tetramethylsilane
TMS-Cl: trimethylsilyl chloride
DMSO: dimethyl sulfoxide
DMF: dimethylformamide
THF: tetrahydrofuran
DBU: 1,8-diazabicyclo[5.4.0]undec-7-ene
NMP: N-methyl-2-pyrrolidone
HOAt: 1-hydroxy-7-azabenzotriazole
HATU: 2-(7-azabenzotriazol-1-yl)-1,1,3,3-tetramethyluronium hexafluorophosphate
PyBOP: benzotriazole-1-yl-oxy-trispyrrolidinophosphonium hexafluorophosphate
rt: room temperature Example 1

Preparation of 6-(ethylthio)-1-(4-fluorobenzyl)-3-isopropyl-1,3,5-triazine-2,4(1H,3H)-dione

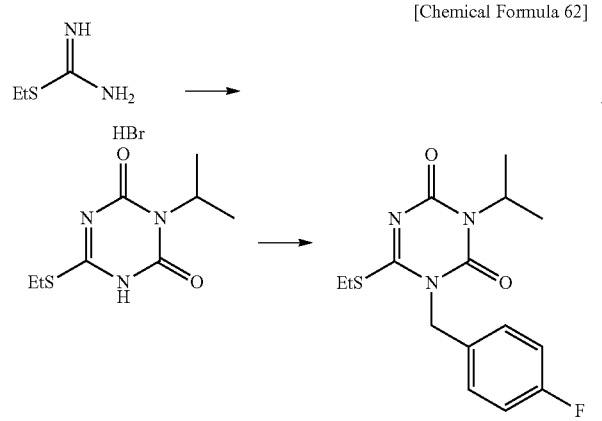

[Chemical Formula 62]

To a mixture of S-ethylthiourea hydrobromide (14.8 g, 80 mmol) and DMF (75 mL) were added isopropylisocyanate (8.2 mL, 84 mmol) and DBU (12.6 mL, 84 mmol) under ice-cooling, and the resulting mixture was stirred under ice-cooling for 6 hours. 1,1'-carbonyldiimidazole (15.57 g, 96 mmol) and DBU (18.0 mL, 120 mmol) were added to the reaction mixture under ice-cooling, and the resulting mixture was stirred for 2 hours. Then, 2 mol/L hydrochloric acid (240 mL) was added to the reaction mixture under ice-cooling for about 50 minutes, and the precipitated solid was collected by filtration. The resulting solid was dissolved in ethyl acetate, and the mixture was dried over anhydrous magnesium sulphate and then concentrated in vacuo to give 6-(ethylthio)-3-isopropyl-1,3,5-triazine-2,4(1H,3H)-dione (12.29 g, yield: 71%) as light brown solid.

1H-NMR (δ ppm TMS/DMSO-d6): 1.27 (6H, t, J=7.2 Hz), 1.33 (6H, d, J=6.9 Hz), 3.05 (2H, q, J=7.2 Hz), 4.81 (1H, sept, J=6.9 Hz).

To a mixture of 6-(ethylthio)-3-isopropyl-1,3,5-triazine-2,4(1H,3H)-dione (4.09 g, 19 mmol), potassium carbonate (7.88 g, 57 mmol) and acetonitrile (80 mL) was added 4-fluorobenzylbromide (3.55 mL, 28.5 mmol), and the resulting mixture was stirred at reflux for 1.5 hours. Then, ice-water (20 mL) was poured into the reaction mixture, and the resulting mixture was extracted with ethyl acetate (10 mL). The extract was dried over anhydrous sodium sulphate, and then concentrated in vacuo. The resulting residue was purified on a silica gel column chromatography (ethyl acetate/hexane). The aimed compound was triturated with ethyl acetate and hexane to give 6-(ethylthio)-1-(4-fluorobenzyl)-3-isopropyl-1,3,5-triazine-2,4(1H,3H)-dione (5.96 g, yield: 97%) as colorless solid.

1H-NMR (δ ppm TMS/CDCl$_3$): 1.37 (3H, t, J=7.5 Hz), 1.47 (6H, d, J=6.9 Hz), 3.21 (2H, q, J=7.5 Hz), 5.02 (1H, sept, J=6.9), 5.06 (2H, s), 7.01-7.07 (2H, m), 7.31-7.36 (2H, m).

Example 2

Preparation of 1-(4-fluorobenzyl)-6-(4-isopropoxyphenylamino)-3-isopropyl-1,3,5-triazine-2,4(1H,3H)-dione

[Chemical Formula 63]

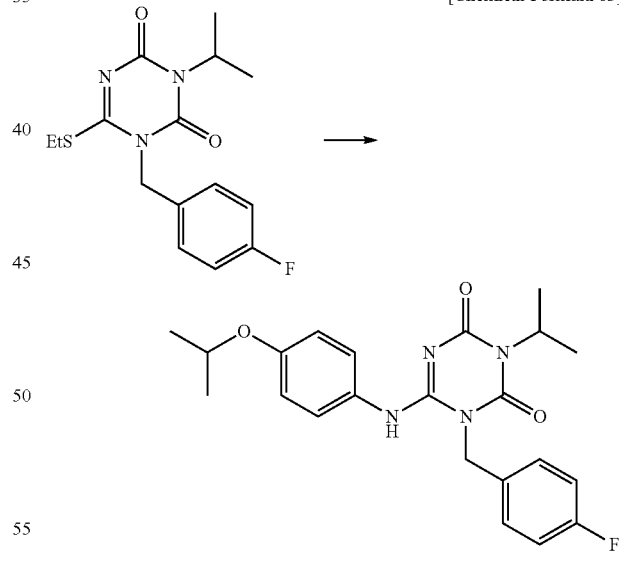

A mixture of 6-(ethylthio)-1-(4-fluorobenzyl)-3-isopropyl-1,3,5-triazine-2,4(1H,3H)-dione (0.323 g, 1 mmol), 4-isopropoxyaniline (0.907 g, 6 mmol) and 1-methyl-2-pyrolidone (1 mL) was heated at 230° C. for 30 min under microwave radiation. Then, water (10 mL) was poured into the reaction mixture, and the resulting mixture was extracted with ethyl acetate (10 mL). The extract was dried over anhydrous sodium sulphate, and then concentrated in vacuo. The resulting residue was purified on a silica gel column chromatography (ethyl acetate/hexane). The aimed compound was triturated with ethyl acetate and hexane to give 1-(4-fluorobenzyl)-6-(4-isopropoxyphenylamino)-3-isopropyl-1,3,5-triazine-2,4(1H,3H)-dione (0.21 g, yield: 51%) as colorless solid.

Melting point: 176-177° C.

1H-NMR (δ ppm TMS/CDCl$_3$): 1.34 (6H, d, J=6.0 Hz), 1.44 (6H, d, J=6.9 Hz), 4.49 (1H, sept, J=6.0 Hz), 4.96 (1H, sept, J=6.9 Hz), 5.18 (2H, s), 6.75-7.06 (6H, m), 7.53-7.57 (2H, m).

Example 3

Preparation of 6-(3-chloro-4-isopropoxyphenylamino)-1-(4-chlorobenzyl)-3-isopropyl-1,3,5-triazine-2,4(1H, 3H)-dione

[Chemical Formula 64]

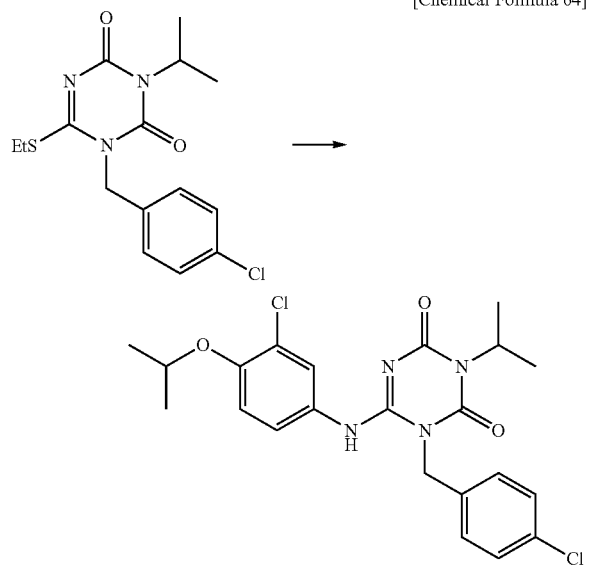

A mixture of 1-(4-chlorobenzyl)-6-(ethylthio)-3-isopropyl-1,3,5-triazine-2,4(1H,3H)-dione (0.60 g, 1.78 mmol), 3-chloro-4-isopropoxyaniline (0.99 g, 5.3 mmol) and acetic acid (10 mL) was heated at 90° C. for 6 hours. Then, the reaction mixture was poured into saturated sodium hydrogen carbonate solution (10 mL), and the resulting mixture was extracted with ethyl acetate (10 mL). The extract was washed with saturated sodium hybrogen carbonate solution (10 mL) and brine (10 mL), dried over anhydrous sodium sulphate, and then concentrated in vacuo. The resulting residue was purified on a silica gel column chromatography (ethyl acetate/hexane). The aimed compound was triturated with diethyl ether and hexane to give 6-(3-chloro-4-isopropoxyphenylamino)-1-(4-chlorobenzyl)-3-isopropyl-1,3,5-triazine-2,4(1H,3H)-dione (0.605 g, yield: 73%) as colorless solid.

Melting point: 167° C.

1H-NMR (δ ppm TMS/DMSO-d6): 1.28 (6H, d, J=6.0 Hz), 1.34 (6H, d, J=6.9 Hz), 4.62 (1H, m), 4.83 (1H, sept, J=6.9 Hz), 5.18 (2H, brs), 7.12-7.15 (2H, m), 7.34-7.37 (3H, m), 7.43 (2H, d, J=8.7 Hz), 9.23 (1H, brs).

Example 4

Preparation of 1-(4-chlorobenzyl)-6-(methylthio)-1,3,5-triazine-2,4(1H,3H)-dione

[Chemical Formula 65]

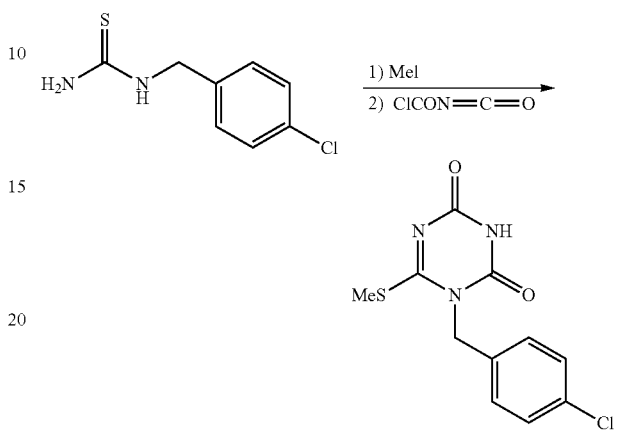

To a mixture of 1-(4-chlorobenzyl)thiourea (11.19 g, 55.8 mmol) and methanol (50 mL) was added methyl iodide (4.18 mL, 66.9 mmol) under ice-cooling, and the resulting mixture was stirred at room temperature for 5 hours. Then, the reaction mixture was concentrated in vacuo. To the resulting residue were added dichloromethane (60 mL) and N,N-diisopropylethylamine (29.2 mL, 167 mmol), and then a solution of N-(chlorocarbonyl) isocyanate (4.94 mL, 61.4 mmol) in dichloromethane (20 mL) was added to the resulting mixture under ice-cooling gradually. The resulting mixture was stirred at room temperature for 1 hour. Then, the precipitated solid was collected by filtration. The obtained solid was washed with a small amount of dichloromethane and dried under reduced pressure to give 1-(4-chlorobenzyl)-6-(methylthio)-1,3,5-triazine-2,4(1H,3H)-dione (9.19 g, yield: 58%) as colorless solid.

1H-NMR (δ ppm TMS/DMSO-d6): 2.46 (3H, s), 5.04 (2H, s), 7.31-7.43 (4H, m), 11.60 (1H, brs).

Example 5

Preparation of 1-(4-chlorobenzyl)-6-(3-fluoro-4-isopropoxyphenylamino)-1,3,5-triazine-2,4(1H, 31)-dione

[Chemical Formula 66]

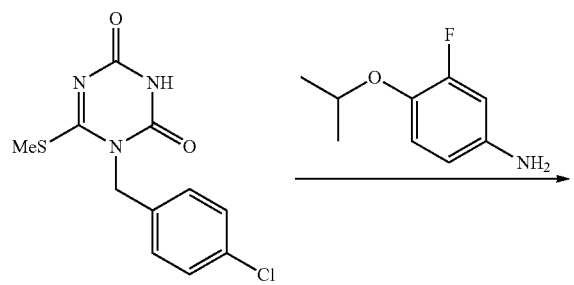

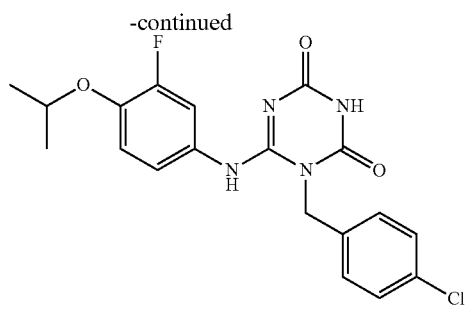

A mixture of 1-(4-chlorobenzyl)-6-(methylthio)-1,3,5-triazine-2,4(1H,3H)-dione (4.21 g, 14.8 mmol), 3-fluoro-4-isopropoxyaniline (3.77 g, 22.3 mmol), t-butanol (84 mL) and acetic acid (17 mL) was heated at reflux for 8 hours. Then, the reaction mixture was poured into saturated sodium hybrogen carbonate solution (30 mL), and the resulting mixture was extracted with ethyl acetate (10 mL). The extract was washed with saturated sodium hybrogen carbonate solution (10 mL) and brine (10 mL), dried over anhydrous sodium sulphate, and then concentrated in vacuo. The resulting residue was purified on a silica gel column chromatography (ethyl acetate/hexane). The aimed compound was triturated with diisopropyl ether to give 1-(4-chlorobenzyl)-6-(3-fluoro-4-isopropoxyphenylamino)-1,3,5-triazine-2,4(1H,3H)-dione (4.54 g, yield: 76%) as colorless solid.

1H-NMR (δ ppm TMS/CDCl$_3$): 1.36 (6H, d, J=6.1 Hz), 4.49 (1H, sept, J=6.1 Hz), 5.14 (2H, s), 6.47 (1H, m), 6.59 (1H, m), 6.97 (1H, m), 7.30 (2H, d, J=8.5 Hz), 7.47 (2H, d, J=8.5 Hz), 8.06 (1H, brs).

Example 6

Preparation of 1-(4-chlorobenzyl)-6-(3-fluoro-4-isopropoxyphenylamino)-3-(2-pyridylmethyl)-1,3,5-triazine-2,4(1H,3H)-dione

[Chemical Formula 67]

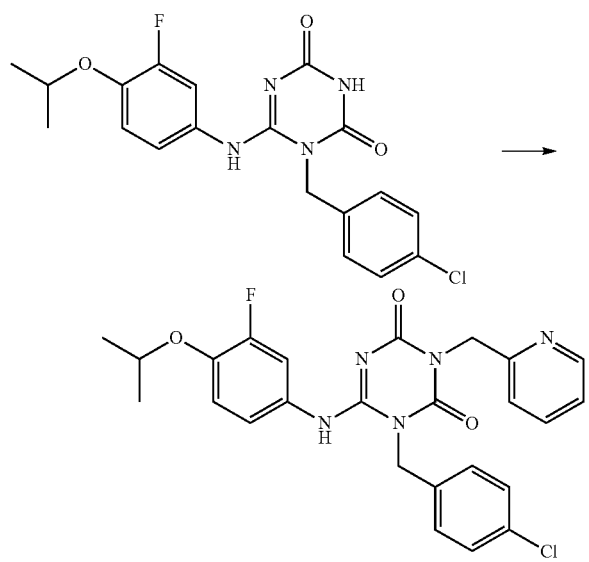

To a mixture of 1-(4-chlorobenzyl)-6-(3-fluoro-4-isopropoxyphenylamino)-1,3,5-triazine-2,4(1H,3H)-dione (0.15 g, 0.37 mmol) and DMF (3 mL) was added potassium t-butoxide (09 mg, 0.82 mmol), and the resulting mixture was stirred at room temperature for 5 minutes. To the mixture was added 2-(bromomethyl)pyridine hydrobromide (0.103 g, 0.41 mmol), and the resulting mixture was stirred at 60° C. for 2 hours. Then, water (20 mL) was poured into the mixture, and the resulting mixture was extracted with ethyl acetate (20 mL×2). The extract was washed with brine (20 mL), dried over anhydrous sodium sulphate, and then concentrated in vacuo. The resulting residue was purified on a silica gel column chromatography (ethyl acetate/hexane). The aimed compound was triturated with hexane to give 1-(4-chlorobenzyl)-6-(3-fluoro-4-isopropoxyphenylamino)-3-(2-pyridylmethyl)-1,3,5-triazine-2,4(1H,3H)-dione (069 g, yield: 37%) as colorless solid.

1H-NMR (δ ppm TMS/CDCl$_3$): 1.36 (2H, d, J=6.2 Hz), 4.47 (1H, sept, J=6.2 Hz), 5.15 (2H, s), 5.19 (2H, s), 6.51 (11H, m), 6.62 (1H, m), 6.97 (11H, m), 7.17-7.48 (7H, m), 7.65 (1H, m), 8.53 (1H, m).

Example 7

Preparation of 1-(4-chlorobenzyl)-6-(3-fluoro-4-isopropoxyphenylamino)-3-(2-hydroxyethyl)-1,3,5-triazine-2,4(1H,3H)-dione

[Chemical Formula 68]

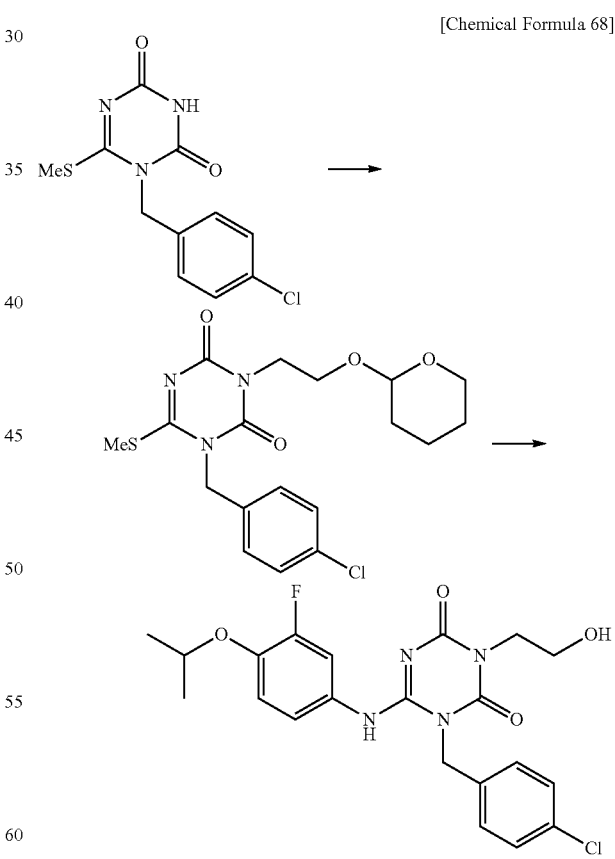

To a mixture of 1-(4-chlorobenzyl)-6-(methylthio)-1,3,5-triazine-2,4(1H,3H)-dione (0.28 g, 1 mmol), 2-(tetrahydro-2H-pyran-2-yloxy)enthanol (0.15 g, 1.00 mmol), triphenylphosphine (0.53 g, 2 mmol) and THF (5 mL) was gradually added diisopropylazocarboxylate (0.23 mL, 1.2 mmol) dropwise under ice-cooling, and the resulting mixture was stirred at room temperature for 3 hours. The mixture was poured into water (20 mL), and the resulting mixture was extracted with ethyl acetate (20 mL×2). The extract was washed with brine (20 mL), dried over anhydrous sodium sulphate, and then concentrated in vacuo. The resulting residue was purified on a silica gel column chromatography (ethyl acetate/hexane) to give 1-(4-chlorobenzyl)-6-(methylthio)-3-[2-(tetrahydro-2H-pyran-2-yloxy)ethyl]-1,3,5-triazine-2,4(1H,3H)-dione (0.32 g, yield: 78%) as colorless amorphous.

1H-NMR (δ ppm TMS/CDCl$_3$): 1.42-1.83 (6H, m), 2.58 (3H, s), 3.47 (1H, m), 3.74-4.32 (5H, m), 4.63 (1H, m), 5.10 (2H, s), 7.28-7.33 (4H, m).

A mixture of 1-(4-chlorobenzyl)-6-(methylthio)-3-[2-(tetrahydro-2H-pyran-2-yloxy)ethyl]-1,3,5-triazine-2,4(1H,3H)-dione (0.32 g, 0.78 mmol), 3-fluoro-4-isopropoxyaniline (0.40 g, 2.4 mmol) and acetic acid (3 mL) was heated at 10° C. for 3 hours. Then, the reaction mixture was poured into saturated sodium hybrogen carbonate solution (10 mL), and the resulting mixture was extracted with chloroform (10 mL×2). The extract was dried over anhydrous sodium sulphate, and then concentrated in vacuo. The resulting residue was purified on a silica gel column chromatography (methanol/chloroform). The aimed compound was triturated with diisopropyl ether and hexane to give 1-(4-chlorobenzyl)-6-(3-fluoro-4-isopropoxyphenylamino)-3-(2-hydroxyethyl)-1,3,5-triazine-2,4(1H,3H)-dione (0.12 g, yield: 33%) as colorless solid.

Example 8

Preparation of 3-(2-aminoethyl)-1-(4-chlorobenzyl)-6-(3-fluoro-4-isopropoxyphenylamino)-1,3,5-triazine-2,4(1H,3H)-dione hydrochloride

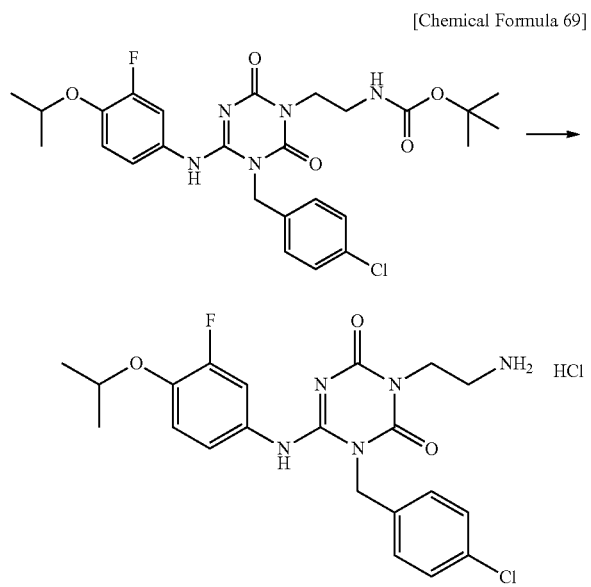

[Chemical Formula 69]

To 3-(2-t-butoxycarbonylaminoethyl)-1-(4-chlorobenzyl)-6-(3-fluoro-4-isopropoxyphenylamino)-1,3,5-triazine-2,4(1H,3H)-dione (0.44 g, 0.8 mmol) was added 4 mol/L solution of hydrochloric acid in dioxane (5 mL) under ice-cooling, and the resulting mixture was stirred at room temperature for 1 hour. Then, the precipitated solid was collected by filtration. The resulting solid was washed with diethyl ether, dried under reduced pressure to give 3-(2-aminoethyl)-1-(4-chlorobenzyl)-6-(3-fluoro-4-isopropoxyphenylamino)-1,3,5-triazine-2,4(1H,3H)-dione hydrochloride (0.31 g, yield: 81%) as colorless solid.

1H-NMR (δ ppm TMS/DMSO-d6): 1.27 (6H, d, J=5.9 Hz), 3.01 (2H, m), 3.98 (2H, m), 4.57 (1H, sept, J=5.9 Hz), 5.27 (2H, brs), 6.98-7.17 (3H, m), 7.42 (3H, s), 7.87 (2H, brs).

Example 9

Preparation of 3-(2-acetylaminoethyl)-1-(4-chlorobenzyl)-6-(3-fluoro-4-isopropoxyphenylamino)-1,3,5-triazine-2,4(1H,3H)-dione

[Chemical Formula 70]

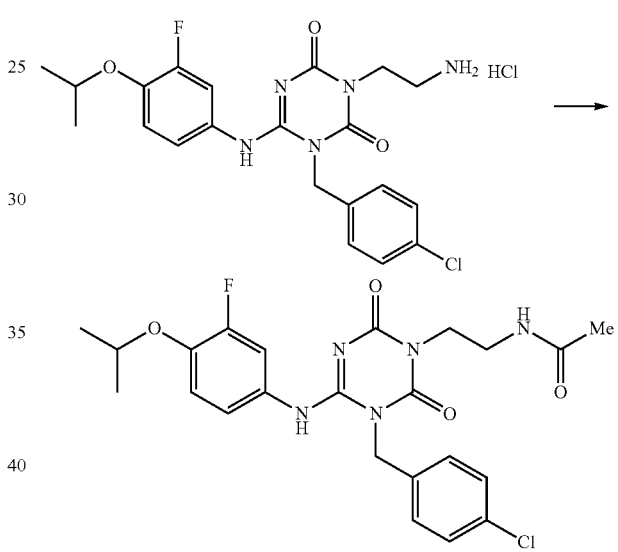

To a mixture of 3-(2-aminoethyl)-1-(4-chlorobenzyl)-6-(3-fluoro-4-isopropoxyphenylamino)-1,3,5-triazine-2,4(1H,3H)-dione hydrochloride (0.104 g, 0.22 mmol), triethylamine (074 mL, 0.54 mmol), dimethylaminopyridine (026 g, 0.22 mmol) and THF (2 mL) was added acetyl chloride (023 mL, 0.32 mmol) dropwise under ice-cooling, and the resulting mixture was stirred at room temperature for 30 minutes. Water (20 mL) was poured into the reaction mixture, and the resulting mixture was extracted with ethyl acetate (10 mL×2). The extract was washed with brine (10 mL), dried over anhydrous sodium sulphate, and then concentrated in vacuo. The resulting residue was purified on a silica gel column chromatography (ethyl acetate/hexane). The aimed compound was triturated with diisopropyl ether and hexane to give 3-(2-acetylaminoethyl)-1-(4-chlorobenzyl)-6-(3-fluoro-4-isopropoxyphenylamino)-1,3,5-triazine-2,4(1H,3H)-dione (0.104 g, yield: 99%) as colorless solid.

1H-NMR (δ ppm TMS/CDCl$_3$): 1.37 (6H, d, J=6.1 Hz), 1.86 (3H, s), 3.51 (2H, m), 4.0 (2H, m), 4.47 (1H, sept, J=6.1 Hz), 5.16 (2H, s), 5.83 (1H, m), 6.51 (11H, m), 6.60 (1H, m), 6.97 (11H, m), 7.27-7.51 (5H, m).

Example 10

Preparation of 1-(4-chlorobenzyl)-6-(3-fluoro-4-isopropoxyphenylamino)-3-(mothoxycarbonylmethyl)-1,3,5-triazine-2,4(1H,3H)-dione

[Chemical Formula 71]

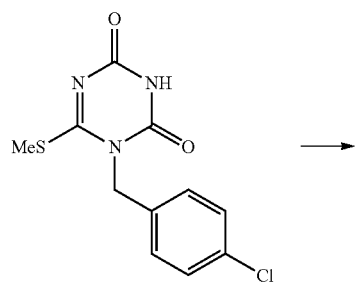

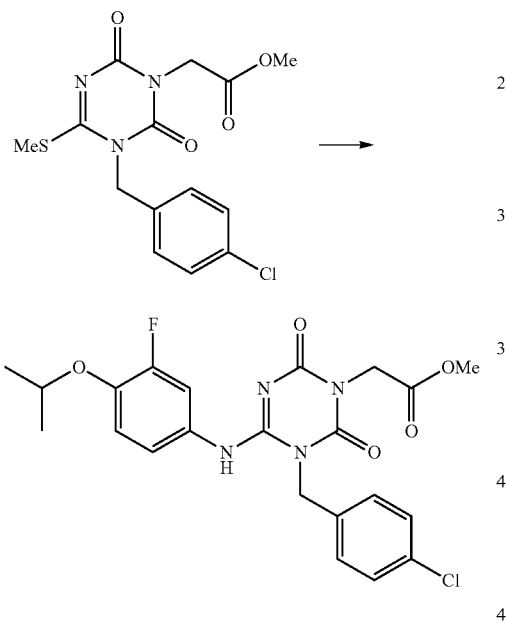

To a mixture of 1-(4-chlorobenzyl)-6-(methylthio)-1,3,5-triazine-2,4(1H,3H)-dione (0.28 g, 1 mmol) and THF (3 mL) was added DBU (0.166 mL, 1.1 mmol), and the resulting mixture was stirred at room temperature for 5 minutes. Bromomethyl acetate (0.104 mL, 1.1 mmol) was added to the mixture, and the resulting mixture was stirred at room temperature for 3 hours. Water (20 mL) was poured into the mixture, and the precipitated solid was collected by filtration. The resulting solid was dried and purified on a silica gel column chromatography (ethyl acetate/hexane) to give 1-(4-chlorobenzyl)-3-(mothoxycarbonylmethyl)-6-(methylthio)-1,3,5-triazine-2,4(1H,3H)-dione (0.25 g, yield: 69%) as colorless solid.

1H-NMR (δ ppm TMS/CDCl$_3$): 2.59 (3H, s), 3.78 (3H, s), 4.69 (2H, s), 5.13 (2H, s), 7.27-7.35 (4H, m).

A mixture of 1-(4-chlorobenzyl)-3-(mothoxycarbonylmethyl)-6-(methylthio)-1,3,5-triazine-2,4(1H,3H)-dione (0.24 g, 0.68 mmol), 3-fluoro-4-isopropoxyaniline (0.17 mg, 1.03 mmol), t-butanol (4.8 mL) and acetic acid (0.4 mL) was heated at reflux for 32 hours. Then, the mixture was poured into saturated sodium hybrogen carbonate solution (20 mL), and the resulting mixture was extracted with ethyl acetate (10 mL). The extract was washed with brine (10 mL), dried over anhydrous sodium sulphate, and concentrated in vacuo. The resulting residue was purified on a silica gel column chromatography (ethyl acetate/hexane). The resulting aimed compound was triturated with diisopropyl ether to give 1-(4-chlorobenzyl)-6-(3-fluoro-4-isopropoxyphenylamino)-3-(mothoxycarbonylmethyl)-1,3,5-triazine-2,4(1H,3H)-dione (0.31 g, yield: 95%) as colorless amorphous.

1H-NMR (δ ppm TMS/CDCls): 1.37 (6H, d, J=5.9 Hz), 3.78 (3H, s), 4.47 (1H, sept, J=5.9 Hz), 4.58 (2H, s), 5.17 (2H, s), 6.50 (1H, m), 6.60 (1H, m), 6.97 (1H, m), 7.28-7.47 (5H, m).

Example 11

Preparation of 1-(4-chlorobenzyl)-6-(3-fluoro-4-isopropoxyphenylamino)-3-(hydroxycarbonylmethyl)-1,3,5-triazine-2,4(1H,3H)-dione

[Chemical Formula 72]

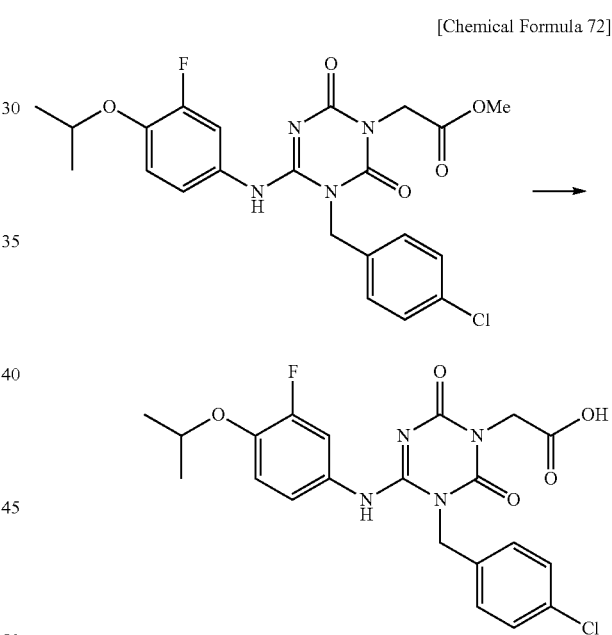

To a mixture of 1-(4-chlorobenzyl)-6-(3-fluoro-4-isopropoxyphenylamino)-3-(methoxycarbonylmethyl)-1,3,5-triazine-2,4(1H,3H)-dione (0.30 g, 0.63 mmol), methanol (3 mL) and THF (3 mL) was added 1 mol/L lithium hydroxide (3.8 mL) under ice-cooling, and the resulting mixture was stirred at room temperature for 1 hour. Then, the mixture was treated with 2 mol/L hydrochloric acid to pH 2 or less. The mixture was poured into brine (20 mL), and the resulting mixture was extracted with chloroform (10 mL×3). The extract was dried over anhydrous sodium sulphate and concentrated in vacuo. The resulting residue was triturated with diethyl ether and hexane to give 1-(4-chlorobenzyl)-6-(3-fluoro-4-isopropoxyphenylamino)-3-(hydroxycarbonylmethyl)-1,3,5-triazine-2,4(1H,3H)-dione (0.28 g, yield: 97%) as colorless solid.

1H-NMR (δ ppm TMS/CDCl$_3$): 1.36 (6H, d, J=6.1 Hz), 4.47 (1H, sept, J=6.1 Hz), 4.62 (2H, s), 5.18 (2H, s), 6.51 (1H, m), 6.60 (1H, m), 6.96 (1H, m), 7.30 (2H, d, J=8.7 Hz), 7.45 (2H, d, J=8.7 Hz), 7.64 (1H, brs).

Example 12

Preparation of 1-(4-chlorobenzyl)-6-(3-fluoro-4-isopropoxyphenylamino)-3-(methylcarbamoylmethyl)-1,3,5-triazine-2,4(1H,3H)-dione

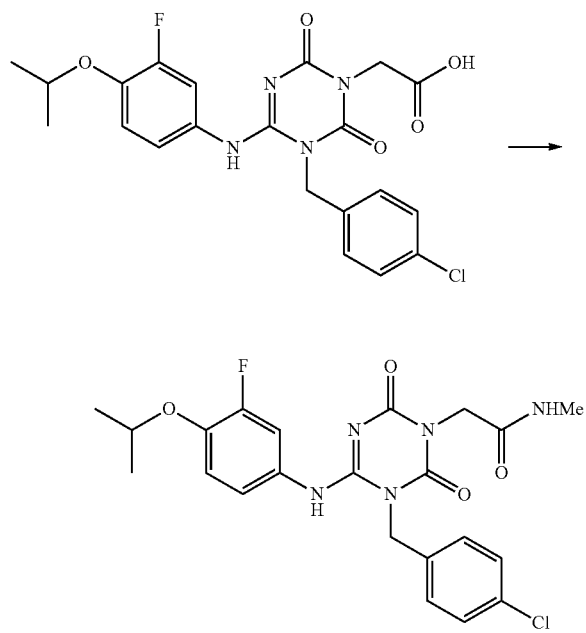

[Chemical Formula 73]

To a mixture of 1-(4-chlorobenzyl)-6-(3-fluoro-4-isopropoxyphenylamino)-3-(hydroxycarbonylmethyl)-1,3,5-triazine-2,4(1H,3H)-dione (083 g, 0.19 mmol) and DMF (2 mL) were added methylamine hydrochloride (015 g, 0.21 mmol), 1-hydroxybenzotriazole hydrate (03 g, 0.2 mmol), 4-dimethylaminopyridine (002 g, 02 mmol), 1-ethyl-3-(3-dimethylanimopropyl)carbodiimide hydrochloride (038 g, 0.2 mmol) and triethylamine (03 mL, 0.21 mmol), and the resulting mixture was stirred at 60° C. for 4 hours. Then, the mixture was poured into water (20 mL), and the resulting mixture was extracted with ethyl acetate (20 mL). The extract was washed with brine (10 mL), dried over anhydrous sodium sulphate and concentrated in vacuo. The resulting residue was purified on a silica gel column chromatography (ethyl acetate/hexane) and the aimed compound was triturated with diisopropyl ether to give 1-(4-chlorobenzyl)-6-(3-fluoro-4-isopropoxyphenylamino)-3-(methylcarbamoylmethyl)-1,3,5-triazine-2,4(1H,3H)-dione (076 g, yield: 89%) as colorless solid.

1H-NMR (δ ppm TMS/CDCl$_3$): 1.37 (6H, d, J=6.1 Hz), 2.85 (3H, d, J=4.9 Hz), 4.37 (2H, s), 4.46 (1H, sept, J=6.1 Hz), 5.15 (2H, s), 5.78 (1H, d, J=4.7 Hz), 6.46 (1H, m), 6.57 (1H, m), 6.95 (1H, m), 7.27-7.46 (4H, m), 7.99 (1H, ms).

Example 13

Preparation of 4-chloro-1-(4-chlorobenzyl)-6-(3-fluoro-4-isopropoxyphenylamino)-1,3,5-triazine-2(1H)-one

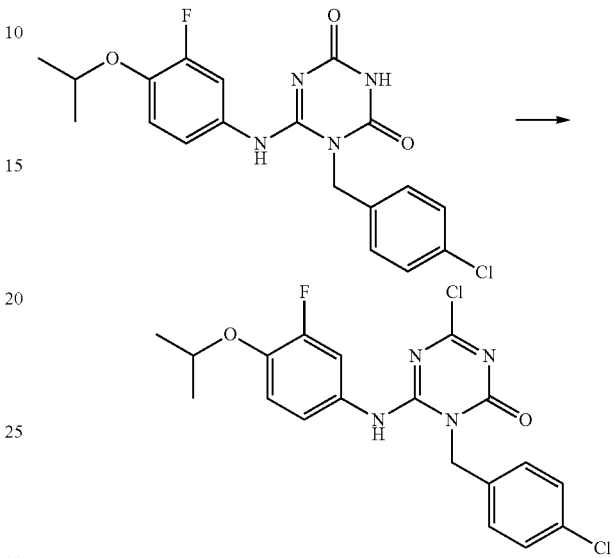

[Chemical Formula 74]

To 1-(4-chlorobenzyl)-6-(3-fluoro-4-isopropoxyphenylamino)-1,3,5-triazine-2,4(1H,3H)-dione (0.486 g, 1.2 mmol) was added phosphorous oxychloride (2.24 mL, 24 mmol), and the resulting mixture was stirred at 50° C. for 2 hours. Then, the mixture was concentrated in vacuo. The resulting residue was dissolved in ethyl acetate (30 mL), washed with saturated sodium hybrogen carbonate solution (10 mL) and brine (10 mL), dried over anhydrous sodium sulphate and concentrated in vacuo to give crude 4-chloro-1-(4-chlorobenzyl)-6-(3-fluoro-4-isopropoxyphenylamino)-1,3,5-triazine-2(1H)-one (0.57 g) as colorless solid.

1H-NMR (δ ppm TMS/CDCl$_3$): 1.35 (6H, d, J=6.3 Hz), 4.51 (1H, sept, J=6.3 Hz), 5.28 (2H, s), 6.72 (1H, brs), 6.80 (1H, m), 6.91 (1H, m), 7.08 (1H, m), 7.30 (2H, d, J=8.4 Hz), 7.44 (2H, d, J=8.4 Hz).

Example 14

Preparation of 1-(4-chlorobenzyl)-6-(3-fluoro-4-isopropoxyphenylamino)-4-(2-hydroxyethoxy)-1,3,5-triazine-2(1H)-one

[Chemical Formula 75]

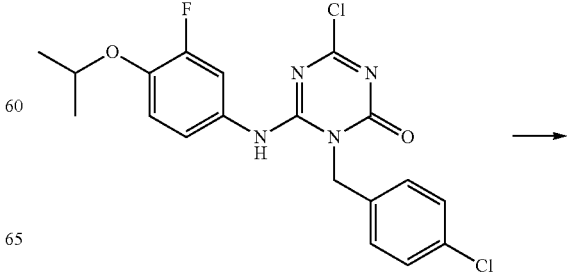

-continued

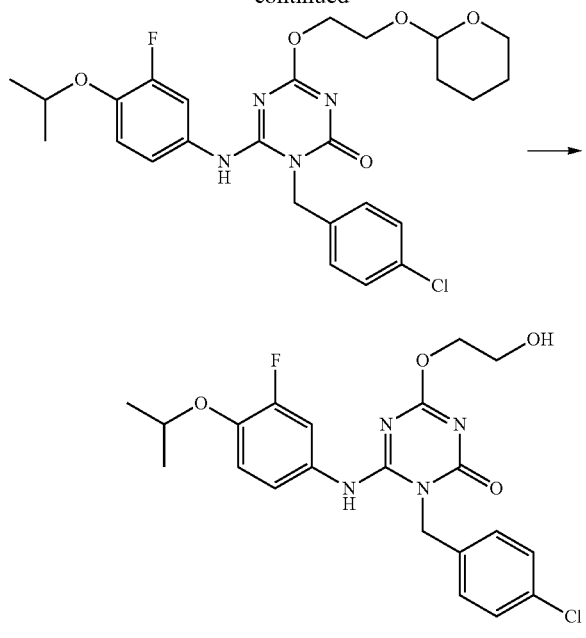

To a mixture of 2-(tetrahydro-2H-pyrane-2-yloxy)ethanol (0.17 mL, about 1.25 mmol) and THF (5.6 mL) was added 60% sodium hydride (05 g, 1.25 mmol), and the resulting mixture was stirred at room temperature for 10 minutes.

A solution of crude 4-chloro-1-(4-chlorobenzyl)-6-(3-fluoro-4-isopropoxyphenylamino)-1,3,5-triazine-2(1H)-one (0.224 g, about 0.5 mmol) in THF (5.6 mL) was added to the mixture under ice-cooling, and the resulting mixture was stirred at room temperature for 5 hours. Then, half-saturated ammonium chloride aqueous solution (50 mL) was poured into the mixture and the resulting mixture was extracted with ethyl acetate (50 mL). The extract was washed with brine (10 mL), dried over anhydrous sodium sulphate, and concentrated in vacuo. The resulting residue was purified on a silica gel column chromatography (ethyl acetate/hexane) and the aimed compound was triturated with hexane to give 1-(4-chlorobenzyl)-6-(3-fluoro-4-isopropoxyphenylamino)-4-[2-(tetrahydro-2H-pyrane-2-yloxy)ethoxy]-1,3,5-triazine-2 (1H)-one (0.166 g, yield: 62%) as colorless oil.

To a mixture of 1-(4-chlorobenzyl)-6-(3-fluoro-4-isopropoxyphenylamino)-4-[2-(tetrahydro-2H-pyrane-2-yloxy)ethoxy]-1,3,5-triazine-2(1H)-one (0.15 g, 0.28 mmol) and methanol (1.5 mL) was added p-toluenesulfonic acid hydrate (08 g, 0.4 mmol), and the resulting mixture was stirred at room temperature for 2 hours. Then, the mixture was poured into half-saturated sodium hydrogen carbonate solution (10 mL) and the resulting mixture was extracted with ethyl acetate (20 mL). The extract was washed with brine (10 mL), dried over anhydrous sodium sulphate, and concentrated in vacuo. The resulting residue was purified on a silica gel column chromatography (methanol/chloroform) and the aimed compound was triturated with hexane to give 1-(4-chlorobenzyl)-6-(3-fluoro-4-isopropoxyphenylamino)-4-(2-hydroxyethoxy)-1,3,5-triazine-2(1H)-one (0.104 g, yield: 83%) as colorless solid.

1H-NMR (δ ppm TMS/CDCl$_3$): 1.34 (6H, d, J=6.1 Hz), 2.53 (1H, brs), 3.91 (2H, brs), 4.44-4.52 (3H, m), 5.30 (2H, s), 6.60 (1H, brs), 6.75-7.10 (3H, m), 7.27-7.43 (4H, m).

Example 15

Preparation of 4-benzylamino-1-(4-chlorobenzyl)-6-(3-fluoro-4-isopropoxyphenylamino)-1,3,5-triazine-2 (1H)-one

[Chemical Formula 76]

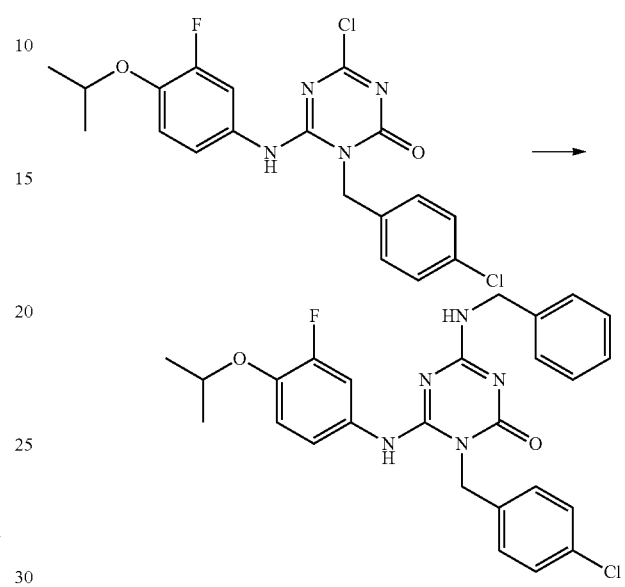

To a mixture of crude 4-chloro-1-(4-chlorobenzyl)-6-(3-fluoro-4-isopropoxyphenylamino)-1,3,5-triazine-2(1H)-one (0.19 g, about 0.4 mmol) and THF (4.7 mL) was added benzylamine (0.108 mL, 1 mmol), and the resulting mixture was stirred at room temperature for 6 hours. Water (10 mL) and ethyl acetate (10 mL) were poured into the mixture and the precipitated solid was collected by filtration. The obtained solid was washed with ethyl acetate, dried under reduced pressure to give 4-benzylamino-1-(4-chlorobenzyl)-6-(3-fluoro-4-isopropoxyphenylamino)-1,3,5-triazine-2(1H)-one (0.102 g, yield: 52%) as colorless solid.

1H-NMR (δ ppm TMS/DMSO-d6): 1.25 (6H, d, J=5.7 Hz), 4.28 (1H, m), 4.41 (1H, m), 4.54 (1H, sept, J=5.7 Hz), 5.22 (2H, m), 7.08-7.52 (8H, m), 7.90 (1H, brs), 8.94 (1H, brs).

Example 16

Preparation of 1-(4-chlorobenzyl)-4-(dodecylthio)-6-(3-fluoro-4-isopropoxyphenylamino)-1,3,5-triazine-2 (1H)-one

[Chemical Formula 77]

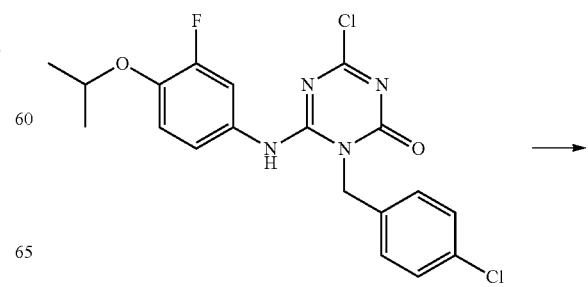

-continued

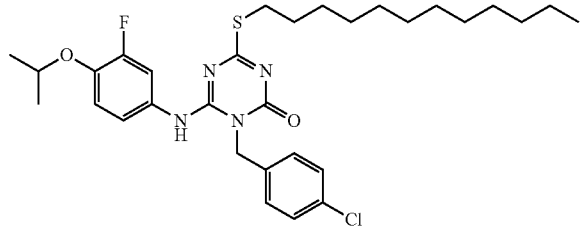

To a mixture of 1-dodecanethiol (0.24 mL, 1.0 mmol) and THF (4.8 mL) was added 60% sodium hydride (045 g, 1.0 mmol), and the resulting mixture was stirred at room temperature for 10 minutes. A solution of crude 4-chloro-1-(4-chlorobenzyl)-6-(3-fluoro-4-isopropoxyphenylamino)-1,3, 5-triazine-2(1H)-one (0.19 g, about 0.4 mmol) in THF (2 mL) was added to the reaction mixture under ice-cooling. After the reaction mixture was stirred at 50° C. for 5 hours, half-saturated ammonium chloride aqueous solution (50 mL) was poured into the mixture and the resulting mixture was extracted with ethyl acetate (50 mL). The extract was washed with brine (10 mL), dried over anhydrous sodium sulphate, and concentrated in vacuo. The resulting residue was purified on a silica gel column chromatography (ethyl acetate/hexane) and the aimed compound was triturated with hexane to give 1-(4-chlorobenzyl)-4-(dodecylthio)-6-(3-fluoro-4-isopropoxyphenylamino)-1,3,5-triazine-2(1H)-one (092 g, yield: 39%) as colorless oil.

1H-NMR (δ ppm TMS/CDCl$_3$): 0.89 (3H, t, J=6.9 Hz), 1.27 (14H, s), 1.34 d, J=6 Hz), 1.50-1.70 (6H, m), 3.02 (2H, t, J=7.5 Hz), 4.48 (1H, sept, J=6 Hz), 5.26 (2H, s), 6.52 (1H, brs), 6.75 (1H, m), 6.88 (1H, m), 7.10 (1H, m), 7.28-7.50 (4H, m).

Example 17

Preparation of 1-(4-chlorobenzyl)-6-(4-hydroxycarbonylphenylamino)-3-isopropyl-1,3,5-triazine-2,4(1H,3H)-dione

[Chemical Formula 78]

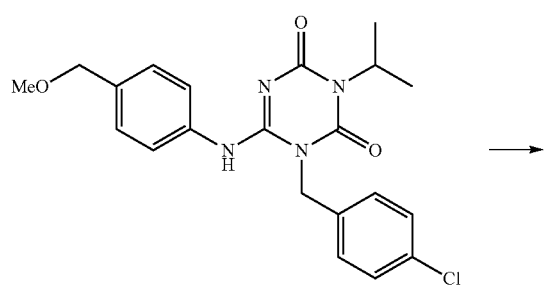

-continued

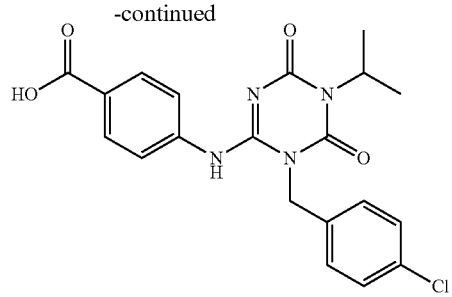

To a mixture of 1-(4-chlorobenzyl)-6-(4-methoxycarbonylphenylamino)-3-isopropyl-1,3,5-triazine-2,4(1H,3h)-dione (0.70 g, 1.63 mmol), methanol (4 mL) and THF (4 mL) was added 2 mol/L lithium hydroxide (4.9 mL) under ice-cooling, and the resulting mixture was stirred at room temperature for 8 hours. The mixture was poured into water (50 mL) and the resulting mixture was treated with 2 mol/L hydrochloric acid to pH3 or less. The resulting mixture was extracted with ethyl acetate (50 mL×2). The extract was washed with brine (50 mL), dried over anhydrous sodium sulphate and concentrated in vacuo. The obtained solid was washed with diethyl ether to give 1-(4-chlorobenzyl)-6-(4-hydroxycarbonylphenylamino)-3-isopropyl-1,3,5-triazine-2,4(1H, 311)-dione (0.60 g, yield: 89%) as colorless solid.

1H-NMR (δ ppm TMS/CDCl$_3$): 1.46 (61-1, d, J=6.9 Hz), 4.98 (1H, sept, J=6.9 Hz), 5.19 (2H, s), 6.90 (2H, d, J=8.1 Hz), 7.31 (2H, d, J=8.7 Hz), 7.50 (2H, d, J=8.7 Hz), 7.90 (2H, d, J=8.1 Hz).

Example 18

Preparation of 1-(4-chlorobenzyl)-6-[4-(N-benzylcarbamoyl)phenylamino]-3-isopropyl-1,3,5-triazine-2,4(1H,3H)-dione

[Chemical Formula 79]

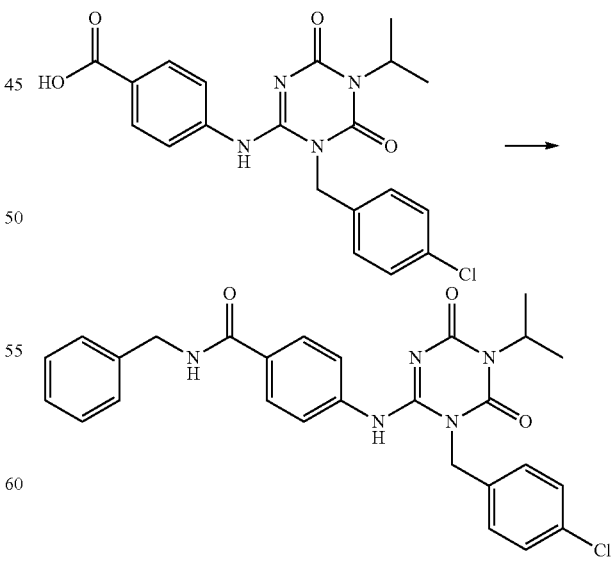

To a mixture of 1-(4-chlorobenzyl)-6-(4-hydroxycarbonylphenylamino)-3-isopropyl-1,3,5-triazine-2,4(1H,3h)-dione (08 g, 0.19 mmol) and THF (2 mL) were added benzylamine (023 mL, 0.21 mmol), 1-hydroxybenzotriazole (03 g, 0.21 mmol), 1-ethyl-3-(3-dimethylaminopropyl)carbodiimide hydrochloride (041 g, 0.2 mmol) and triethylamine (03 mL, 0.21 mmol) under ice-cooling, and the resulting mixture was stirred at room temperature for 4 hours. The mixture was poured into water (30 mL) and the resulting mixture was extracted with ethyl acetate (30 mL). The extract was washed with brine (30 mL), dried over anhydrous sodium sulphate and concentrated in vacuo. The resulting residue was purified on a silica gel column chromatography (ethyl acetate/hexane) and the aimed compound was triturated with diethyl ether to give 1-(4-chlorobenzyl)-6-[4-(N-benzylcarbamoyl)phenylamino]-3-isopropyl-1,3,5-triazine-2,4(1H,3H)-dione (07 g, yield: 72%) as colorless solid.

1H-NMR (δ ppm TMS/CDCl$_3$): 1.43 (6I-1, d, J=6.9 Hz), 4.67 (2H, d, J=4.0 Hz), 4.96 (1H, sept, J=6.9 Hz), 5.18 (2H, s), 6.34 (11H, m), 6.88 (2H, d, J=8.4 Hz), 7.17 brs), 7.29-7.34 (6H, m), 7.50 (2H, d, J=8.4 Hz), 7.80 (2H, d, J=8.4 Hz).

Example 19

Preparation of 1-(4-chlorobenzyl)-6-(3-chloro-4-isopropoxyphenylamino)-4-hydroxycarbonylethyl-1,3,5-triazine-2(1H)-one

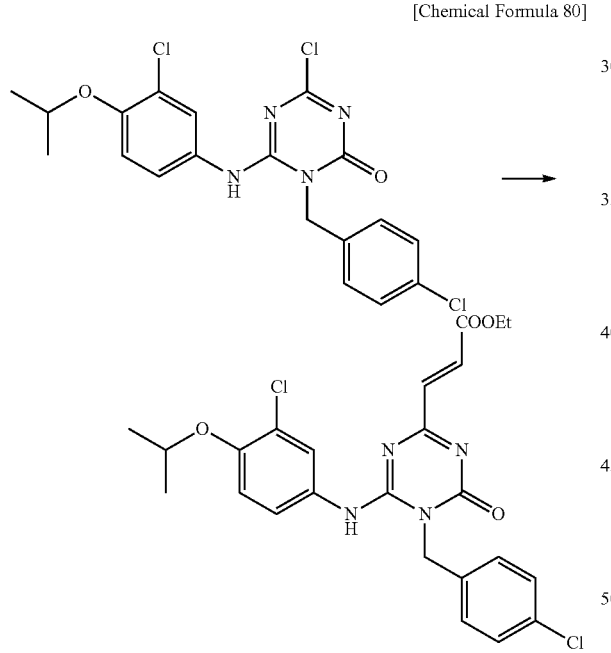

[Chemical Formula 80]

A mixture of 4-chloro-1-(4-chlorobenzyl)-6-(3-fluoro-4-isopropoxyphenylamino)-1,3,5-triazine-2(1H)-one (0.15 g, 0.34 mmol), 1,1'-bis(di-t-butylphosphinoferrocene)palladium(II) dichloride (22.23 mg, 034 mmol), and THF (3 mL) was placed in a flask under nitrogen. To the mixture were added (E)-ethyl-3-(4,4,5,5-tetramethyl-1,3,2-dioxaborolane-2-yl)acrylate (063 g, 0.49 mmol) and 2 mol/L potassium carbonate (0.682 mL, 1.364 mmol), and the resulting mixture was heated at reflux for 7 hours. Then, the mixture was poured into water (30 mL) and the resulting mixture was extracted with chloroform (30 mL). The extract was dried over anhydrous sodium sulphate and concentrated in vacuo. The resulting residue was purified on a hight performance liquid chromatography (0.3% HCO2H H2O/MeCN 50-80%) to give 1-(4-chlorobenzyl)-6-(3-chloro-4-isopropoxyphenylamino)-ethoxycarbonylethenyl-1,3,5-triazine-2(1H)-one (05 g, yield: 30%) as pale orange oil.

1H-NMR (δ ppm TMS/DMSO-d6): 1.20-1.28 (9H, m), 4.17-4.22 (2H, m), 4.54 (1H, brs), 5.10 (2H, brs), 7.40 (8H, brs), 8.14 (1H, s), 9.77 (1H, s).

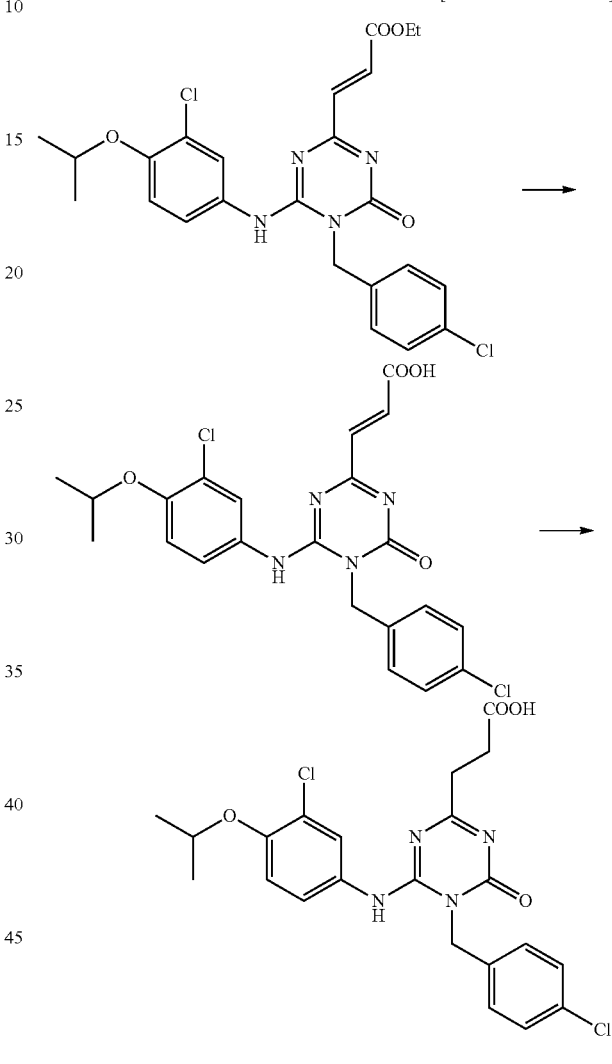

[Chemical Formula 81]

To a mixture of 1-(4-chlorobenzyl)-6-(3-chloro-4-isopropoxyphenylamino)-ethoxycarbonylethenyl-1,3,5-triazine-2(1H)-one (05 g, 0.1 mmol), THF (1 mL), EtOH (1 mL) and water (0.3 mL) was added lithium hydroxide hydrate (12.5 mg, 0.3 mmol), and the resulting mixture was stirred at room temperature for 3 days. The reaction mixture was purified on a hight performance liquid chromatography (0.3% HCO2H H2O/MeCN 40-70%) to give 1-(4-chlorobenzyl)-6-(3-chloro-4-isopropoxyphenylamino)-4-hydroxycarbonylethenyl-1,3,5-triazine-2(1H)-one (27 mg, yield: 57%) as pale orange oil.

The obtained intermediate was dissolved in methanol (3 mL), the resulting solution was conducted a catalytic reduction by using H-Cube (10% Pt—C, H2=1 atm). The reaction mixture was purified on a hight performance liquid chromatography (0.3% HCO2H H2O/MeCN 50-80%) to give 1-(4- chlorobenzyl)-6-(3-chloro-4-isopropoxyphenylamino)-4-hydroxycarbonylethyl-1,3,5-triazine-2(1H)-one (2.3 mg, yield: 8.5%) as colorless oil.

1H-NMR (δ ppm TMS/CDCl₃): 1.36 (6H, d, J=5.7 Hz), 2.22 (1H, t, J=7.8 Hz), 2.74 (3H, brs), 4.48 (1H, sept, J=5.7 Hz), 5.18 (2H, s), 6.88 (2H, s), 7.13 (1H, s), 7.30 (2H, d, J=8.4 Hz), 7.45 (2H, d, J=8.4 Hz).

Example 20

Preparation of (R)-1-(4-chlorobenzyl)-6-(3-fluoro-4-isopropoxyphenylamino)-3-(2-methoxycarbonylpropyl)-1,3,5-triazine-2,4(1H,3H)-dione

[Chemical Formula 82]

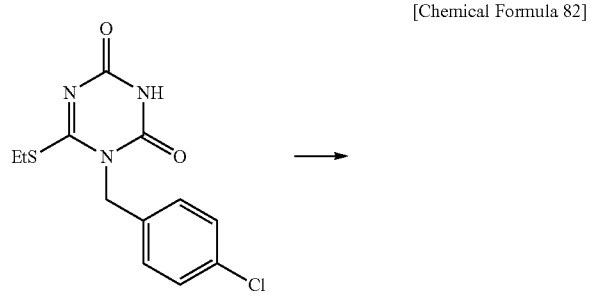

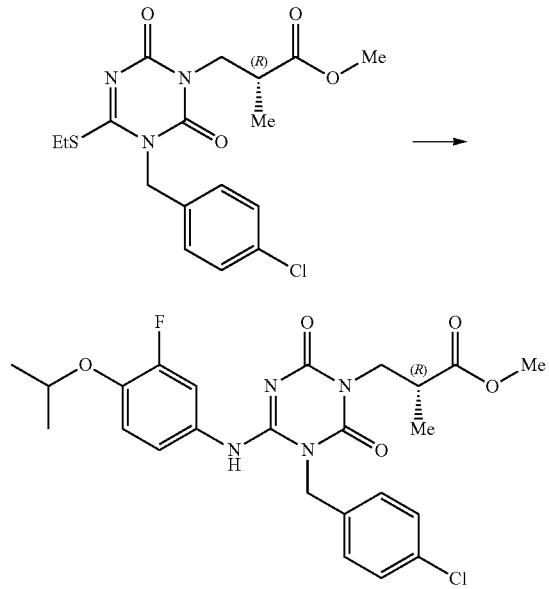

To a mixture of 1-(4-chlorobenzyl)-6-(ethylthio)-1,3,5-triazine-2,4(1H,3H)-dione (1.0 g, 3.4 mmol), di-2-methoxyethyl azocarboxylate (1.02 g, 4.4 mmol), triphenylphosphine (1.15 g, 4.4 mmol) and dioxane (8 mL) was gradually added methyl(R)-(−)-3-hybroxyisobutyrate (0.52 g, 4.4 mmol), and the resulting mixture was stirred at room temperature for 1 hour. Water (20 mL) was poured into the mixture, and the resulting mixture was extracted with ethyl acetate (20 mL×2). The extract was washed with brine (20 mL), dried over anhydrous magnesium sulfate, and then concentrated in vacuo. The resulting residue was purified on a silica gel column chromatography (ethyl acetate/hexane) to give (R)-1-(4-chlorobenzyl)-6-(ethylthio)-3-(2-methoxycarbonylpropyl)-1,3,5-triazine-2,4(1H,3H)-dione (0.98 g, yield: 74%) as colorless amorphous.

1H-NMR (δ ppm TMS/CDCl₃): 1.19 (3H, d, J=5.7 Hz), 1.37 (3H, t, J=7.1 Hz), 2.96 (1H, m), 3.12 (2H, q, J=7.1 Hz), 3.60 (3H, s), 3.98 (1H, m), 4.21 (1H, m), 5.08 (2H, s), 7.29-7.34 (4H, m).

A mixture of (R)-1-(4-chlorobenzyl)-6-(ethylthio)-3-(2-methoxycarbonylpropyl)-1,3,5-triazine-2,4(1H,3H)-dione (0.32 g, 0.8 mmol), 3-fluoro-4-isopropoxyaniline (0.20 g, 1.2 mmol), acetic acid (0.72 g, 12 mmol) and t-butanol (6 mL) was heated at reflux over night. Then, the mixture was poured into saturated sodium hybrogen carbonate solution (40 mL), and the resulting mixture was extracted with ethyl acetate (40 mL×2). The extract was washed with 2 mol/L hydrochloric acid (20 mL×2), dried over anhydrous sodium sulphate, and then concentrated in vacuo. The resulting residue was purified on a silica gel column chromatography (ethyl acetate/hexane). The obtained compound was triturated with diethyl ether to give (R)-1-(4-chlorobenzyl)-6-(3-fluoro-4-isopropoxyphenylamino)-3-(2-methoxycarbonylpropyl)-1,3,5-triazine-2,4(1H,3H)-dione (0.29 g, yield: 71%) as lilac powder.

Example 21

Preparation of (R)-1-(4-chlorobenzyl)-6-(3-fluoro-4-isopropoxyphenylamino)-3-(2-hydroxycarbonylpropyl)-1,3,5-triazine-2,4(1H,3H)-dione

[Chemical Formula 83]

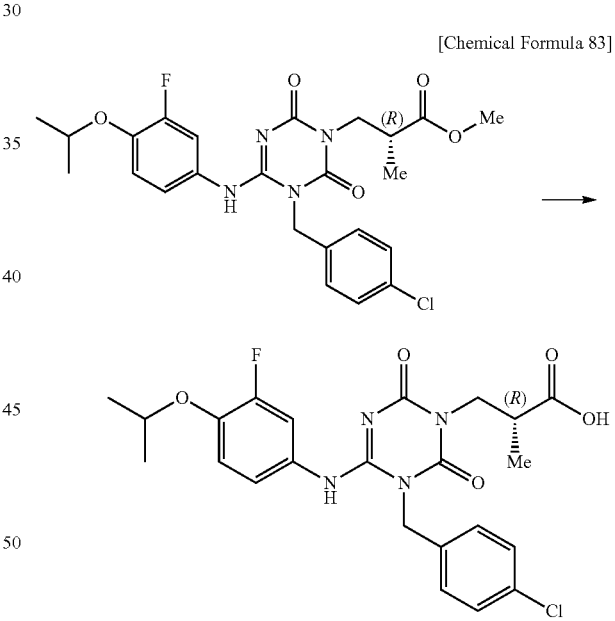

To a mixture of (R)-1-(4-chlorobenzyl)-6-(3-fluoro-4-isopropoxyphenylamino)-3-(2-methoxycarbonylisopropyl)-1,3,5-triazine-2,4(1H,3H)-dione (0.26 g, 0.5 mmol) and dioxane (4 mL) was added 1 mol/L lithium hydroxide (1.6 mL), and the resulting mixture was stirred at 50° C. for 6 hours. Then, water (50 mL) was poured into the mixture. The resulting mixture was treated with 2 mol/L hydrochloric acid to about pH3. The precipitated solid was collected by filtration and the obtained solid was dried under reduced pressure at 40° C. for 2 hours to give (R)-1-(4-chlorobenzyl)-6-(3-fluoro-4-isopropoxyphenylamino)-3-(2-hydroxycarbonylpropyl)-1,3,5-triazine-2,4(1H,3H)-dione (0.21 g, yield: 84%) as colorless solid.

1H-NMR (δ ppm TMS/CDCl$_3$): 1.19 (3H, d, J=5.7 Hz), 1.34 (6H, d, J=5.7 Hz), 2.91 (1H, m), 3.89 (1H, m), 4.11 (1H, m), 4.44 (1H, sept, J=5.7 Hz), 5.16 (2H, s), 6.47-6.60 (2H, m), 6.93 (11H, m), 7.28-7.44 (4H, m), 7.94 (1H, brs).

Example 22

Preparation of 1-(4-chlorobenzyl)-6-(3-fluoro-4-isopropoxyphenylamino)-3-[2,2-di(hydroxymethyl)propyl]-1,3,5-triazine-2,4(1H,3H)-dione

[Chemical Formula 84]

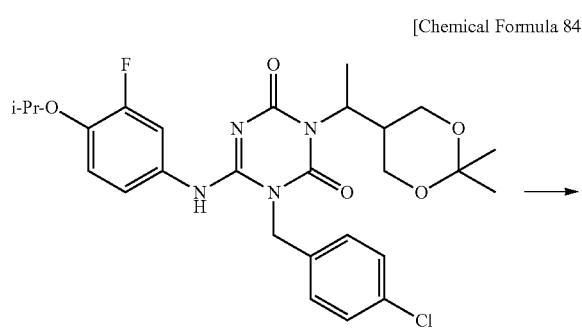

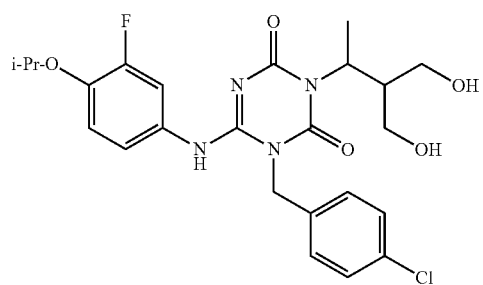

To a mixture of 1-(4-chlorobenzyl)-6-(3-fluoro-4-isopropoxyphenylamino)-3-(2,2,5-trimethyl-1,3-dioxane-5-yl)methyl-1,3,5-triazine-2,4(1H,3H)-dione (7.9 g, 14.44 mmol) and methanol (160 mL) was added p-toluenesulfonic acid monohydrate (5.49 g, 28.9 mmol), and the resulting mixture was stirred at room temperature for 1 hour. Then, the mixture was poured into saturated sodium hybrogen carbonate solution (20 mL) and the resulting mixture was extracted with ethyl acetate (30 mL×2). The extract was washed with brine (30 mL), dried over anhydrous sodium sulphate, and concentrated in vacuo. The resulting residue was purified on a silica gel column chromatography (ethyl acetate/hexane). The obtained compound was triturated with water. The precipitated solid was collected by filtration and the obtained solid was dried under reduced pressure at 70° C. for 6 hours to give 1-(4-chlorobenzyl)-6-(3-fluoro-4-isopropoxyphenylamino)-3-[2,2-di(hydroxymethyl)propyl]-1,3,5-triazine-2,4(1H,3H)-dione (5.12 g, yield: 70%) as white powder.

1H-NMR (δ ppm TMS/CDCl$_3$): 1.37 (6H, d, J=6.0 Hz), 3.26-3.46 (6H, m), 3.99 (2H, s), 4.48 (1H, sept, J=6.0 Hz), 5.19 (2H, s), 6.49-6.64 (2H, m), 6.99 (1H, m), 7.30-7.51 (5H, m).

Elemental Analysis

Calculated value C24H28ClFN4O5.⅓H2O, C, 56.19; H, 5.63, Cl: 6.91, F: 3.70, N, 10.92

Water: 1.18%

Measured value C, 56.33; H, 5.60, Cl: 6.79, F: 3.58, N, 11.06

Karl Fischer moisture measurement: 1.02%

The following compounds were synthesized in a manner similar to those described in the general procedures and Examples. The chemical structure of the compounds and the physical properties of them are described below.

(Method of Identification for the Compound)

LC/MS data of the compounds were measured under any one of the following 3 conditions (Method A, B and C), and a retention time and [M+H]$^+$ are shown.

(Method 1)

Column: Luna C18(2) (5 μm, i.d. 4.6×50 mm) (Phenomenex)

Flow rate: 3 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 10% solvent [B] for 3 minutes was performed, and 10% solvent [B] was maintained for 1 minute.

(Method 2)

Column: Xbridge C18(5 μm, i.d. 4.6×50 mm) (Waters)

Flow rate: 3 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 10% solvent [B] for 3 minutes was performed, and 10% solvent [B] was maintained for 1 minute.

(Method 3)

Column: Shim-pack XR-ODS (2.2 μm, i.d. 50×3.0 mm) (Shimadzu)

Flow rate: 1.6 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 10% solvent [B] for 3 minutes was performed, and 10% solvent [B] was maintained for 1 minute.

(Method 4)

Column: Develosil RPAq, (50×4.5 mm)

Flow rate: 1.5 mL/min

UV detection wavelength: 254 nm

Mobile phase: [A] is 0.1% formic acid-containing aqueous solution, and [B] is 0.1% formic acid-containing acetonitrile solution Gradient: 60% solvent [B] was maintained for 0.5 minute, linear gradient of 60% to 10% solvent [B] for 4.5 minutes was performed, and 10% solvent [B] was maintained for 1.0 minute.

TABLE 4

| Chemical Structure | Compound No. | [M + H] | Retention time (min) | Method |
|---|---|---|---|---|
| 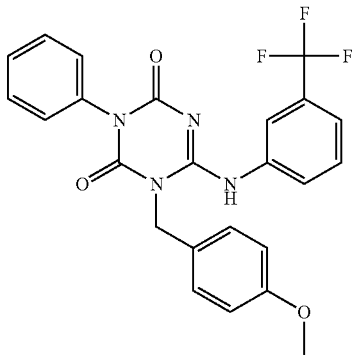 [SMILES: COc1ccc(Cn2c(Nc3cccc(C(F)(F)F)c3)nc(=O)n(-c3ccccc3)c2=O)cc1] | I-001 | 469 | 2.46 | 3 |
| 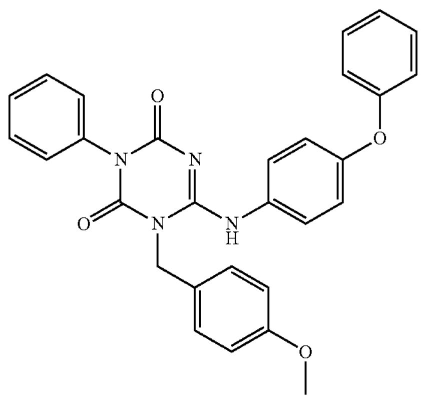 [SMILES: COc1ccc(Cn2c(Nc3ccc(Oc4ccccc4)cc3)nc(=O)n(-c3ccccc3)c2=O)cc1] | I-002 | 493 | 2.49 | 3 |
| 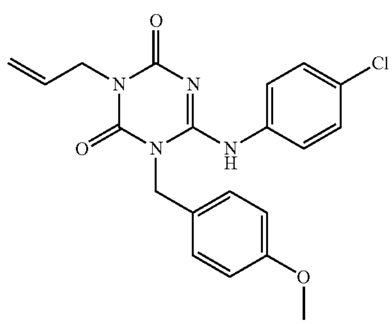 [SMILES: C=CCn1c(=O)nc(Nc2ccc(Cl)cc2)n(Cc2ccc(OC)cc2)c1=O] | I-003 | 399 | 2.31 | 3 |
| 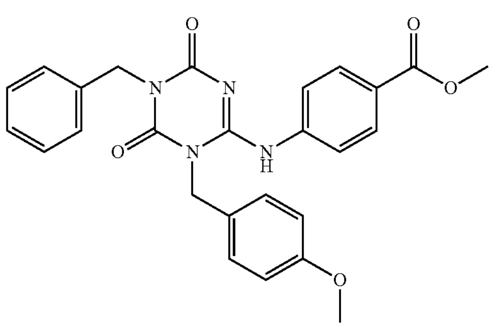 [SMILES: COC(=O)c1ccc(Nc2nc(=O)n(Cc3ccccc3)c(=O)n2Cc2ccc(OC)cc2)cc1] | I-004 | 473 | 2.47 | 3 |

TABLE 4-continued

| Chemical Structure | Compound No. | [M + H] | Retention time (min) | Method |
|---|---|---|---|---|
| 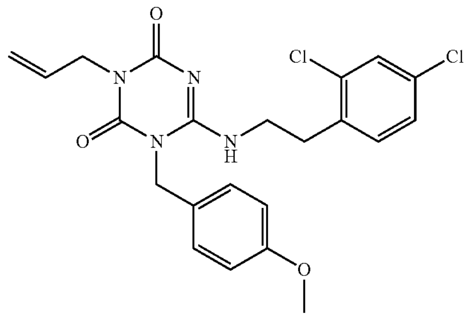 [SMILES: C=CCn1c(=O)nc(NCCc2ccc(Cl)cc2Cl)n(Cc2ccc(OC)cc2)c1=O] | I-005 | 461 | 2.37 | 3 |

TABLE 5

| Chemical Structure | Compound No. | [M + H] | Retention time (min) | Method |
|---|---|---|---|---|
| 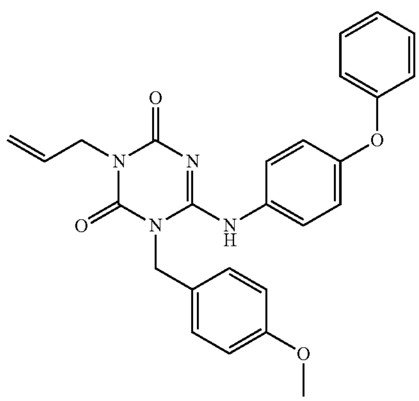 [SMILES: C=CCn1c(=O)nc(Nc2ccc(Oc3ccccc3)cc2)n(Cc2ccc(OC)cc2)c1=O] | I-006 | 457 | 2.48 | 3 |
| 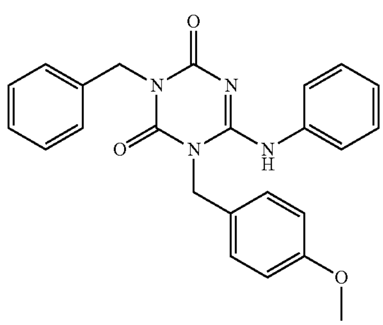 [SMILES: COc1ccc(Cn2c(Nc3ccccc3)nc(=O)n(Cc3ccccc3)c2=O)cc1] | I-007 | 415 | 2.34 | 3 |
| 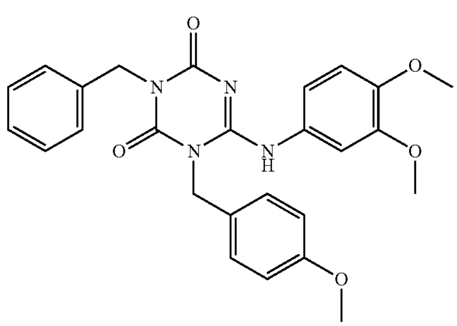 [SMILES: COc1ccc(Cn2c(Nc3ccc(OC)c(OC)c3)nc(=O)n(Cc3ccccc3)c2=O)cc1] | I-008 | 475 | 2.22 | 3 |

TABLE 5-continued

| Chemical Structure | Compound No. | [M + H] | Retention time (min) | Method |
|---|---|---|---|---|
| 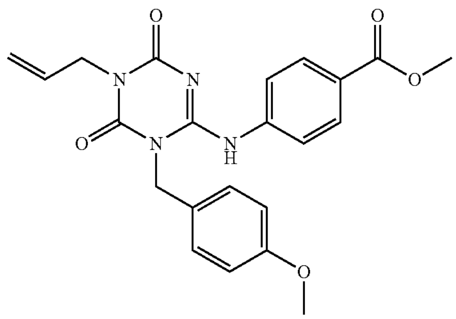 [SMILES: C=CCn1c(=O)nc(Nc2ccc(C(=O)OC)cc2)n(Cc2ccc(OC)cc2)c1=O] | I-009 | 423 | 2.23 | 3 |
| 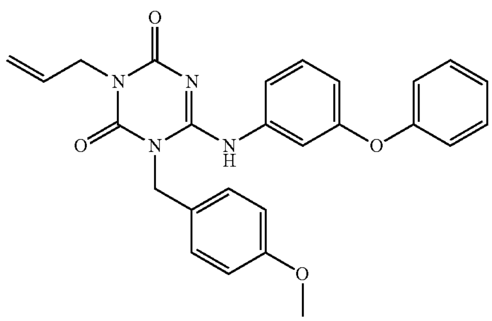 [SMILES: C=CCn1c(=O)nc(Nc2cccc(Oc3ccccc3)c2)n(Cc2ccc(OC)cc2)c1=O] | I-010 | 457 | 2.48 | 3 |

TABLE 6

| Chemical Structure | Compound No. | [M + H] | Retention time (min) | Method |
|---|---|---|---|---|
| 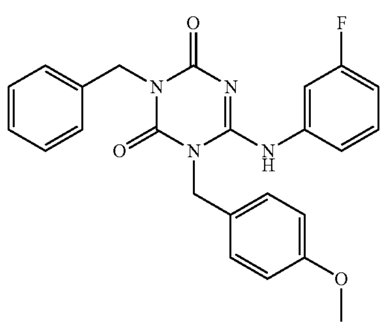 [SMILES: COc1ccc(Cn2c(Nc3cccc(F)c3)nc(=O)n(Cc3ccccc3)c2=O)cc1] | I-011 | 433 | 2.47 | 3 |
| 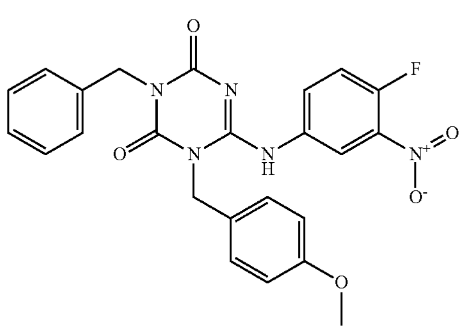 [SMILES: COc1ccc(Cn2c(Nc3ccc(F)c([N+](=O)[O-])c3)nc(=O)n(Cc3ccccc3)c2=O)cc1] | I-012 | 478 | 2.51 | 3 |

TABLE 6-continued

| Chemical Structure | Compound No. | [M + H] | Retention time (min) | Method |
|---|---|---|---|---|
| 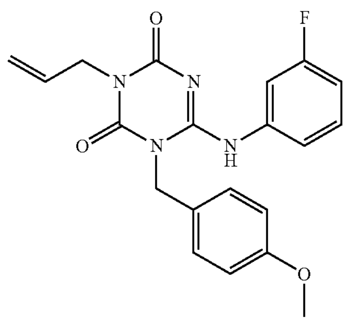 [SMILES: C=CCn1c(=O)nc(Nc2cccc(F)c2)n(Cc2ccc(OC)cc2)c1=O] | I-013 | 383 | 2.23 | 3 |
| 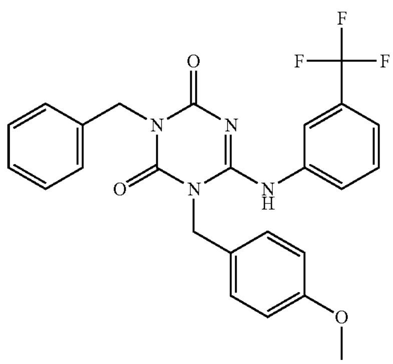 [SMILES: COc1ccc(Cn2c(Nc3cccc(C(F)(F)F)c3)nc(=O)n(Cc3ccccc3)c2=O)cc1] | I-014 | 483 | 2.65 | 3 |
| 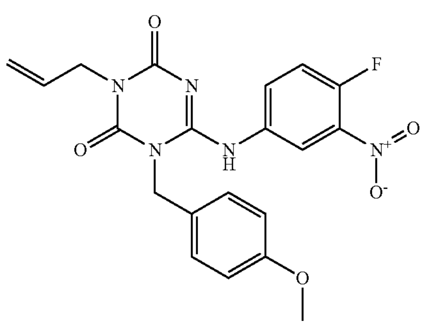 [SMILES: C=CCn1c(=O)nc(Nc2ccc(F)c([N+](=O)[O-])c2)n(Cc2ccc(OC)cc2)c1=O] | I-015 | 428 | 2.29 | 3 |

TABLE 7

| Chemical Structure | Compound No. | [M + H] | Retention time (min) | Method |
|---|---|---|---|---|
| 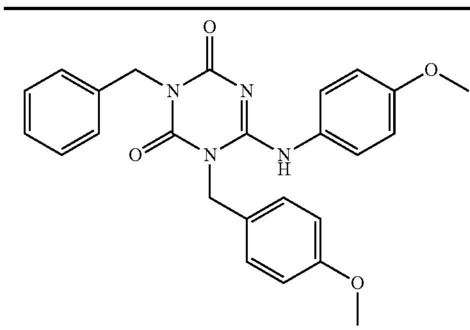 | I-016 | 445 | 2.29 | 3 |

TABLE 7-continued

| Chemical Structure | Compound No. | [M + H] | Retention time (min) | Method |
|---|---|---|---|---|
| (structure) | I-017 | 433 | 2.45 | 3 |
| (structure) | I-018 | 494 | 2.09 | 3 |
| (structure) | I-019 | 405 | 2.16 | 4 |
| (structure) | I-020 | 439 | 3.88 | 4 |

TABLE 8

| Chemical Structure | Compound No. | [M + H] | Retention time (min) | Method |
|---|---|---|---|---|
| 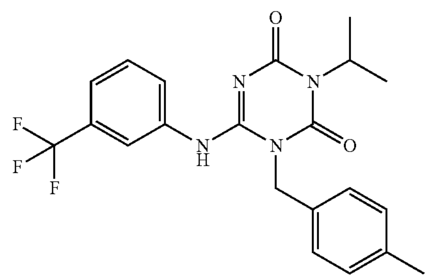 [SMILES: Cc1ccc(Cn2c(Nc3cccc(C(F)(F)F)c3)nc(=O)n(C(C)C)c2=O)cc1] | I-021 | 419 | 3.63 | 4 |
| 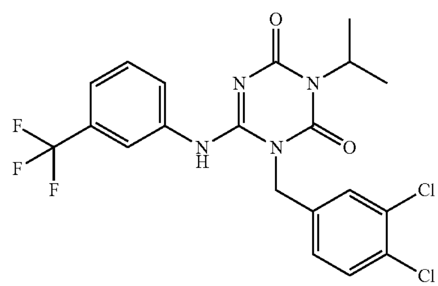 [SMILES: CC(C)n1c(=O)nc(Nc2cccc(C(F)(F)F)c2)n(Cc2ccc(Cl)c(Cl)c2)c1=O] | I-022 | 474 | 4.43 | 4 |
| 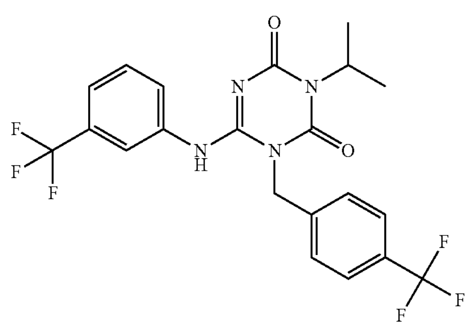 [SMILES: CC(C)n1c(=O)nc(Nc2cccc(C(F)(F)F)c2)n(Cc2ccc(C(F)(F)F)cc2)c1=O] | I-023 | 473 | 3.91 | 4 |
| 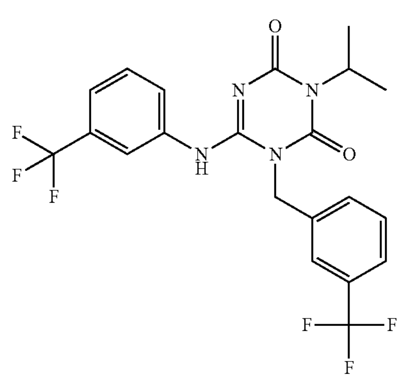 [SMILES: CC(C)n1c(=O)nc(Nc2cccc(C(F)(F)F)c2)n(Cc2cccc(C(F)(F)F)c2)c1=O] | I-024 | 473 | 3.93 | 4 |

TABLE 8-continued
| Chemical Structure | Compound No. | [M + H] | Retention time (min) | Method |
|---|---|---|---|---|
| 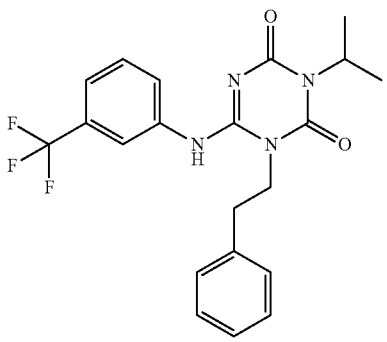 [SMILES: CC(C)n1c(=O)nc(Nc2cccc(C(F)(F)F)c2)n(CCc2ccccc2)c1=O] | I-025 | 419 | 3.33 | 4 |
TABLE 9
| Chemical Structure | Compound No. | [M + H] | Retention time (min) | Method |
|---|---|---|---|---|
| 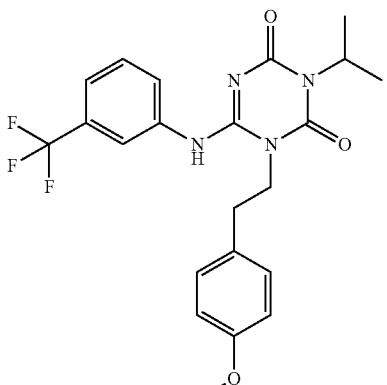 | I-026 | 449 | 3.16 | 4 |
| 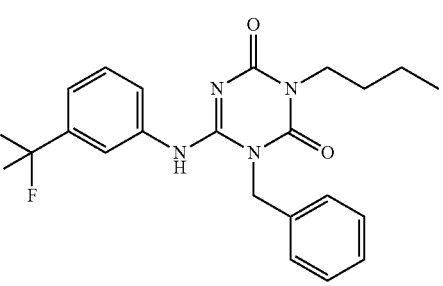 | I-027 | 419 | 2.46 | 4 |
| 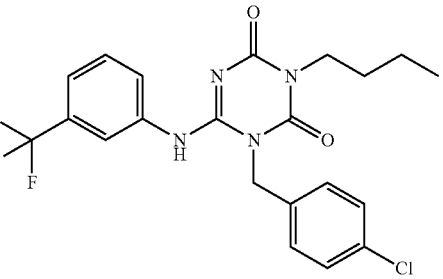 | I-028 | 453 | 3.27 | 4 |

TABLE 9-continued

| Chemical Structure | Compound No. | [M + H] | Retention time (min) | Method |
|---|---|---|---|---|
| 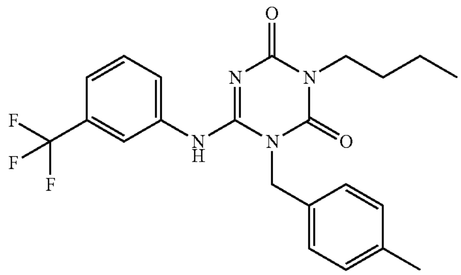 [SMILES: CCCCn1c(=O)nc(Nc2cccc(C(F)(F)F)c2)n(Cc2ccc(C)cc2)c1=O] | I-029 | 433 | 2.95 | 4 |
| 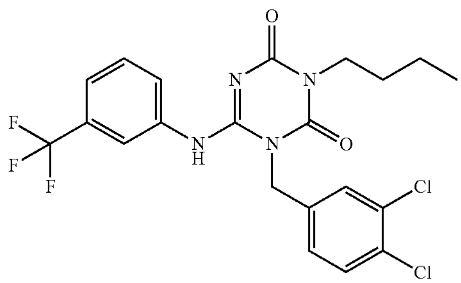 [SMILES: CCCCn1c(=O)nc(Nc2cccc(C(F)(F)F)c2)n(Cc2ccc(Cl)c(Cl)c2)c1=O] | I-030 | 488 | 3.94 | 4 |

TABLE 10

| Chemical Structure | Compound No. | [M + H] | Retention time (min) | Method |
|---|---|---|---|---|
| 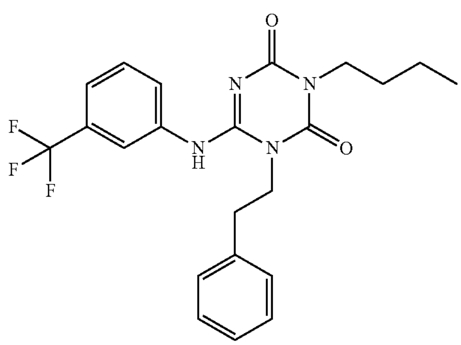 [SMILES: CCCCn1c(=O)nc(Nc2cccc(C(F)(F)F)c2)n(CCc2ccccc2)c1=O] | I-031 | 433 | 2.61 | 4 |
| 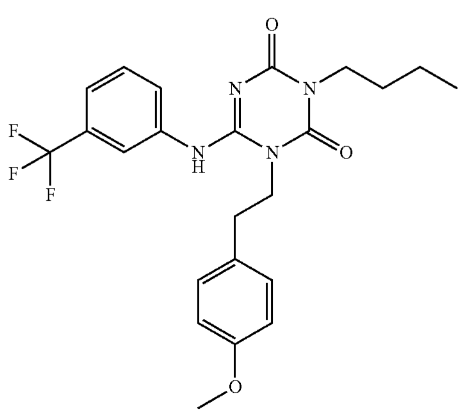 [SMILES: CCCCn1c(=O)nc(Nc2cccc(C(F)(F)F)c2)n(CCc2ccc(OC)cc2)c1=O] | I-032 | 463 | 2.39 | 4 |

TABLE 10-continued
| Chemical Structure | Compound No. | [M + H] | Retention time (min) | Method |
|---|---|---|---|---|
| 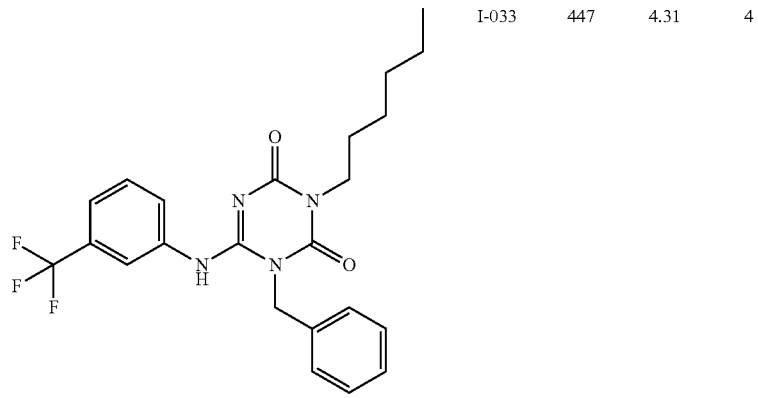 | I-033 | 447 | 4.31 | 4 |
| 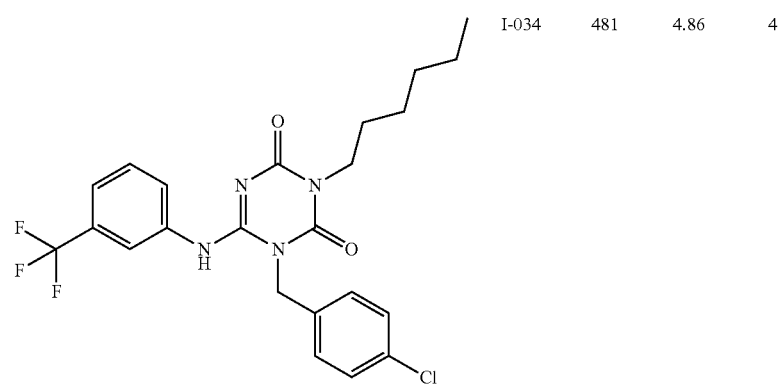 | I-034 | 481 | 4.86 | 4 |
| 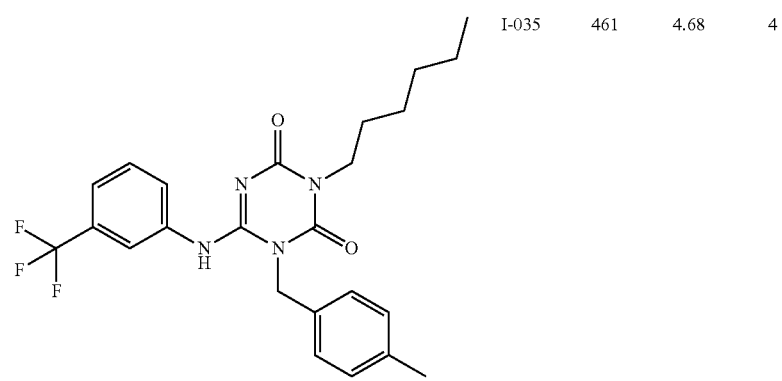 | I-035 | 461 | 4.68 | 4 |

TABLE 11
| Chemical Structure | Compound No. | [M + H] | Retention time (min) | Method |
|---|---|---|---|---|
| 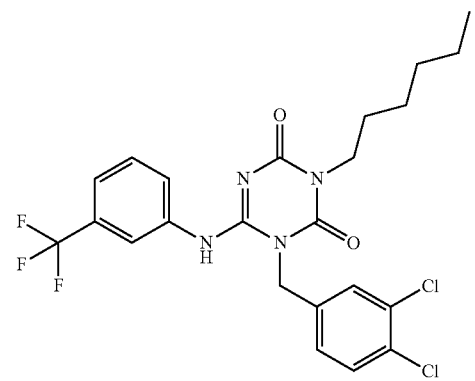 [SMILES: CCCCCCn1c(=O)nc(Nc2cccc(C(F)(F)F)c2)n(Cc2ccc(Cl)c(Cl)c2)c1=O] | I-036 | 516 | 3.73 | 4 |
| 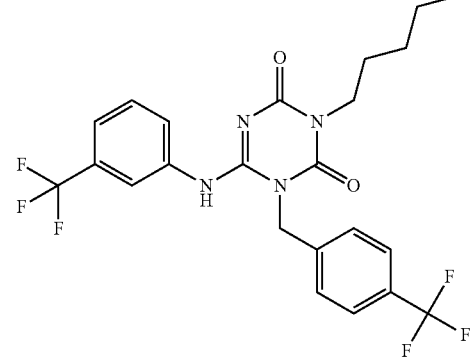 | I-037 | 515 | 4.80 | 4 |
| 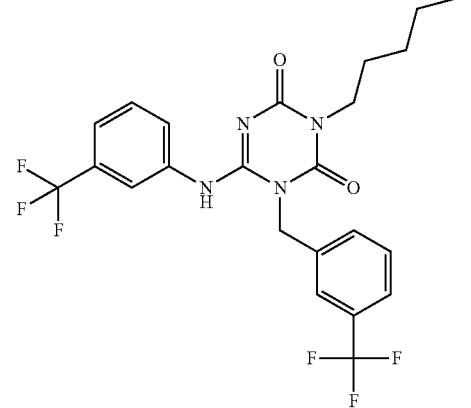 | I-038 | 515 | 4.83 | 4 |

TABLE 11-continued
| Chemical Structure | Compound No. | [M + H] | Retention time (min) | Method |
|---|---|---|---|---|
| 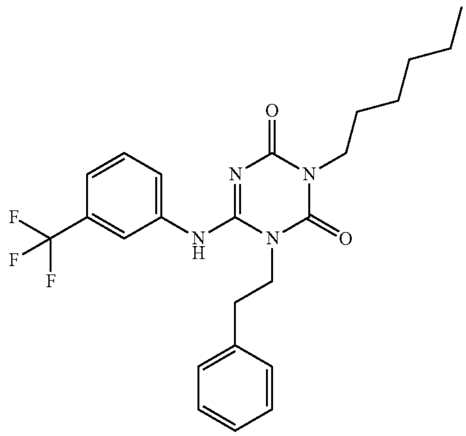 [SMILES: CCCCCCn1c(=O)nc(Nc2cccc(C(F)(F)F)c2)n(CCc2ccccc2)c1=O] | I-039 | 461 | 3.67 | 4 |
| 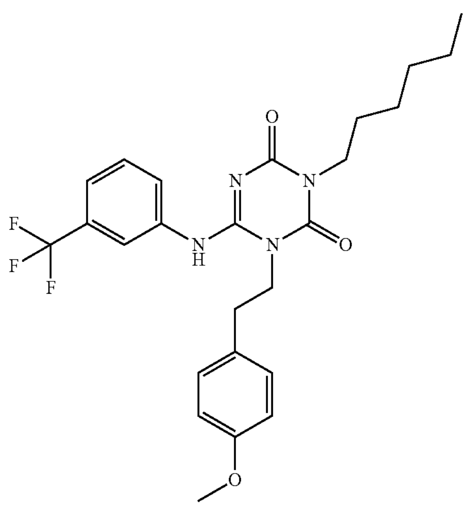 [SMILES: CCCCCCn1c(=O)nc(Nc2cccc(C(F)(F)F)c2)n(CCc2ccc(OC)cc2)c1=O] | I-040 | 491 | 3.47 | 4 |
TABLE 12
| Chemical Structure | Compound No. | [M + H] | Retention time (min) | Method |
|---|---|---|---|---|
| 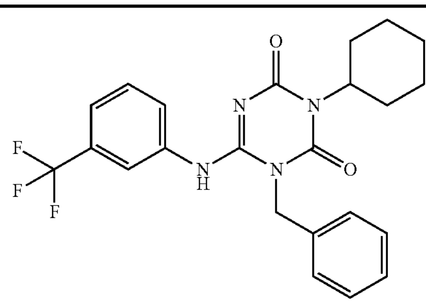 | I-041 | 445 | 4.09 | 4 |
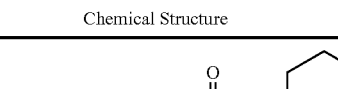

TABLE 12-continued

| Chemical Structure | Compound No. | [M + H] | Retention time (min) | Method |
|---|---|---|---|---|
| 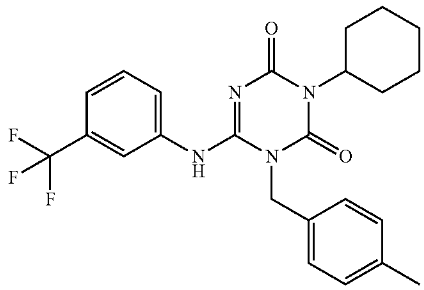 [SMILES: Cc1ccc(Cn2c(Nc3cccc(C(F)(F)F)c3)nc(=O)n(C3CCCCC3)c2=O)cc1] | I-042 | 459 | 4.45 | 4 |
| 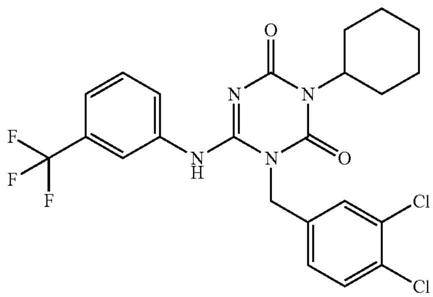 [SMILES: O=c1nc(Nc2cccc(C(F)(F)F)c2)n(Cc2ccc(Cl)c(Cl)c2)c(=O)n1C1CCCCC1] | I-043 | 514 | 3.51 | 4 |
| 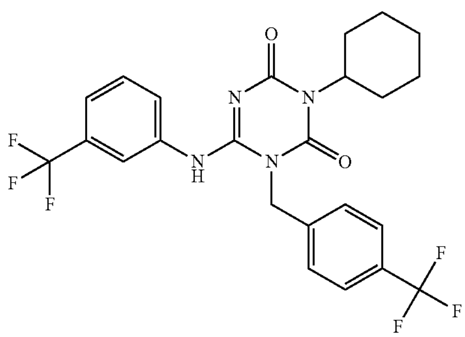 [SMILES: O=c1nc(Nc2cccc(C(F)(F)F)c2)n(Cc2ccc(C(F)(F)F)cc2)c(=O)n1C1CCCCC1] | I-044 | 513 | 4.62 | 4 |
| 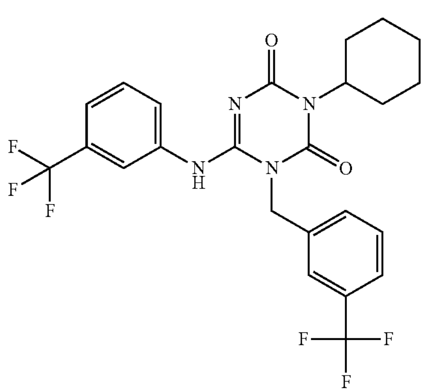 [SMILES: O=c1nc(Nc2cccc(C(F)(F)F)c2)n(Cc2cccc(C(F)(F)F)c2)c(=O)n1C1CCCCC1] | I-045 | 513 | 4.65 | 4 |

TABLE 13

| Chemical Structure | Compound No. | [M + H] | Retention time (min) | Method |
|---|---|---|---|---|
| 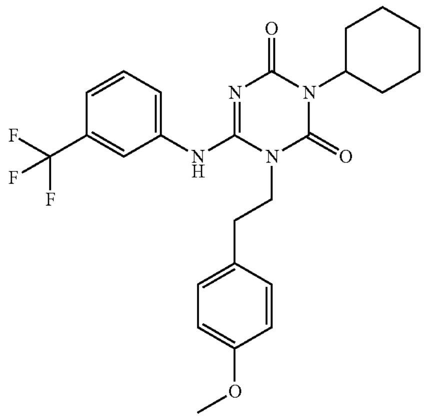 [SMILES: COc1ccc(CCn2c(Nc3cccc(C(F)(F)F)c3)nc(=O)n(C3CCCCC3)c2=O)cc1] | I-046 | 489 | 3.17 | 4 |
| 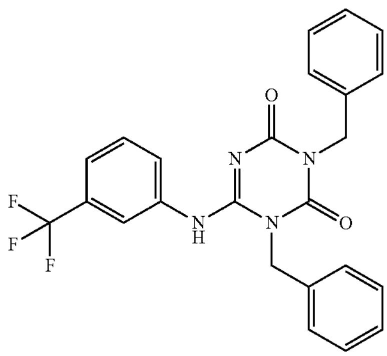 [SMILES: O=c1nc(Nc2cccc(C(F)(F)F)c2)n(Cc2ccccc2)c(=O)n1Cc1ccccc1] | I-047 | 453 | 3.46 | 4 |
| 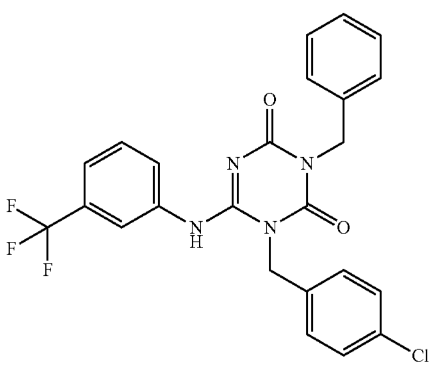 [SMILES: O=c1nc(Nc2cccc(C(F)(F)F)c2)n(Cc2ccc(Cl)cc2)c(=O)n1Cc1ccccc1] | I-048 | 487 | 4.09 | 4 |
| 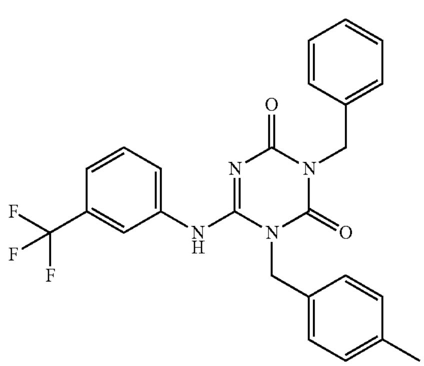 [SMILES: Cc1ccc(Cn2c(Nc3cccc(C(F)(F)F)c3)nc(=O)n(Cc3ccccc3)c2=O)cc1] | I-049 | 467 | 3.83 | 4 |

TABLE 13-continued

| Chemical Structure | Compound No. | [M + H] | Retention time (min) | Method |
|---|---|---|---|---|
| 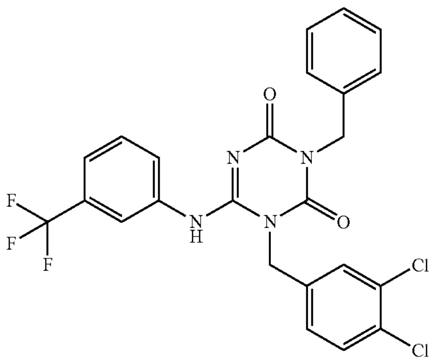 [SMILES: O=c1nc(Nc2cccc(C(F)(F)F)c2)n(Cc2ccc(Cl)c(Cl)c2)c(=O)n1Cc1ccccc1] | I-050 | 522 | 4.56 | 4 |

TABLE 14

| Chemical Structure | Compound No. | [M + H] | Retention time (min) | Method |
|---|---|---|---|---|
| 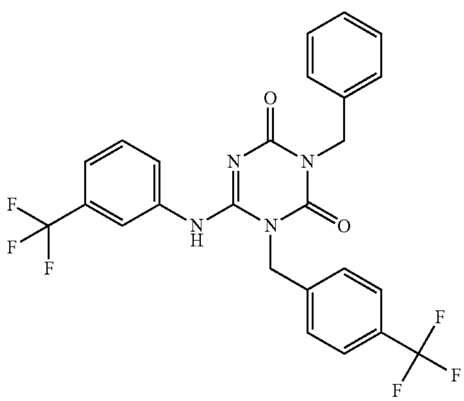 [SMILES: O=c1nc(Nc2cccc(C(F)(F)F)c2)n(Cc2ccc(C(F)(F)F)cc2)c(=O)n1Cc1ccccc1] | I-051 | 521 | 4.09 | 4 |
| 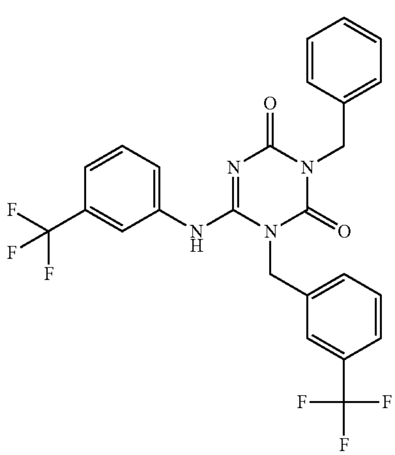 [SMILES: O=c1nc(Nc2cccc(C(F)(F)F)c2)n(Cc2cccc(C(F)(F)F)c2)c(=O)n1Cc1ccccc1] | I-052 | 521 | 4.12 | 4 |

TABLE 14-continued

| Chemical Structure | Compound No. | [M + H] | Retention time (min) | Method |
|---|---|---|---|---|
| 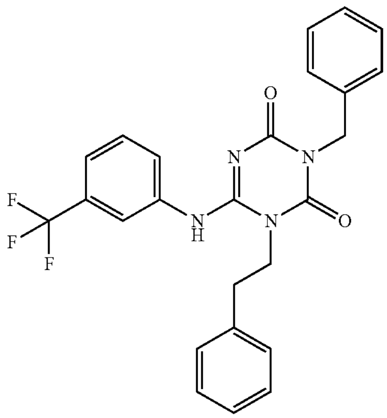 [SMILES: O=c1nc(Nc2cccc(C(F)(F)F)c2)n(CCc2ccccc2)c(=O)n1Cc1ccccc1] | I-053 | 467 | 3.57 | 4 |
| 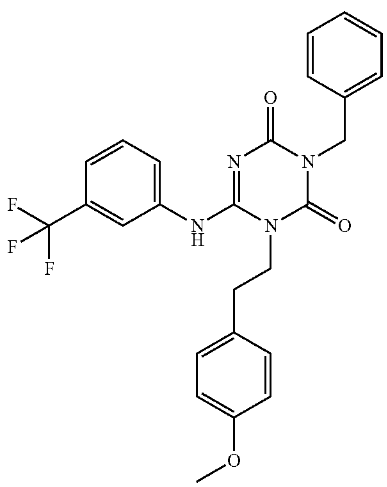 [SMILES: COc1ccc(CCn2c(Nc3cccc(C(F)(F)F)c3)nc(=O)n(Cc3ccccc3)c2=O)cc1] | I-054 | 497 | 3.42 | 4 |
| 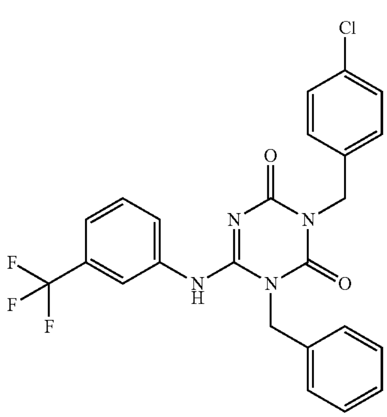 [SMILES: O=c1nc(Nc2cccc(C(F)(F)F)c2)n(Cc2ccccc2)c(=O)n1Cc1ccc(Cl)cc1] | I-055 | 487 | 3.90 | 4 |

TABLE 15

| Chemical Structure | Compound No. | [M + H] | Retention time (min) | Method |
|---|---|---|---|---|
| (structure) | I-056 | 522 | 4.49 | 4 |
| (structure) | I-057 | 501 | 4.26 | 4 |
| (structure) | I-058 | 556 | 4.94 | 4 |

TABLE 15-continued
| Chemical Structure | Compound No. | [M + H] | Retention time (min) | Method |
|---|---|---|---|---|
| 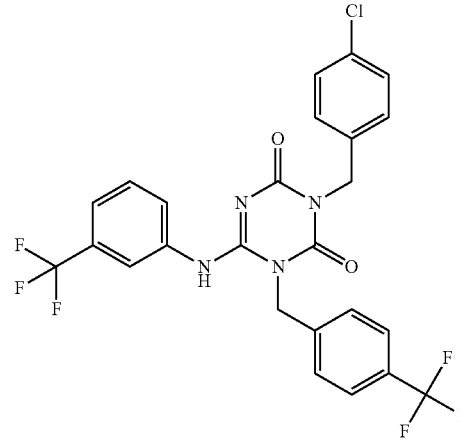 | I-059 | 555 | 4.45 | 4 |
| 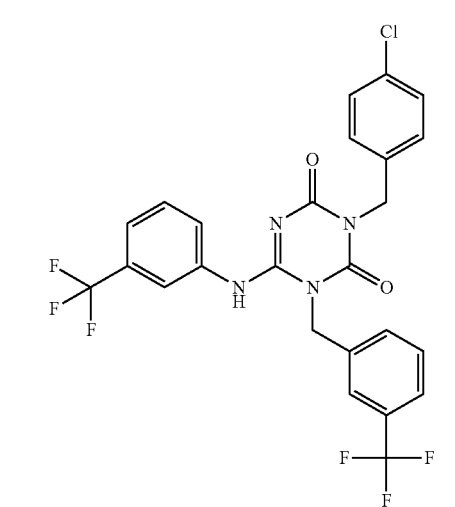 [SMILES: O=c1nc(Nc2cccc(C(F)(F)F)c2)n(Cc2cccc(C(F)(F)F)c2)c(=O)n1Cc1ccc(Cl)cc1] | I-060 | 555 | 4.50 | 4 |
TABLE 16
| Chemical Structure | Compound No. | [M + H] | Retention time (min) | Method |
|---|---|---|---|---|
| 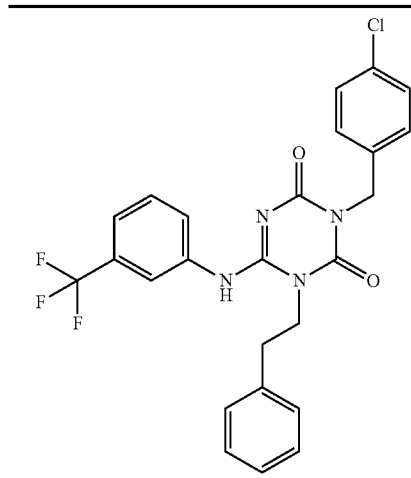 | I-061 | 501 | 3.99 | 4 |

TABLE 16-continued
| Chemical Structure | Compound No. | [M + H] | Retention time (min) | Method |
|---|---|---|---|---|
| 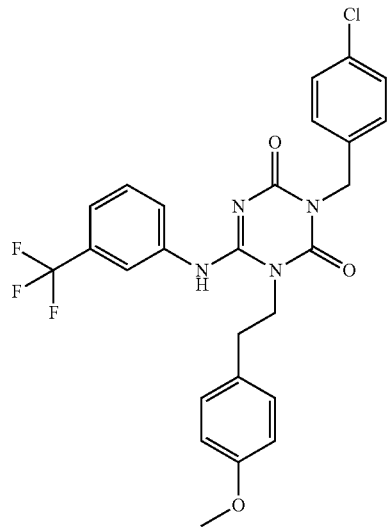 [SMILES: COc1ccc(CCn2c(Nc3cccc(C(F)(F)F)c3)nc(=O)n(Cc3ccc(Cl)cc3)c2=O)cc1] | I-062 | 531 | 3.86 | 4 |
| 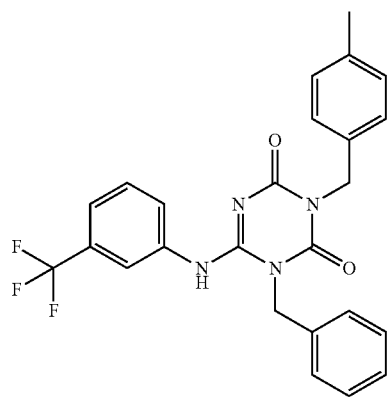 [SMILES: Cc1ccc(Cn2c(=O)nc(Nc3cccc(C(F)(F)F)c3)n(Cc3ccccc3)c2=O)cc1] | I-063 | 467 | 2.81 | 4 |
| 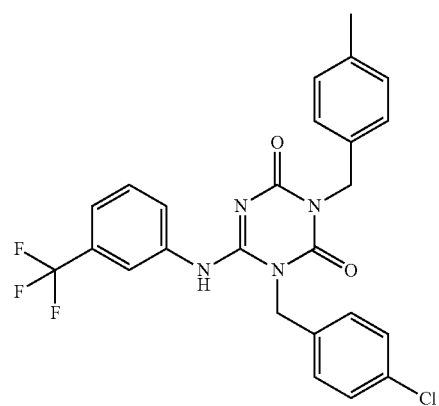 [SMILES: Cc1ccc(Cn2c(=O)nc(Nc3cccc(C(F)(F)F)c3)n(Cc3ccc(Cl)cc3)c2=O)cc1] | I-064 | 501 | 2.40 | 4 |

TABLE 16-continued
| Chemical Structure | Compound No. | [M + H] | Retention time (min) | Method |
|---|---|---|---|---|
| 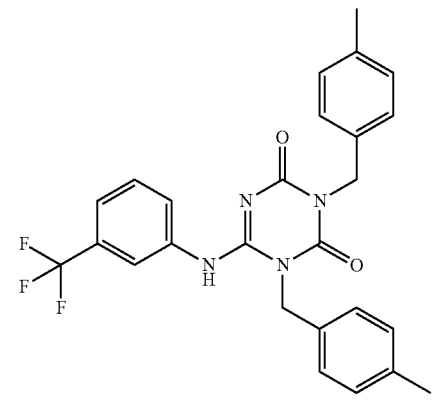 [SMILES: Cc1ccc(Cn2c(Nc3cccc(C(F)(F)F)c3)nc(=O)n(Cc3ccc(C)cc3)c2=O)cc1] | I-065 | 481 | 3.32 | 4 |
TABLE 17
| Chemical Structure | Compound No. | [M + H] | Retention time (min) | Method |
|---|---|---|---|---|
| 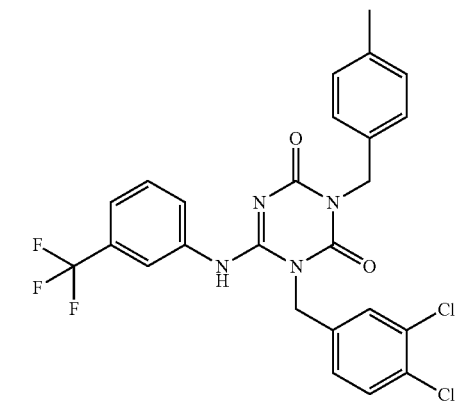 [SMILES: Cc1ccc(Cn2c(=O)nc(Nc3cccc(C(F)(F)F)c3)n(Cc3ccc(Cl)c(Cl)c3)c2=O)cc1] | I-066 | 534 | 4.30 | 4 |
| 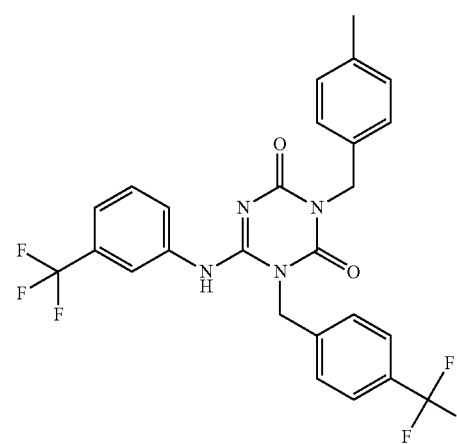 | I-067 | 535 | 3.60 | 4 |

TABLE 17-continued

| Chemical Structure | Compound No. | [M + H] | Retention time (min) | Method |
| --- | --- | --- | --- | --- |
| 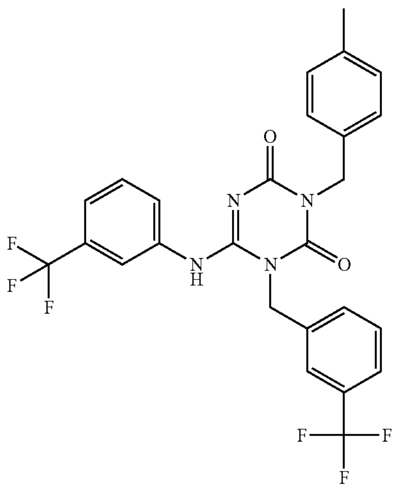 [SMILES: Cc1ccc(Cn2c(=O)nc(Nc3cccc(C(F)(F)F)c3)n(Cc3cccc(C(F)(F)F)c3)c2=O)cc1] | I-068 | 535 | 3.60 | 4 |
| 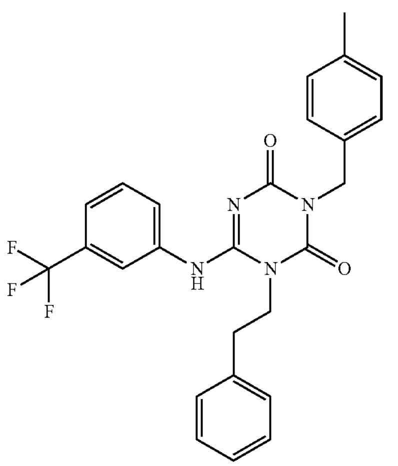 [SMILES: Cc1ccc(Cn2c(=O)nc(Nc3cccc(C(F)(F)F)c3)n(CCc3ccccc3)c2=O)cc1] | I-069 | 481 | 3.91 | 4 |
| 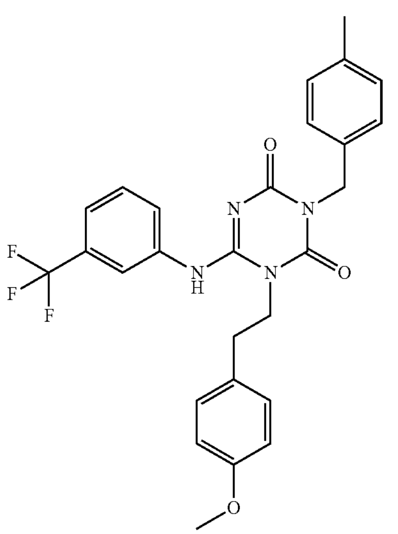 [SMILES: COc1ccc(CCn2c(Nc3cccc(C(F)(F)F)c3)nc(=O)n(Cc3ccc(C)cc3)c2=O)cc1] | I-070 | 511 | 2.76 | 4 |

TABLE 18

| Chemical Structure | Compound No. | [M + H] | Retention time (min) | Method |
|---|---|---|---|---|
| 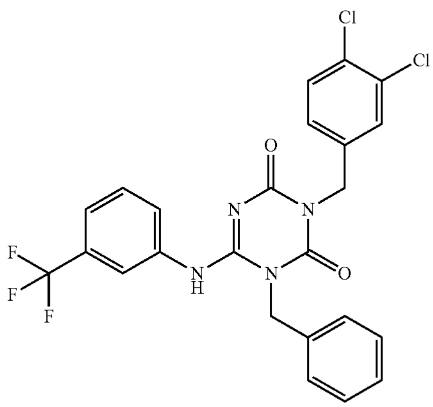 [SMILES: O=c1nc(Nc2cccc(C(F)(F)F)c2)n(Cc2ccccc2)c(=O)n1Cc1ccc(Cl)c(Cl)c1] | I-071 | 522 | 3.43 | 4 |
| 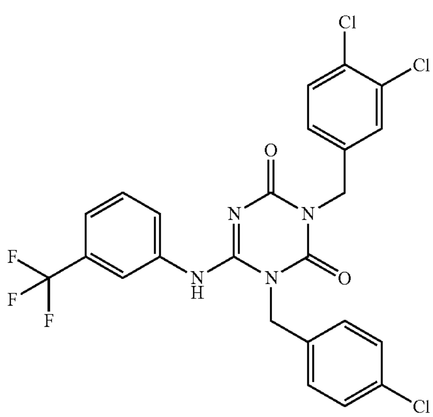 [SMILES: O=c1nc(Nc2cccc(C(F)(F)F)c2)n(Cc2ccc(Cl)cc2)c(=O)n1Cc1ccc(Cl)c(Cl)c1] | I-072 | 556 | 4.12 | 4 |
| 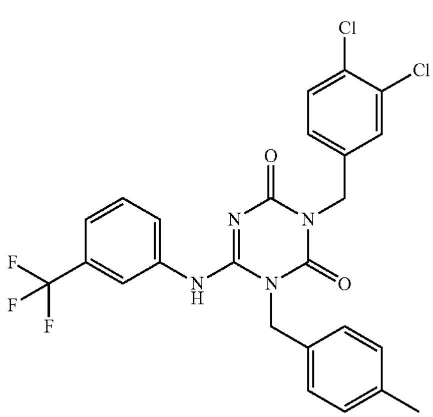 [SMILES: Cc1ccc(Cn2c(Nc3cccc(C(F)(F)F)c3)nc(=O)n(Cc3ccc(Cl)c(Cl)c3)c2=O)cc1] | I-073 | 536 | 3.86 | 4 |

TABLE 18-continued

| Chemical Structure | Compound No. | [M + H] | Retention time (min) | Method |
|---|---|---|---|---|
| 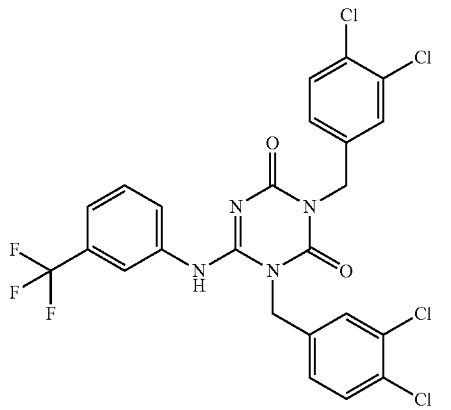 [SMILES: O=c1nc(Nc2cccc(C(F)(F)F)c2)n(Cc2ccc(Cl)c(Cl)c2)c(=O)n1Cc1ccc(Cl)c(Cl)c1] | I-074 | 591 | 4.68 | 4 |
| 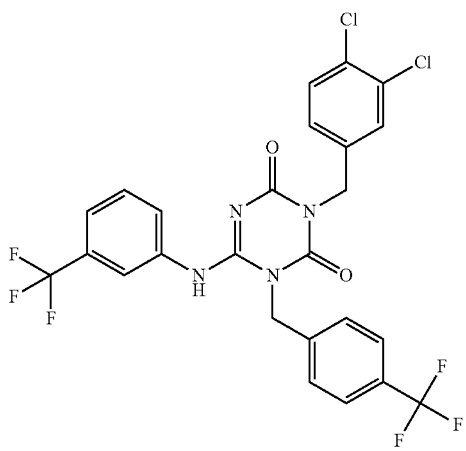 [SMILES: O=c1nc(Nc2cccc(C(F)(F)F)c2)n(Cc2ccc(C(F)(F)F)cc2)c(=O)n1Cc1ccc(Cl)c(Cl)c1] | I-075 | 590 | 4.07 | 4 |

TABLE 19

| Chemical Structure | Compound No. | [M + H] | Retention time (min) | Method |
|---|---|---|---|---|
| 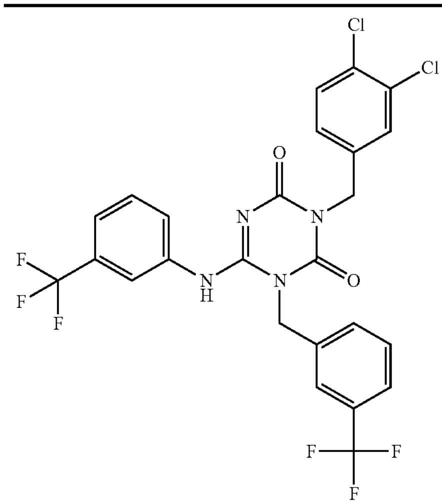 | I-076 | 590 | 4.11 | 4 |

TABLE 19-continued

| Chemical Structure | Compound No. | [M + H] | Retention time (min) | Method |
|---|---|---|---|---|
| 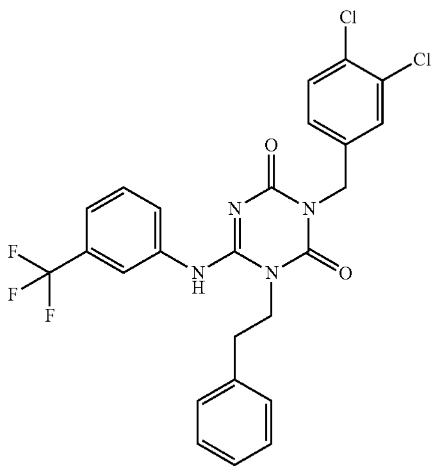 [SMILES: O=c1nc(Nc2cccc(C(F)(F)F)c2)n(CCc2ccccc2)c(=O)n1Cc1ccc(Cl)c(Cl)c1] | I-077 | 536 | 3.55 | 4 |
| 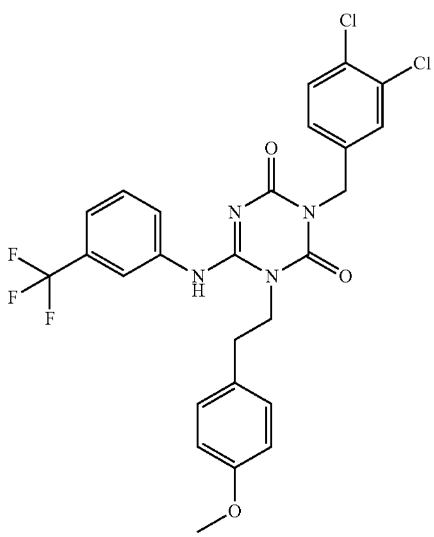 [SMILES: COc1ccc(CCn2c(Nc3cccc(C(F)(F)F)c3)nc(=O)n(Cc3ccc(Cl)c(Cl)c3)c2=O)cc1] | I-078 | 566 | 3.49 | 4 |
| 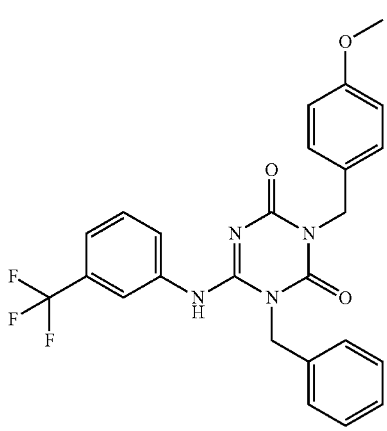 [SMILES: COc1ccc(Cn2c(=O)nc(Nc3cccc(C(F)(F)F)c3)n(Cc3ccccc3)c2=O)cc1] | I-079 | 483 | 2.38 | 4 |

TABLE 19-continued
| Chemical Structure | Compound No. | [M + H] | Retention time (min) | Method |
|---|---|---|---|---|
| 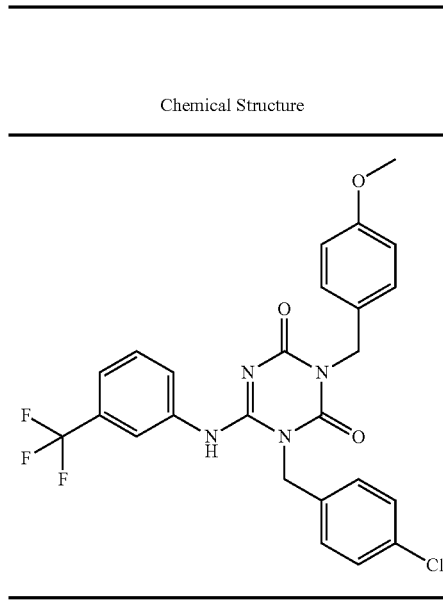 | I-080 | 517 | 3.21 | 4 |
TABLE 20
| Chemical Structure | Compound No. | [M + H] | Retention time (min) | Method |
|---|---|---|---|---|
| 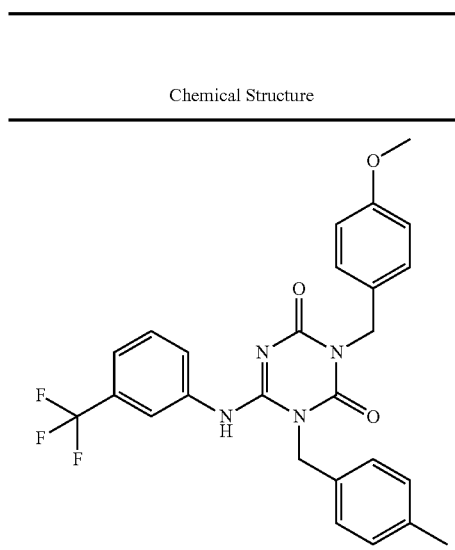 | I-081 | 497 | 2.85 | 4 |
| 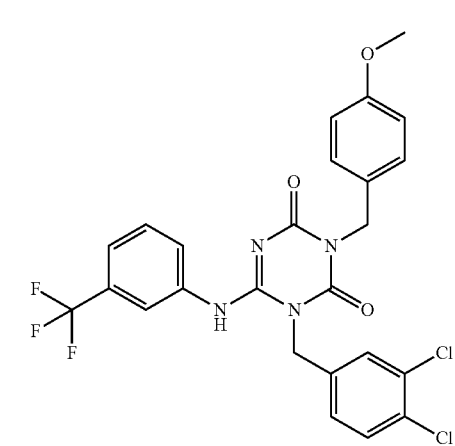 [SMILES: COc1ccc(Cn2c(=O)nc(Nc3cccc(C(F)(F)F)c3)n(Cc3ccc(Cl)c(Cl)c3)c2=O)cc1] | I-082 | 552 | 3.85 | 4 |

TABLE 20-continued

| Chemical Structure | Compound No. | [M + H] | Retention time (min) | Method |
|---|---|---|---|---|
| 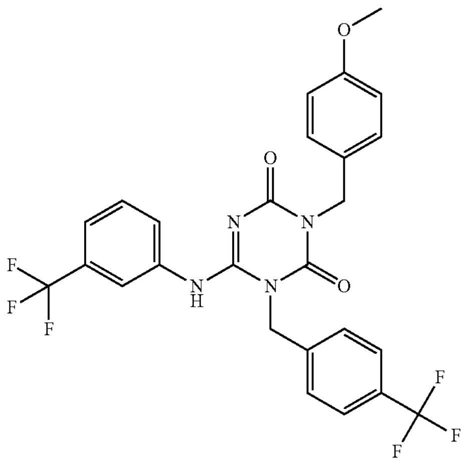 [SMILES: COc1ccc(Cn2c(=O)nc(Nc3cccc(C(F)(F)F)c3)n(Cc3ccc(C(F)(F)F)cc3)c2=O)cc1] | I-083 | 551 | 3.22 | 4 |
| 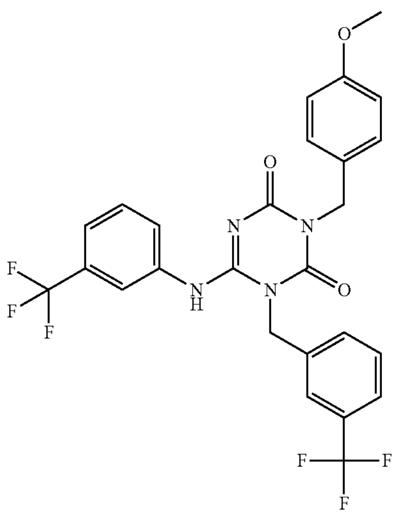 [SMILES: COc1ccc(Cn2c(=O)nc(Nc3cccc(C(F)(F)F)c3)n(Cc3cccc(C(F)(F)F)c3)c2=O)cc1] | I-084 | 551 | 3.23 | 4 |
| 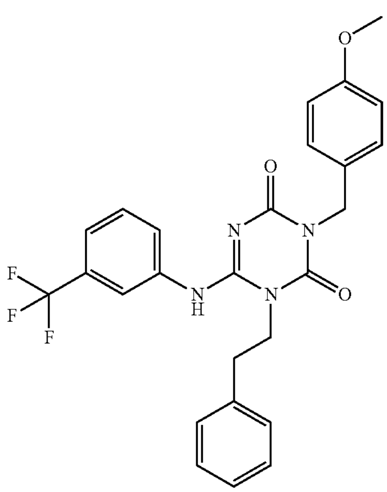 [SMILES: COc1ccc(Cn2c(=O)nc(Nc3cccc(C(F)(F)F)c3)n(CCc3ccccc3)c2=O)cc1] | I-085 | 497 | 2.48 | 4 |

TABLE 21

| Chemical Structure | Compound No. | [M + H] | Retention time (min) | Method |
|---|---|---|---|---|
| 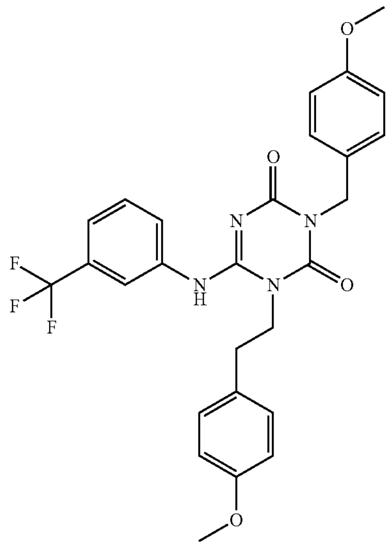 [SMILES: COc1ccc(CCn2c(Nc3cccc(C(F)(F)F)c3)nc(=O)n(Cc3ccc(OC)cc3)c2=O)cc1] | I-086 | 527 | 2.29 | 4 |
| 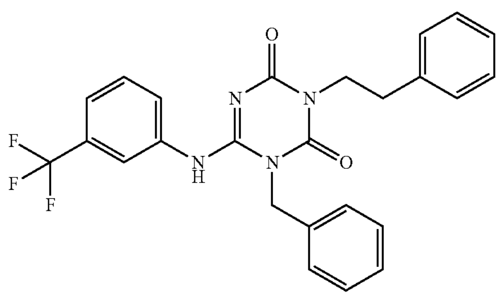 [SMILES: O=c1nc(Nc2cccc(C(F)(F)F)c2)n(Cc2ccccc2)c(=O)n1CCc1ccccc1] | I-087 | 467 | 2.75 | 4 |
| 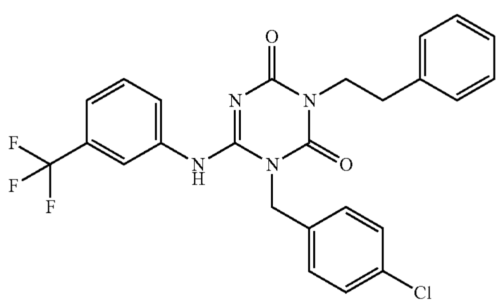 [SMILES: O=c1nc(Nc2cccc(C(F)(F)F)c2)n(Cc2ccc(Cl)cc2)c(=O)n1CCc1ccccc1] | I-088 | 501 | 3.54 | 4 |
| 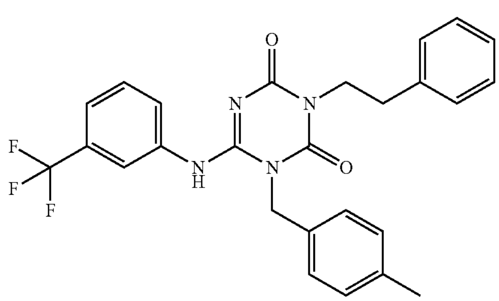 [SMILES: Cc1ccc(Cn2c(Nc3cccc(C(F)(F)F)c3)nc(=O)n(CCc3ccccc3)c2=O)cc1] | I-089 | 481 | 3.19 | 4 |

TABLE 21-continued

| Chemical Structure | Compound No. | [M + H] | Retention time (min) | Method |
|---|---|---|---|---|
| 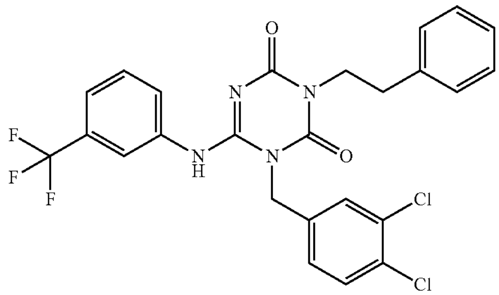 [SMILES: O=c1nc(Nc2cccc(C(F)(F)F)c2)n(Cc2ccc(Cl)c(Cl)c2)c(=O)n1CCc1ccccc1] | I-090 | 536 | 4.15 | 4 |

TABLE 22

| Chemical Structure | Compound No. | [M + H] | Retention time (min) | Method |
|---|---|---|---|---|
| 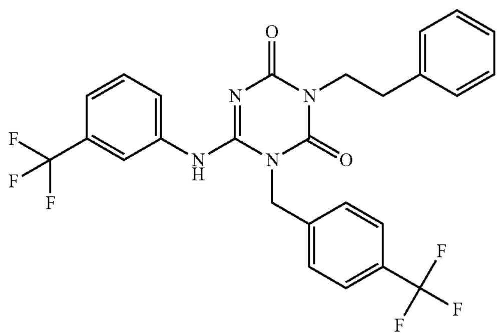 [SMILES: O=c1nc(Nc2cccc(C(F)(F)F)c2)n(Cc2ccc(C(F)(F)F)cc2)c(=O)n1CCc1ccccc1] | I-091 | 535 | 3.49 | 4 |
| 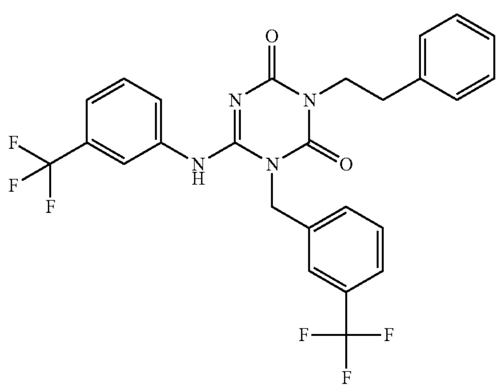 [SMILES: O=c1nc(Nc2cccc(C(F)(F)F)c2)n(Cc2cccc(C(F)(F)F)c2)c(=O)n1CCc1ccccc1] | I-092 | 535 | 3.57 | 4 |
| 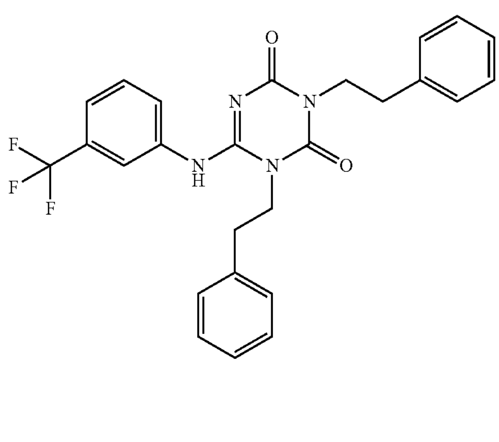 [SMILES: O=c1nc(Nc2cccc(C(F)(F)F)c2)n(CCc2ccccc2)c(=O)n1CCc1ccccc1] | I-093 | 481 | 3.03 | 4 |

TABLE 22-continued

| Chemical Structure | Compound No. | [M + H] | Retention time (min) | Method |
| --- | --- | --- | --- | --- |
| 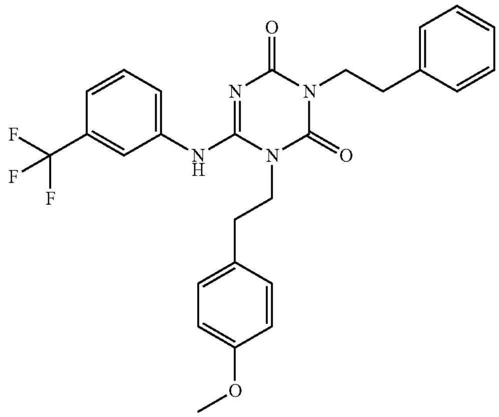 [SMILES: COc1ccc(CCn2c(Nc3cccc(C(F)(F)F)c3)nc(=O)n(CCc3ccccc3)c2=O)cc1] | I-094 | 511 | 2.79 | 4 |
| 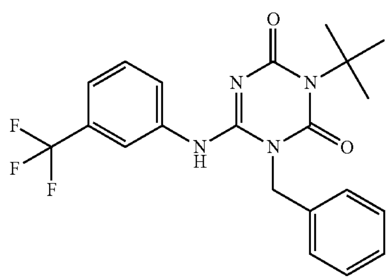 [SMILES: CC(C)(C)n1c(=O)nc(Nc2cccc(C(F)(F)F)c2)n(Cc2ccccc2)c1=O] | I-095 | 419 | 3.58 | 4 |

TABLE 23

| Chemical Structure | Compound No. | [M + H] | Retention time (min) | Method |
| --- | --- | --- | --- | --- |
| 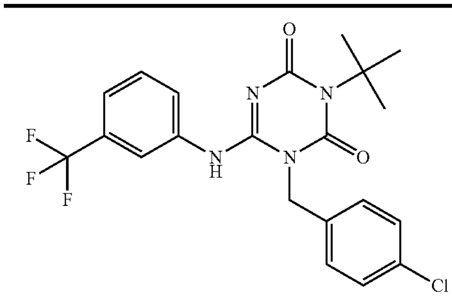 | I-096 | 453 | 4.22 | 4 |
| 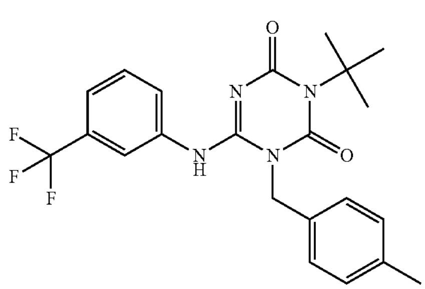 [SMILES: Cc1ccc(Cn2c(Nc3cccc(C(F)(F)F)c3)nc(=O)n(C(C)(C)C)c2=O)cc1] | I-097 | 433 | 4.21 | 4 |

TABLE 23-continued
| Chemical Structure | Compound No. | [M + H] | Retention time (min) | Method |
|---|---|---|---|---|
| 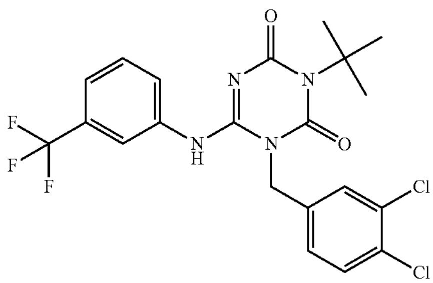 [SMILES: CC(C)(C)n1c(=O)nc(Nc2cccc(C(F)(F)F)c2)n(Cc2ccc(Cl)c(Cl)c2)c1=O] | I-098 | 488 | 4.03 | 4 |
| 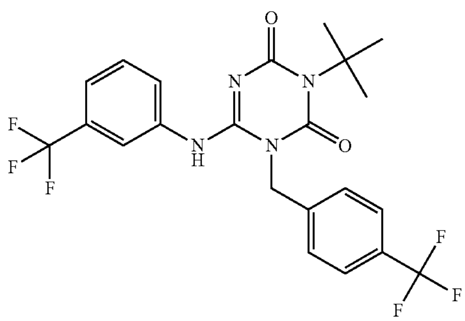 [SMILES: CC(C)(C)n1c(=O)nc(Nc2cccc(C(F)(F)F)c2)n(Cc2ccc(C(F)(F)F)cc2)c1=O] | I-099 | 487 | 3.38 | 4 |
| 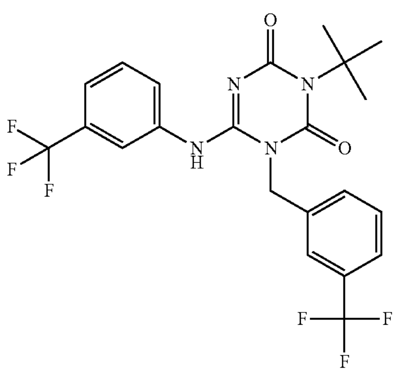 [SMILES: CC(C)(C)n1c(=O)nc(Nc2cccc(C(F)(F)F)c2)n(Cc2cccc(C(F)(F)F)c2)c1=O] | I-100 | 487 | 4.24 | 4 |
TABLE 24
| Chemical Structure | Compound No. | [M + H] | Retention time (min) | Method |
|---|---|---|---|---|
| 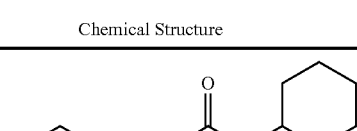 | I-101 | 459 | 3.38 | 4 |

TABLE 24-continued

| Chemical Structure | Compound No. | [M + H] | Retention time (min) | Method |
| --- | --- | --- | --- | --- |
| 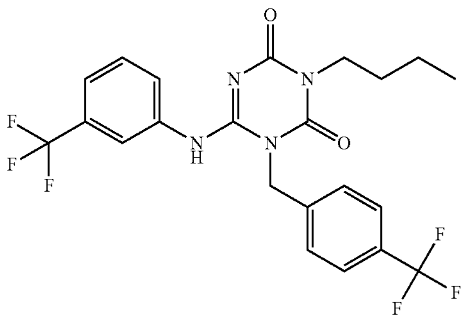 [SMILES: CCCCn1c(=O)nc(Nc2cccc(C(F)(F)F)c2)n(Cc2ccc(C(F)(F)F)cc2)c1=O] | I-102 | 487 | 4.16 | 4 |
| 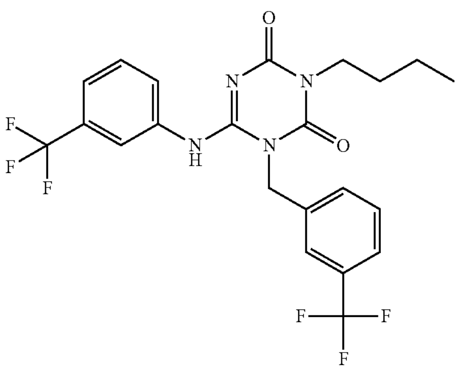 [SMILES: CCCCn1c(=O)nc(Nc2cccc(C(F)(F)F)c2)n(Cc2cccc(C(F)(F)F)c2)c1=O] | I-103 | 487 | 4.18 | 4 |
| 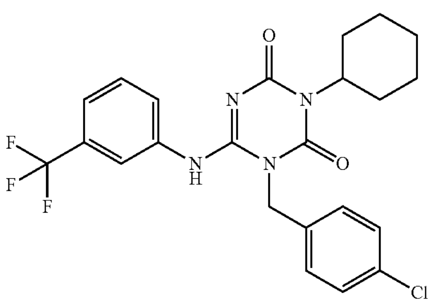 [SMILES: O=c1nc(Nc2cccc(C(F)(F)F)c2)n(Cc2ccc(Cl)cc2)c(=O)n1C1CCCCC1] | I-104 | 479 | 4.69 | 4 |
| 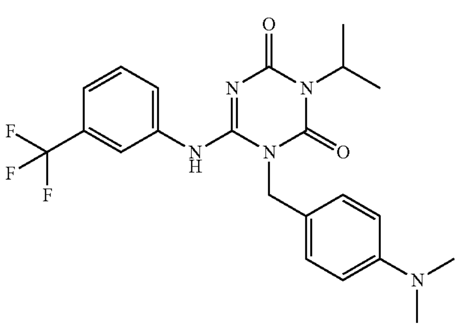 [SMILES: CC(C)n1c(=O)nc(Nc2cccc(C(F)(F)F)c2)n(Cc2ccc(N(C)C)cc2)c1=O] | I-105 | 448 | 3.38 | 4 |

TABLE 25
| Chemical Structure | Compound No. | [M + H] | Retention time (min) | Method |
|---|---|---|---|---|
| 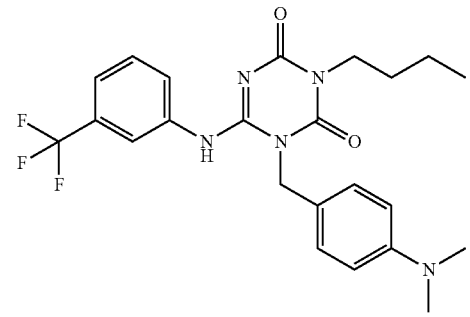 [SMILES: CCCCn1c(=O)nc(Nc2cccc(C(F)(F)F)c2)n(Cc2ccc(N(C)C)cc2)c1=O] | I-106 | 462 | 3.59 | 4 |
| 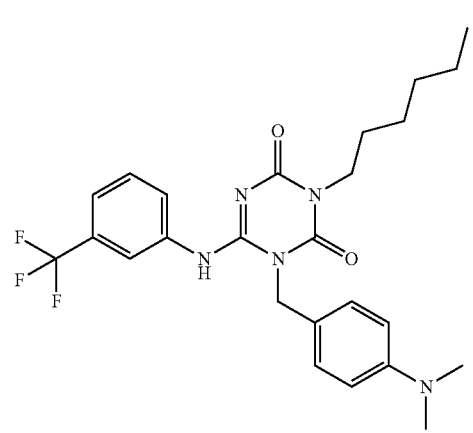 [SMILES: CCCCCCn1c(=O)nc(Nc2cccc(C(F)(F)F)c2)n(Cc2ccc(N(C)C)cc2)c1=O] | I-107 | 490 | 4.05 | 4 |
| 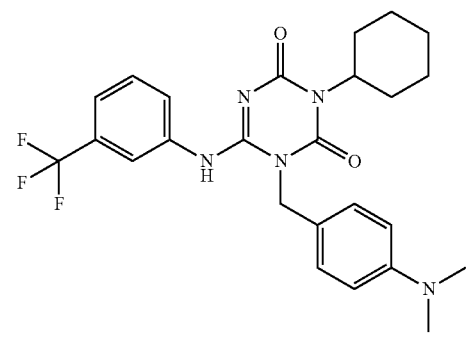 [SMILES: CN(C)c1ccc(Cn2c(Nc3cccc(C(F)(F)F)c3)nc(=O)n(C3CCCCC3)c2=O)cc1] | I-108 | 488 | 3.85 | 4 |
| 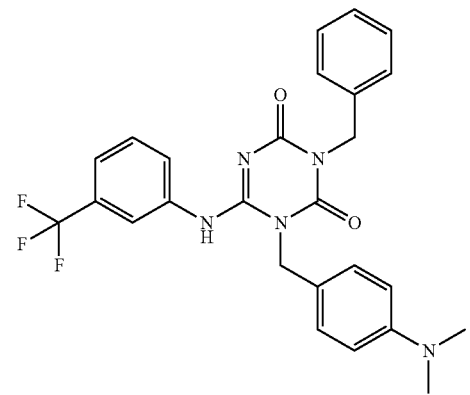 [SMILES: CN(C)c1ccc(Cn2c(Nc3cccc(C(F)(F)F)c3)nc(=O)n(Cc3ccccc3)c2=O)cc1] | I-109 | 496 | 3.66 | 4 |

TABLE 25-continued
| Chemical Structure | Compound No. | [M + H] | Retention time (min) | Method |
|---|---|---|---|---|
| 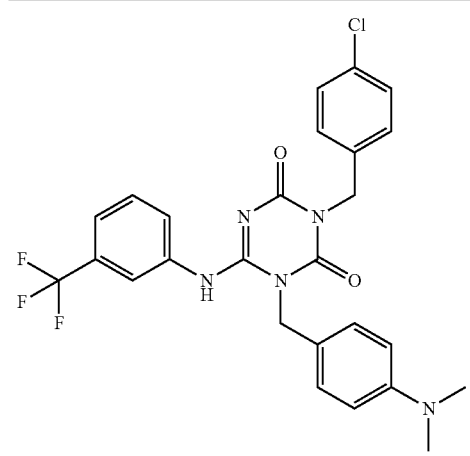 [SMILES: CN(C)c1ccc(Cn2c(Nc3cccc(C(F)(F)F)c3)nc(=O)n(Cc3ccc(Cl)cc3)c2=O)cc1] | I-110 | 530 | 3.97 | 4 |
TABLE 26
| Chemical Structure | Compound No. | [M + H] | Retention time (min) | Method |
|---|---|---|---|---|
| 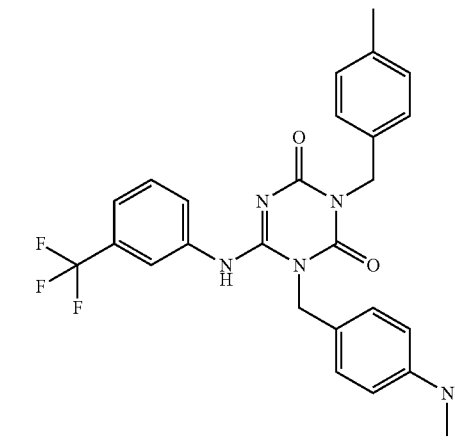 | I-111 | 510 | 3.84 | 4 |
| 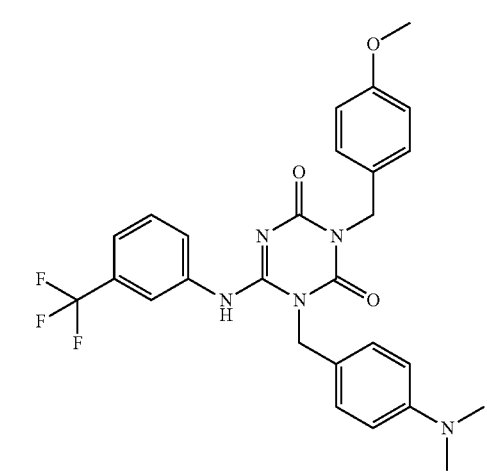 [SMILES: COc1ccc(Cn2c(=O)nc(Nc3cccc(C(F)(F)F)c3)n(Cc3ccc(N(C)C)cc3)c2=O)cc1] | I-112 | 526 | 3.67 | 4 |

TABLE 26-continued

| Chemical Structure | Compound No. | [M + H] | Retention time (min) | Method |
|---|---|---|---|---|
| 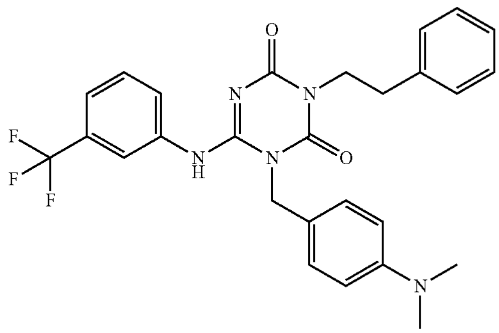 [SMILES: CN(C)c1ccc(Cn2c(Nc3cccc(C(F)(F)F)c3)nc(=O)n(CCc3ccccc3)c2=O)cc1] | I-113 | 510 | 3.77 | 4 |
| 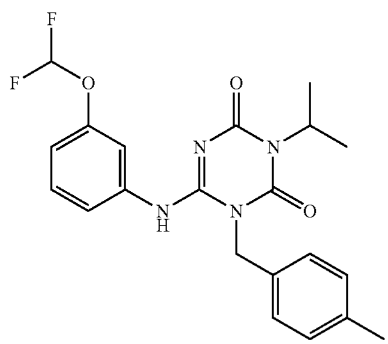 [SMILES: Cc1ccc(Cn2c(Nc3cccc(OC(F)F)c3)nc(=O)n(C(C)C)c2=O)cc1] | I-114 | 417 | 2.44 | 1 |
| 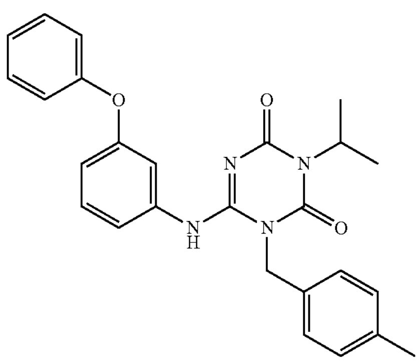 [SMILES: Cc1ccc(Cn2c(Nc3cccc(Oc4ccccc4)c3)nc(=O)n(C(C)C)c2=O)cc1] | I-115 | 443 | 2.67 | 1 |

TABLE 27

| Chemical Structure | Compound No. | [M + H] | Retention time (min) | Method |
|---|---|---|---|---|
| 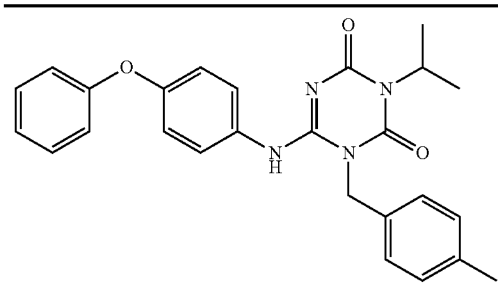 | I-116 | 443 | 2.59 | 1 |

TABLE 27-continued

| Chemical Structure | Compound No. | [M + H] | Retention time (min) | Method |
|---|---|---|---|---|
| (3-chlorophenyl)amino triazine with isopropyl and 4-methylbenzyl | I-117 | 385 | 2.52 | 1 |
| (3-methylthiophenyl)amino triazine with isopropyl and 4-methylbenzyl | I-118 | 397 | 2.44 | 1 |
| (3-isopropoxyphenyl)amino triazine with isopropyl and 4-methylbenzyl | I-119 | 409 | 2.52 | 1 |
| (3-tert-butylphenyl)amino triazine with isopropyl and 4-methylbenzyl | I-120 | 407 | 2.70 | 1 |

TABLE 28

| Chemical Structure | Compound No. | [M + H] | Retention time (min) | Method |
|---|---|---|---|---|
| 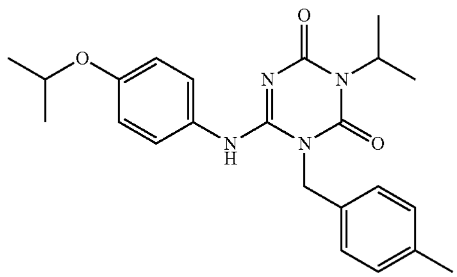 [SMILES: Cc1ccc(Cn2c(Nc3ccc(OC(C)C)cc3)nc(=O)n(C(C)C)c2=O)cc1] | I-121 | 409 | 2.40 | 1 |
| 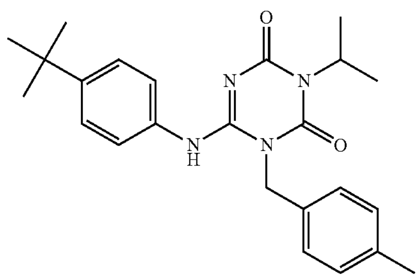 [SMILES: Cc1ccc(Cn2c(Nc3ccc(C(C)(C)C)cc3)nc(=O)n(C(C)C)c2=O)cc1] | I-122 | 407 | 2.68 | 1 |
| 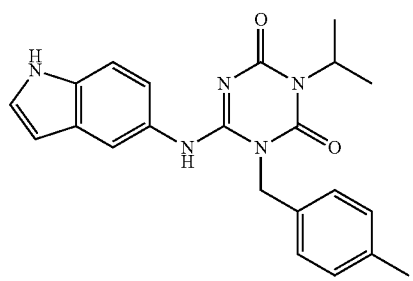 [SMILES: Cc1ccc(Cn2c(Nc3ccc4[nH]ccc4c3)nc(=O)n(C(C)C)c2=O)cc1] | I-123 | 390 | 2.05 | 1 |
| 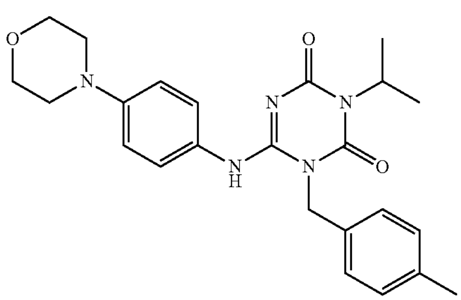 [SMILES: Cc1ccc(Cn2c(Nc3ccc(N4CCOCC4)cc3)nc(=O)n(C(C)C)c2=O)cc1] | I-124 | 436 | 2.04 | 1 |
| 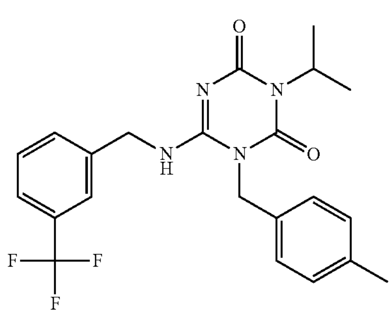 [SMILES: Cc1ccc(Cn2c(NCc3cccc(C(F)(F)F)c3)nc(=O)n(C(C)C)c2=O)cc1] | I-125 | 433 | 2.31 | 1 |

TABLE 29

| Chemical Structure | Compound No. | [M + H] | Retention time (min) | Method |
|---|---|---|---|---|
| 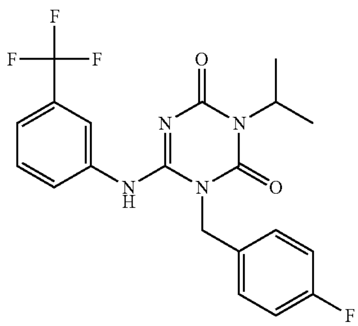 [SMILES: CC(C)n1c(=O)nc(Nc2cccc(C(F)(F)F)c2)n(Cc2ccc(F)cc2)c1=O] | I-126 | 423 | 2.51 | 1 |
| 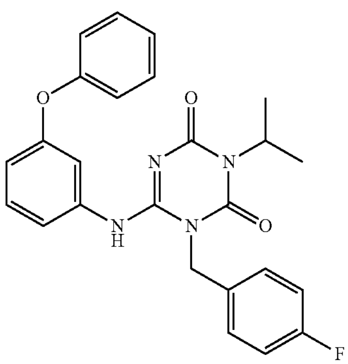 [SMILES: CC(C)n1c(=O)nc(Nc2cccc(Oc3ccccc3)c2)n(Cc2ccc(F)cc2)c1=O] | I-127 | 447 | 2.60 | 1 |
| 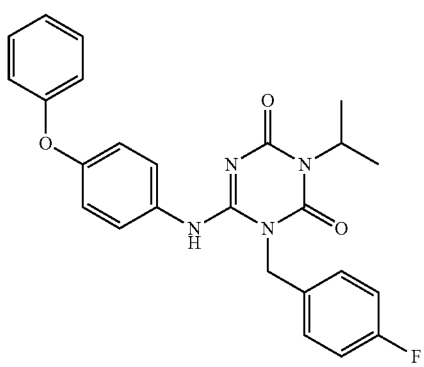 [SMILES: CC(C)n1c(=O)nc(Nc2ccc(Oc3ccccc3)cc2)n(Cc2ccc(F)cc2)c1=O] | I-128 | 447 | 2.52 | 1 |
| 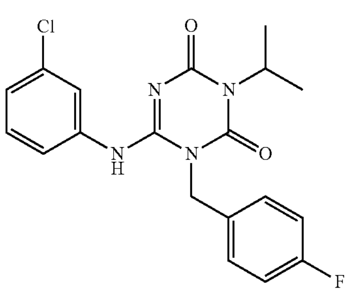 [SMILES: CC(C)n1c(=O)nc(Nc2cccc(Cl)c2)n(Cc2ccc(F)cc2)c1=O] | I-129 | 389 | 2.44 | 1 |

TABLE 29-continued

| Chemical Structure | Compound No. | [M + H] | Retention time (min) | Method |
|---|---|---|---|---|
| (3-methylthiophenyl-NH linked to triazinedione with N-isopropyl and N-(4-fluorobenzyl)) | I-130 | 401 | 2.36 | 1 |

TABLE 30

| Chemical Structure | Compound No. | [M + H] | Retention time (min) | Method |
|---|---|---|---|---|
| (3-isopropoxyphenyl-NH linked to triazinedione with N-isopropyl and N-(4-fluorobenzyl)) | I-131 | 413 | 2.44 | 1 |
| (3-tert-butylphenyl-NH linked to triazinedione with N-isopropyl and N-(4-fluorobenzyl)) | I-132 | 411 | 2.60 | 1 |
| (4-isopropoxyphenyl-NH linked to triazinedione with N-isopropyl and N-(4-fluorobenzyl)) | I-133 | 413 | 2.31 | 1 |

TABLE 30-continued

| Chemical Structure | Compound No. | [M + H] | Retention time (min) | Method |
|---|---|---|---|---|
| 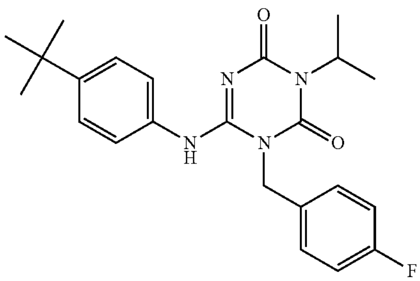 [SMILES: CC(C)n1c(=O)nc(Nc2ccc(C(C)(C)C)cc2)n(Cc2ccc(F)cc2)c1=O] | I-134 | 411 | 2.58 | 1 |
| 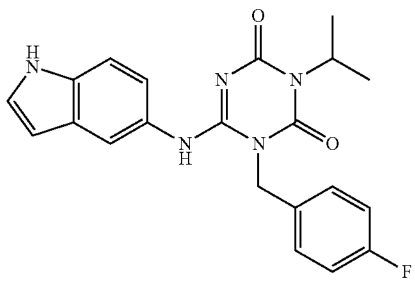 [SMILES: CC(C)n1c(=O)nc(Nc2ccc3[nH]ccc3c2)n(Cc2ccc(F)cc2)c1=O] | I-135 | 394 | 1.96 | 1 |

TABLE 31

| Chemical Structure | Compound No. | [M + H] | Retention time (min) | Method |
|---|---|---|---|---|
| 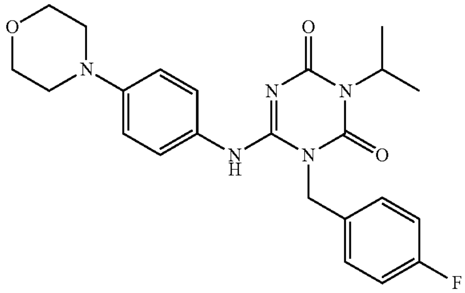 [SMILES: CC(C)n1c(=O)nc(Nc2ccc(N3CCOCC3)cc2)n(Cc2ccc(F)cc2)c1=O] | I-136 | 440 | 1.93 | 1 |
| 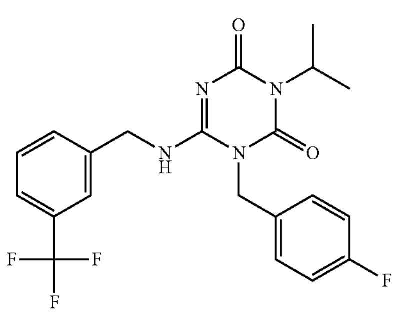 | I-137 | 437 | 2.18 | 1 |

TABLE 31-continued

| Chemical Structure | Compound No. | [M + H] | Retention time (min) | Method |
|---|---|---|---|---|
| 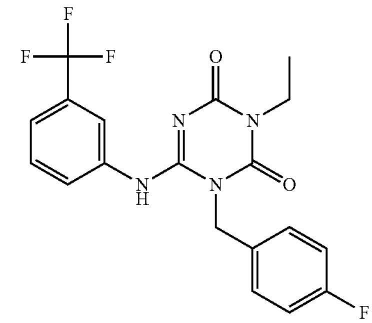 [SMILES: CCn1c(=O)nc(Nc2cccc(C(F)(F)F)c2)n(Cc2ccc(F)cc2)c1=O] | I-138 | 409 | 2.35 | 1 |
| 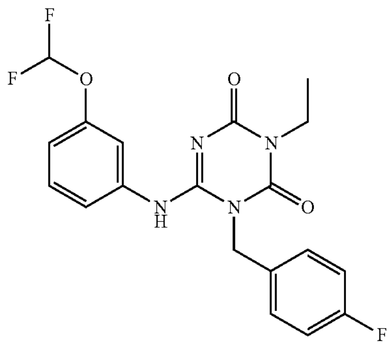 [SMILES: CCn1c(=O)nc(Nc2cccc(OC(F)F)c2)n(Cc2ccc(F)cc2)c1=O] | I-139 | 407 | 2.18 | 1 |
| 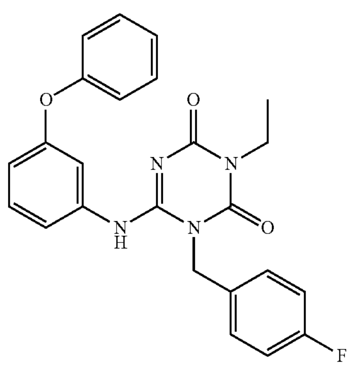 [SMILES: CCn1c(=O)nc(Nc2cccc(Oc3ccccc3)c2)n(Cc2ccc(F)cc2)c1=O] | I-140 | 433 | 2.44 | 1 |

TABLE 32

| Chemical Structure | Compound No. | [M + H] | Retention time (min) | Method |
|---|---|---|---|---|
| 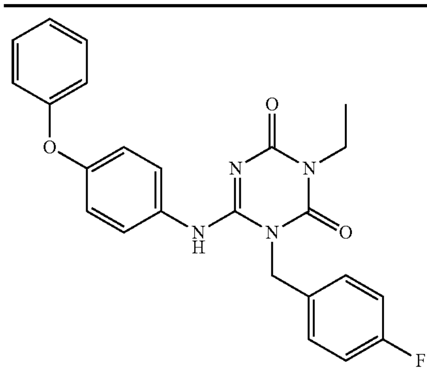 | I-141 | 433 | 2.37 | 1 |

TABLE 32-continued

| Chemical Structure | Compound No. | [M + H] | Retention time (min) | Method |
|---|---|---|---|---|
| (3-chlorophenyl)amino, 1-ethyl, 3-(4-fluorobenzyl) triazinedione | I-142 | 374 | 2.26 | 1 |
| (3-methylthiophenyl)amino, 1-ethyl, 3-(4-fluorobenzyl) triazinedione | I-143 | 387 | 2.17 | 1 |
| (3-isopropoxyphenyl)amino, 1-ethyl, 3-(4-fluorobenzyl) triazinedione | I-144 | 399 | 2.27 | 1 |
| (3-tert-butylphenyl)amino, 1-ethyl, 3-(4-fluorobenzyl) triazinedione | I-145 | 397 | 2.45 | 1 |

TABLE 33

| Chemical Structure | Compound No. | [M + H] | Retention time (min) | Method |
|---|---|---|---|---|
| 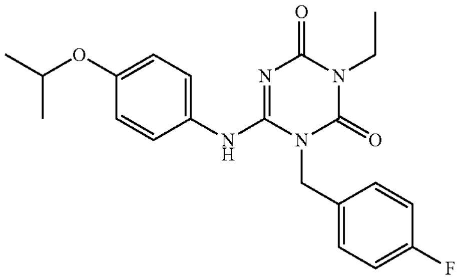 [SMILES: CCn1c(=O)nc(Nc2ccc(OC(C)C)cc2)n(Cc2ccc(F)cc2)c1=O] | I-146 | 399 | 2.13 | 1 |
| 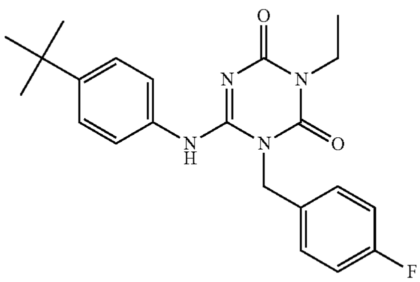 [SMILES: CCn1c(=O)nc(Nc2ccc(C(C)(C)C)cc2)n(Cc2ccc(F)cc2)c1=O] | I-147 | 397 | 2.42 | 1 |
| 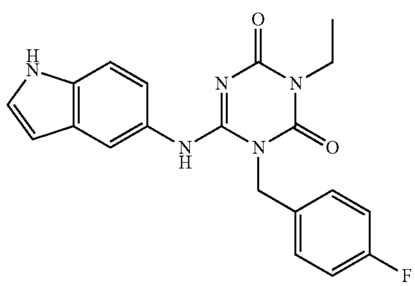 [SMILES: CCn1c(=O)nc(Nc2ccc3[nH]ccc3c2)n(Cc2ccc(F)cc2)c1=O] | I-148 | 380 | 1.78 | 1 |
| 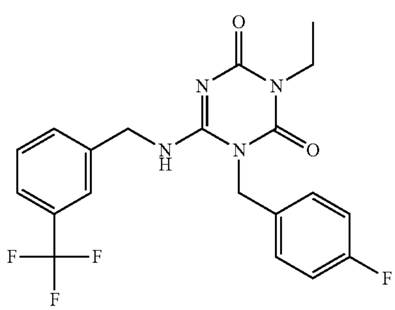 [SMILES: CCn1c(=O)nc(NCc2cccc(C(F)(F)F)c2)n(Cc2ccc(F)cc2)c1=O] | I-149 | 423 | 2.04 | 1 |
| 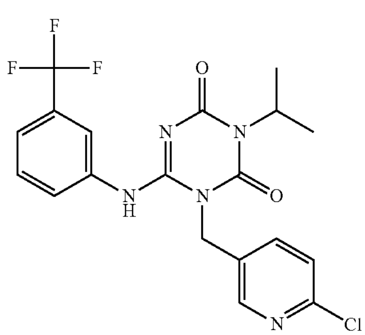 [SMILES: CC(C)n1c(=O)nc(Nc2cccc(C(F)(F)F)c2)n(Cc2ccc(Cl)nc2)c1=O] | I-150 | 440 | 2.40 | 1 |

TABLE 34
| Chemical Structure | Compound No. | [M + H] | Retention time (min) | Method |
|---|---|---|---|---|
| 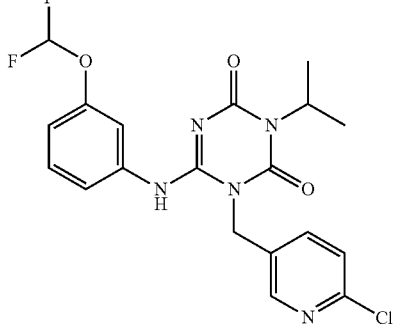 | I-151 | 438 | 2.24 | 1 |
| 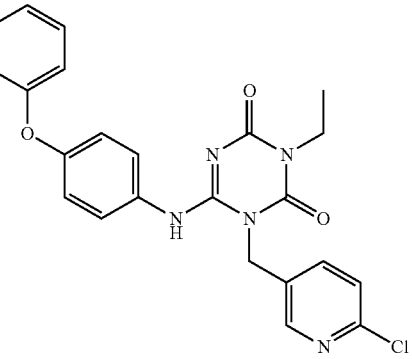 | I-152 | 464 | 2.44 | 1 |
| 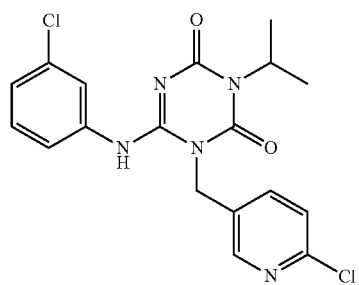 [SMILES: CC(C)n1c(=O)nc(Nc2cccc(Cl)c2)n(Cc2ccc(Cl)nc2)c1=O] | I-153 | 407 | 2.30 | 1 |
| 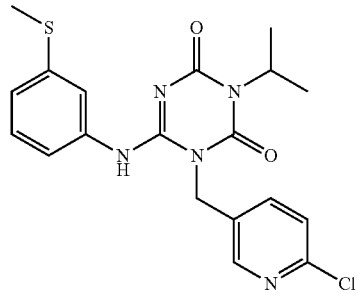 [SMILES: CSc1cccc(Nc2nc(=O)n(C(C)C)c(=O)n2Cc2ccc(Cl)nc2)c1] | I-154 | 418 | 2.25 | 1 |

TABLE 34-continued

| Chemical Structure | Compound No. | [M + H] | Retention time (min) | Method |
|---|---|---|---|---|
| (3-isopropoxyphenyl)amino-triazinedione-N-isopropyl-N-(6-chloropyridin-3-yl)methyl | I-155 | 430 | 2.34 | 1 |

TABLE 35

| Chemical Structure | Compound No. | [M + H] | Retention time (min) | Method |
|---|---|---|---|---|
| (3-tert-butylphenyl)amino-triazinedione-N-isopropyl-N-(6-chloropyridin-3-yl)methyl | I-156 | 428 | 2.53 | 1 |
| (4-isopropoxyphenyl)amino-triazinedione-N-isopropyl-N-(6-chloropyridin-3-yl)methyl | I-157 | 430 | 2.21 | 1 |
| (4-tert-butylphenyl)amino-triazinedione-N-isopropyl-N-(6-chloropyridin-3-yl)methyl | I-158 | 428 | 2.51 | 1 |

TABLE 35-continued

| Chemical Structure | Compound No. | [M + H] | Retention time (min) | Method |
|---|---|---|---|---|
| 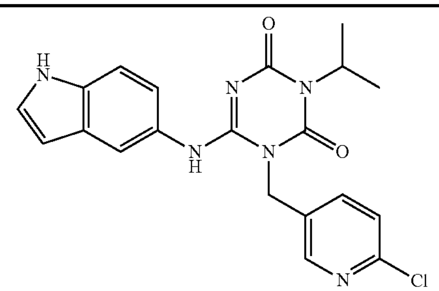 | I-159 | 411 | 1.83 | 1 |
| 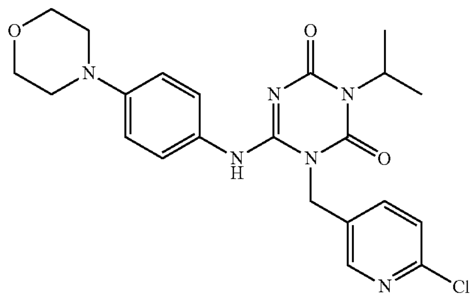 [SMILES: CC(C)n1c(=O)nc(Nc2ccc(N3CCOCC3)cc2)n(Cc2ccc(Cl)nc2)c1=O] | I-160 | 457 | 1.77 | 1 |

TABLE 36

| Chemical Structure | Compound No. | [M + H] | Retention time (min) | Method |
|---|---|---|---|---|
| 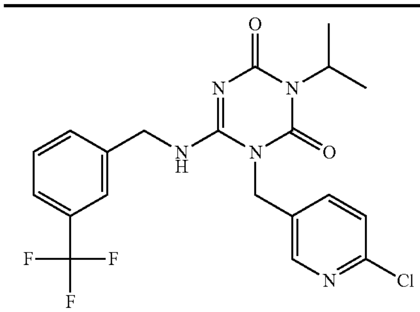 | I-161 | 454 | 2.04 | 1 |
| 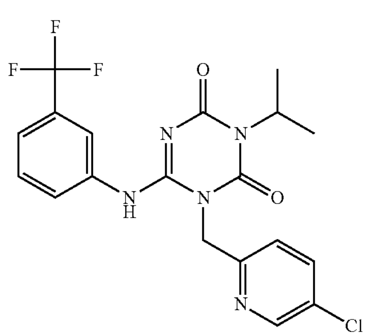 [SMILES: CC(C)n1c(=O)nc(Nc2cccc(C(F)(F)F)c2)n(Cc2ccc(Cl)cn2)c1=O] | I-162 | 440 | 2.40 | 1 |

TABLE 36-continued

| Chemical Structure | Compound No. | [M + H] | Retention time (min) | Method |
|---|---|---|---|---|
| 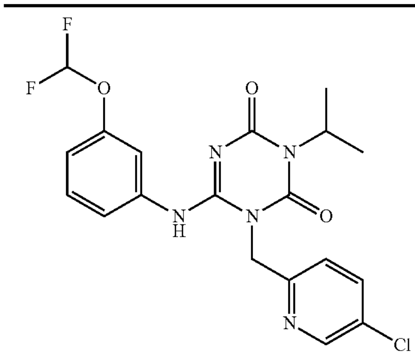 | I-163 | 438 | 2.24 | 1 |
| 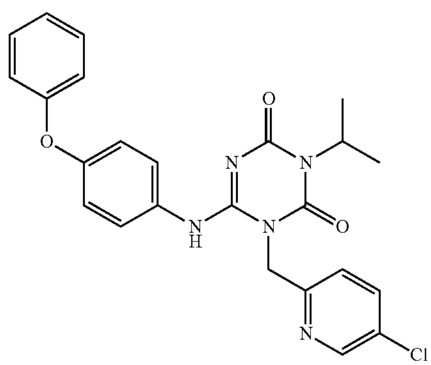 [SMILES: CC(C)n1c(=O)nc(Nc2ccc(Oc3ccccc3)cc2)n(Cc2ccc(Cl)cn2)c1=O] | I-164 | 464 | 2.48 | 1 |
| 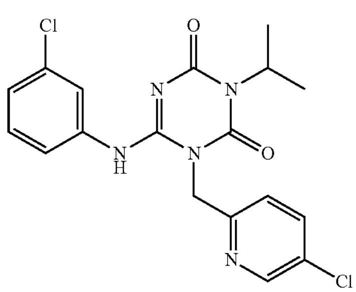 [SMILES: CC(C)n1c(=O)nc(Nc2cccc(Cl)c2)n(Cc2ccc(Cl)cn2)c1=O] | I-165 | 407 | 2.31 | 1 |

TABLE 37

| Chemical Structure | Compound No. | [M + H] | Retention time (min) | Method |
|---|---|---|---|---|
| 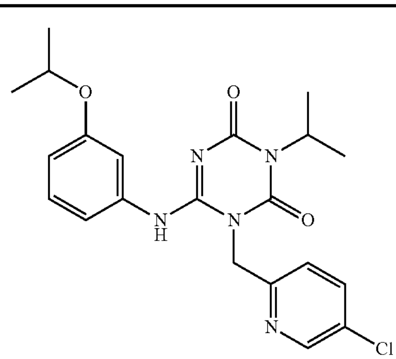 | I-166 | 430 | 2.38 | 1 |

TABLE 37-continued

| Chemical Structure | Compound No. | [M + H] | Retention time (min) | Method |
|---|---|---|---|---|
| (structure) | I-167 | 428 | 2.58 | 1 |
| (structure) | I-168 | 430 | 2.31 | 1 |
| (structure) | I-169 | 430 | 2.60 | 1 |

TABLE 38

| Chemical Structure | Compound No. | [M + H] | Retention time (min) | Method |
|---|---|---|---|---|
| (structure) | I-171 | 457 | 1.92 | 1 |

TABLE 38-continued

| Chemical Structure | Compound No. | [M + H] | Retention time (min) | Method |
|---|---|---|---|---|
| 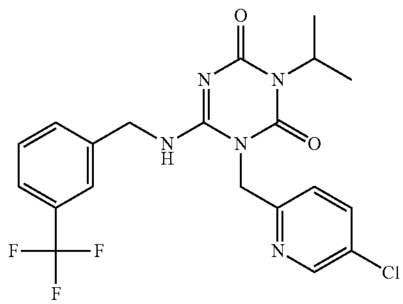 [SMILES: CC(C)n1c(=O)nc(NCc2cccc(C(F)(F)F)c2)n(Cc2ccc(Cl)cn2)c1=O] | I-172 | 454 | 2.20 | 1 |
| 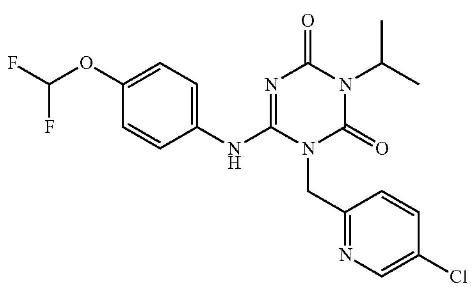 [SMILES: CC(C)n1c(=O)nc(Nc2ccc(OC(F)F)cc2)n(Cc2ccc(Cl)cn2)c1=O] | I-173 | 438 | 2.30 | 3 |
| 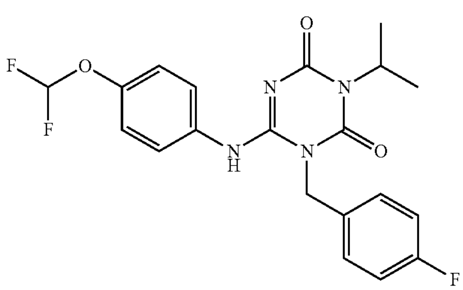 [SMILES: CC(C)n1c(=O)nc(Nc2ccc(OC(F)F)cc2)n(Cc2ccc(F)cc2)c1=O] | I-174 | 421 | 2.38 | 3 |
| 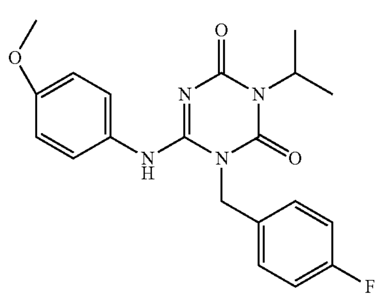 [SMILES: COc1ccc(Nc2nc(=O)n(C(C)C)c(=O)n2Cc2ccc(F)cc2)cc1] | I-175 | 385 | 2.20 | 3 |

TABLE 39

| Chemical Structure | Compound No. | [M + H] | Retention time (min) | Method |
|---|---|---|---|---|
| (4-trifluoromethylphenyl)amino isopropyl 4-fluorobenzyl triazine-2,4-dione | I-176 | 423 | 2.70 | 3 |
| (4-trifluoromethoxyphenyl)amino isopropyl 4-fluorobenzyl triazine-2,4-dione | I-177 | 439 | 2.70 | 3 |
| (4-fluorophenyl)amino isopropyl 4-fluorobenzyl triazine-2,4-dione | I-178 | 373 | 2.30 | 3 |
| (4-chlorophenyl)amino isopropyl 4-fluorobenzyl triazine-2,4-dione | I-179 | 389 | 2.50 | 3 |
| (3-methoxyphenyl)amino isopropyl 4-fluorobenzyl triazine-2,4-dione | I-180 | 385 | 2.40 | 3 |

TABLE 40

| Chemical Structure | Compound No. | [M + H] | Retention time (min) | Method |
|---|---|---|---|---|
| 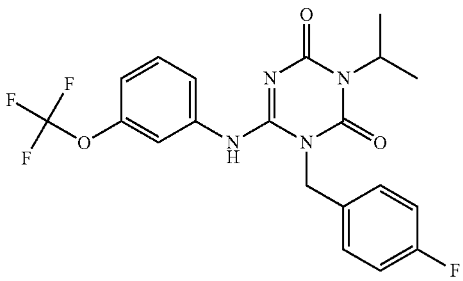 [SMILES: CC(C)n1c(=O)nc(Nc2cccc(OC(F)(F)F)c2)n(Cc2ccc(F)cc2)c1=O] | I-181 | 439 | 2.70 | 3 |
| 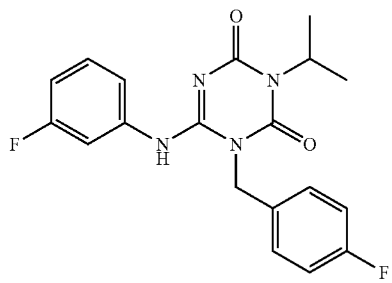 [SMILES: CC(C)n1c(=O)nc(Nc2cccc(F)c2)n(Cc2ccc(F)cc2)c1=O] | I-182 | 373 | 2.40 | 3 |
| 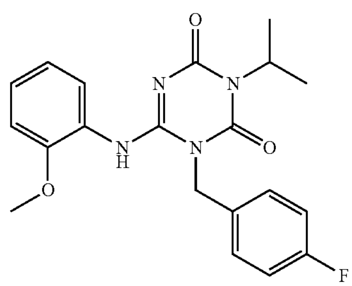 [SMILES: COc1ccccc1Nc1nc(=O)n(C(C)C)c(=O)n1Cc1ccc(F)cc1] | I-183 | 385 | 2.30 | 3 |
| 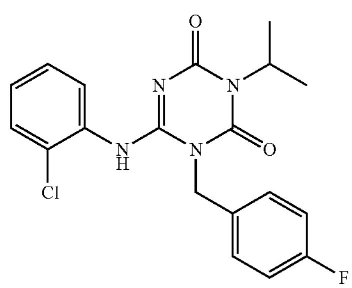 [SMILES: CC(C)n1c(=O)nc(Nc2ccccc2Cl)n(Cc2ccc(F)cc2)c1=O] | I-184 | 389 | 2.60 | 3 |
| 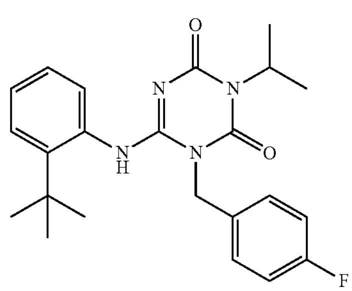 [SMILES: CC(C)n1c(=O)nc(Nc2ccccc2C(C)(C)C)n(Cc2ccc(F)cc2)c1=O] | I-185 | 411 | 2.90 | 3 |

TABLE 41

| Chemical Structure | Compound No. | [M + H] | Retention time (min) | Method |
|---|---|---|---|---|
| 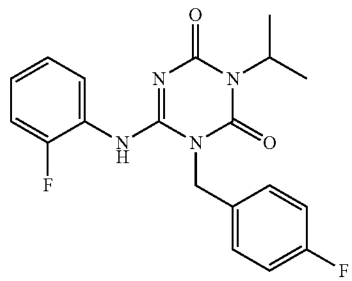 [SMILES: CC(C)n1c(=O)nc(Nc2ccccc2F)n(Cc2ccc(F)cc2)c1=O] | I-186 | 373 | 2.40 | 3 |
| 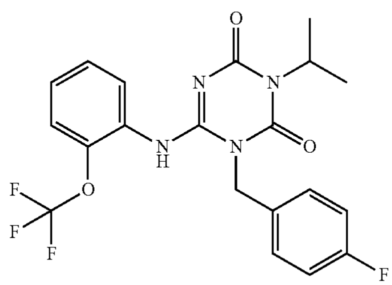 [SMILES: CC(C)n1c(=O)nc(Nc2ccccc2OC(F)(F)F)n(Cc2ccc(F)cc2)c1=O] | I-187 | 439 | 2.70 | 3 |
| 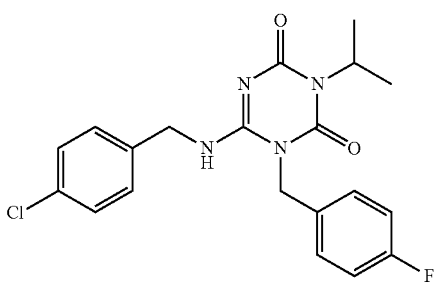 [SMILES: CC(C)n1c(=O)nc(NCc2ccc(Cl)cc2)n(Cc2ccc(F)cc2)c1=O] | I-188 | 403 | 1.20 | 3 |
| 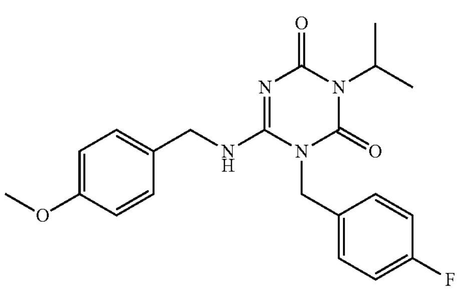 [SMILES: COc1ccc(CNc2nc(=O)n(C(C)C)c(=O)n2Cc2ccc(F)cc2)cc1] | I-189 | 399 | 1.20 | 3 |
| 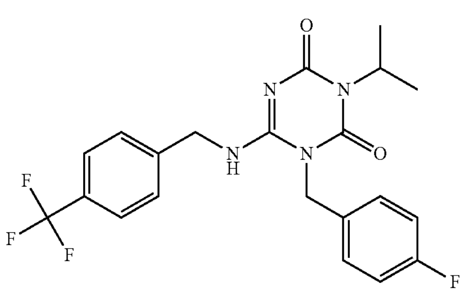 [SMILES: CC(C)n1c(=O)nc(NCc2ccc(C(F)(F)F)cc2)n(Cc2ccc(F)cc2)c1=O] | I-190 | 437 | 2.10 | 3 |

TABLE 42

| Chemical Structure | Compound No. | [M + H] | Retention time (min) | Method |
|---|---|---|---|---|
| (3-methoxybenzyl) structure | I-191 | 399 | 1.90 | 3 |
| (2-methoxybenzyl) structure | I-192 | 399 | 1.90 | 3 |
| (3-chlorobenzyl) structure | I-193 | 403 | 2.20 | 3 |
| (2-chlorobenzyl) structure | I-194 | 403 | 2.20 | 3 |
| (2-trifluoromethylbenzyl) structure | I-195 | 437 | 2.30 | 3 |

TABLE 43

| Chemical Structure | Compound No. | [M + H] | Retention time (min) | Method |
|---|---|---|---|---|
| (4-fluorobenzyl, isopropyl triazinedione with 2-methoxyethylamino) | I-196 | 337 | 1.70 | 3 |
| (4-fluorobenzyl, isopropyl triazinedione with 3,4-dichloroanilino) | I-197 | 424 | 2.80 | 3 |
| (4-fluorobenzyl, isopropyl triazinedione with 4-chloro-3-trifluoromethylanilino) | I-198 | 457 | 2.80 | 3 |
| (4-fluorobenzyl, isopropyl triazinedione with 1-benzylpiperidin-4-ylamino) | I-199 | 452 | 1.40 | 3 |
| (4-chlorobenzyl, isopropyl triazinedione with 4-isopropoxyanilino) | I-200 | 429 | 2.60 | 3 |

TABLE 44
| Chemical Structure | Compound No. | [M + H] | Retention time (min) | Method |
|---|---|---|---|---|
| 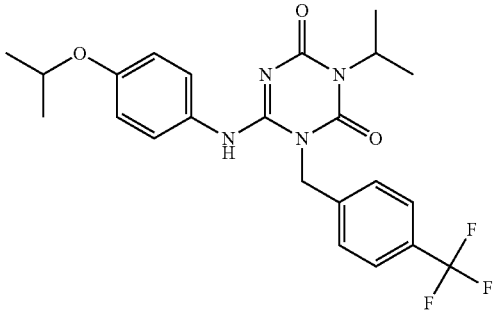 [SMILES: CC(C)Oc1ccc(Nc2nc(=O)n(C(C)C)c(=O)n2Cc2ccc(C(F)(F)F)cc2)cc1] | I-201 | 463 | 2.70 | 3 |
| 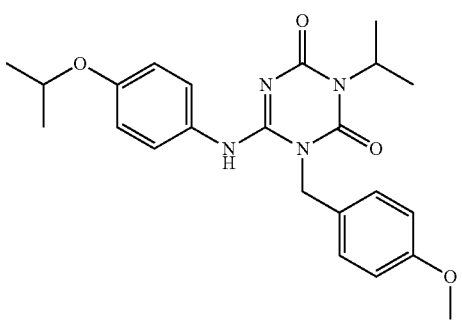 [SMILES: COc1ccc(Cn2c(Nc3ccc(OC(C)C)cc3)nc(=O)n(C(C)C)c2=O)cc1] | I-202 | 425 | 2.40 | 3 |
| 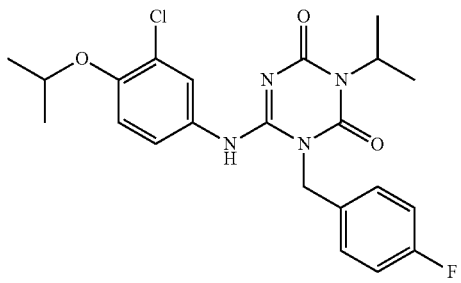 | I-203 | 447 | 2.70 | 3 |
| 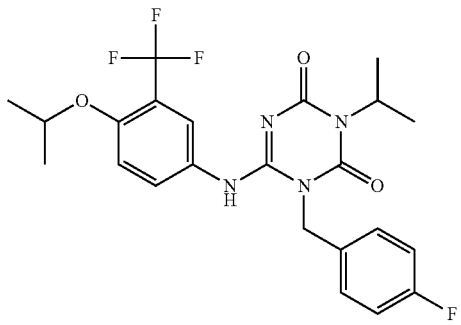 [SMILES: CC(C)Oc1ccc(Nc2nc(=O)n(C(C)C)c(=O)n2Cc2ccc(F)cc2)cc1C(F)(F)F] | I-204 | 481 | 2.80 | 3 |
| 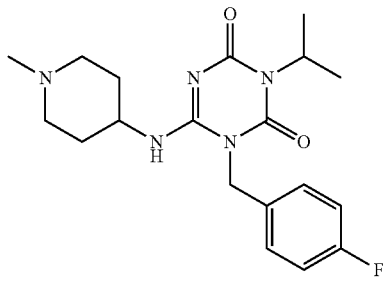 [SMILES: CC(C)n1c(=O)nc(NC2CCN(C)CC2)n(Cc2ccc(F)cc2)c1=O] | I-205 | 376 | 1.20 | 3 |

TABLE 45

| Chemical Structure | Compound No. | [M + H] | Retention time (min) | Method |
|---|---|---|---|---|
| (structure) | I-206 | 398 | 1.80 | 3 |
| (structure) | I-207 | 413 | 2.20 | 3 |
| (structure) | I-208 | 420 | 2.30 | 3 |
| (structure) | I-209 | 429 | 2.60 | 3 |
| (structure) | I-210 | 425 | 2.40 | 3 |

TABLE 46
| Chemical Structure | Compound No. | [M + H] | Retention time (min) | Method |
|---|---|---|---|---|
| 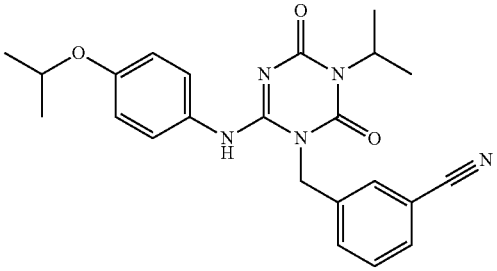 [SMILES: CC(C)Oc1ccc(Nc2nc(=O)n(C(C)C)c(=O)n2Cc2cccc(C#N)c2)cc1] | I-211 | 420 | 2.40 | 3 |
| 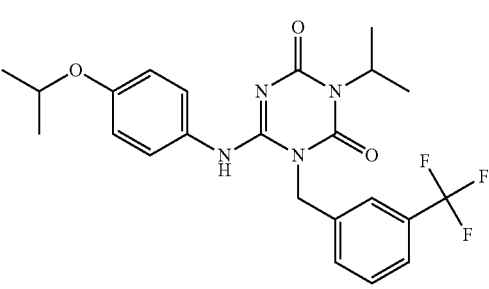 [SMILES: CC(C)Oc1ccc(Nc2nc(=O)n(C(C)C)c(=O)n2Cc2cccc(C(F)(F)F)c2)cc1] | I-212 | 463 | 2.70 | 3 |
| 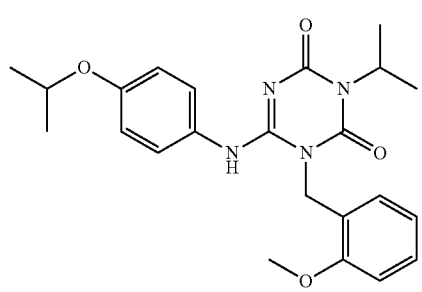 [SMILES: COc1ccccc1Cn1c(Nc2ccc(OC(C)C)cc2)nc(=O)n(C(C)C)c1=O] | I-213 | 425 | 2.40 | 3 |
| 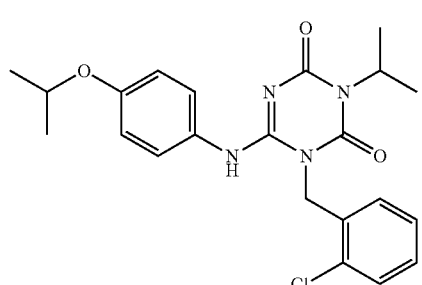 | I-214 | 429 | 2.60 | 3 |
| 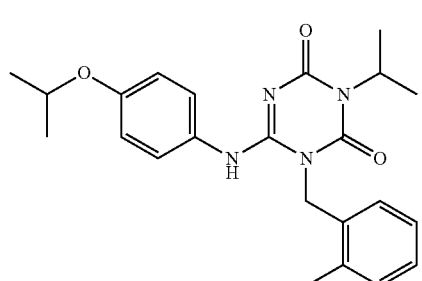 | I-215 | 420 | 2.40 | 3 |

TABLE 47

| Chemical Structure | Compound No. | [M + H] | Retention time (min) | Method |
|---|---|---|---|---|
| 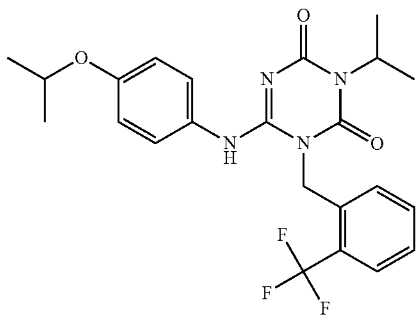 [SMILES: CC(C)Oc1ccc(Nc2nc(=O)n(C(C)C)c(=O)n2Cc2ccccc2C(F)(F)F)cc1] | I-216 | 463 | 2.70 | 3 |
| 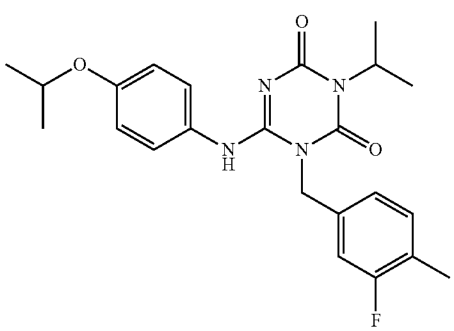 [SMILES: Cc1ccc(Cn2c(Nc3ccc(OC(C)C)cc3)nc(=O)n(C(C)C)c2=O)cc1F] | I-217 | 427 | 2.60 | 3 |
| 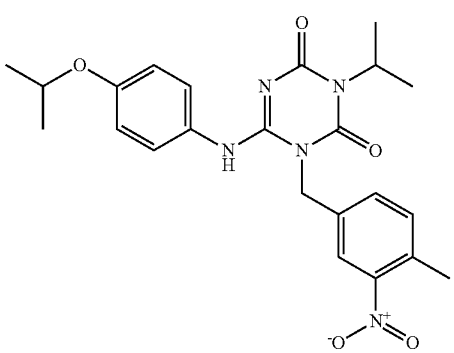 | I-218 | 454 | 2.50 | 3 |
| 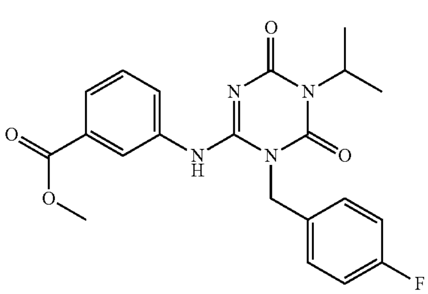 [SMILES: COC(=O)c1cccc(Nc2nc(=O)n(C(C)C)c(=O)n2Cc2ccc(F)cc2)c1] | I-219 | 413 | 2.40 | 3 |

TABLE 47-continued

| Chemical Structure | Compound No. | [M + H] | Retention time (min) | Method |
|---|---|---|---|---|
| (structure) | I-220 | 451 | 2.90 | 3 |

TABLE 48

| Chemical Structure | Compound No. | [M + H] | Retention time (min) | Method |
|---|---|---|---|---|
| (structure) | I-221 | 413 | 2.40 | 3 |
| (structure) | I-222 | 427 | 2.40 | 3 |
| (structure) | I-223 | 417 | 2.40 | 3 |

TABLE 48-continued

| Chemical Structure | Compound No. | [M + H] | Retention time (min) | Method |
|---|---|---|---|---|
| 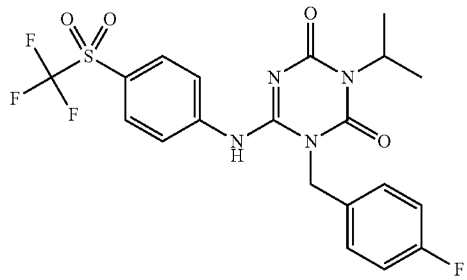 [SMILES: CC(C)n1c(=O)nc(Nc2ccc(S(=O)(=O)C(F)(F)F)cc2)n(Cc2ccc(F)cc2)c1=O] | I-224 | 487 | 2.70 | 3 |
| 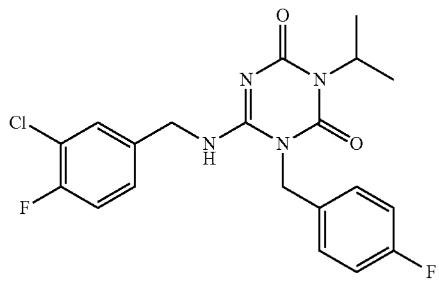 [SMILES: CC(C)n1c(=O)nc(NCc2ccc(F)c(Cl)c2)n(Cc2ccc(F)cc2)c1=O] | I-225 | 421 | 2.30 | 3 |

TABLE 49

| Chemical Structure | Compound No. | [M + H] | Retention time (min) | Method |
|---|---|---|---|---|
| 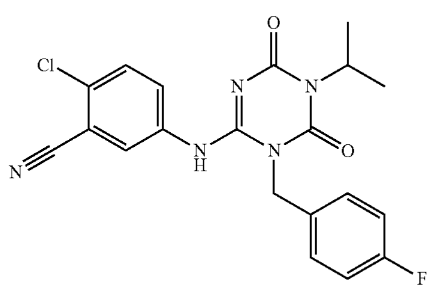 [SMILES: CC(C)n1c(=O)nc(Nc2ccc(Cl)c(C#N)c2)n(Cc2ccc(F)cc2)c1=O] | I-226 | 414 | 2.60 | 3 |
| 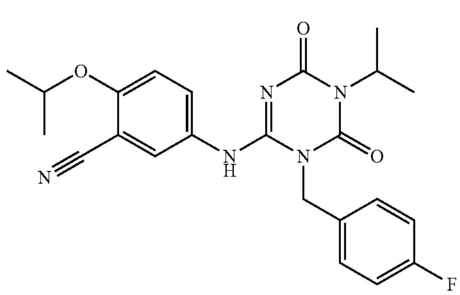 [SMILES: CC(C)Oc1ccc(Nc2nc(=O)n(C(C)C)c(=O)n2Cc2ccc(F)cc2)cc1C#N] | I-227 | 438 | 2.50 | 3 |

TABLE 49-continued
| Chemical Structure | Compound No. | [M + H] | Retention time (min) | Method |
|---|---|---|---|---|
| 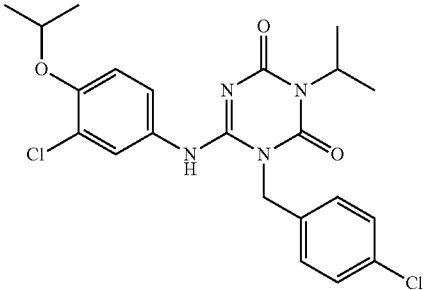 [SMILES: CC(C)Oc1ccc(Nc2nc(=O)n(C(C)C)c(=O)n2Cc2ccc(Cl)cc2)cc1Cl] | I-228 | 463 | 2.90 | 3 |
| 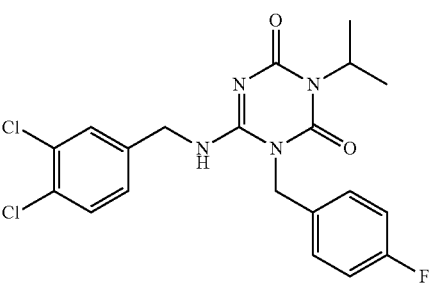 [SMILES: CC(C)n1c(=O)nc(NCc2ccc(Cl)c(Cl)c2)n(Cc2ccc(F)cc2)c1=O] | I-229 | 437 | 2.40 | 3 |
| 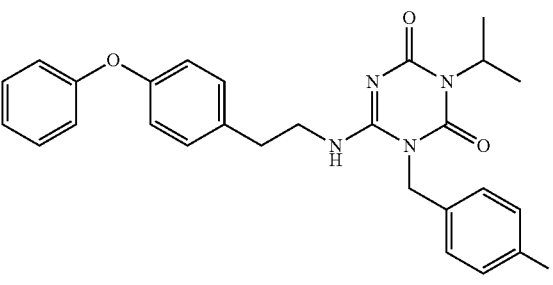 | I-230 | 475 | 2.60 | 3 |
TABLE 50
| Chemical Structure | Compound No. | [M + H] | Retention time (min) | Method |
|---|---|---|---|---|
| 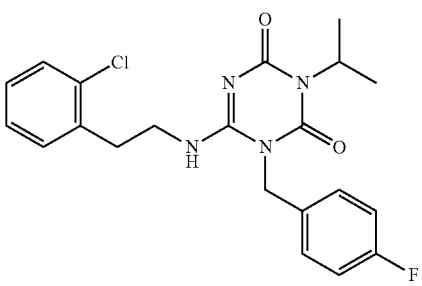 [SMILES: CC(C)n1c(=O)nc(NCCc2ccccc2Cl)n(Cc2ccc(F)cc2)c1=O] | I-231 | 417 | 2.40 | 3 |

TABLE 50-continued

| Chemical Structure | Compound No. | [M + H] | Retention time (min) | Method |
|---|---|---|---|---|
| (structure) | I-232 | 447 | 2.40 | 3 |
| (structure) | I-233 | 417 | 2.40 | 3 |
| (structure) | I-234 | 465 | 2.60 | 3 |
| (structure) | I-235 | 464 | 2.60 | 3 |

TABLE 51

| Chemical Structure | Compound No. | [M + H] | Retention time (min) | Method |
|---|---|---|---|---|
| 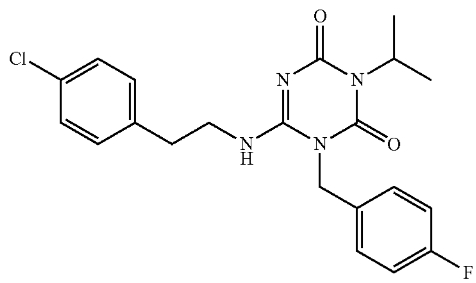 [SMILES: CC(C)n1c(=O)nc(NCCc2ccc(Cl)cc2)n(Cc2ccc(F)cc2)c1=O] | I-236 | 417 | 2.40 | 3 |
| 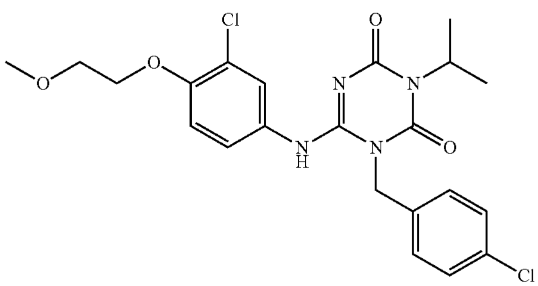 [SMILES: COCCOc1ccc(Nc2nc(=O)n(C(C)C)c(=O)n2Cc2ccc(Cl)cc2)cc1Cl] | I-237 | 479 | 2.60 | 3 |
| 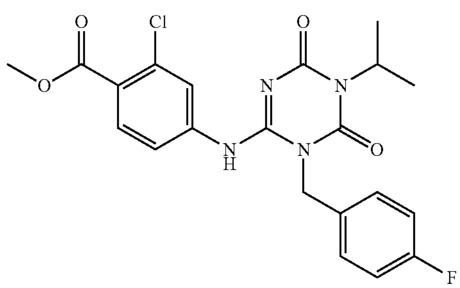 [SMILES: COC(=O)c1ccc(Nc2nc(=O)n(C(C)C)c(=O)n2Cc2ccc(F)cc2)cc1Cl] | I-238 | 447 | 2.70 | 3 |
| 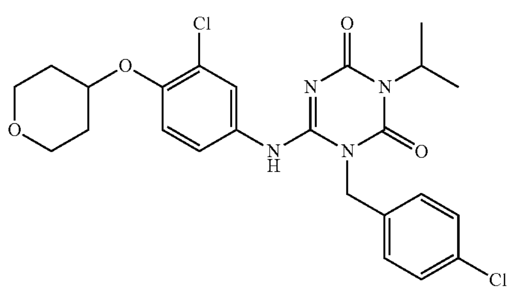 [SMILES: CC(C)n1c(=O)nc(Nc2ccc(OC3CCOCC3)c(Cl)c2)n(Cc2ccc(Cl)cc2)c1=O] | I-239 | 505 | 2.70 | 3 |
| 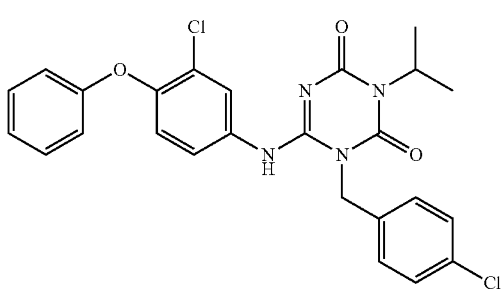 [SMILES: CC(C)n1c(=O)nc(Nc2ccc(Oc3ccccc3)c(Cl)c2)n(Cc2ccc(Cl)cc2)c1=O] | I-240 | 497 | 3.10 | 3 |

TABLE 52

| Chemical Structure | Compound No. | [M + H] | Retention time (min) | Method |
|---|---|---|---|---|
| 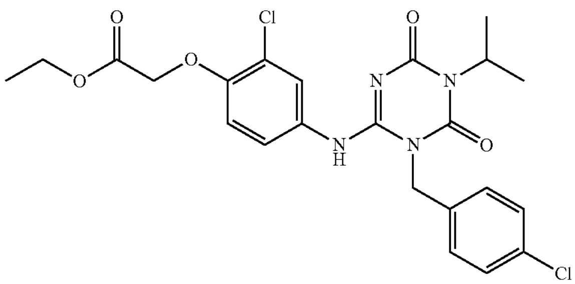 [SMILES: CCOC(=O)COc1ccc(Nc2nc(=O)n(C(C)C)c(=O)n2Cc2ccc(Cl)cc2)cc1Cl] | I-241 | 507 | 2.70 | 3 |
| 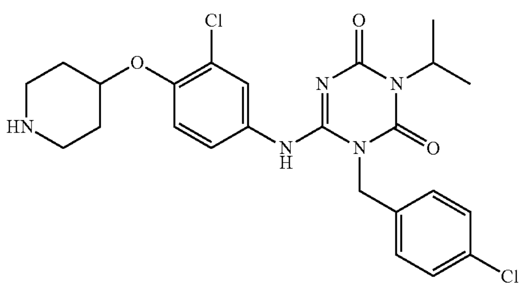 [SMILES: CC(C)n1c(=O)nc(Nc2ccc(OC3CCNCC3)c(Cl)c2)n(Cc2ccc(Cl)cc2)c1=O] | I-242 | 505 | 1.60 | 3 |
| 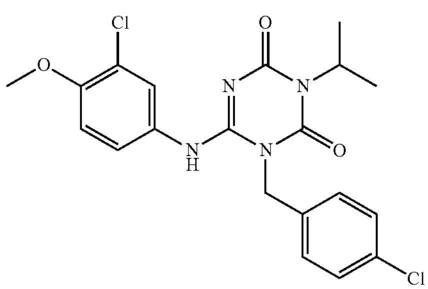 [SMILES: COc1ccc(Nc2nc(=O)n(C(C)C)c(=O)n2Cc2ccc(Cl)cc2)cc1Cl] | I-243 | 435 | 2.60 | 3 |
| 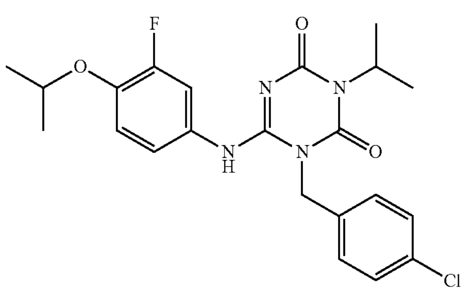 [SMILES: CC(C)Oc1ccc(Nc2nc(=O)n(C(C)C)c(=O)n2Cc2ccc(Cl)cc2)cc1F] | I-244 | 447 | 2.80 | 3 |
| 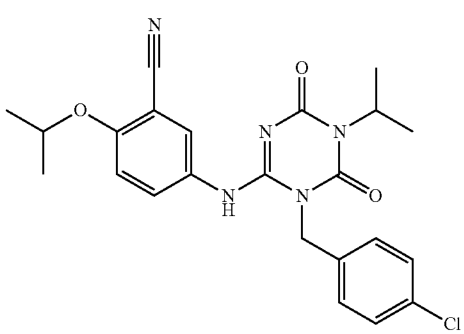 [SMILES: CC(C)Oc1ccc(Nc2nc(=O)n(C(C)C)c(=O)n2Cc2ccc(Cl)cc2)cc1C#N] | I-245 | 454 | 2.70 | 3 |

TABLE 53

| Chemical Structure | Compound No. | [M + H] | Retention time (min) | Method |
|---|---|---|---|---|
| (structure) | I-246 | 428 | 2.20 | 3 |
| (structure) | I-247 | 470 | 2.50 | 3 |
| (structure) | I-248 | 429 | 2.60 | 3 |
| (structure) | I-249 | 428 | 2.20 | 3 |
| (structure) | I-250 | 470 | 2.60 | 3 |

TABLE 54

| Chemical Structure | Compound No. | [M + H] | Retention time (min) | Method |
|---|---|---|---|---|
| 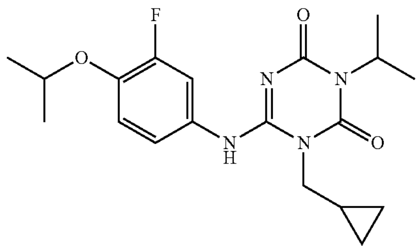 [SMILES: CC(C)Oc1ccc(Nc2nc(=O)n(C(C)C)c(=O)n2CC2CC2)cc1F] | I-251 | 377 | 2.40 | 3 |
| 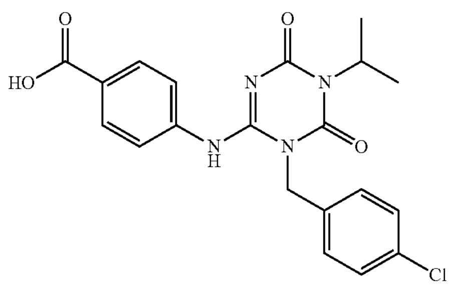 [SMILES: CC(C)n1c(=O)nc(Nc2ccc(C(=O)O)cc2)n(Cc2ccc(Cl)cc2)c1=O] | I-252 | 415 | 2.30 | 3 |
| 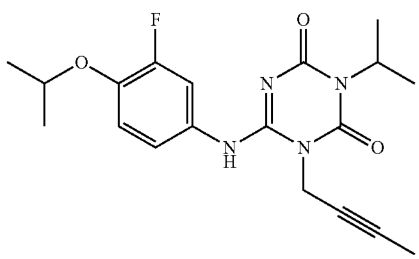 [SMILES: CC#CCn1c(Nc2ccc(OC(C)C)c(F)c2)nc(=O)n(C(C)C)c1=O] | I-253 | 375 | 2.30 | 3 |
| 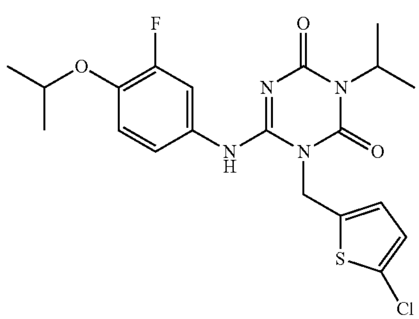 [SMILES: CC(C)Oc1ccc(Nc2nc(=O)n(C(C)C)c(=O)n2Cc2ccc(Cl)s2)cc1F] | I-254 | 453 | 2.90 | 3 |
| 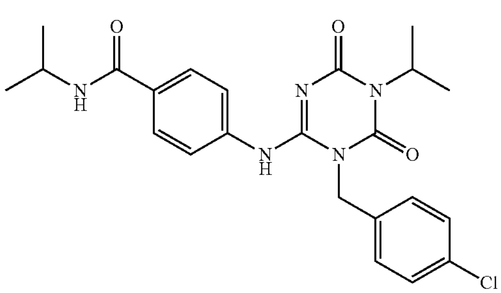 [SMILES: CC(C)NC(=O)c1ccc(Nc2nc(=O)n(C(C)C)c(=O)n2Cc2ccc(Cl)cc2)cc1] | I-255 | 456 | 2.40 | 3 |

TABLE 55

| Chemical Structure | Compound No. | [M + H] | Retention time (min) | Method |
|---|---|---|---|---|
| 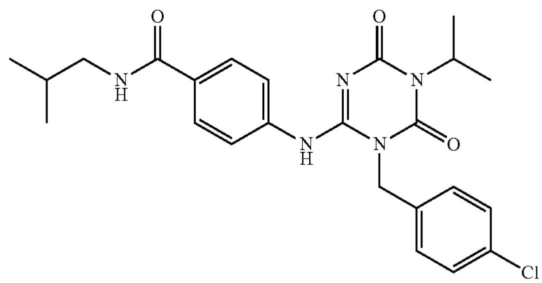 [SMILES: CC(C)CNC(=O)c1ccc(Nc2nc(=O)n(C(C)C)c(=O)n2Cc2ccc(Cl)cc2)cc1] | I-256 | 470 | 2.50 | 3 |
| 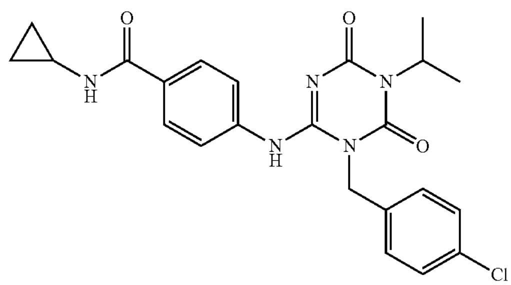 [SMILES: CC(C)n1c(=O)nc(Nc2ccc(C(=O)NC3CC3)cc2)n(Cc2ccc(Cl)cc2)c1=O] | I-257 | 454 | 2.20 | 3 |
| 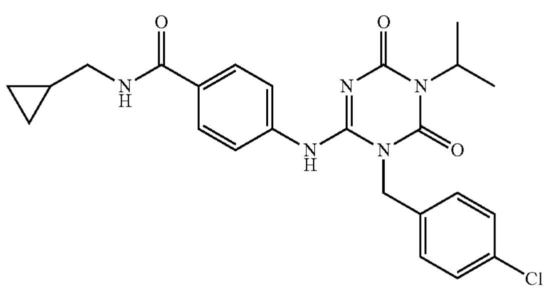 [SMILES: CC(C)n1c(=O)nc(Nc2ccc(C(=O)NCC3CC3)cc2)n(Cc2ccc(Cl)cc2)c1=O] | I-258 | 468 | 2.40 | 3 |
| 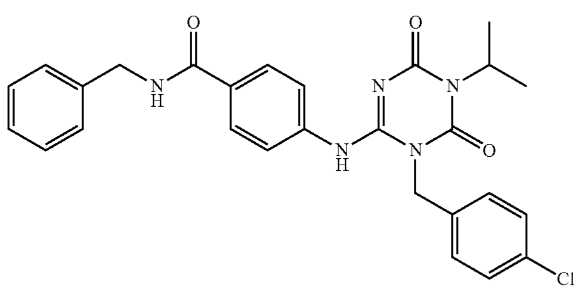 [SMILES: CC(C)n1c(=O)nc(Nc2ccc(C(=O)NCc3ccccc3)cc2)n(Cc2ccc(Cl)cc2)c1=O] | I-259 | 504 | 2.50 | 3 |
| 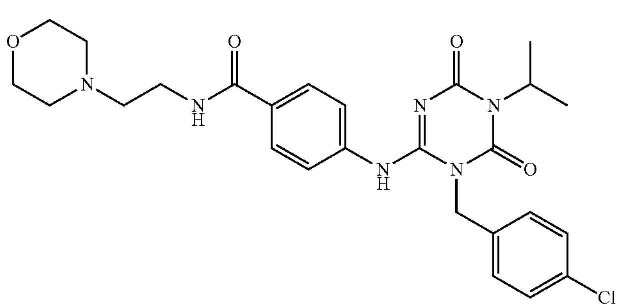 [SMILES: CC(C)n1c(=O)nc(Nc2ccc(C(=O)NCCN3CCOCC3)cc2)n(Cc2ccc(Cl)cc2)c1=O] | I-260 | 528 | 1.50 | 3 |

TABLE 56

| Chemical Structure | Compound No. | [M + H] | Retention time (min) | Method |
|---|---|---|---|---|
| 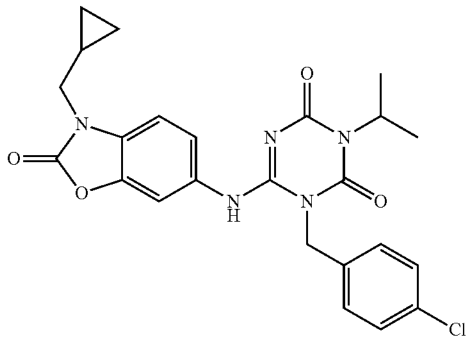 [SMILES: CC(C)n1c(=O)nc(Nc2ccc3c(c2)oc(=O)n3CC2CC2)n(Cc2ccc(Cl)cc2)c1=O] | I-261 | 482 | 2.60 | 3 |
| 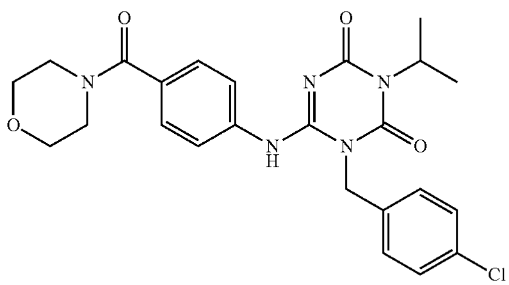 [SMILES: CC(C)n1c(=O)nc(Nc2ccc(C(=O)N3CCOCC3)cc2)n(Cc2ccc(Cl)cc2)c1=O] | I-262 | 484 | 2.20 | 3 |
| 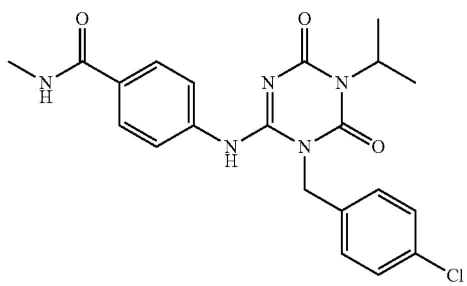 [SMILES: CNC(=O)c1ccc(Nc2nc(=O)n(C(C)C)c(=O)n2Cc2ccc(Cl)cc2)cc1] | I-263 | 428 | 2.10 | 3 |
| 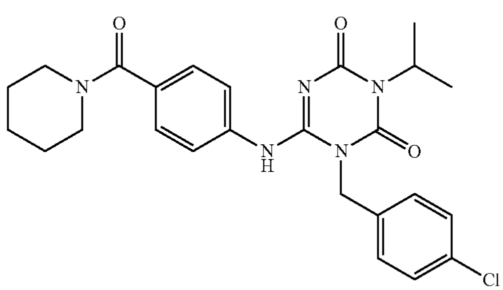 [SMILES: CC(C)n1c(=O)nc(Nc2ccc(C(=O)N3CCCCC3)cc2)n(Cc2ccc(Cl)cc2)c1=O] | I-264 | 482 | 2.50 | 3 |
| 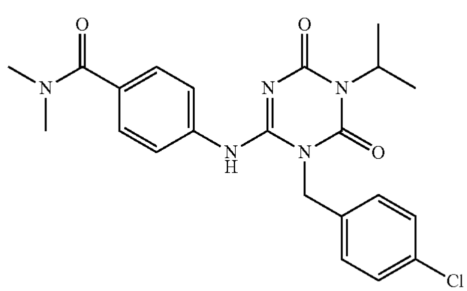 [SMILES: CC(C)n1c(=O)nc(Nc2ccc(C(=O)N(C)C)cc2)n(Cc2ccc(Cl)cc2)c1=O] | I-265 | 442 | 2.30 | 3 |

TABLE 57

| Chemical Structure | Compound No. | [M + H] | Retention time (min) | Method |
|---|---|---|---|---|
| (structure) | I-266 | 490 | 2.60 | 3 |
| (structure) | I-267 | 458 | 2.00 | 3 |
| (structure) | I-268 | 484 | 2.60 | 3 |
| (structure) | I-269 | 405 | 2.03 | 1 |
| (structure) | I-270 | 477 | 2.42 | 1 |

TABLE 58

| Chemical Structure | Compound No. | [M + H] | Retention time (min) | Method |
|---|---|---|---|---|
| 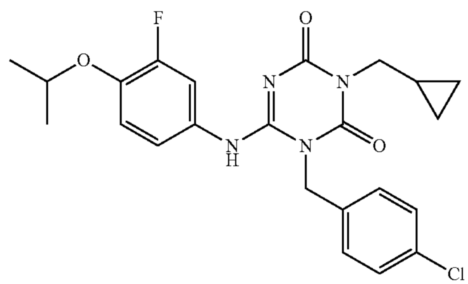 [SMILES: CC(C)Oc1ccc(Nc2nc(=O)n(CC3CC3)c(=O)n2Cc2ccc(Cl)cc2)cc1F] | I-271 | 459 | 2.49 | 1 |
| 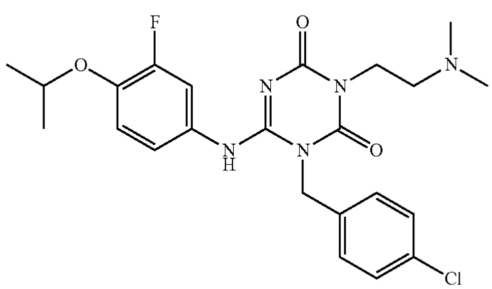 [SMILES: CC(C)Oc1ccc(Nc2nc(=O)n(CCN(C)C)c(=O)n2Cc2ccc(Cl)cc2)cc1F] | I-272 | 476 | 1.44 | 1 |
| 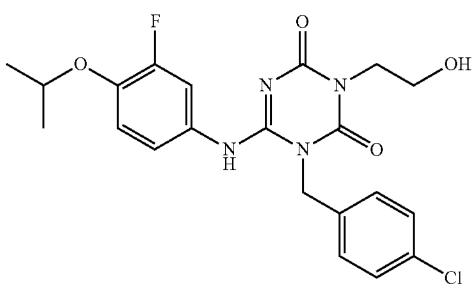 | I-273 | 449 | 1.96 | 1 |
| 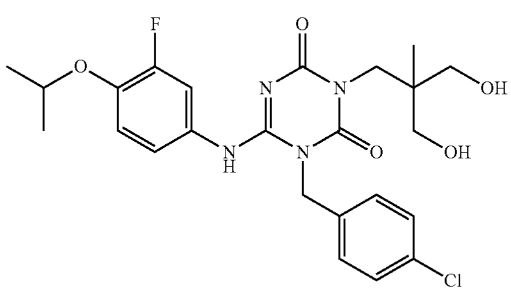 | I-274 | 507 | 1.98 | 1 |
| 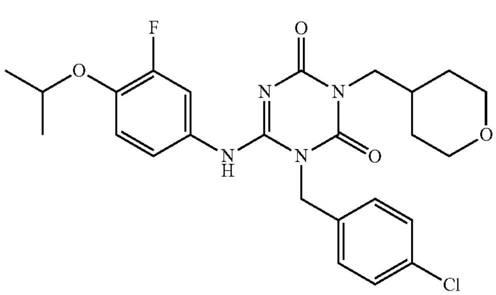 [SMILES: CC(C)Oc1ccc(Nc2nc(=O)n(CC3CCOCC3)c(=O)n2Cc2ccc(Cl)cc2)cc1F] | I-275 | 503 | 2.27 | 1 |

TABLE 59
| Chemical Structure | Compound No. | [M + H] | Retention time (min) | Method |
|---|---|---|---|---|
| 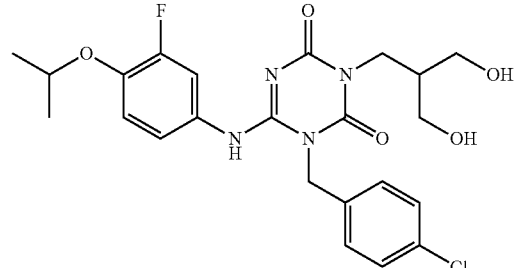 | I-276 | 493 | 1.85 | 1 |
| 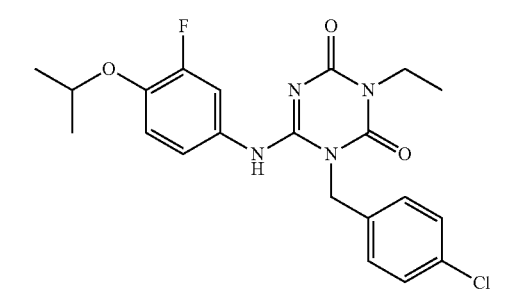 [SMILES: CCn1c(=O)nc(Nc2ccc(OC(C)C)c(F)c2)n(Cc2ccc(Cl)cc2)c1=O] | I-277 | 433 | 2.34 | 1 |
| 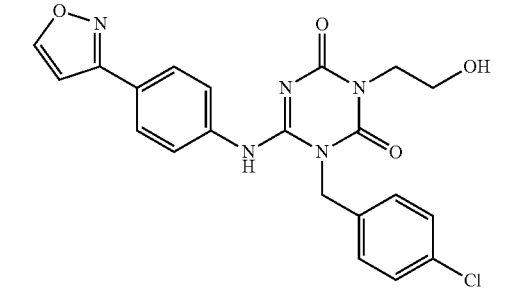 [SMILES: O=c1nc(Nc2ccc(-c3ccon3)cc2)n(Cc2ccc(Cl)cc2)c(=O)n1CCO] | I-278 | 440 | 1.70 | 1 |
| 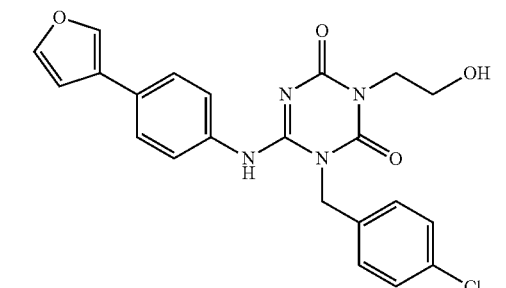 | I-279 | 439 | 1.90 | 1 |
| 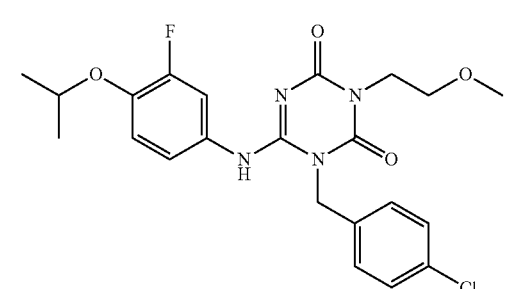 | I-280 | 463 | 2.21 | 1 |

TABLE 60

| Chemical Structure | Compound No. | [M + H] | Retention time (min) | Method |
|---|---|---|---|---|
| 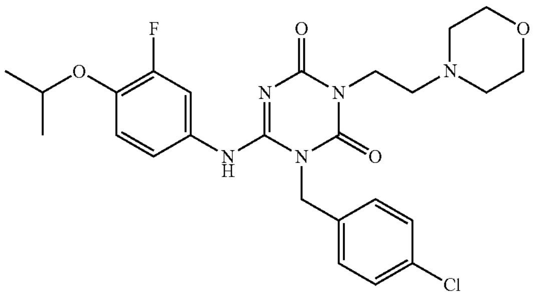 [SMILES: CC(C)Oc1ccc(Nc2nc(=O)n(CCN3CCOCC3)c(=O)n2Cc2ccc(Cl)cc2)cc1F] | I-281 | 518 | 1.47 | 1 |
| 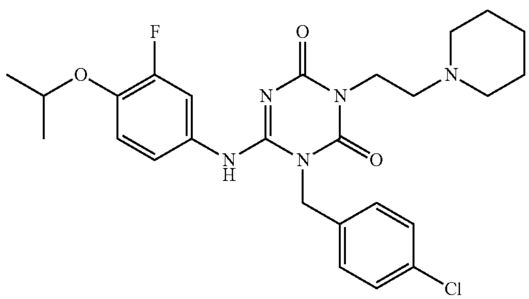 [SMILES: CC(C)Oc1ccc(Nc2nc(=O)n(CCN3CCCCC3)c(=O)n2Cc2ccc(Cl)cc2)cc1F] | I-282 | 516 | 1.50 | 1 |
| 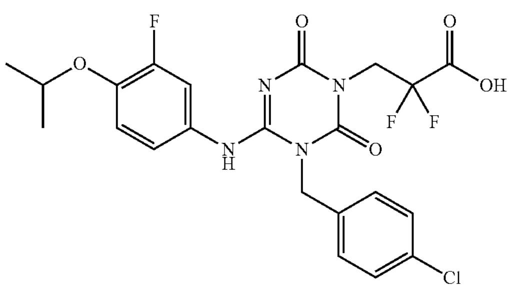 [SMILES: CC(C)Oc1ccc(Nc2nc(=O)n(CC(F)(F)C(=O)O)c(=O)n2Cc2ccc(Cl)cc2)cc1F] | I-283 | 513 | 1.82 | 1 |
| 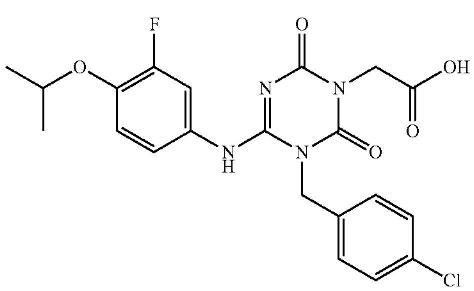 [SMILES: CC(C)Oc1ccc(Nc2nc(=O)n(CC(=O)O)c(=O)n2Cc2ccc(Cl)cc2)cc1F] | I-284 | 463 | 1.96 | 1 |
| 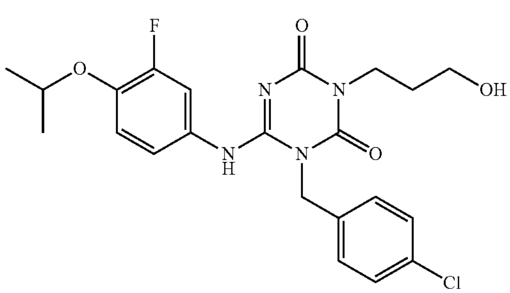 [SMILES: CC(C)Oc1ccc(Nc2nc(=O)n(CCCO)c(=O)n2Cc2ccc(Cl)cc2)cc1F] | I-285 | 463 | 2.00 | 1 |

TABLE 61

| Chemical Structure | Compound No. | [M + H] | Retention time (min) | Method |
|---|---|---|---|---|
| 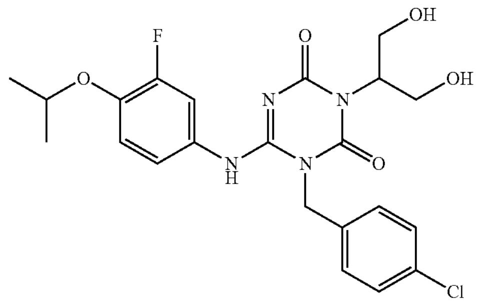 [SMILES: CC(C)Oc1ccc(Nc2nc(=O)n(C(CO)CO)c(=O)n2Cc2ccc(Cl)cc2)cc1F] | I-286 | 479 | 1.80 | 1 |
| 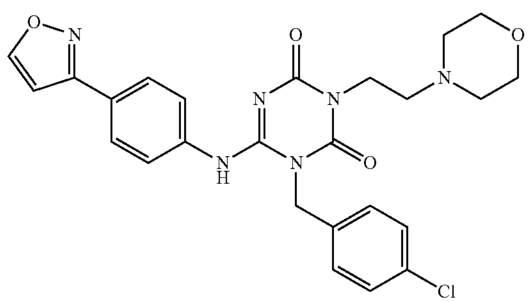 [SMILES: O=c1nc(Nc2ccc(-c3ccon3)cc2)n(Cc2ccc(Cl)cc2)c(=O)n1CCN1CCOCC1] | I-287 | 509 | 1.30 | 1 |
| 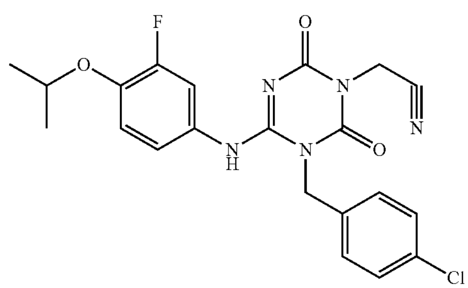 [SMILES: CC(C)Oc1ccc(Nc2nc(=O)n(CC#N)c(=O)n2Cc2ccc(Cl)cc2)cc1F] | I-288 | 444 | 2.15 | 1 |
| 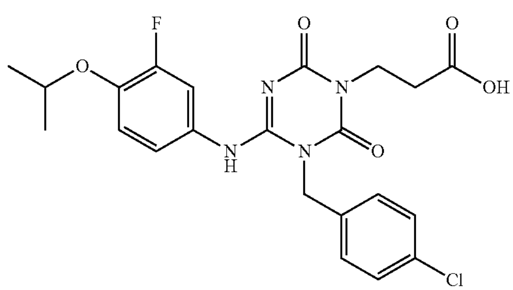 [SMILES: CC(C)Oc1ccc(Nc2nc(=O)n(CCC(=O)O)c(=O)n2Cc2ccc(Cl)cc2)cc1F] | I-289 | 477 | 2.00 | 1 |
| 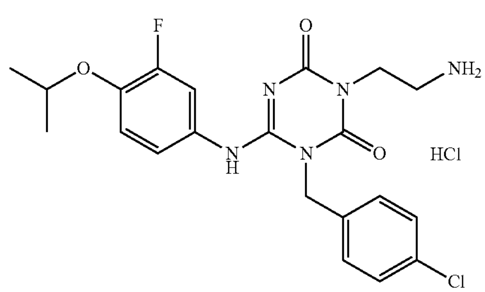 [SMILES: CC(C)Oc1ccc(Nc2nc(=O)n(CCN)c(=O)n2Cc2ccc(Cl)cc2)cc1F ; Cl] | I-290 | 448 | 1.40 | 1 |

TABLE 62

| Chemical Structure | Compound No. | [M + H] | Retention time (min) | Method |
|---|---|---|---|---|
| 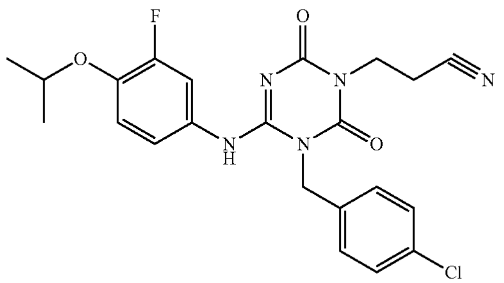 [SMILES: CC(C)Oc1ccc(Nc2nc(=O)n(CCC#N)c(=O)n2Cc2ccc(Cl)cc2)cc1F] | I-291 | 458 | 2.15 | 1 |
| 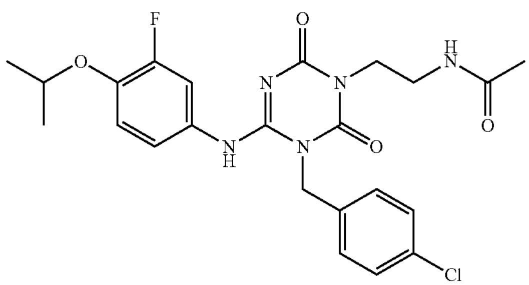 [SMILES: CC(=O)NCCn1c(=O)nc(Nc2ccc(OC(C)C)c(F)c2)n(Cc2ccc(Cl)cc2)c1=O] | I-292 | 489 | 1.90 | 1 |
| 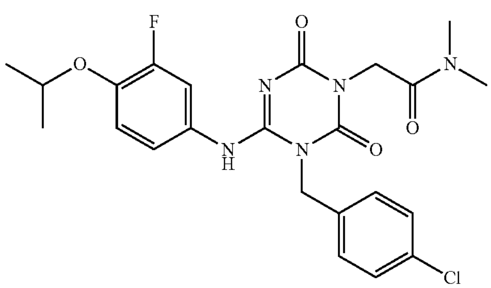 [SMILES: CC(C)Oc1ccc(Nc2nc(=O)n(CC(=O)N(C)C)c(=O)n2Cc2ccc(Cl)cc2)cc1F] | I-293 | 490 | 2.00 | 1 |
| 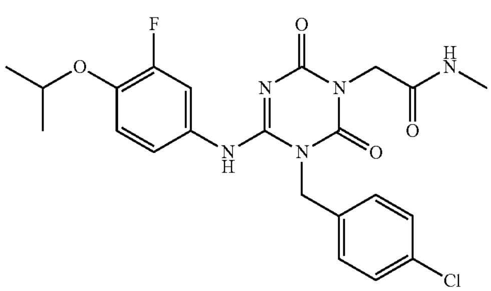 [SMILES: CNC(=O)Cn1c(=O)nc(Nc2ccc(OC(C)C)c(F)c2)n(Cc2ccc(Cl)cc2)c1=O] | I-294 | 476 | 1.91 | 1 |
| 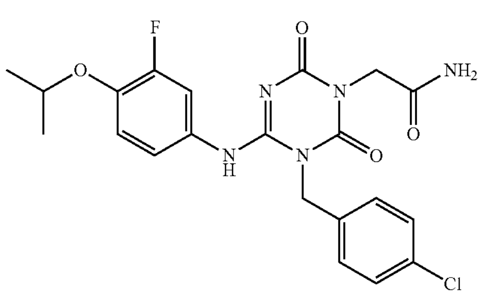 [SMILES: CC(C)Oc1ccc(Nc2nc(=O)n(CC(N)=O)c(=O)n2Cc2ccc(Cl)cc2)cc1F] | I-295 | 462 | 1.85 | 1 |

TABLE 63

| Chemical Structure | Compound No. | [M + H] | Retention time (min) | Method |
|---|---|---|---|---|
| 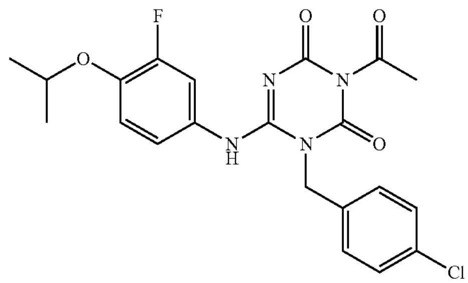 [SMILES: CC(=O)n1c(=O)nc(Nc2ccc(OC(C)C)c(F)c2)n(Cc2ccc(Cl)cc2)c1=O] | I-296 | 447 | 2.18 | 1 |
| 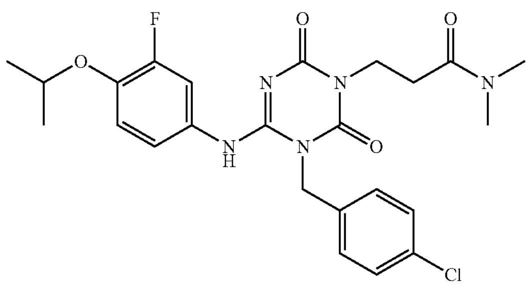 [SMILES: CC(C)Oc1ccc(Nc2nc(=O)n(CCC(=O)N(C)C)c(=O)n2Cc2ccc(Cl)cc2)cc1F] | I-297 | 504 | 2.04 | 1 |
| 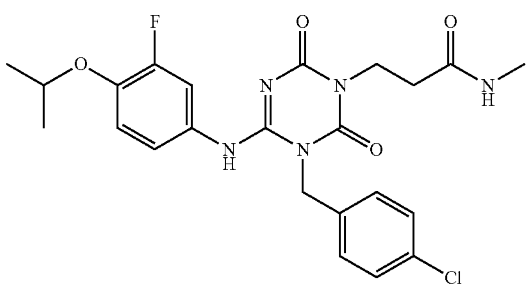 [SMILES: CNC(=O)CCn1c(=O)nc(Nc2ccc(OC(C)C)c(F)c2)n(Cc2ccc(Cl)cc2)c1=O] | I-298 | 490 | 1.90 | 1 |
| 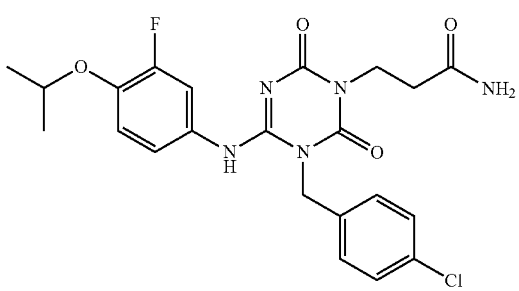 [SMILES: CC(C)Oc1ccc(Nc2nc(=O)n(CCC(N)=O)c(=O)n2Cc2ccc(Cl)cc2)cc1F] | I-299 | 476 | 1.86 | 1 |
| 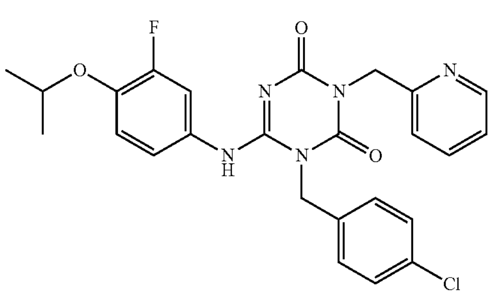 [SMILES: CC(C)Oc1ccc(Nc2nc(=O)n(Cc3ccccn3)c(=O)n2Cc2ccc(Cl)cc2)cc1F] | I-300 | 496 | 2.06 | 1 |

TABLE 64

| Chemical Structure | Compound No. | [M + H] | Retention time (min) | Method |
|---|---|---|---|---|
| 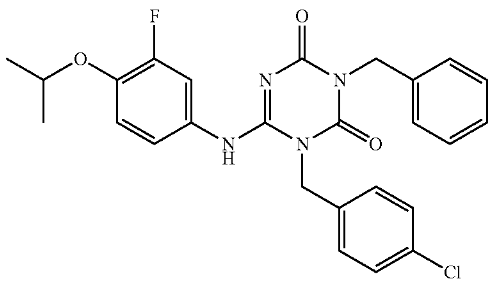 [SMILES: CC(C)Oc1ccc(Nc2nc(=O)n(Cc3ccccc3)c(=O)n2Cc2ccc(Cl)cc2)cc1F] | I-301 | 495 | 2.53 | 1 |
| 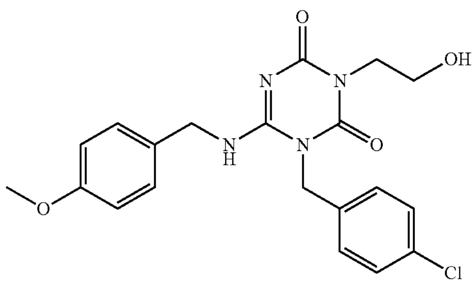 [SMILES: COc1ccc(CNc2nc(=O)n(CCO)c(=O)n2Cc2ccc(Cl)cc2)cc1] | I-302 | 417 | 1.50 | 1 |
| | I-303 | 417 | 1.60 | 1 |
| 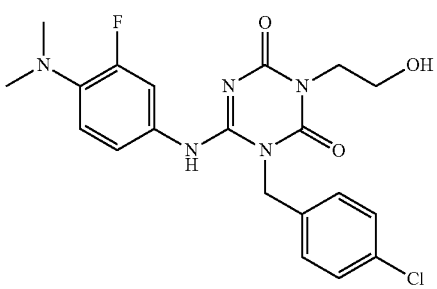 [SMILES: CN(C)c1ccc(Nc2nc(=O)n(CCO)c(=O)n2Cc2ccc(Cl)cc2)cc1F] | I-304 | 434 | 1.50 | 1 |
| 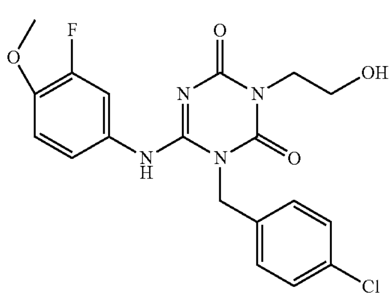 [SMILES: COc1ccc(Nc2nc(=O)n(CCO)c(=O)n2Cc2ccc(Cl)cc2)cc1F] | I-305 | 421 | 1.69 | 1 |

TABLE 65

| Chemical Structure | Compound No. | [M + H] | Retention time (min) | Method |
|---|---|---|---|---|
| 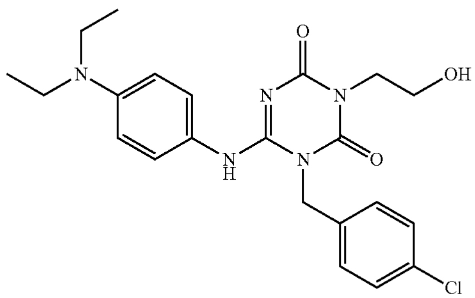 [SMILES: CCN(CC)c1ccc(Nc2nc(=O)n(CCO)c(=O)n2Cc2ccc(Cl)cc2)cc1] | I-306 | 444 | 1.11 | 1 |
| 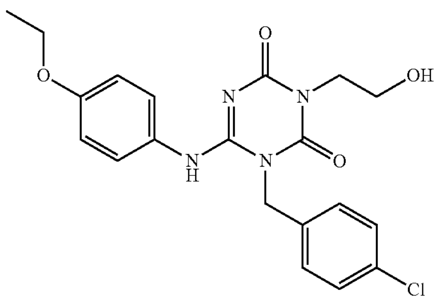 [SMILES: CCOc1ccc(Nc2nc(=O)n(CCO)c(=O)n2Cc2ccc(Cl)cc2)cc1] | I-307 | 417 | 1.72 | 1 |
| 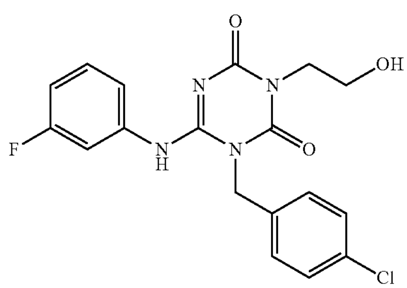 [SMILES: O=c1nc(Nc2cccc(F)c2)n(Cc2ccc(Cl)cc2)c(=O)n1CCO] | I-308 | 391 | 1.80 | 1 |
| 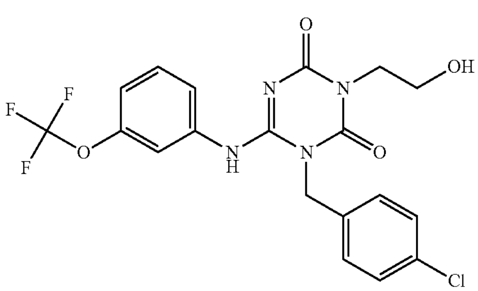 [SMILES: O=c1nc(Nc2cccc(OC(F)(F)F)c2)n(Cc2ccc(Cl)cc2)c(=O)n1CCO] | I-309 | 457 | 2.09 | 1 |
| 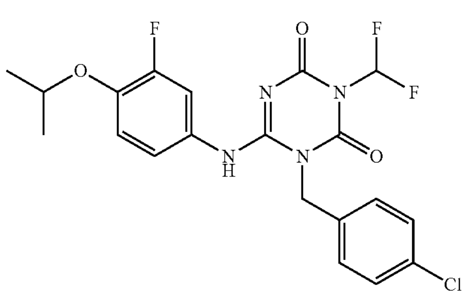 [SMILES: CC(C)Oc1ccc(Nc2nc(=O)n(C(F)F)c(=O)n2Cc2ccc(Cl)cc2)cc1F] | I-310 | 455 | 2.21 | 1 |

TABLE 66

| Chemical Structure | Compound No. | [M + H] | Retention time (min) | Method |
|---|---|---|---|---|
| (piperidinyl-phenyl-NH-triazinedione-N-CH2CH2OH, N-CH2-C6H4-Cl) | I-311 | 456 | 1.14 | 1 |
| (3-fluoro-4-ethoxyphenyl-NH-triazinedione-N-CH2CH2OH, N-CH2-C6H4-Cl) | I-312 | 435 | 1.83 | 1 |
| (3-trifluoromethylphenyl-NH-triazinedione-N-CH2CH2OH, N-CH2-C6H4-Cl) | I-313 | 441 | 2.00 | 2 |
| (3-isoxazolyl-phenyl-NH-triazinedione-N-CH2CH2OH, N-CH2-C6H4-Cl) | I-314 | 440 | 1.70 | 2 |
| (3-fluoro-4-trifluoromethylphenyl-NH-triazinedione-N-CH2CH2OH, N-CH2-C6H4-Cl) | I-315 | 459 | 2.09 | 2 |

TABLE 67
| Chemical Structure | Compound No. | [M + H] | Retention time (min) | Method |
|---|---|---|---|---|
| 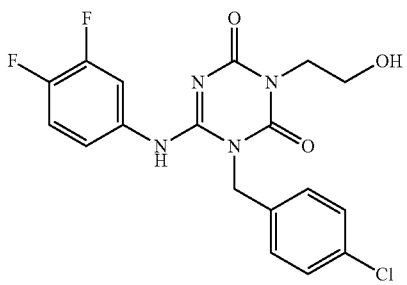 [SMILES: O=c1nc(Nc2ccc(F)c(F)c2)n(Cc2ccc(Cl)cc2)c(=O)n1CCO] | I-316 | 409 | 1.84 | 2 |
| 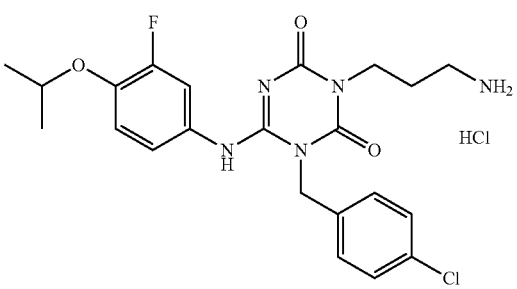 [SMILES: CC(C)Oc1ccc(Nc2nc(=O)n(CCCN)c(=O)n2Cc2ccc(Cl)cc2)cc1F ; Cl] | I-317 | 462 | 1.40 | 2 |
| 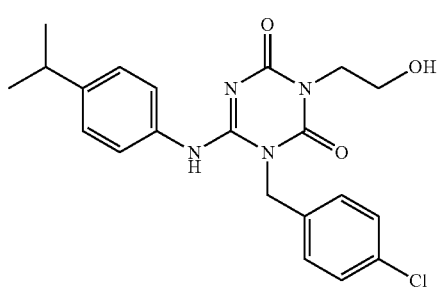 [SMILES: CC(C)c1ccc(Nc2nc(=O)n(CCO)c(=O)n2Cc2ccc(Cl)cc2)cc1] | I-318 | 415 | 2.01 | 2 |
| 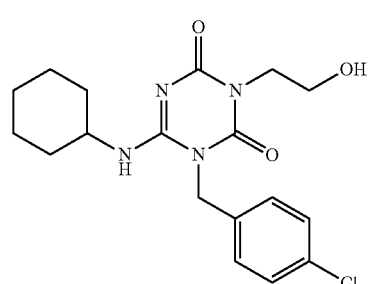 | I-319 | 379 | 1.68 | 2 |
| 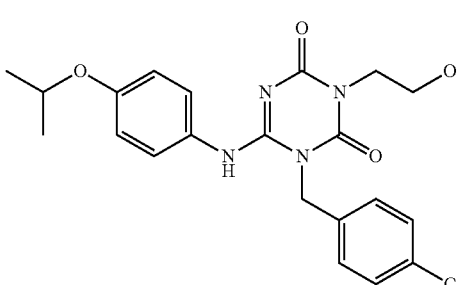 | I-320 | 431 | 1.83 | 2 |

TABLE 68

| Chemical Structure | Compound No. | [M + H] | Retention time (min) | Method |
|---|---|---|---|---|
| 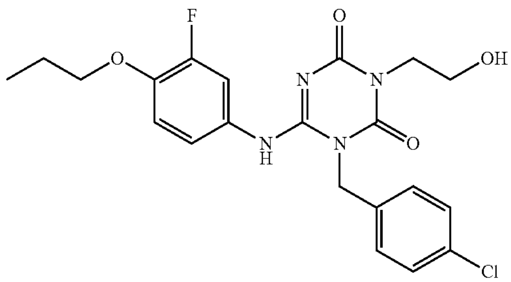 [SMILES: CCCOc1ccc(Nc2nc(=O)n(CCO)c(=O)n2Cc2ccc(Cl)cc2)cc1F] | I-321 | 449 | 1.99 | 2 |
| 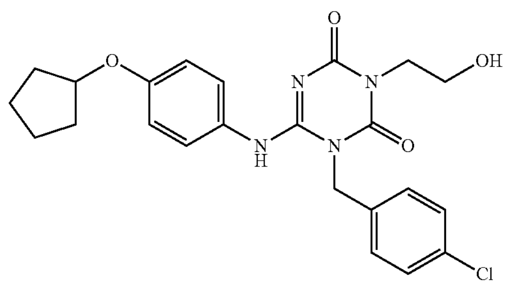 [SMILES: O=c1nc(Nc2ccc(OC3CCCC3)cc2)n(Cc2ccc(Cl)cc2)c(=O)n1CCO] | I-322 | 457 | 2.03 | 2 |
| 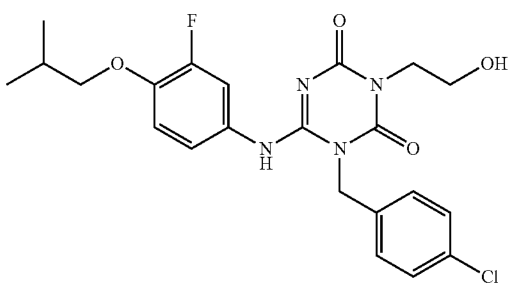 [SMILES: CC(C)COc1ccc(Nc2nc(=O)n(CCO)c(=O)n2Cc2ccc(Cl)cc2)cc1F] | I-323 | 463 | 2.16 | 2 |
| 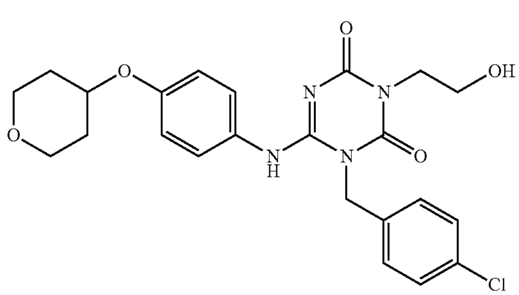 [SMILES: O=c1nc(Nc2ccc(OC3CCOCC3)cc2)n(Cc2ccc(Cl)cc2)c(=O)n1CCO] | I-324 | 473 | 1.61 | 2 |
| 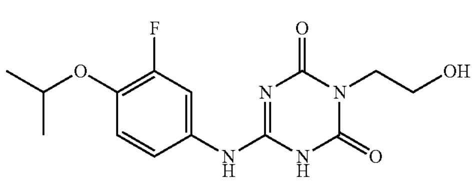 [SMILES: CC(C)Oc1ccc(Nc2nc(=O)n(CCO)c(=O)[nH]2)cc1F] | I-325 | 325 | 1.10 | 2 |

TABLE 69

| Chemical Structure | Compound No. | [M + H] | Retention time (min) | Method |
|---|---|---|---|---|
| 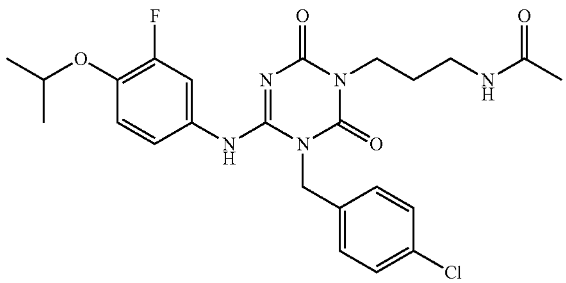 [SMILES: CC(=O)NCCCn1c(=O)nc(Nc2ccc(OC(C)C)c(F)c2)n(Cc2ccc(Cl)cc2)c1=O] | I-326 | 504 | 1.93 | 2 |
| 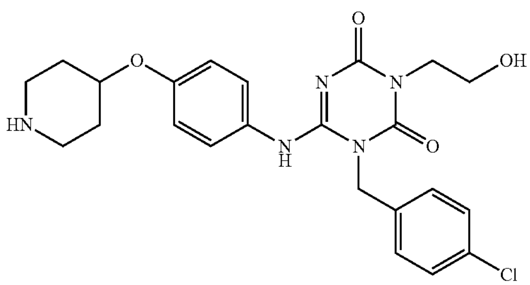 [SMILES: O=c1nc(Nc2ccc(OC3CCNCC3)cc2)n(Cc2ccc(Cl)cc2)c(=O)n1CCO] | I-327 | 472 | 1.03 | 2 |
| 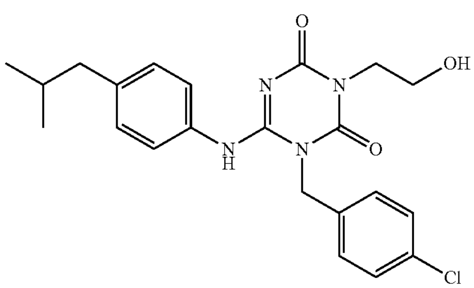 [SMILES: CC(C)Cc1ccc(Nc2nc(=O)n(CCO)c(=O)n2Cc2ccc(Cl)cc2)cc1] | I-328 | 429 | 2.15 | 2 |
| 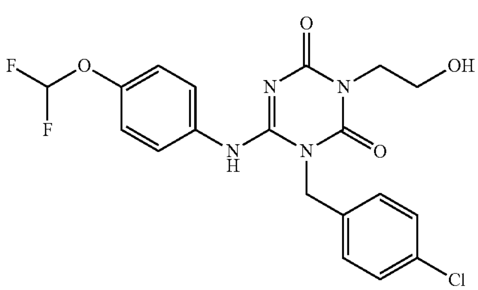 [SMILES: O=c1nc(Nc2ccc(OC(F)F)cc2)n(Cc2ccc(Cl)cc2)c(=O)n1CCO] | I-329 | 439 | 1.80 | 2 |
| 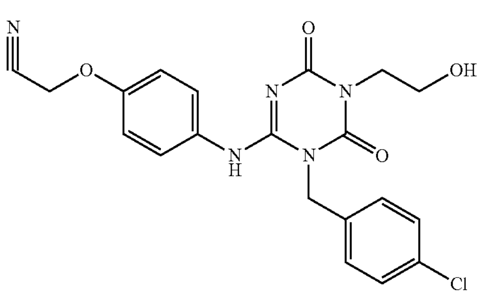 [SMILES: N#CCOc1ccc(Nc2nc(=O)n(CCO)c(=O)n2Cc2ccc(Cl)cc2)cc1] | I-330 | 428 | 1.56 | 2 |

TABLE 70

| Chemical Structure | Compound No. | [M + H] | Retention time (min) | Method |
|---|---|---|---|---|
| 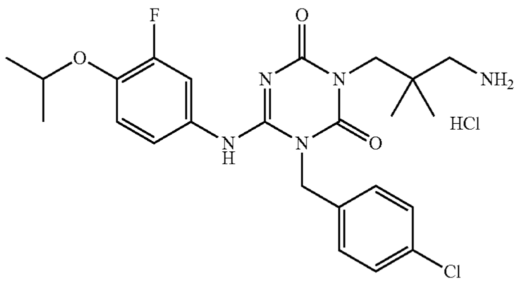 [SMILES: CC(C)Oc1ccc(Nc2nc(=O)n(CC(C)(C)CN)c(=O)n2Cc2ccc(Cl)cc2)cc1F ; Cl] | I-331 | 490 | 1.49 | 2 |
| 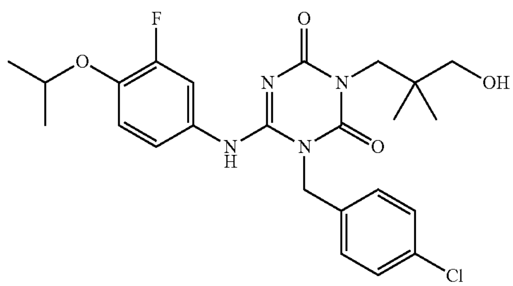 [SMILES: CC(C)Oc1ccc(Nc2nc(=O)n(CC(C)(C)CO)c(=O)n2Cc2ccc(Cl)cc2)cc1F] | I-332 | 491 | 2.26 | 2 |
| 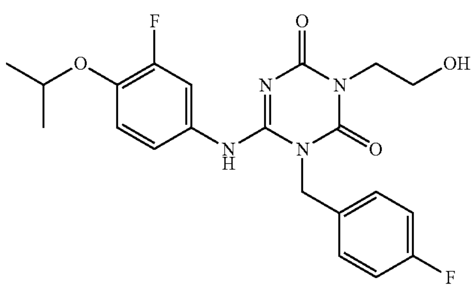 [SMILES: CC(C)Oc1ccc(Nc2nc(=O)n(CCO)c(=O)n2Cc2ccc(F)cc2)cc1F] | I-333 | 433 | 1.80 | 2 |
| 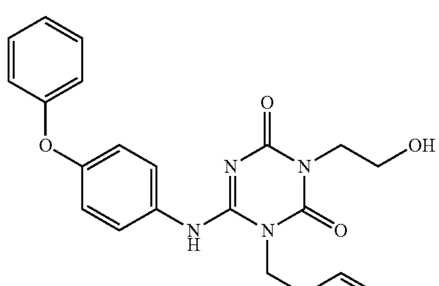 | I-334 | 465 | 2.35 | 3 |
| 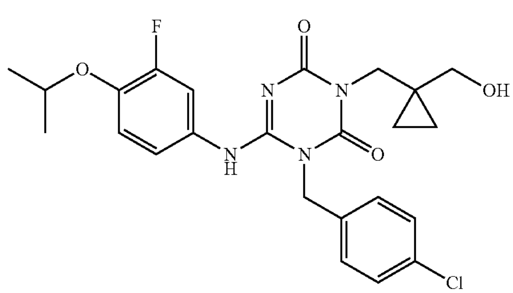 [SMILES: CC(C)Oc1ccc(Nc2nc(=O)n(CC3(CO)CC3)c(=O)n2Cc2ccc(Cl)cc2)cc1F] | I-335 | 489 | 2.19 | 2 |

TABLE 71

| Chemical Structure | Compound No. | [M + H] | Retention time (min) | Method |
|---|---|---|---|---|
| 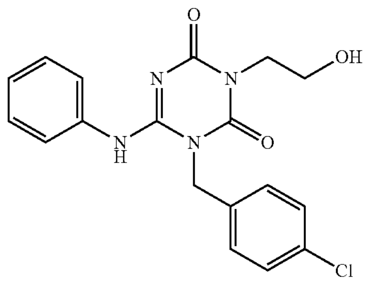 [SMILES: O=c1nc(Nc2ccccc2)n(Cc2ccc(Cl)cc2)c(=O)n1CCO] | I-336 | 373 | 1.61 | 2 |
| 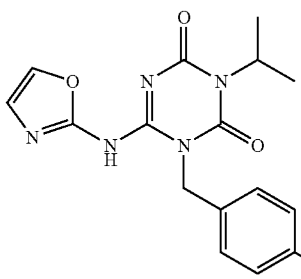 | I-337 | 362 | 2.39 | 2 |
| 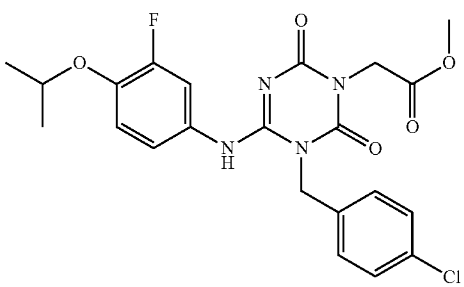 [SMILES: COC(=O)Cn1c(=O)nc(Nc2ccc(OC(C)C)c(F)c2)n(Cc2ccc(Cl)cc2)c1=O] | I-338 | 477 | 2.45 | 3 |
| 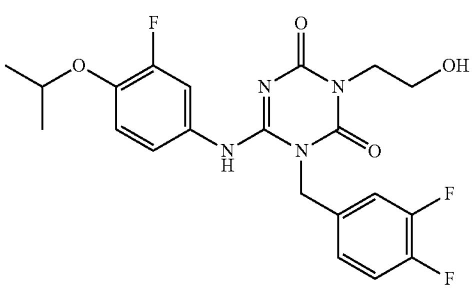 [SMILES: CC(C)Oc1ccc(Nc2nc(=O)n(CCO)c(=O)n2Cc2ccc(F)c(F)c2)cc1F] | I-339 | 451 | 1.88 | 2 |
| 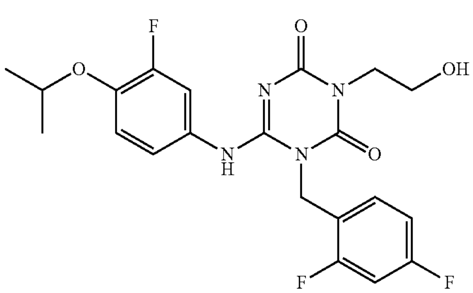 [SMILES: CC(C)Oc1ccc(Nc2nc(=O)n(CCO)c(=O)n2Cc2ccc(F)cc2F)cc1F] | I-340 | 451 | 1.84 | 2 |

TABLE 72

| Chemical Structure | Compound No. | [M + H] | Retention time (min) | Method |
|---|---|---|---|---|
| 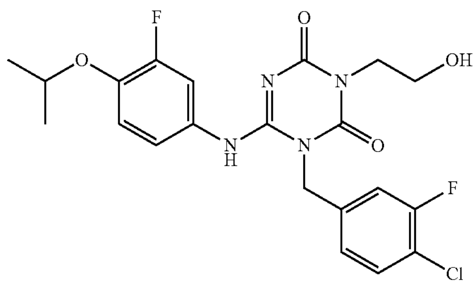 [SMILES: CC(C)Oc1ccc(Nc2nc(=O)n(CCO)c(=O)n2Cc2ccc(Cl)c(F)c2)cc1F] | I-341 | 467 | 2.01 | 2 |
| 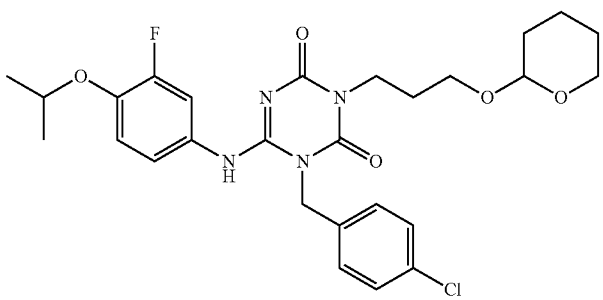 [SMILES: CC(C)Oc1ccc(Nc2nc(=O)n(CCCOC3CCCCO3)c(=O)n2Cc2ccc(Cl)cc2)cc1F] | I-342 | 548 | 2.81 | 3 |
| 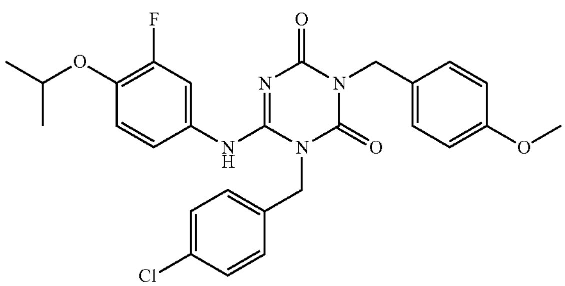 [SMILES: COc1ccc(Cn2c(=O)nc(Nc3ccc(OC(C)C)c(F)c3)n(Cc3ccc(Cl)cc3)c2=O)cc1] | I-343 | 525 | 2.50 | 2 |
| 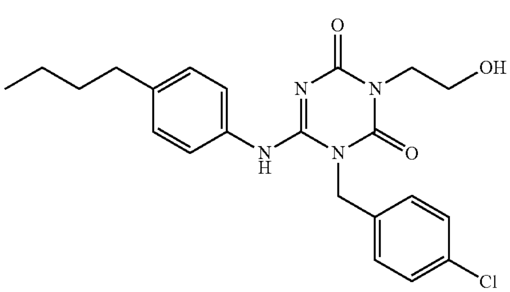 [SMILES: CCCCc1ccc(Nc2nc(=O)n(CCO)c(=O)n2Cc2ccc(Cl)cc2)cc1] | I-344 | 429 | 2.48 | 3 |
| 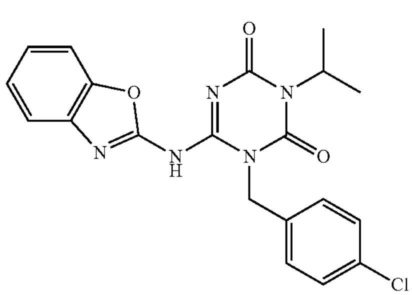 [SMILES: CC(C)n1c(=O)nc(Nc2nc3ccccc3o2)n(Cc2ccc(Cl)cc2)c1=O] | I-345 | 412 | 2.74 | 2 |

TABLE 73

| Chemical Structure | Compound No. | [M + H] | Retention time (min) | Method |
|---|---|---|---|---|
| 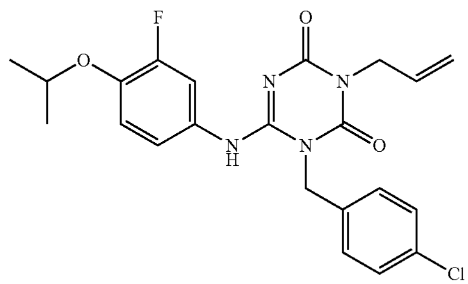 [SMILES: C=CCn1c(=O)nc(Nc2ccc(OC(C)C)c(F)c2)n(Cc2ccc(Cl)cc2)c1=O] | I-346 | 445 | 2.34 | 2 |
| 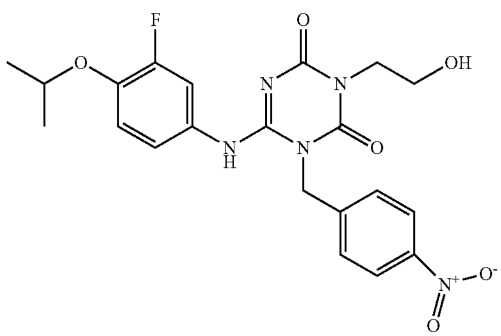 [SMILES: CC(C)Oc1ccc(Nc2nc(=O)n(CCO)c(=O)n2Cc2ccc([N+](=O)[O-])cc2)cc1F] | I-347 | 460 | 1.78 | 2 |
| 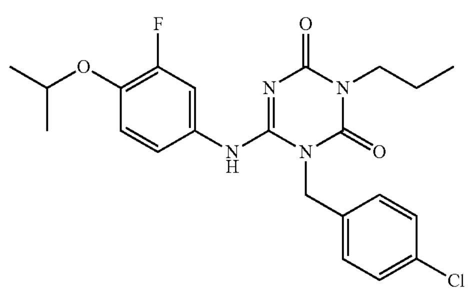 [SMILES: CCCn1c(=O)nc(Nc2ccc(OC(C)C)c(F)c2)n(Cc2ccc(Cl)cc2)c1=O] | I-348 | 447 | 2.45 | 2 |
| 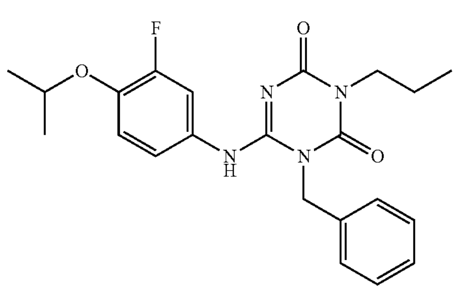 [SMILES: CCCn1c(=O)nc(Nc2ccc(OC(C)C)c(F)c2)n(Cc2ccccc2)c1=O] | I-349 | 413 | 2.20 | 2 |

TABLE 73-continued

| Chemical Structure | Compound No. | [M + H] | Retention time (min) | Method |
|---|---|---|---|---|
| 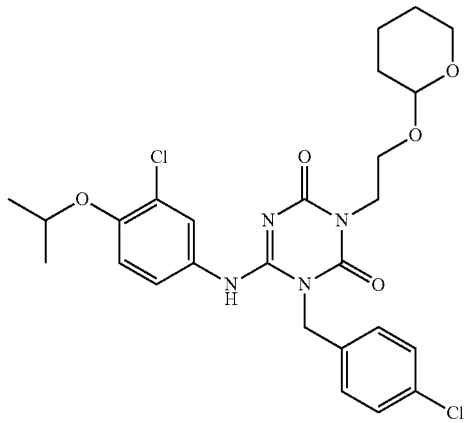 [SMILES: CC(C)Oc1ccc(Nc2nc(=O)n(CCOC3CCCCO3)c(=O)n2Cc2ccc(Cl)cc2)cc1Cl] | I-350 | 549 | 2.55 | 2 |

TABLE 74

| Chemical Structure | Compound No. | [M + H] | Retention time (min) | Method |
|---|---|---|---|---|
| 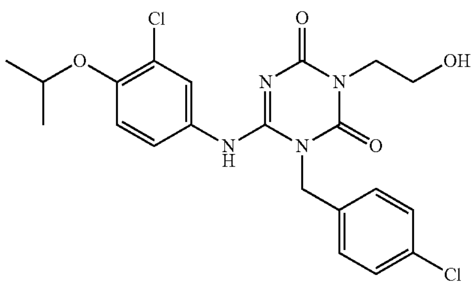 [SMILES: CC(C)Oc1ccc(Nc2nc(=O)n(CCO)c(=O)n2Cc2ccc(Cl)cc2)cc1Cl] | I-351 | 465 | 2.06 | 2 |
| 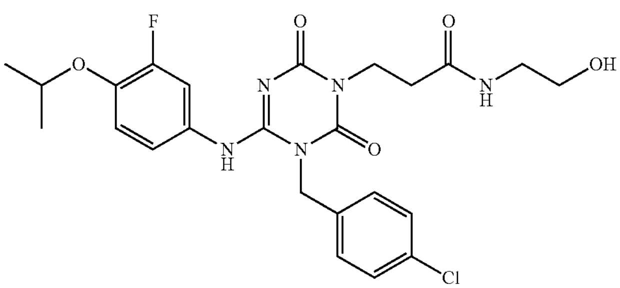 [SMILES: CC(C)Oc1ccc(Nc2nc(=O)n(CCC(=O)NCCO)c(=O)n2Cc2ccc(Cl)cc2)cc1F] | I-352 | 520 | 1.78 | 2 |
| 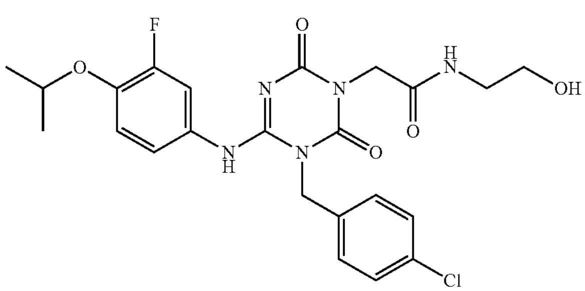 [SMILES: CC(C)Oc1ccc(Nc2nc(=O)n(CC(=O)NCCO)c(=O)n2Cc2ccc(Cl)cc2)cc1F] | I-353 | 506 | 1.77 | 2 |

TABLE 74-continued

| Chemical Structure | Compound No. | [M + H] | Retention time (min) | Method |
|---|---|---|---|---|
| (structure) | I-354 | 521 | 2.47 | 2 |
| (structure) | I-355 | 493 | 2.10 | 2 |

TABLE 75

| Chemical Structure | Compound No. | [M + H] | Retention time (min) | Method |
|---|---|---|---|---|
| (structure) | I-356 | 505 | 2.33 | 2 |
| (structure) | I-357 | 455 | 2.07 | 2 |

TABLE 75-continued

| Chemical Structure | Compound No. | [M + H] | Retention time (min) | Method |
|---|---|---|---|---|
| (isobutyl-phenyl-NH / triazine-dione / 3-hydroxypropyl / 4-chlorobenzyl) | I-358 | 442 | 2.23 | 2 |
| (isopropoxy-phenyl-NH / triazine-dione / 3-hydroxypropyl / 4-chlorobenzyl) | I-359 | 445 | 1.85 | 2 |
| (difluoromethoxy-phenyl-NH / triazine-dione / 3-hydroxypropyl / 4-chlorobenzyl) | I-360 | 453 | 1.84 | 2 |

TABLE 76

| Chemical Structure | Compound No. | [M + H] | Retention time (min) | Method |
|---|---|---|---|---|
| (ethoxy-phenyl-NH / triazine-dione / 3-hydroxypropyl / 4-chlorobenzyl) | I-361 | 431 | 1.77 | 2 |

TABLE 76-continued

| Chemical Structure | Compound No. | [M + H] | Retention time (min) | Method |
|---|---|---|---|---|
| (structure) | I-362 | 479 | 2.12 | 2 |
| (structure) | I-363 | 491 | 2.05 | 2 |
| (structure) | I-364 | 505 | 2.12 | 2 |
| (structure) | I-365 | 477 | 2.03 | 2 |

TABLE 77

| Chemical Structure | Compound No. | [M + H] | Retention time (min) | Method |
|---|---|---|---|---|
| (structure) | I-366 | 473 | 2.33 | 3 |

TABLE 77-continued

| Chemical Structure | Compound No. | [M + H] | Retention time (min) | Method |
|---|---|---|---|---|
| (structure) | I-367 | 485 | 2.17 | 3 |
| (structure) | I-368 | 475 | 2.00 | 3 |
| (structure) | I-369 | 510 | 2.24 | 3 |
| (structure) | I-370 | 483 | 1.98 | 3 |

TABLE 78

| Chemical Structure | Compound No. | [M + H] | Retention time (min) | Method |
|---|---|---|---|---|
| 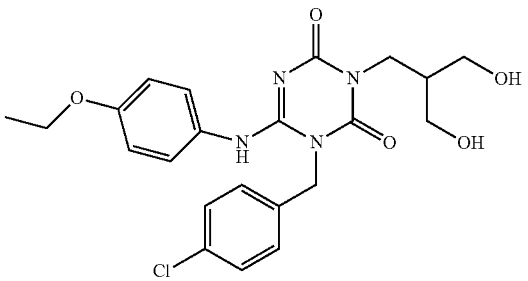 [SMILES: CCOc1ccc(Nc2nc(=O)n(CC(CO)CO)c(=O)n2Cc2ccc(Cl)cc2)cc1] | I-371 | 461 | 1.88 | 3 |
| 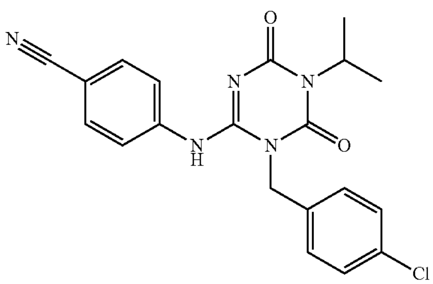 [SMILES: CC(C)n1c(=O)nc(Nc2ccc(C#N)cc2)n(Cc2ccc(Cl)cc2)c1=O] | I-372 | 396 | 2.27 | 2 |
| 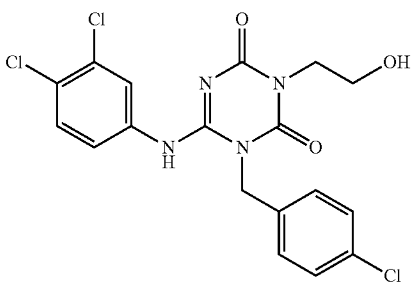 [SMILES: O=c1nc(Nc2ccc(Cl)c(Cl)c2)n(Cc2ccc(Cl)cc2)c(=O)n1CCO] | I-373 | 443 | 2.17 | 2 |
| 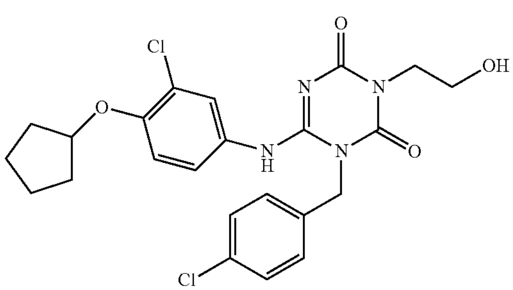 [SMILES: O=c1nc(Nc2ccc(OC3CCCC3)c(Cl)c2)n(Cc2ccc(Cl)cc2)c(=O)n1CCO] | I-374 | 491 | 2.28 | 2 |
| 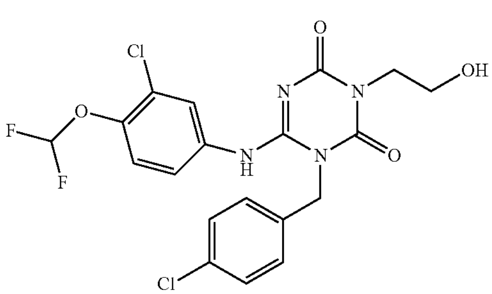 [SMILES: O=c1nc(Nc2ccc(OC(F)F)c(Cl)c2)n(Cc2ccc(Cl)cc2)c(=O)n1CCO] | I-375 | 473 | 2.32 | 3 |

TABLE 79

| Chemical Structure | Compound No. | [M + H] | Retention time (min) | Method |
|---|---|---|---|---|
| 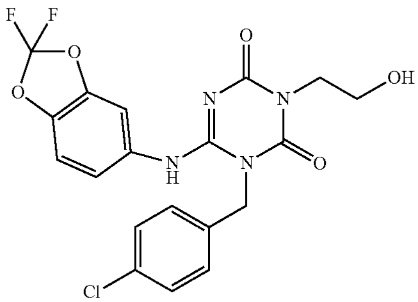 [SMILES: O=c1nc(Nc2ccc3c(c2)OC(F)(F)O3)n(Cc2ccc(Cl)cc2)c(=O)n1CCO] | I-376 | 453 | 2.30 | 3 |
| 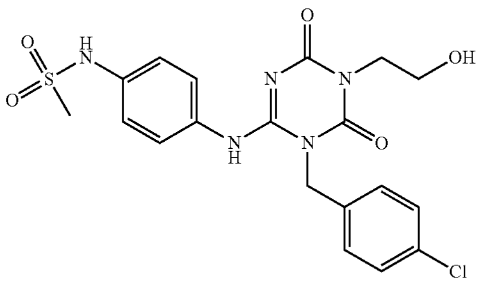 [SMILES: CS(=O)(=O)Nc1ccc(Nc2nc(=O)n(CCO)c(=O)n2Cc2ccc(Cl)cc2)cc1] | I-377 | 446 | 1.41 | 2 |
| 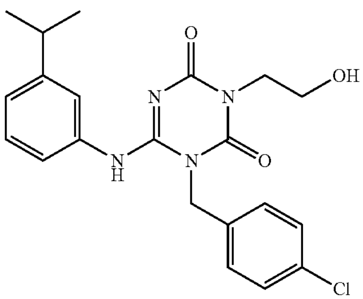 [SMILES: CC(C)c1cccc(Nc2nc(=O)n(CCO)c(=O)n2Cc2ccc(Cl)cc2)c1] | I-378 | 415 | 2.02 | 2 |
| 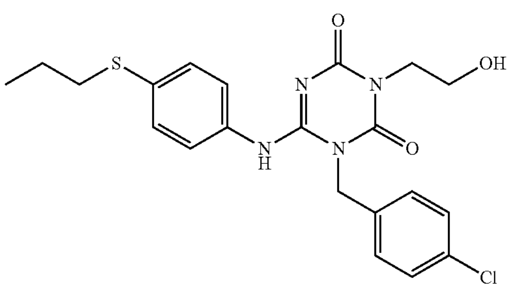 | I-379 | 447 | 2.11 | 2 |
| 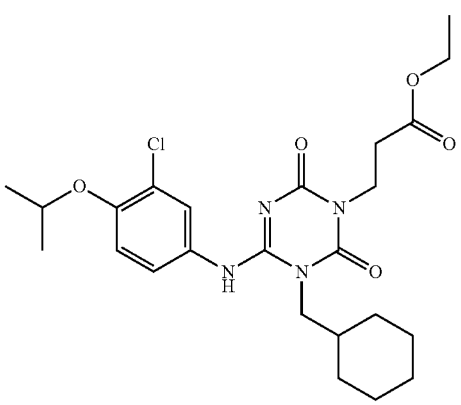 [SMILES: CCOC(=O)CCn1c(=O)nc(Nc2ccc(OC(C)C)c(Cl)c2)n(CC2CCCCC2)c1=O] | I-380 | 493 | 2.49 | 2 |

TABLE 80
| Chemical Structure | Compound No. | [M + H] | Retention time (min) | Method |
|---|---|---|---|---|
| 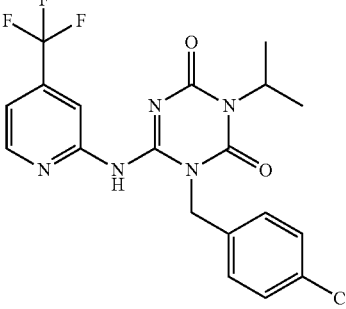 | I-381 | 440 | 3.04 | 3 |
| 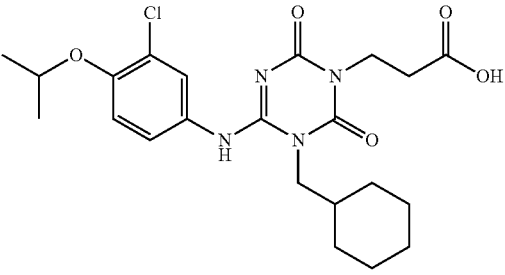 [SMILES: CC(C)Oc1ccc(Nc2nc(=O)n(CCC(=O)O)c(=O)n2CC2CCCCC2)cc1Cl] | I-382 | 465 | 2.09 | 2 |
| 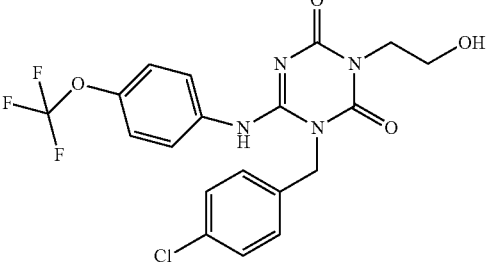 | I-383 | 457 | 2.32 | 3 |
| 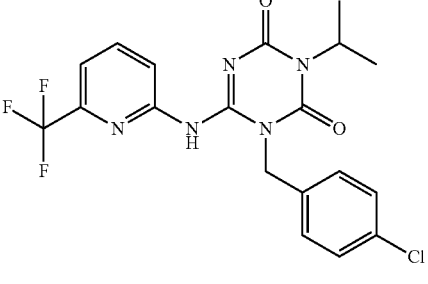 | I-384 | 440 | 2.77 | 2 |
| 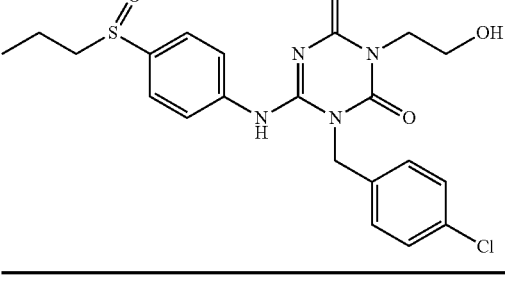 | I-385 | 463 | 1.56 | 2 |

TABLE 81

| Chemical Structure | Compound No. | [M + H] | Retention time (min) | Method |
|---|---|---|---|---|
| 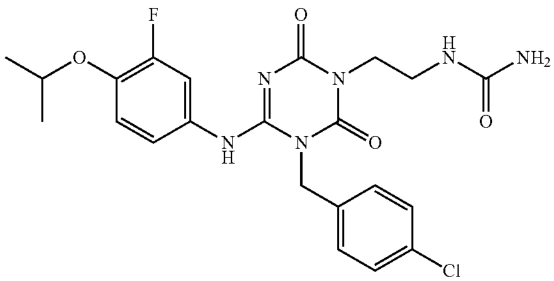 [SMILES: CC(C)Oc1ccc(Nc2nc(=O)n(CCNC(N)=O)c(=O)n2Cc2ccc(Cl)cc2)cc1F] | I-386 | 491 | 1.81 | 2 |
| 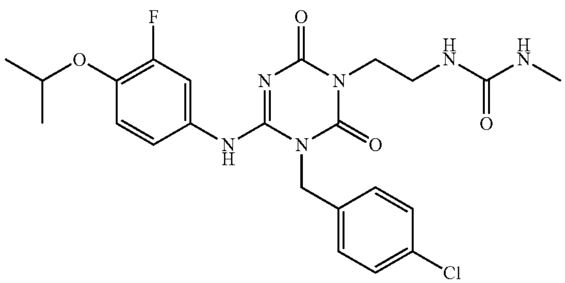 [SMILES: CNC(=O)NCCn1c(=O)nc(Nc2ccc(OC(C)C)c(F)c2)n(Cc2ccc(Cl)cc2)c1=O] | I-387 | 505 | 1.86 | 2 |
| 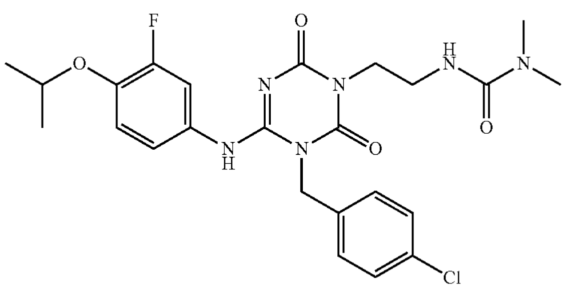 [SMILES: CC(C)Oc1ccc(Nc2nc(=O)n(CCNC(=O)N(C)C)c(=O)n2Cc2ccc(Cl)cc2)cc1F] | I-388 | 519 | 1.98 | 2 |
| 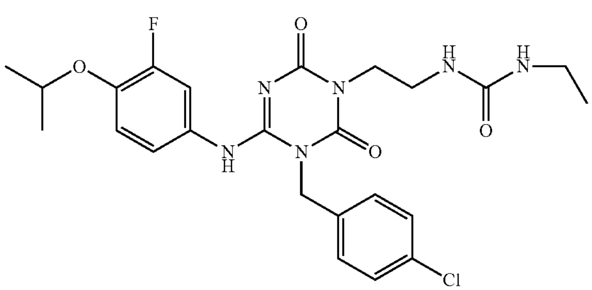 [SMILES: CCNC(=O)NCCn1c(=O)nc(Nc2ccc(OC(C)C)c(F)c2)n(Cc2ccc(Cl)cc2)c1=O] | I-389 | 519 | 1.94 | 2 |
| 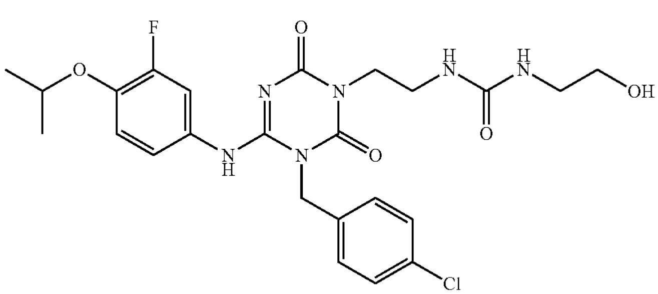 [SMILES: CC(C)Oc1ccc(Nc2nc(=O)n(CCNC(=O)NCCO)c(=O)n2Cc2ccc(Cl)cc2)cc1F] | I-390 | 535 | 1.77 | 2 |

TABLE 82
| Chemical Structure | Compound No. | [M + H] | Retention time (min) | Method |
|---|---|---|---|---|
| 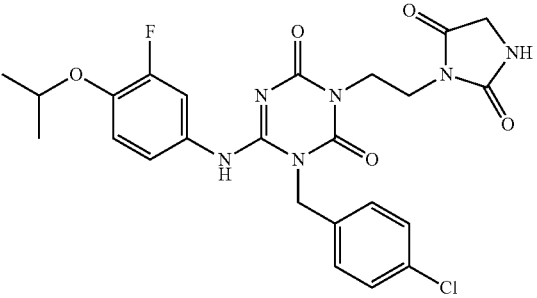 [SMILES: CC(C)Oc1ccc(Nc2nc(=O)n(CCN3C(=O)CNC3=O)c(=O)n2Cc2ccc(Cl)cc2)cc1F] | I-391 | 531 | 1.89 | 2 |
| 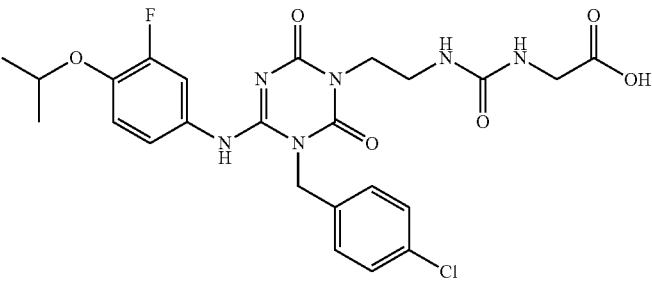 [SMILES: CC(C)Oc1ccc(Nc2nc(=O)n(CCNC(=O)NCC(=O)O)c(=O)n2Cc2ccc(Cl)cc2)cc1F] | I-392 | 549 | 1.77 | 2 |
| 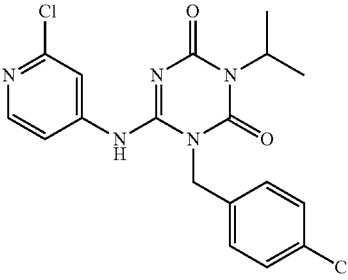 | I-393 | 406 | 2.28 | 2 |
| 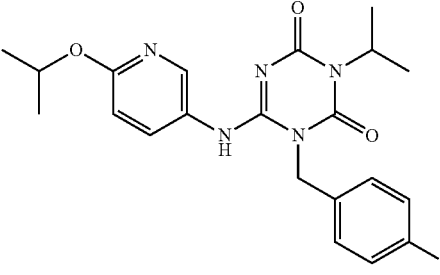 | I-394 | 430 | 2.30 | 2 |
| 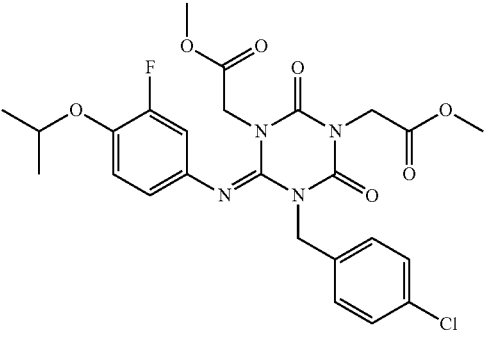 [SMILES: COC(=O)Cn1c(=O)n(CC(=O)OC)/c(=N\c2ccc(OC(C)C)c(F)c2)n(Cc2ccc(Cl)cc2)c1=O] | I-395 | 549 | 2.77 | 3 |

TABLE 83

| Chemical Structure | Compound No. | [M + H] | Retention time (min) | Method |
|---|---|---|---|---|
| 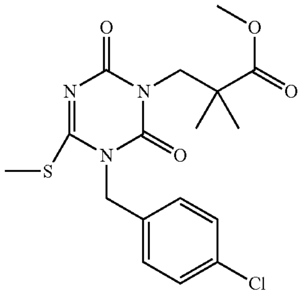 [SMILES: COC(=O)C(C)(C)Cn1c(=O)nc(SC)n(Cc2ccc(Cl)cc2)c1=O] | I-396 | 398 | 2.03 | 2 |
| 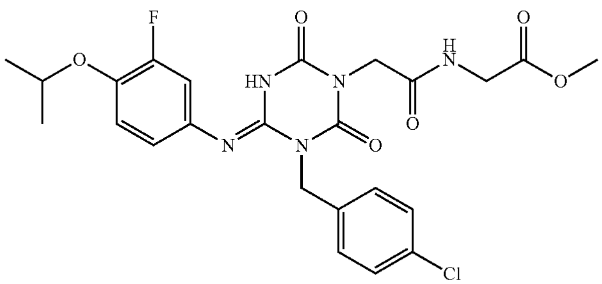 [SMILES: COC(=O)CNC(=O)Cn1c(=O)[nH]/c(=N\c2ccc(OC(C)C)c(F)c2)n(Cc2ccc(Cl)cc2)c1=O] | I-397 | 534 | 1.94 | 2 |
| 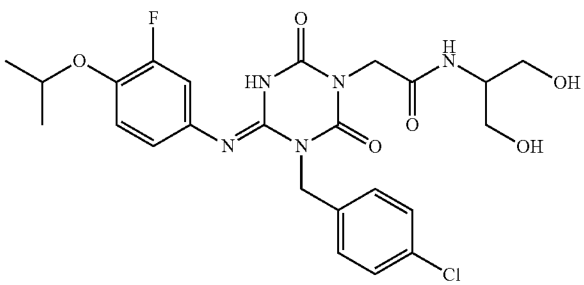 [SMILES: CC(C)Oc1ccc(/N=c2\[nH]c(=O)n(CC(=O)NC(CO)CO)c(=O)n2Cc2ccc(Cl)cc2)cc1F] | I-398 | 536 | 1.69 | 2 |
| 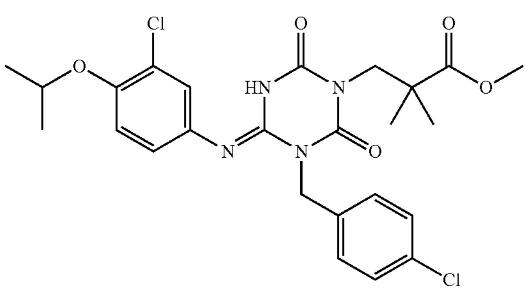 [SMILES: COC(=O)C(C)(C)Cn1c(=O)[nH]/c(=N\c2ccc(OC(C)C)c(Cl)c2)n(Cc2ccc(Cl)cc2)c1=O] | I-399 | 535 | 2.51 | 2 |
| 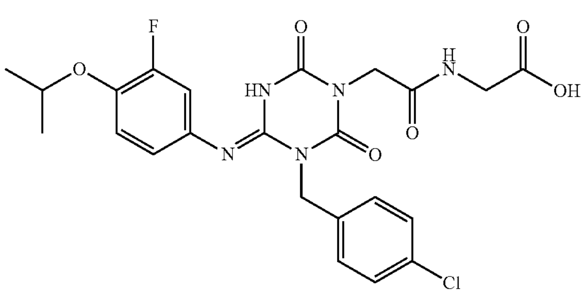 [SMILES: CC(C)Oc1ccc(/N=c2\[nH]c(=O)n(CC(=O)NCC(=O)O)c(=O)n2Cc2ccc(Cl)cc2)cc1F] | I-400 | 520 | 1.81 | 2 |

TABLE 84

| Chemical Structure | Compound No. | [M + H] | Retention time (min) | Method |
|---|---|---|---|---|
| 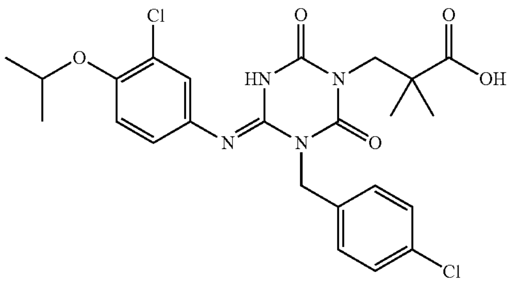 [SMILES: CC(C)Oc1ccc(/N=c2\[nH]c(=O)n(CC(C)(C)C(=O)O)c(=O)n2Cc2ccc(Cl)cc2)cc1Cl] | I-401 | 521 | 2.24 | 2 |
| 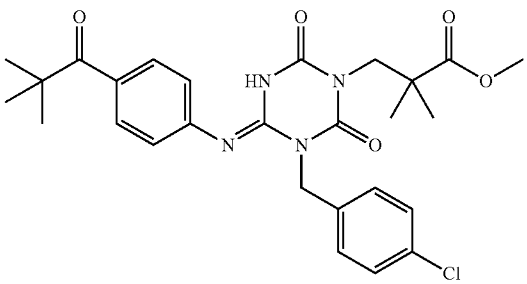 [SMILES: COC(=O)C(C)(C)Cn1c(=O)[nH]/c(=N\c2ccc(C(=O)C(C)(C)C)cc2)n(Cc2ccc(Cl)cc2)c1=O] | I-402 | 527 | 2.49 | 2 |
| 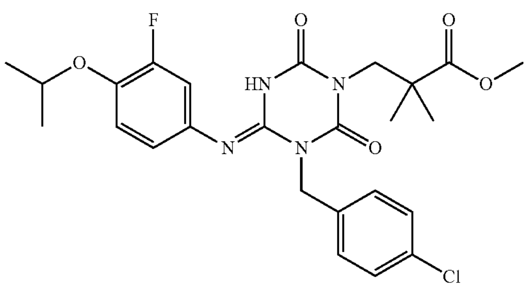 [SMILES: COC(=O)C(C)(C)Cn1c(=O)[nH]/c(=N\c2ccc(OC(C)C)c(F)c2)n(Cc2ccc(Cl)cc2)c1=O] | I-403 | 519 | 2.40 | 2 |
| 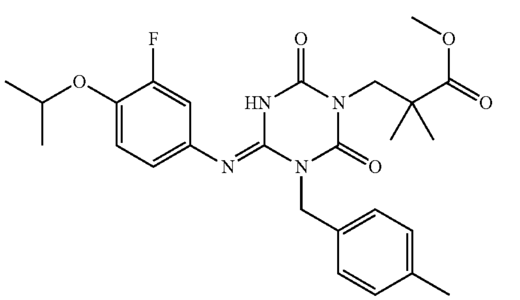 [SMILES: COC(=O)C(C)(C)Cn1c(=O)[nH]/c(=N\c2ccc(OC(C)C)c(F)c2)n(Cc2ccc(C)cc2)c1=O] | I-404 | 499 | 2.32 | 2 |
| 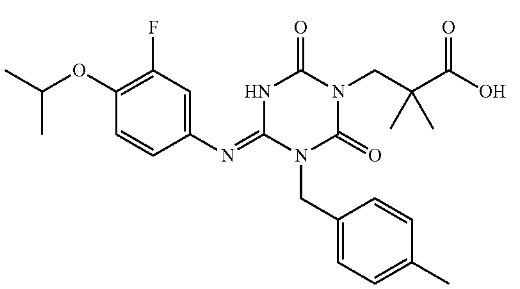 [SMILES: Cc1ccc(Cn2c(=O)n(CC(C)(C)C(=O)O)c(=O)[nH]/c2=N\c2ccc(OC(C)C)c(F)c2)cc1] | I-405 | 485 | 2.04 | 2 |

TABLE 85

| Chemical Structure | Compound No. | [M + H] | Retention time (min) | Method |
|---|---|---|---|---|
| 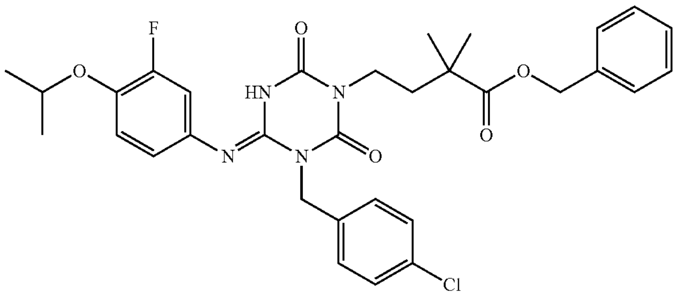 [SMILES: CC(C)Oc1ccc(/N=c2\[nH]c(=O)n(CCC(C)(C)C(=O)OCc3ccccc3)c(=O)n2Cc2ccc(Cl)cc2)cc1F] | I-406 | 609 | 2.74 | 2 |
| 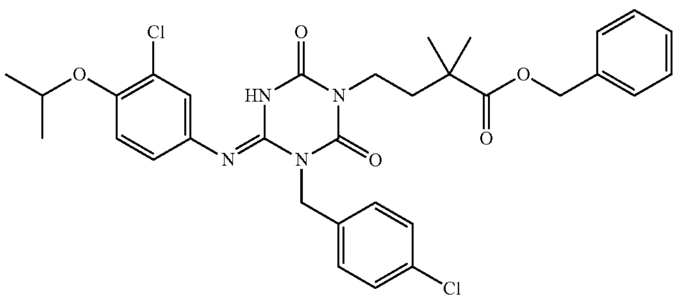 | I-407 | 625 | 2.84 | 2 |
| 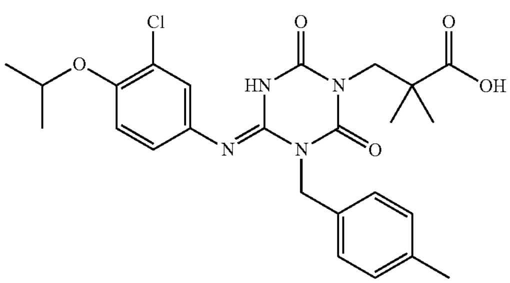 [SMILES: Cc1ccc(Cn2c(=O)n(CC(C)(C)C(=O)O)c(=O)[nH]/c2=N\c2ccc(OC(C)C)c(Cl)c2)cc1] | I-408 | 501 | 2.16 | 2 |
| 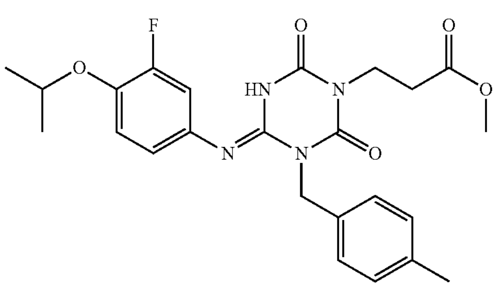 [SMILES: COC(=O)CCn1c(=O)[nH]/c(=N\c2ccc(OC(C)C)c(F)c2)n(Cc2ccc(C)cc2)c1=O] | I-409 | 471 | 2.13 | 2 |
| 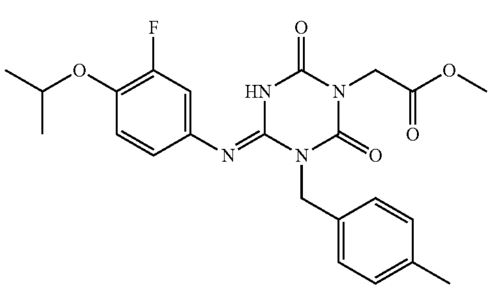 [SMILES: COC(=O)Cn1c(=O)[nH]/c(=N\c2ccc(OC(C)C)c(F)c2)n(Cc2ccc(C)cc2)c1=O] | I-410 | 457 | 2.09 | 2 |

TABLE 86
| Chemical Structure | Compound No. | [M + H] | Retention time (min) | Method |
|---|---|---|---|---|
| 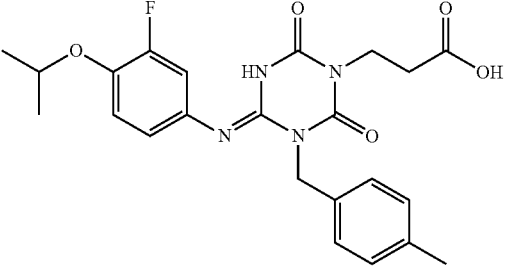 [SMILES: Cc1ccc(Cn2c(=O)n(CCC(=O)O)c(=O)[nH]/c2=N\c2ccc(OC(C)C)c(F)c2)cc1] | I-411 | 457 | 1.92 | 2 |
| 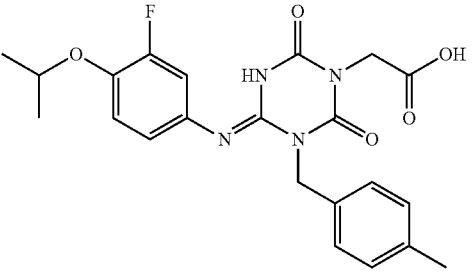 [SMILES: Cc1ccc(Cn2c(=O)n(CC(=O)O)c(=O)[nH]/c2=N\c2ccc(OC(C)C)c(F)c2)cc1] | I-412 | 443 | 1.87 | 2 |
| 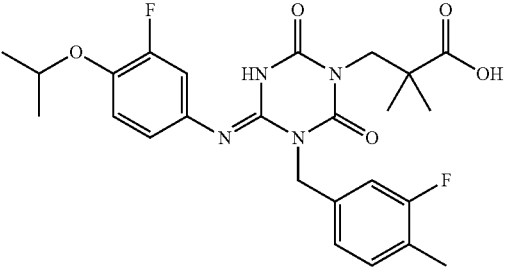 [SMILES: Cc1ccc(Cn2c(=O)n(CC(C)(C)C(=O)O)c(=O)[nH]/c2=N\c2ccc(OC(C)C)c(F)c2)cc1F] | I-413 | 503 | 2.10 | 2 |
| 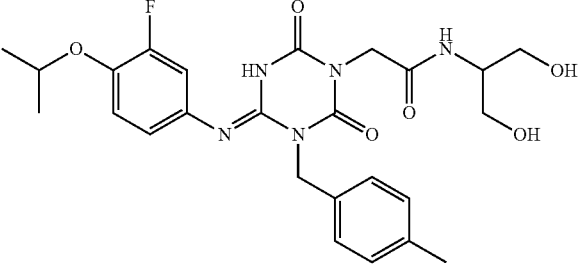 [SMILES: Cc1ccc(Cn2c(=O)n(CC(=O)NC(CO)CO)c(=O)[nH]/c2=N\c2ccc(OC(C)C)c(F)c2)cc1] | I-414 | 516 | 1.63 | 2 |
| 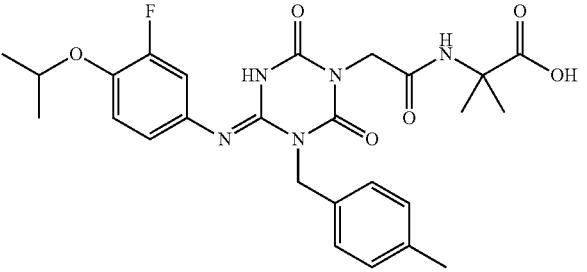 [SMILES: Cc1ccc(Cn2c(=O)n(CC(=O)NC(C)(C)C(=O)O)c(=O)[nH]/c2=N\c2ccc(OC(C)C)c(F)c2)cc1] | I-415 | 528 | 1.84 | 2 |

TABLE 87

| Chemical Structure | Compound No. | [M + H] | Retention time (min) | Method |
|---|---|---|---|---|
| (structure) | I-416 | 500 | 1.74 | 2 |
| (structure) | I-417 | 514 | 1.78 | 2 |
| (structure) | I-418 | 514 | 1.79 | 2 |
| (structure) | I-419 | 526 | 1.78 | 2 |
| (structure) | I-420 | 519 | 2.21 | 2 |

TABLE 88

| Chemical Structure | Compound No. | [M + H] | Retention time (min) | Method |
|---|---|---|---|---|
| 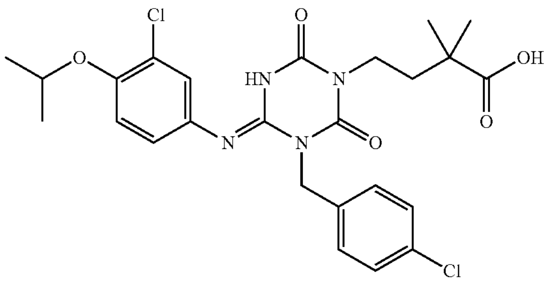 [SMILES: CC(C)Oc1ccc(/N=c2\[nH]c(=O)n(CCC(C)(C)C(=O)O)c(=O)n2Cc2ccc(Cl)cc2)cc1Cl] | I-421 | 535 | 2.32 | 2 |
| 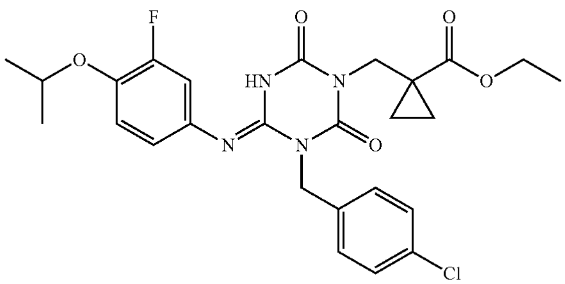 [SMILES: CCOC(=O)C1(Cn2c(=O)[nH]/c(=N\c3ccc(OC(C)C)c(F)c3)n(Cc3ccc(Cl)cc3)c2=O)CC1] | I-422 | 531 | 2.45 | 2 |
| 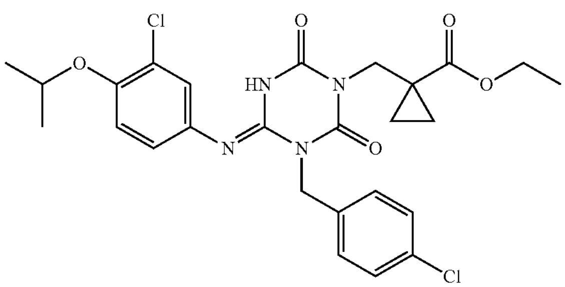 | I-423 | 547 | 2.53 | 2 |
| 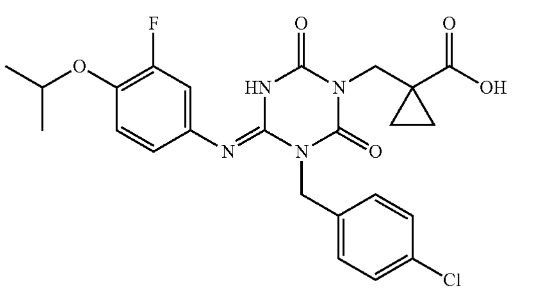 | I-424 | 503 | 2.09 | 2 |
| 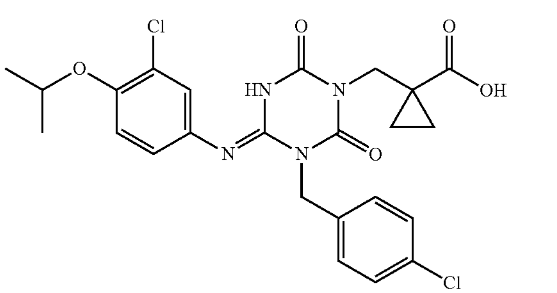 [SMILES: CC(C)Oc1ccc(/N=c2\[nH]c(=O)n(CC3(C(=O)O)CC3)c(=O)n2Cc2ccc(Cl)cc2)cc1F] | I-425 | 519 | 2.20 | 2 |

TABLE 89

| Chemical Structure | Compound No. | [M + H] | Retention time (min) | Method |
|---|---|---|---|---|
| (structure) | I-426 | 493 | 1.99 | 2 |
| (structure) | I-427 | 496 | 2.12 | 2 |
| (structure) | I-428 | 500 | 1.25 | 2 |
| (structure) | I-429 | 479 | 1.72 | 2 |
| (structure) | I-430 | 482 | 1.85 | 2 |

TABLE 90

| Chemical Structure | Compound No. | [M + H] | Retention time (min) | Method |
|---|---|---|---|---|
| 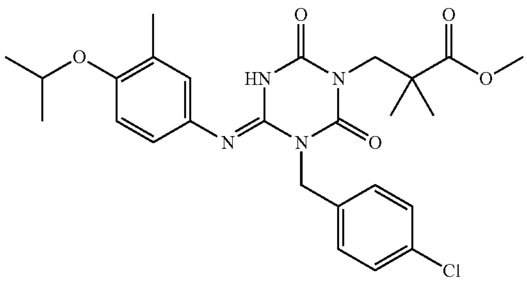 [SMILES: COC(=O)C(C)(C)Cn1c(=O)[nH]/c(=N\c2ccc(OC(C)C)c(C)c2)n(Cc2ccc(Cl)cc2)c1=O] | I-431 | 515 | 2.44 | 2 |
| 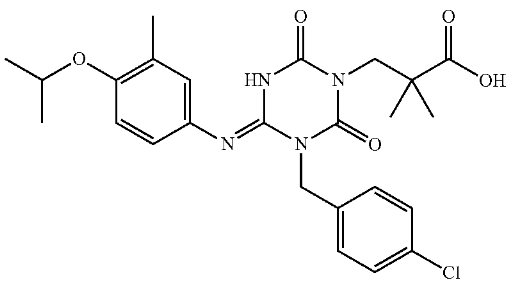 [SMILES: Cc1cc(/N=c2\[nH]c(=O)n(CC(C)(C)C(=O)O)c(=O)n2Cc2ccc(Cl)cc2)ccc1OC(C)C] | I-432 | 501 | 2.15 | 2 |
| 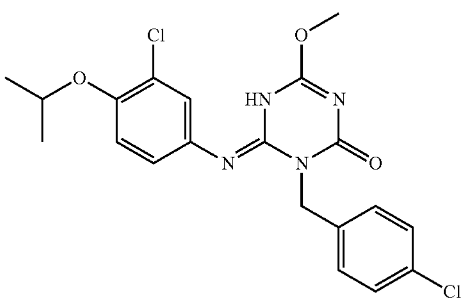 [SMILES: COc1nc(=O)n(Cc2ccc(Cl)cc2)/c(=N/c2ccc(OC(C)C)c(Cl)c2)[nH]1] | I-433 | 435 | 2.10 | 1 |
| 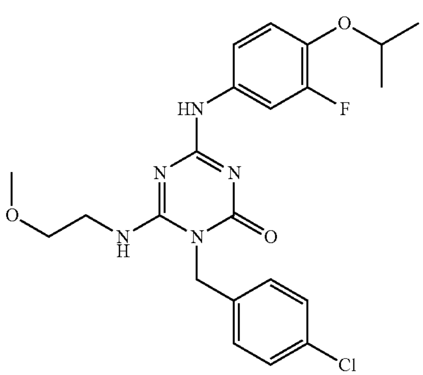 [SMILES: COCCNc1nc(Nc2ccc(OC(C)C)c(F)c2)nc(=O)n1Cc1ccc(Cl)cc1] | II-001 | 462 | 1.79 | 1 |
| 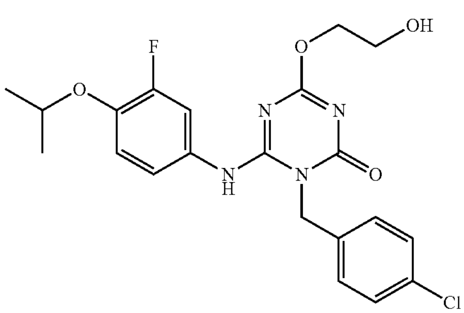 [SMILES: CC(C)Oc1ccc(Nc2nc(OCCO)nc(=O)n2Cc2ccc(Cl)cc2)cc1F] | II-002 | 449 | 1.80 | 1 |

TABLE 91

| Chemical Structure | Compound No. | [M + H] | Retention time (min) | Method |
|---|---|---|---|---|
| (structure) | II-003 | 494 | 1.90 | 1 |
| (structure) | II-004 | 590 | 3.40 | 1 |
| (structure) | II-005 | 448 | 1.50 | 2 |
| (structure) | II-006 | 464 | 1.80 | 2 |
| (structure) | II-007 | 462 | 1.50 | 2 |

TABLE 92

| Chemical Structure | Compound No. | [M + H] | Retention time (min) | Method |
|---|---|---|---|---|
| (structure) | II-008 | 493 | 1.70 | 2 |
| (structure) | II-009 | 479 | 1.88 | 1 |
| (structure) | II-010 | 521 | 2.09 | 1 |

TABLE 93

| Chemical Structure | Compound No. | [M + H] | Retention time (min) | Method |
|---|---|---|---|---|
| (structure) | I-434 | 479 | 2.06 | 2 |

TABLE 93-continued

| Chemical Structure | Compound No. | [M + H] | Retention time (min) | Method |
|---|---|---|---|---|
| (structure) | I-435 | 517 | 2.21 | 3 |
| (structure) | I-436 | 492 | 2.16 | 3 |
| (structure) | I-437 | 522 | 2.03 | 3 |
| (structure) | I-438 | 535 | 1.98 | 3 |

TABLE 94

| Chemical Structure | Compound No. | [M + H] | Retention time (min) | Method |
|---|---|---|---|---|
| (structure) | I-439 | 515 | 2.11 | 3 |

TABLE 94-continued

| Chemical Structure | Compound No. | [M + H] | Retention time (min) | Method |
|---|---|---|---|---|
| 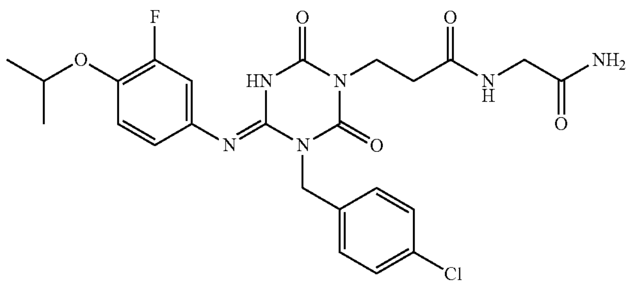 [SMILES: CC(C)Oc1ccc(/N=c2\[nH]c(=O)n(CCC(=O)NCC(N)=O)c(=O)n2Cc2ccc(Cl)cc2)cc1F] | I-440 | 533 | 1.87 | 3 |
| 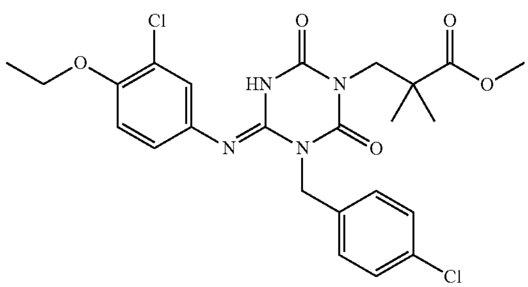 | I-441 | 521 | 2.43 | 2 |
| 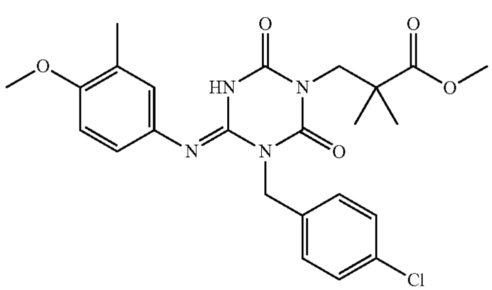 | I-442 | 487 | 2.23 | 2 |
| 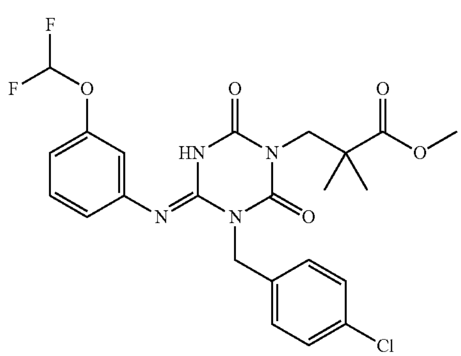 [SMILES: COC(=O)C(C)(C)Cn1c(=O)[nH]/c(=N\c2cccc(OC(F)F)c2)n(Cc2ccc(Cl)cc2)c1=O] | I-443 | 509 | 2.5 | 3 |

TABLE 95

| Chemical Structure | Compound No. | [M + H] | Retention time (min) | Method |
|---|---|---|---|---|
| 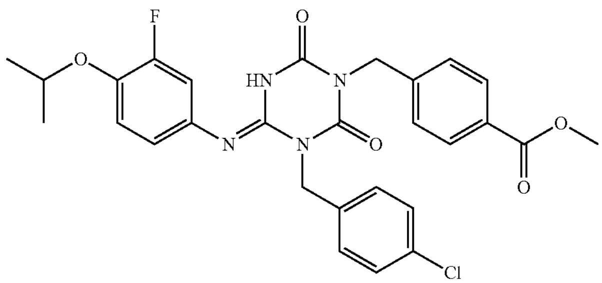 [SMILES: COC(=O)c1ccc(Cn2c(=O)[nH]/c(=N\c3ccc(OC(C)C)c(F)c3)n(Cc3ccc(Cl)cc3)c2=O)cc1] | I-444 | 553 | 2.61 | 3 |
| 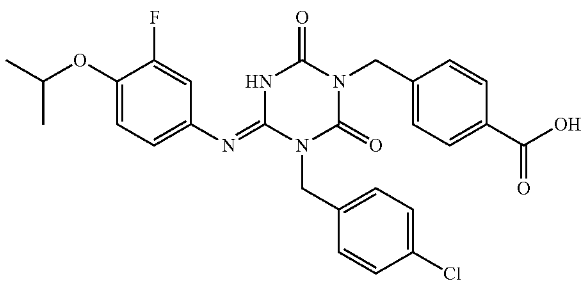 [SMILES: CC(C)Oc1ccc(/N=c2\[nH]c(=O)n(Cc3ccc(C(=O)O)cc3)c(=O)n2Cc2ccc(Cl)cc2)cc1F] | I-445 | 539 | 2.33 | 3 |
| 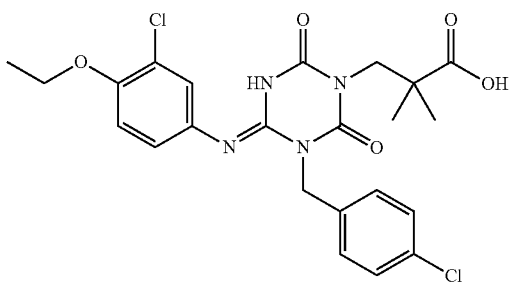 | I-446 | 507 | 2.31 | 2 |
| 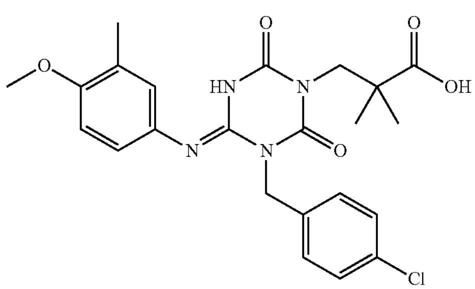 [SMILES: COc1ccc(/N=c2\[nH]c(=O)n(CC(C)(C)C(=O)O)c(=O)n2Cc2ccc(Cl)cc2)cc1C] | I-447 | 473 | 2.1 | 2 |
| 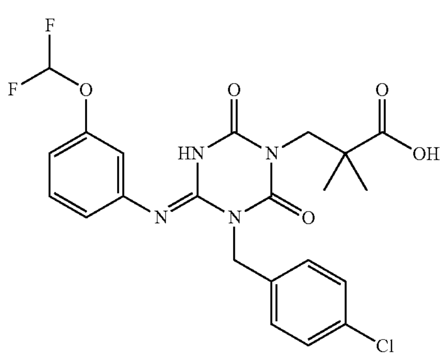 [SMILES: CC(C)(Cn1c(=O)[nH]/c(=N\c2cccc(OC(F)F)c2)n(Cc2ccc(Cl)cc2)c1=O)C(=O)O] | I-448 | 495 | 2.22 | 2 |

TABLE 96

| Chemical Structure | Compound No. | [M + H] | Retention time (min) | Method |
|---|---|---|---|---|
| 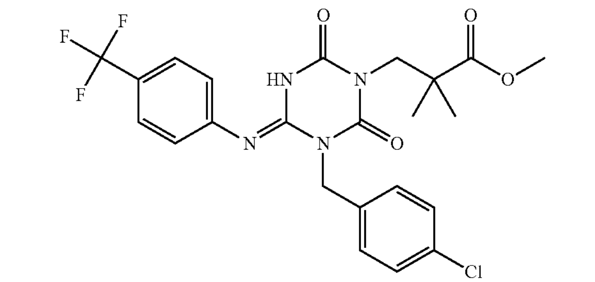 [SMILES: COC(=O)C(C)(C)Cn1c(=O)[nH]/c(=N\c2ccc(C(F)(F)F)cc2)n(Cc2ccc(Cl)cc2)c1=O] | I-449 | 511 | 2.67 | 2 |
| 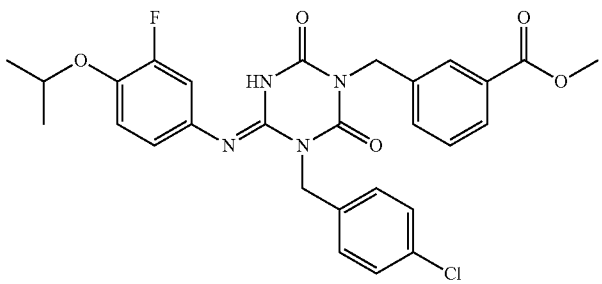 [SMILES: COC(=O)c1cccc(Cn2c(=O)[nH]/c(=N\c3ccc(OC(C)C)c(F)c3)n(Cc3ccc(Cl)cc3)c2=O)c1] | I-450 | 553 | 2.63 | 3 |
| 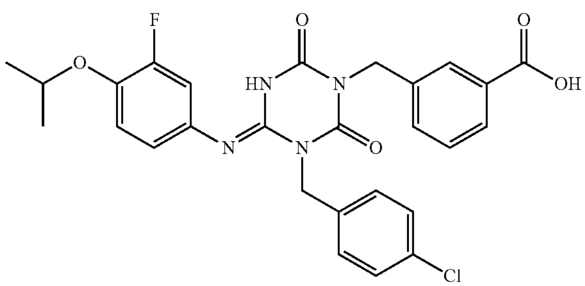 [SMILES: CC(C)Oc1ccc(/N=c2\[nH]c(=O)n(Cc3cccc(C(=O)O)c3)c(=O)n2Cc2ccc(Cl)cc2)cc1F] | I-451 | 539 | 2.36 | 3 |
| 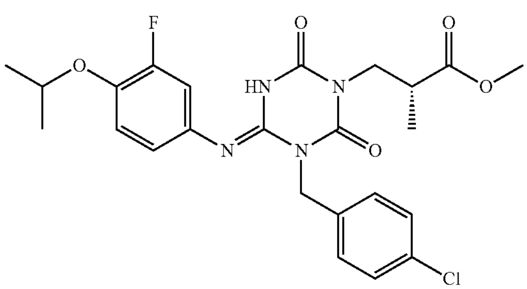 [SMILES: COC(=O)[C@H](C)Cn1c(=O)[nH]/c(=N\c2ccc(OC(C)C)c(F)c2)n(Cc2ccc(Cl)cc2)c1=O] | I-452 | 505 | 2.29 | 2 |
| 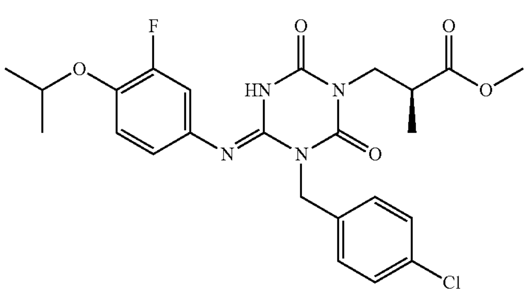 [SMILES: COC(=O)[C@@H](C)Cn1c(=O)[nH]/c(=N\c2ccc(OC(C)C)c(F)c2)n(Cc2ccc(Cl)cc2)c1=O] | I-453 | 505 | 2.3 | 2 |

TABLE 97
| Chemical Structure | Compound No. | [M + H] | Retention time (min) | Method |
|---|---|---|---|---|
| 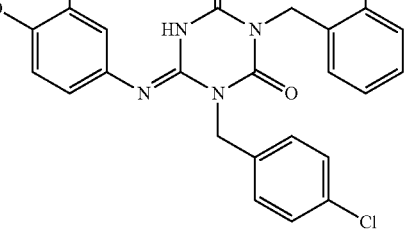 | I-454 | 567 | 2.74 | 3 |
| 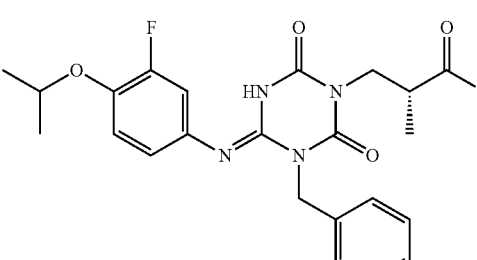 | I-455 | 491 | 2.22 | 3 |
| 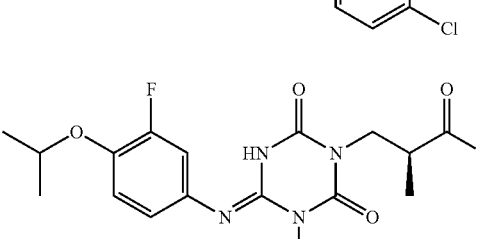 | I-456 | 491 | 2.22 | 3 |
| 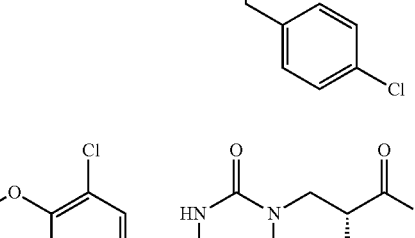 | I-457 | 521 | 2.41 | 2 |
| 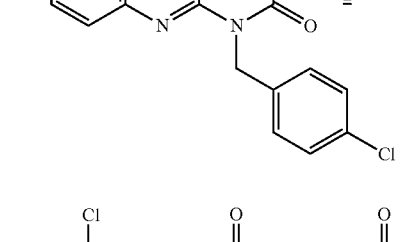 | I-458 | 521 | 2.41 | 2 |

TABLE 98

| Chemical Structure | Compound No. | [M + H] | Retention time (min) | Method |
|---|---|---|---|---|
| (structure) | I-459 | 539 | 2.38 | 3 |
| (structure) | I-460 | 507 | 2.34 | 3 |
| (structure) | I-461 | 507 | 2.33 | 3 |
| (structure) | I-462 | 501 | 2.33 | 2 |
| (structure) | I-463 | 471 | 2.31 | 2 |

TABLE 99

| Chemical Structure | Compound No. | [M + H] | Retention time (min) | Method |
|---|---|---|---|---|
| 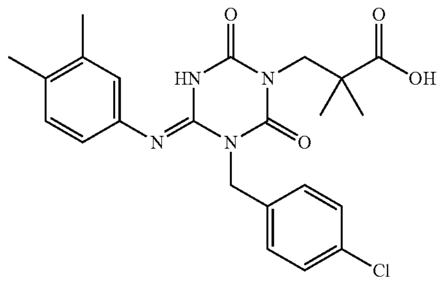 [SMILES: Cc1ccc(/N=c2\[nH]c(=O)n(CC(C)(C)C(=O)O)c(=O)n2Cc2ccc(Cl)cc2)cc1C] | I-464 | 457 | 2.02 | 2 |
| 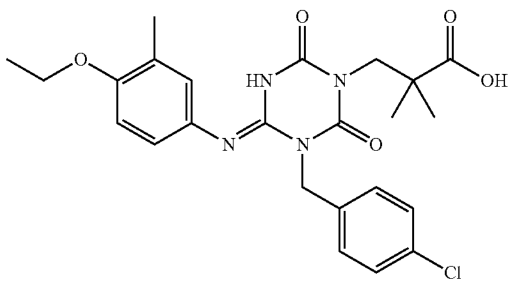 [SMILES: CCOc1ccc(/N=c2\[nH]c(=O)n(CC(C)(C)C(=O)O)c(=O)n2Cc2ccc(Cl)cc2)cc1C] | I-465 | 487 | 2.06 | 2 |
| 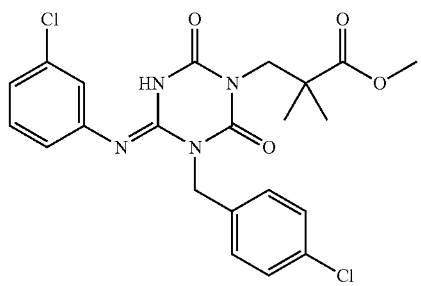 [SMILES: COC(=O)C(C)(C)Cn1c(=O)[nH]/c(=N\c2cccc(Cl)c2)n(Cc2ccc(Cl)cc2)c1=O] | I-466 | 477 | 2.41 | 2 |
| 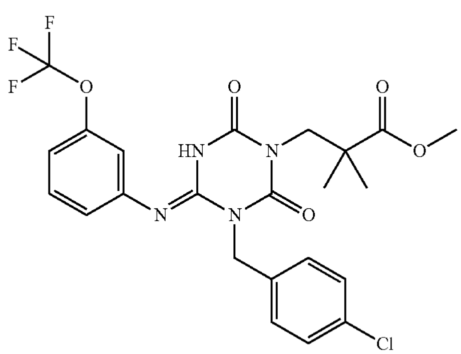 [SMILES: COC(=O)C(C)(C)Cn1c(=O)[nH]/c(=N\c2cccc(OC(F)(F)F)c2)n(Cc2ccc(Cl)cc2)c1=O] | I-467 | 527 | 2.5 | 2 |
| 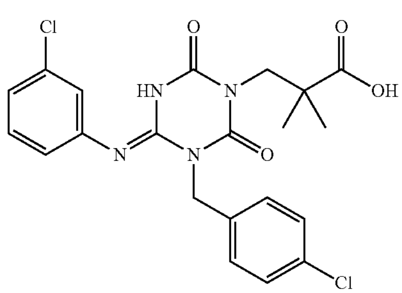 [SMILES: CC(C)(Cn1c(=O)[nH]/c(=N\c2cccc(Cl)c2)n(Cc2ccc(Cl)cc2)c1=O)C(=O)O] | I-468 | 463 | 2.29 | 3 |

TABLE 100

| Chemical Structure | Compound No. | [M + H] | Retention time (min) | Method |
|---|---|---|---|---|
| 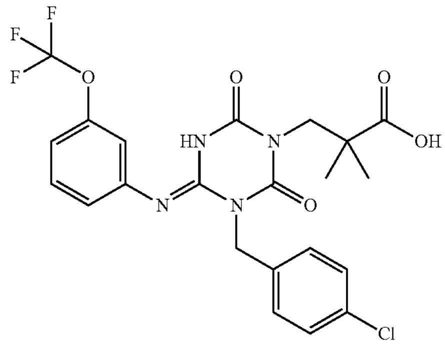 [SMILES: CC(C)(Cn1c(=O)[nH]/c(=N\c2cccc(OC(F)(F)F)c2)n(Cc2ccc(Cl)cc2)c1=O)C(=O)O] | I-469 | 513 | 2.41 | 3 |
| 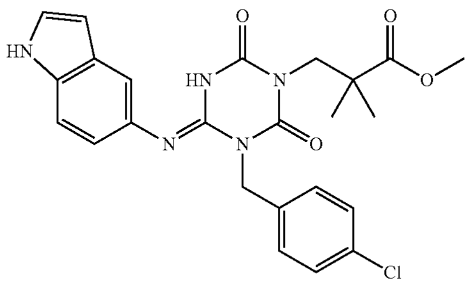 [SMILES: COC(=O)C(C)(C)Cn1c(=O)[nH]/c(=N\c2ccc3[nH]ccc3c2)n(Cc2ccc(Cl)cc2)c1=O] | I-470 | 482 | 2.15 | 3 |
| 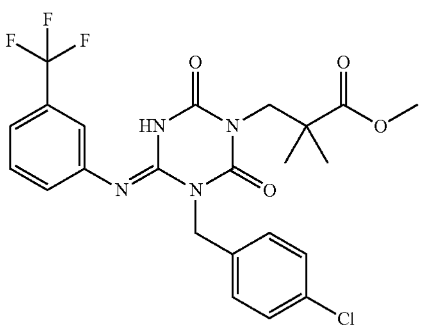 [SMILES: COC(=O)C(C)(C)Cn1c(=O)[nH]/c(=N\c2cccc(C(F)(F)F)c2)n(Cc2ccc(Cl)cc2)c1=O] | I-471 | 511 | 2.63 | 3 |
| 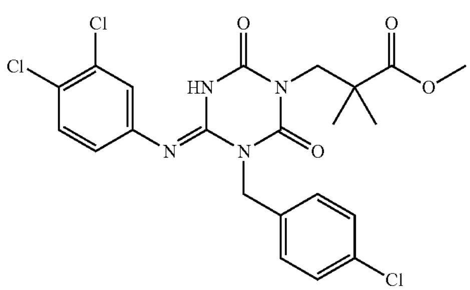 [SMILES: COC(=O)C(C)(C)Cn1c(=O)[nH]/c(=N\c2ccc(Cl)c(Cl)c2)n(Cc2ccc(Cl)cc2)c1=O] | I-472 | 512 | 2.75 | 3 |
| 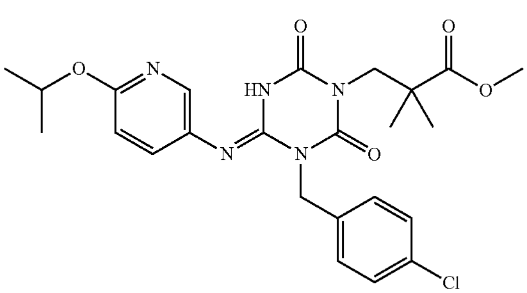 [SMILES: COC(=O)C(C)(C)Cn1c(=O)[nH]/c(=N\c2ccc(OC(C)C)nc2)n(Cc2ccc(Cl)cc2)c1=O] | I-473 | 502 | 1.78 | 2 |

TABLE 101

| Chemical Structure | Compound No. | [M + H] | Retention time (min) | Method |
|---|---|---|---|---|
| 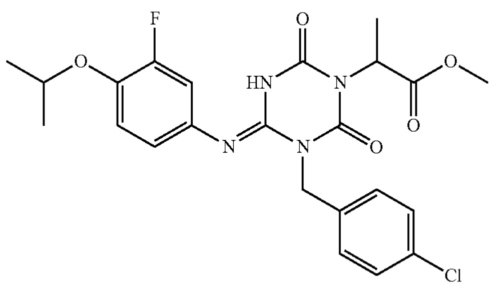 [SMILES: COC(=O)C(C)n1c(=O)[nH]/c(=N\c2ccc(OC(C)C)c(F)c2)n(Cc2ccc(Cl)cc2)c1=O] | I-474 | 491 | 2.42 | 3 |
| 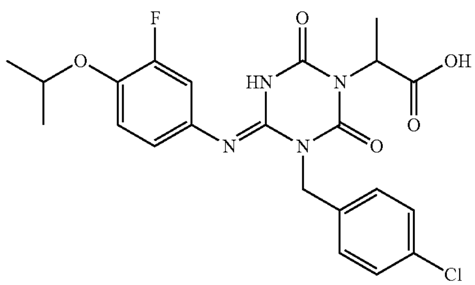 [SMILES: CC(C)Oc1ccc(/N=c2\[nH]c(=O)n(C(C)C(=O)O)c(=O)n2Cc2ccc(Cl)cc2)cc1F] | I-475 | 477 | 2.18 | 3 |
| 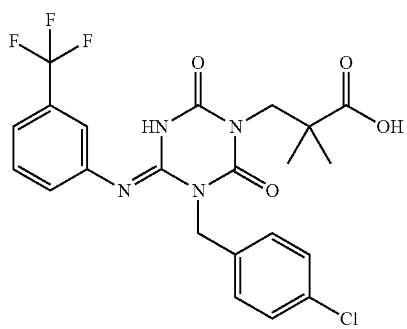 [SMILES: CC(C)(Cn1c(=O)[nH]/c(=N\c2cccc(C(F)(F)F)c2)n(Cc2ccc(Cl)cc2)c1=O)C(=O)O] | I-476 | 497 | 2.2 | 2 |
| 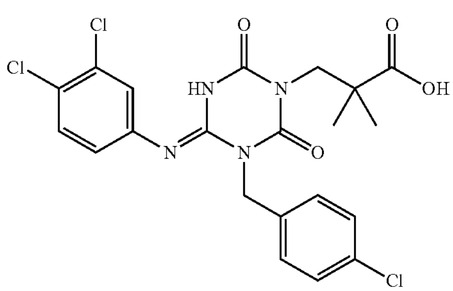 [SMILES: CC(C)(Cn1c(=O)[nH]/c(=N\c2ccc(Cl)c(Cl)c2)n(Cc2ccc(Cl)cc2)c1=O)C(=O)O] | I-477 | 499 | 2.31 | 2 |
| 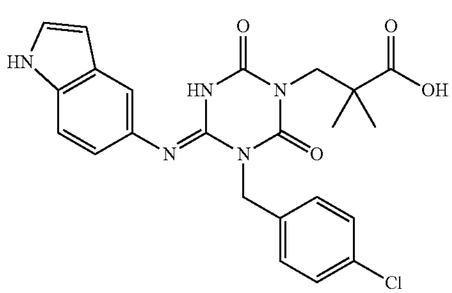 [SMILES: CC(C)(Cn1c(=O)[nH]/c(=N\c2ccc3[nH]ccc3c2)n(Cc2ccc(Cl)cc2)c1=O)C(=O)O] | I-478 | 468 | 1.71 | 2 |

TABLE 102

| Chemical Structure | Compound No. | [M + H] | Retention time (min) | Method |
|---|---|---|---|---|
| 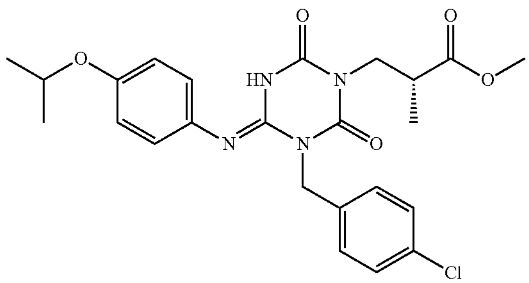 [SMILES: COC(=O)[C@H](C)Cn1c(=O)[nH]/c(=N\c2ccc(OC(C)C)cc2)n(Cc2ccc(Cl)cc2)c1=O] | I-479 | 487 | 2.17 | 2 |
| 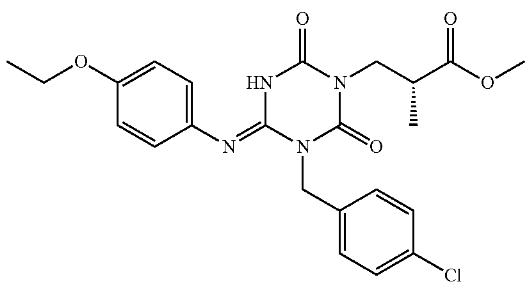 [SMILES: CCOc1ccc(/N=c2\[nH]c(=O)n(C[C@@H](C)C(=O)OC)c(=O)n2Cc2ccc(Cl)cc2)cc1] | I-480 | 473 | 2.06 | 2 |
| 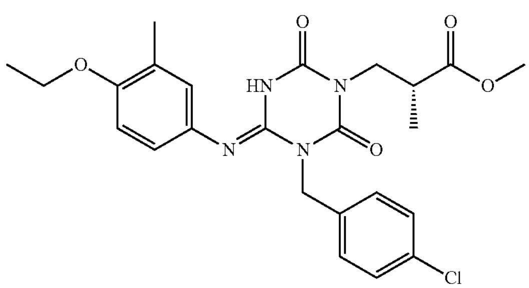 [SMILES: CCOc1ccc(/N=c2\[nH]c(=O)n(C[C@@H](C)C(=O)OC)c(=O)n2Cc2ccc(Cl)cc2)cc1C] | I-481 | 487 | 2.22 | 2 |
| 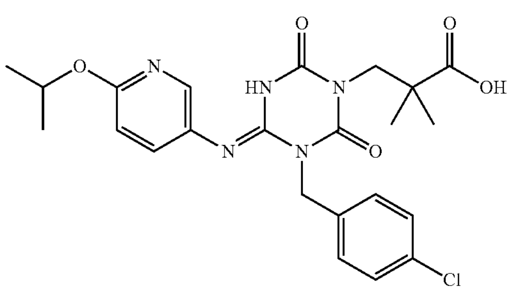 [SMILES: CC(C)Oc1ccc(/N=c2\[nH]c(=O)n(CC(C)(C)C(=O)O)c(=O)n2Cc2ccc(Cl)cc2)cn1] | I-482 | 488 | 1.53 | 2 |
| 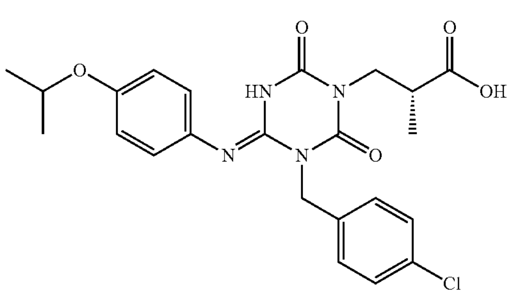 [SMILES: CC(C)Oc1ccc(/N=c2\[nH]c(=O)n(C[C@@H](C)C(=O)O)c(=O)n2Cc2ccc(Cl)cc2)cc1] | I-483 | 473 | 1.93 | 2 |

TABLE 103
| Chemical Structure | Compound No. | [M + H] | Retention time (min) | Method |
|---|---|---|---|---|
| 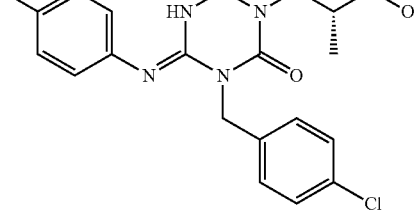 | I-484 | 459 | 1.82 | 2 |
| 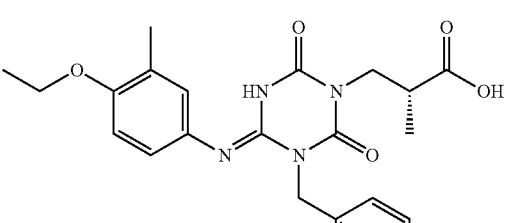 | I-485 | 473 | 1.98 | 2 |
| 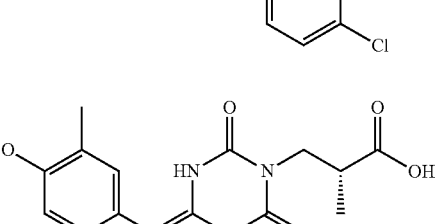 | I-486 | 487 | 2.08 | 2 |
| 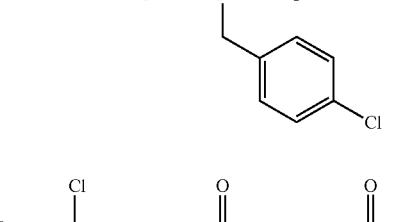 | I-487 | 493 | 2.03 | 2 |
| 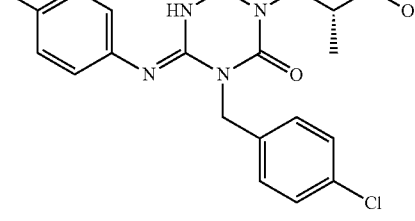 | I-488 | 498 | 1.98 | 2 |

TABLE 104

| Chemical Structure | Compound No. | [M + H] | Retention time (min) | Method |
|---|---|---|---|---|
| 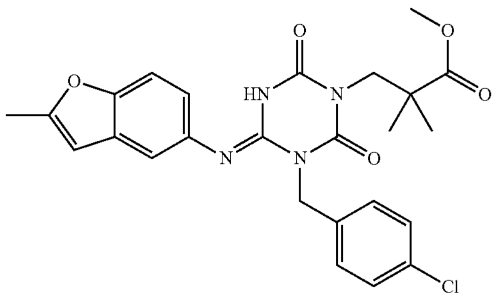 [SMILES: COC(=O)C(C)(C)Cn1c(=O)[nH]/c(=N\c2ccc3oc(C)cc3c2)n(Cc2ccc(Cl)cc2)c1=O] | I-489 | 497 | 2.28 | 2 |
| 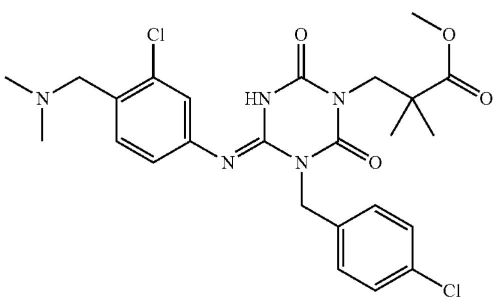 [SMILES: COC(=O)C(C)(C)Cn1c(=O)[nH]/c(=N\c2ccc(CN(C)C)c(Cl)c2)n(Cc2ccc(Cl)cc2)c1=O] | I-490 | 534 | 1.62 | 2 |
| 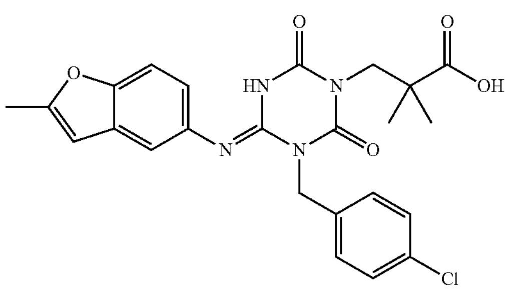 [SMILES: Cc1cc2cc(/N=c3\[nH]c(=O)n(CC(C)(C)C(=O)O)c(=O)n3Cc3ccc(Cl)cc3)ccc2o1] | I-491 | 483 | 2 | 2 |
| 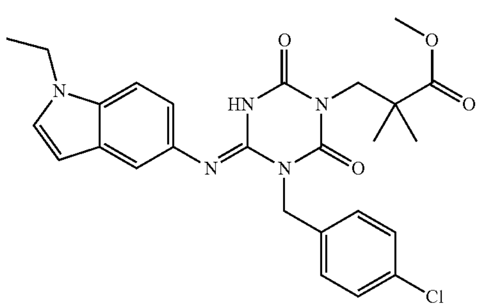 [SMILES: CCn1ccc2cc(/N=c3\[nH]c(=O)n(CC(C)(C)C(=O)OC)c(=O)n3Cc3ccc(Cl)cc3)ccc21] | I-492 | 510 | 2.23 | 2 |
| 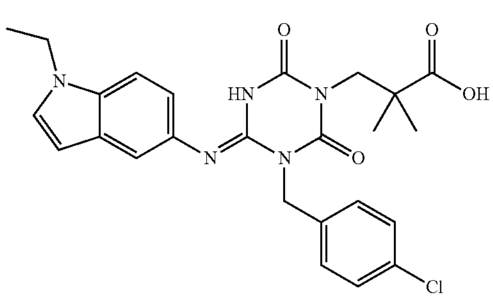 [SMILES: CCn1ccc2cc(/N=c3\[nH]c(=O)n(CC(C)(C)C(=O)O)c(=O)n3Cc3ccc(Cl)cc3)ccc21] | I-493 | 496 | 1.96 | 2 |

TABLE 105

| Chemical Structure | Compound No. | [M + H] | Retention time (min) | Method |
|---|---|---|---|---|
| 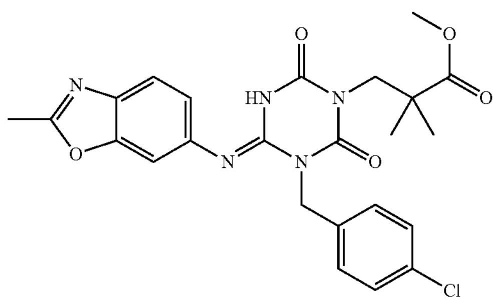 [SMILES: COC(=O)C(C)(C)Cn1c(=O)[nH]/c(=N\c2ccc3nc(C)oc3c2)n(Cc2ccc(Cl)cc2)c1=O] | I-494 | 498 | 2.04 | 2 |
| 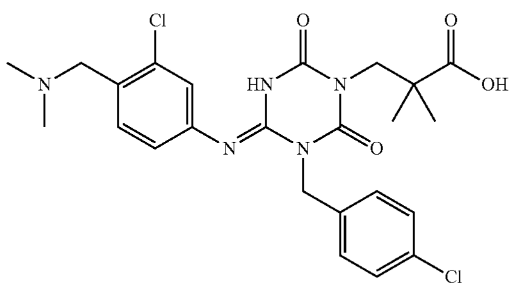 [SMILES: CN(C)Cc1ccc(/N=c2\[nH]c(=O)n(CC(C)(C)C(=O)O)c(=O)n2Cc2ccc(Cl)cc2)cc1Cl] | I-495 | 520 | 1.43 | 2 |
| 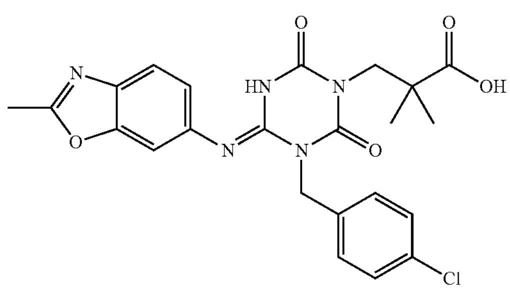 [SMILES: Cc1nc2ccc(/N=c3\[nH]c(=O)n(CC(C)(C)C(=O)O)c(=O)n3Cc3ccc(Cl)cc3)cc2o1] | I-496 | 484 | 1.75 | 2 |
| 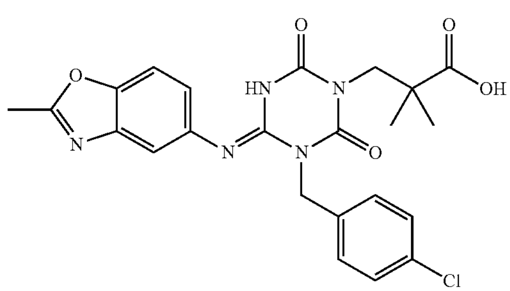 | I-497 | 484 | 1.74 | 2 |
| 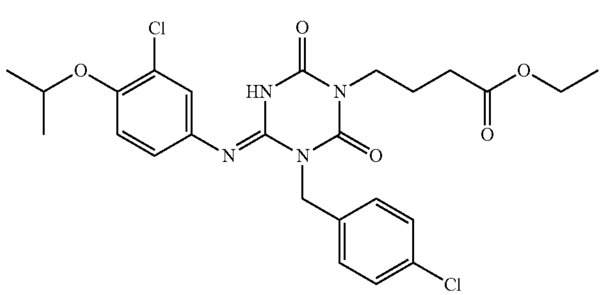 [SMILES: CCOC(=O)CCCn1c(=O)[nH]/c(=N\c2ccc(OC(C)C)c(Cl)c2)n(Cc2ccc(Cl)cc2)c1=O] | I-498 | 535 | 2.5 | 2 |

TABLE 106

| Chemical Structure | Compound No. | [M + H] | Retention time (min) | Method |
|---|---|---|---|---|
| 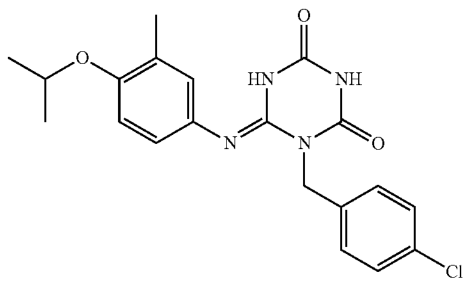 [SMILES: Cc1cc(/N=c2\[nH]c(=O)[nH]c(=O)n2Cc2ccc(Cl)cc2)ccc1OC(C)C] | I-499 | 401 | 2.03 | 2 |
| 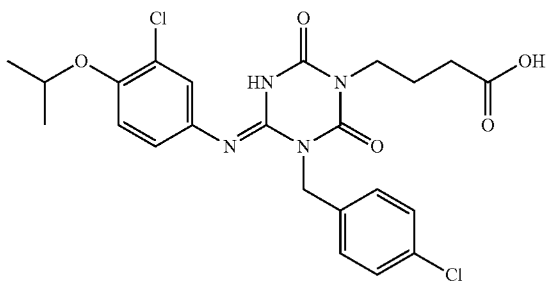 [SMILES: CC(C)Oc1ccc(/N=c2\[nH]c(=O)n(CCCC(=O)O)c(=O)n2Cc2ccc(Cl)cc2)cc1Cl] | I-500 | 507 | 2.13 | 2 |
| 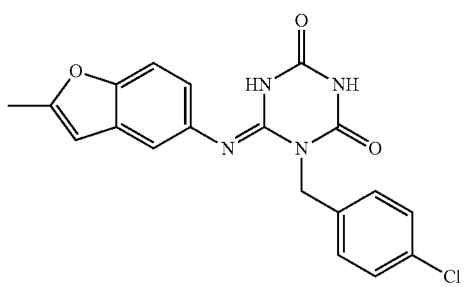 [SMILES: Cc1cc2cc(/N=c3\[nH]c(=O)[nH]c(=O)n3Cc3ccc(Cl)cc3)ccc2o1] | I-501 | 383 | 1.85 | 2 |
| 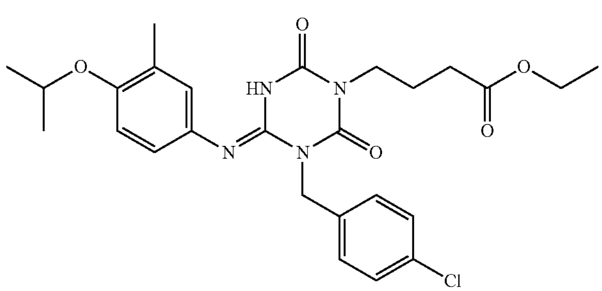 [SMILES: CCOC(=O)CCCn1c(=O)[nH]/c(=N\c2ccc(OC(C)C)c(C)c2)n(Cc2ccc(Cl)cc2)c1=O] | I-502 | 515 | 2.41 | 2 |
| 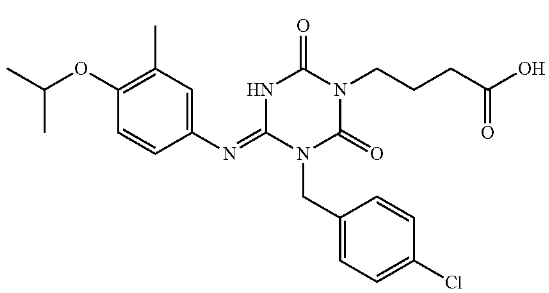 [SMILES: Cc1cc(/N=c2\[nH]c(=O)n(CCCC(=O)O)c(=O)n2Cc2ccc(Cl)cc2)ccc1OC(C)C] | I-503 | 487 | 2.06 | 2 |

TABLE 107

| Chemical Structure | Compound No. | [M + H] | Retention time (min) | Method |
|---|---|---|---|---|
| 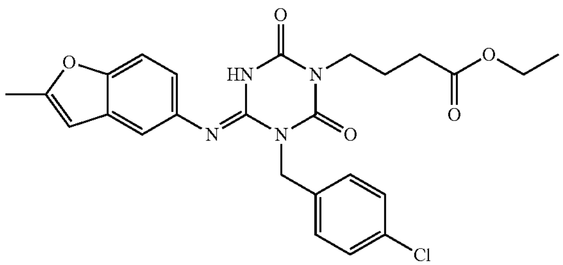 [SMILES: CCOC(=O)CCCn1c(=O)[nH]/c(=N\c2ccc3oc(C)cc3c2)n(Cc2ccc(Cl)cc2)c1=O] | I-504 | 497 | 2.25 | 2 |
| 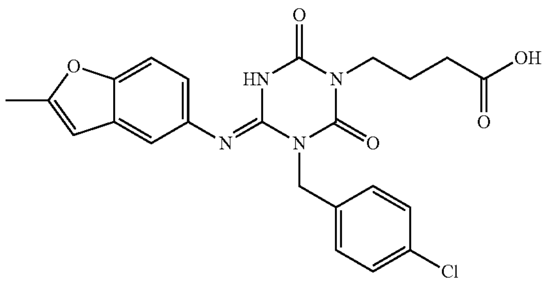 [SMILES: Cc1cc2cc(/N=c3\[nH]c(=O)n(CCCC(=O)O)c(=O)n3Cc3ccc(Cl)cc3)ccc2o1] | I-505 | 469 | 1.89 | 2 |
| 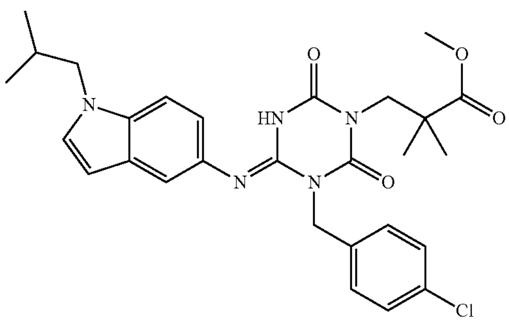 [SMILES: COC(=O)C(C)(C)Cn1c(=O)[nH]/c(=N\c2ccc3c(ccn3CC(C)C)c2)n(Cc2ccc(Cl)cc2)c1=O] | I-506 | 538 | 2.44 | 2 |
| 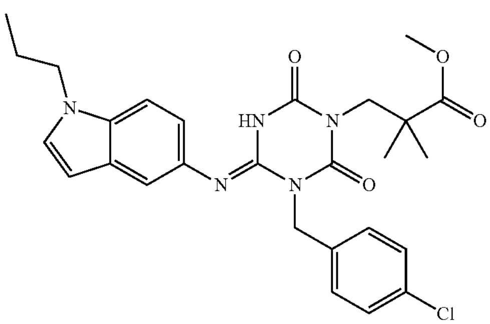 [SMILES: CCCn1ccc2cc(/N=c3\[nH]c(=O)n(CC(C)(C)C(=O)OC)c(=O)n3Cc3ccc(Cl)cc3)ccc21] | I-507 | 524 | 2.34 | 2 |
| 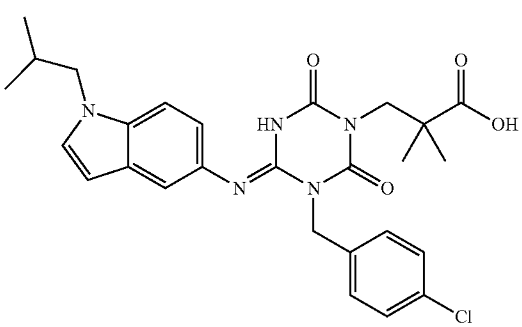 [SMILES: CC(C)Cn1ccc2cc(/N=c3\[nH]c(=O)n(CC(C)(C)C(=O)O)c(=O)n3Cc3ccc(Cl)cc3)ccc21] | I-508 | 524 | 2.17 | 2 |

TABLE 108

| Chemical Structure | Compound No. | [M + H] | Retention time (min) | Method |
|---|---|---|---|---|
| 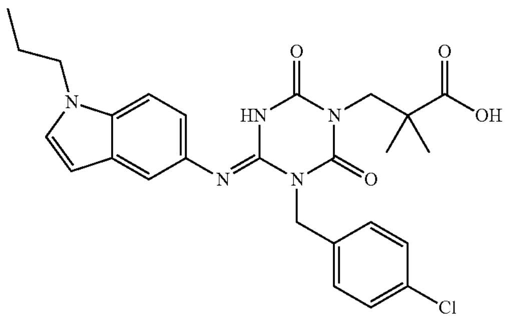 [SMILES: CCCn1ccc2cc(/N=c3\[nH]c(=O)n(CC(C)(C)C(=O)O)c(=O)n3Cc3ccc(Cl)cc3)ccc21] | I-509 | 510 | 2.07 | 2 |
| 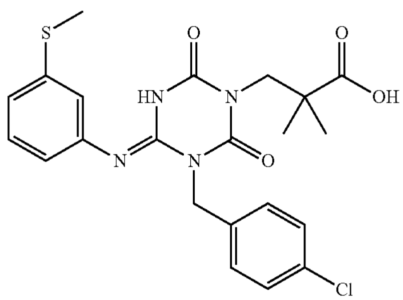 [SMILES: CSc1cccc(/N=c2\[nH]c(=O)n(CC(C)(C)C(=O)O)c(=O)n2Cc2ccc(Cl)cc2)c1] | I-510 | 475 | 2.23 | 3 |
| 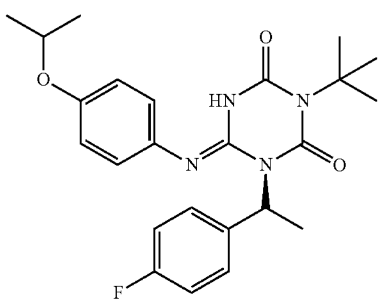 | I-511 | 441 | 2.67 | 3 |
| 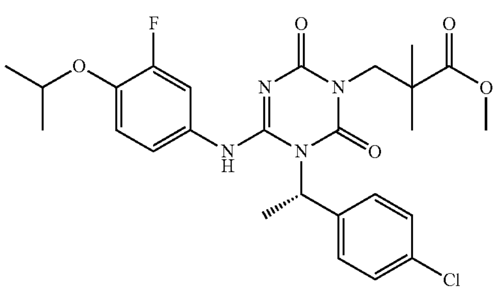 [SMILES: COC(=O)C(C)(C)Cn1c(=O)nc(Nc2ccc(OC(C)C)c(F)c2)n([C@@H](C)c2ccc(Cl)cc2)c1=O] | I-512 | 533 | 2.75 | 3 |
| 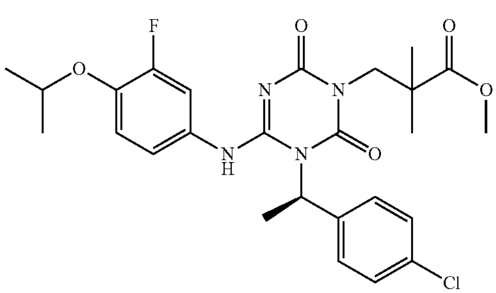 [SMILES: COC(=O)C(C)(C)Cn1c(=O)nc(Nc2ccc(OC(C)C)c(F)c2)n([C@H](C)c2ccc(Cl)cc2)c1=O] | I-513 | 533 | 2.75 | 3 |

TABLE 109

| Chemical Structure | Compound No. | [M + H] | Retention time (min) | Method |
|---|---|---|---|---|
| 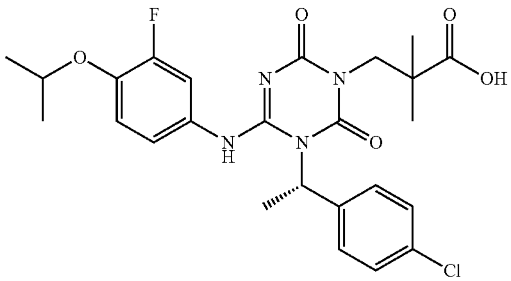 [SMILES: CC(C)Oc1ccc(Nc2nc(=O)n(CC(C)(C)C(=O)O)c(=O)n2[C@@H](C)c2ccc(Cl)cc2)cc1F] | I-514 | 519 | 2.5 | 3 |
| 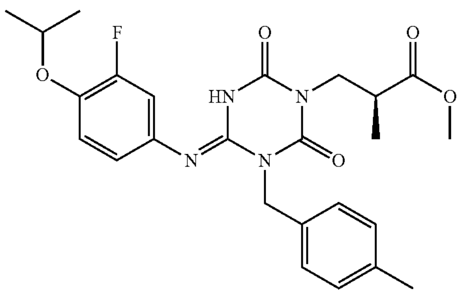 [SMILES: COC(=O)[C@@H](C)Cn1c(=O)[nH]/c(=N\c2ccc(OC(C)C)c(F)c2)n(Cc2ccc(C)cc2)c1=O] | I-515 | 485 | 2.4 | 3 |
| 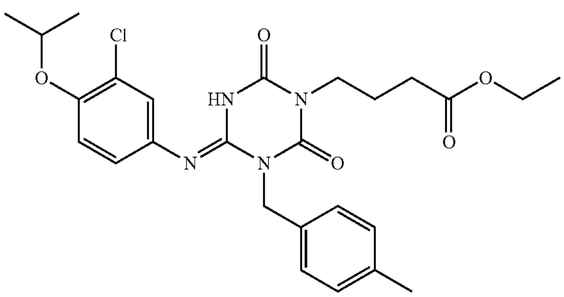 [SMILES: CCOC(=O)CCCn1c(=O)[nH]/c(=N\c2ccc(OC(C)C)c(Cl)c2)n(Cc2ccc(C)cc2)c1=O] | I-516 | 516 | 2.62 | 3 |
| 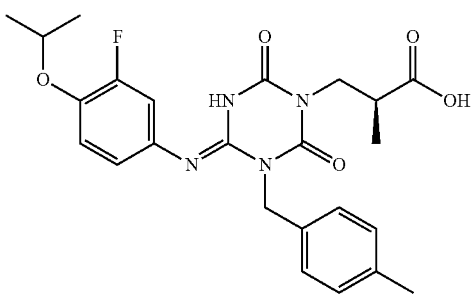 [SMILES: Cc1ccc(Cn2c(=O)n(C[C@H](C)C(=O)O)c(=O)[nH]/c2=N\c2ccc(OC(C)C)c(F)c2)cc1] | I-517 | 471 | 2.18 | 3 |
| 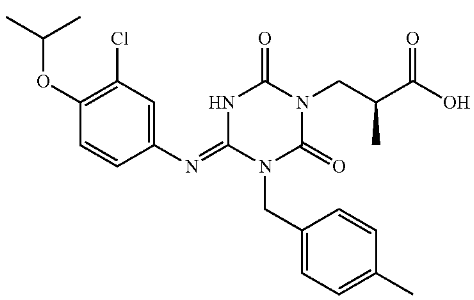 [SMILES: Cc1ccc(Cn2c(=O)n(C[C@H](C)C(=O)O)c(=O)[nH]/c2=N\c2ccc(OC(C)C)c(Cl)c2)cc1] | I-518 | 487 | 2.28 | 3 |

TABLE 110

| Chemical Structure | Compound No. | [M + H] | Retention time (min) | Method |
|---|---|---|---|---|
| 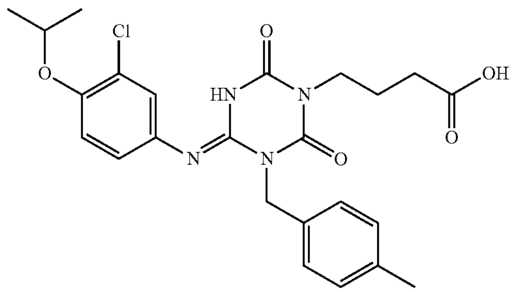 [SMILES: Cc1ccc(Cn2c(=O)n(CCCC(=O)O)c(=O)[nH]/c2=N\c2ccc(OC(C)C)c(Cl)c2)cc1] | I-519 | 487 | 2.25 | 3 |
| 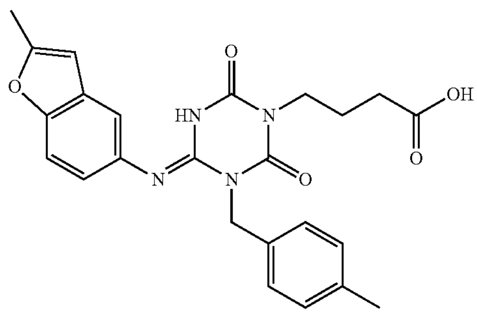 [SMILES: Cc1ccc(Cn2c(=O)n(CCCC(=O)O)c(=O)[nH]/c2=N\c2ccc3oc(C)cc3c2)cc1] | I-520 | 449 | 2 | 3 |
| 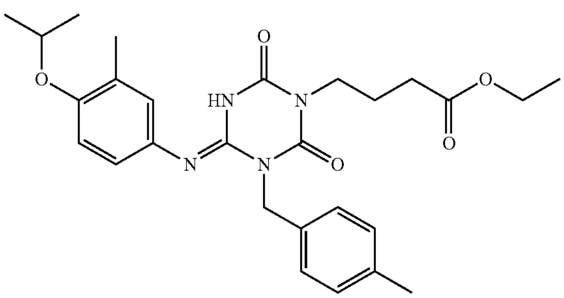 [SMILES: CCOC(=O)CCCn1c(=O)[nH]/c(=N\c2ccc(OC(C)C)c(C)c2)n(Cc2ccc(C)cc2)c1=O] | I-521 | 495 | 2.55 | 3 |
| 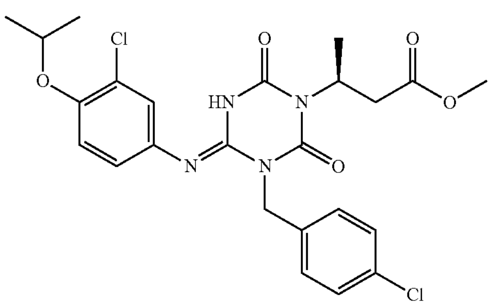 [SMILES: COC(=O)C[C@H](C)n1c(=O)[nH]/c(=N\c2ccc(OC(C)C)c(Cl)c2)n(Cc2ccc(Cl)cc2)c1=O] | I-522 | 521 | 2.64 | 3 |
| 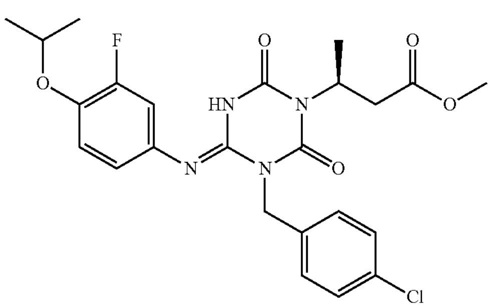 [SMILES: COC(=O)C[C@H](C)n1c(=O)[nH]/c(=N\c2ccc(OC(C)C)c(F)c2)n(Cc2ccc(Cl)cc2)c1=O] | I-523 | 505 | 2.53 | 3 |

TABLE 111

| Chemical Structure | Compound No. | [M + H] | Retention time (min) | Method |
|---|---|---|---|---|
| 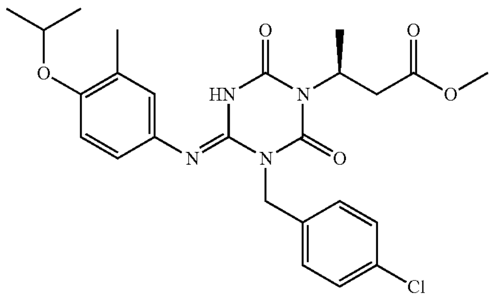 [SMILES: COC(=O)C[C@H](C)n1c(=O)[nH]/c(=N\c2ccc(OC(C)C)c(C)c2)n(Cc2ccc(Cl)cc2)c1=O] | I-524 | 501 | 2.57 | 3 |
| 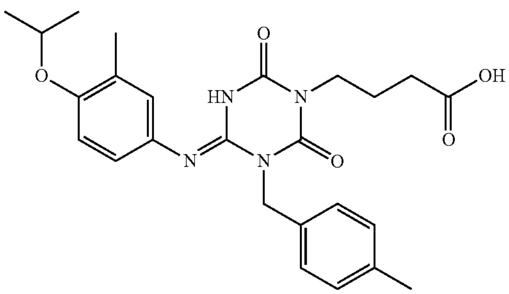 [SMILES: Cc1ccc(Cn2c(=O)n(CCCC(=O)O)c(=O)[nH]/c2=N\c2ccc(OC(C)C)c(C)c2)cc1] | I-525 | 467 | 2.2 | 3 |
| 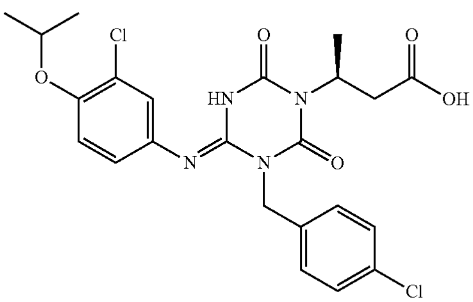 [SMILES: CC(C)Oc1ccc(/N=c2\[nH]c(=O)n([C@@H](C)CC(=O)O)c(=O)n2Cc2ccc(Cl)cc2)cc1Cl] | I-526 | 507 | 2.38 | 3 |
| 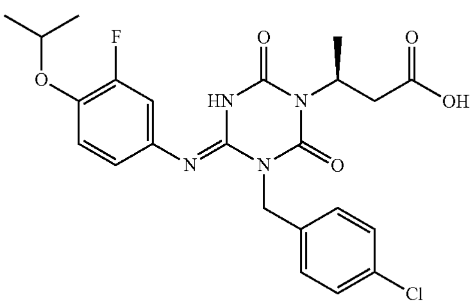 [SMILES: CC(C)Oc1ccc(/N=c2\[nH]c(=O)n([C@@H](C)CC(=O)O)c(=O)n2Cc2ccc(Cl)cc2)cc1F] | I-527 | 491 | 2.26 | 3 |
| 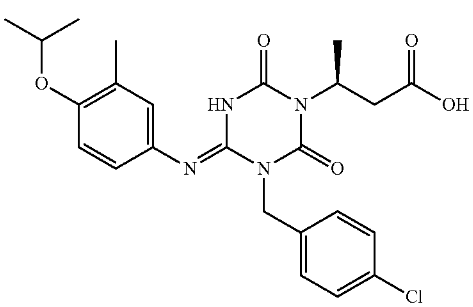 | I-528 | 487 | 2.3 | 3 |

TABLE 112

| Chemical Structure | Compound No. | [M + H] | Retention time (min) | Method |
|---|---|---|---|---|
| 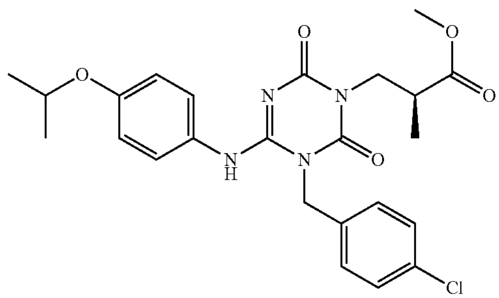 [SMILES: COC(=O)[C@@H](C)Cn1c(=O)nc(Nc2ccc(OC(C)C)cc2)n(Cc2ccc(Cl)cc2)c1=O] | I-529 | 487 | 2.18 | 2 |
| 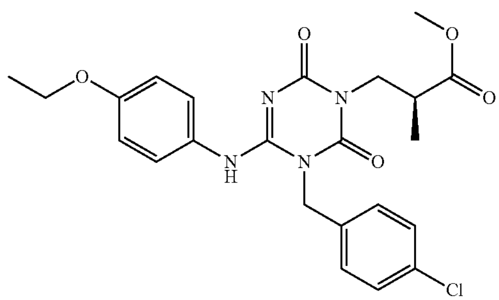 [SMILES: CCOc1ccc(Nc2nc(=O)n(C[C@H](C)C(=O)OC)c(=O)n2Cc2ccc(Cl)cc2)cc1] | I-530 | 473 | 2.07 | 2 |
| 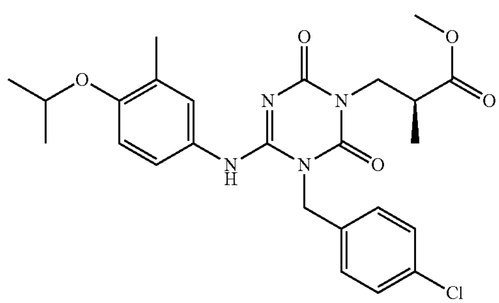 | I-531 | 501 | 2.33 | 2 |
| 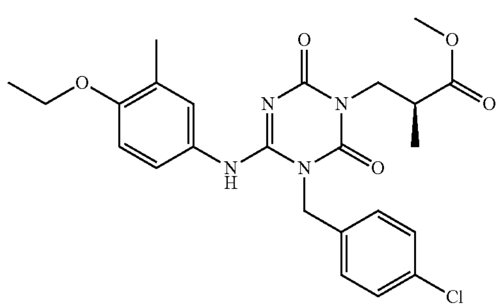 [SMILES: CCOc1ccc(Nc2nc(=O)n(C[C@H](C)C(=O)OC)c(=O)n2Cc2ccc(Cl)cc2)cc1C] | I-532 | 487 | 2.23 | 2 |
| 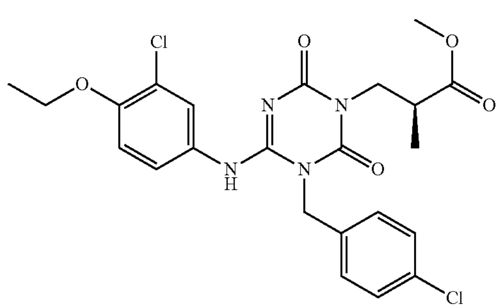 | I-533 | 507 | 2.29 | 2 |

TABLE 113

| Chemical Structure | Compound No. | [M + H] | Retention time (min) | Method |
|---|---|---|---|---|
| 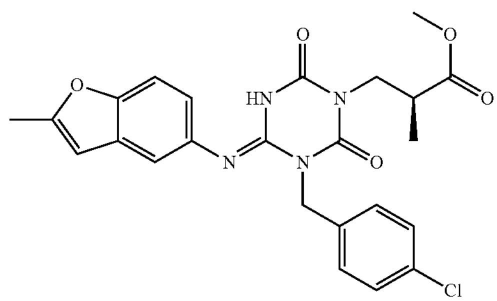 [SMILES: COC(=O)[C@@H](C)Cn1c(=O)[nH]/c(=N\c2ccc3oc(C)cc3c2)n(Cc2ccc(Cl)cc2)c1=O] | I-534 | 483 | 2.16 | 2 |
| 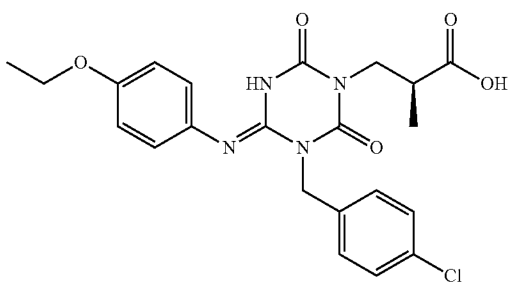 [SMILES: CCOc1ccc(/N=c2\[nH]c(=O)n(C[C@H](C)C(=O)O)c(=O)n2Cc2ccc(Cl)cc2)cc1] | I-535 | 459 | 1.82 | 2 |
| 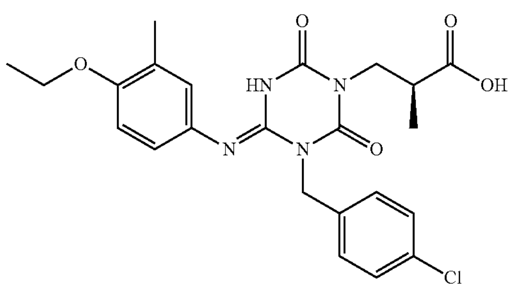 [SMILES: CCOc1ccc(/N=c2\[nH]c(=O)n(C[C@H](C)C(=O)O)c(=O)n2Cc2ccc(Cl)cc2)cc1C] | I-536 | 473 | 1.98 | 2 |
| 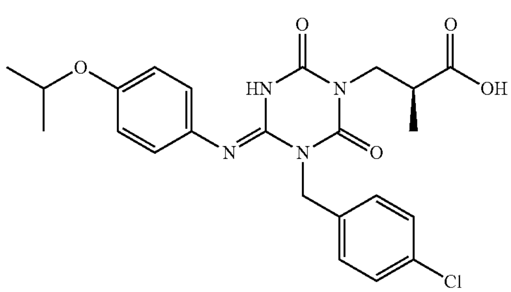 [SMILES: CC(C)Oc1ccc(/N=c2\[nH]c(=O)n(C[C@H](C)C(=O)O)c(=O)n2Cc2ccc(Cl)cc2)cc1] | I-537 | 473 | 1.91 | 2 |
| 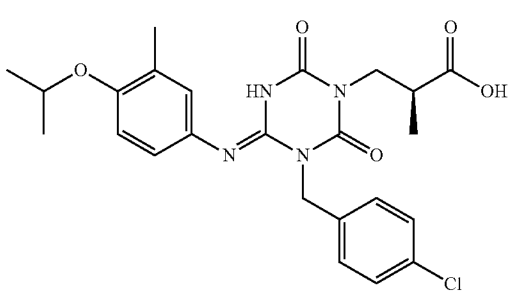 | I-538 | 487 | 2.09 | 2 |

TABLE 114

| Chemical Structure | Compound No. | [M + H] | Retention time (min) | Method |
|---|---|---|---|---|
| 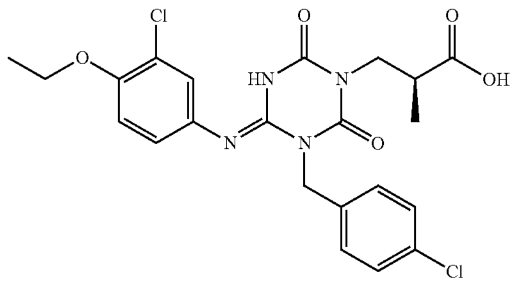 [SMILES: CCOc1ccc(/N=c2\[nH]c(=O)n(C[C@H](C)C(=O)O)c(=O)n2Cc2ccc(Cl)cc2)cc1Cl] | I-539 | 493 | 2.03 | 2 |
| 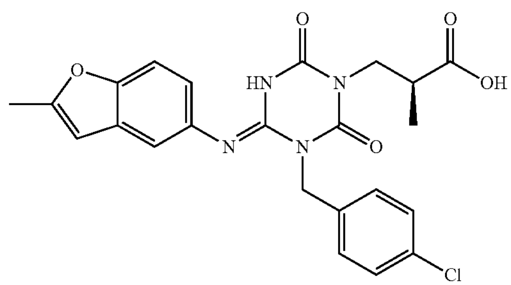 [SMILES: Cc1cc2cc(/N=c3\[nH]c(=O)n(C[C@H](C)C(=O)O)c(=O)n3Cc3ccc(Cl)cc3)ccc2o1] | I-540 | 469 | 1.91 | 2 |
| 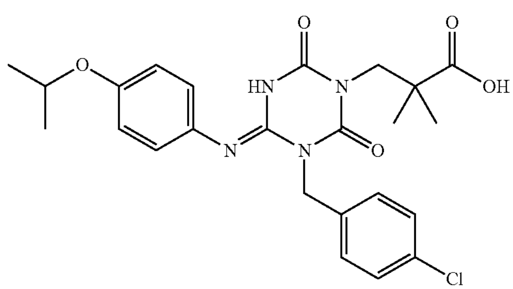 [SMILES: CC(C)Oc1ccc(/N=c2\[nH]c(=O)n(CC(C)(C)C(=O)O)c(=O)n2Cc2ccc(Cl)cc2)cc1] | I-541 | 487 | 1.99 | 2 |
| 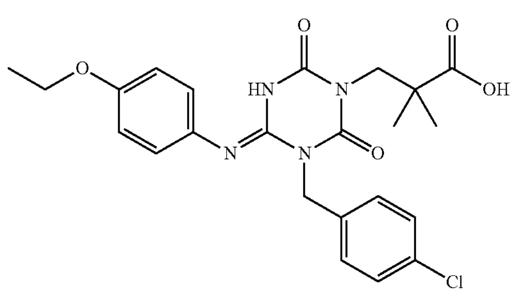 [SMILES: CCOc1ccc(/N=c2\[nH]c(=O)n(CC(C)(C)C(=O)O)c(=O)n2Cc2ccc(Cl)cc2)cc1] | I-542 | 473 | 1.9 | 2 |
| 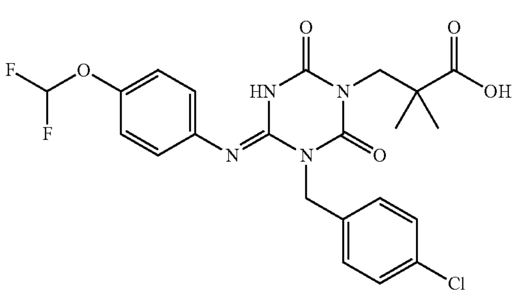 | I-543 | 495 | 1.97 | 2 |

TABLE 115

| Chemical Structure | Compound No. | [M + H] | Retention time (min) | Method |
|---|---|---|---|---|
| 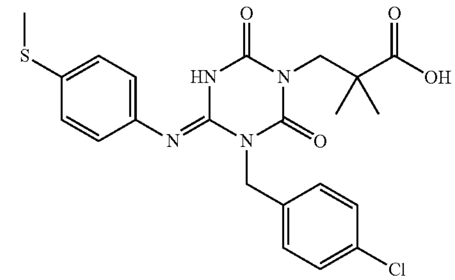 [SMILES: CSc1ccc(/N=c2\[nH]c(=O)n(CC(C)(C)C(=O)O)c(=O)n2Cc2ccc(Cl)cc2)cc1] | I-544 | 475 | 1.99 | 2 |
| 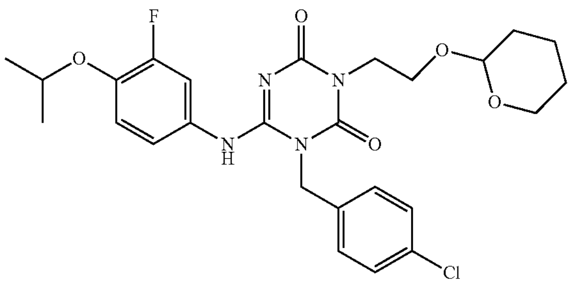 [SMILES: CC(C)Oc1ccc(Nc2nc(=O)n(CCOC3CCCCO3)c(=O)n2Cc2ccc(Cl)cc2)cc1F] | I-545 | 533 | 2.41 | 2 |
| 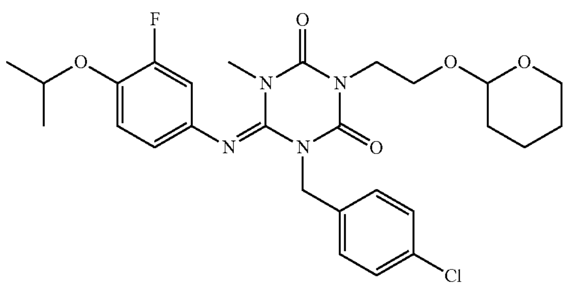 [SMILES: CC(C)Oc1ccc(/N=c2\n(C)c(=O)n(CCOC3CCCCO3)c(=O)n2Cc2ccc(Cl)cc2)cc1F] | I-546 | 547 | 2.76 | 2 |
| 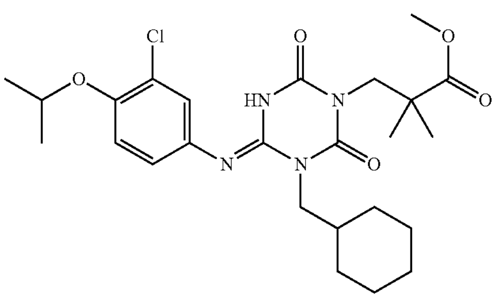 [SMILES: COC(=O)C(C)(C)Cn1c(=O)[nH]/c(=N\c2ccc(OC(C)C)c(Cl)c2)n(CC2CCCCC2)c1=O] | I-547 | 507 | 2.53 | 2 |
| 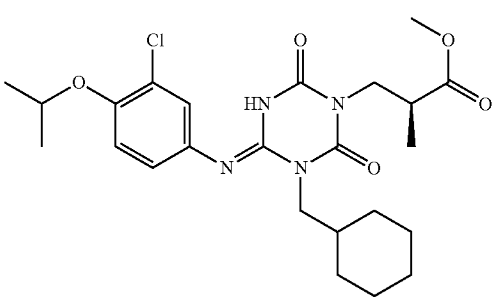 | I-548 | 493 | 2.42 | 2 |

TABLE 116

| Chemical Structure | Compound No. | [M + H] | Retention time (min) | Method |
|---|---|---|---|---|
| 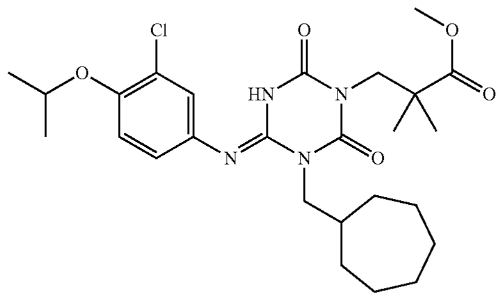 [SMILES: COC(=O)C(C)(C)Cn1c(=O)[nH]/c(=N\c2ccc(OC(C)C)c(Cl)c2)n(CC2CCCCCC2)c1=O] | I-549 | 521 | 2.65 | 2 |
| 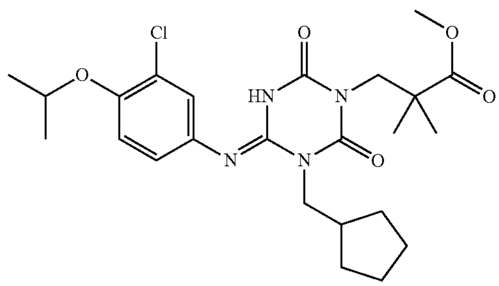 [SMILES: COC(=O)C(C)(C)Cn1c(=O)[nH]/c(=N\c2ccc(OC(C)C)c(Cl)c2)n(CC2CCCC2)c1=O] | I-550 | 493 | 2.43 | 2 |
| 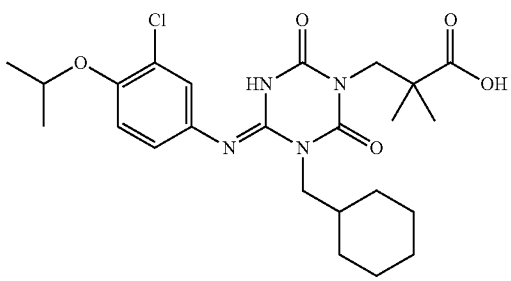 [SMILES: CC(C)Oc1ccc(/N=c2\[nH]c(=O)n(CC(C)(C)C(=O)O)c(=O)n2CC2CCCCC2)cc1Cl] | I-551 | 493 | 2.23 | 2 |
| 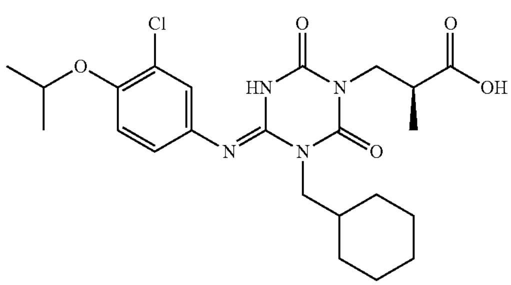 [SMILES: CC(C)Oc1ccc(/N=c2\[nH]c(=O)n(C[C@H](C)C(=O)O)c(=O)n2CC2CCCCC2)cc1Cl] | I-552 | 479 | 2.16 | 2 |
| 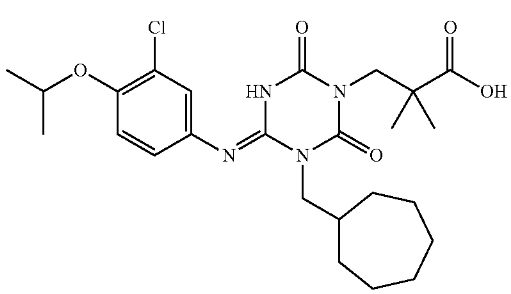 [SMILES: CC(C)Oc1ccc(/N=c2\[nH]c(=O)n(CC(C)(C)C(=O)O)c(=O)n2CC2CCCCCC2)cc1Cl] | I-553 | 507 | 2.35 | 2 |

TABLE 117

| Chemical Structure | Compound No. | [M + H] | Retention time (min) | Method |
|---|---|---|---|---|
| 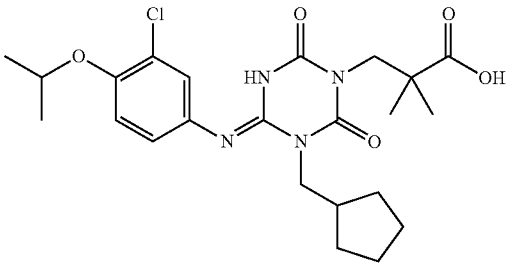 [SMILES: CC(C)Oc1ccc(/N=c2\[nH]c(=O)n(CC(C)(C)C(=O)O)c(=O)n2CC2CCCC2)cc1Cl] | I-554 | 479 | 2.12 | 2 |
| 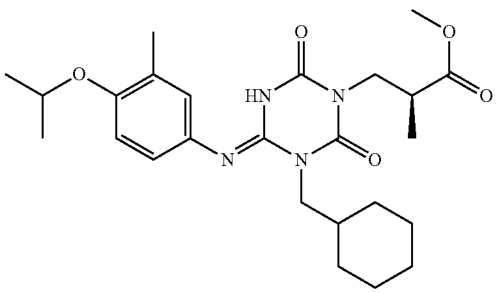 [SMILES: COC(=O)[C@@H](C)Cn1c(=O)[nH]/c(=N\c2ccc(OC(C)C)c(C)c2)n(CC2CCCCC2)c1=O] | I-555 | 473 | 2.37 | 2 |
| 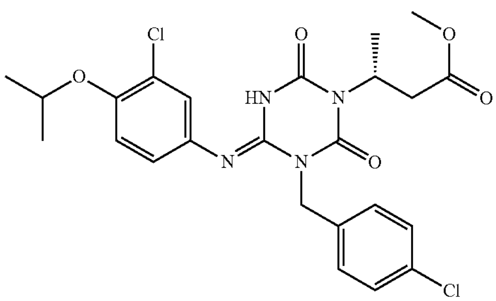 [SMILES: COC(=O)C[C@@H](C)n1c(=O)[nH]/c(=N\c2ccc(OC(C)C)c(Cl)c2)n(Cc2ccc(Cl)cc2)c1=O] | I-556 | 521 | 2.44 | 2 |
| 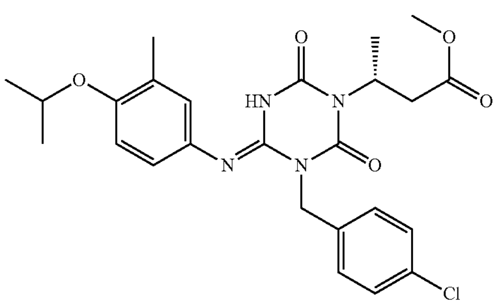 [SMILES: COC(=O)C[C@@H](C)n1c(=O)[nH]/c(=N\c2ccc(OC(C)C)c(C)c2)n(Cc2ccc(Cl)cc2)c1=O] | I-557 | 501 | 2.37 | 2 |
| 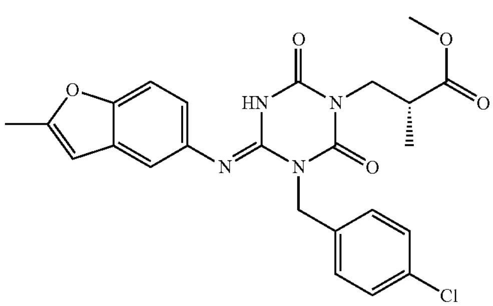 [SMILES: COC(=O)[C@H](C)Cn1c(=O)[nH]/c(=N\c2ccc3oc(C)cc3c2)n(Cc2ccc(Cl)cc2)c1=O] | I-558 | 483 | 2.16 | 2 |

TABLE 118

| Chemical Structure | Compound No. | [M + H] | Retention time (min) | Method |
|---|---|---|---|---|
| 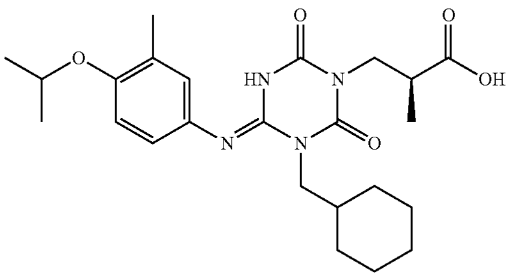 [SMILES: Cc1cc(/N=c2\[nH]c(=O)n(C[C@H](C)C(=O)O)c(=O)n2CC2CCCCC2)ccc1OC(C)C] | I-559 | 459 | 2.09 | 2 |
| 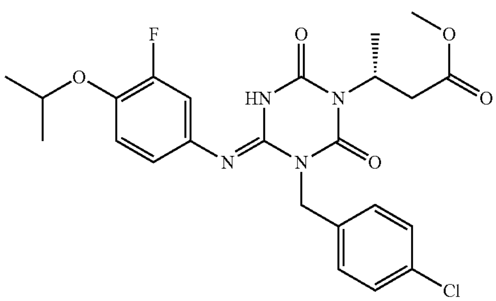 | I-560 | 505 | 2.34 | 2 |
| 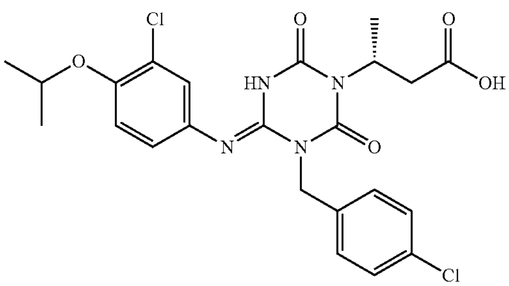 [SMILES: CC(C)Oc1ccc(/N=c2\[nH]c(=O)n([C@H](C)CC(=O)O)c(=O)n2Cc2ccc(Cl)cc2)cc1F] | I-561 | 507 | 2.18 | 2 |
| 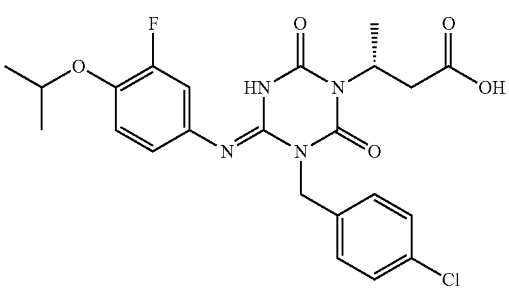 | I-562 | 491 | 2.28 | 2 |
| 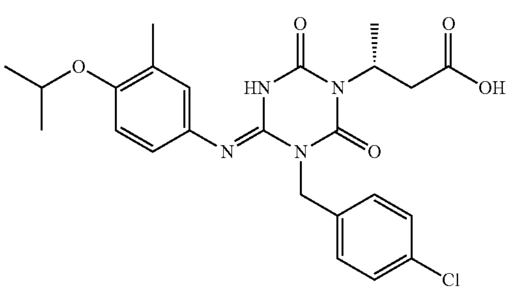 [SMILES: Cc1cc(/N=c2\[nH]c(=O)n([C@H](C)CC(=O)O)c(=O)n2Cc2ccc(Cl)cc2)ccc1OC(C)C] | I-563 | 487 | 2.32 | 2 |

TABLE 119
| Chemical Structure | Compound No. | [M + H] | Retention time (min) | Method |
|---|---|---|---|---|
| 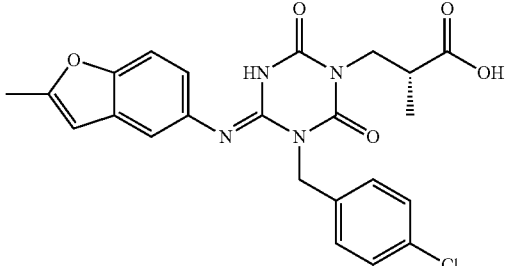 | I-564 | 469 | 2.11 | 3 |
| 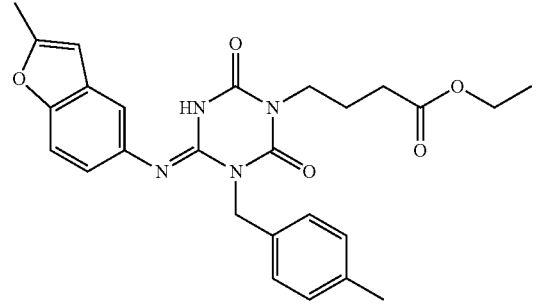 [SMILES: CCOC(=O)CCCn1c(=O)[nH]/c(=N\c2ccc3oc(C)cc3c2)n(Cc2ccc(C)cc2)c1=O] | I-565 | 477 | 2.41 | 3 |
| 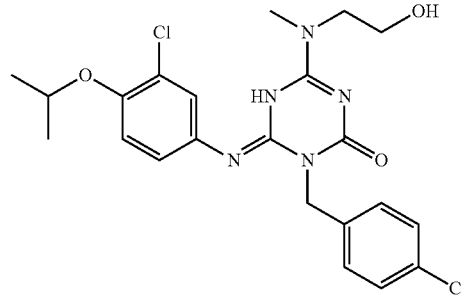 | II-011 | 478 | 1.74 | 2 |
| 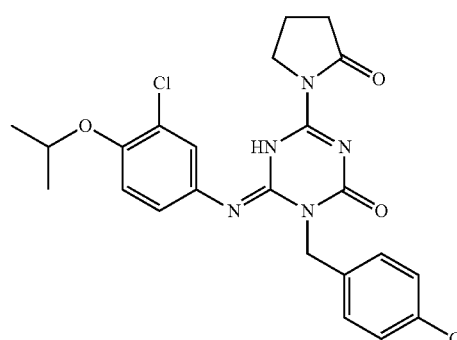 | II-012 | 488 | 2.44 | 2 |
| 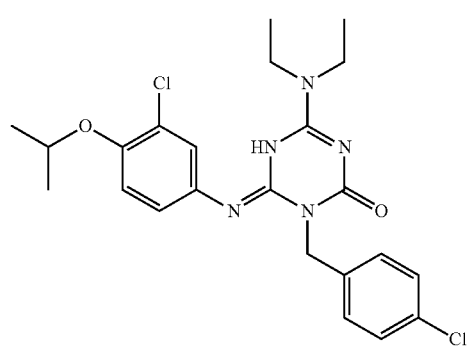 [SMILES: CCN(CC)c1nc(=O)n(Cc2ccc(Cl)cc2)/c(=N/c2ccc(OC(C)C)c(Cl)c2)[nH]1] | II-013 | 476 | 2.04 | 2 |

TABLE 119-continued

| Chemical Structure | Compound No. | [M + H] | Retention time (min) | Method |
|---|---|---|---|---|

TABLE 120

| Chemical Structure | Compound No. | [M + H] | Retention time (min) | Method |
|---|---|---|---|---|
| 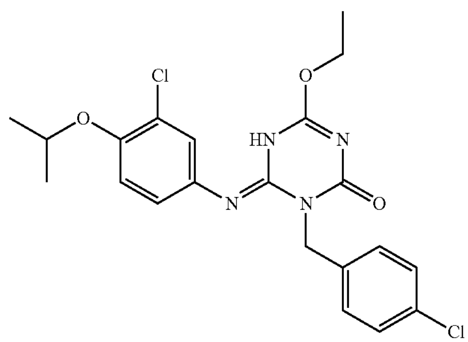 [SMILES: CCOc1nc(=O)n(Cc2ccc(Cl)cc2)/c(=N/c2ccc(OC(C)C)c(Cl)c2)[nH]1] | II-014 | 449 | 2.21 | 2 |
| 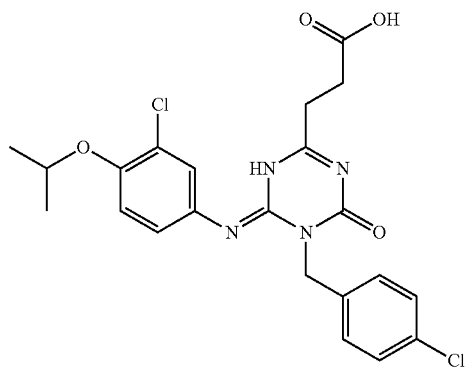 [SMILES: CC(C)Oc1ccc(/N=c2\[nH]c(CCC(=O)O)nc(=O)n2Cc2ccc(Cl)cc2)cc1Cl] | II-015 | 477 | 2.07 | 2 |
| 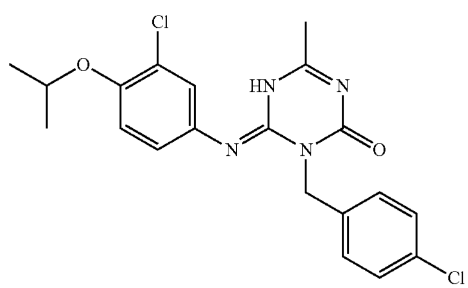 [SMILES: Cc1nc(=O)n(Cc2ccc(Cl)cc2)/c(=N/c2ccc(OC(C)C)c(Cl)c2)[nH]1] | II-016 | 419 | 2.28 | 2 |
| 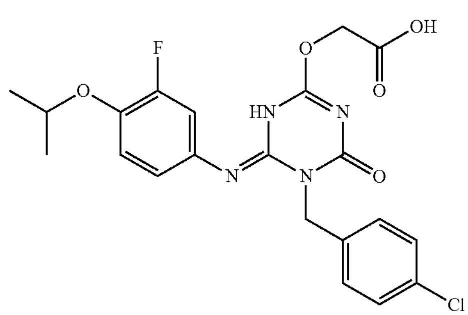 [SMILES: CC(C)Oc1ccc(/N=c2\[nH]c(OCC(=O)O)nc(=O)n2Cc2ccc(Cl)cc2)cc1F] | II-017 | 463 | 1.78 | 2 |

TABLE 120-continued

| Chemical Structure | Compound No. | [M + H] | Retention time (min) | Method |
|---|---|---|---|---|
| (structure) | II-018 | 506 | 1.62 | 2 |

TABLE 121

| Chemical Structure | Compound No. | [M + H] | Retention time (min) | Method |
|---|---|---|---|---|
| (structure) | II-019 | 505 | 1.72 | 2 |
| (structure) | II-020 | 536 | 1.56 | 2 |
| (structure) | II-021 | 533 | 1.4 | 2 |

TABLE 121-continued

| Chemical Structure | Compound No. | [M + H] | Retention time (min) | Method |
|---|---|---|---|---|
| 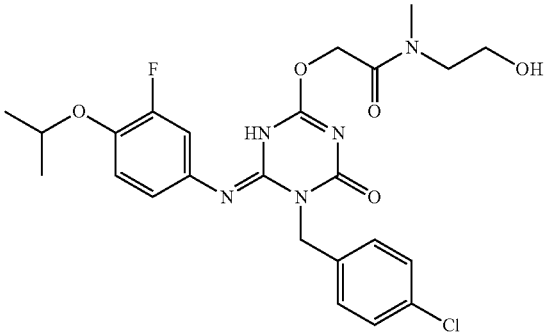 [SMILES: CC(C)Oc1ccc(/N=c2\[nH]c(OCC(=O)N(C)CCO)nc(=O)n2Cc2ccc(Cl)cc2)cc1F] | II-022 | 520 | 1.65 | 2 |
| 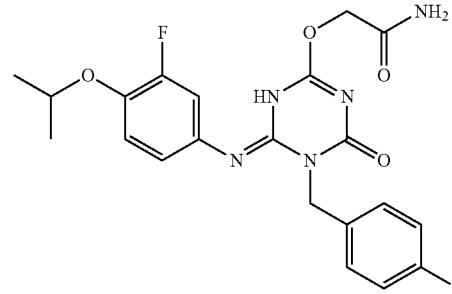 | II-023 | 462 | 1.66 | 2 |

Test Examples

Stably expressing cell line (C6BU-1 cell transfected with human $P2X_3$ receptor gene (GenBank accession number Y07683)) was used. The cells were seeded in a 96-well microtiter plate at a concentration of 8000 cells/well and cultured in the medium (8.3% fetal bovine serum, 8.3% horse serum, 1% antibiotic and antifungal in DMEM) for one day at 37° C. under 5% carbon dioxide atmosphere. The medium was replaced with 4 μM Fluo-3-AM solution (pH 7.5) containing 20 mM HEPES, 137 mM NaCl, 2.7 mM KCl, 0.9 mM $MgCl_2$, 5.0 mM $CaCl_2$, 5.6 mM D-glucose, 2.5 mM probenecid, 10% BSA, and 0.08% Pluronic F-127, and incubated at 37° C. under 5% dioxide carbon atmosphere for one hour. The plate was washed with washing buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH 7.5), and each well was added with 40 μL of this buffer. The plate was placed in High-Throughput Screening System FDSS 3000 (Hamamatsu Photonics K.K.). Measurement of fluorescence intensity by FDSS 3000 was started, and 40 μL of DMSO solutions containing different concentrations of the test compound as prepared by dilution with dilution buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, 0.1% Pluronic F-127, pH 7.5) were dispensed to each well through the built-in automatic dispenser. Five minutes after, 40 nM ATP solution (50 μL) prepared by dilution with the dilution buffer was dispensed through the built-in automatic dispenser, and the measurement of fluorescence intensity was continued for 3 min. For each well, the specific maximum fluorescence intensity was calculated as the ratio of the maximum fluorescence intensity after addition of the ATP solution to the fluorescence intensity at the starting of the measurement. The 50% inhibitory concentration ($IC_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. $IC_{50}$ was calculated using Microsoft™ Excel™ (Microsoft Corporation) and XLfit™ (ID Business Solutions Ltd.)

The results of the compounds of the invention are shown in the following tables.

TABLE 122

| Compound No. | P2X3 IC50(μM) |
|---|---|
| I-020 | 0.389 |
| I-021 | 0.197 |
| I-029 | 0.595 |
| I-097 | 0.505 |
| I-116 | 0.484 |
| I-117 | 0.387 |
| I-118 | 0.231 |
| I-121 | 0.246 |
| I-123 | 0.815 |
| I-126 | 0.689 |
| I-128 | 0.840 |
| I-130 | 0.953 |
| I-133 | 0.339 |
| I-138 | 0.619 |
| I-141 | 0.685 |
| I-162 | 0.379 |
| I-164 | 0.860 |
| I-181 | 0.985 |
| I-182 | 0.714 |
| I-200 | 0.128 |
| I-203 | 0.110 |
| I-204 | 0.558 |

TABLE 122-continued

| Compound No. | P2X3 IC50(μM) |
|---|---|
| I-217 | 0.268 |
| I-218 | 0.505 |
| I-221 | 0.276 |
| I-223 | 0.909 |
| I-227 | 0.970 |
| I-228 | 0.031 |
| I-234 | 0.298 |
| I-235 | 0.985 |
| I-237 | 0.230 |
| I-238 | 0.658 |
| I-239 | 0.116 |
| I-240 | 0.953 |
| I-241 | 0.447 |
| I-242 | 0.787 |
| I-243 | 0.450 |
| I-244 | 0.045 |
| I-245 | 0.168 |
| I-246 | 0.996 |
| I-248 | 0.420 |
| I-254 | 0.144 |
| I-255 | 0.520 |
| I-256 | 0.867 |
| I-257 | 0.682 |
| I-258 | 0.683 |
| I-266 | 0.861 |
| I-269 | 0.415 |
| I-270 | 0.271 |
| I-271 | 0.032 |
| I-272 | 0.180 |
| I-273 | 0.038 |
| I-274 | 0.009 |
| I-275 | 0.021 |
| I-276 | 0.012 |
| I-277 | 0.038 |
| I-278 | 0.931 |
| I-280 | 0.030 |
| I-281 | 0.012 |
| I-282 | 0.027 |
| I-283 | 0.019 |
| I-284 | 0.629 |
| I-285 | 0.014 |
| I-286 | 0.277 |
| I-287 | 0.222 |
| I-288 | 0.093 |
| I-289 | 0.066 |
| I-290 | 0.266 |
| I-291 | 0.009 |
| I-292 | 0.034 |
| I-293 | 0.351 |
| I-294 | 0.040 |
| I-295 | 0.046 |
| I-296 | 0.176 |
| I-297 | 0.045 |
| I-298 | 0.027 |
| I-299 | 0.046 |
| I-300 | 0.025 |
| I-301 | 0.048 |
| I-305 | 0.946 |
| I-307 | 0.250 |
| I-309 | 0.357 |
| I-310 | 0.389 |
| I-311 | 0.142 |
| I-312 | 0.104 |
| I-313 | 0.178 |
| I-314 | 0.555 |
| I-315 | 0.183 |
| I-316 | 0.712 |
| I-317 | 0.137 |
| I-320 | 0.083 |
| I-321 | 0.033 |
| I-322 | 0.112 |
| I-323 | 0.148 |
| I-324 | 0.309 |
| I-325 | 0.665 |
| I-326 | 0.011 |
| I-328 | 0.124 |
| I-329 | 0.266 |

TABLE 122-continued

| Compound No. | P2X3 IC50(μM) |
|---|---|
| I-330 | 0.594 |
| I-331 | 0.066 |
| I-332 | 0.008 |
| I-333 | 0.192 |
| I-334 | 0.099 |
| I-335 | 0.007 |
| I-338 | 0.053 |
| I-339 | 0.775 |
| I-340 | 0.336 |
| I-341 | 0.149 |
| I-342 | 0.005 |
| I-343 | 0.021 |
| I-344 | 0.128 |
| I-346 | 0.016 |
| I-347 | 0.251 |
| I-348 | 0.013 |
| I-349 | 0.113 |
| I-350 | 0.010 |
| I-351 | 0.015 |
| I-352 | 0.036 |
| I-353 | 0.018 |
| I-354 | 0.008 |
| I-355 | 0.020 |
| I-356 | 0.012 |
| I-357 | 0.047 |
| I-358 | 0.055 |
| I-359 | 0.040 |
| I-360 | 0.148 |
| I-361 | 0.076 |
| I-362 | 0.007 |
| I-363 | 0.078 |
| I-364 | 0.030 |
| I-365 | 0.018 |
| I-366 | 0.046 |
| I-367 | 0.040 |
| I-368 | 0.041 |
| I-369 | 0.007 |
| I-370 | 0.154 |
| I-371 | 0.063 |
| I-372 | 0.964 |
| I-373 | 0.185 |
| I-374 | 0.080 |
| I-375 | 0.152 |
| I-377 | 0.755 |
| I-378 | 0.347 |
| I-379 | 0.330 |
| I-380 | 0.034 |
| I-382 | 0.096 |
| I-383 | 0.532 |
| I-385 | 0.908 |
| I-386 | 0.041 |
| I-387 | 0.037 |
| I-388 | 0.036 |
| I-389 | 0.064 |
| I-390 | 0.067 |
| I-391 | 0.133 |
| I-392 | 0.038 |
| I-394 | 0.435 |
| I-397 | 0.019 |
| I-398 | 0.007 |
| I-399 | 0.008 |
| I-400 | 0.044 |
| I-401 | 0.007 |
| I-402 | 0.443 |
| I-403 | 0.015 |
| I-404 | 0.012 |
| I-405 | 0.032 |
| I-406 | 0.030 |
| I-407 | 0.027 |
| I-408 | 0.010 |
| I-409 | 0.012 |
| I-410 | 0.044 |
| I-411 | 0.061 |
| I-413 | 0.099 |
| I-414 | 0.007 |
| I-415 | 0.314 |
| I-416 | 0.035 |

TABLE 122-continued

| Compound No. | P2X3 IC50(μM) |
|---|---|
| I-417 | 0.035 |
| I-418 | 0.200 |
| I-419 | 0.071 |
| I-420 | 0.053 |
| I-421 | 0.019 |
| I-422 | 0.006 |
| I-423 | 0.004 |
| I-424 | 0.049 |
| I-425 | 0.016 |
| I-426 | 0.211 |
| I-427 | 0.678 |
| I-429 | 0.779 |
| I-431 | 0.004 |
| I-432 | 0.026 |
| I-433 | 0.199 |
| II-002 | 0.079 |
| II-006 | 0.398 |
| II-008 | 0.943 |
| II-009 | 0.034 |
| II-010 | 0.349 |
| I-434 | 0.407 |
| I-435 | 0.006 |
| I-436 | 0.008 |
| I-437 | 0.006 |
| I-438 | 0.005 |
| I-439 | 0.018 |
| I-440 | 0.055 |
| I-441 | 0.011 |
| I-442 | 0.117 |
| I-443 | 0.207 |
| I-444 | 0.017 |
| I-445 | 0.008 |
| I-446 | 0.020 |
| I-447 | 0.279 |
| I-448 | 0.388 |
| I-450 | 0.036 |
| I-451 | 0.016 |
| I-452 | 0.003 |
| I-453 | 0.005 |
| I-454 | 0.024 |
| I-455 | 0.030 |
| I-456 | 0.008 |
| I-457 | 0.003 |
| I-458 | 0.004 |
| I-459 | 0.039 |
| I-460 | 0.016 |
| I-461 | 0.009 |
| I-462 | 0.004 |
| I-463 | 0.074 |
| I-464 | 0.564 |
| I-465 | 0.057 |
| I-466 | 0.037 |
| I-467 | 0.037 |
| I-468 | 0.137 |
| I-469 | 0.101 |
| I-470 | 0.080 |
| I-471 | 0.024 |
| I-472 | 0.047 |
| I-473 | 0.583 |
| I-474 | 0.014 |
| I-475 | 0.571 |
| I-476 | 0.035 |
| I-477 | 0.056 |
| I-478 | 0.629 |
| I-479 | 0.007 |
| I-480 | 0.012 |
| I-481 | 0.012 |
| I-483 | 0.100 |
| I-484 | 0.290 |
| I-485 | 0.198 |
| I-486 | 0.042 |
| I-487 | 0.027 |
| I-488 | 0.124 |
| I-489 | 0.010 |
| I-490 | 0.046 |
| I-491 | 0.027 |
| I-492 | 0.102 |
| I-493 | 0.952 |
| I-494 | 0.034 |
| I-495 | 0.125 |
| I-496 | 0.125 |
| I-497 | 0.458 |
| I-498 | 0.009 |
| I-499 | 0.137 |
| I-500 | 0.013 |
| I-501 | 0.191 |
| I-502 | 0.020 |
| I-503 | 0.050 |
| I-504 | 0.015 |
| I-505 | 0.120 |
| I-506 | 0.279 |
| I-507 | 0.301 |
| I-508 | 0.511 |
| I-509 | 0.652 |
| I-510 | 0.098 |
| I-515 | 0.006 |
| I-516 | 0.005 |
| I-517 | 0.015 |
| I-518 | 0.007 |
| I-519 | 0.012 |
| I-520 | 0.080 |
| I-521 | 0.004 |
| I-522 | 0.029 |
| I-523 | 0.072 |
| I-524 | 0.060 |
| I-525 | 0.054 |
| I-526 | 0.024 |
| I-527 | 0.033 |
| I-528 | 0.053 |
| I-529 | 0.022 |
| I-530 | 0.034 |
| I-531 | 0.010 |
| I-532 | 0.029 |
| I-533 | 0.010 |
| I-534 | 0.018 |
| I-535 | 0.052 |
| I-536 | 0.046 |
| I-537 | 0.019 |
| I-538 | 0.016 |
| I-539 | 0.007 |
| I-540 | 0.027 |
| I-541 | 0.058 |
| I-542 | 0.096 |
| I-543 | 0.172 |
| I-544 | 0.601 |
| I-545 | 0.006 |
| I-546 | 0.459 |
| I-547 | 0.011 |
| I-548 | 0.012 |
| I-549 | 0.019 |
| I-550 | 0.033 |
| I-551 | 0.034 |
| I-552 | 0.023 |
| I-553 | 0.034 |
| I-554 | 0.139 |
| I-555 | 0.013 |
| I-556 | 0.005 |
| I-557 | 0.019 |
| I-558 | 0.005 |
| I-559 | 0.097 |
| I-560 | 0.007 |
| I-561 | 0.008 |
| I-562 | 0.027 |
| I-563 | 0.040 |
| I-564 | 0.048 |
| II-012 | 0.568 |
| II-013 | 0.430 |
| II-014 | 0.254 |
| II-015 | 0.614 |

Test Examples 2

CYP3A4 Fluorescent MBI test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 µmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris(trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (−).

Test Examples 3

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

Test Examples 4

FAT Test

20 µL of freezing-stored rat typhoid *bacillus* (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution, the bacteria was suspended in 9 mL of a Micro F buffer ($K_2HPO_4$: 3.5 g/L, $KH2PO_4$: 1 g/L, $(NH_4)_2SO_4$: 1 g/L, trisodium citrate dehydrate: 0.25 g/L, $MgSO_4.7H_2O$: 0.1 g/L), the suspension was added to 110 mL of an Exposure medium (Micro F buffer containing Biotin: 8 µg/mL, histidine 0.2 µg/mL, glucose: 8 mg/mL), and the TA100 strain was added to 120 mL of the Exposure medium relative to 3.16 mL of the bacterial solution to prepare a test bacterial solution. Each 12 µl of a test substance DMSO solution (8 stage dilution from maximum dose 50 mg/mL at 2-fold ratio), DMSO as a negative control, 50 µg/mL of 4-nitroquinoline-1-oxide DMSO solution for the TA98 strain, 0.25 µg/mL of 2-(furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/m L of 2-aminoanthracene DMSO solution for the TA100 strain under the metabolism activating condition as a positive control, and 588 µL of the test bacterial solution (a mixed solution of 498 µl of the test bacterial solution and 90 µL of S9 mix under the metabolism activating condition) were mixed, and this was shaking-cultured at 37° C. for 90 minutes. 460 µL of the bacterial solution exposed to the test substance was mixed with 2300 µL of an Indicator medium (Micro F buffer containing biotin: 8 µg/mL, histidine 0.2 µg/mL, glucose: 8 mg/mL, Bromo Cresol Purple: 37.5 µg/mL), each 50 µL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group.

Test Examples 5

Solubility Test

The solubility of a compound is determined under a condition in which 1% DMSO is added. 10 mM compound solution is prepared using DMSO, and then 6 μL of the compound solution is added to 594 μL of artificial intestinal juice in pH 6.8 (to 250 mL of 0.2 mol/L potassium dihydrogen phosphate reagent solution is added 118 mL of 0.2 mol/L NaOH reagent solution and water to provide a final volume of 1000 mL). After standing at 25 degrees Celsius for 16 hours, the mixed solution is filtrated with suction. The filtrate is diluted twice with methanol/water (1/1), and then a concentration in the filtration is measured with HPLC or LC/MS/MS by the absolute calibration method.

Test Examples 6

Metabolism Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%.

Test Examples 7 hERG Test

For the purpose of assessing risk of an electrocardiogram QT interval prolongation, effects on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, NaH$_2$PO$_4$: 0.3 mmol/L, CaCl$_2$.2H$_2$O: 1.8 mmol/L, MgCl$_2$.6H$_2$O:1 mmol/L, glucose: 10 mmol/L, HEPES (4-(2-hydroxyethyl)-1-piperazineethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

Test Example 8

Metabolism Stability Test

Using a prepared frozen rat hepatocyte, a test compound is reacted for a constant time, a remaining rate is calculated by comparing a reacted sample and an unreacted sample, thereby, a degree of metabolism in liver is assessed.

A reaction is performed at 37° C. for 0, 1 or 2 hours in William's E medium containing rat frozen hepatocyte 1.0× $10^6$ cells/mL. After the reaction, 50 μL of the reaction solution is added to 100 μL of a methanol/acetonitrile=1/1 (v/v), mixed and centrifuged at 3000 rpm for 15 minutes. The test compound in the supernatant is quantified by LC/MS/MS, and a remaining amount of the test coin pound after the reaction is calculated, letting a compound amount at 0 minute reaction time to be 100%.

As shown, the compounds of the invention showed inhibiting activity on P2X$_3$ receptor. Furthermore, as the compounds of the invention can be effective to P2X$_3$ subtype, the compounds also have inhibiting activity on P2X$_{2/3}$ receptor, which comprises P2X$_3$ subtype.

INDUSTRIAL APPLICABILITY

The compound of the invention has antagonizing effect on P2X$_3$ and/or P2X$_{2/3}$ receptor and is useful in the treatment of diseases or conditions associated with a P2X$_3$ and/or P2X$_{2/3}$ receptor, such as chronic pain, overactive bladder, etc.

The invention claimed is:
1. A compound represented by formula (II):

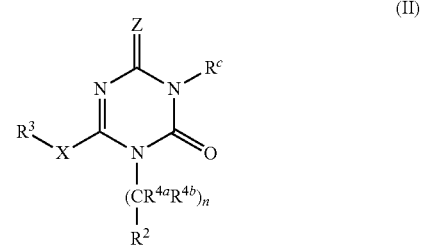

or a pharmaceutically acceptable salt thereof,
wherein
R$^{1c}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
R$^{4a}$ and R$^{4b}$ are each independently hydrogen;
—X— is N(R$^5$)—;
R$^5$ is hydrogen;
═Z is ═O;
n is an integer of 1 to 2;

$R^2$ is substituted or unsubstituted aryl, or substituted or unsubstituted heteroaryl;

$R^3$ is a group represented by the formula:

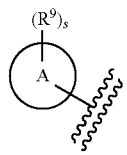

wherein ring A is aryl or heteroaryl;

s is an integer of 0 to 3; and $R^9$ is each independently halogen, hydroxy, cyano, nitro, substituted or unsubstituted alkyl, substituted or unsubstituted alkenyl, substituted or unsubstituted alkenyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy.

2. The compound according to claim 1, wherein $R^{1c}$ is hydrogen; unsubstituted alkyl; or alkyl substituted with one or more substituents selected from the group consisting of halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclic ring-oxy-carbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl and substituted or unsubstituted heteroaryl, or a pharmaceutically acceptable salt thereof.

3. The compound according to claim 1, wherein $R^3$ is a group represented by the formula:

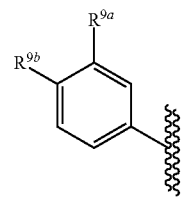

wherein $R^{9a}$ and $R^{9b}$ are each independently halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy, or a pharmaceutically acceptable salt thereof.

4. The compound according to claim 1, wherein $R^3$ is a group represented by the formula:

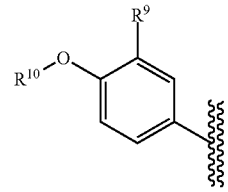

wherein $R^9$ is halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy, or a pharmaceutically acceptable salt thereof; and $R^{10}$ is substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or a pharmaceutically acceptable salt thereof.

5. A pharmaceutical composition comprising a compound represented by formula (II):

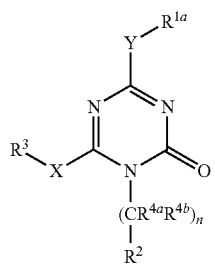

(III)

or a pharmaceutically acceptable salt thereof, wherein $R^{1c}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^{4a}$ and $R^{4b}$ are each independently hydrogen;

—X— is —O—, —S— or —N($R^5$)—;

$R^5$ is hydrogen;

=Z is =O;

n is an integer of 1 to 2;

$R^2$ is substituted or unsubstituted aryl, or substituted or unsubstituted heteroaryl;

$R^3$ is a group represented by the formula:

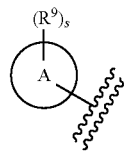

wherein ring A is aryl or heteroaryl;

s is an integer of 0 to 3; and $R^9$ is each independently halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclic ring-oxy, substituted or unsubstituted aryloxy, or substituted or unsubstituted heteroaryloxy.

* * * * *